United States Patent
Bear et al.

(10) Patent No.: US 10,478,189 B2
(45) Date of Patent: Nov. 19, 2019

(54) METHOD OF APPLYING AN ANNULAR ARRAY OF STAPLES TO TISSUE

(71) Applicant: Ethicon Endo-Surgery, LLC, Guaynabo, PR (US)

(72) Inventors: Brian W. Bear, Cincinnati, OH (US); Matthew H. Bolton, West Chester, OH (US); Rodney V. Clingaman, Mason, OH (US); Brian F. DiNardo, Cincinnati, OH (US); William D. Fox, New Richmond, OH (US); Kevin L. Houser, Springboro, OH (US); John P. Measamer, Cincinnati, OH (US); Christopher C. Miller, Loveland, OH (US); Mark D. Overmyer, Cincinnati, OH (US); Kevin D. Sackett, Independence, KY (US); Charles J. Scheib, Loveland, OH (US); Emily A. Schellin, Cincinnati, OH (US); Richard F. Schwemberger, Cincinnati, OH (US); Frederick E. Shelton, IV, Hillsboro, OH (US); Craig S. Smith, Cincinnati, OH (US); Omar J. Vakharia, Cincinnati, OH (US); Jason E. Zerkle, Blanchester, OH (US)

(73) Assignee: Ethicon LLC, Guaynabo, PR (US)

( * ) Notice: Subject to any disclaimer, the term of this patent is extended or adjusted under 35 U.S.C. 154(b) by 701 days.

(21) Appl. No.: 14/751,612

(22) Filed: Jun. 26, 2015

(65) Prior Publication Data
US 2016/0374672 A1 Dec. 29, 2016

(51) Int. Cl.
*A61B 17/115* (2006.01)
*H02J 7/00* (2006.01)
(Continued)

(52) U.S. Cl.
CPC ............ *A61B 17/1155* (2013.01); *H02J 7/00* (2013.01); *A61B 2017/00039* (2013.01);
(Continued)

(58) Field of Classification Search
None
See application file for complete search history.

(56) References Cited

U.S. PATENT DOCUMENTS 5,205,459 A 4/1993 Brinkerhoff et al.
5,271,544 A 12/1993 Fox et al.
(Continued)

*Primary Examiner* — Shuan L David
(74) *Attorney, Agent, or Firm* — Frost Brown Todd LLC

(57) ABSTRACT

A surgical instrument includes a body, a shaft assembly, a stapling head assembly, an anvil, an anvil adjustment assembly, a trigger, and a lockout assembly. The stapling head assembly is operable to drive an annular array of staples. The anvil is configured to couple with the stapling head assembly. The anvil adjustment assembly includes a translating member, which translates relative to the body to thereby adjust the longitudinal position of the anvil relative to the stapling head assembly. The trigger is operable to actuate the stapling head assembly. The lockout assembly includes an electrically powered braking feature. A method of operating the surgical instrument includes providing the lockout assembly in a first state to permit translation of the translating member. The translating member is then translated. The lockout assembly is then transitioned to a second state to prevent further translation of the translating member.

20 Claims, 228 Drawing Sheets

(51) Int. Cl.
*A61B 17/00* (2006.01)
*A61B 90/00* (2016.01)

(52) U.S. Cl.
CPC .............. *A61B 2017/00115* (2013.01); *A61B 2017/00367* (2013.01); *A61B 2017/00398* (2013.01); *A61B 2017/00407* (2013.01); *A61B 2017/00477* (2013.01); *A61B 2017/00734* (2013.01); *A61B 2017/00876* (2013.01); *A61B 2090/031* (2016.02); *A61B 2090/0811* (2016.02)

(56) References Cited

U.S. PATENT DOCUMENTS

| | | |
|---|---|---|
| 5,275,322 A | 1/1994 | Wolf et al. |
| 5,285,945 A | 2/1994 | Brinkerhoff et al. |
| 5,292,053 A | 3/1994 | Smith et al. |
| 5,333,773 A | 8/1994 | Main et al. |
| 5,350,104 A | 9/1994 | Main et al. |
| 5,533,661 A | 7/1996 | Victor |
| 6,945,444 B2 | 9/2005 | Gresham et al. |
| 7,794,475 B2 | 9/2010 | Hess et al. |
| 8,408,439 B2 | 4/2013 | Huang et al. |
| 8,453,914 B2 | 6/2013 | Laurent et al. |
| 8,910,847 B2 | 12/2014 | Nalagatla et al. |
| 9,161,803 B2 | 10/2015 | Yates et al. |
| 2010/0096431 A1* | 4/2010 | Smith .................... A61B 17/00 227/175.2 |
| 2013/0153630 A1* | 6/2013 | Miller .................. A61B 17/115 227/175.2 |
| 2013/0153631 A1 | 6/2013 | Vasudevan et al. |
| 2014/0144968 A1 | 5/2014 | Shelton |
| 2014/0144969 A1 | 5/2014 | Scheib et al. |
| 2014/0151429 A1 | 6/2014 | Scheib et al. |
| 2014/0151430 A1 | 6/2014 | Scheib et al. |
| 2014/0158747 A1 | 6/2014 | Measamer et al. |
| 2014/0166717 A1 | 6/2014 | Swayze et al. |
| 2014/0166718 A1 | 6/2014 | Swayze et al. |
| 2014/0166728 A1 | 6/2014 | Swayze et al. |
| 2015/0083772 A1 | 3/2015 | Miller et al. |
| 2015/0083773 A1 | 3/2015 | Measamer et al. |
| 2015/0083774 A1* | 3/2015 | Measamer ........... A61B 17/068 227/175.1 |
| 2015/0083775 A1 | 3/2015 | Leimbach et al. |
| 2015/0272575 A1 | 10/2015 | Leimbach et al. |

* cited by examiner

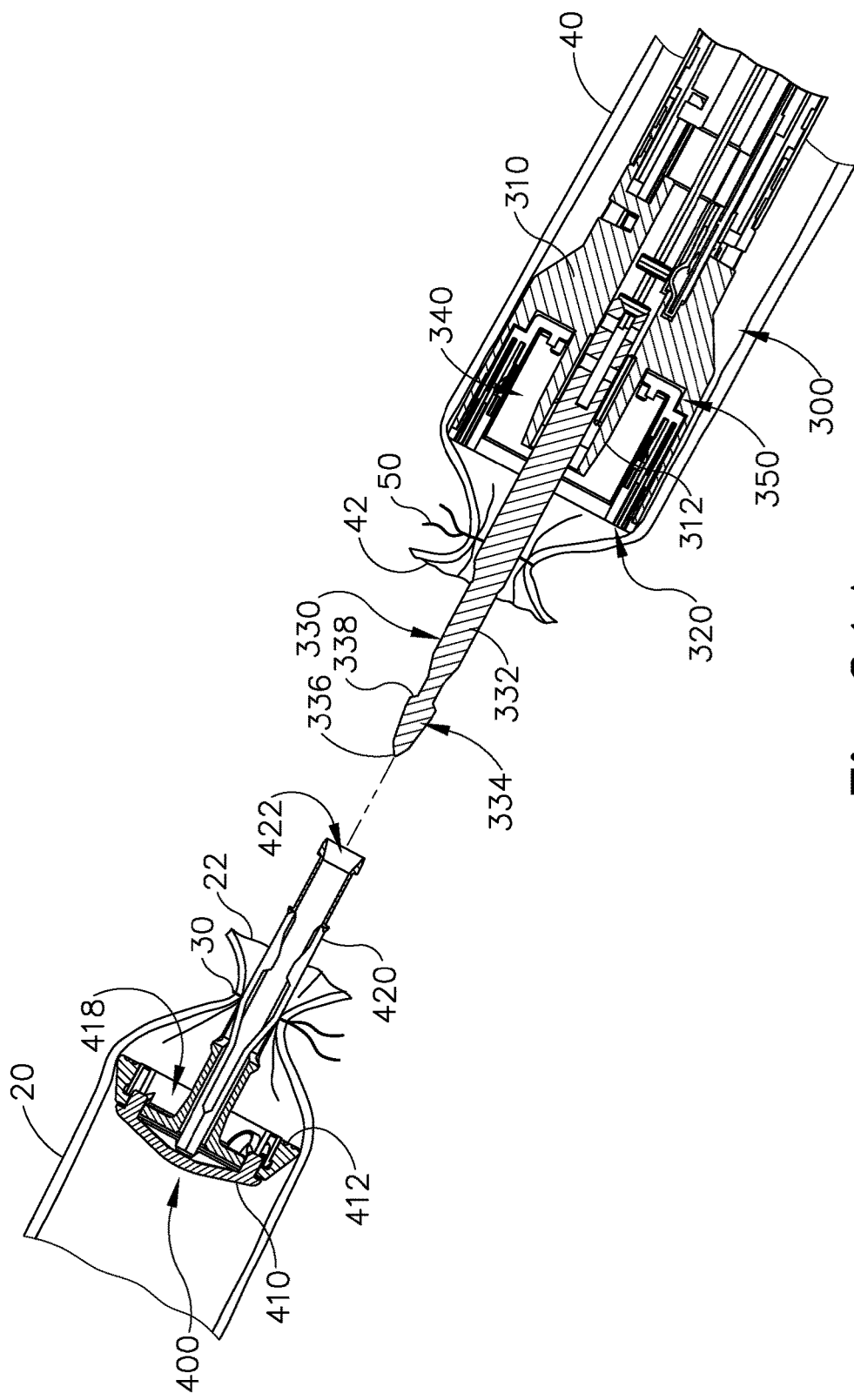

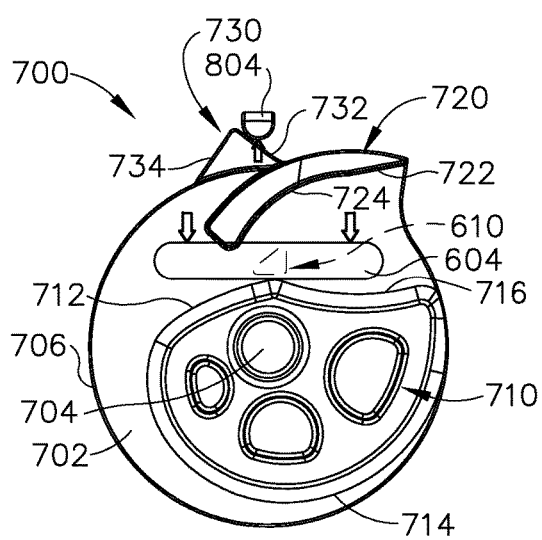
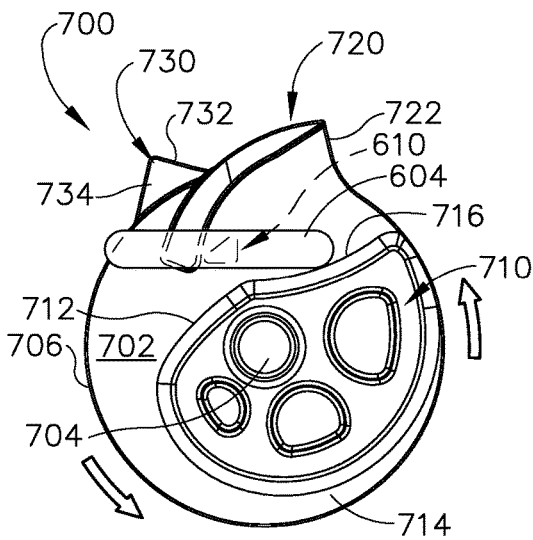
FIG. 50A
FIG. 50B
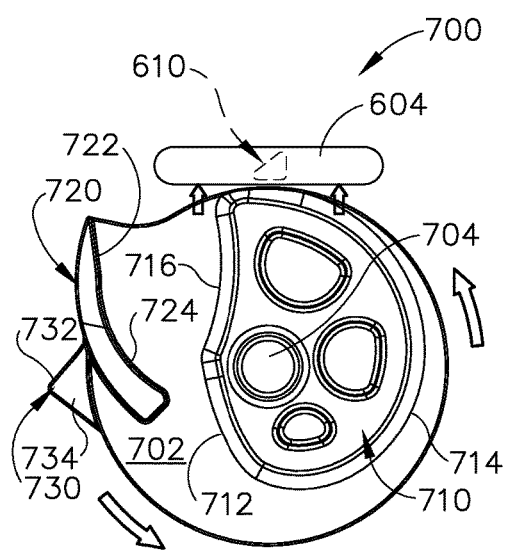
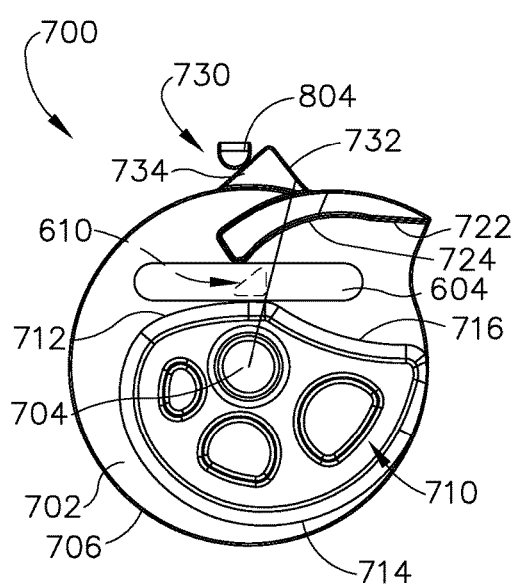
FIG. 50C
FIG. 50D

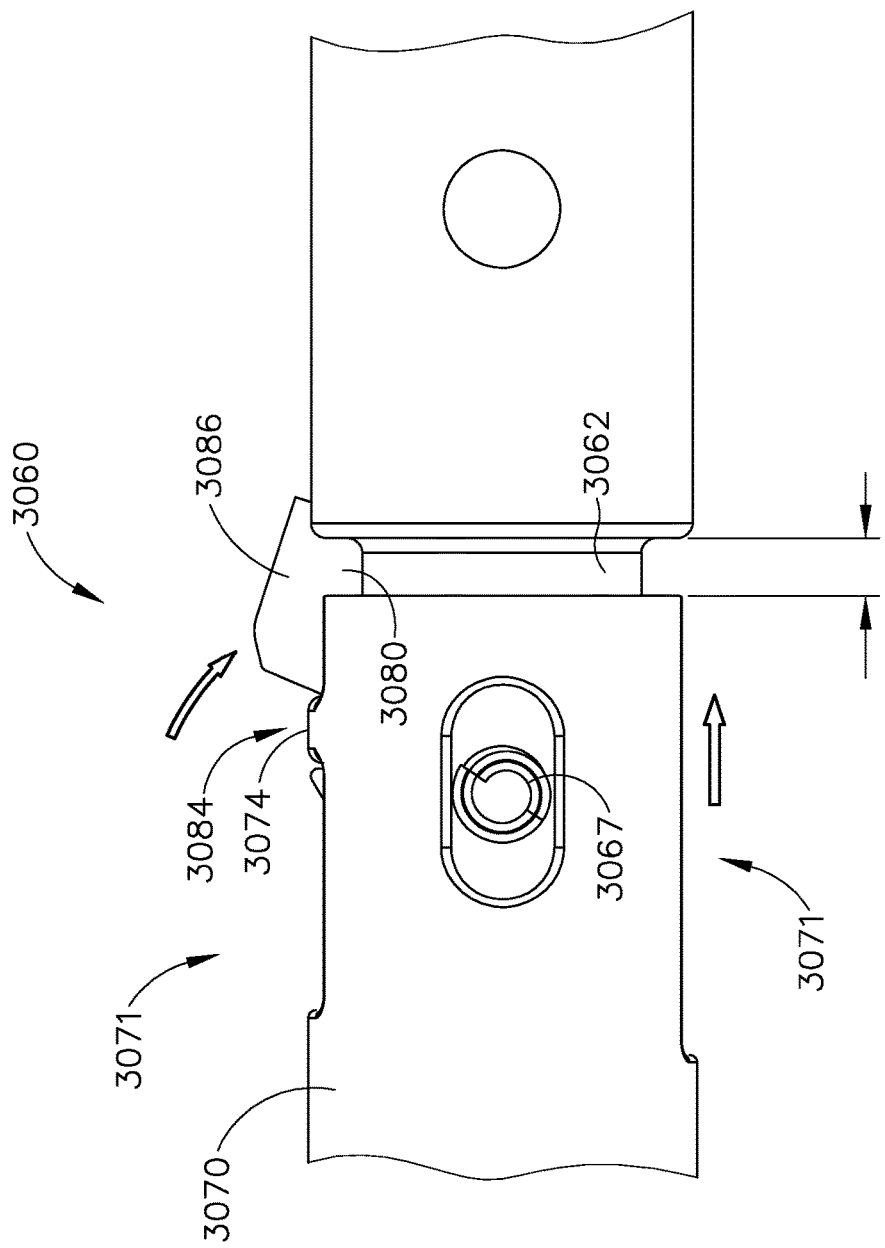

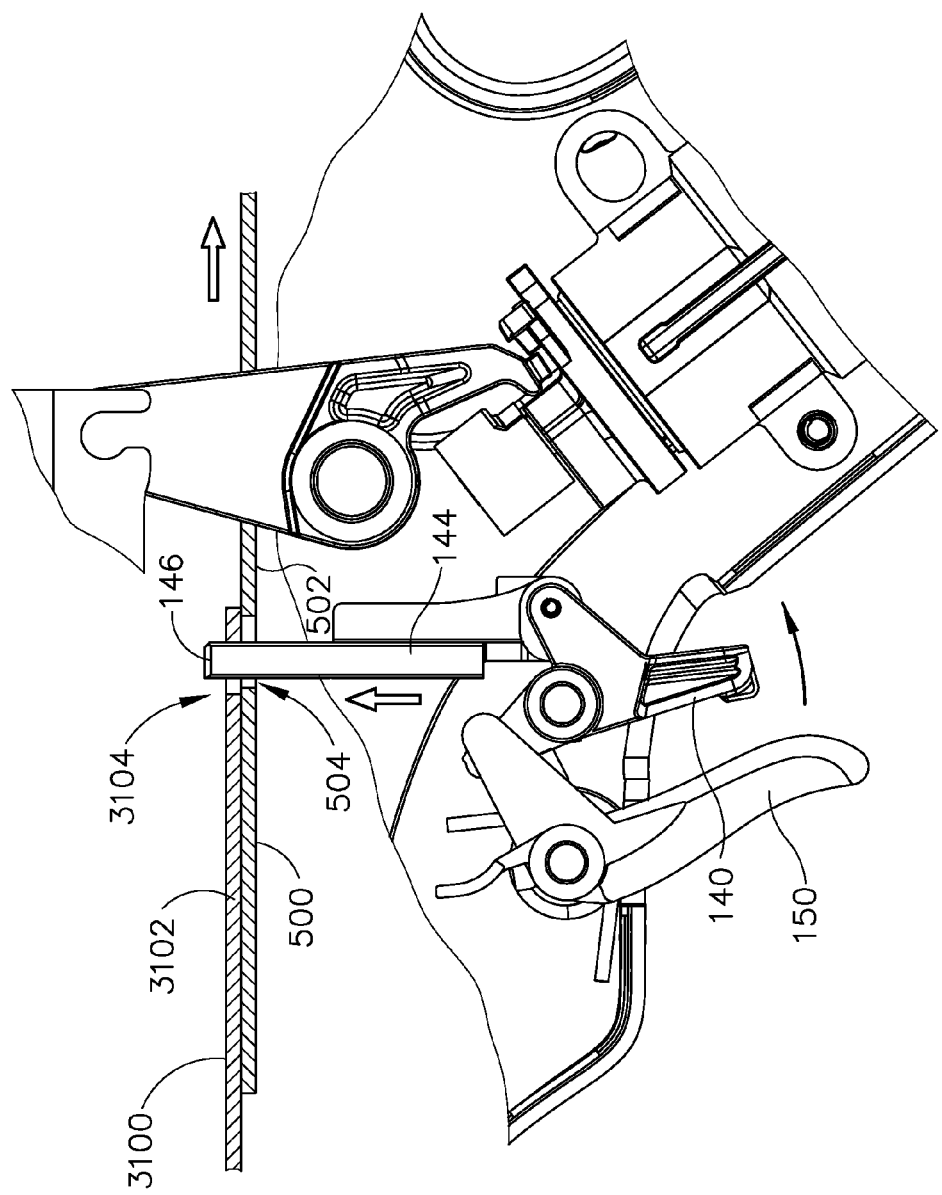

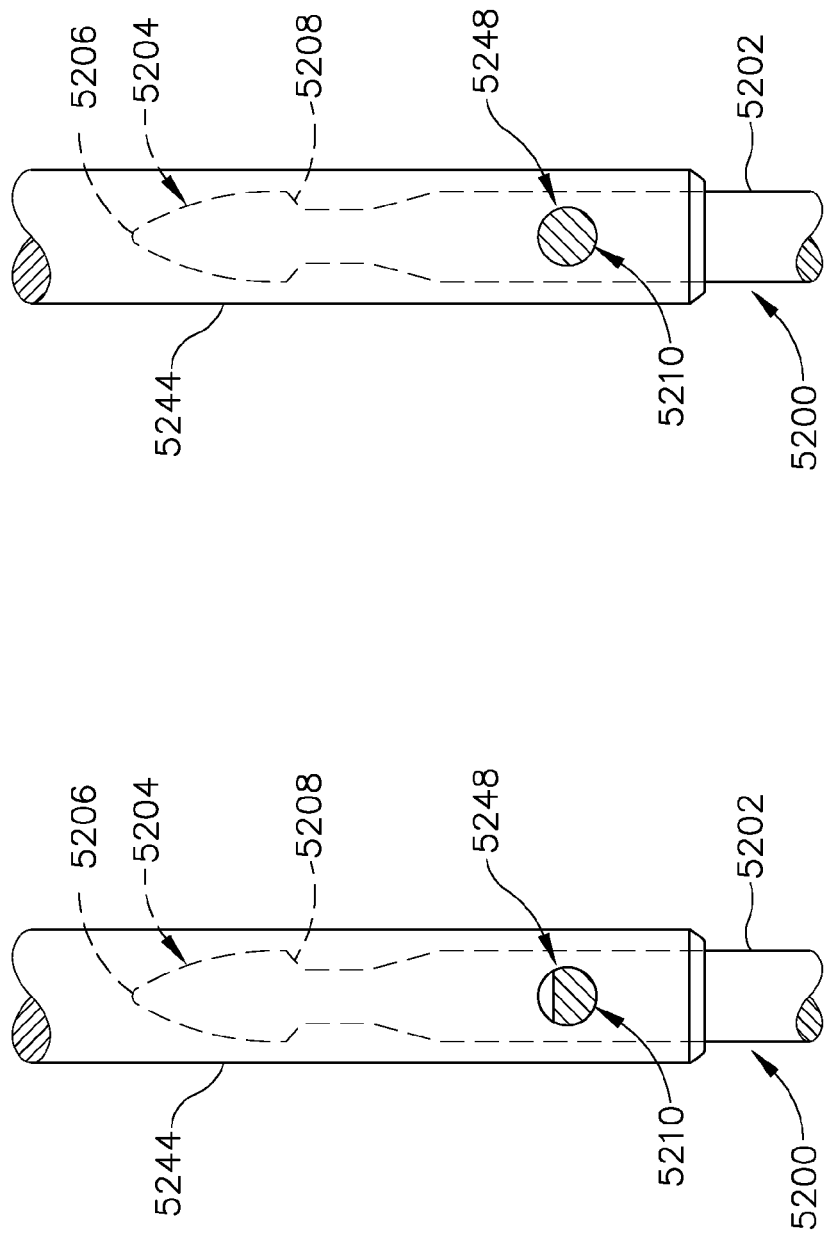

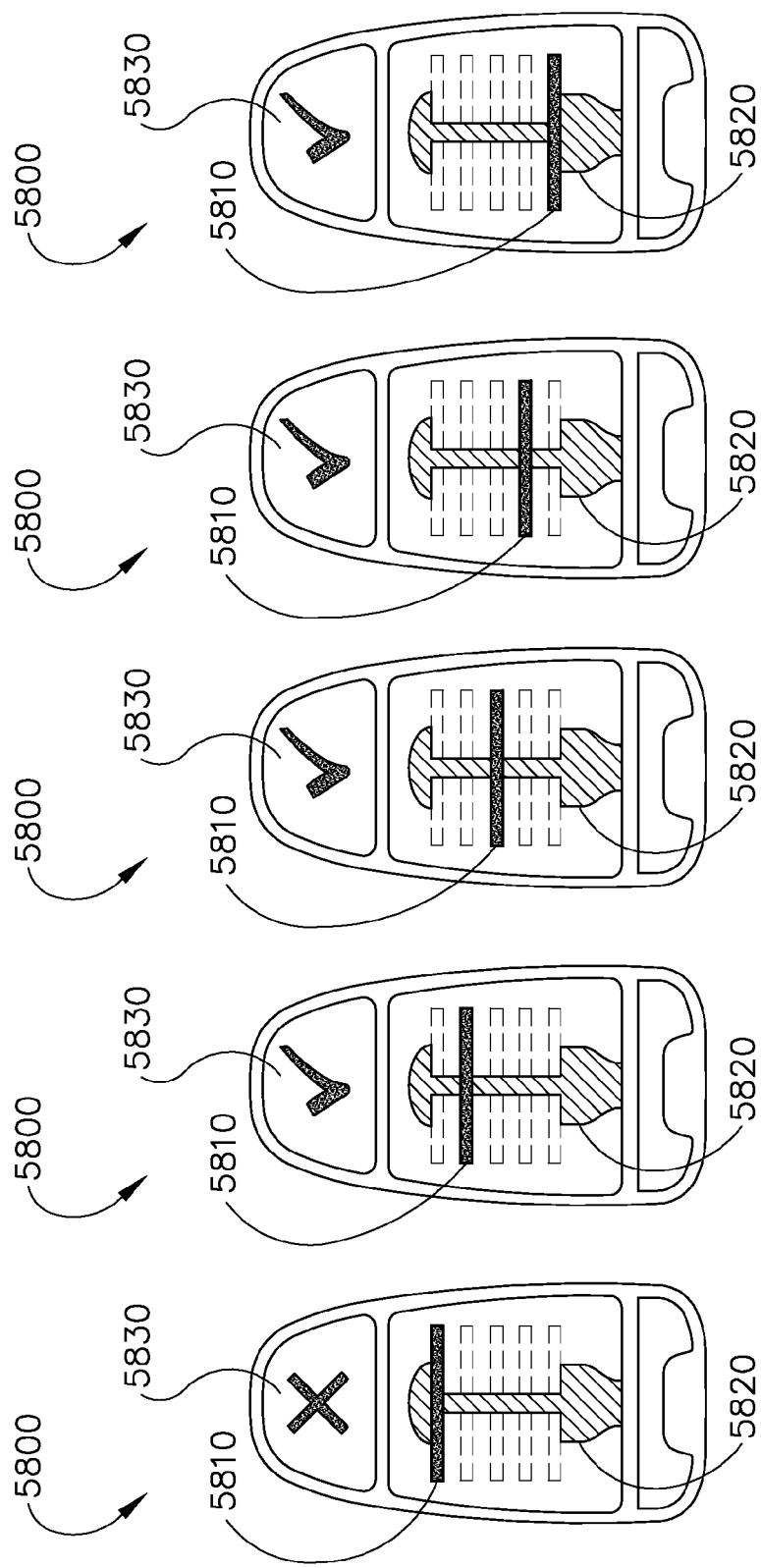

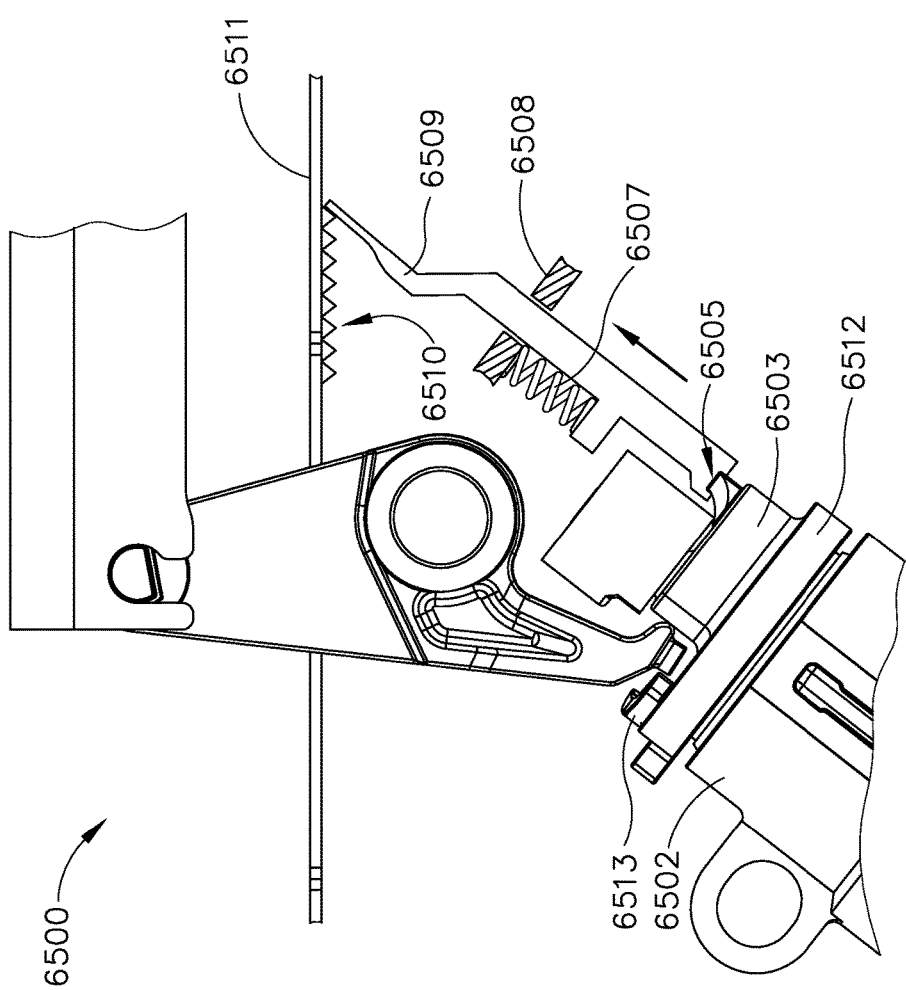

METHOD OF APPLYING AN ANNULAR ARRAY OF STAPLES TO TISSUE

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 21A depicts a cross-sectional side view of the anvil of FIG. 3 positioned within a first section of a digestive tract and the stapling head assembly of FIG. 6 positioned in a second section of the digestive tract, with the anvil separated from the stapling head assembly;

FIG. 50A depicts a schematic end view of the rotary cam of FIG. 16, the cam follower of FIG. 14, and the rocker member of FIG. 19A, with the rotary cam in the fourth angular position, the cam follower in the first pivotal position, and the rocker member in the second pivotal position;

FIG. 50B depicts a schematic end view of the rotary cam of FIG. 16 and the cam follower of FIG. 14, with the rotary cam in the third angular position, the cam follower transitioning toward the second pivotal position, and the rocker member of FIG. 19A in the first pivotal position;

FIG. 50C depicts a schematic end view of the rotary cam of FIG. 16 and the cam follower of FIG. 14, with the rotary cam in the second angular position, the cam follower in the second pivotal position, and the rocker member of FIG. 19A in the first pivotal position;

FIG. 50D depicts a schematic end view of the rotary cam of FIG. 16, the cam follower of FIG. 14, and the rocker member of FIG. 19A, with the rotary cam in the first angular position, the cam follower in the first pivotal position, and the rocker member in a second pivotal position;

FIG. 61B depicts a detailed side elevational view of the trocar of FIG. 57, with the sleeve member of FIG. 60A moved to the second position of FIG. 60B, and with the lockout member of FIG. 60A moved to the second rotational position of FIG. 60B by movement of the sleeve member to the second position;

FIG. 70B depicts a side view of the anvil actuation assembly of FIG. 70A, with the actuation rod moved to a second position, and with the lockout rod moved to a second position;

FIG. 78C depicts a schematic view of the control circuit of FIG. 78A, in a third state of operation;

FIG. 78D depicts a schematic view of the control circuit of FIG. 78A, in a fourth state of operation;

FIG. 78E depicts a schematic view of the control circuit of FIG. 78A, in a fifth state of operation;

FIG. 78F depicts a schematic view of the control circuit of FIG. 78A, in a sixth state of operation;

FIG. 79 depicts a schematic view of an exemplary alternative control circuit that may be incorporated into the circular stapler of FIG. 1;

FIG. 80 depicts a schematic view of another exemplary alternative control circuit that may be incorporated into the circular stapler of FIG. 1;

FIG. 81 depicts a schematic view of another exemplary alternative control circuit that may be incorporated into the circular stapler of FIG. 1;

FIG. 82 depicts a perspective view of a handle assembly of an exemplary alternative circular stapler;

FIG. 83A depicts a detailed cross-sectional side view of the handle assembly of FIG. 82 with a battery pack of the handle assembly in a proximal position;

FIG. 83B depicts a detailed cross-sectional side view of the handle assembly of FIG. 83A with the battery pack of FIG. 83A moved to a distal position;

FIG. 84 depicts a perspective view of the distal end of another exemplary alternative circular stapler with an anvil of the circular stapler spaced apart from a trocar of the circular stapler;

FIG. 85A depicts a side view of the anvil of FIG. 84 in a first position relative to the trocar of FIG. 84;

Figure 1:
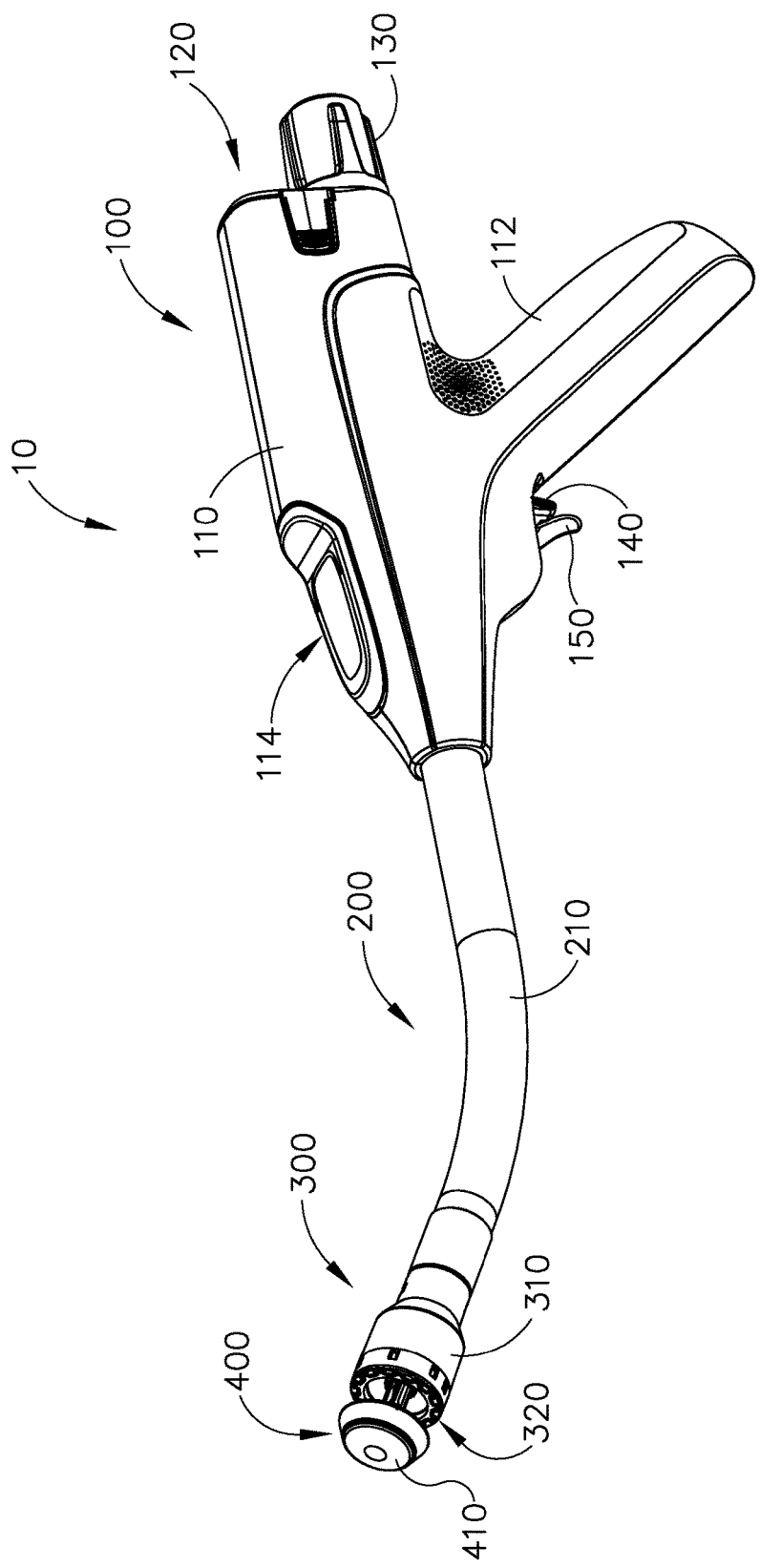
FIG. 1 depicts a perspective view of an exemplary circular stapler.
Figure 6:
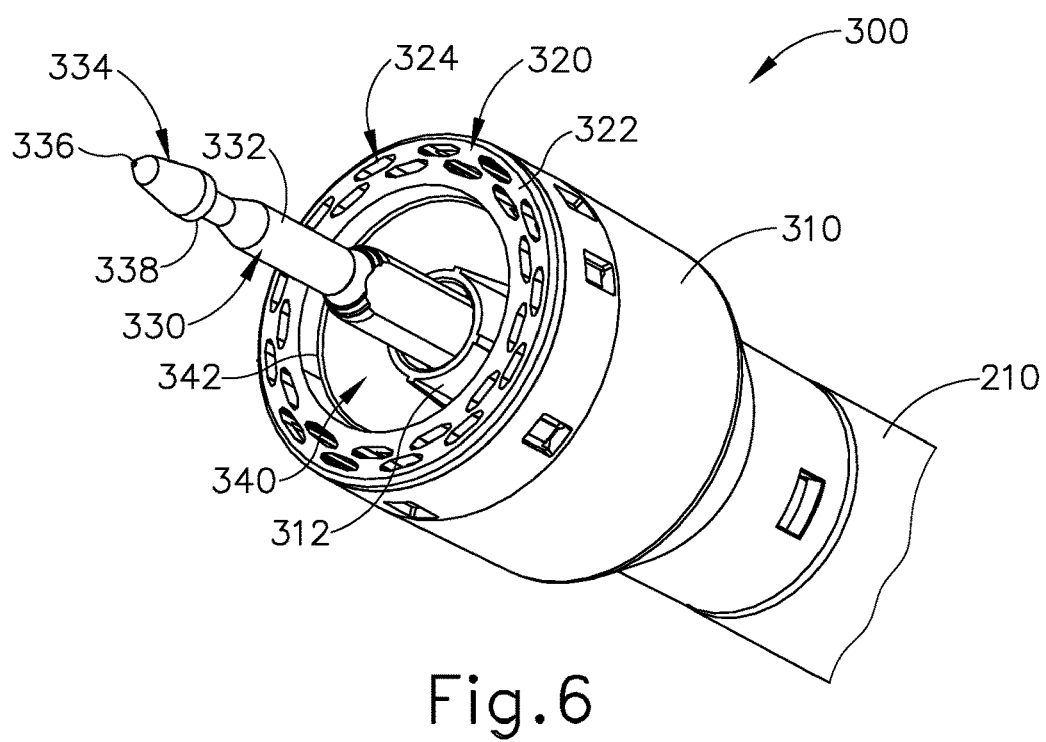
FIG. 6 depicts a perspective view of the stapling head assembly of the circular stapler of FIG. 1.
Figure 13:
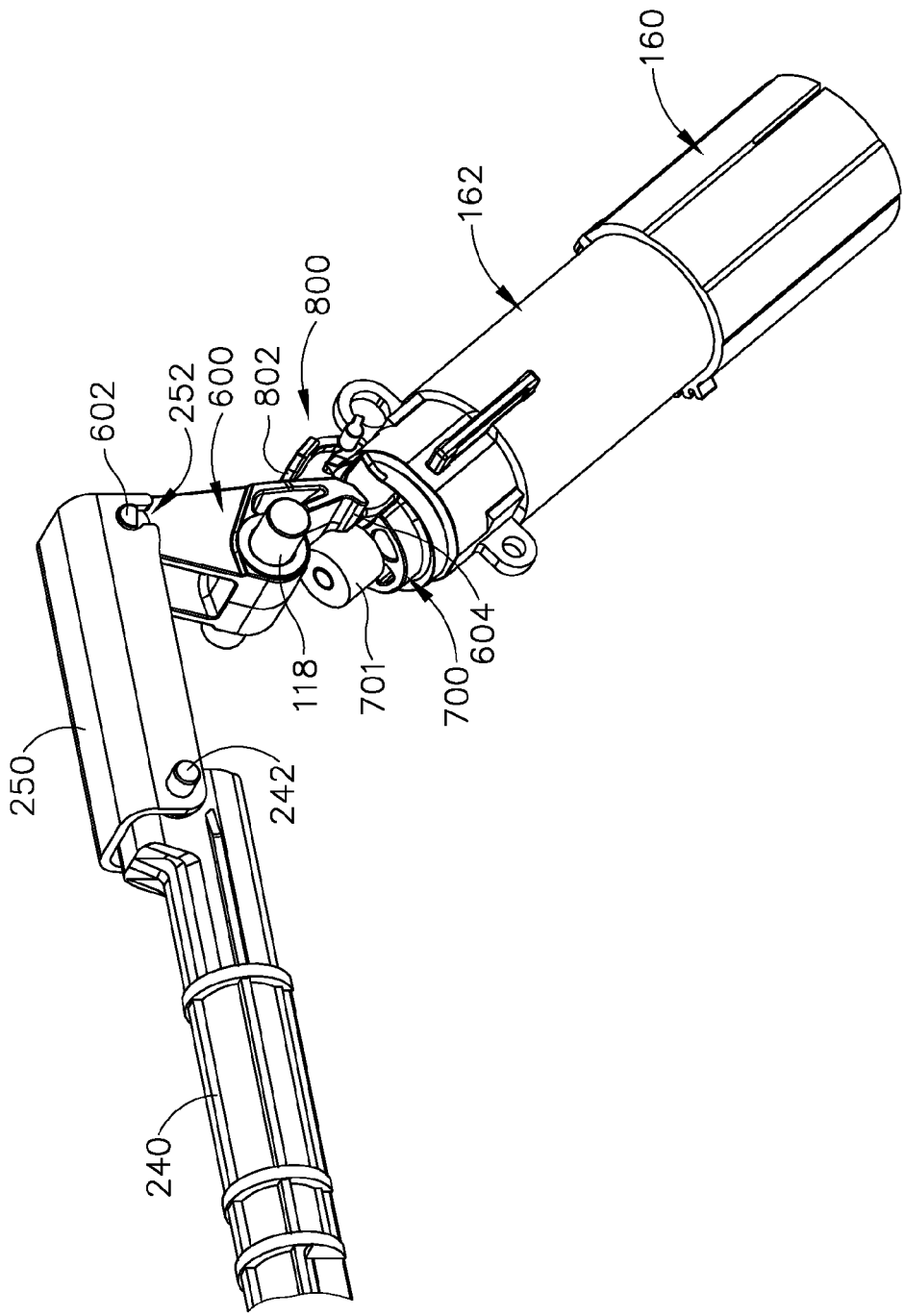
FIG. 13 depicts a perspective view of a stapling head actuation assembly of the circular stapler of FIG. 1.
Figure 22:
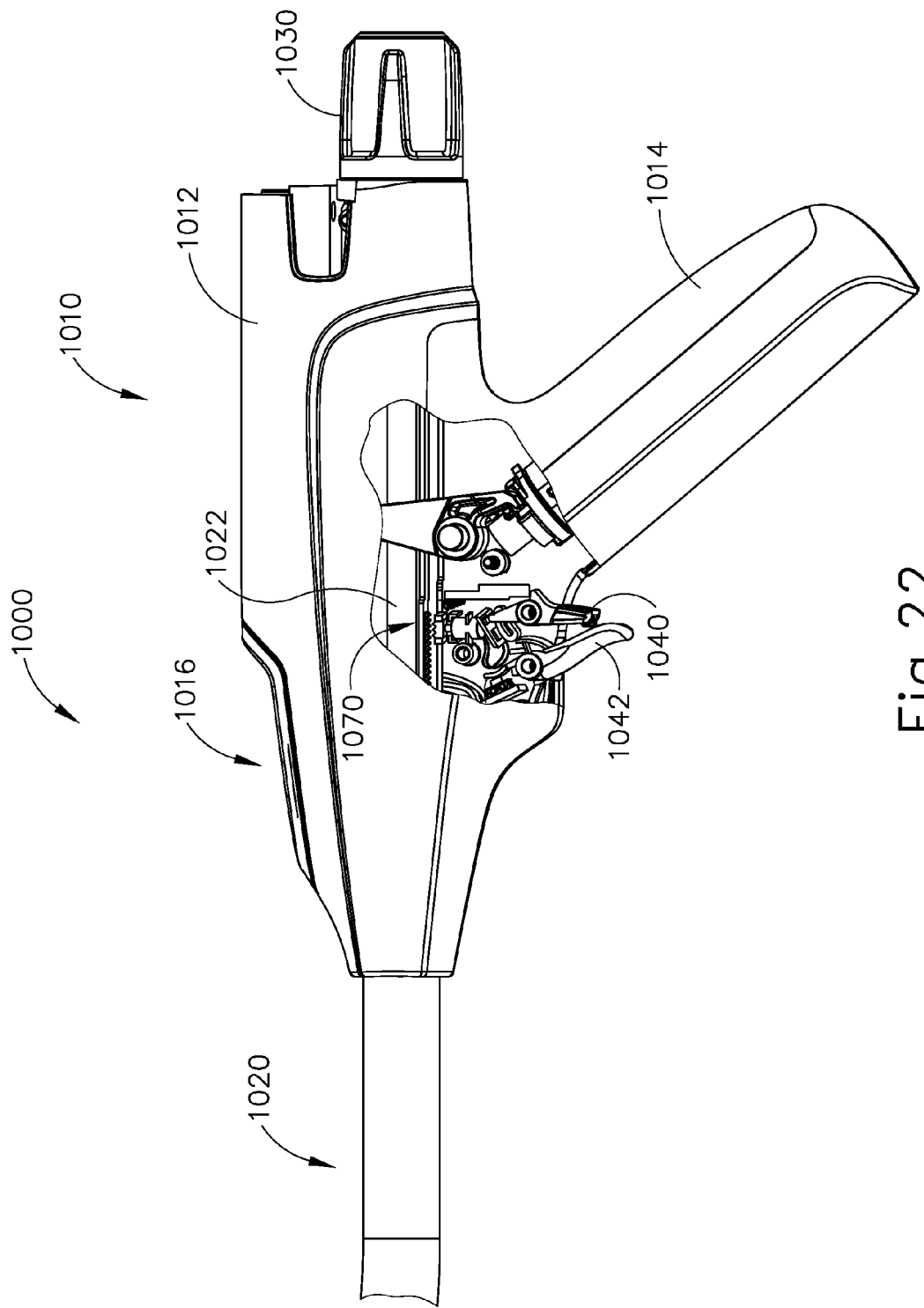
FIG. 22 depicts a side cut-away view of a handle assembly of an exemplary alternative circular stapler.
Figure 84:
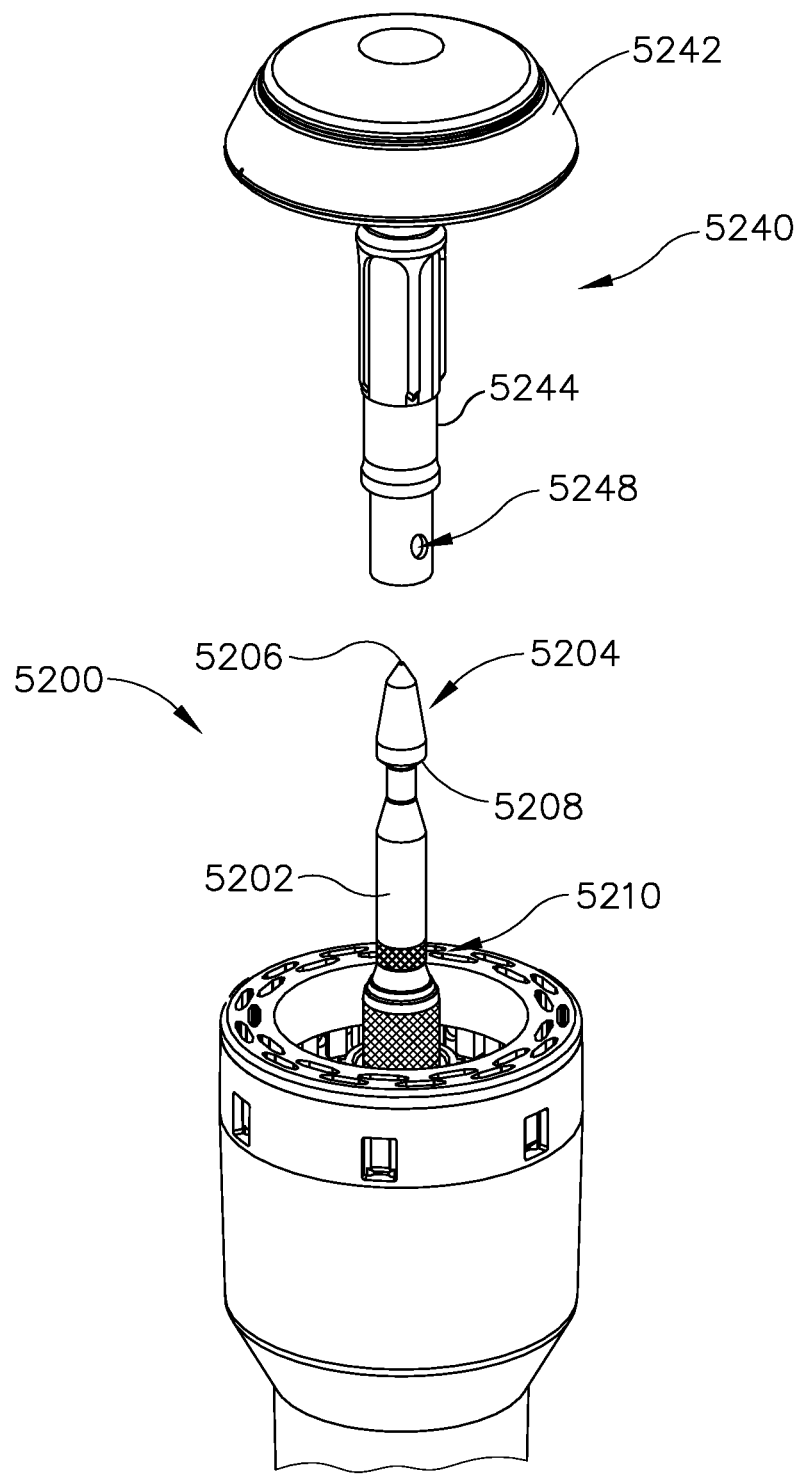
Figure 86A:
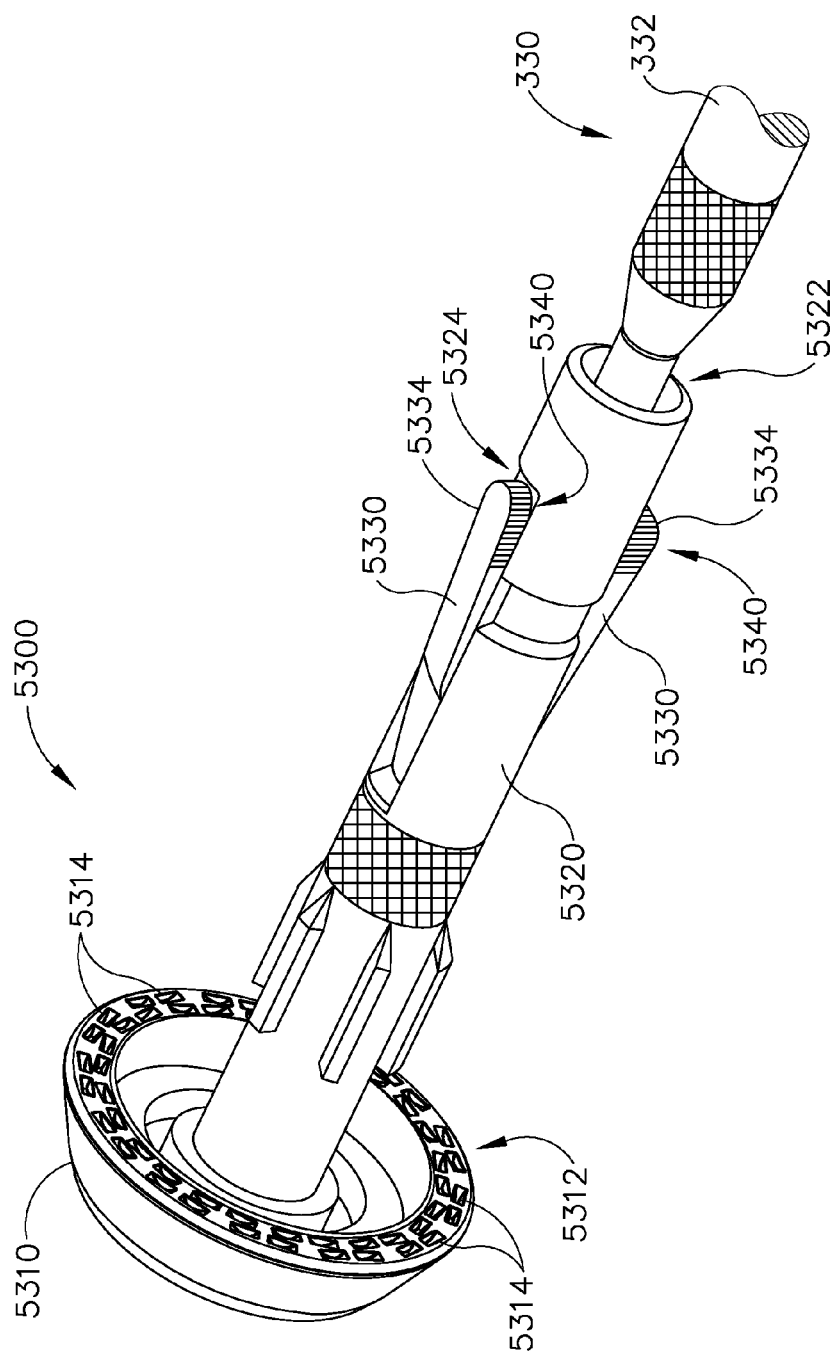
Figure 86B:
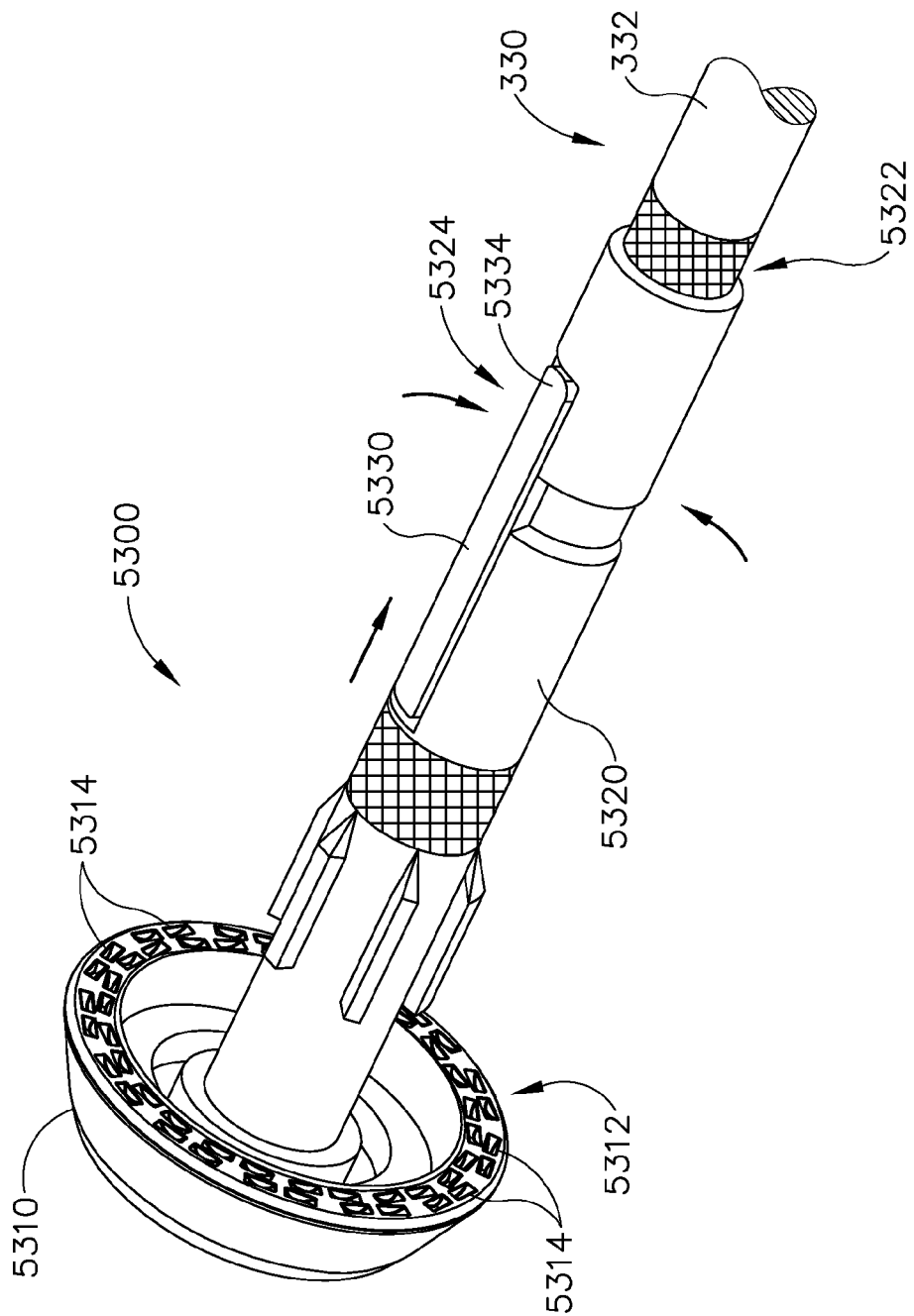
Figure 87:
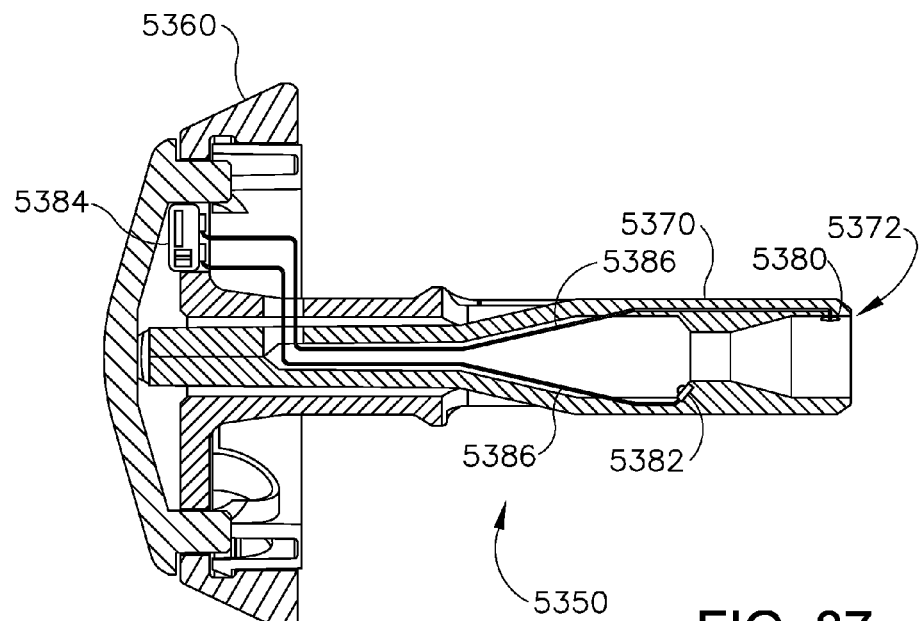
Figure 88:
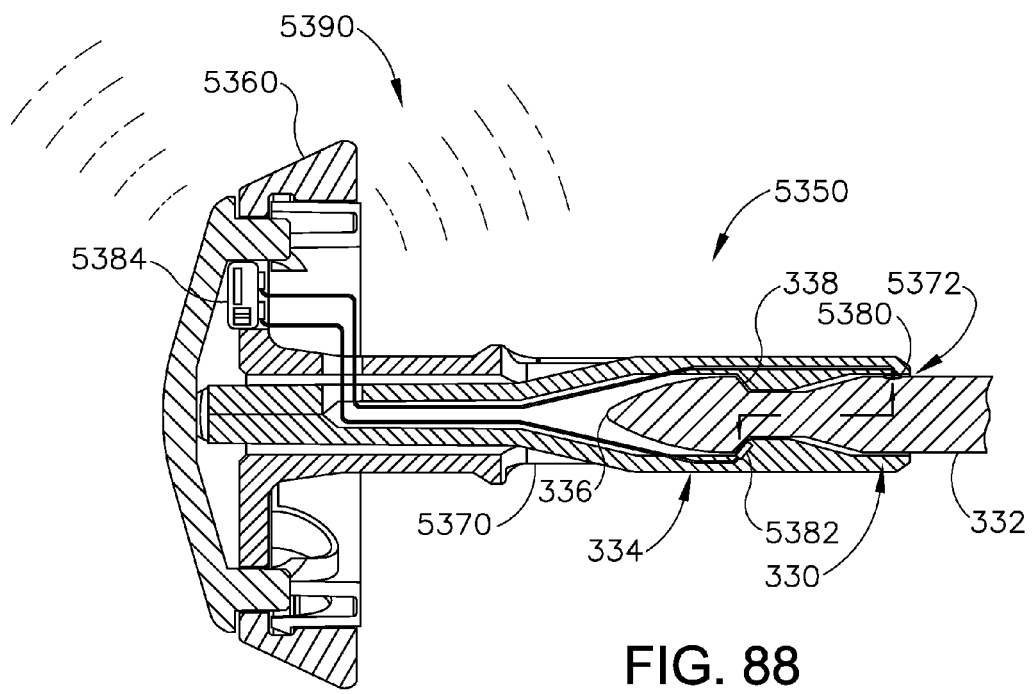
Figure 89:
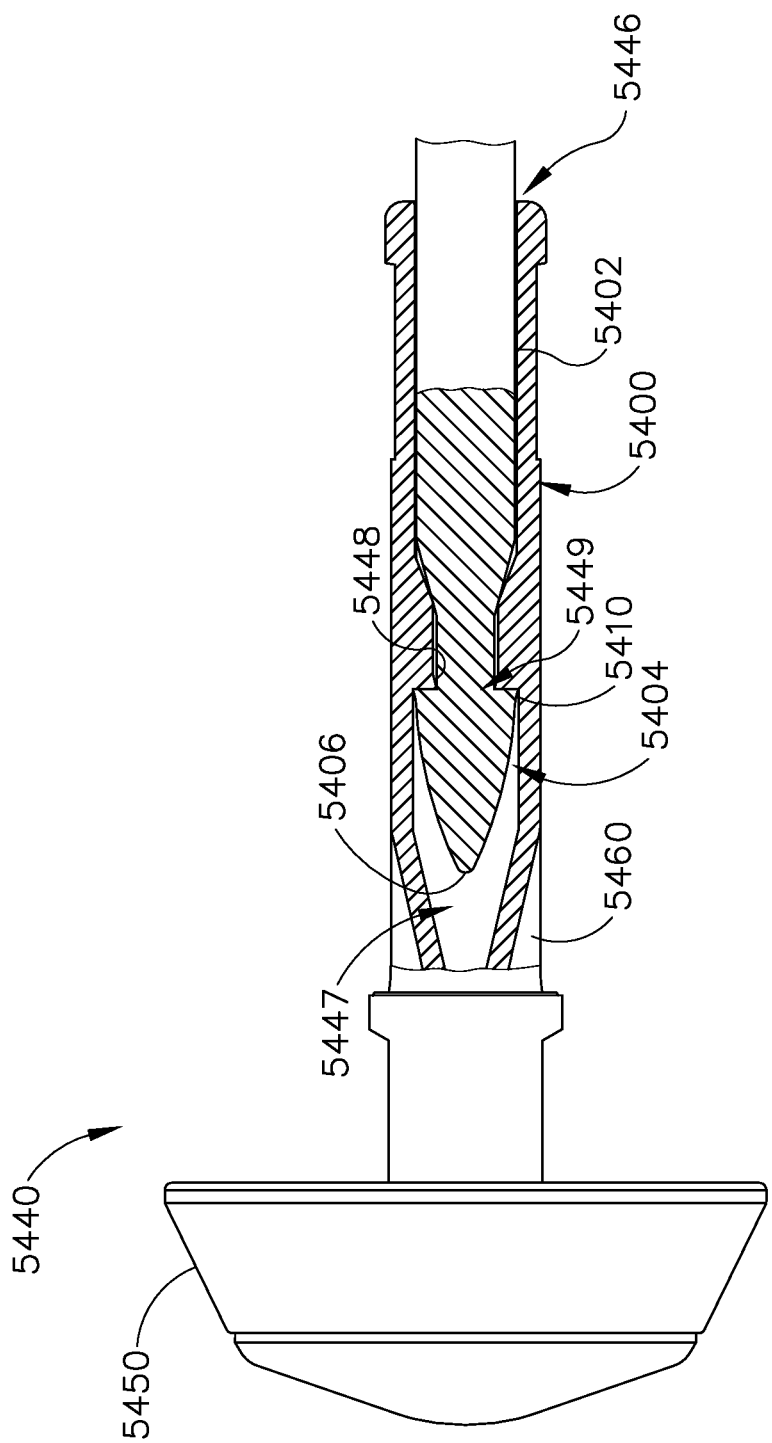
Figure 90A:
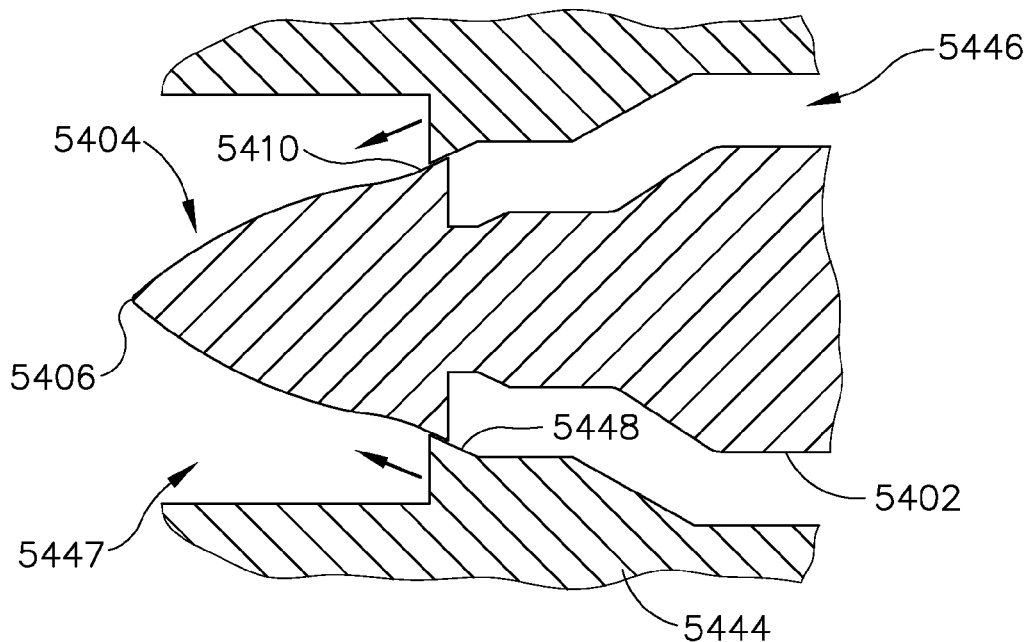
Figure 90B:
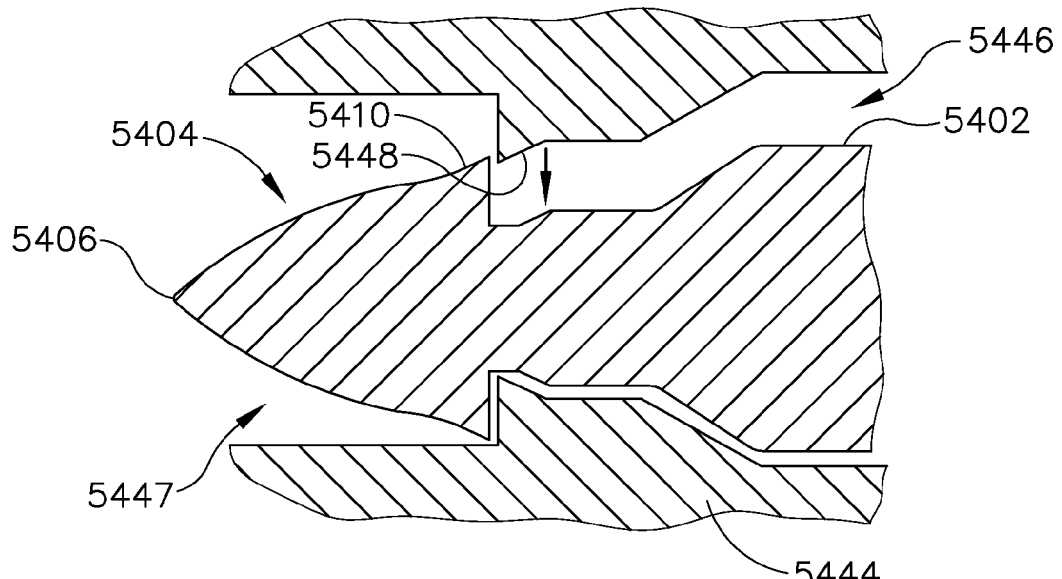
Figure 91:
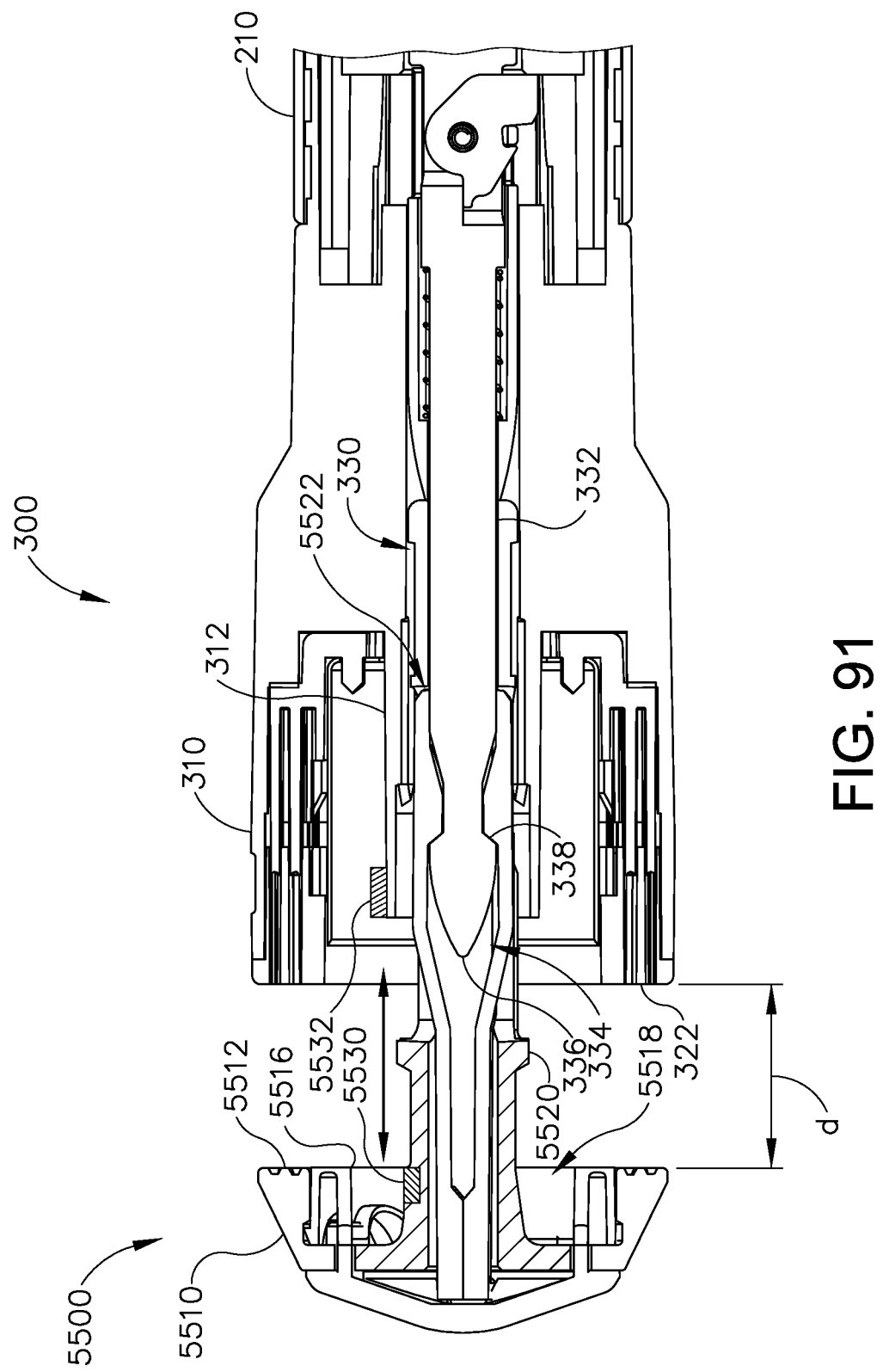
Figure 92A:
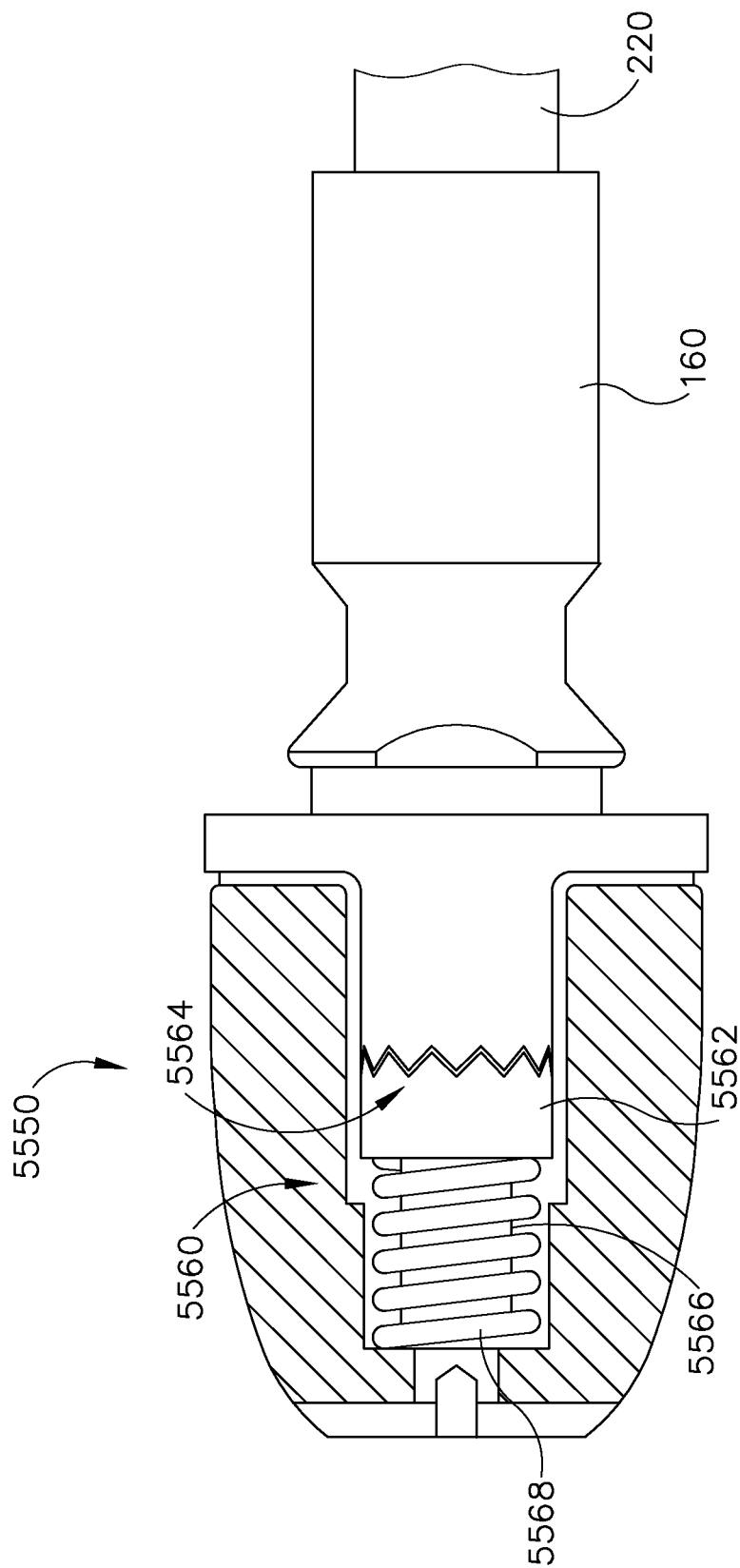
Figure 92B:
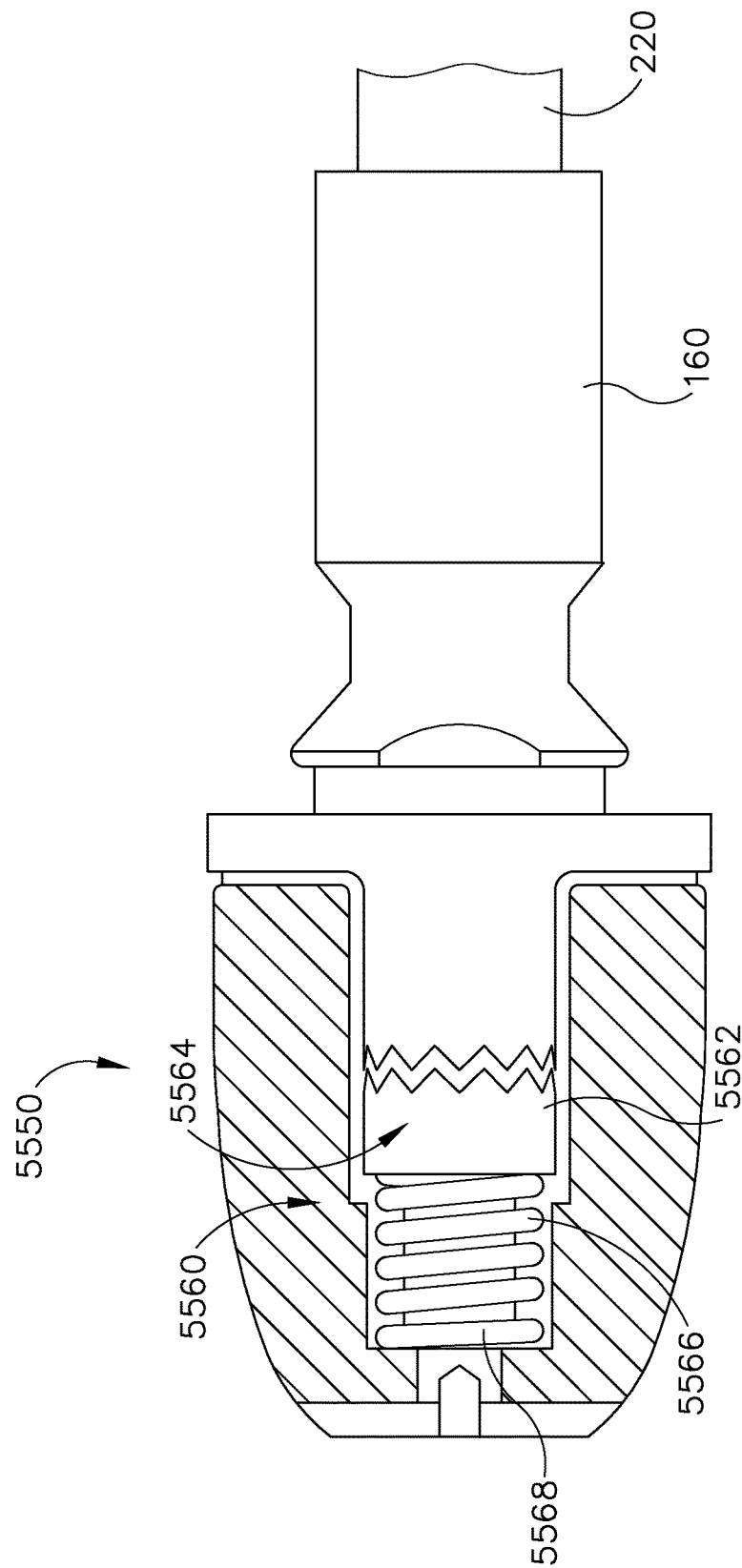
Figure 93:
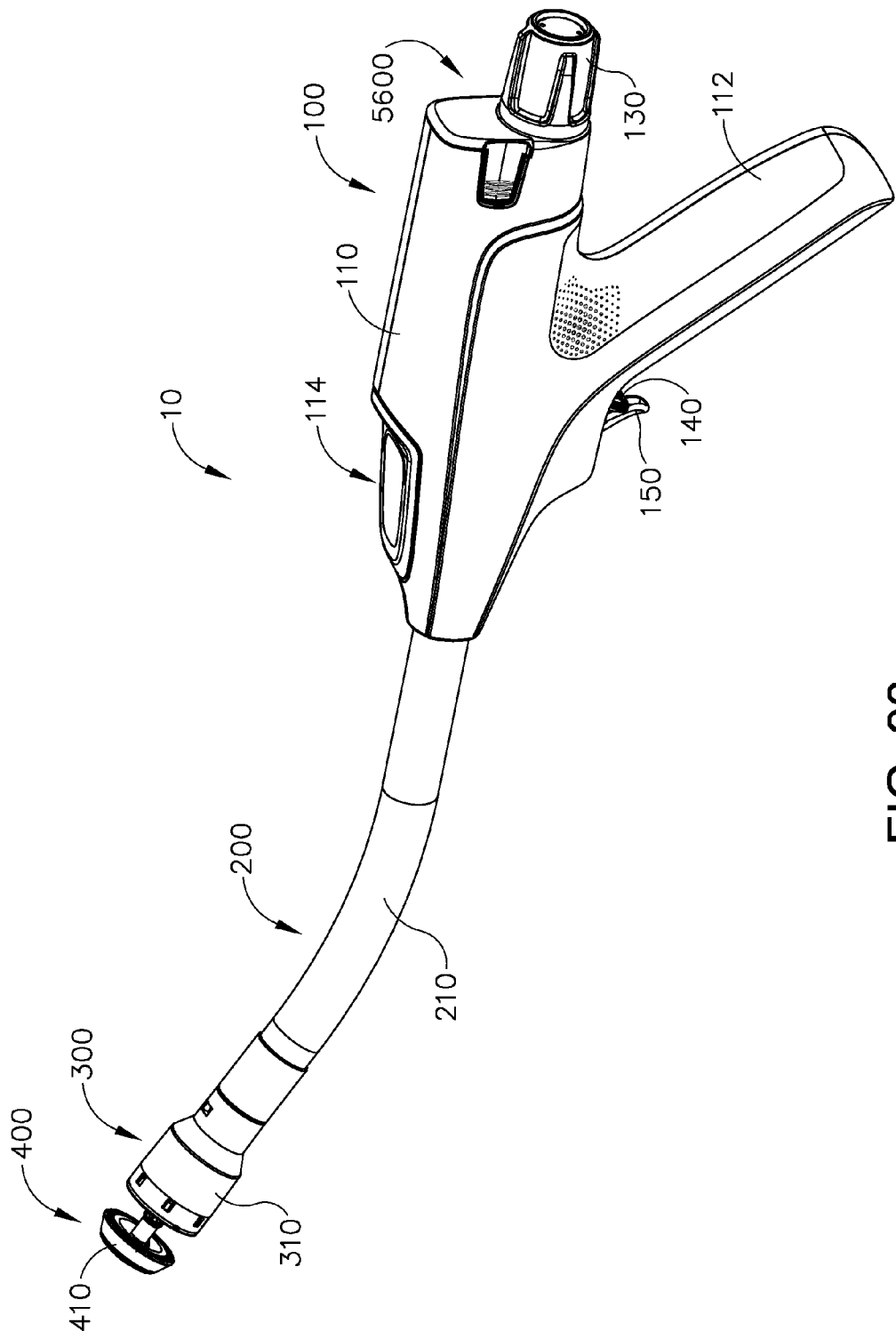
Figure 94:
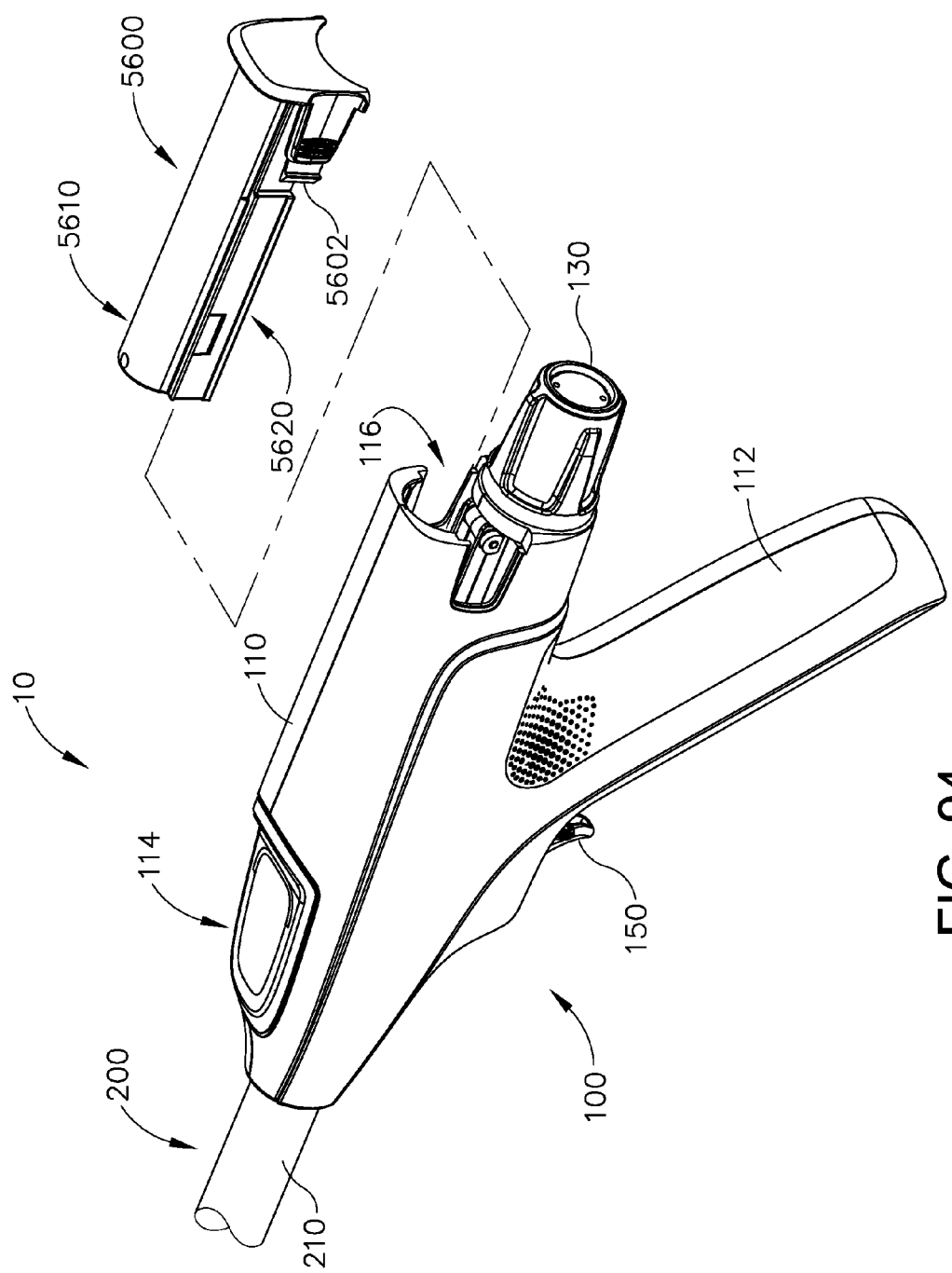
Figure 95:
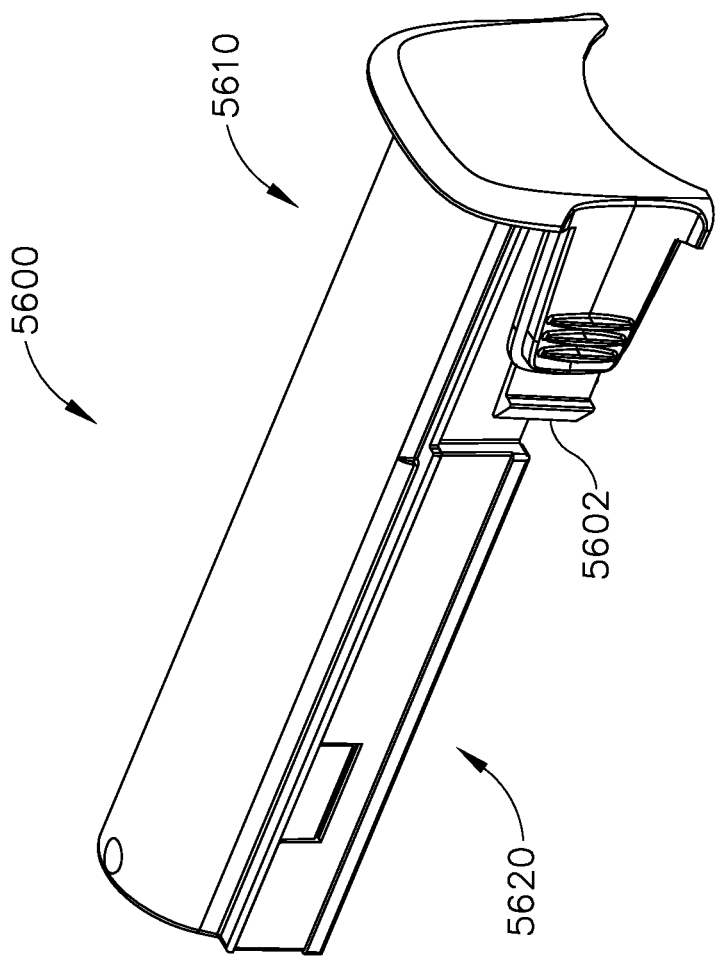
Figure 96:
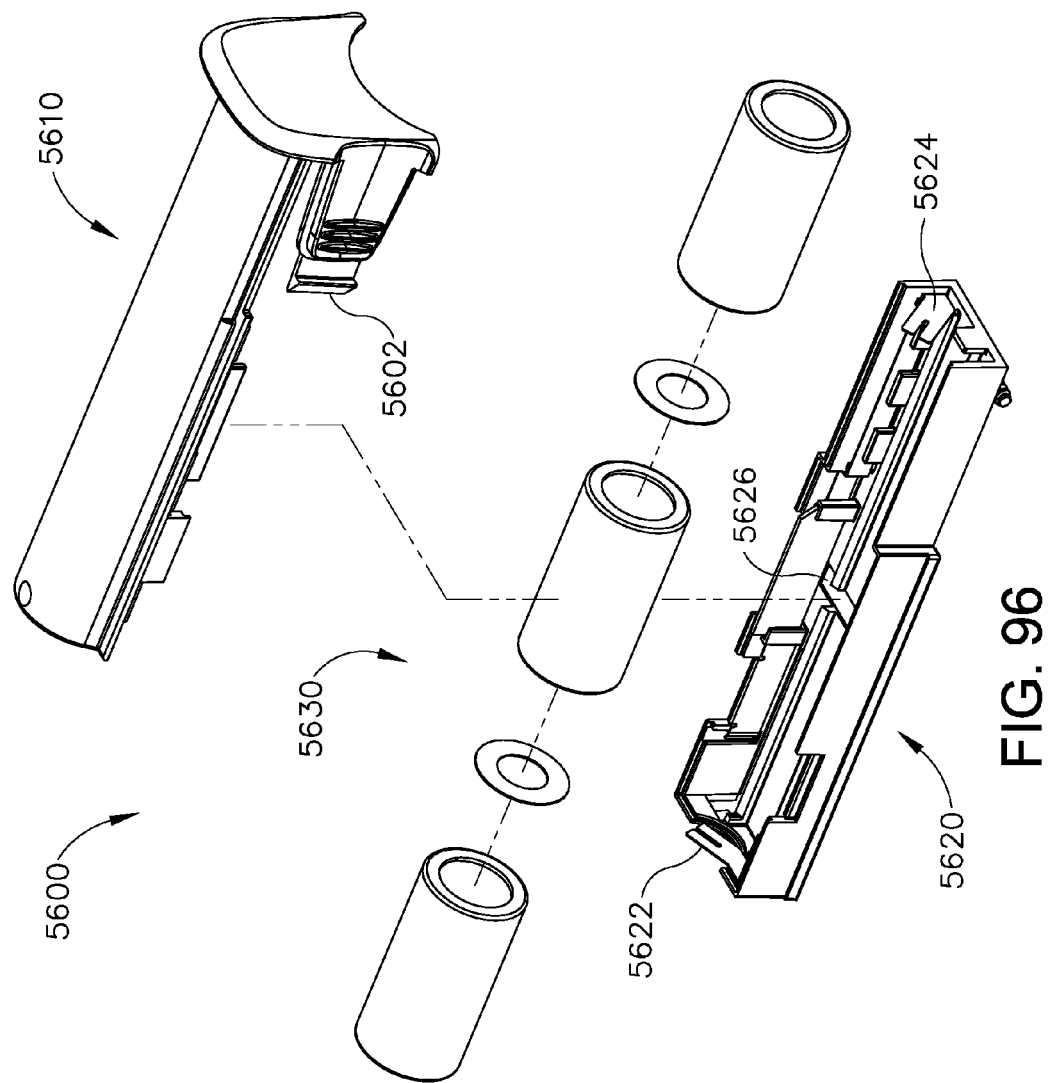
Figure 97A:
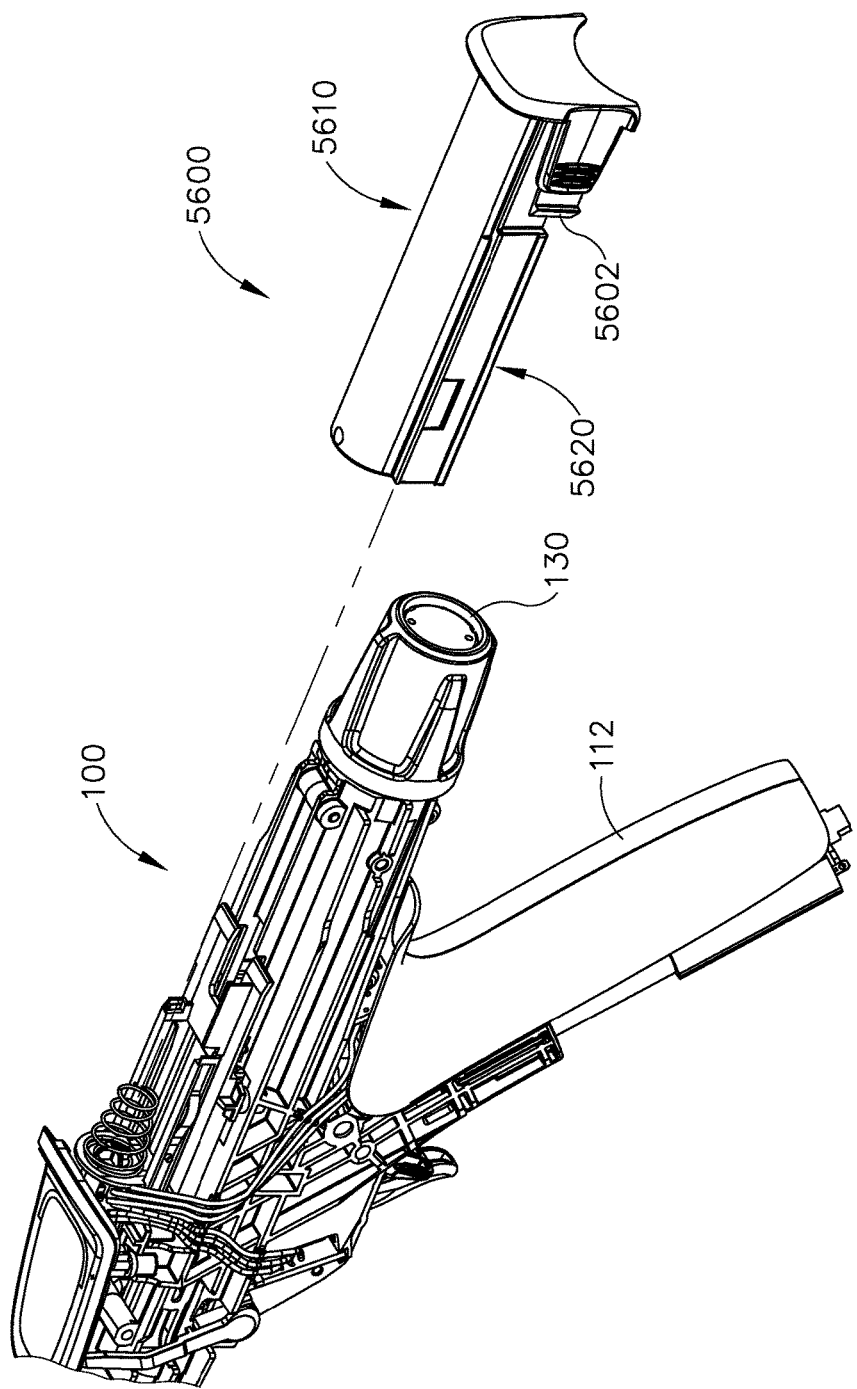
Figure 97B:
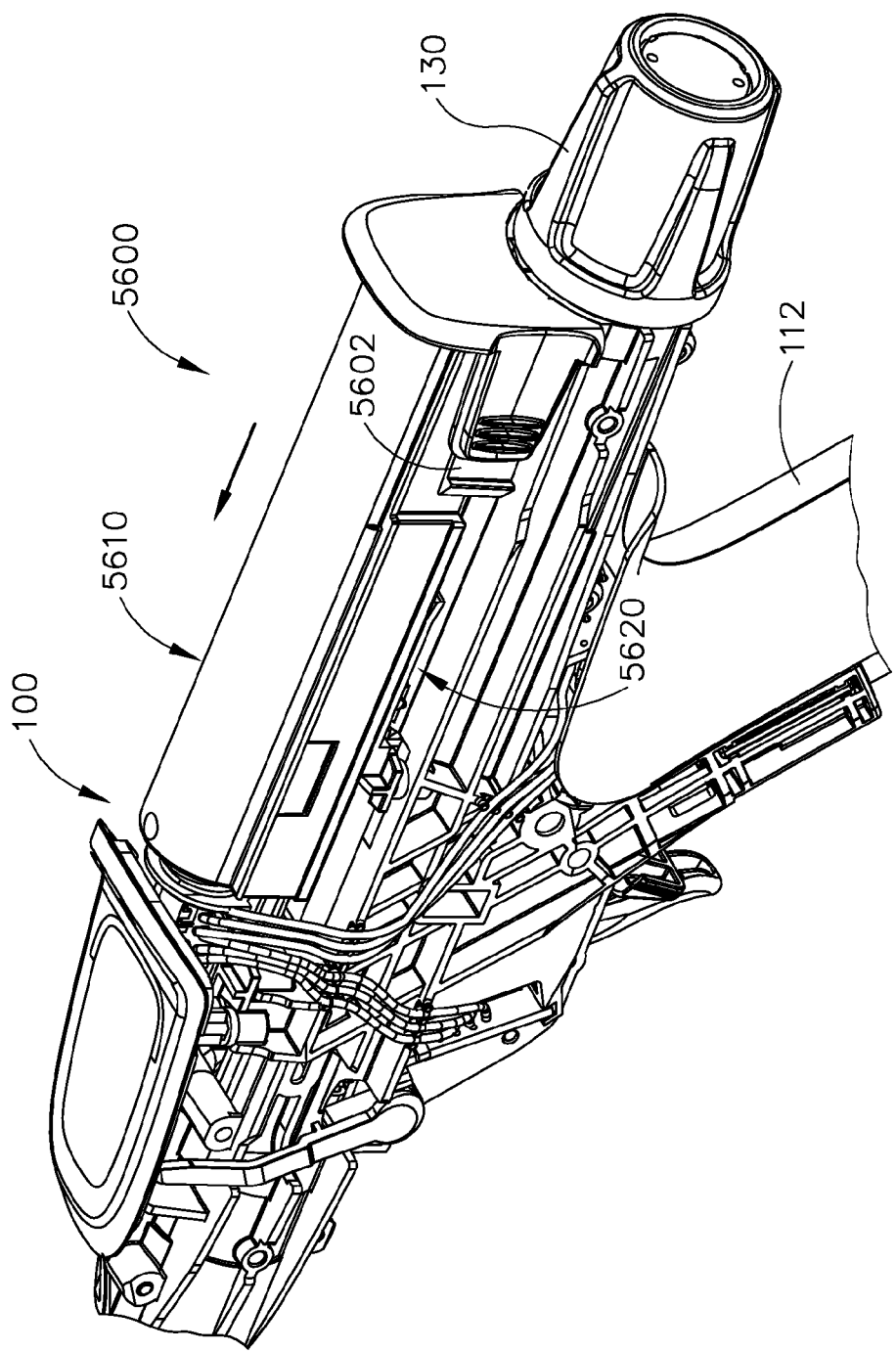
Figure 98:
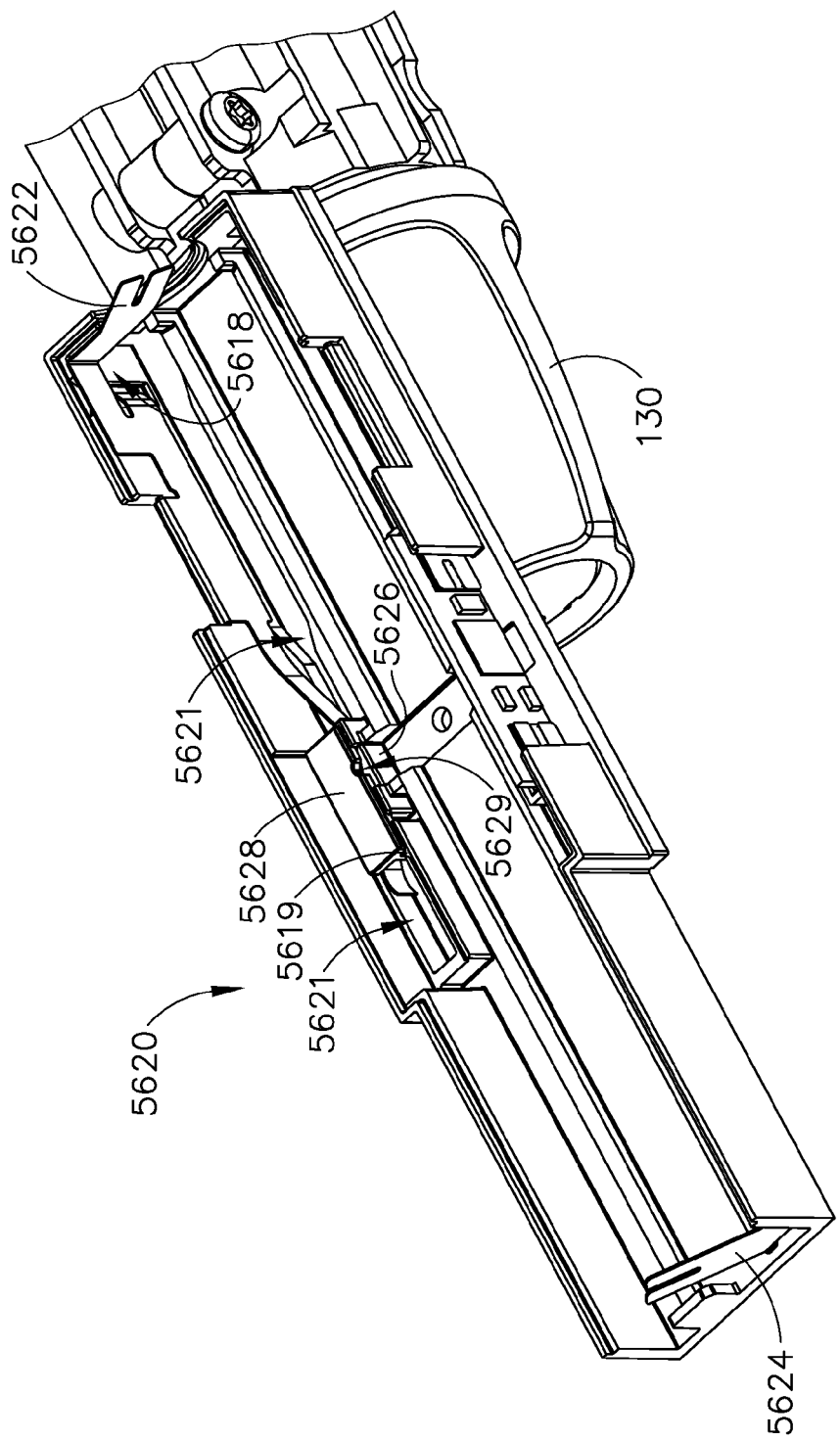
Figure 99:
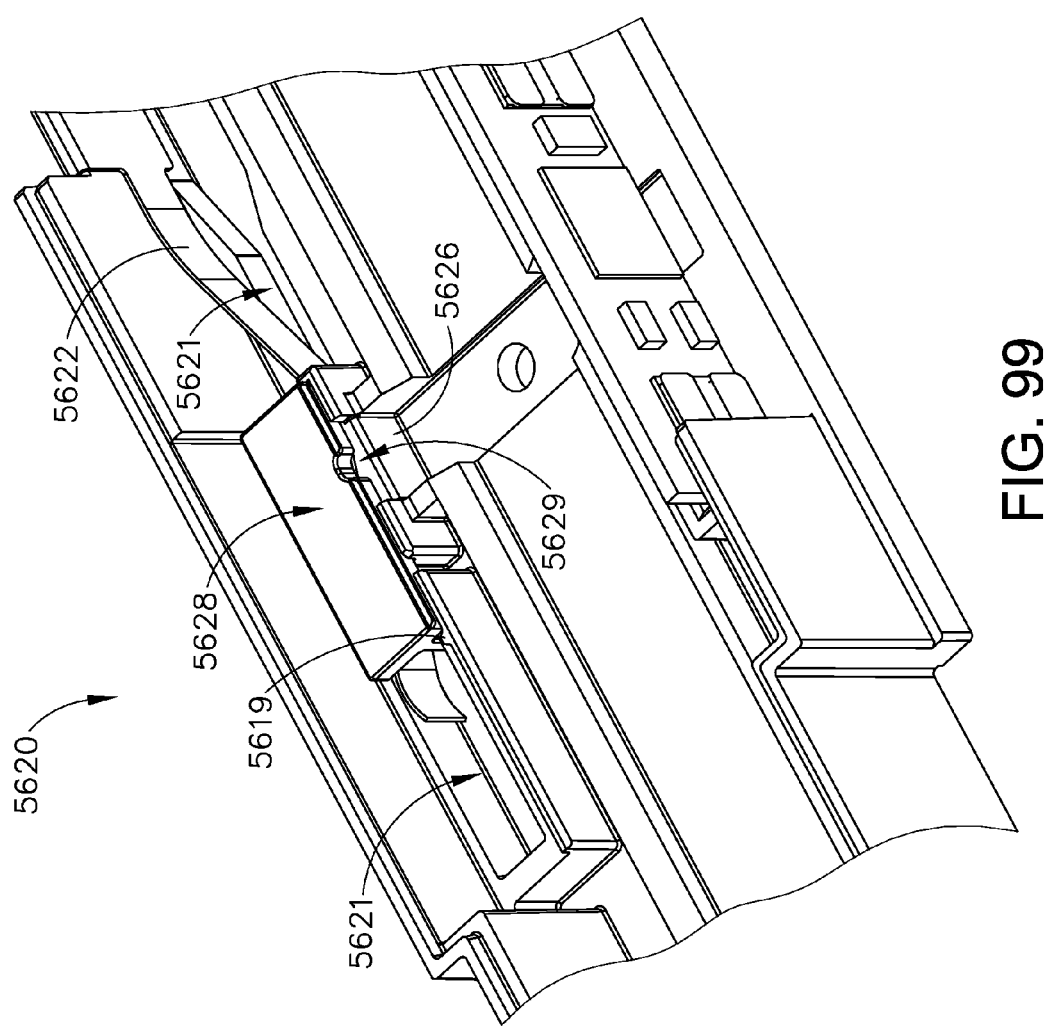
Figure 100:
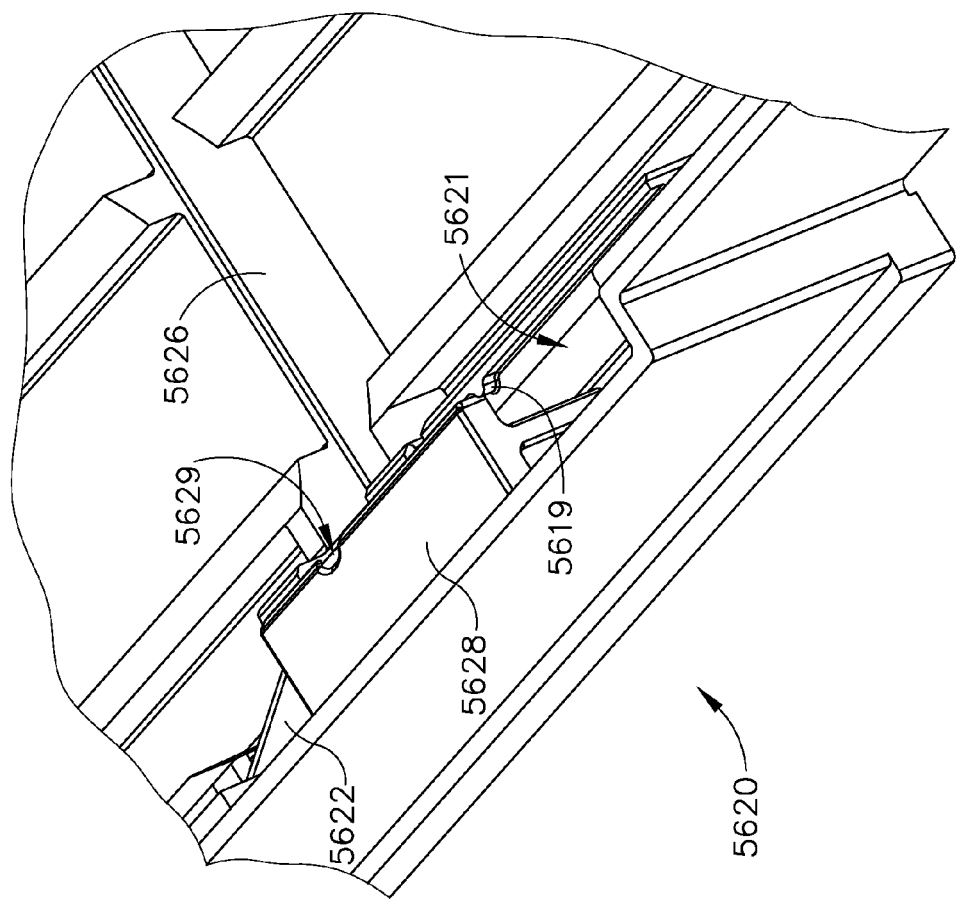
Figure 101:
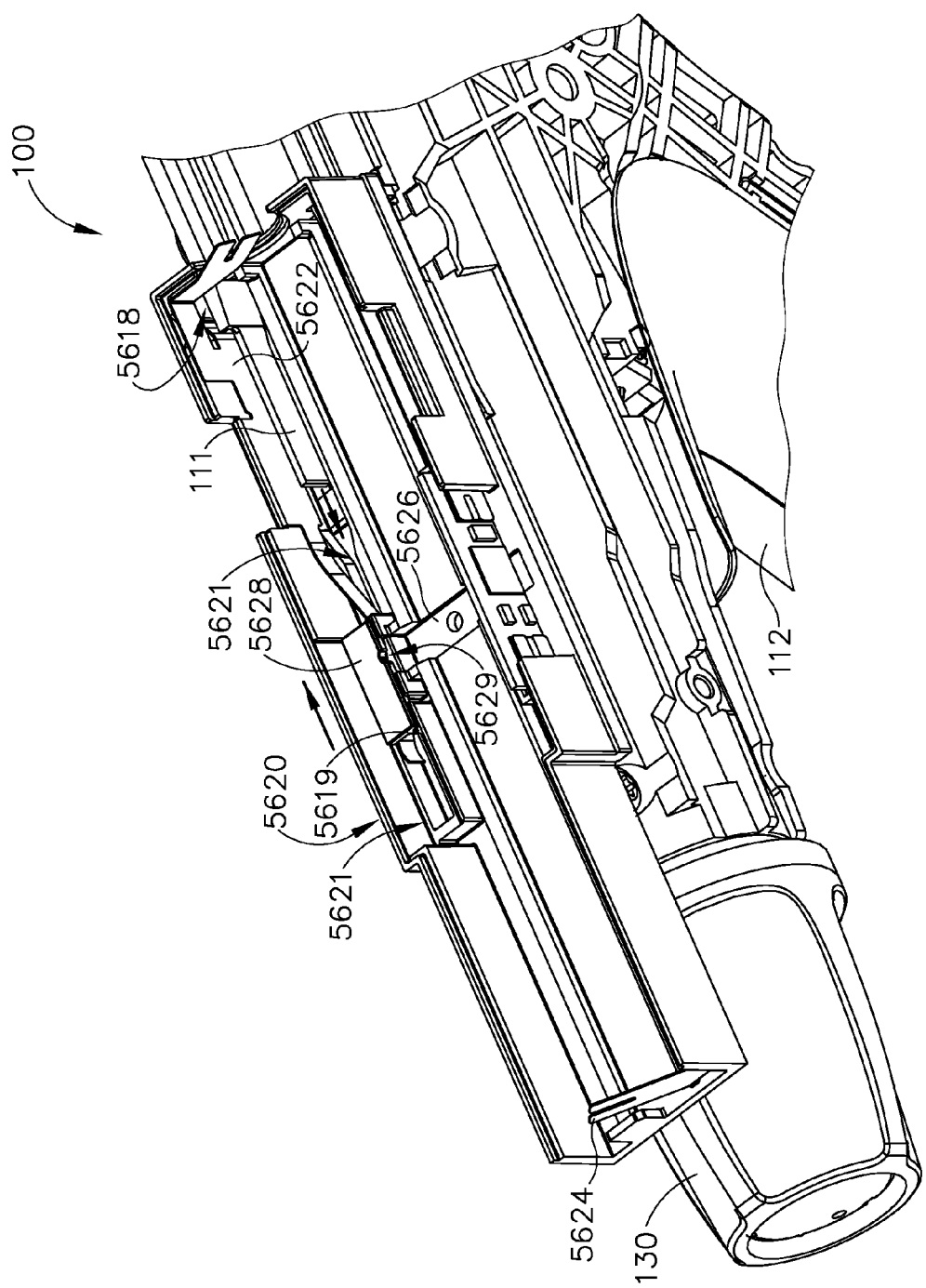
Figure 102:
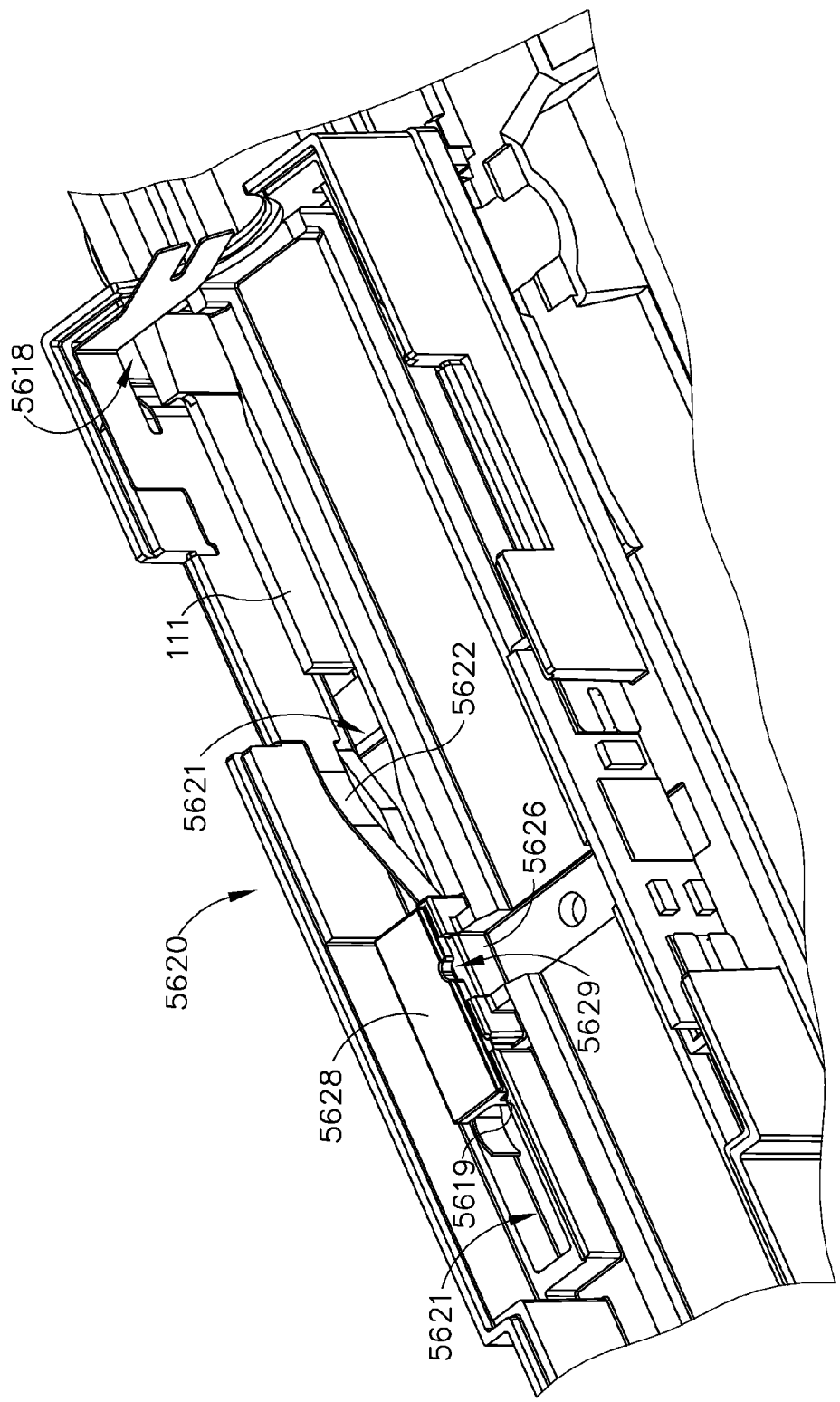
Figure 103:
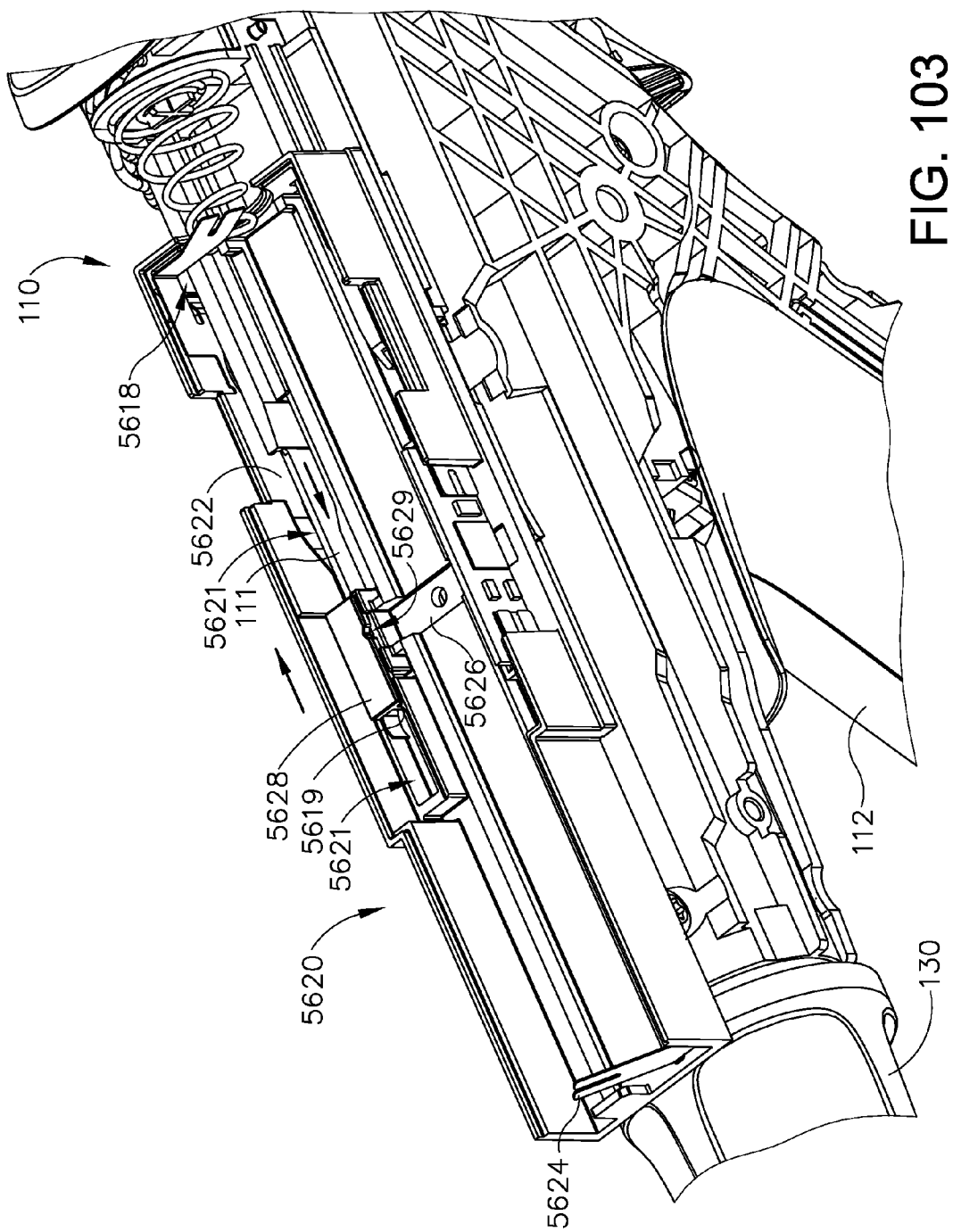
Figure 104:
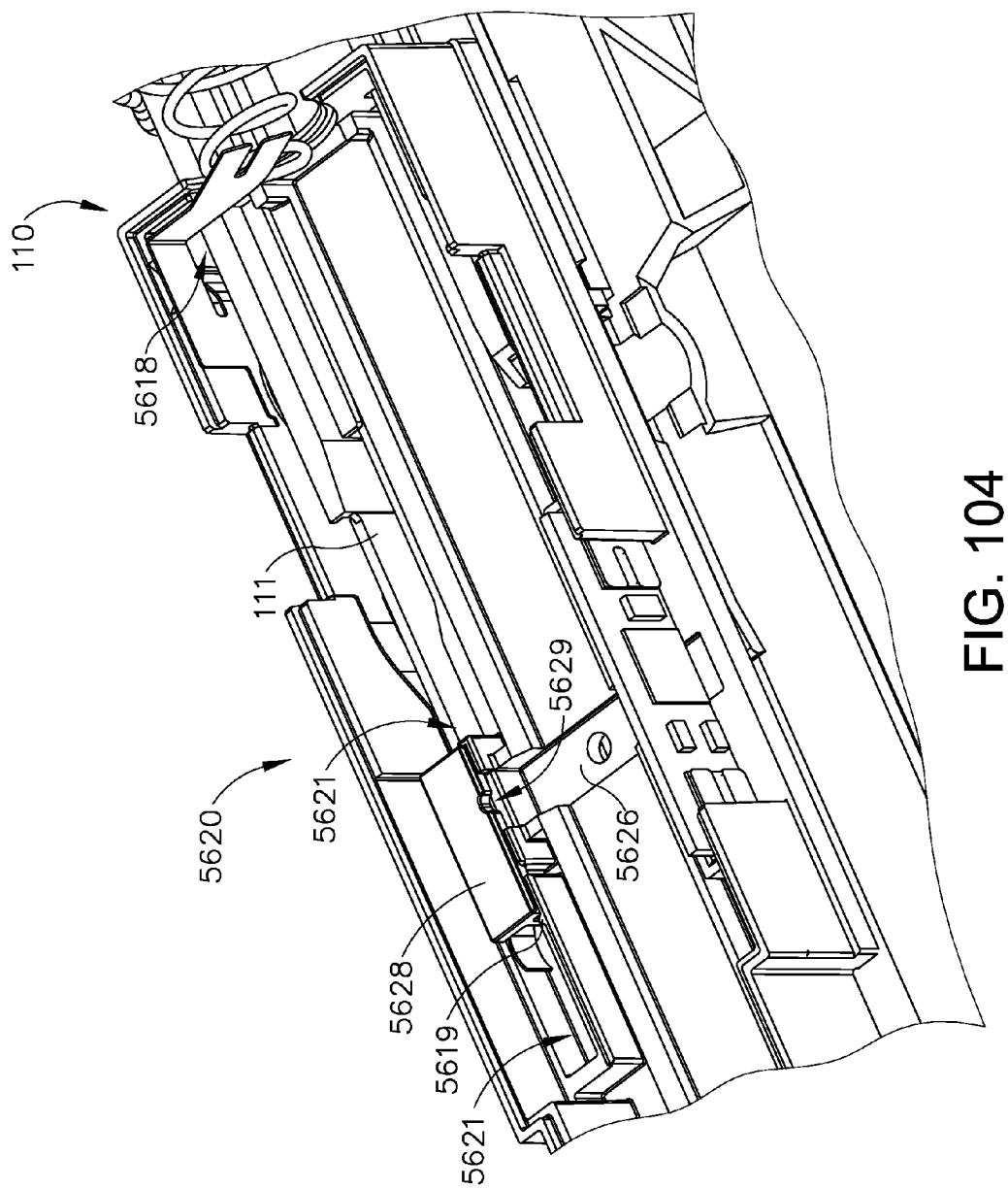
Figure 105:
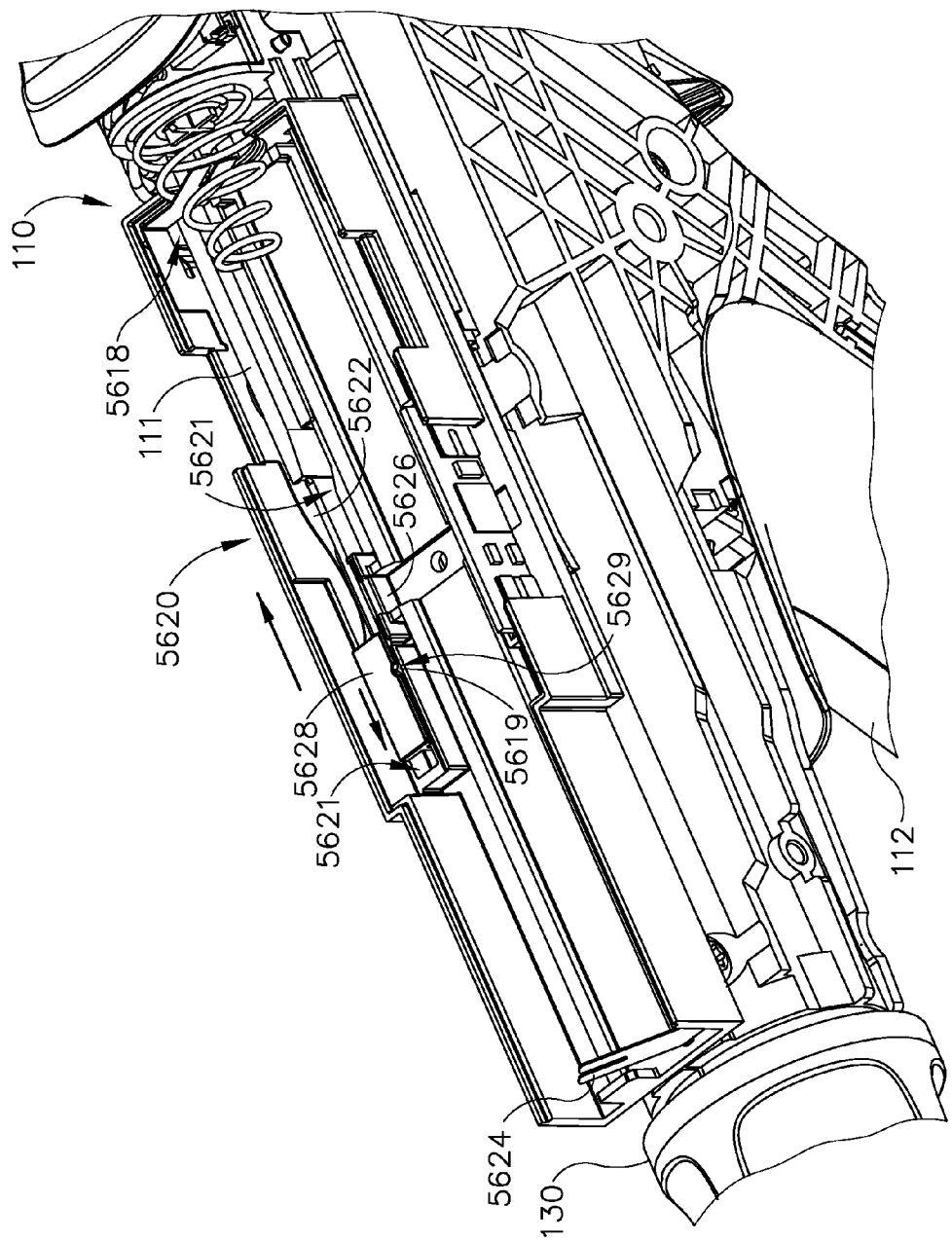
Figure 106:
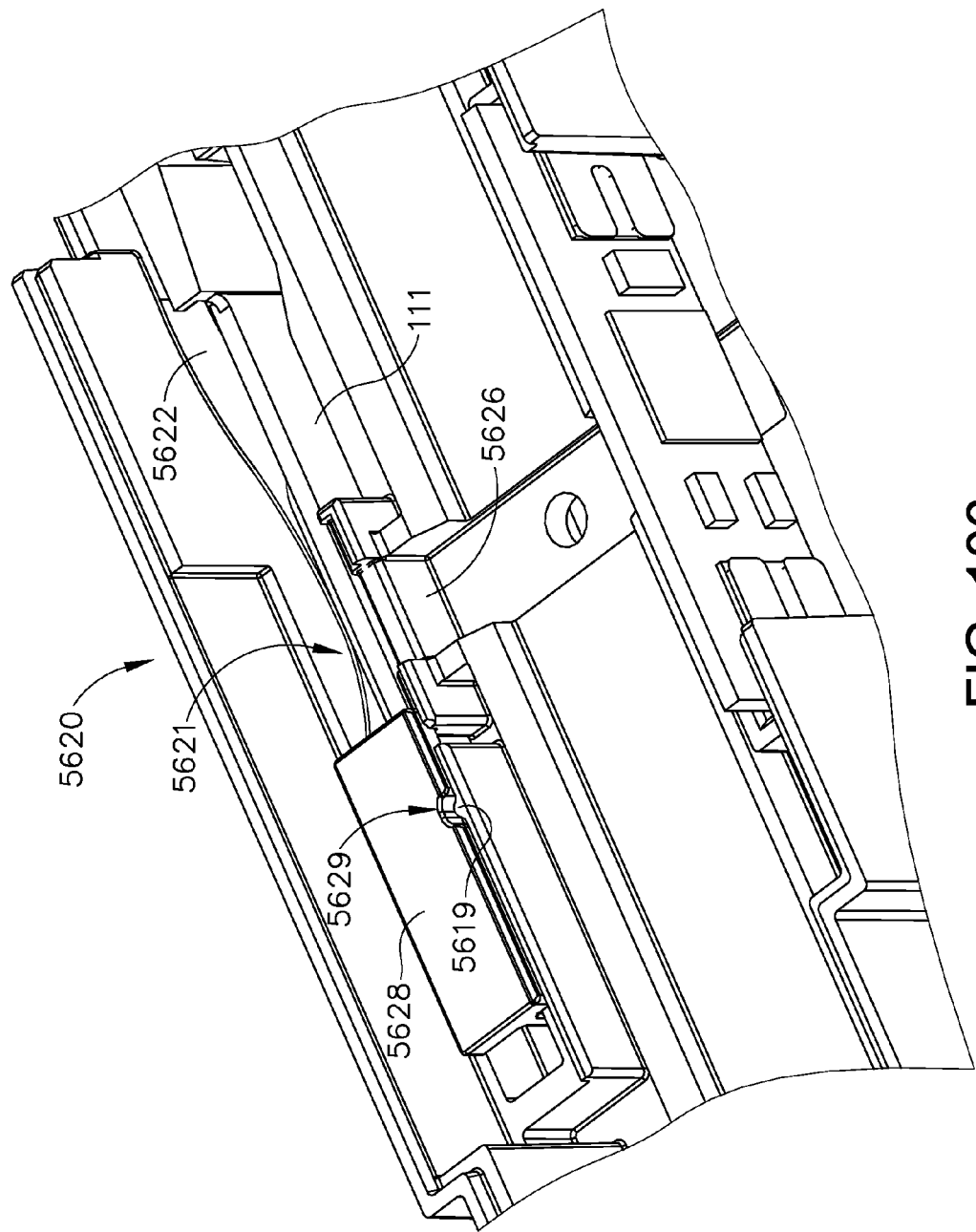
Figure 107:
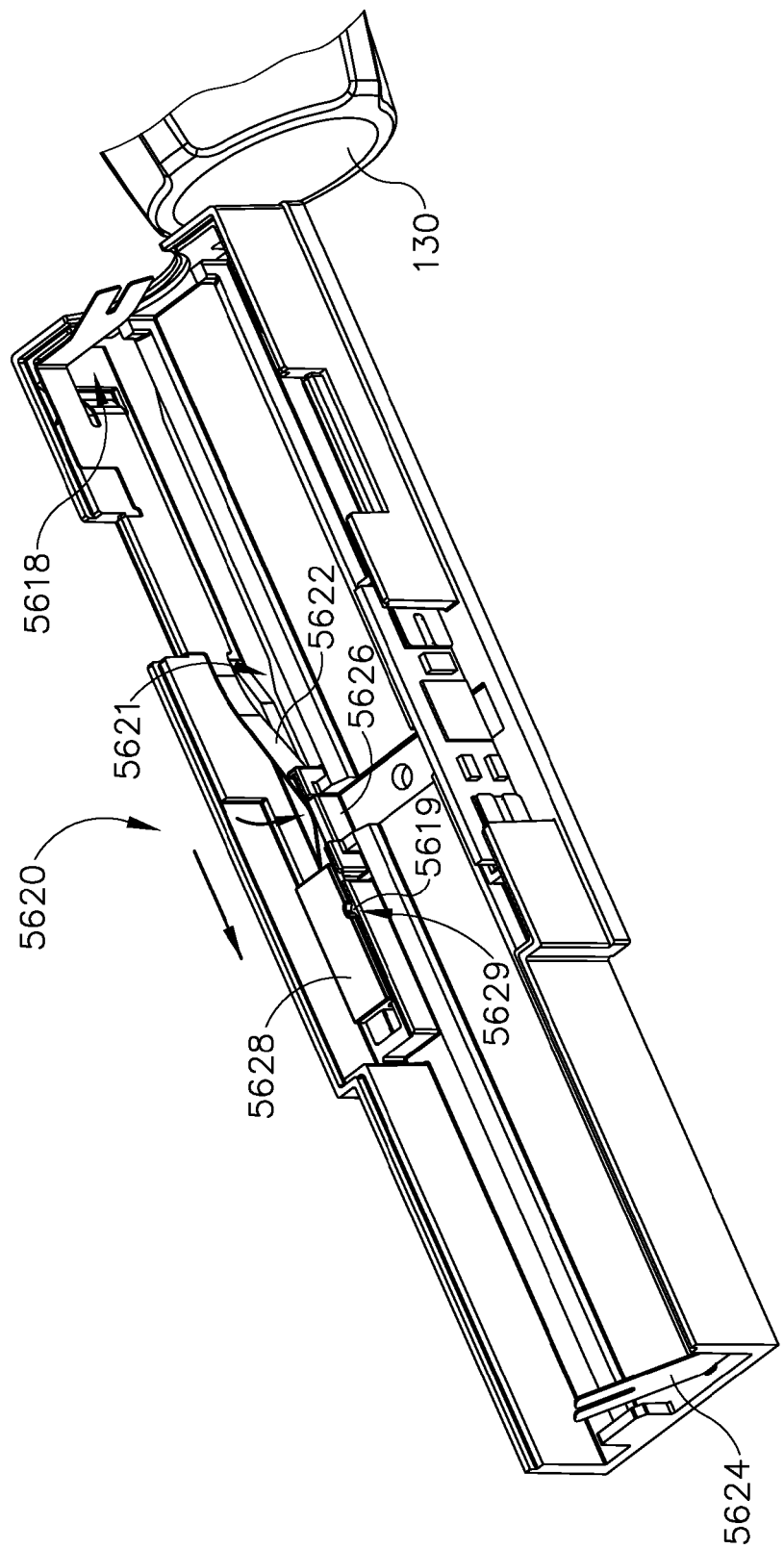
Figure 108:
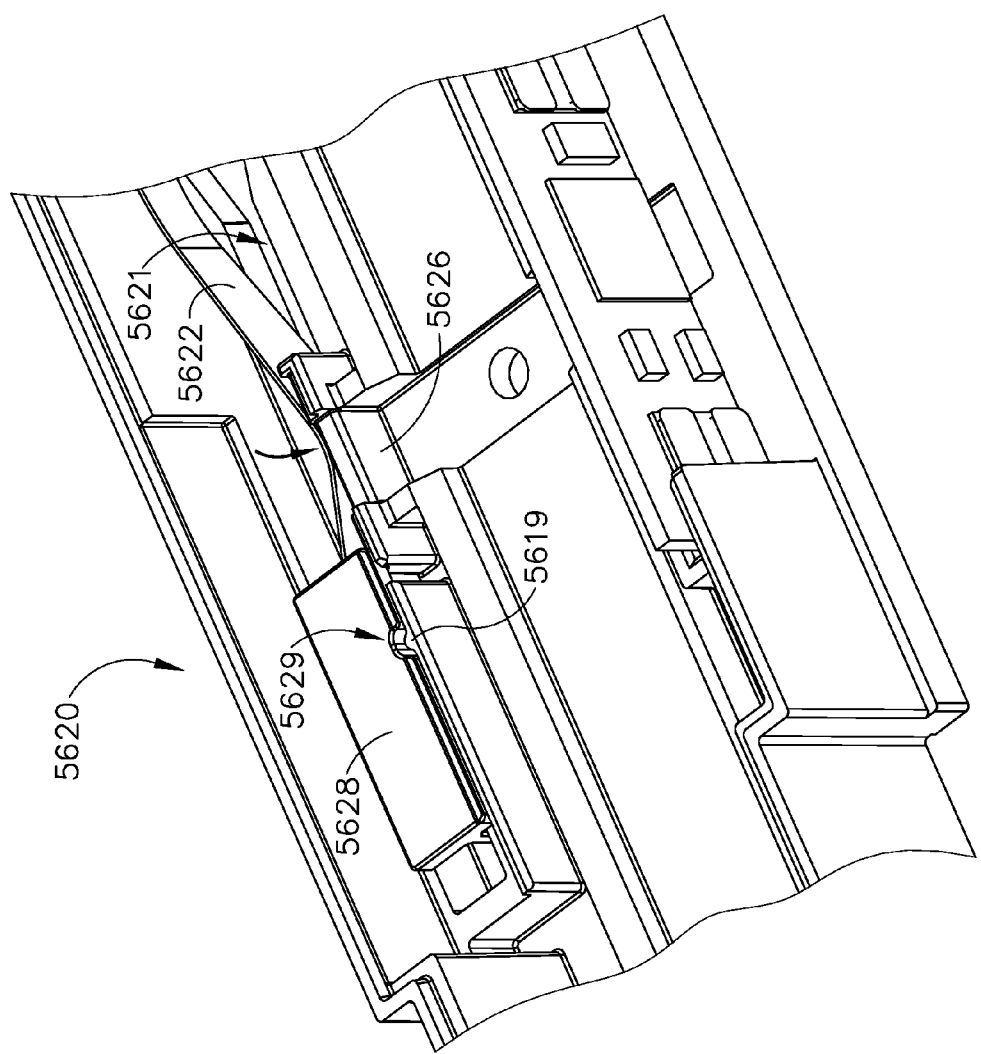
Figure 109:
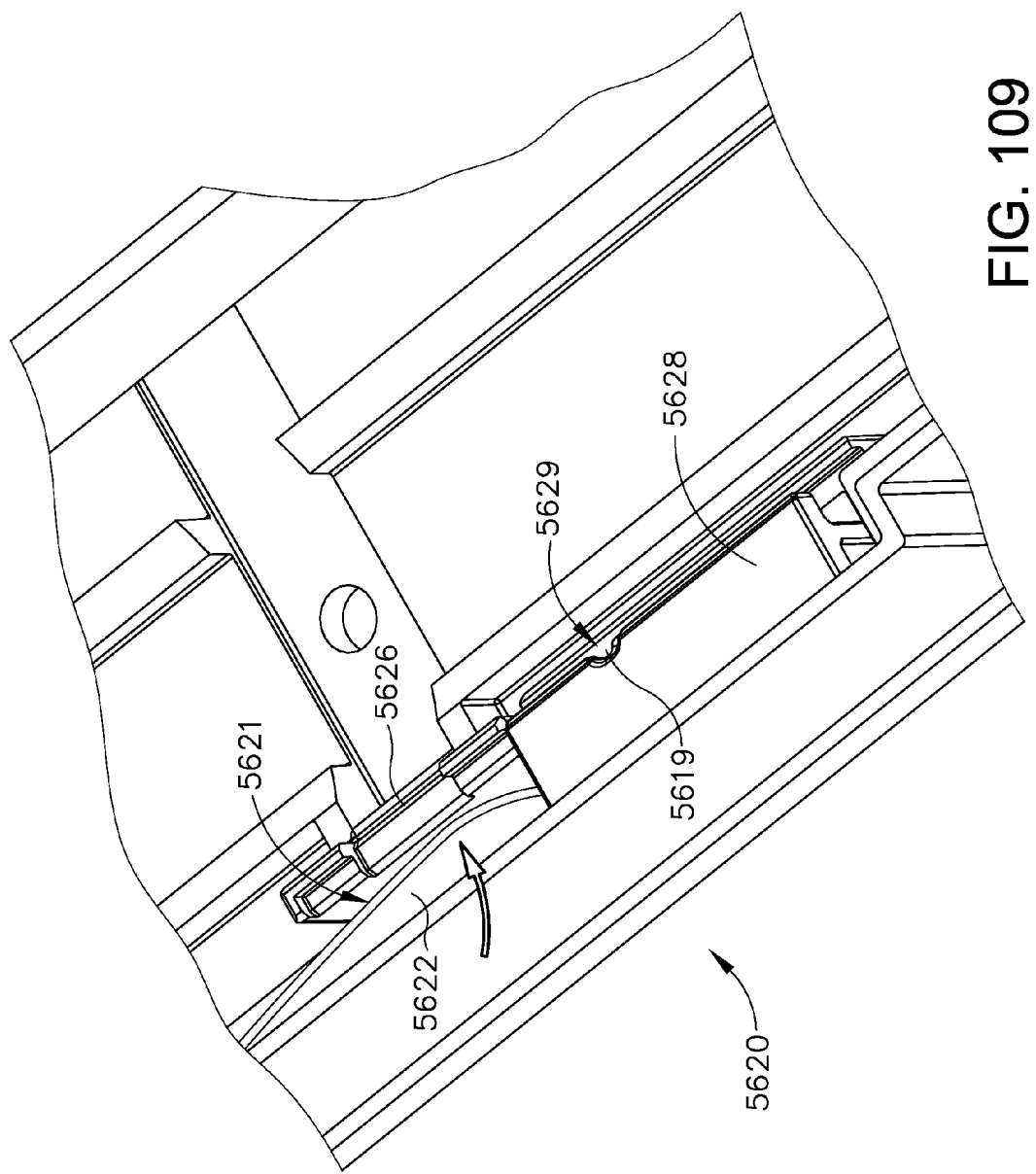
Figure 110:
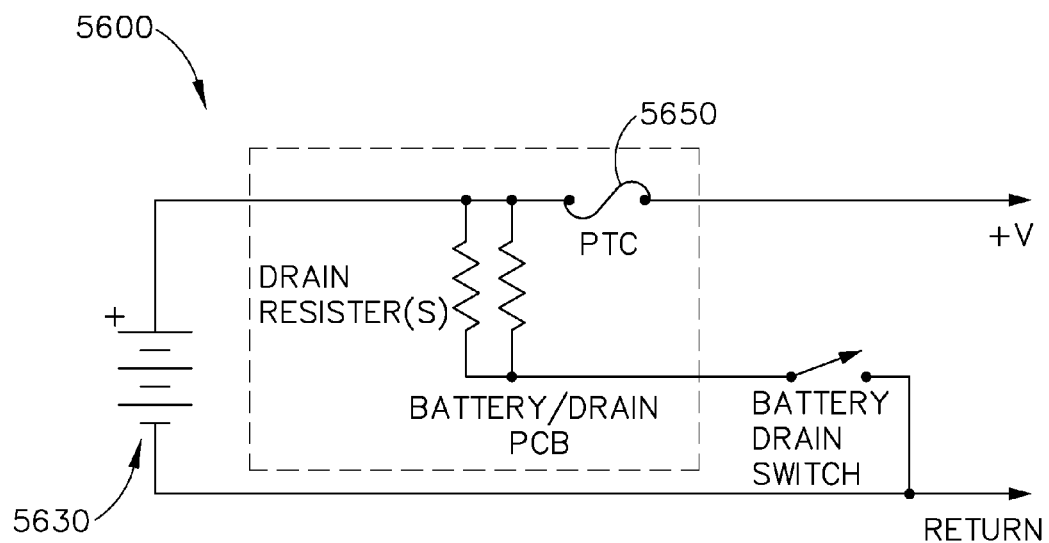
Figure 111:
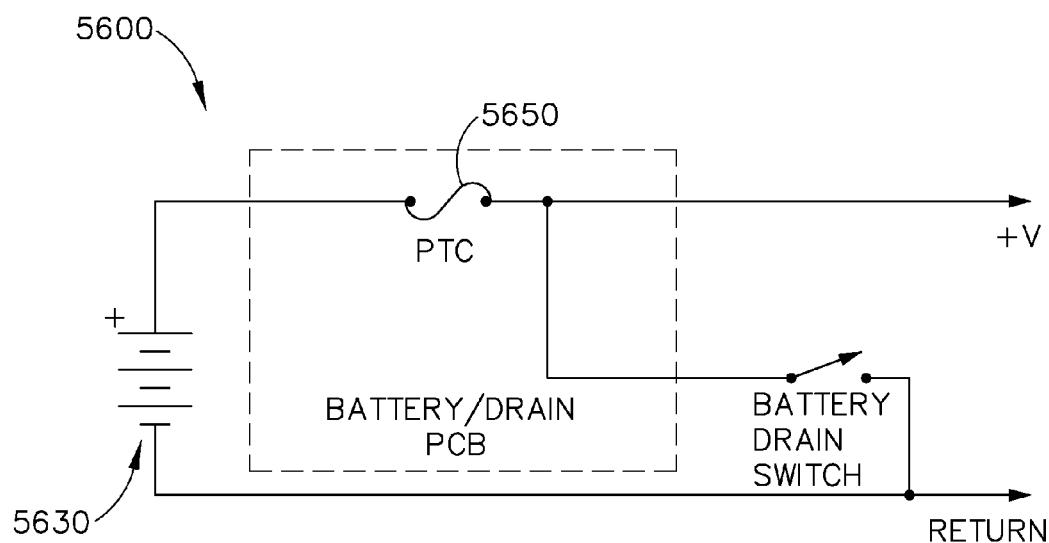
Figure 112A:
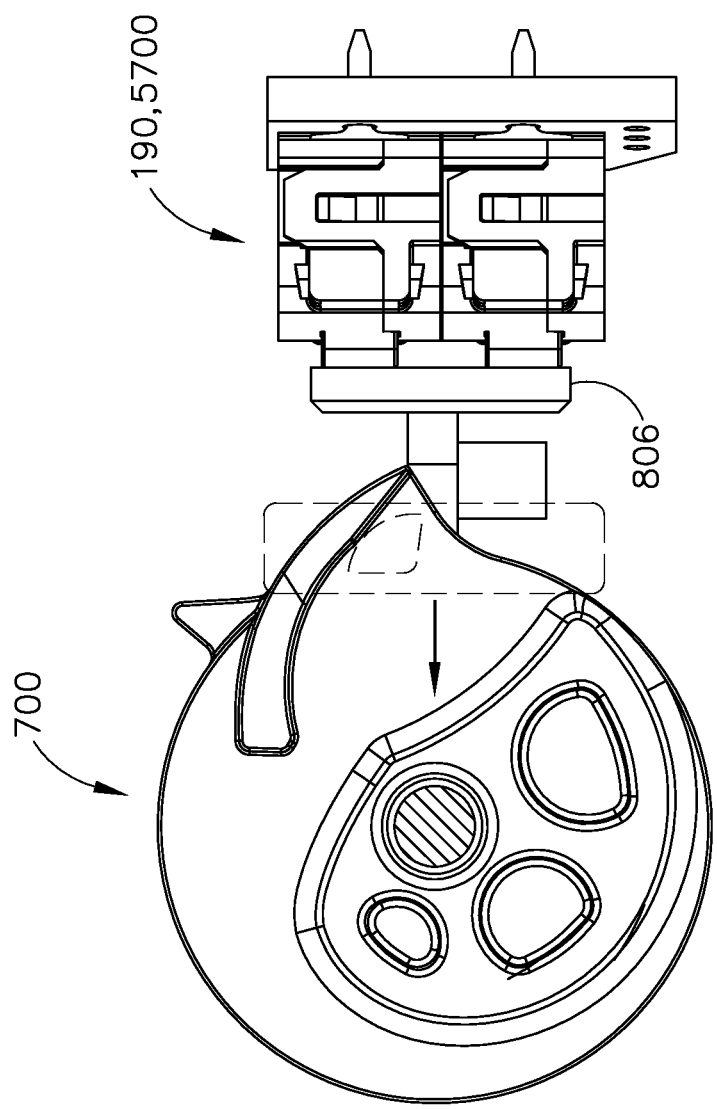
Figure 112B:
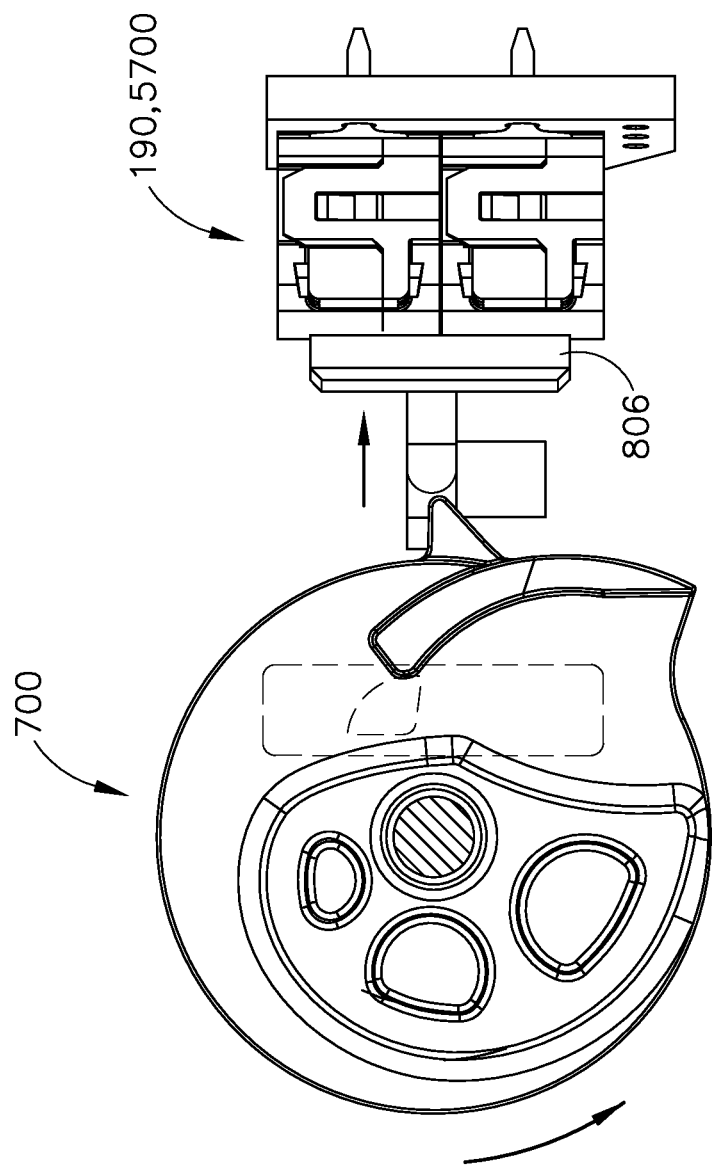
Figure 114:
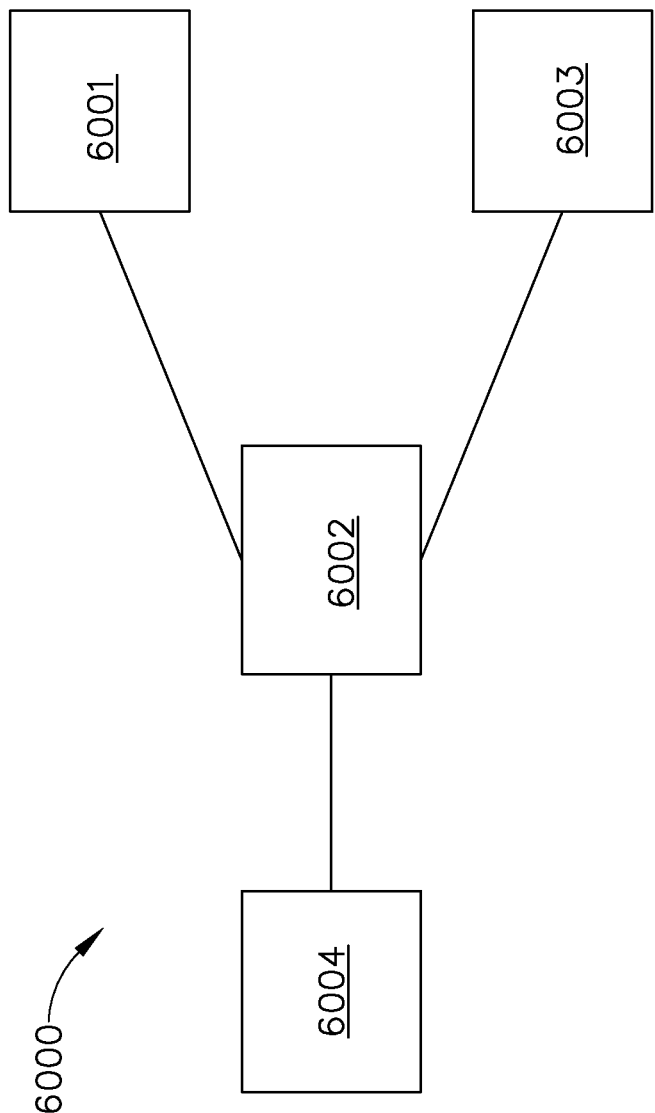
Figure 115:
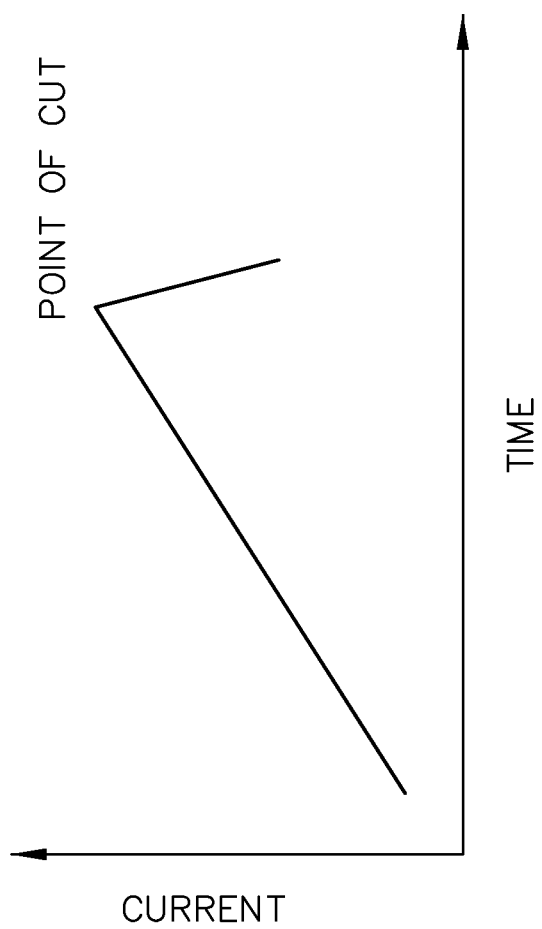
Figure 116:
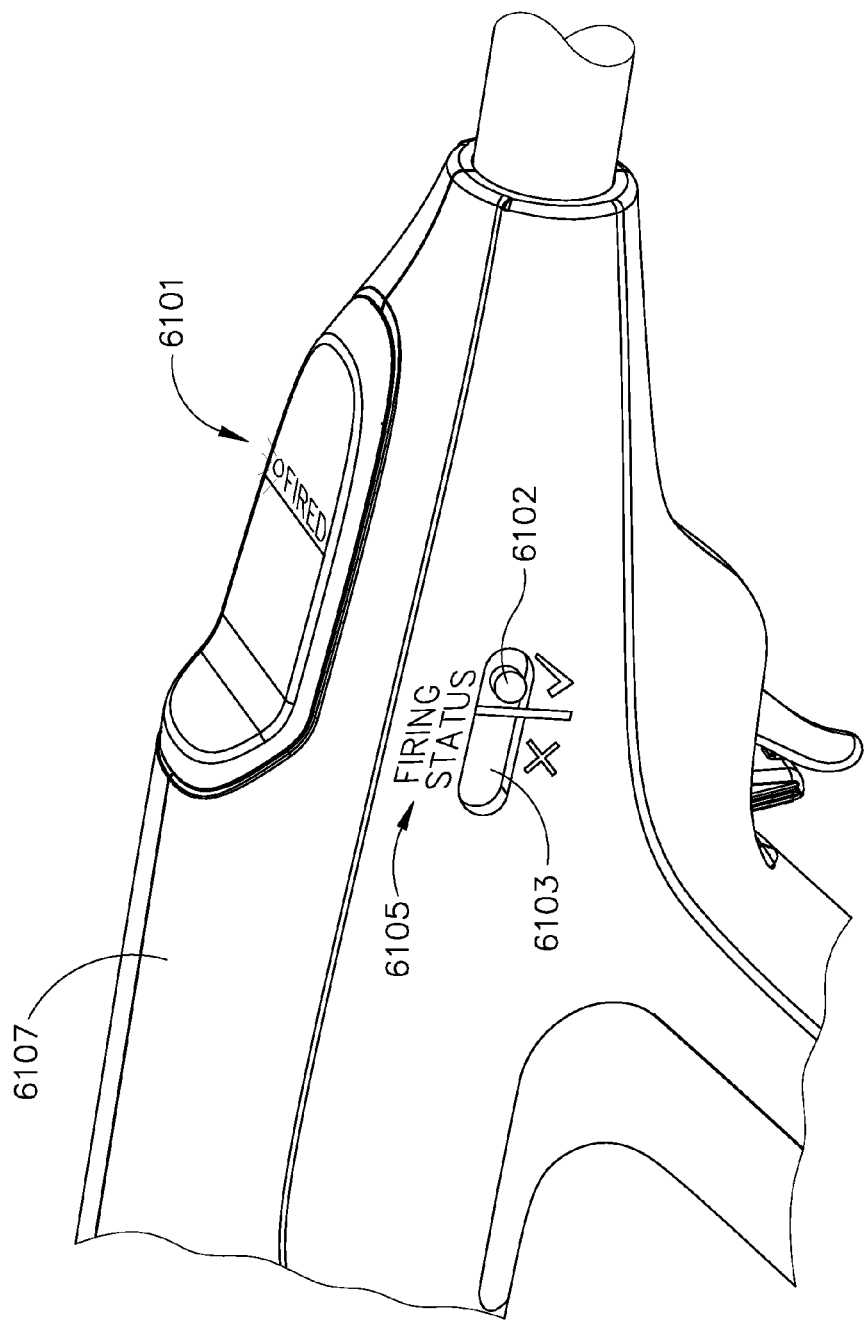
Figure 117:
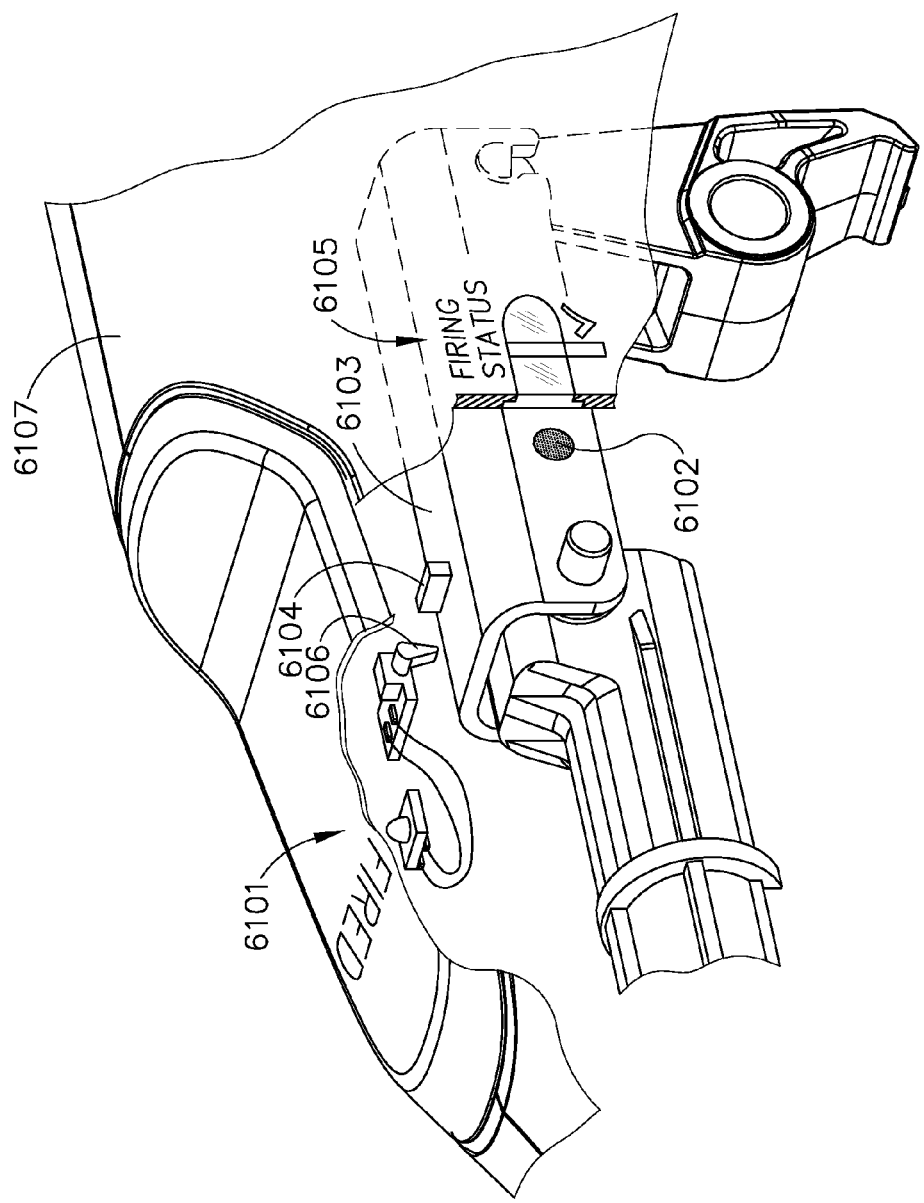
Figure 118:
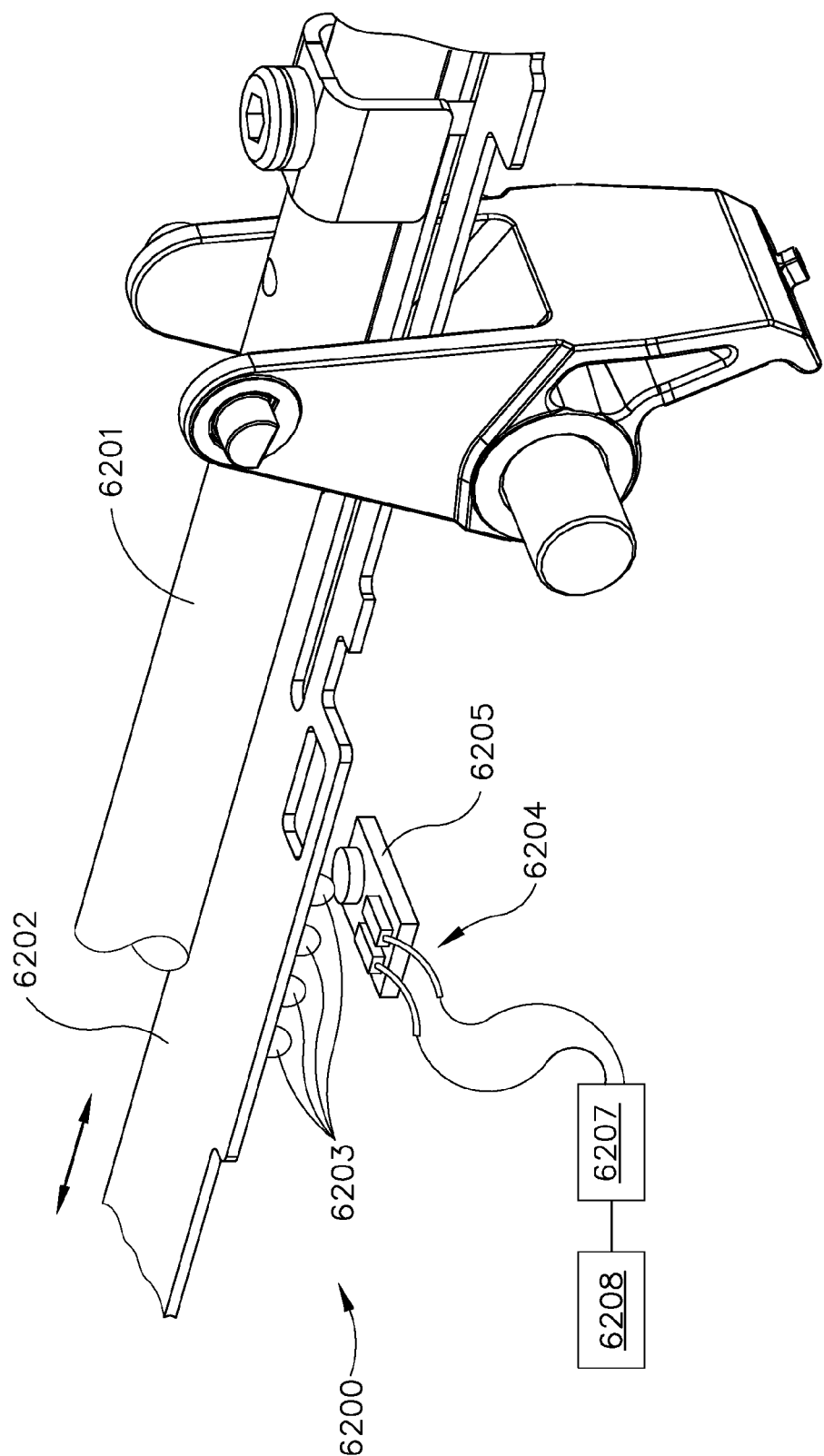
Figure 119:
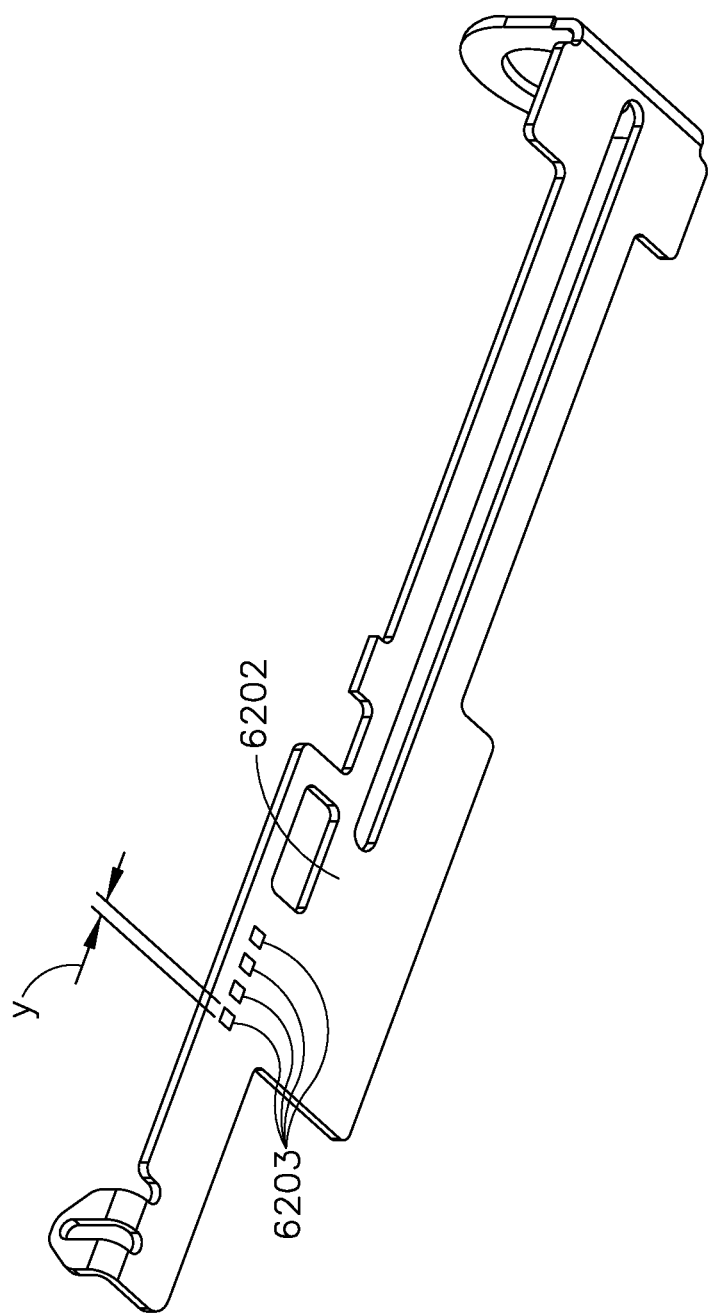
Figure 120:
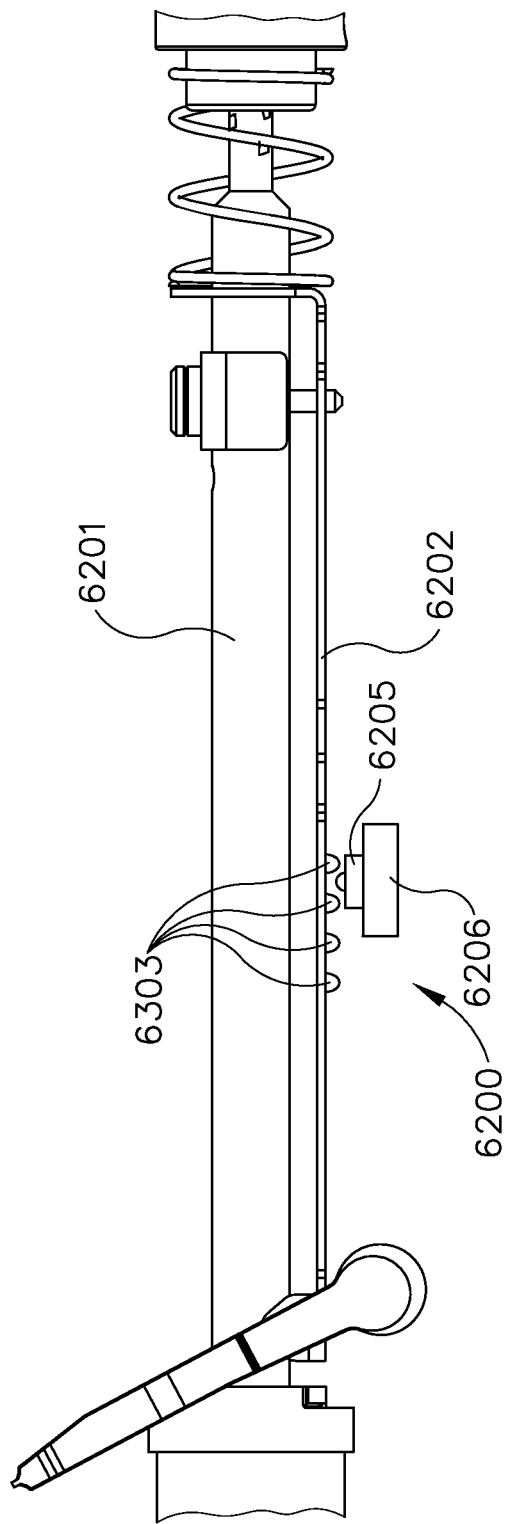
Figure 121:
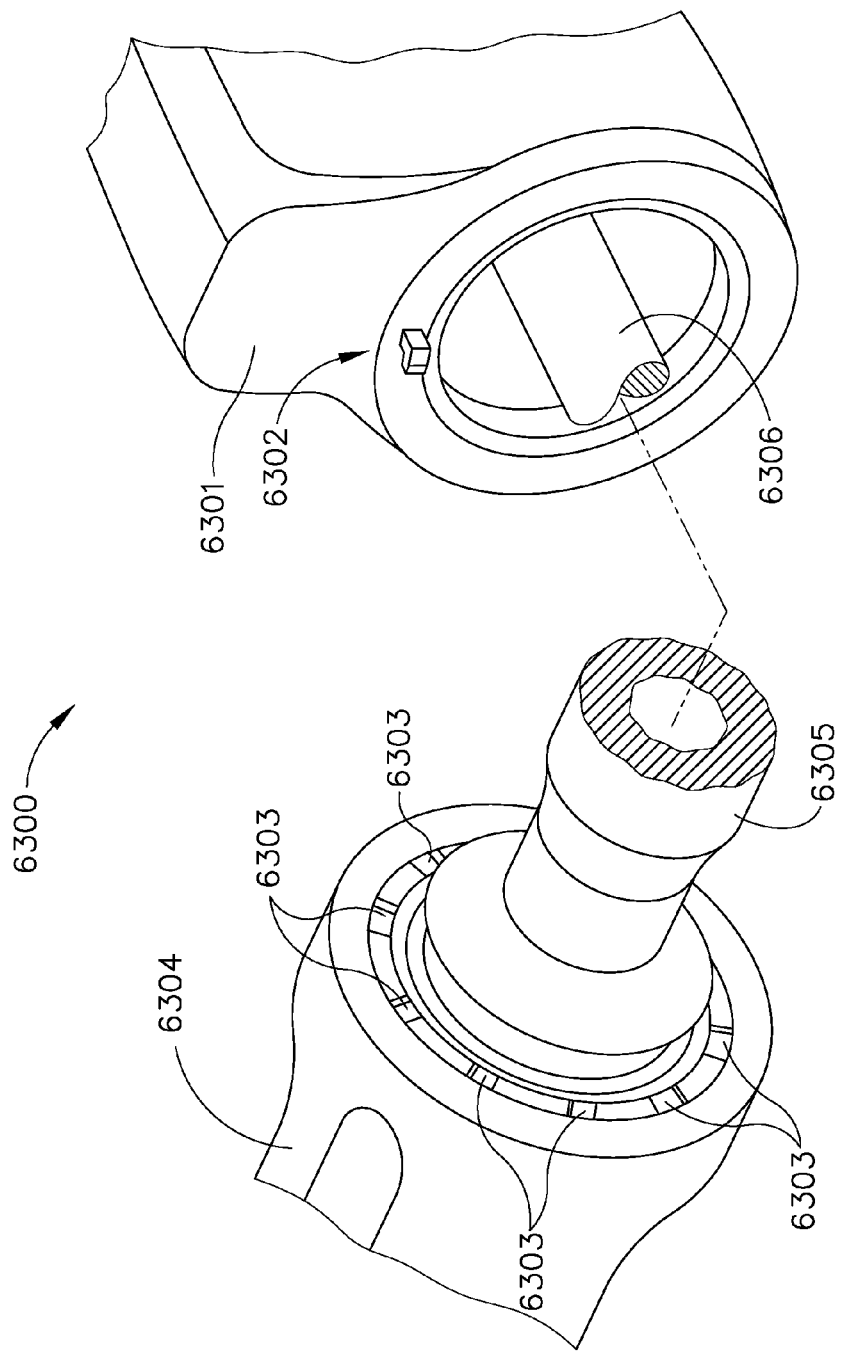
Figure 122A:
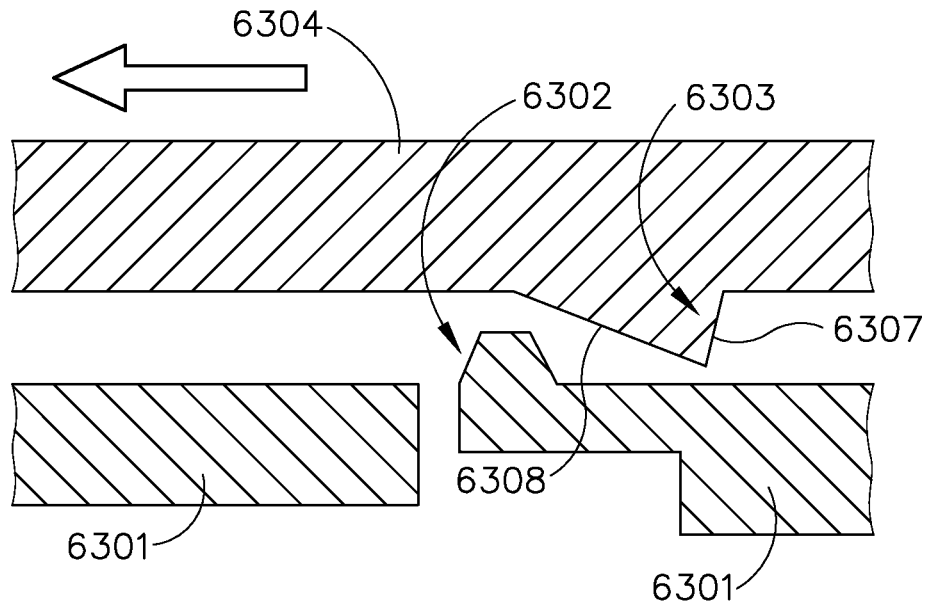
Figure 122B:
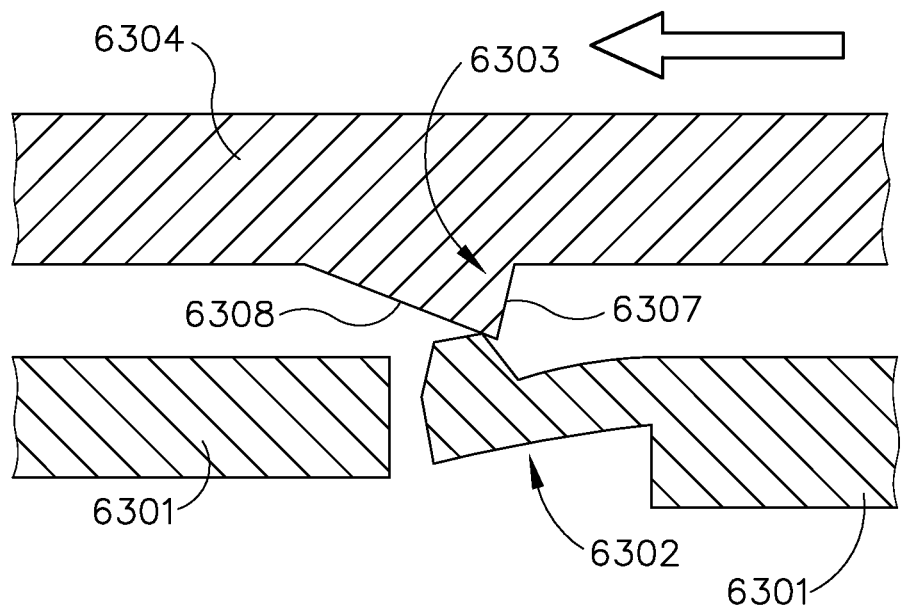
Figure 122C:
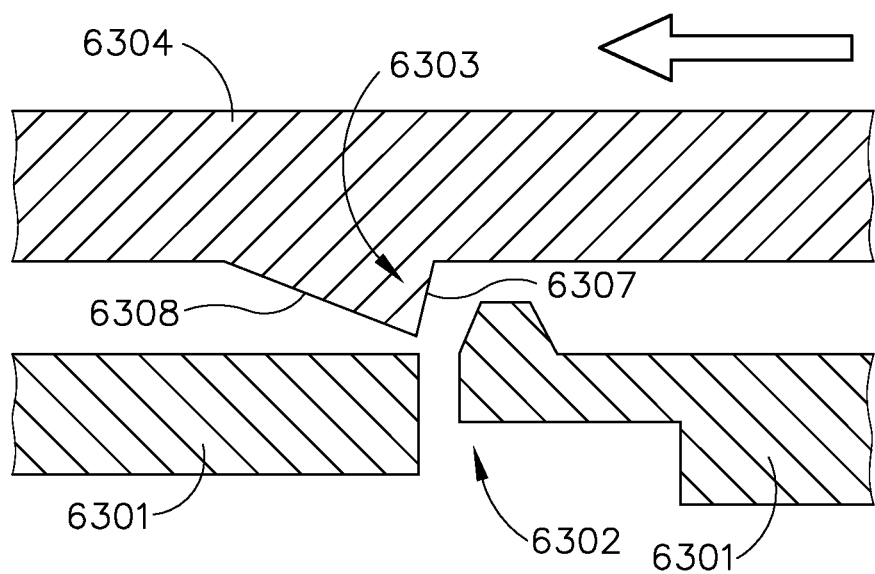
Figure 123A:
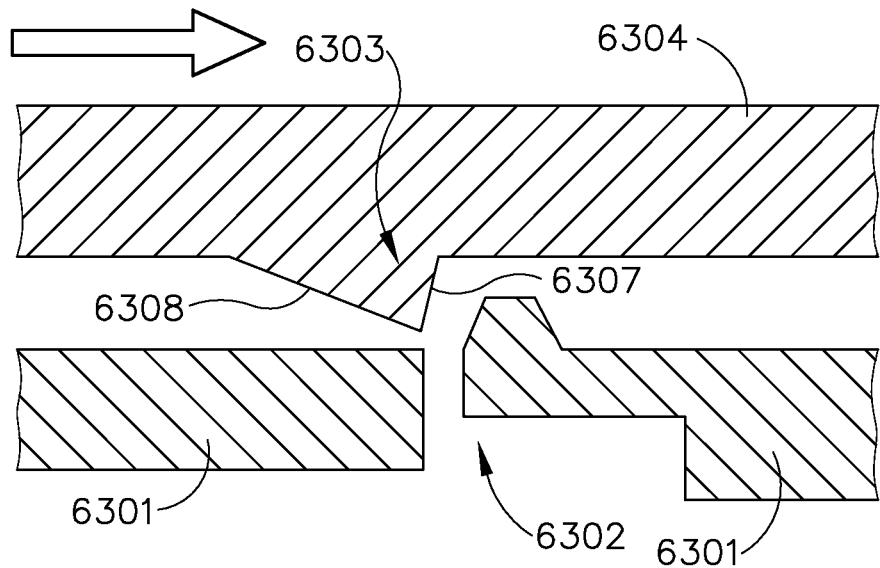
Figure 123B:
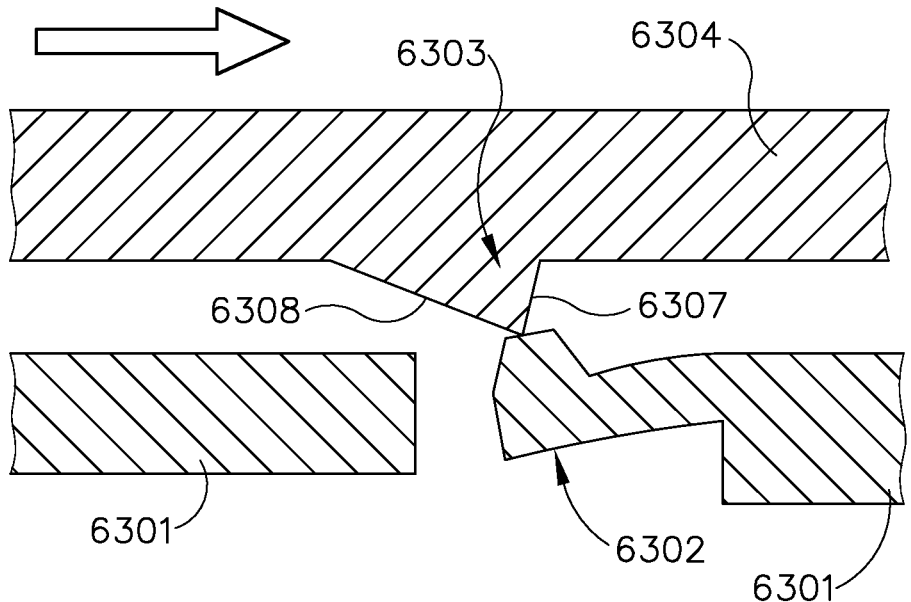
Figure 123C:
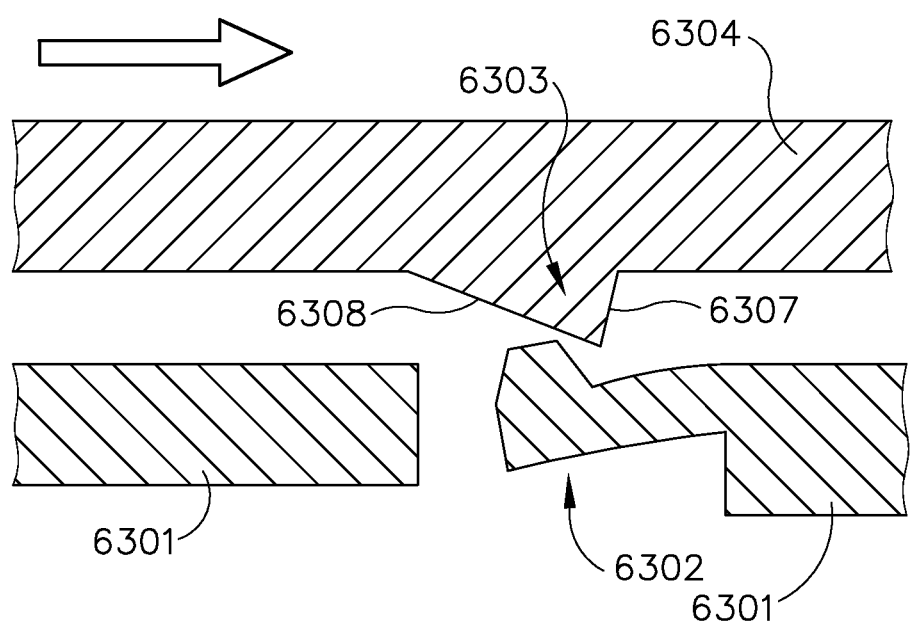
Figure 124A:
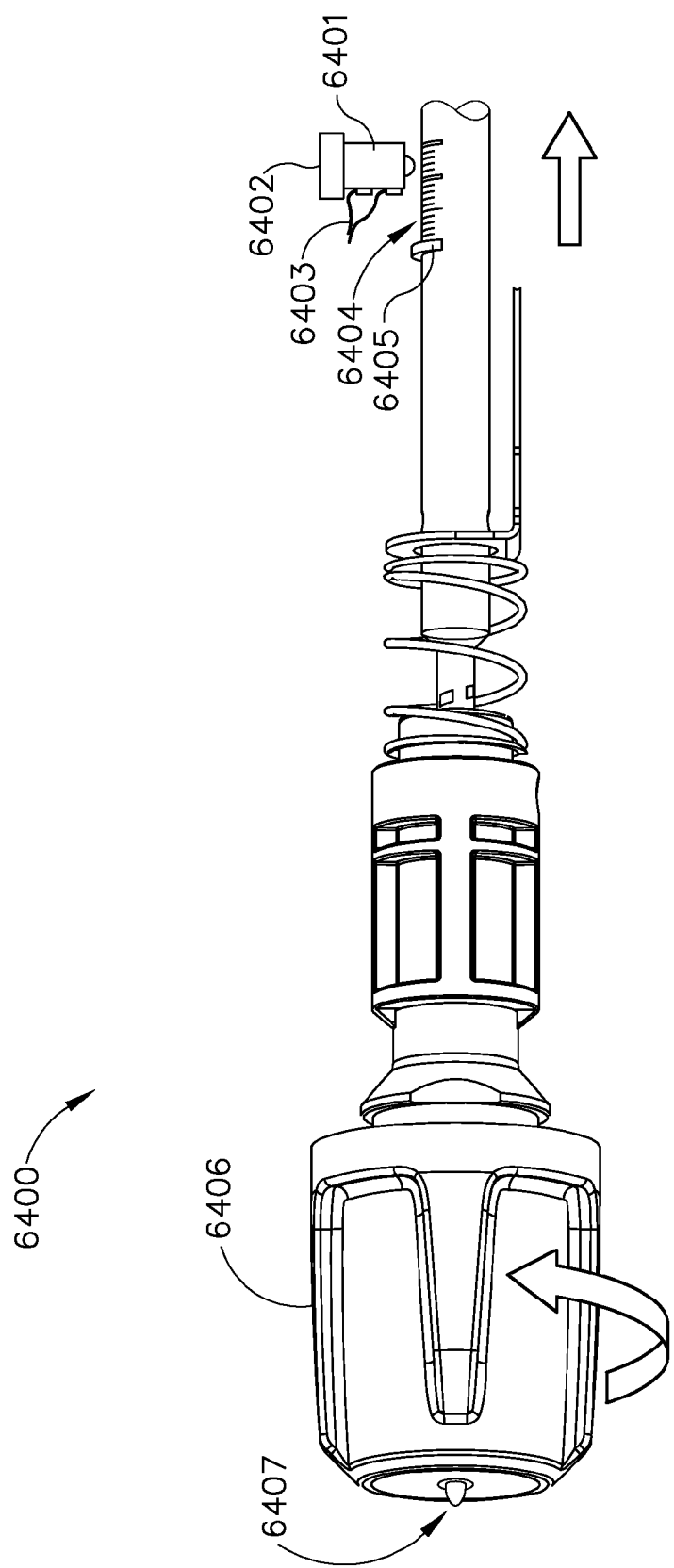
Figure 124B:
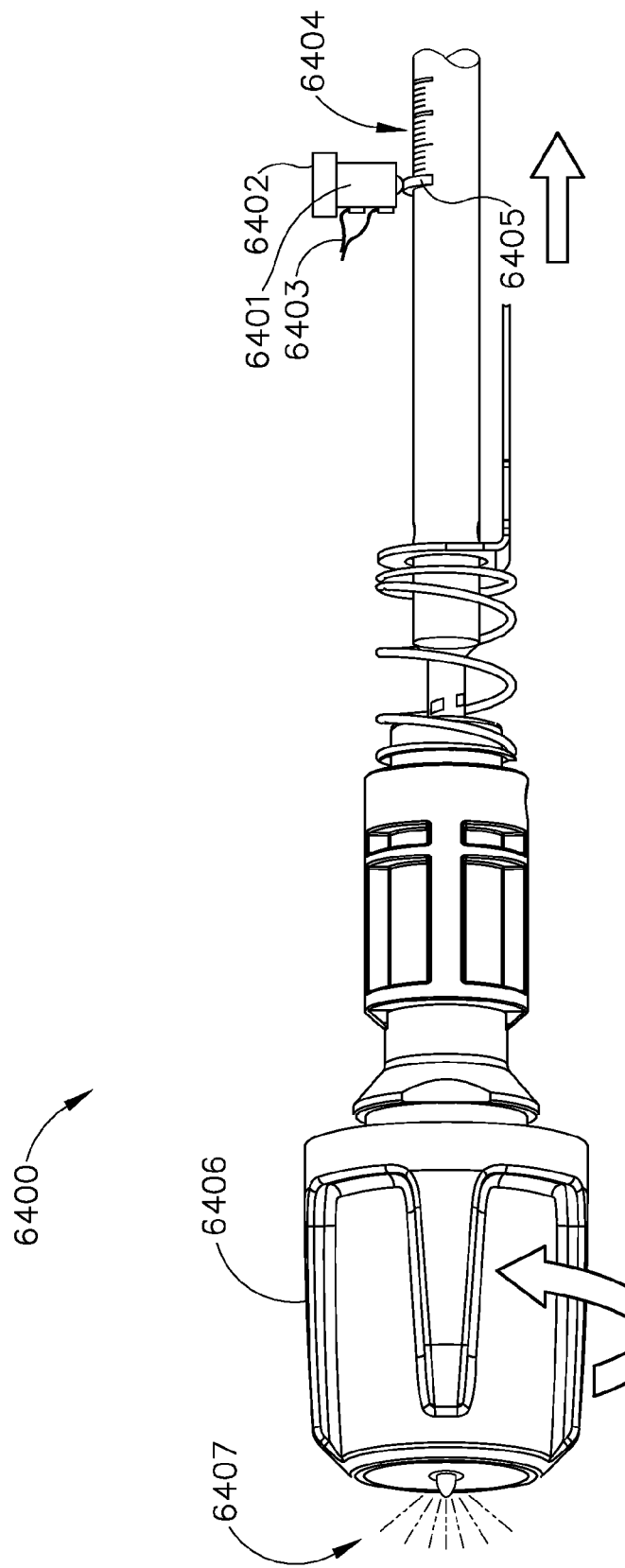
Figure 125:
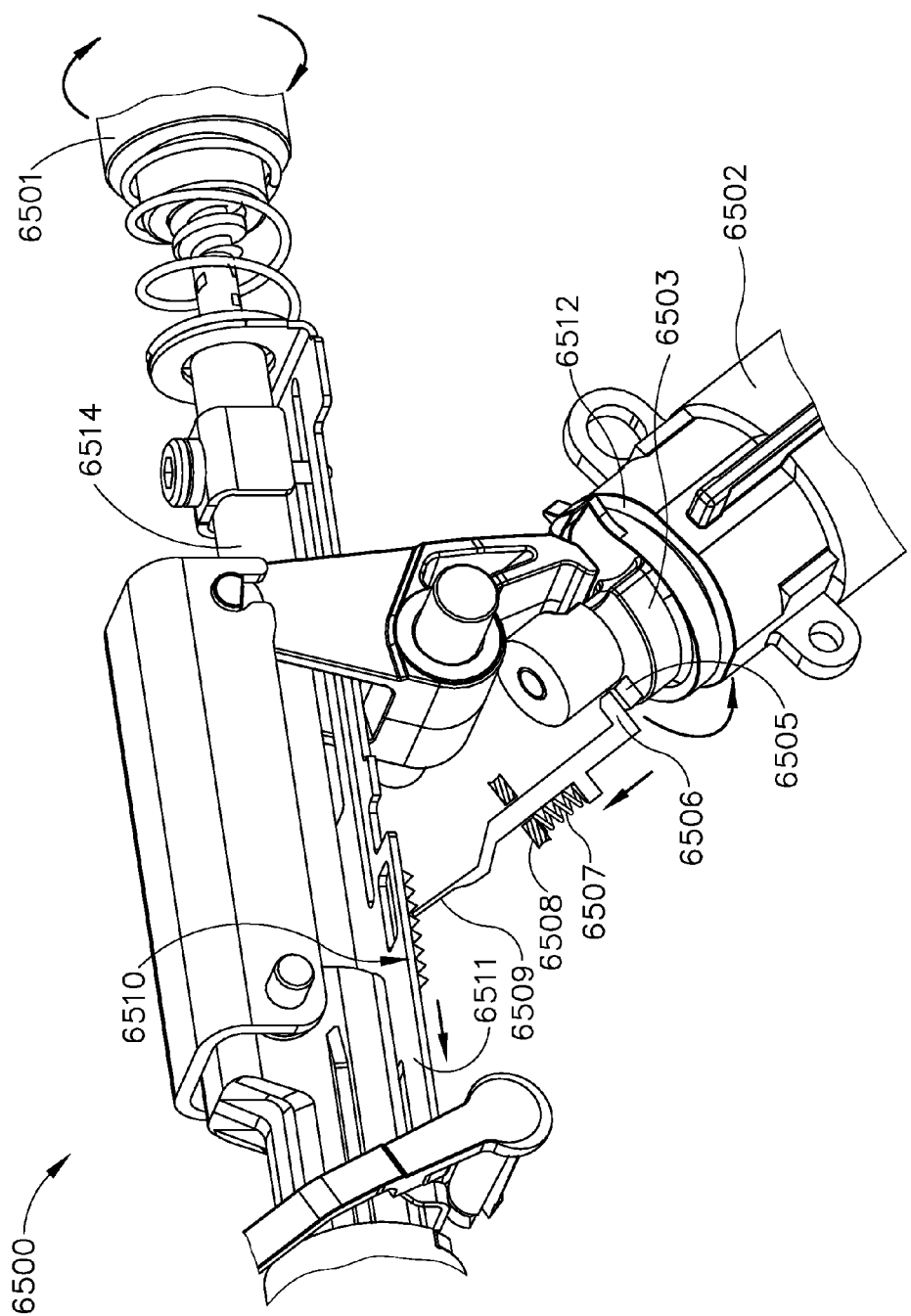
Figure 126A:
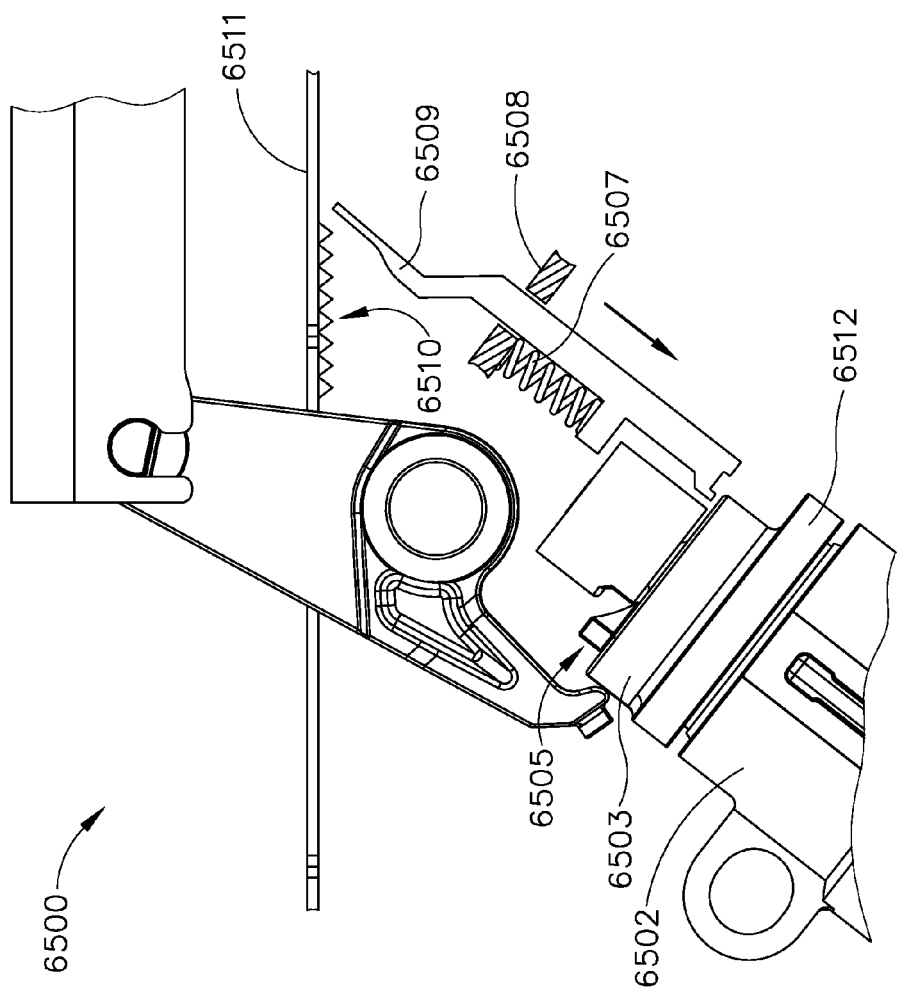
Figure 126C:
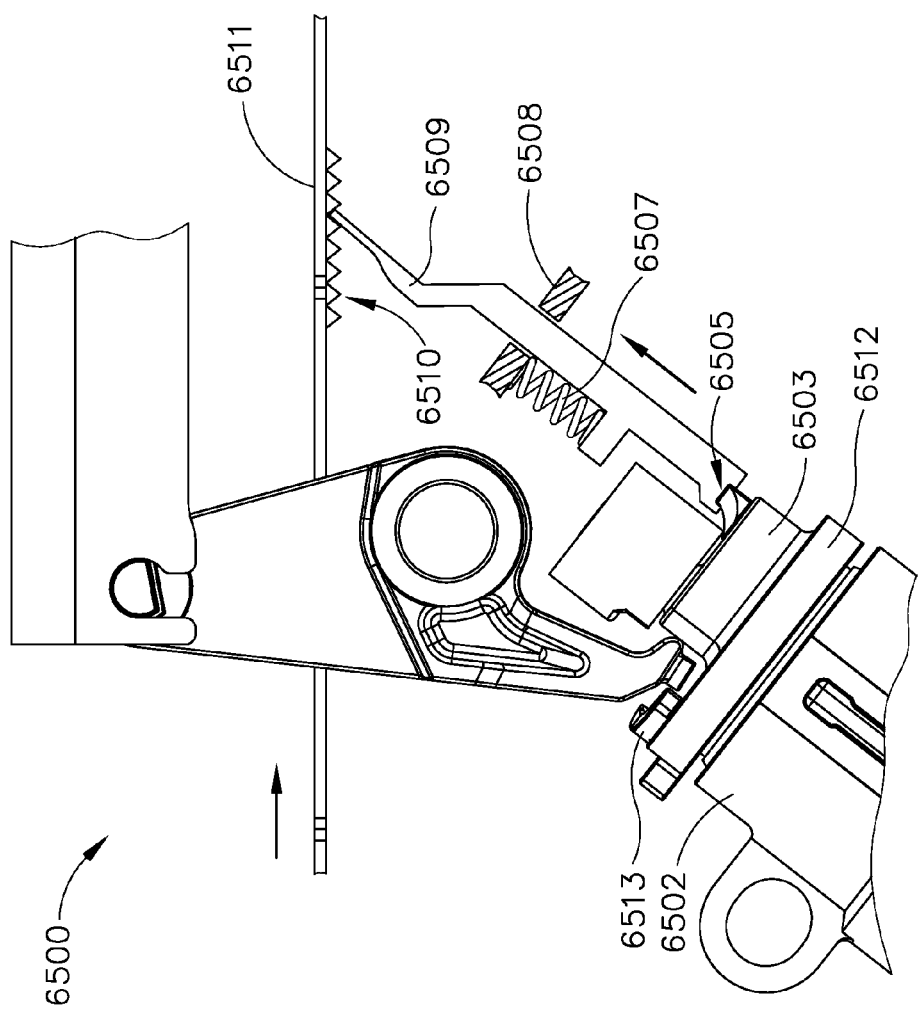
Figure 127:
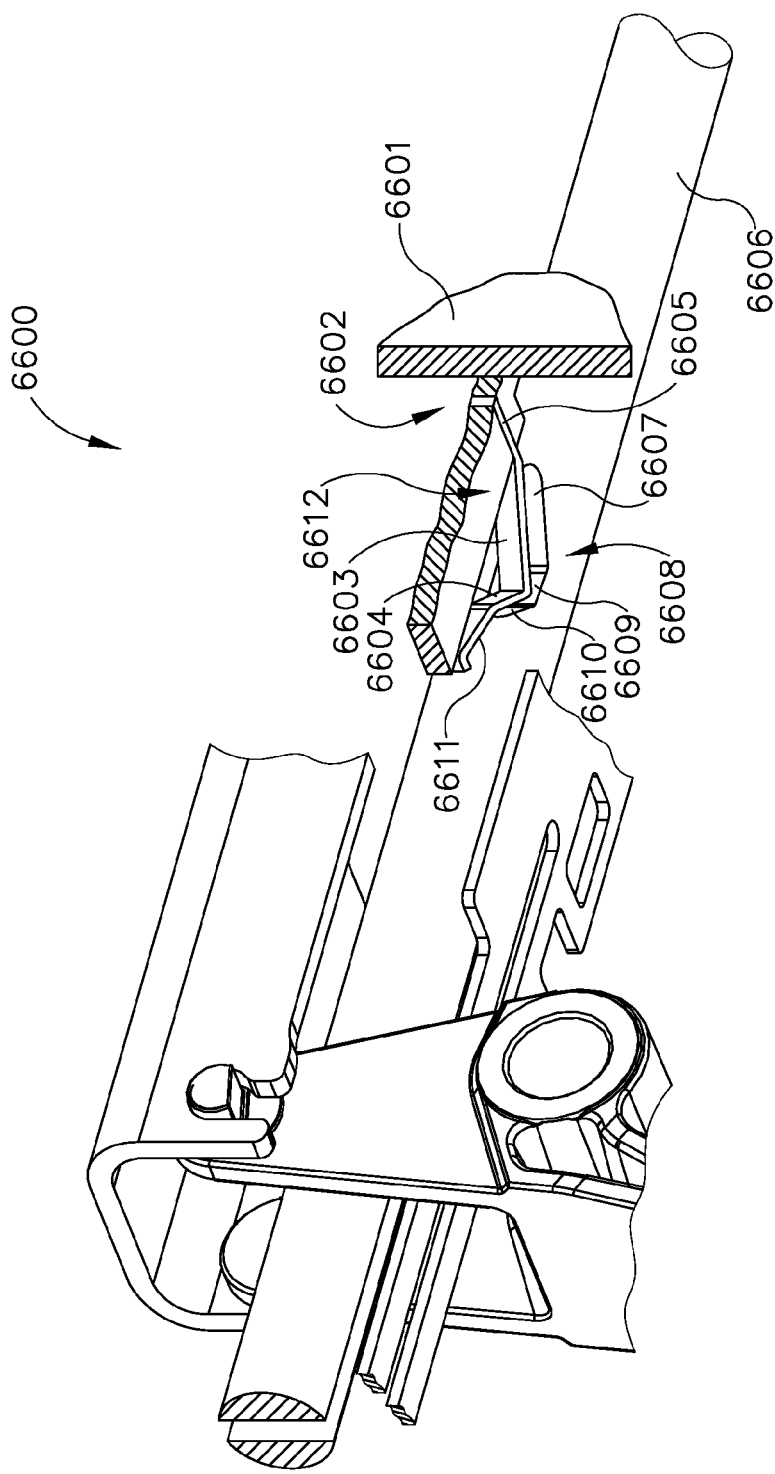
Figure 128A:
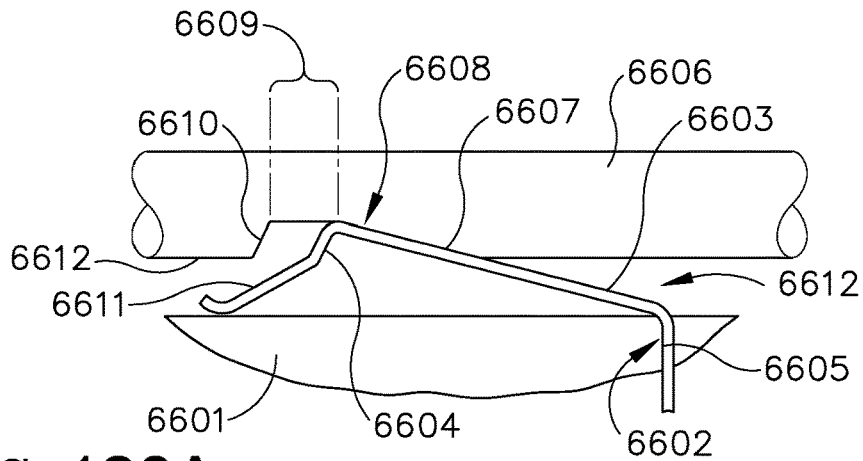
Figure 128B:
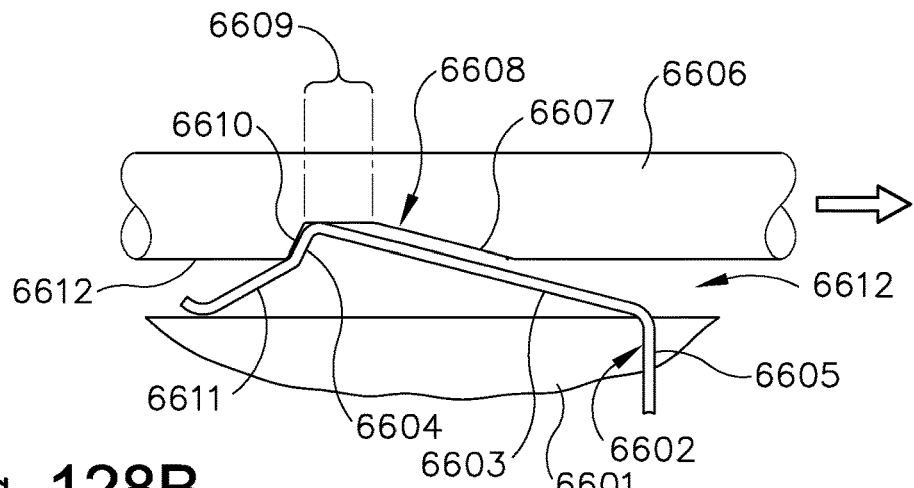
Figure 128C:
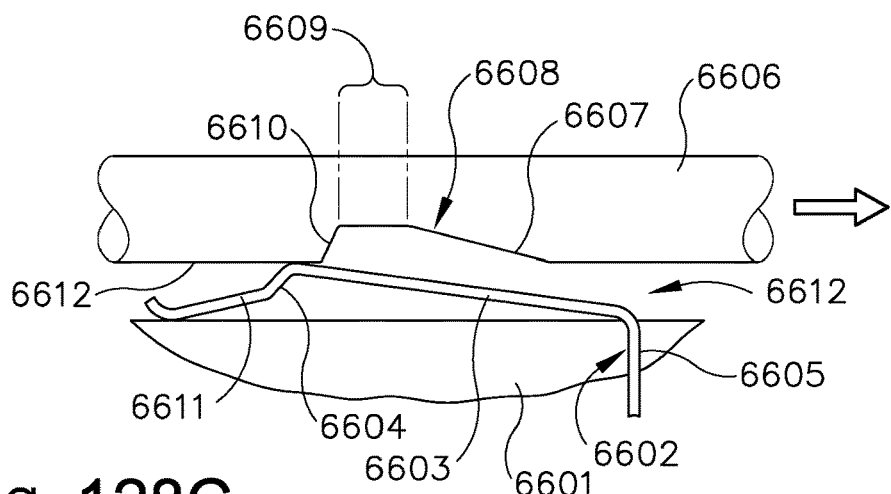
Figure 129:
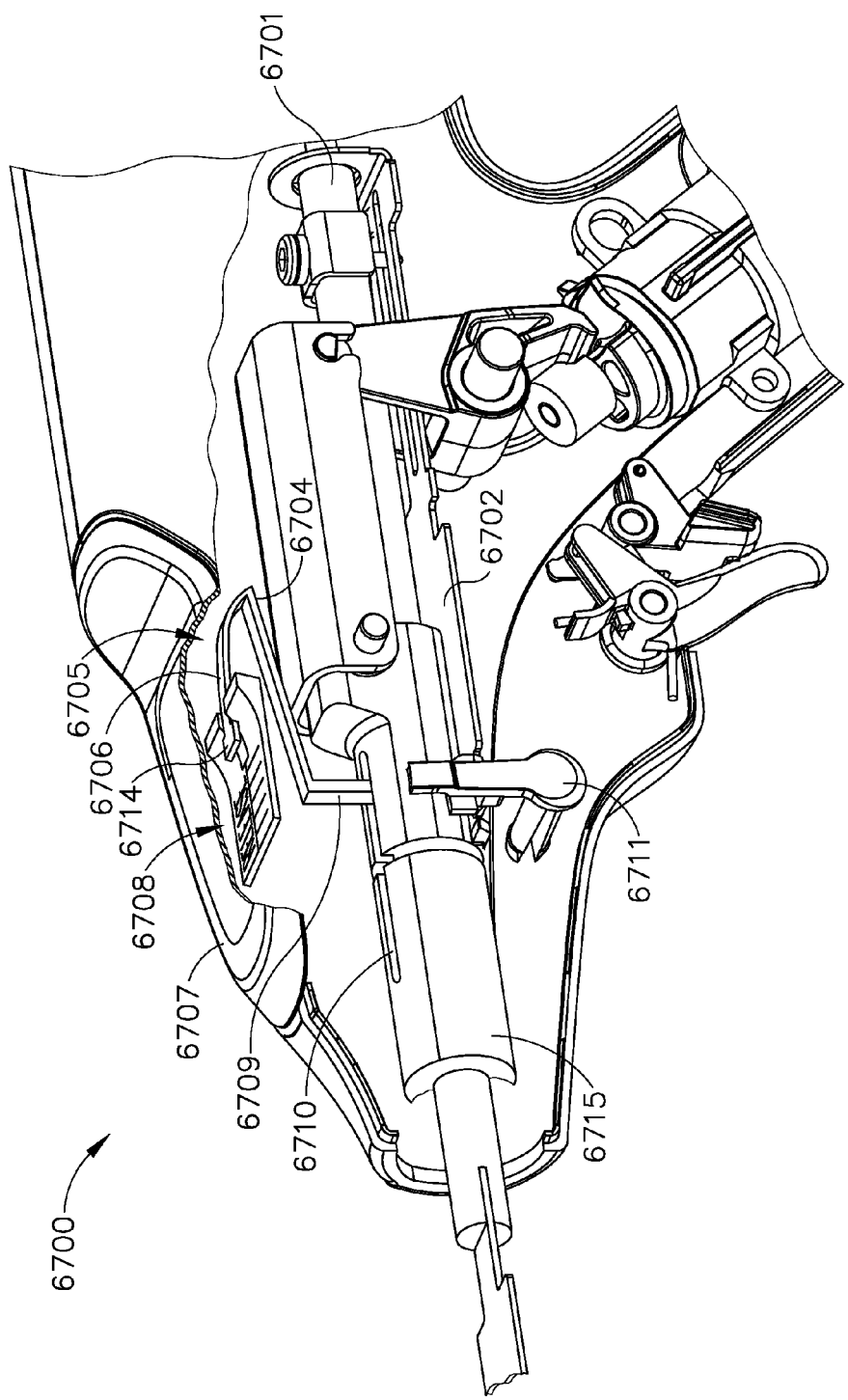
Figure 130A:
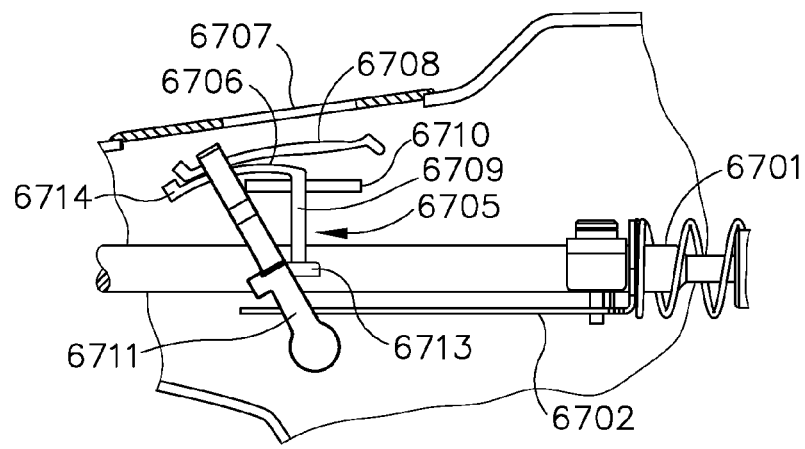
Figure 130B:
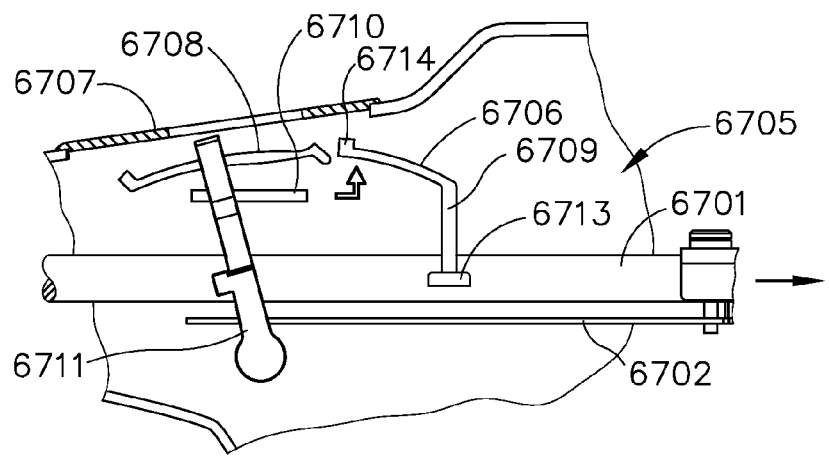
Figure 130C:
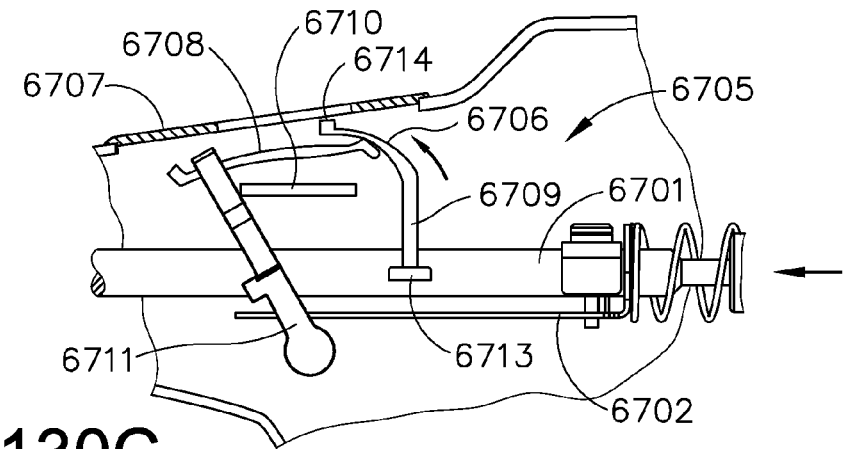
Figure 131:
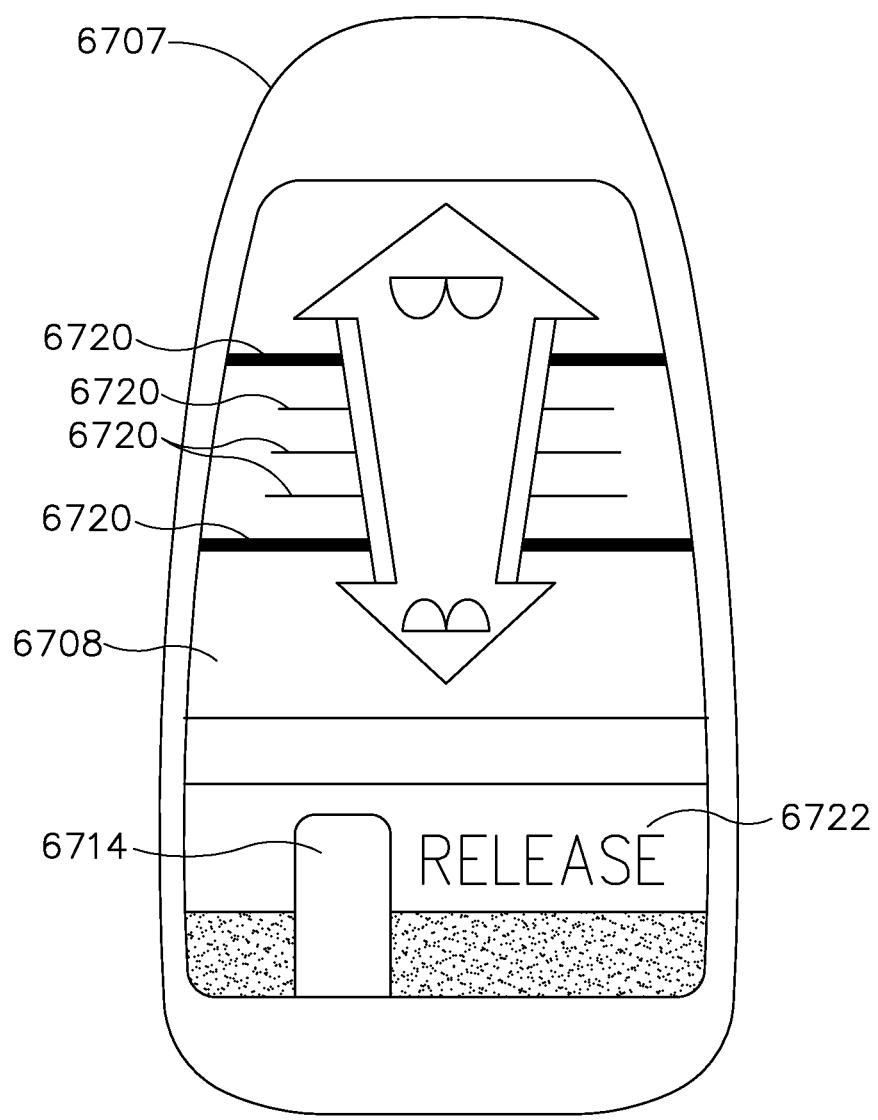
Figure 132:
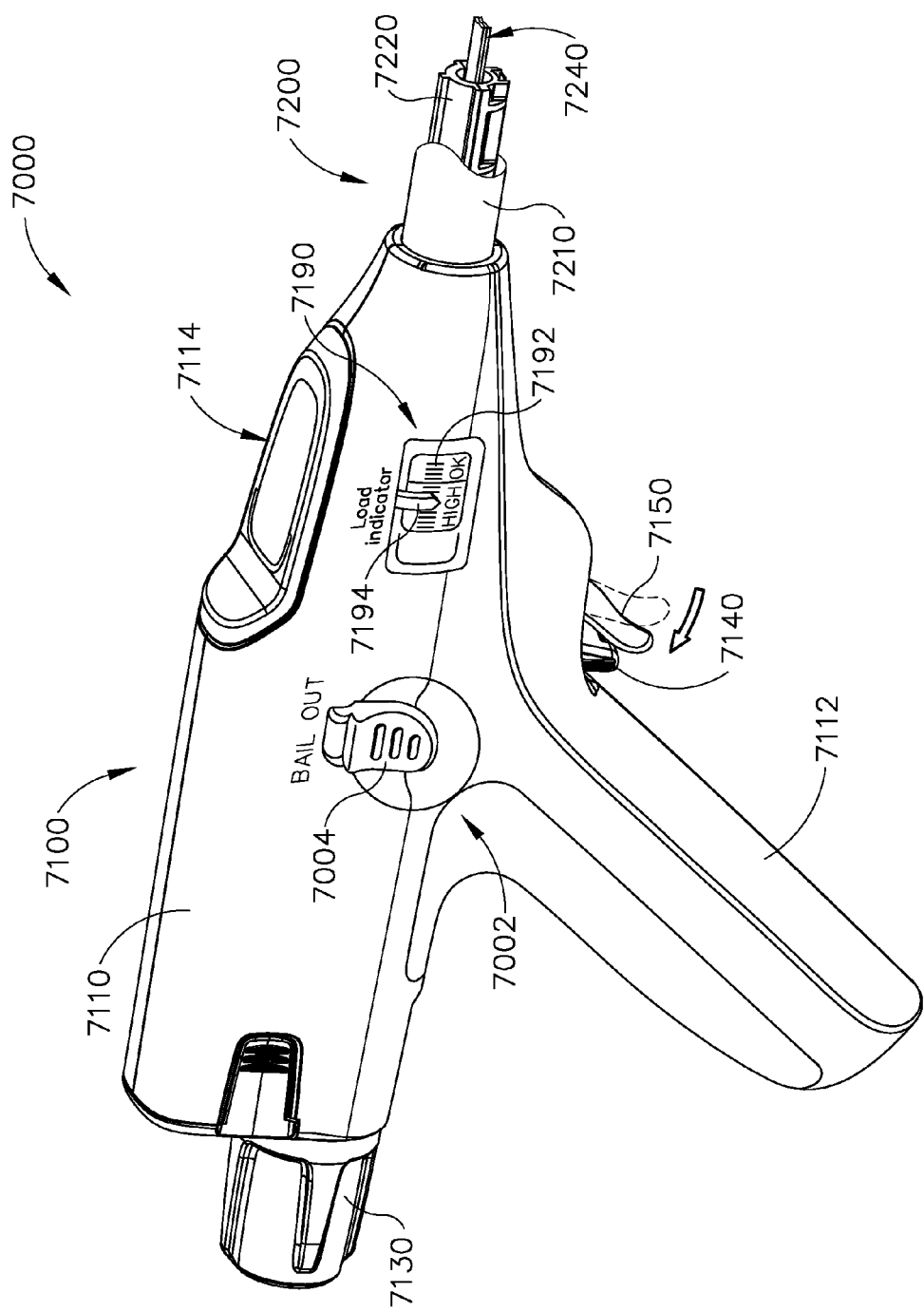
Figure 133:
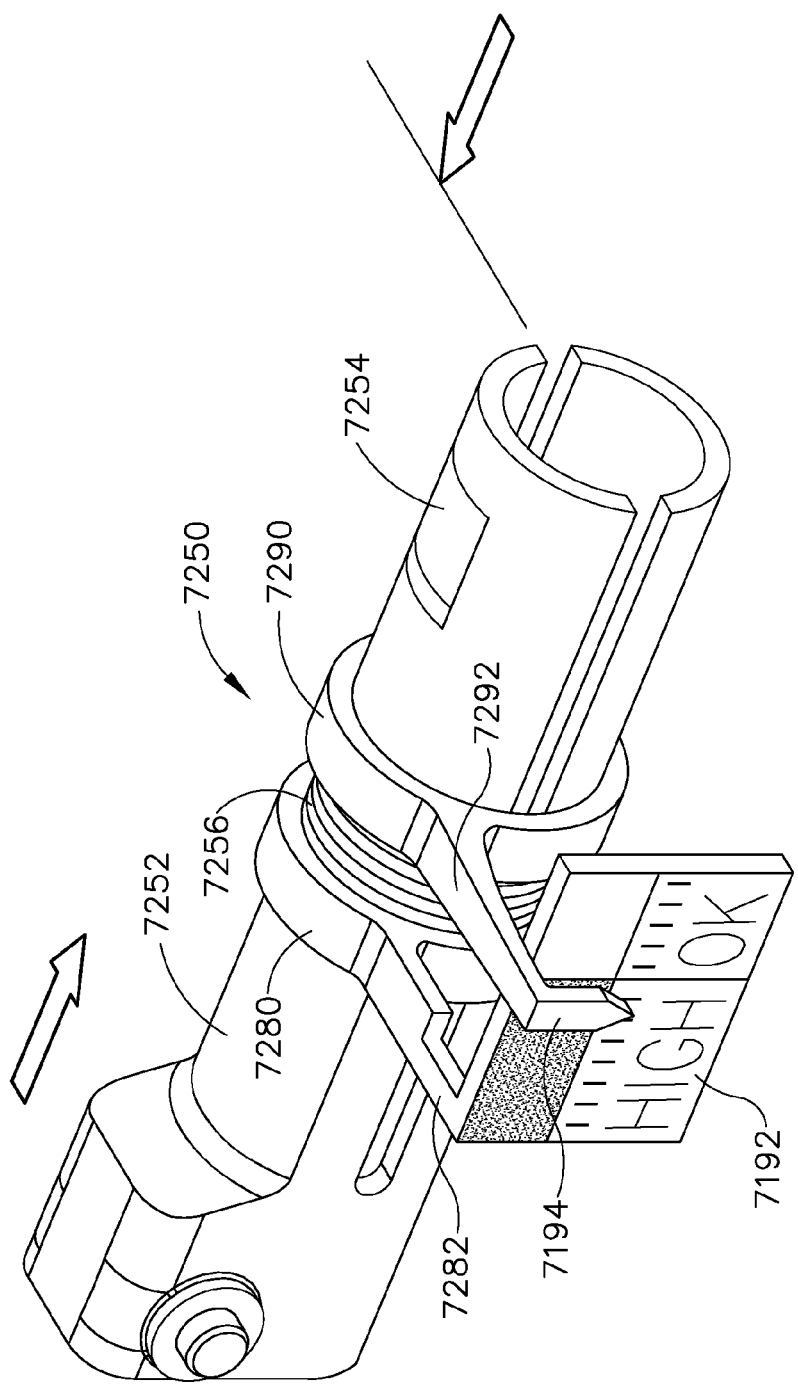
Figure 134:
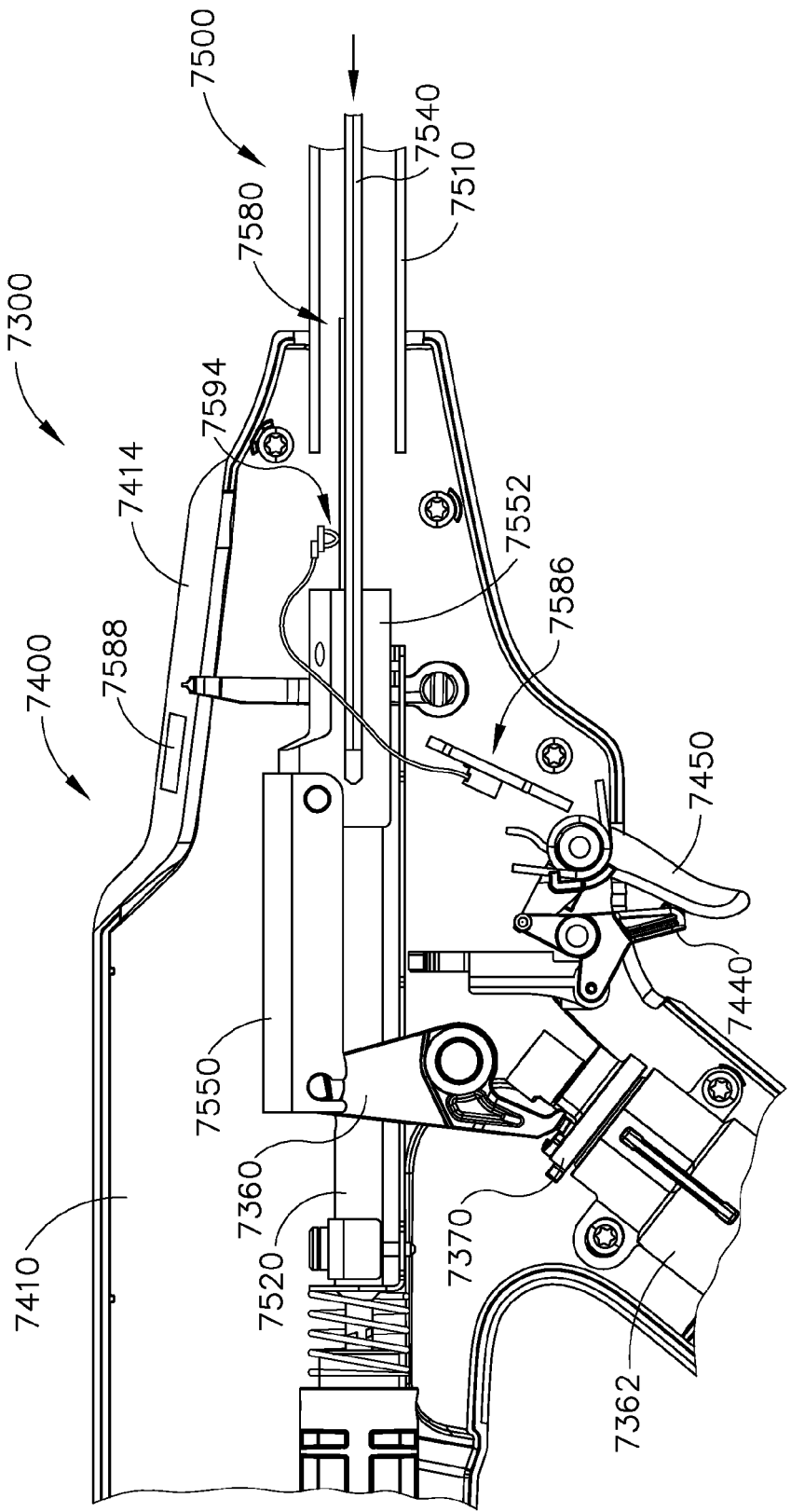
Figure 135:
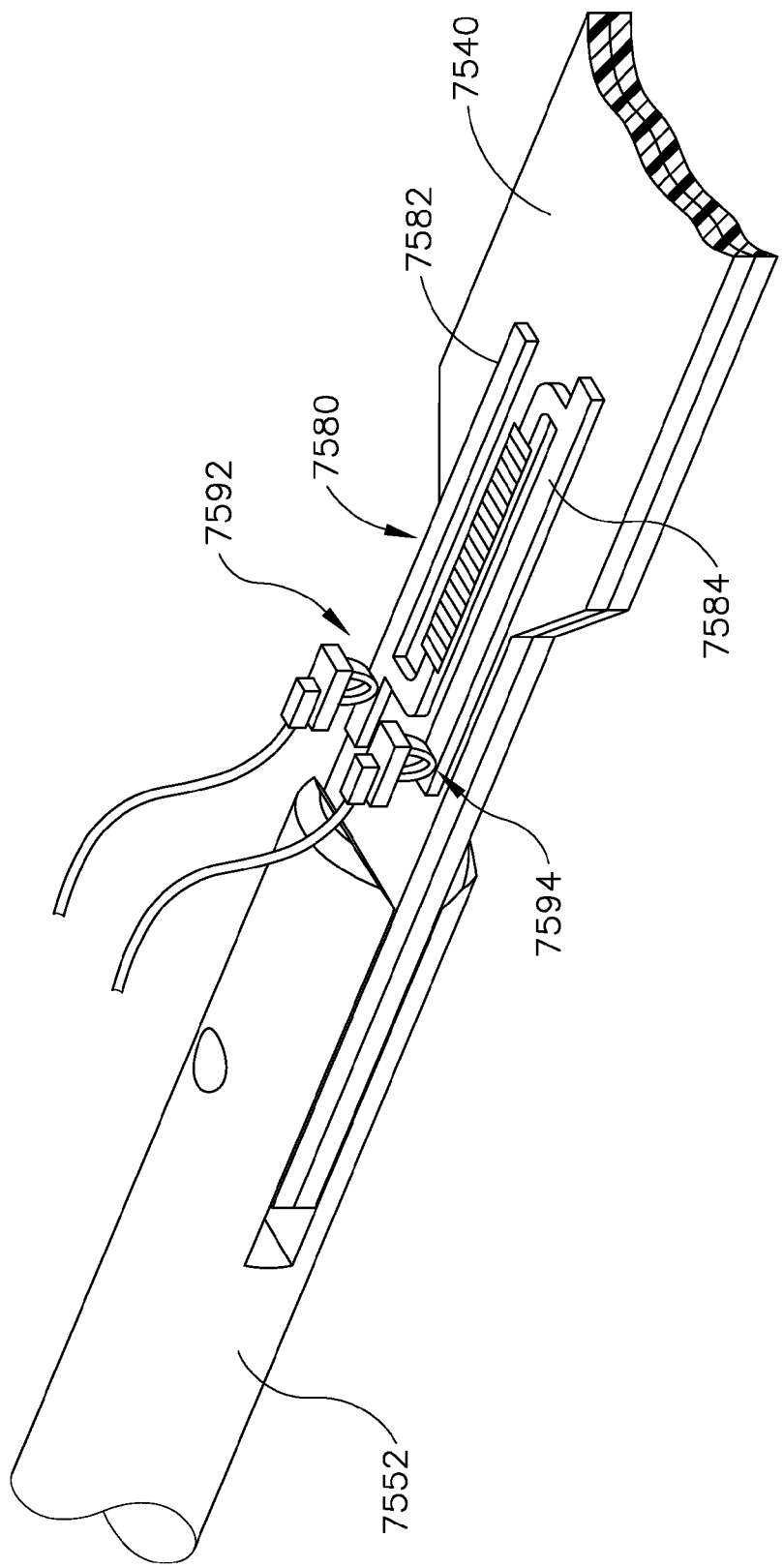
Figure 136:
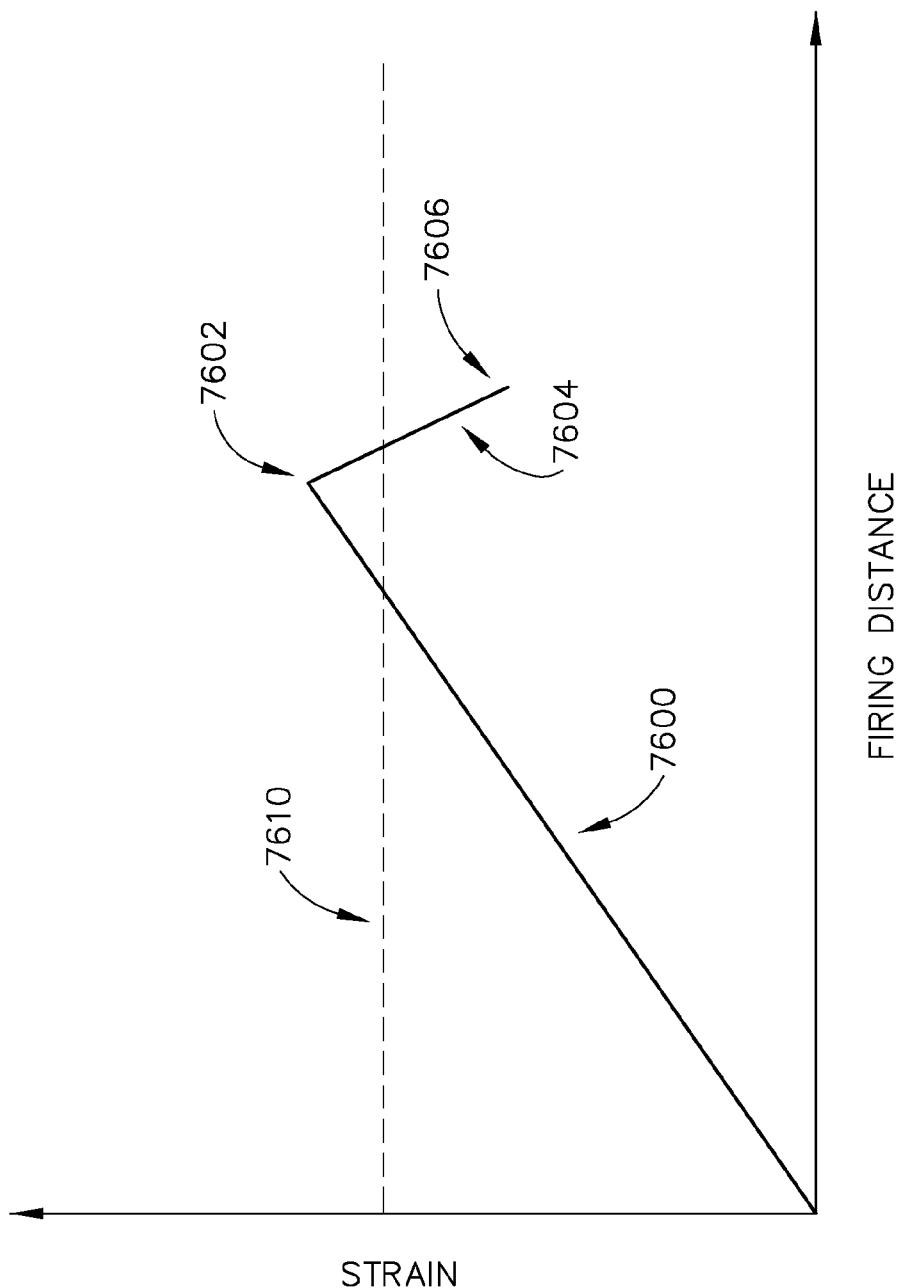
Figure 137A:
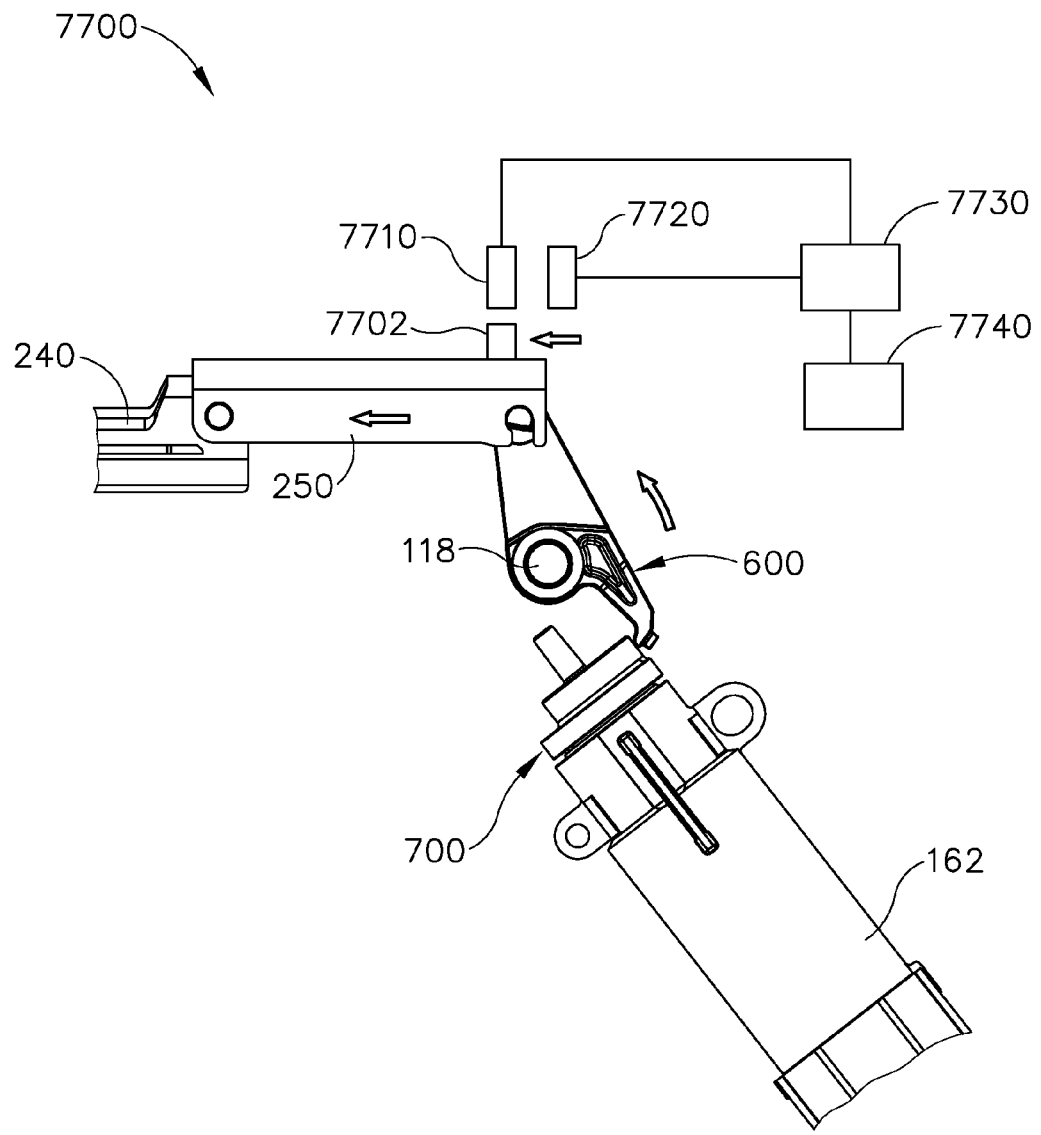
Figure 137B:
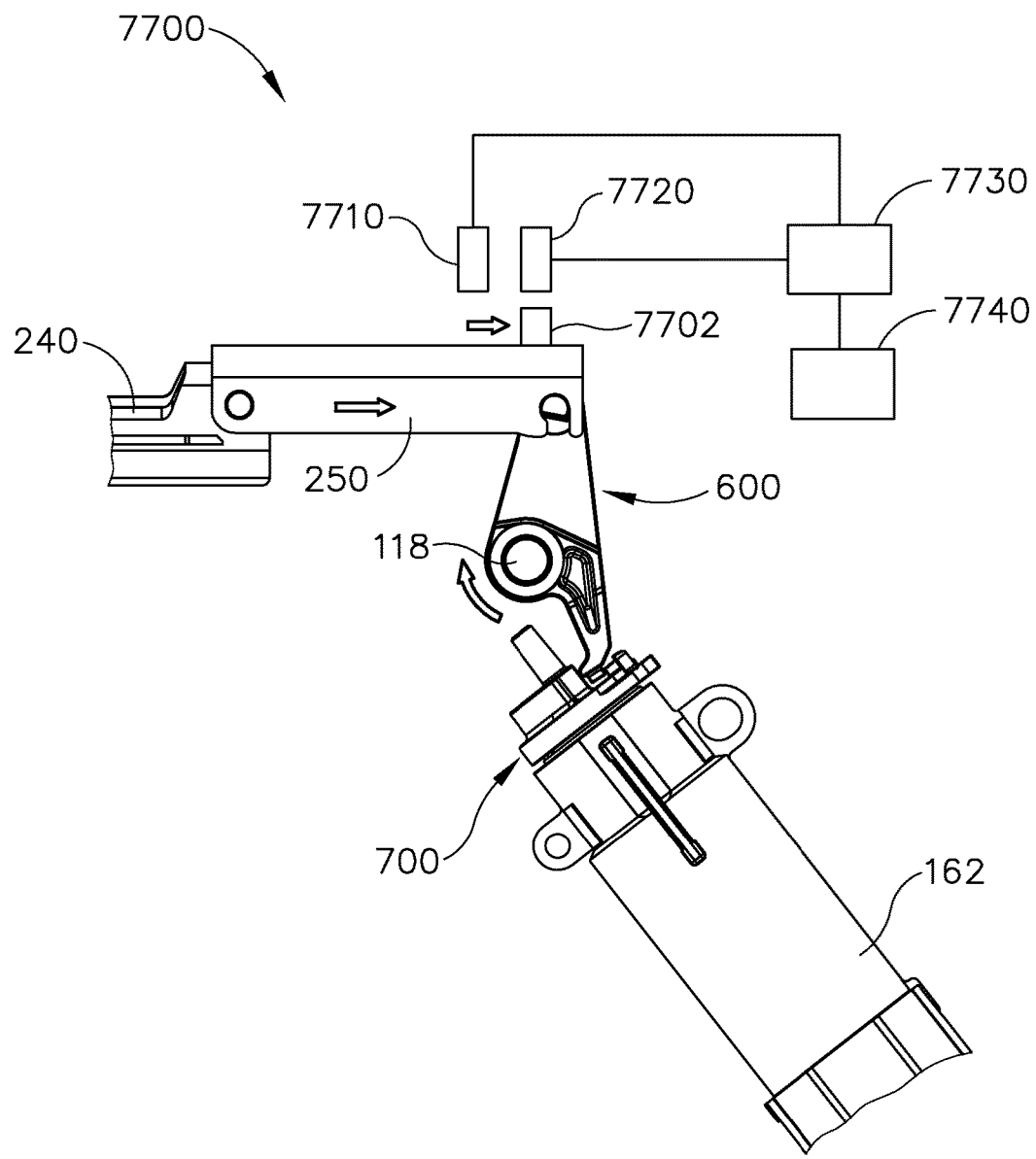
Figure 138:
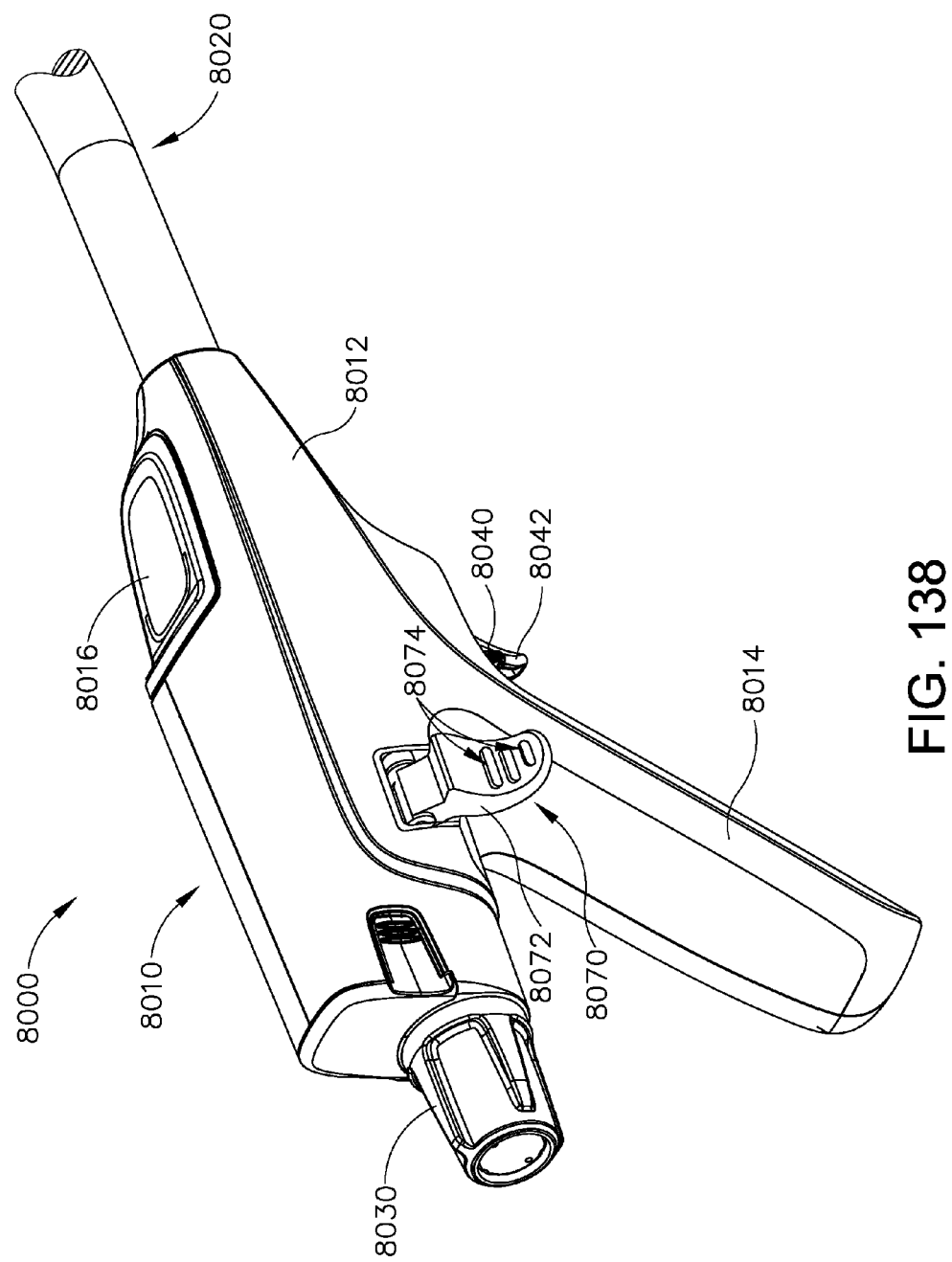
Figure 139:
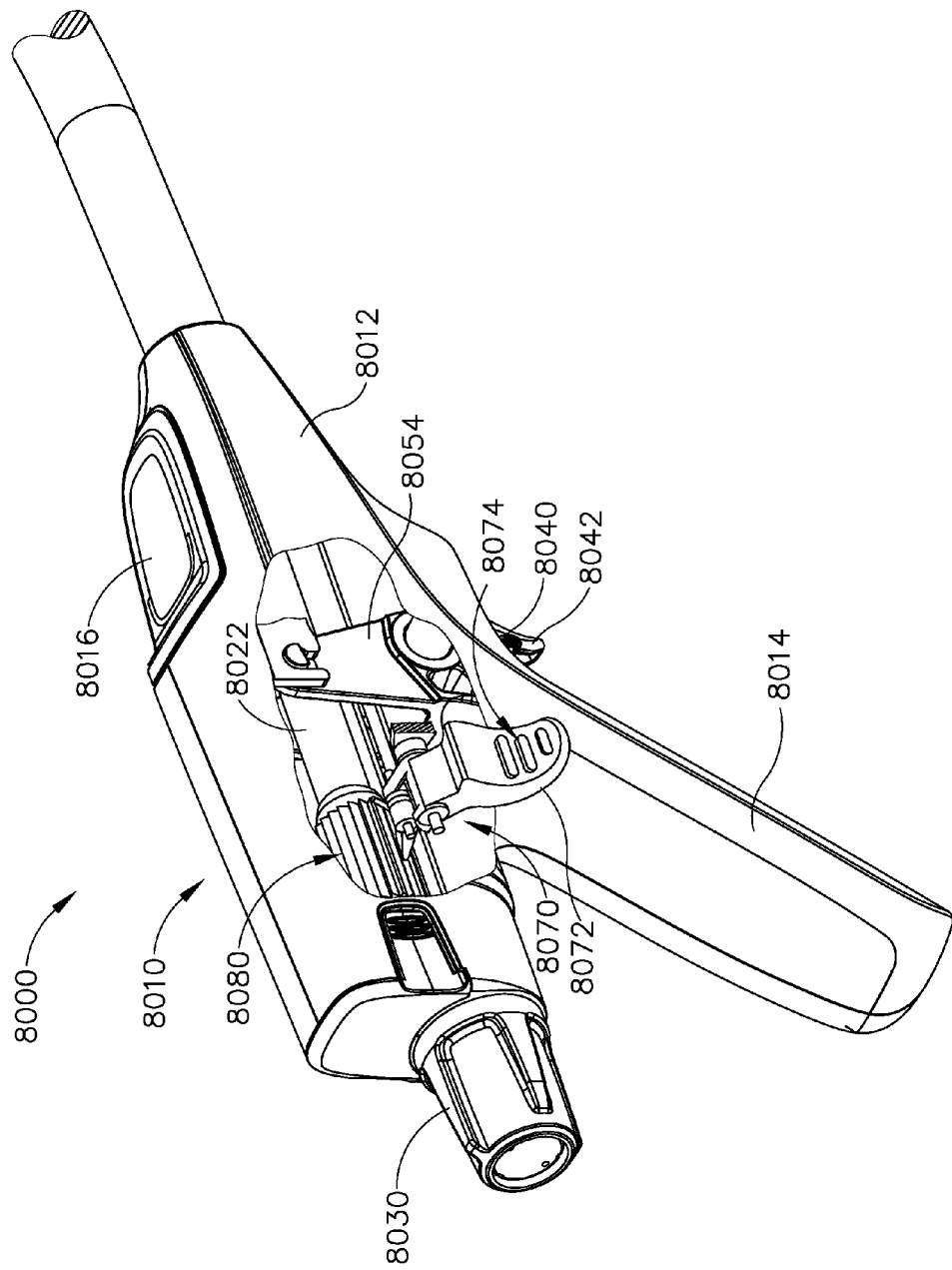
Figure 140:
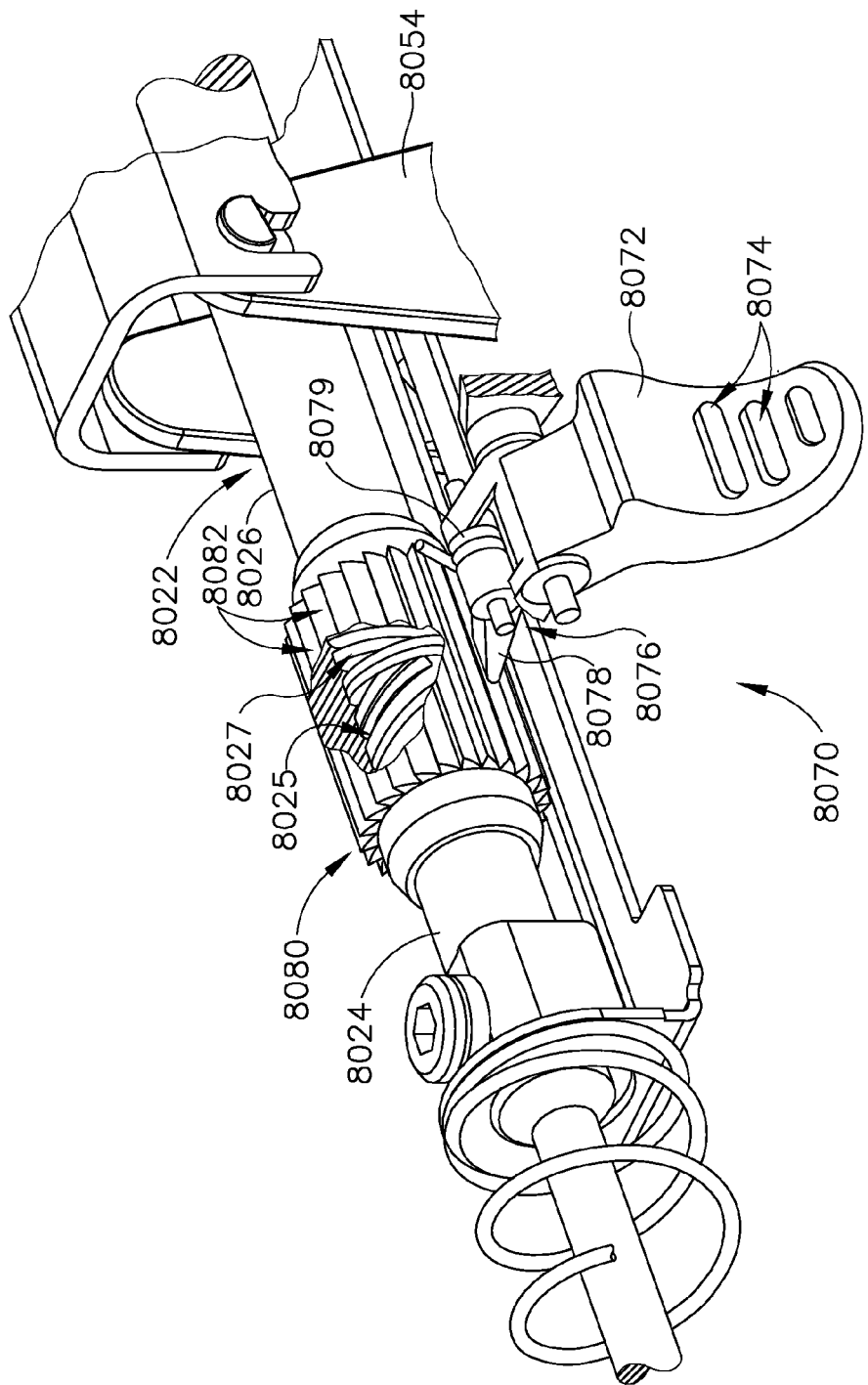
Figure 141:
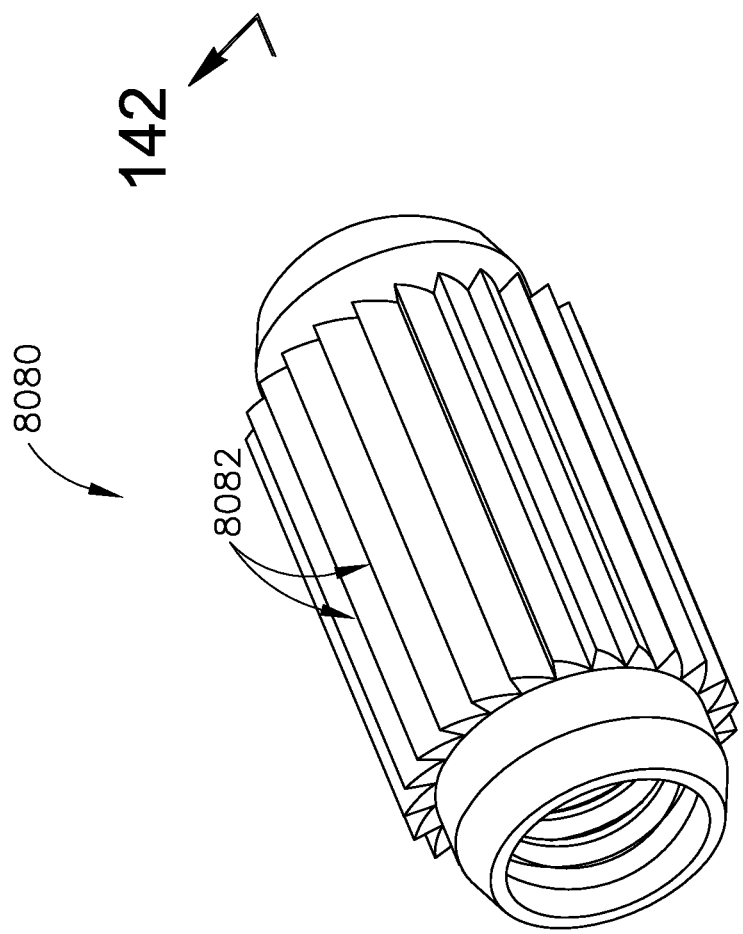
Figure 142:
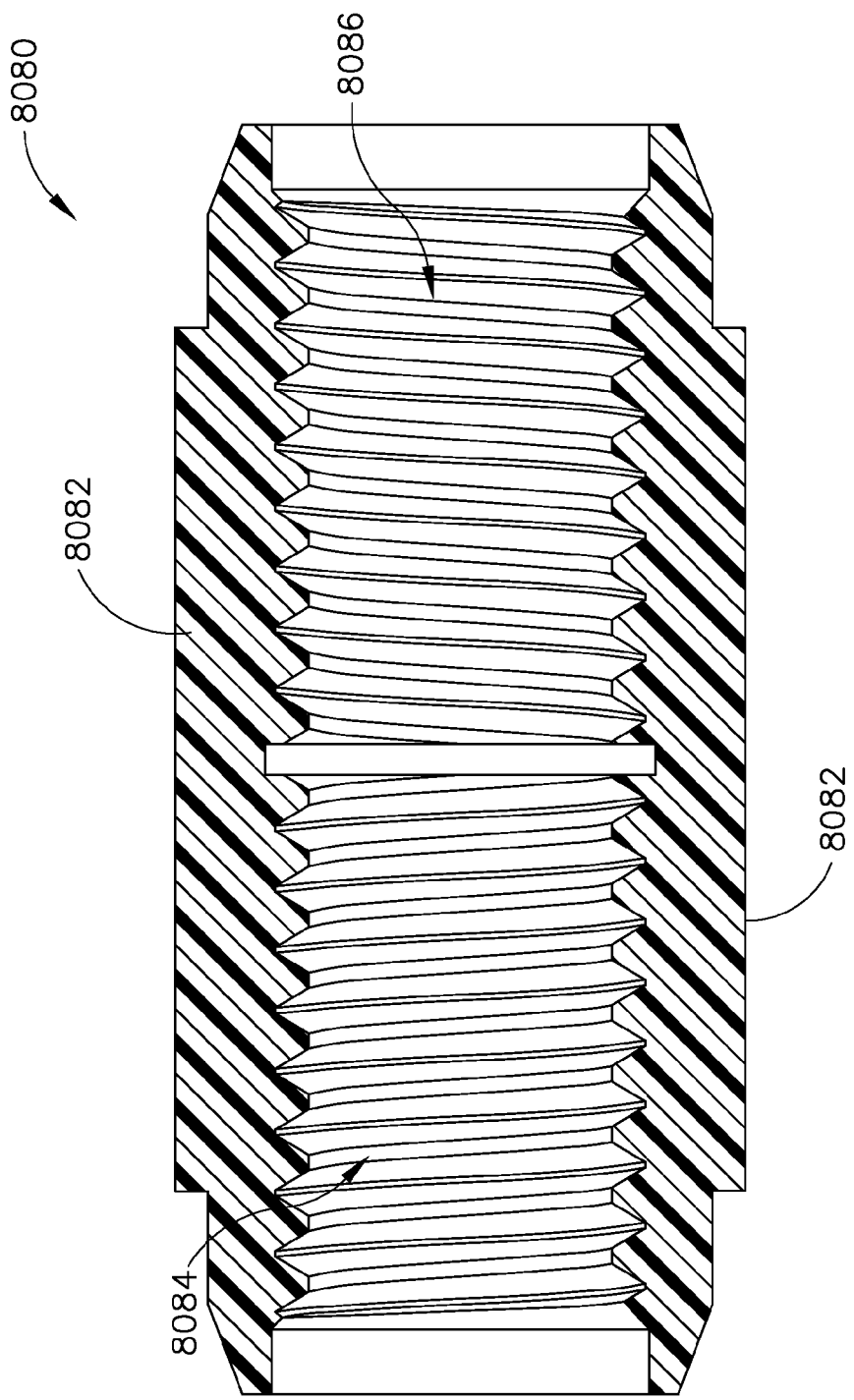
Figure 143:
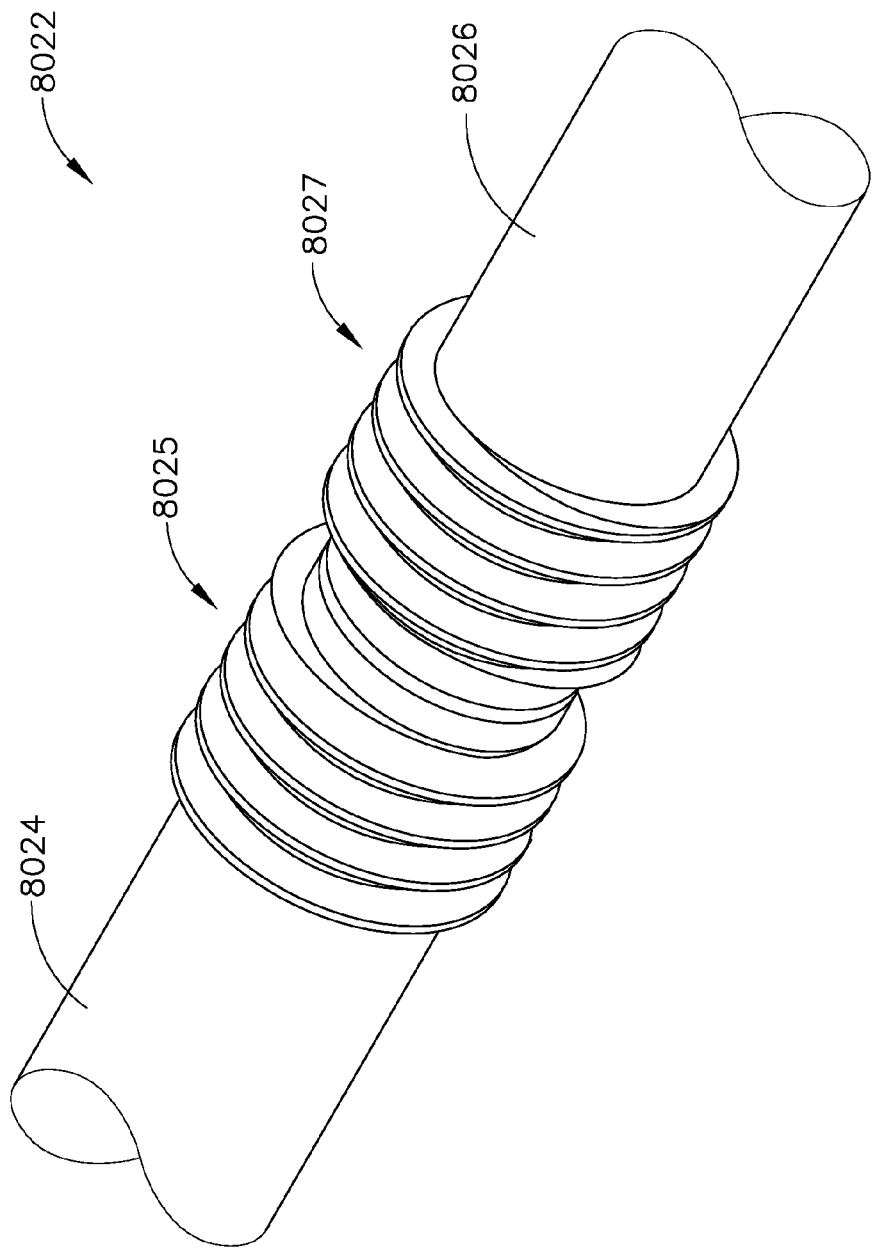
Figure 144:
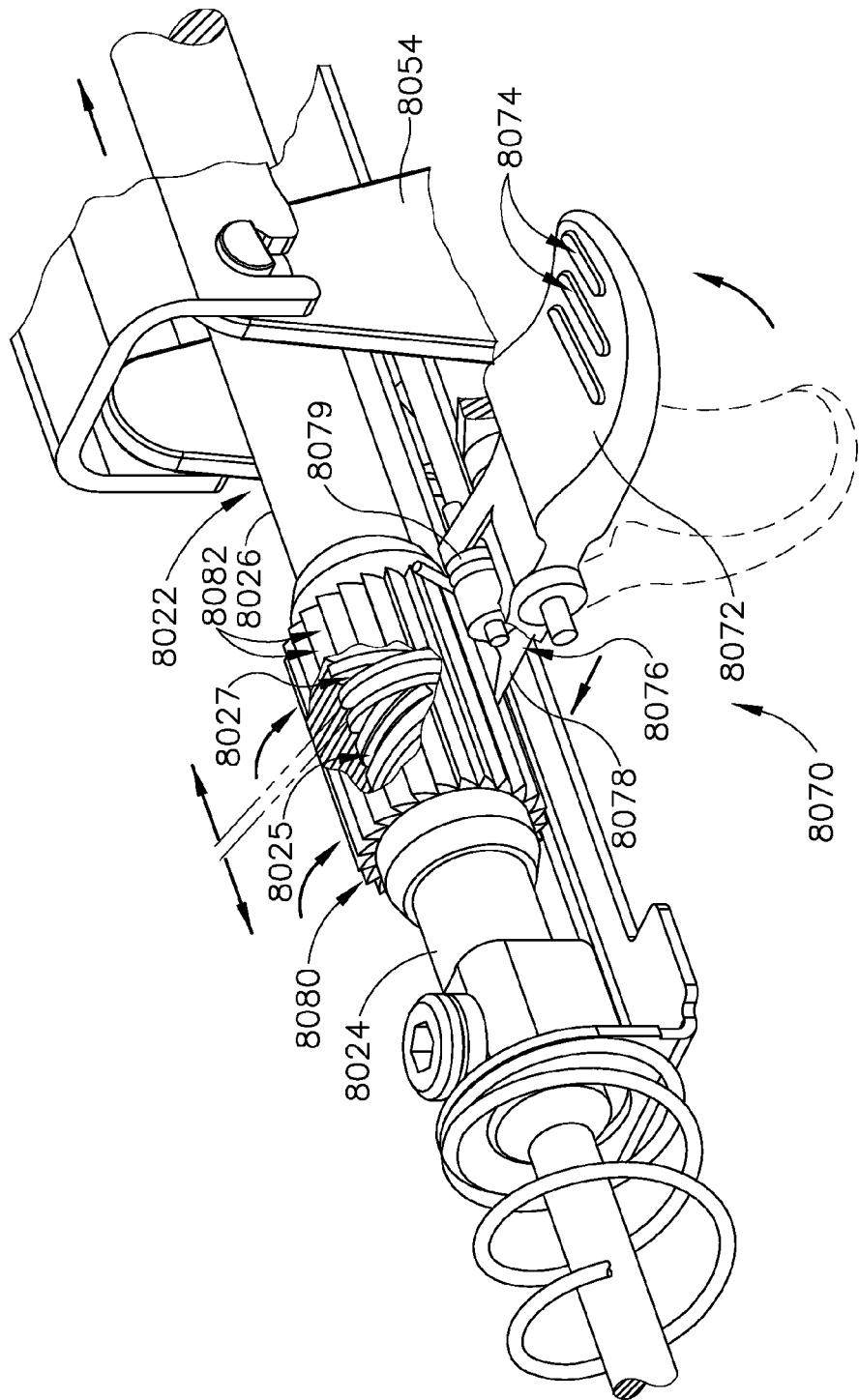
Figure 145:
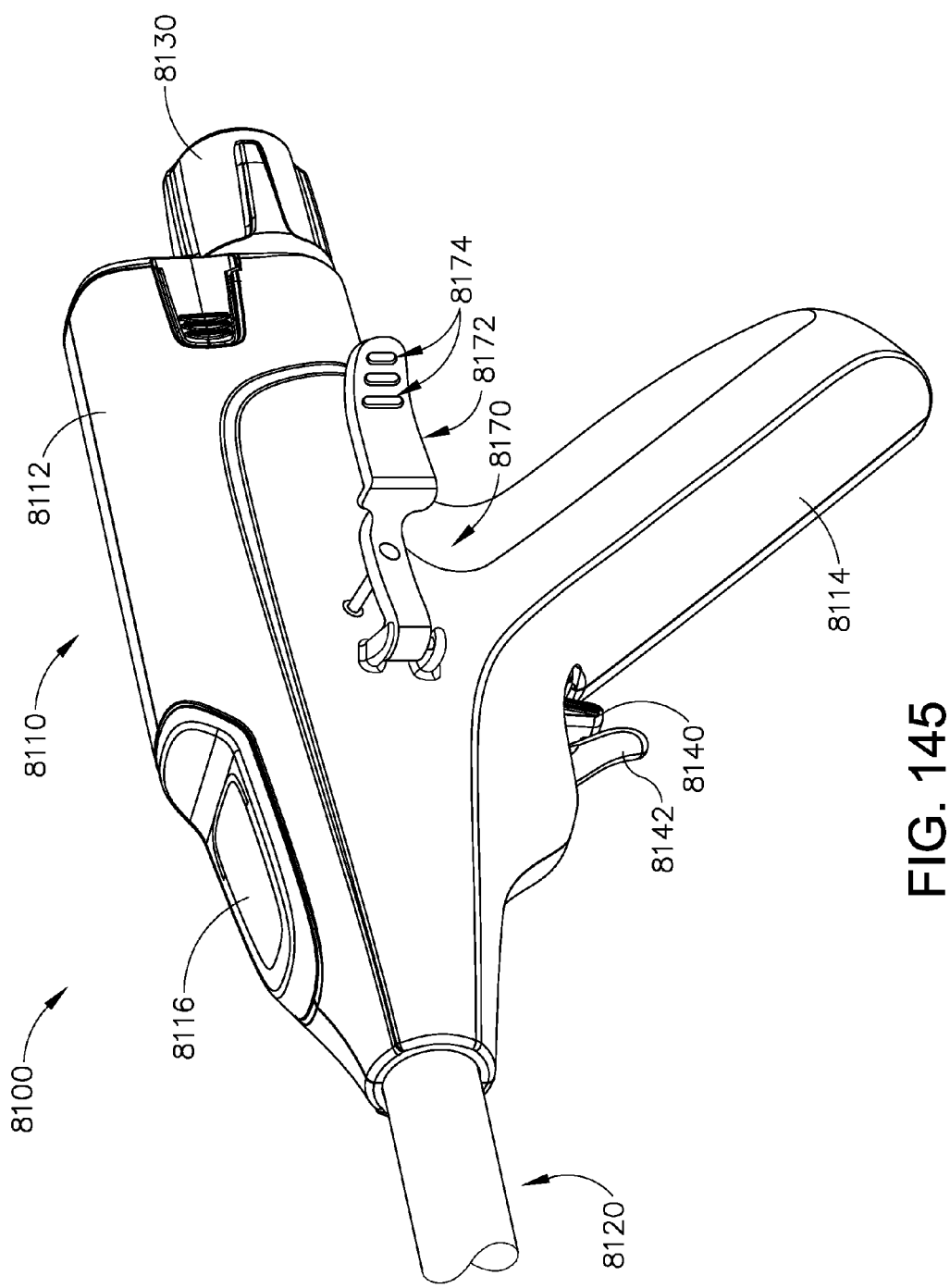
Figure 146:
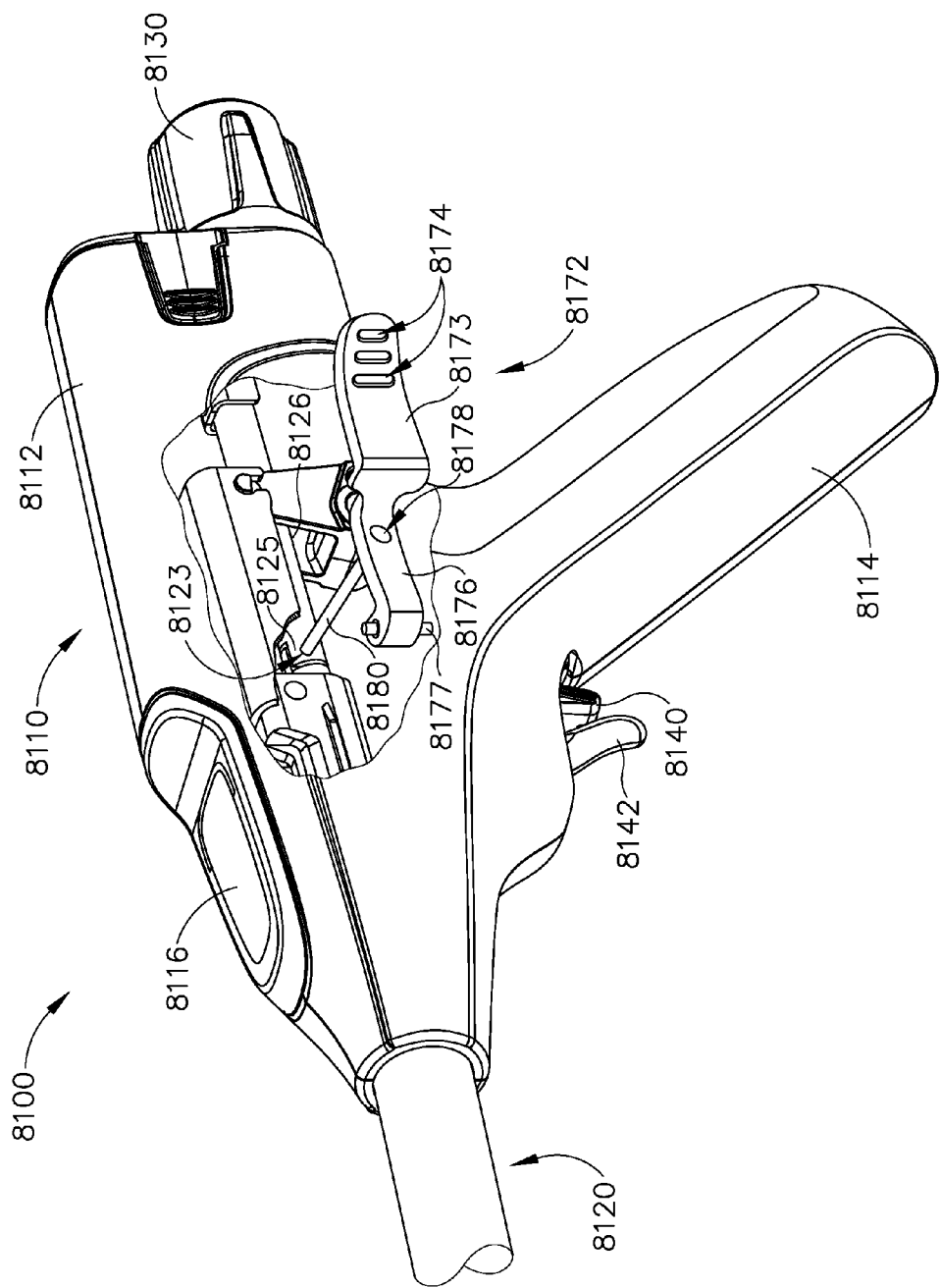
Figure 147:
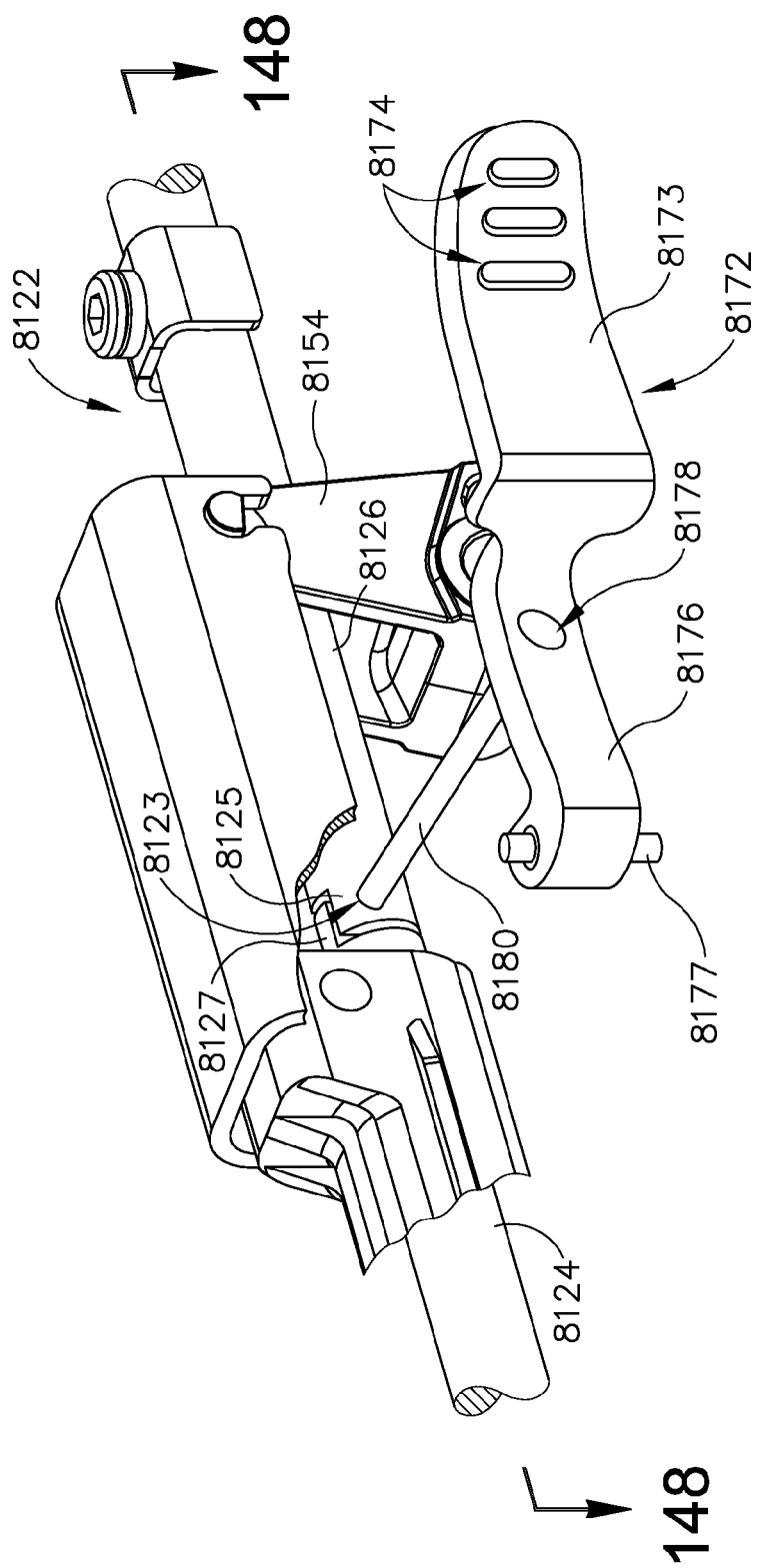
Figure 148:
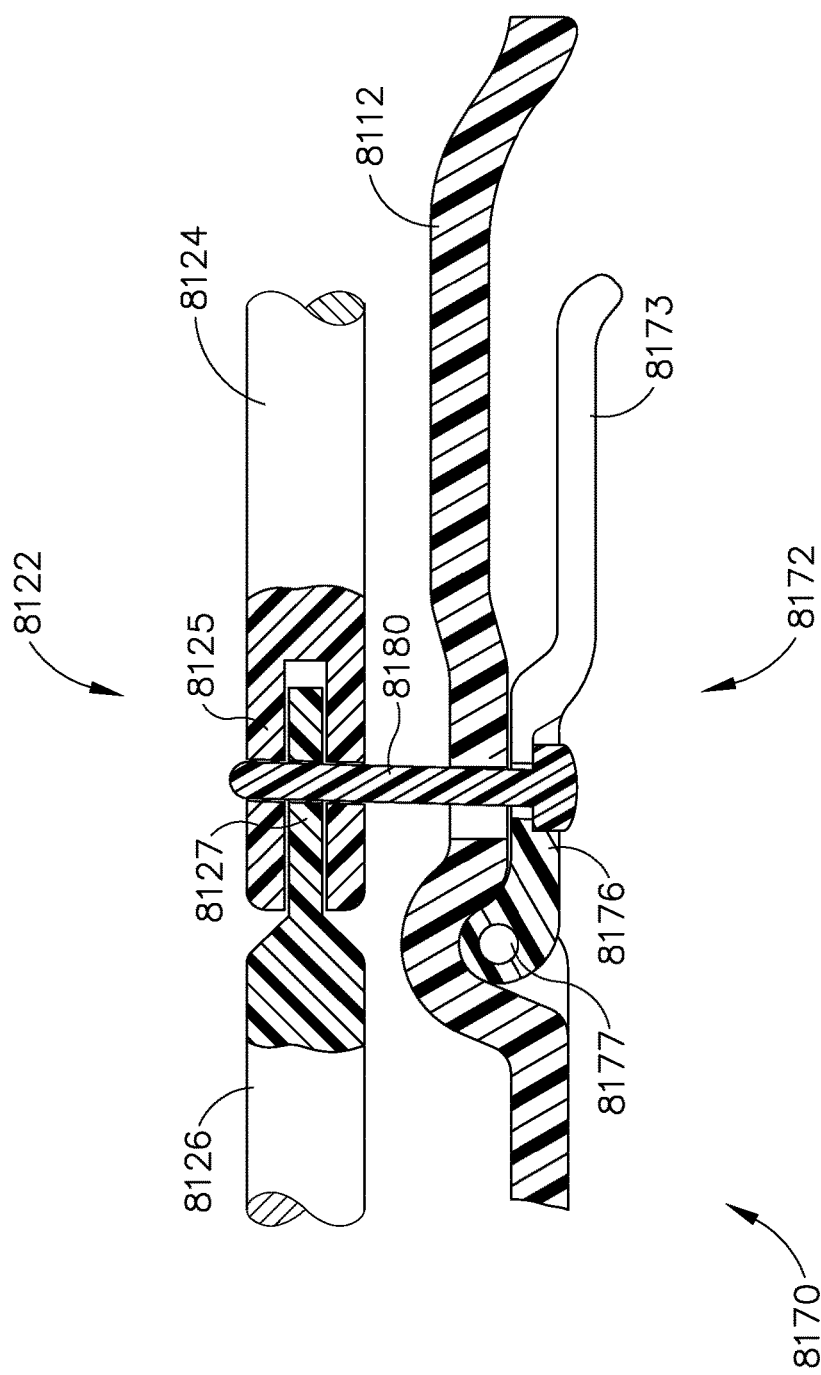
Figure 149:
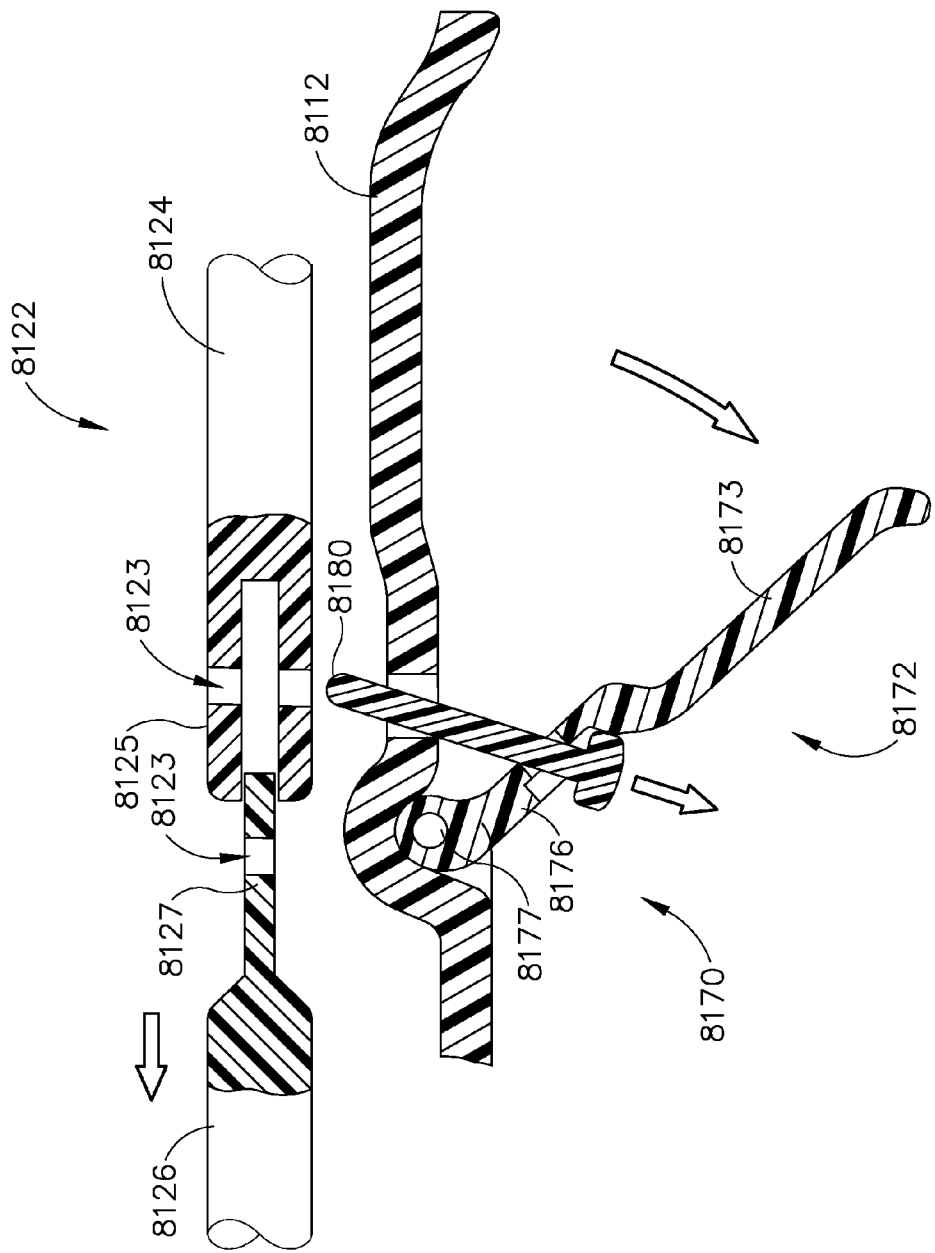
Figure 150:
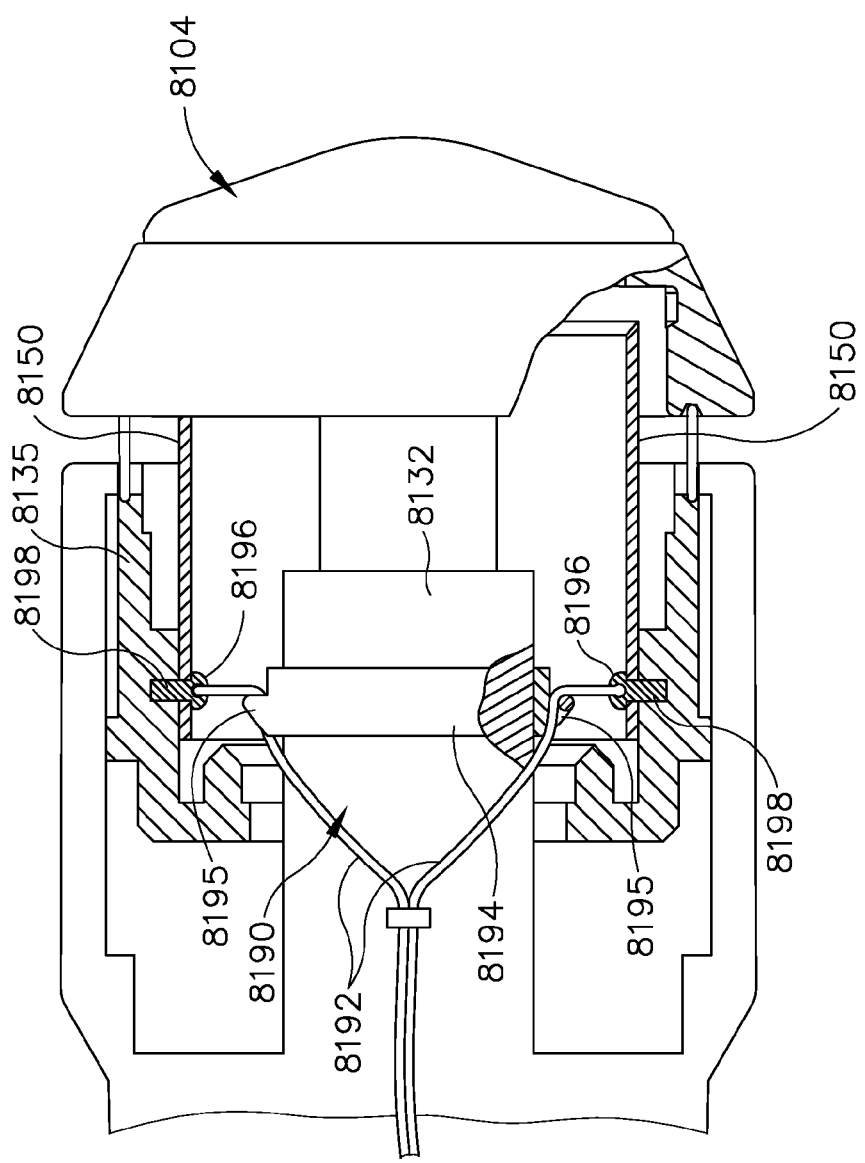
Figure 152:
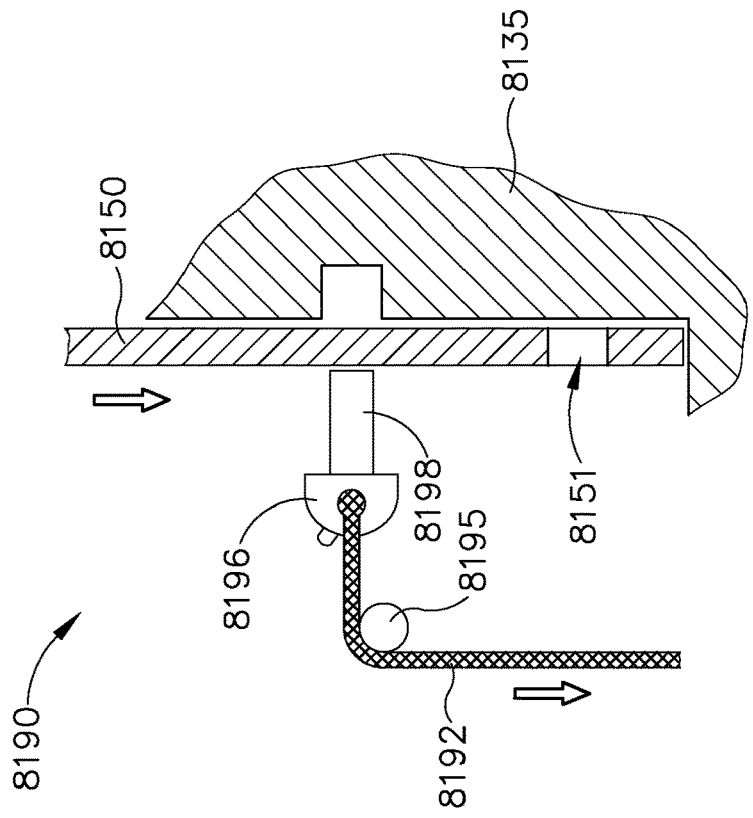
Figure 151:
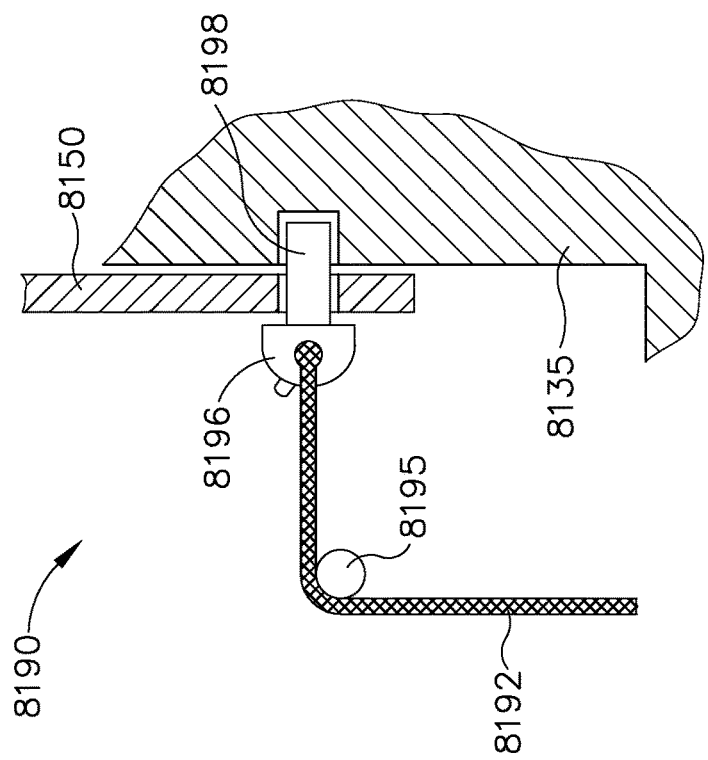
Figure 153:
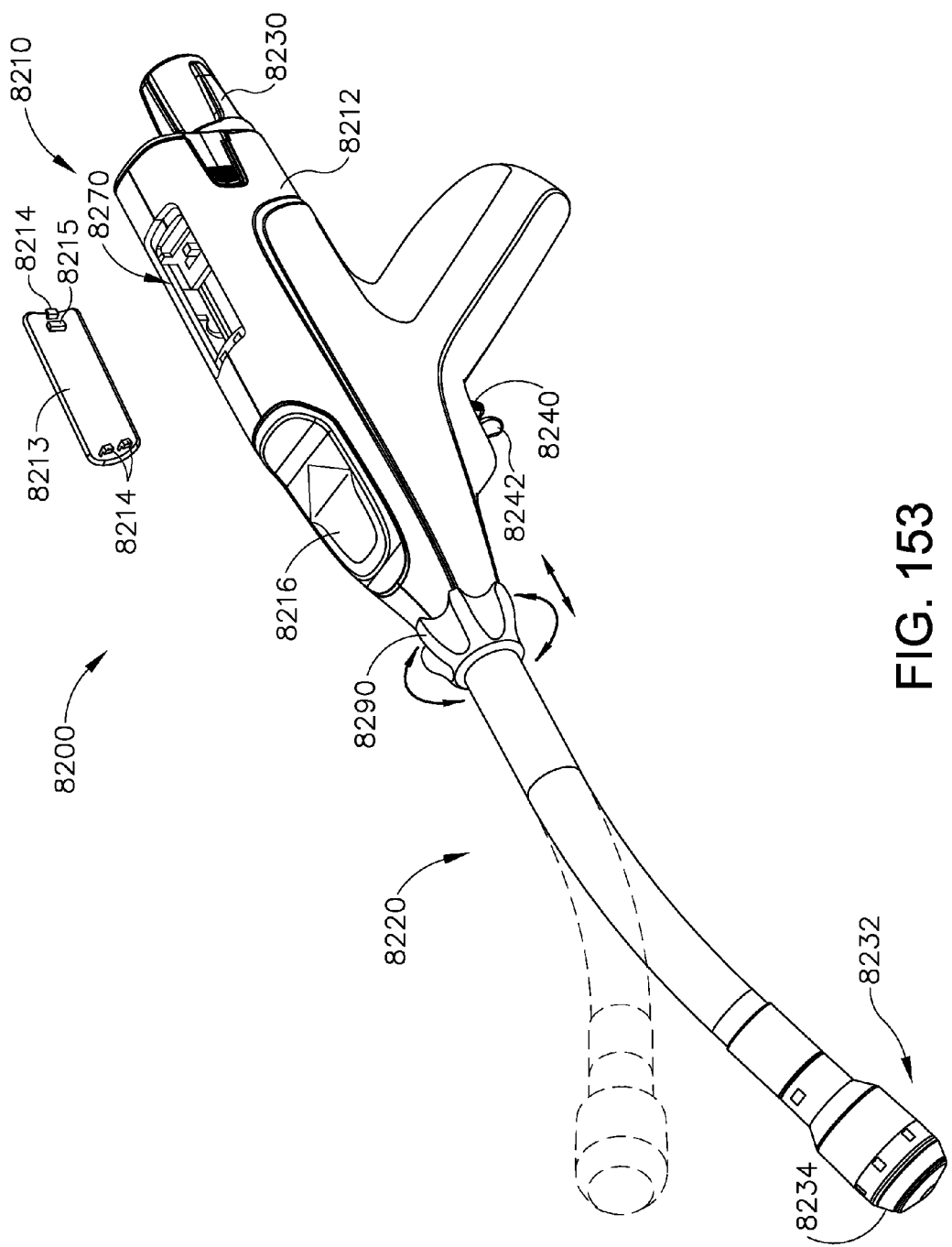
Figure 154:
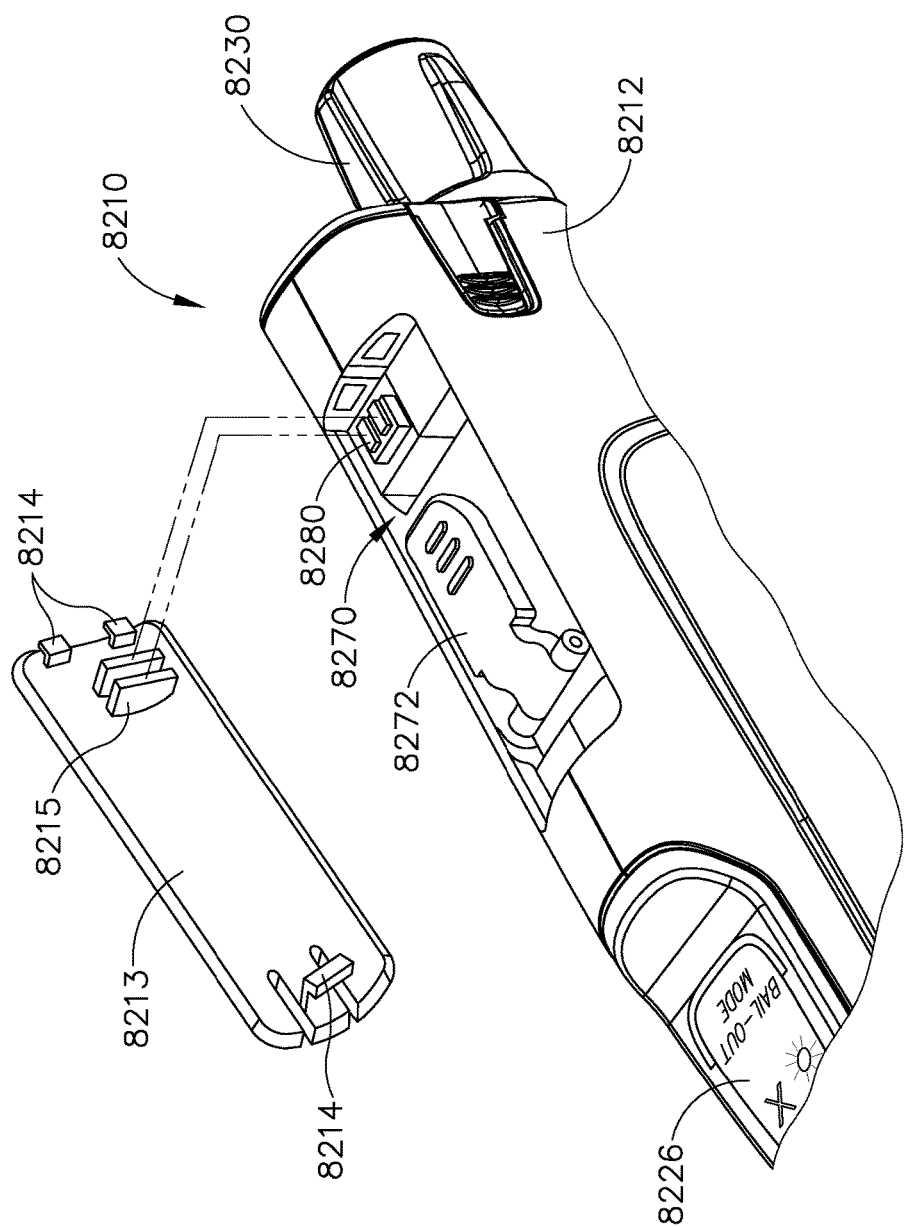
Figure 155:
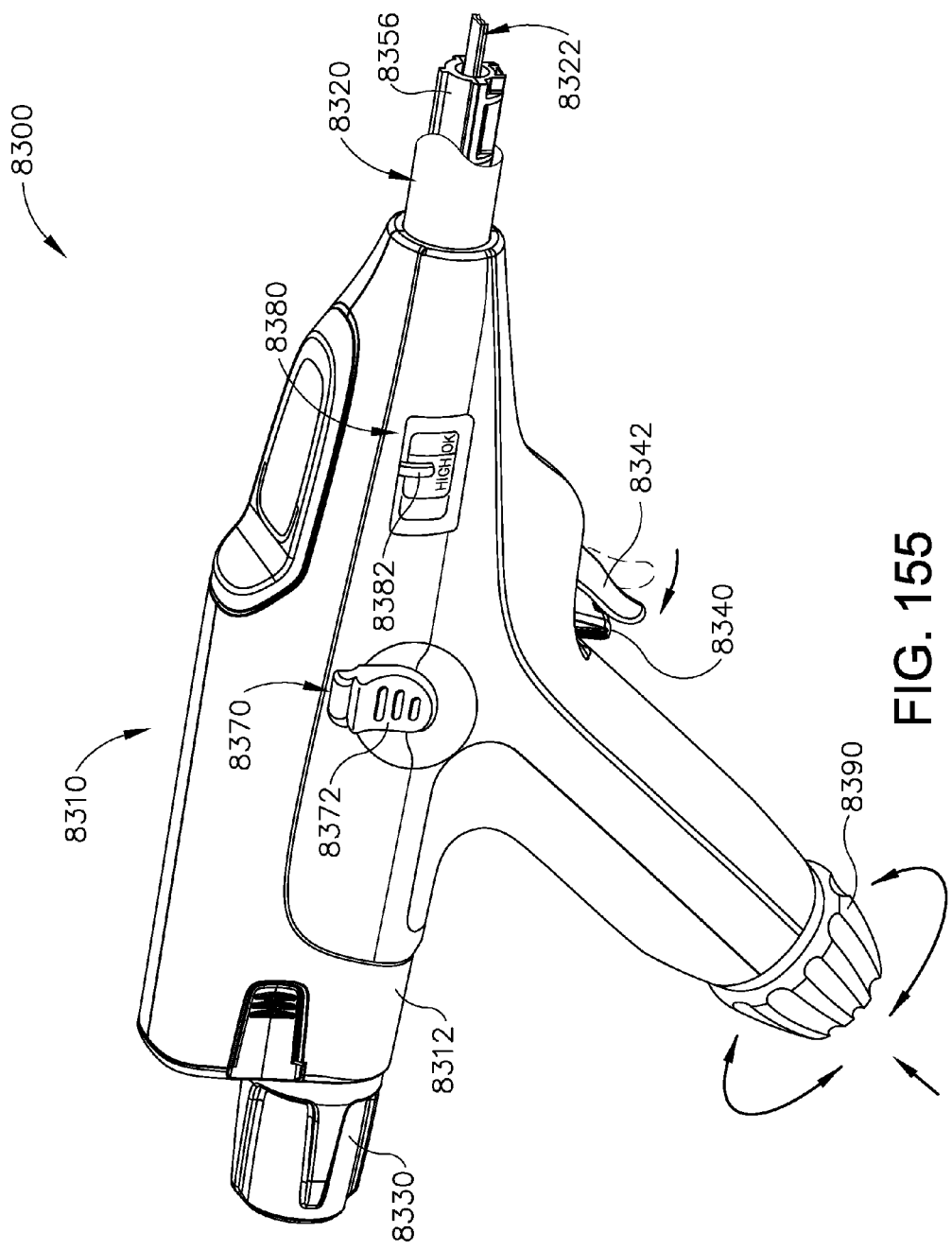
Figure 156:
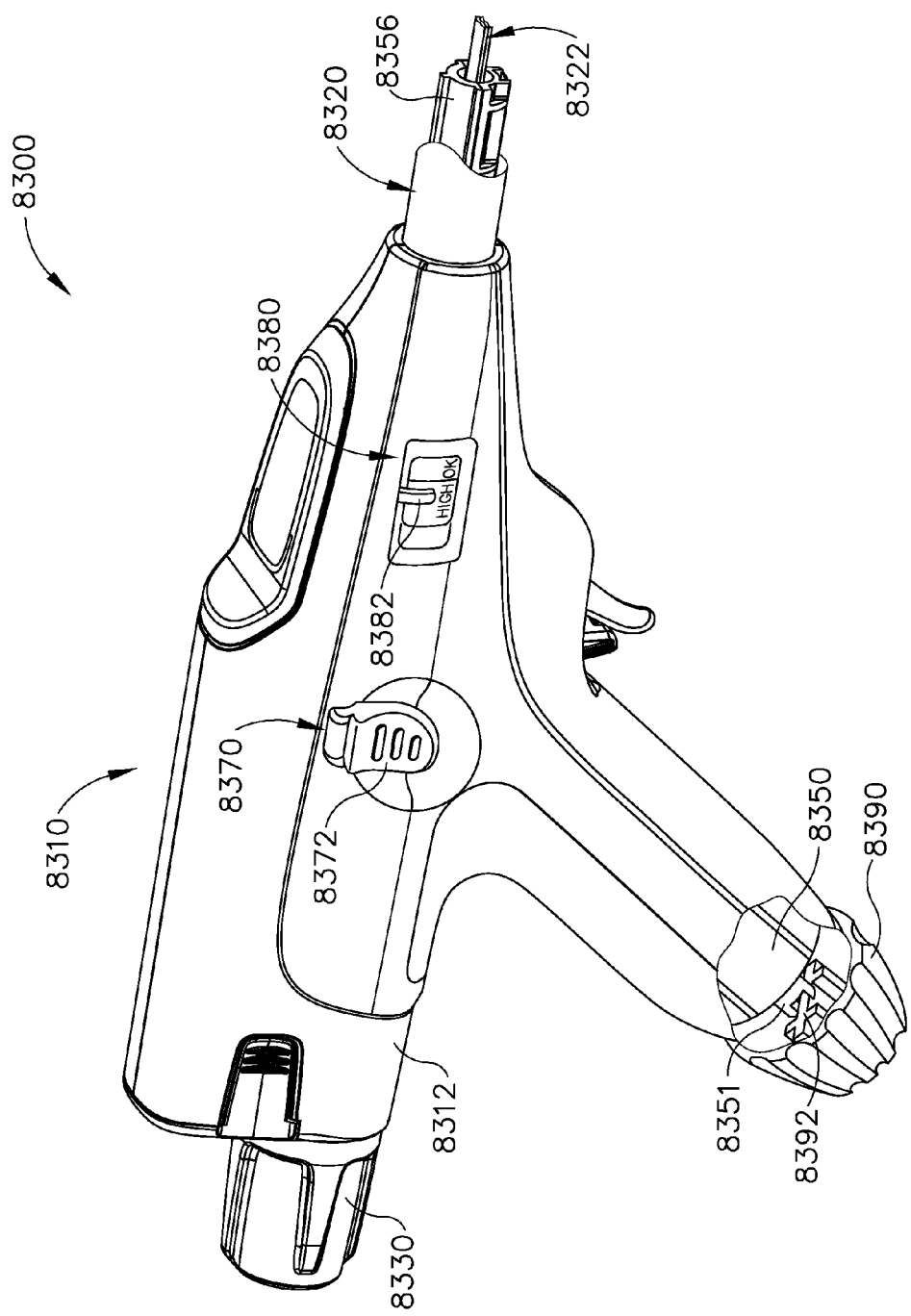
Figure 157:
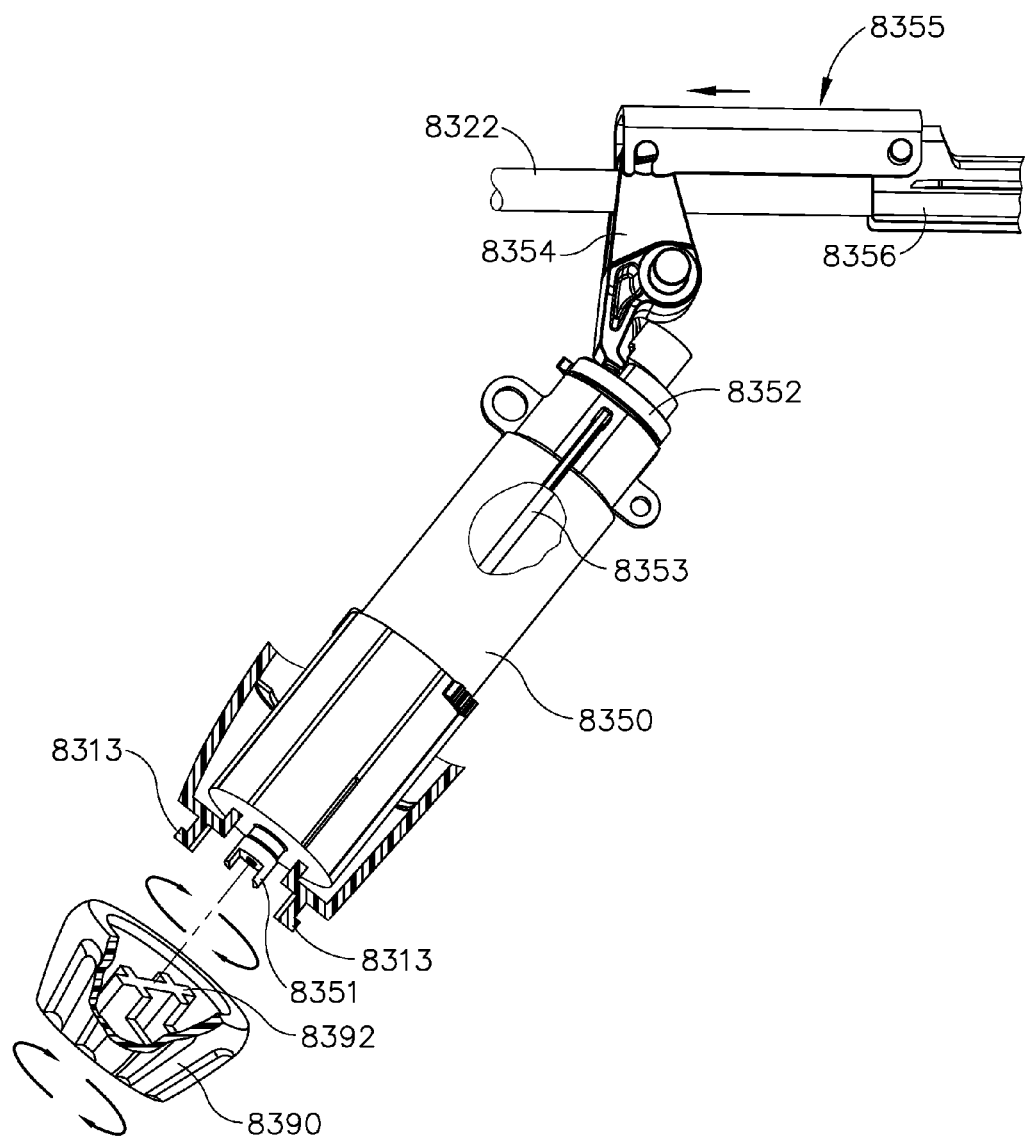
Figure 158:
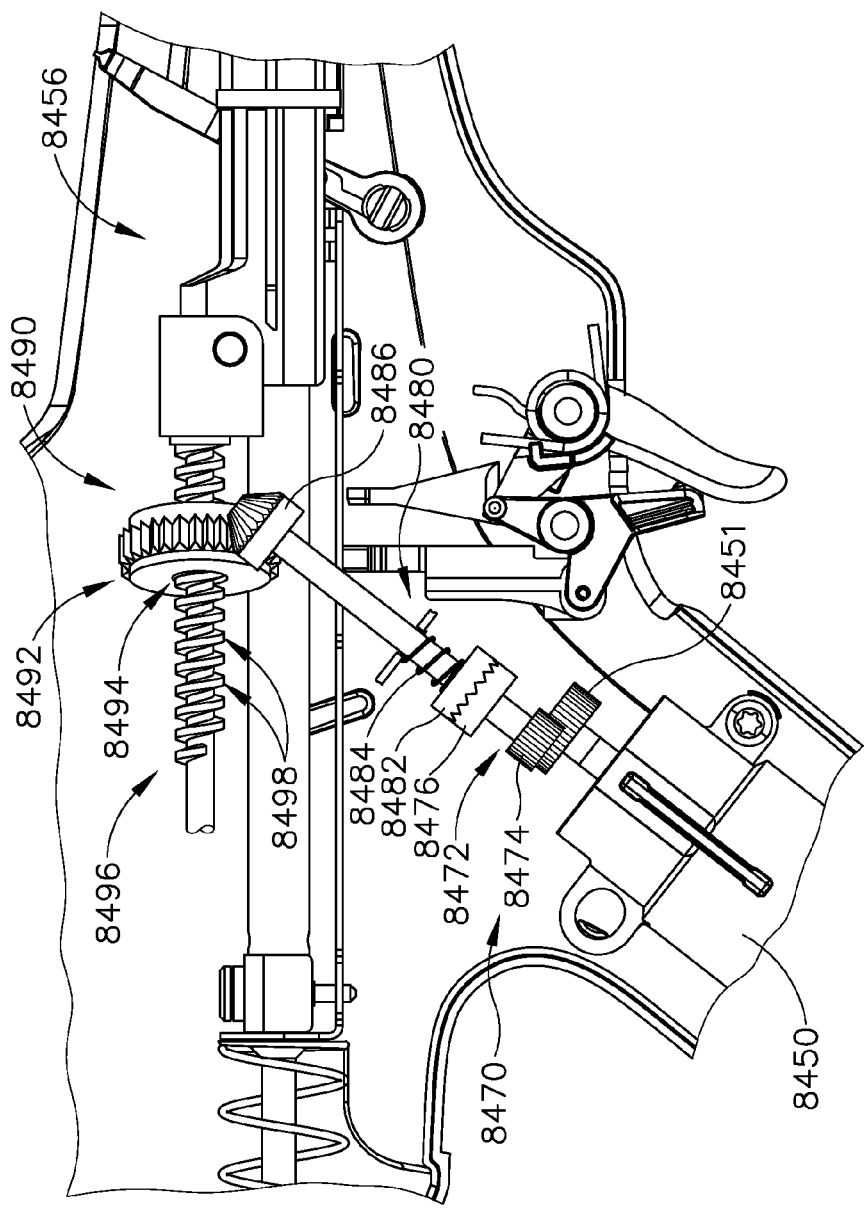
Figure 160:
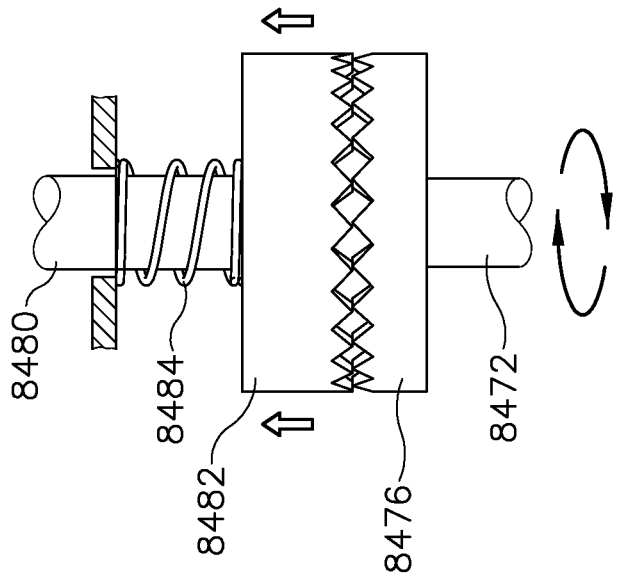
Figure 159:
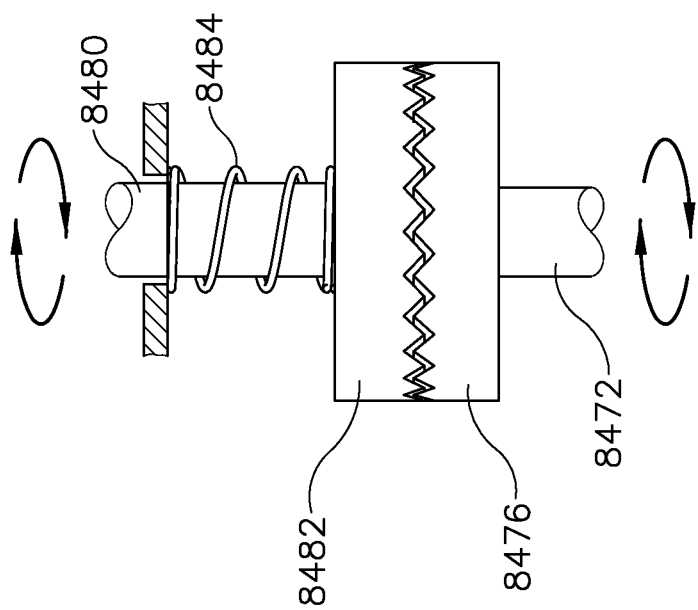
Figure 161:
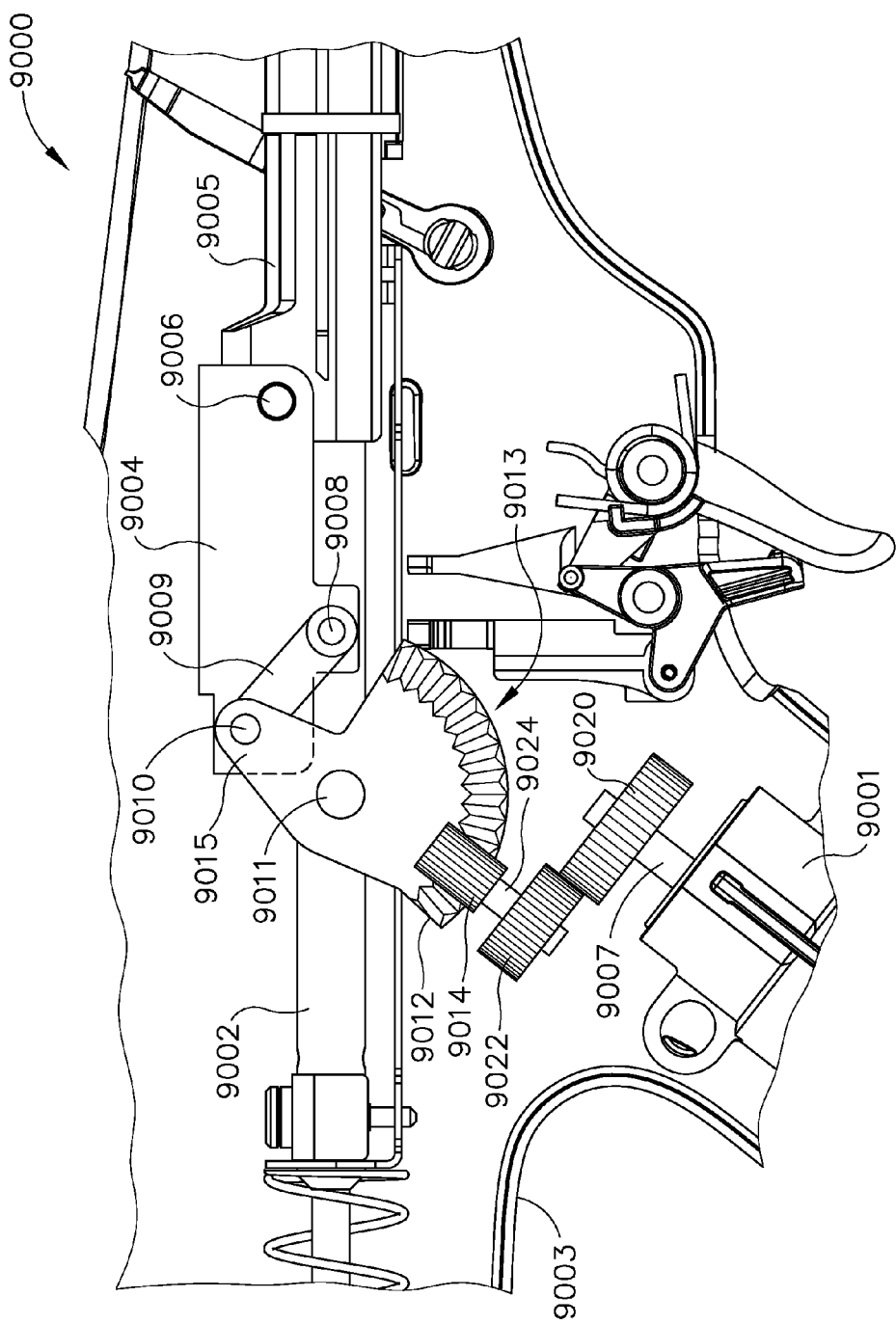
Figure 162A:
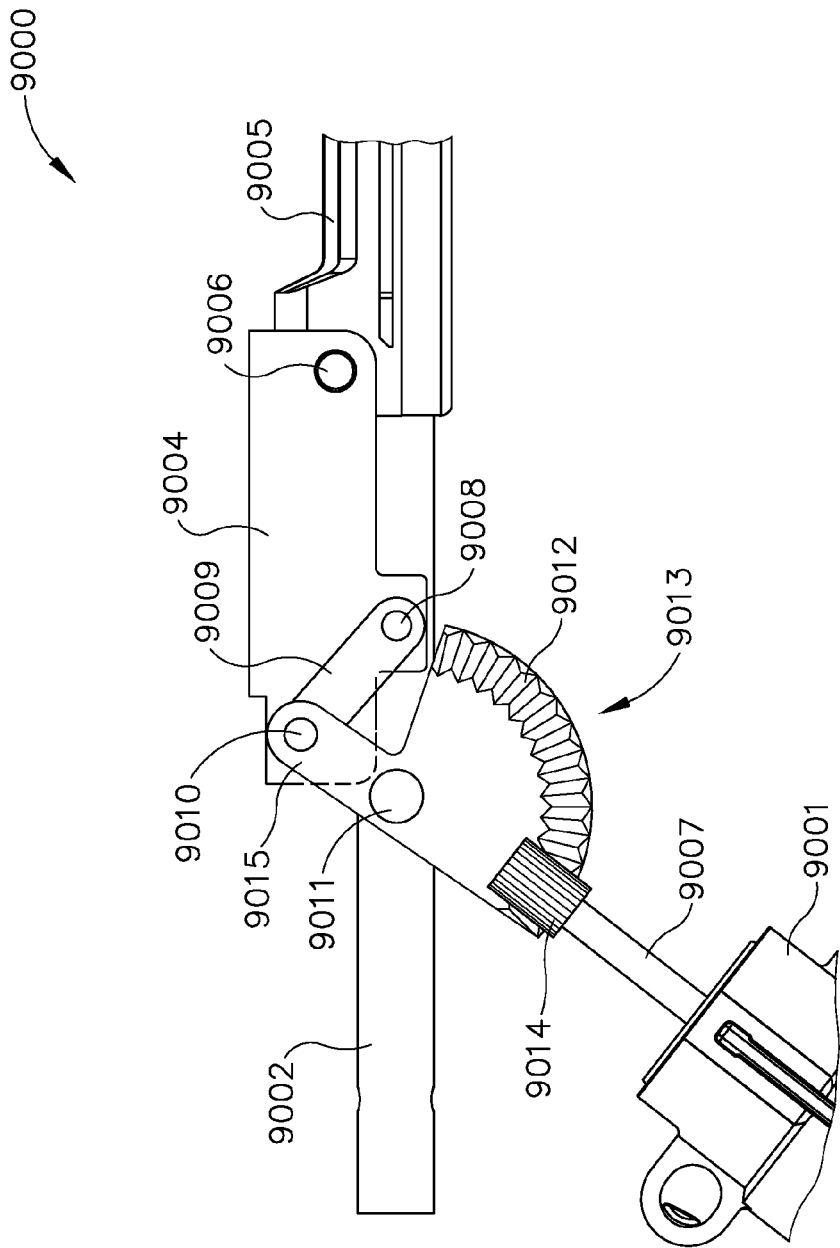
Figure 162B:
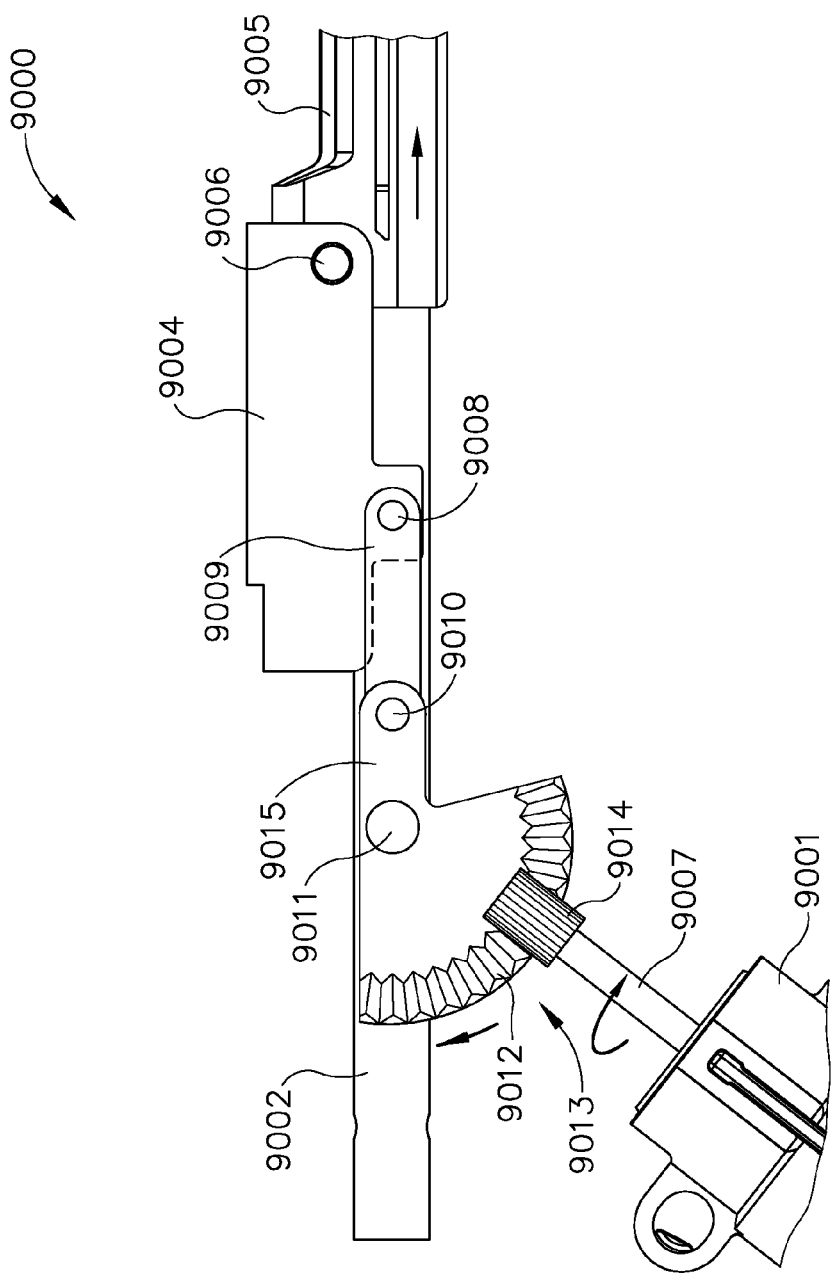
Figure 162C:
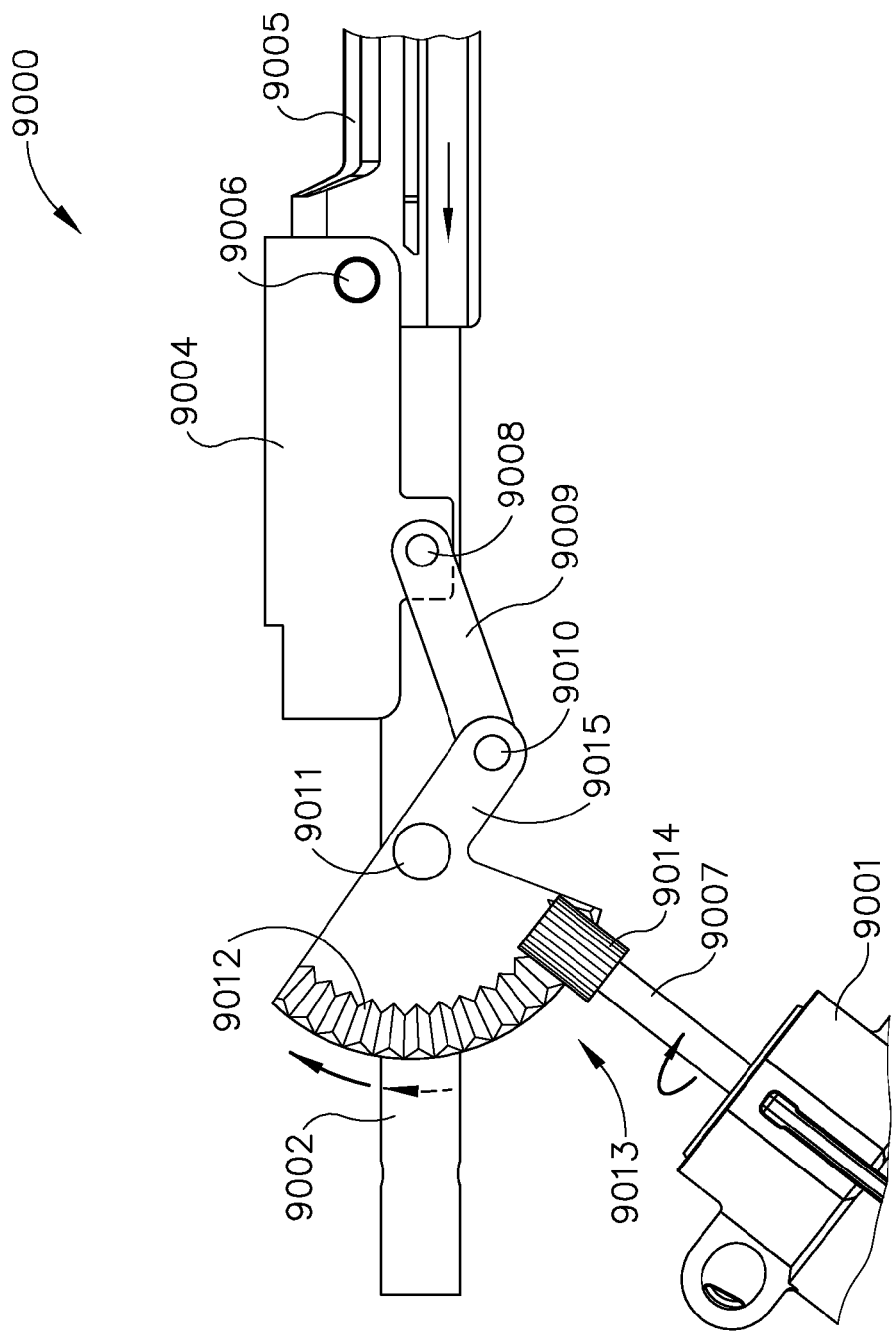
Figure 163A:
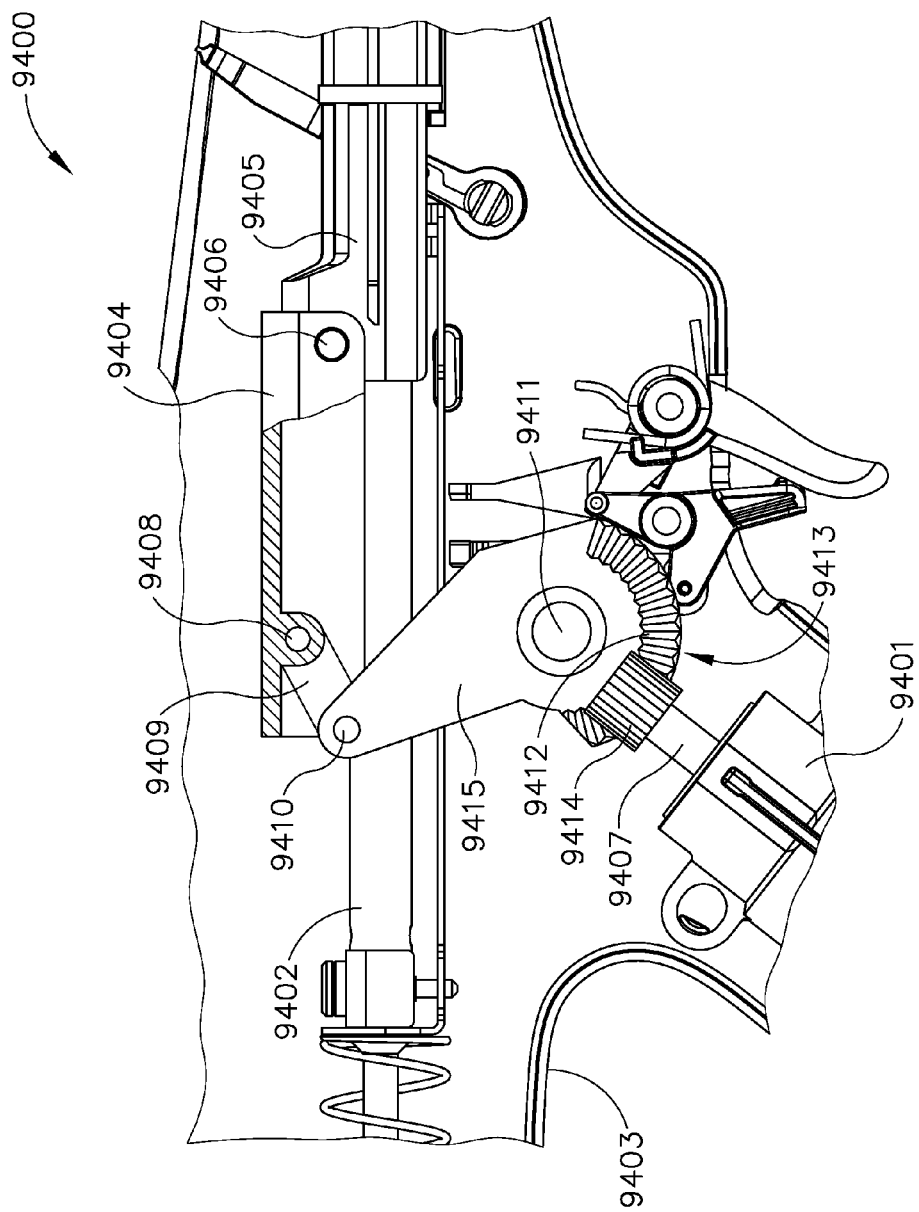
Figure 163B:
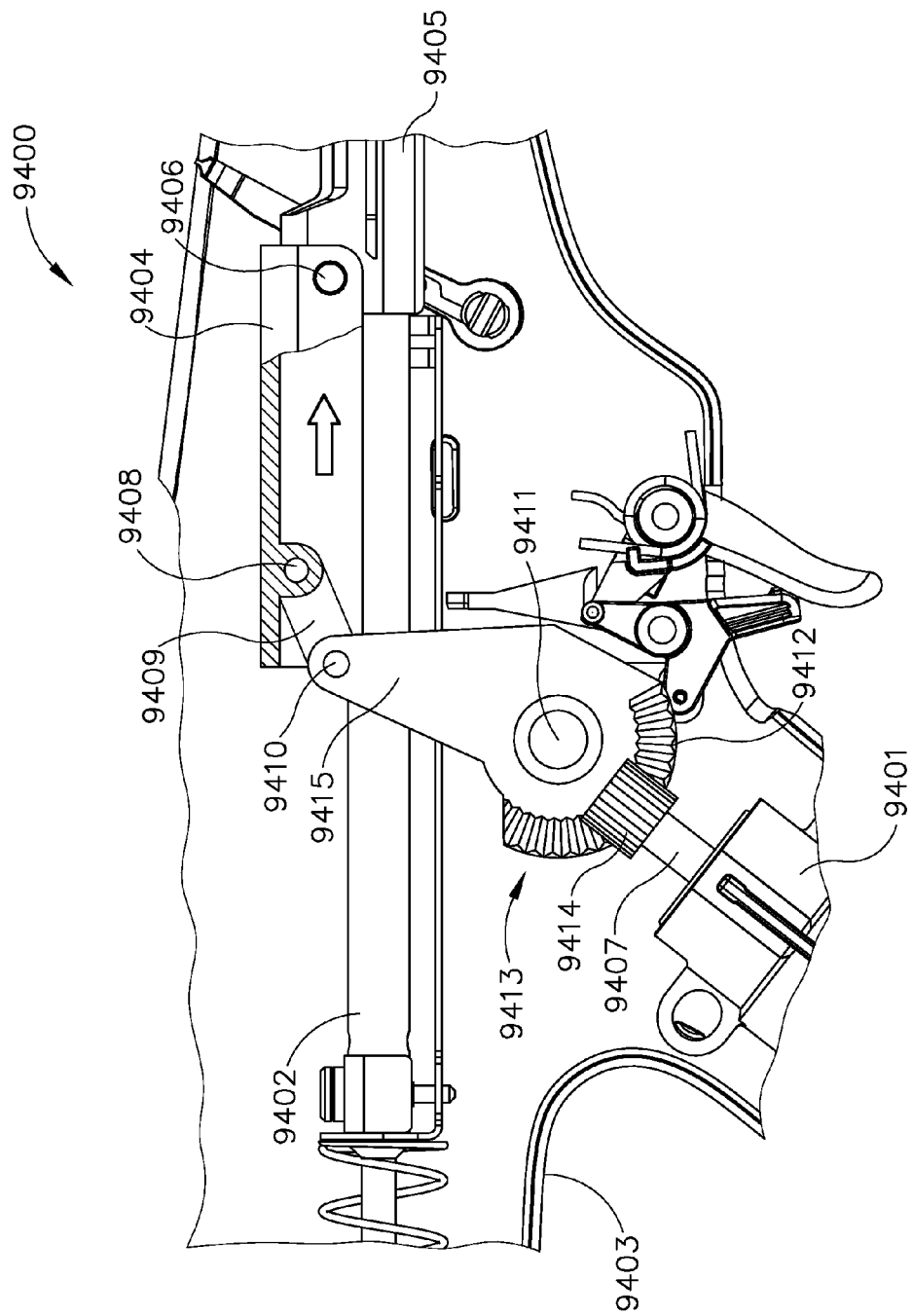
Figure 163C:
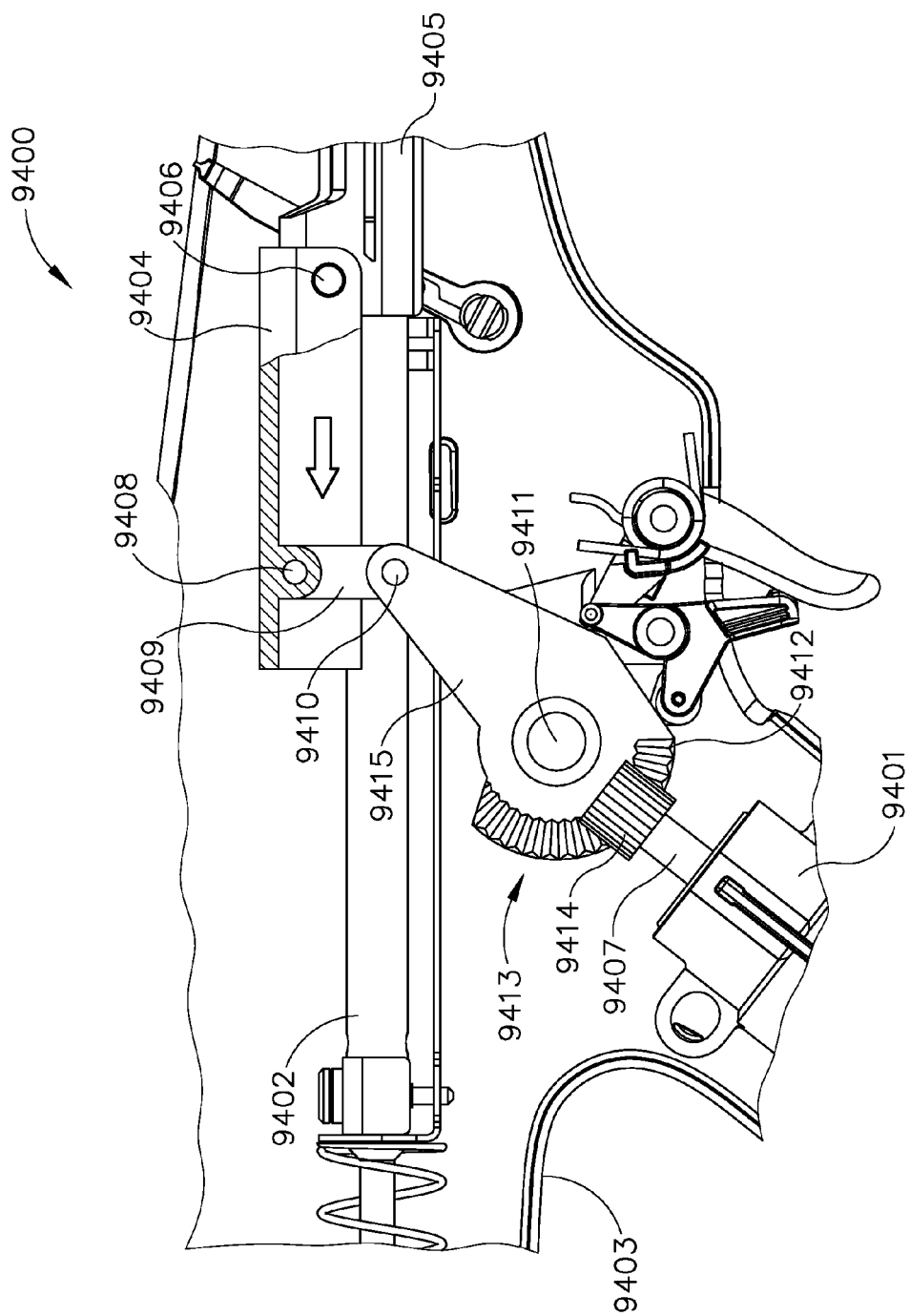
Figure 164A:
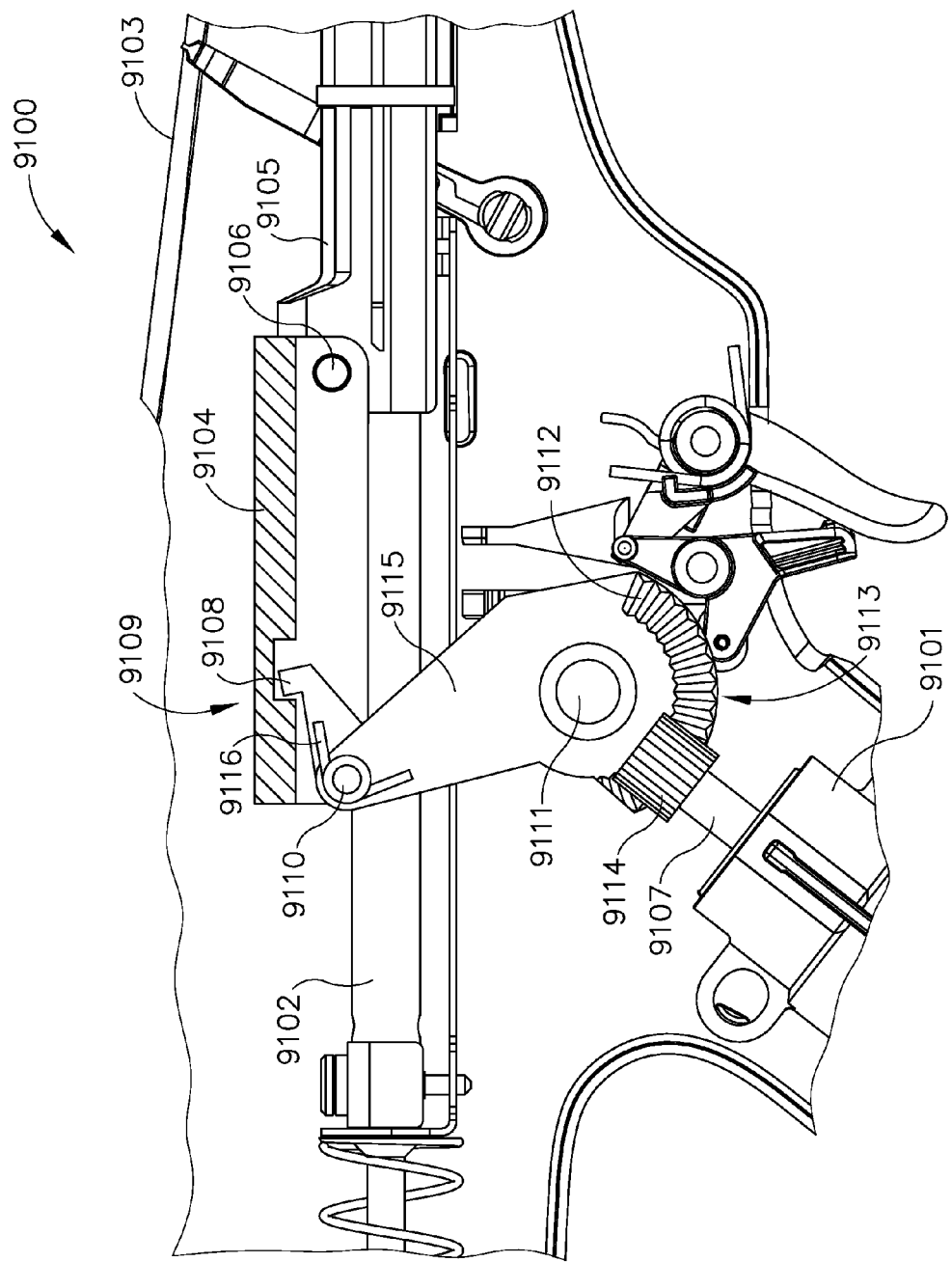
Figure 164B:
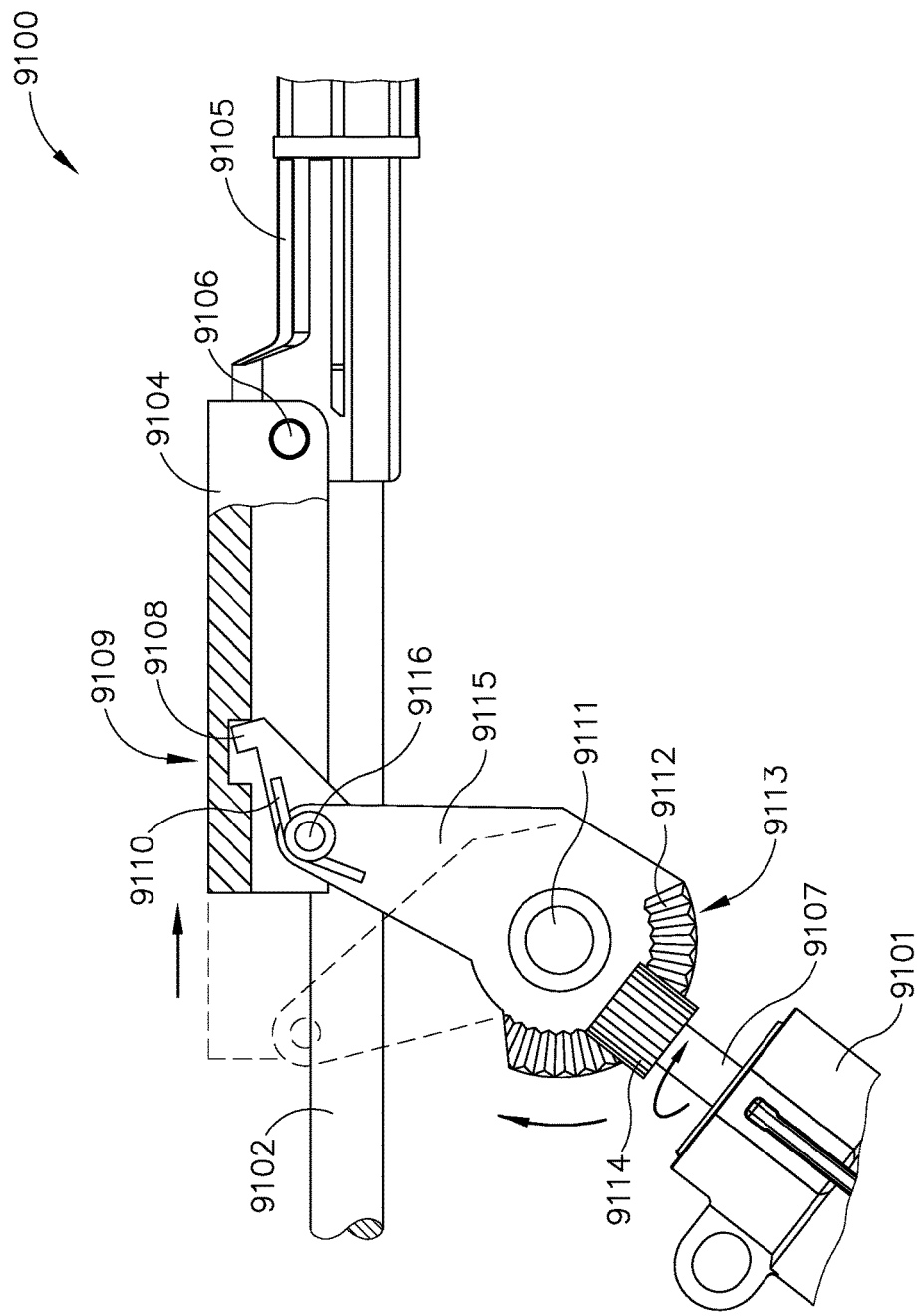
Figure 165A:
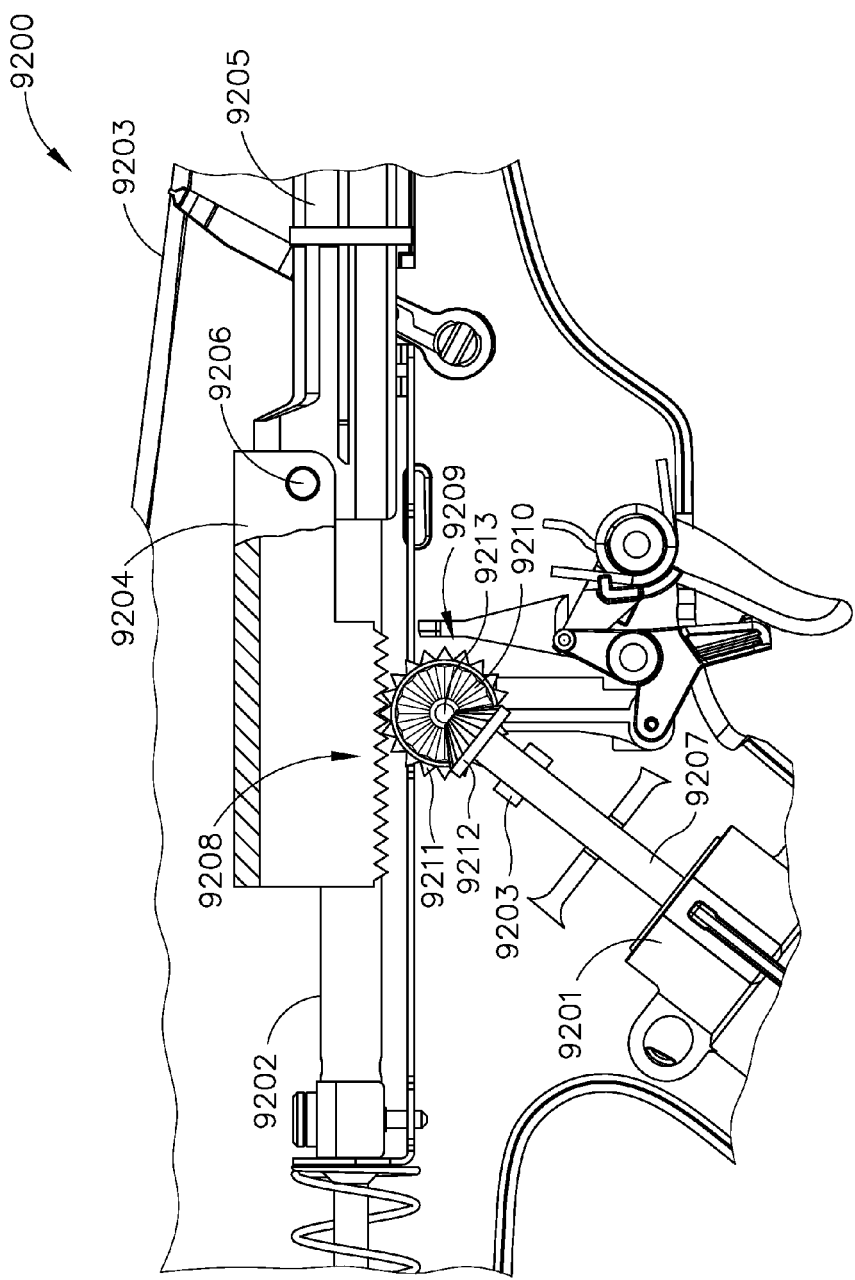
Figure 165B:
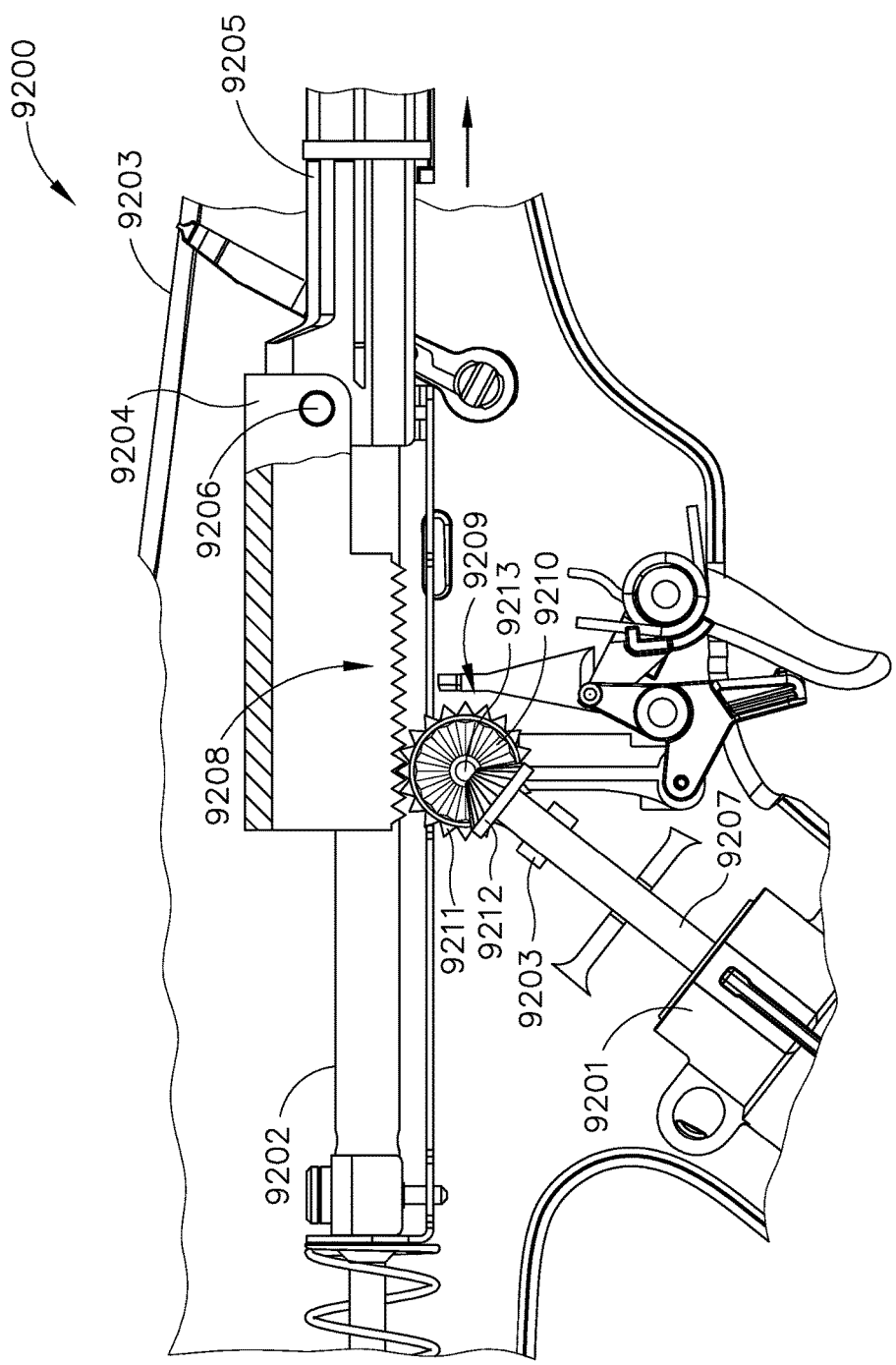
Figure 165C:
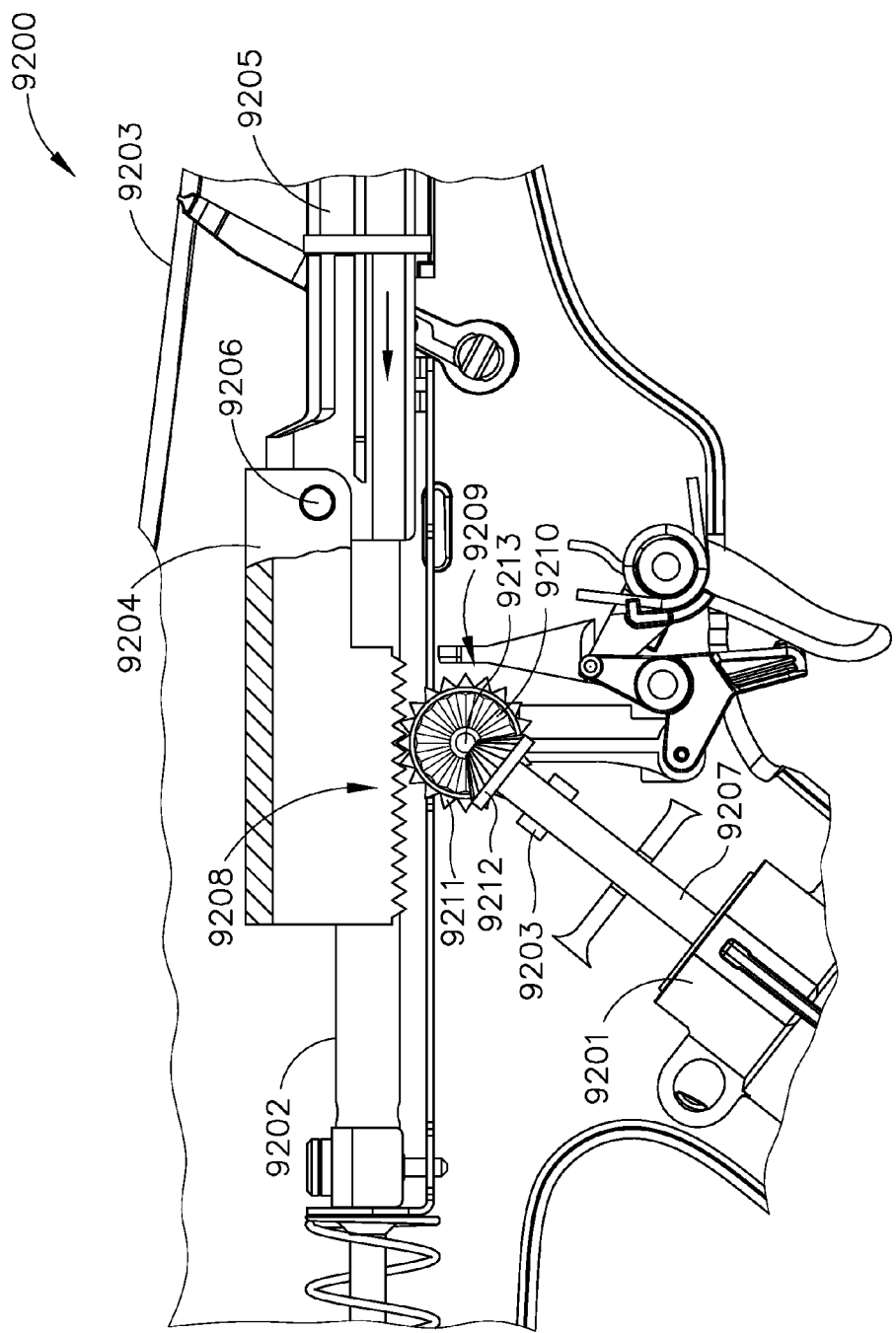
Figure 166A:
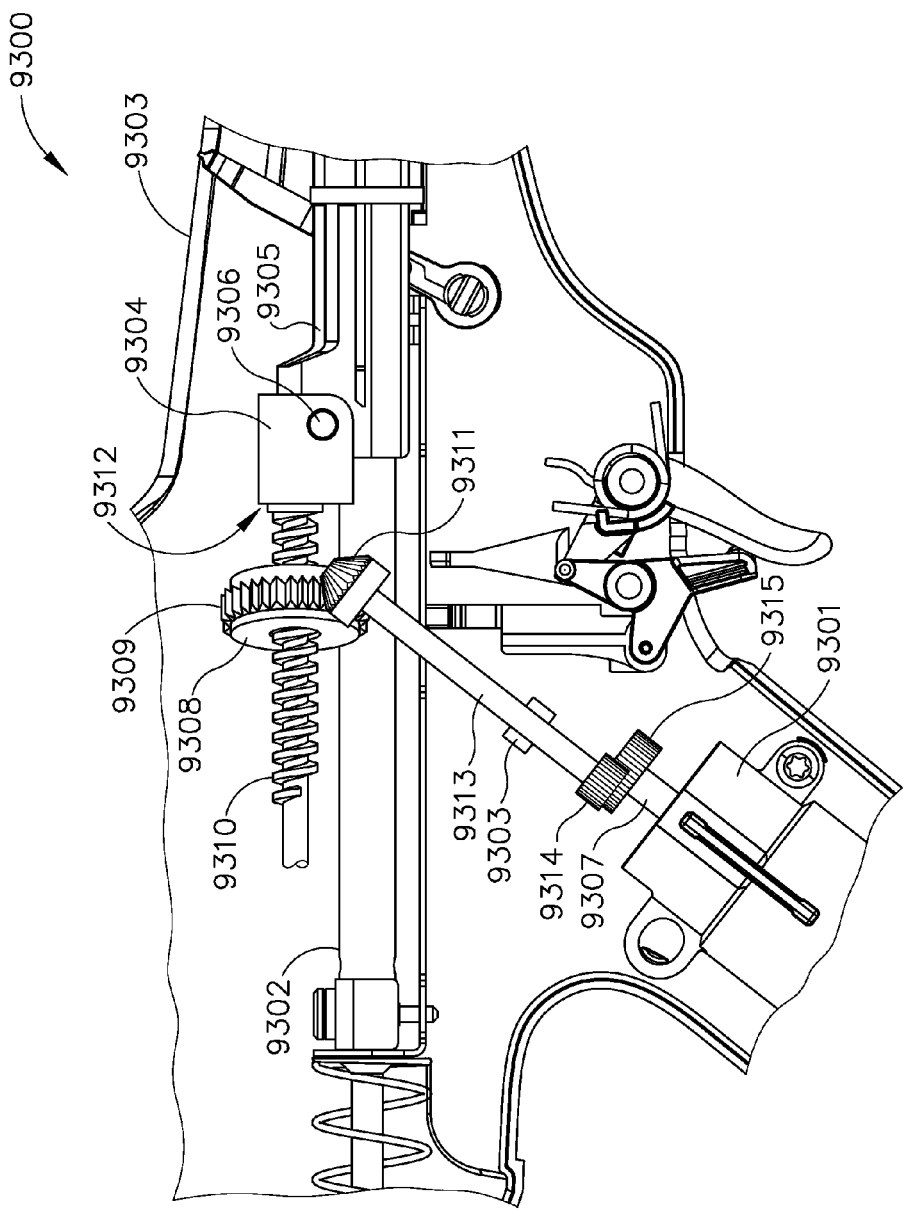
Figure 166B:
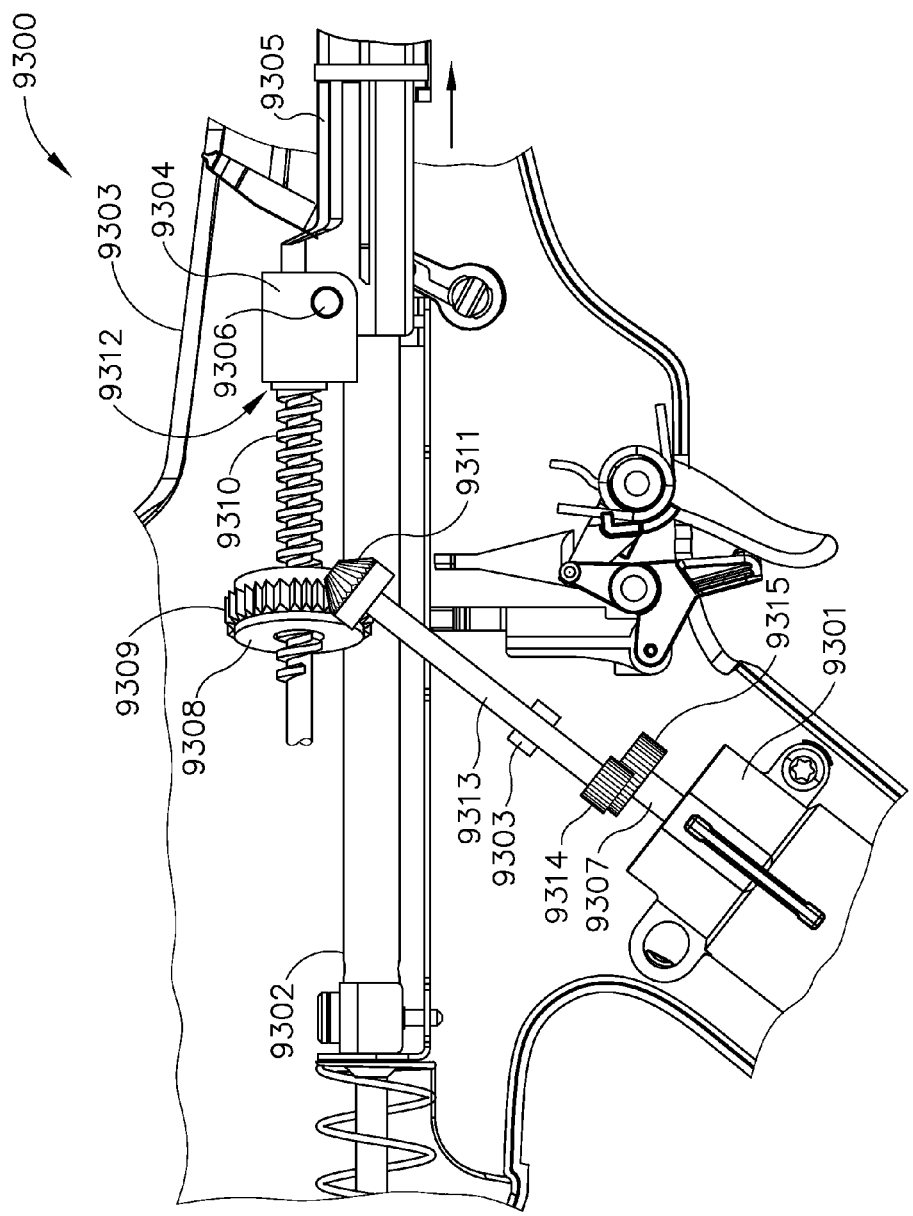
Figure 166C:
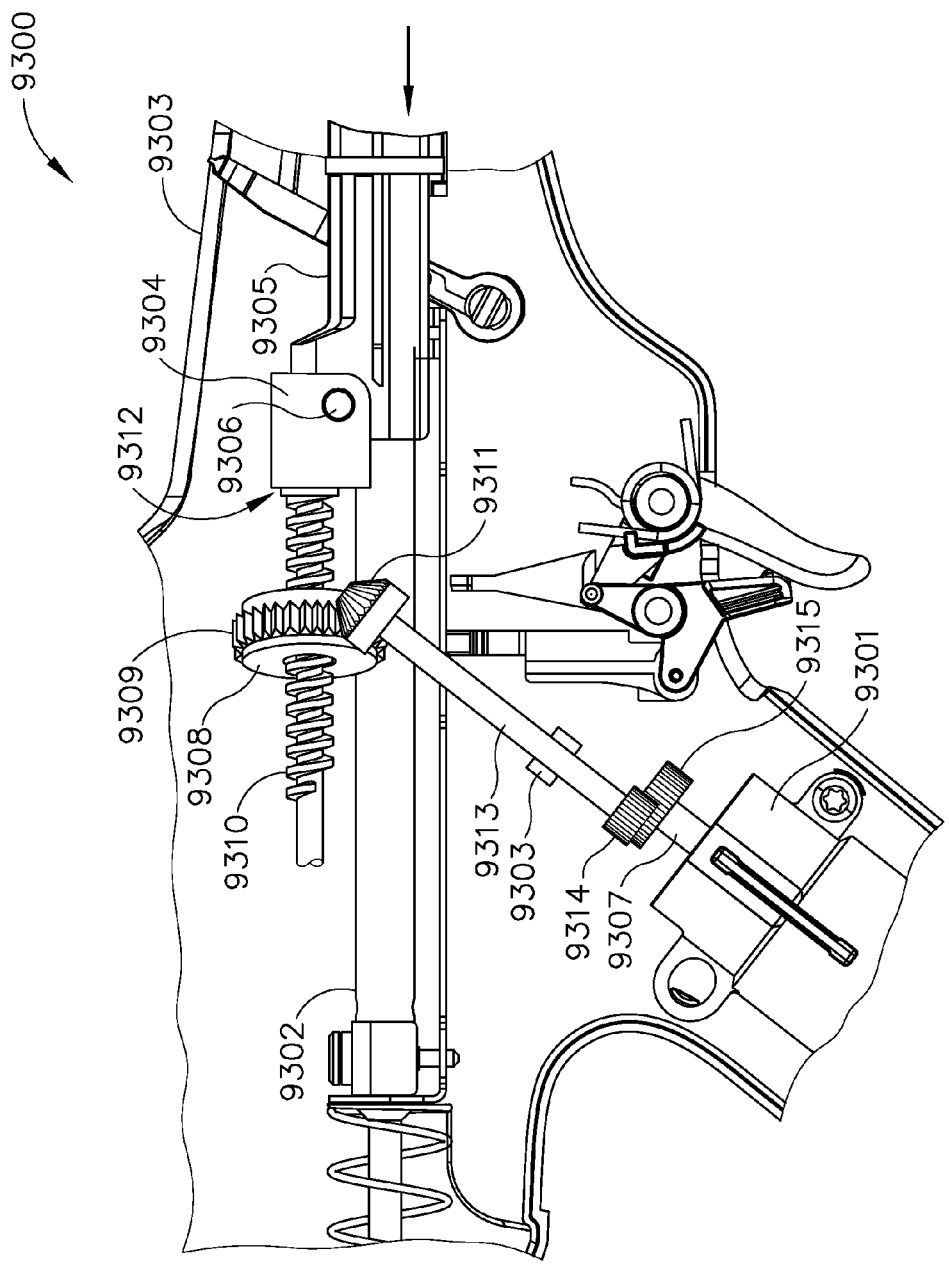
Figure 167:
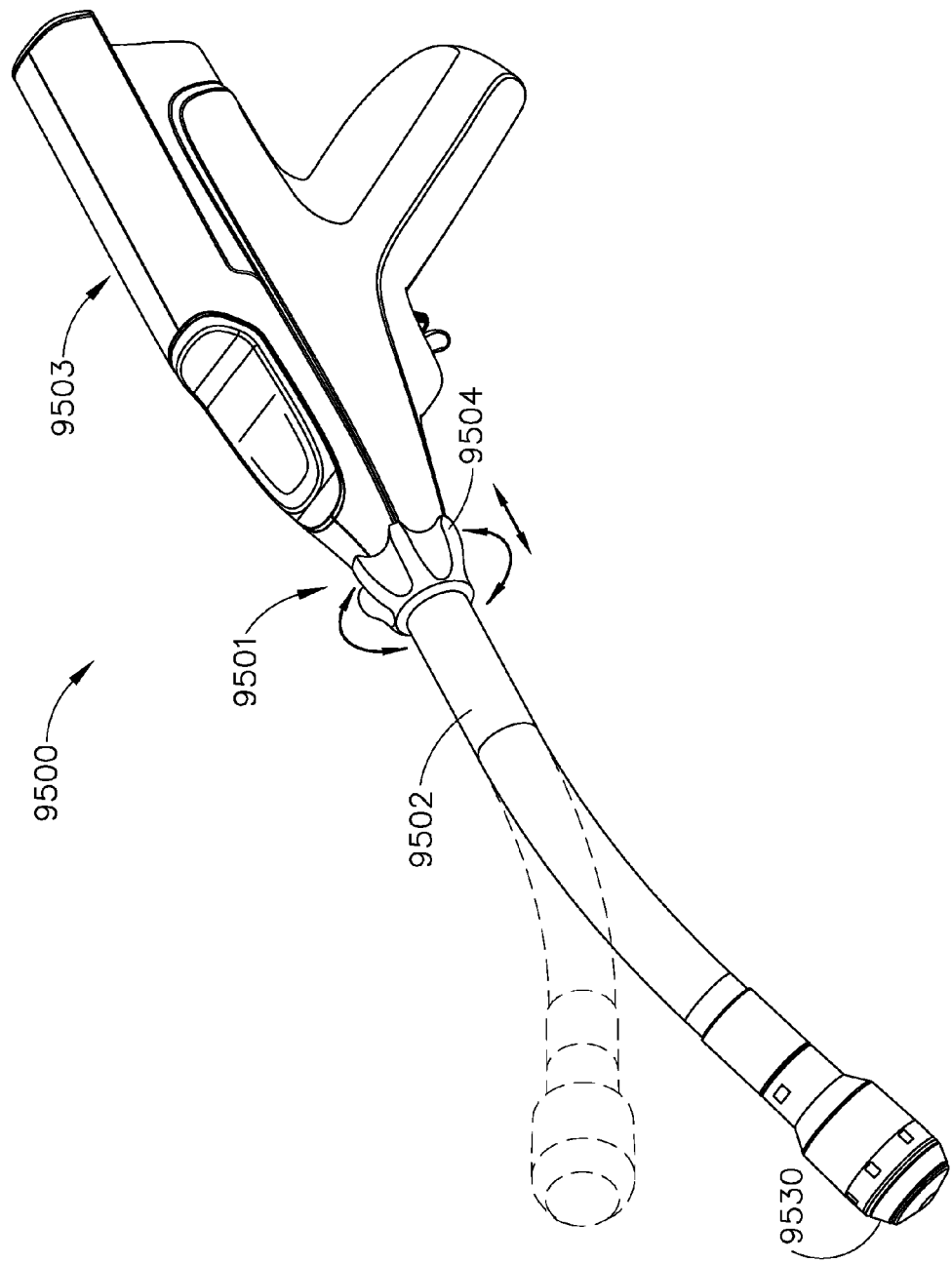
Figure 168:
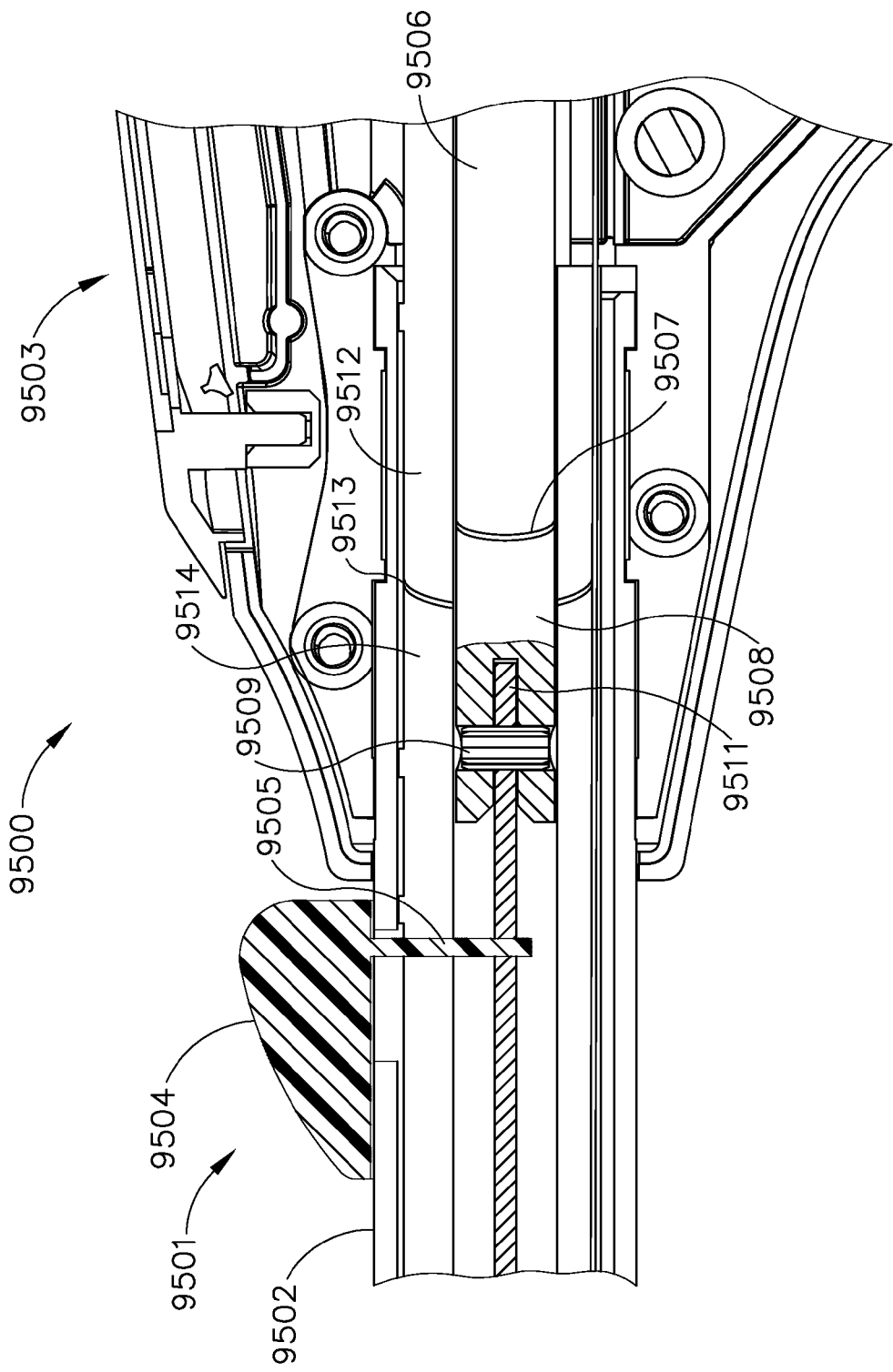
Figure 169:
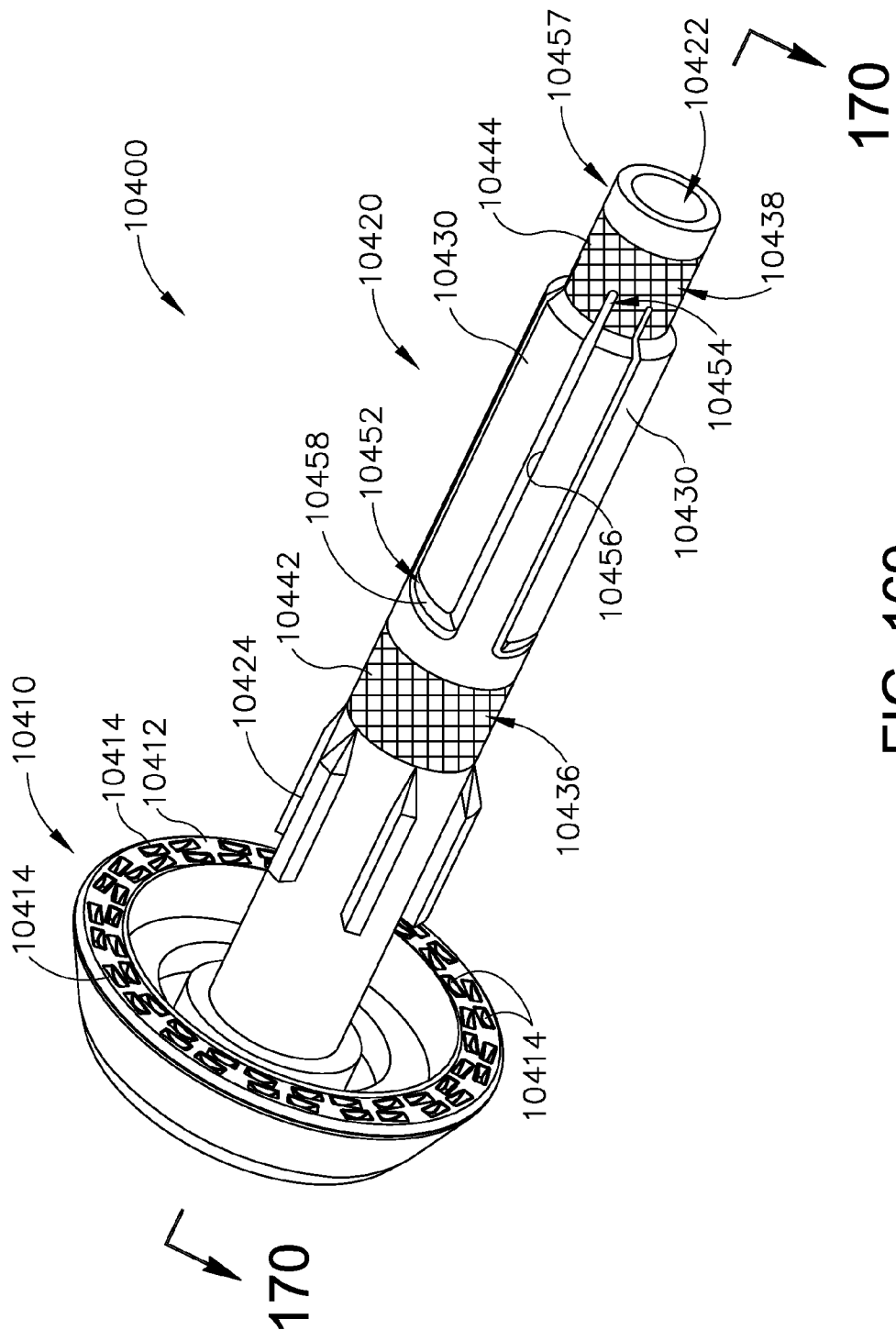
Figure 170A:
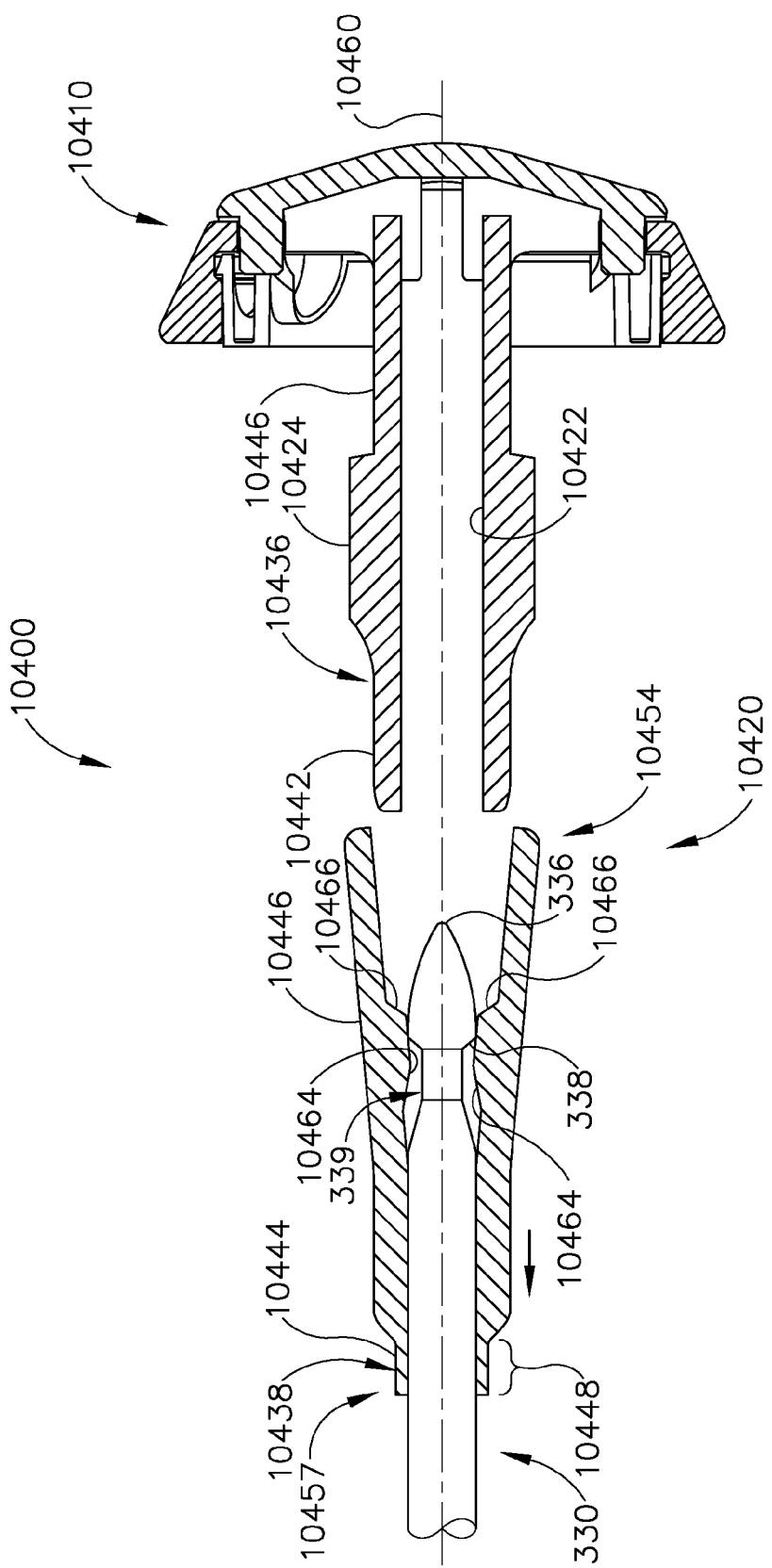
Figure 170B:
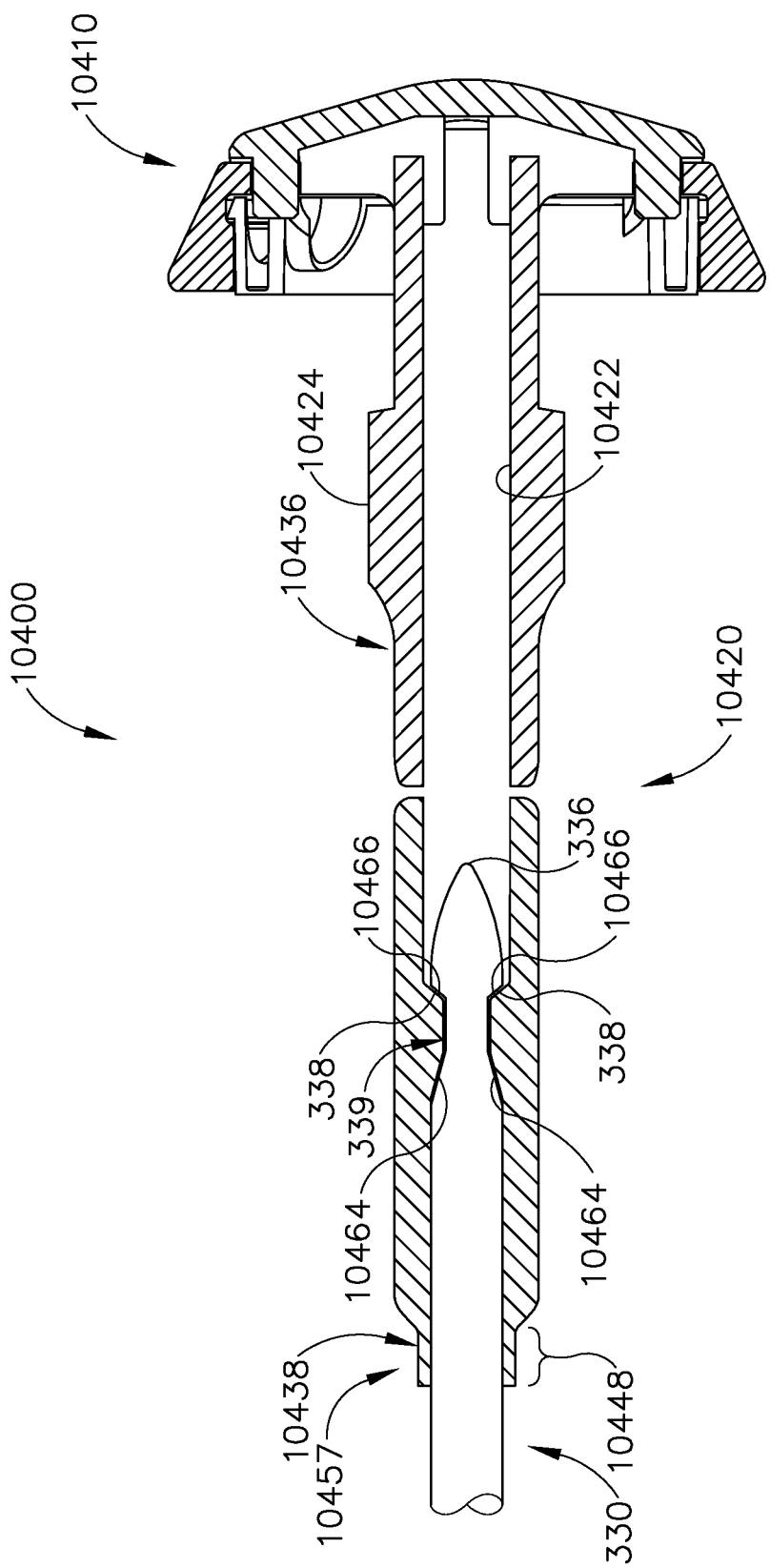
Figure 171:
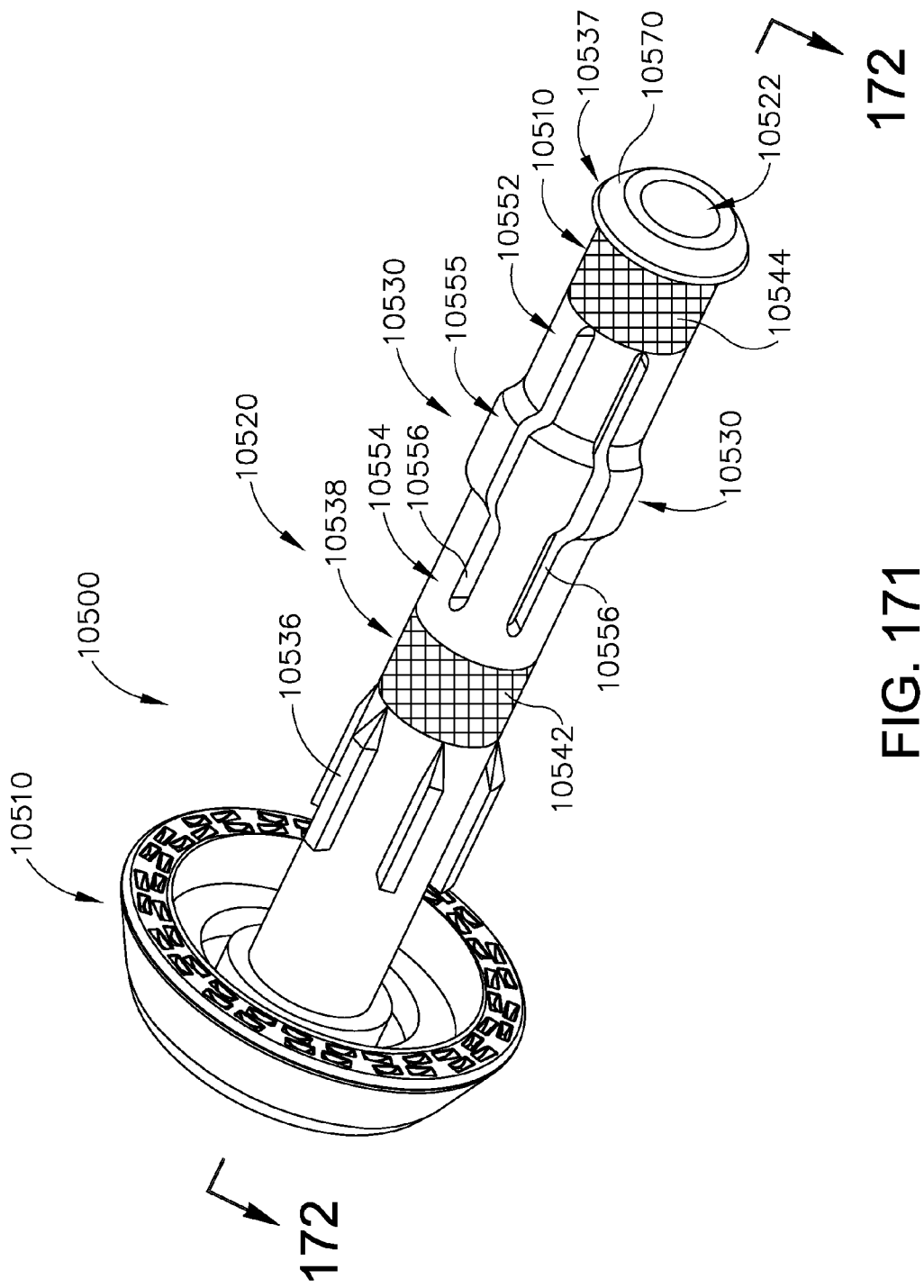
Figure 172A:
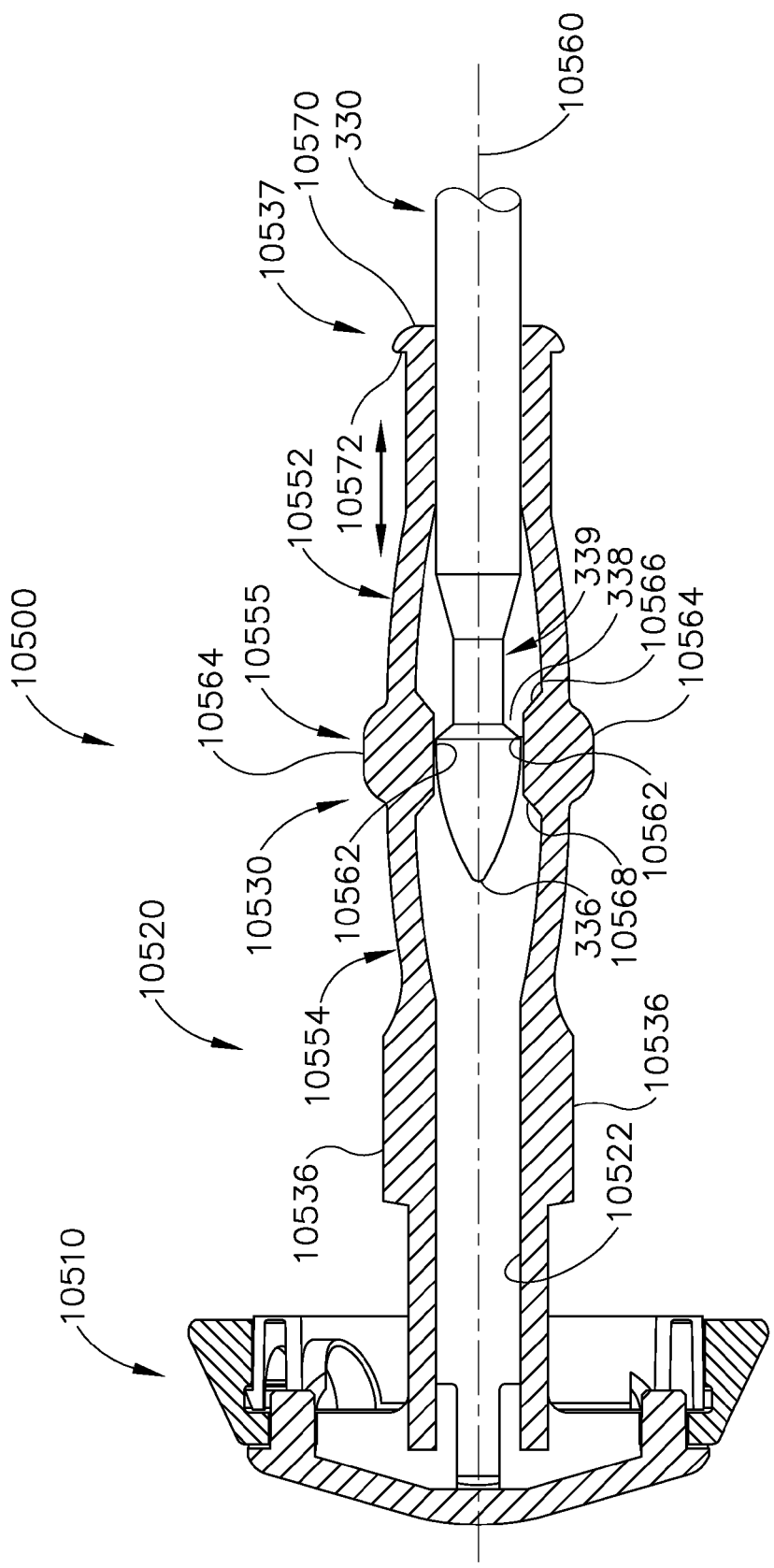
Figure 172B:
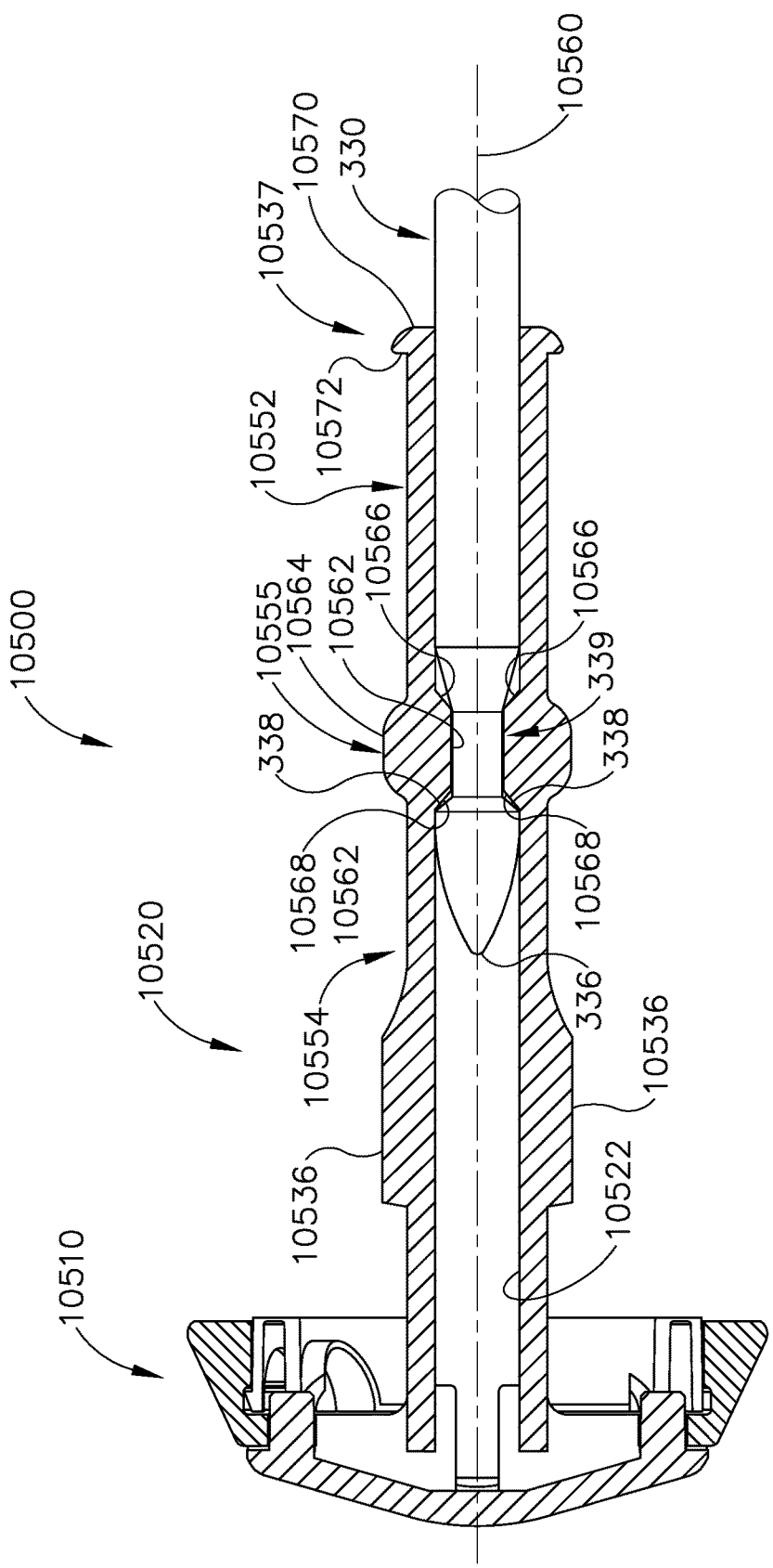
Figure 173:
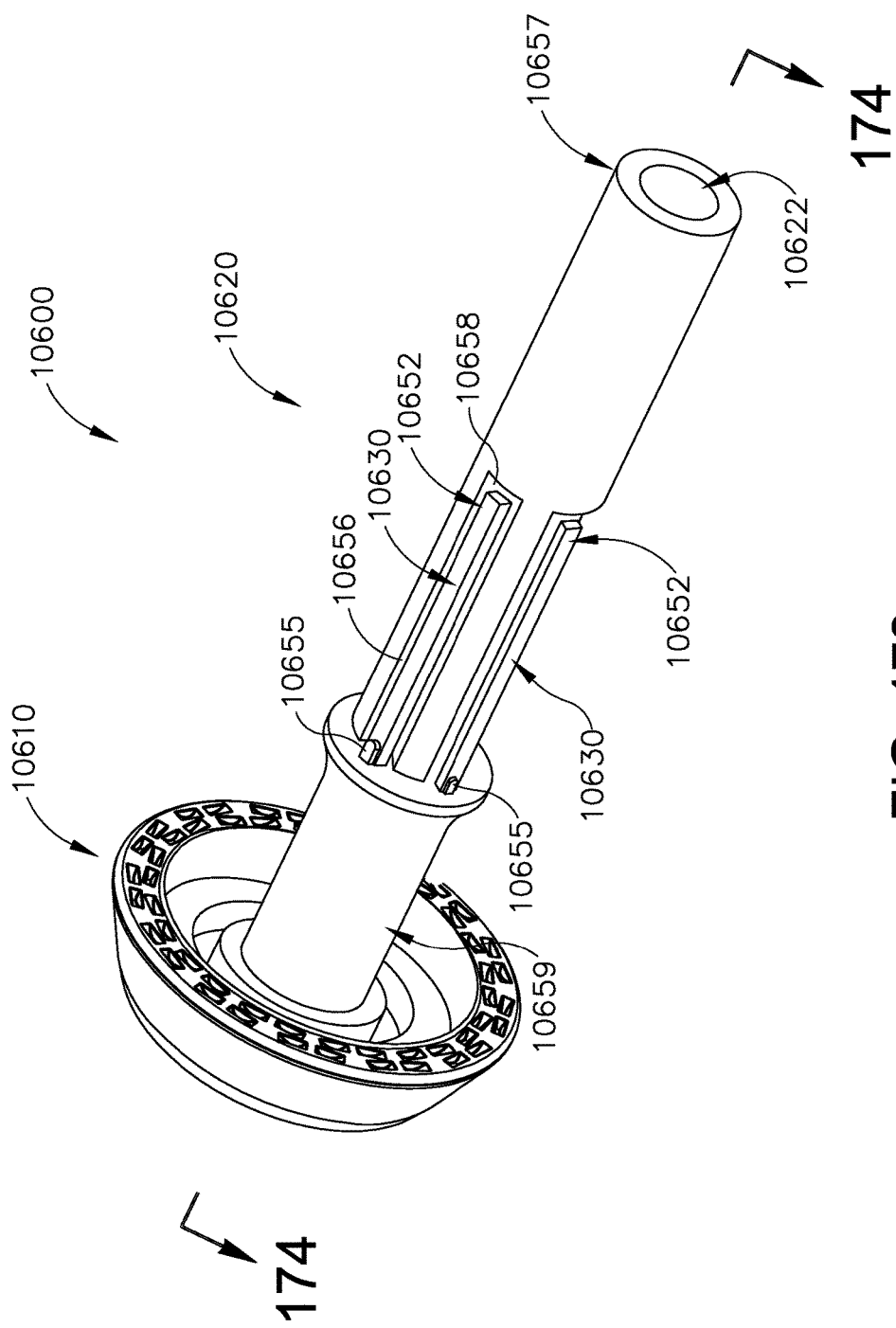
Figure 174A:
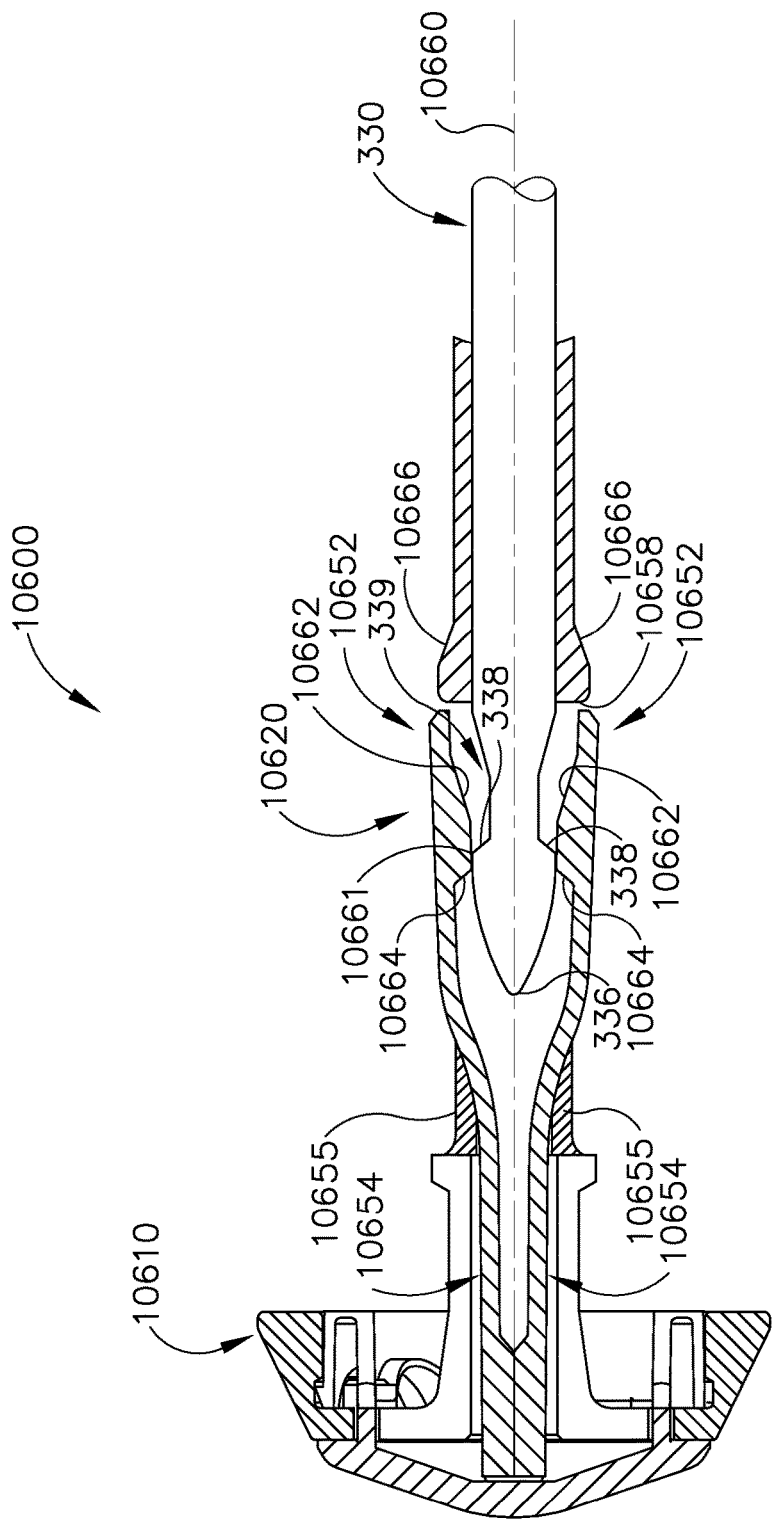
Figure 174B:
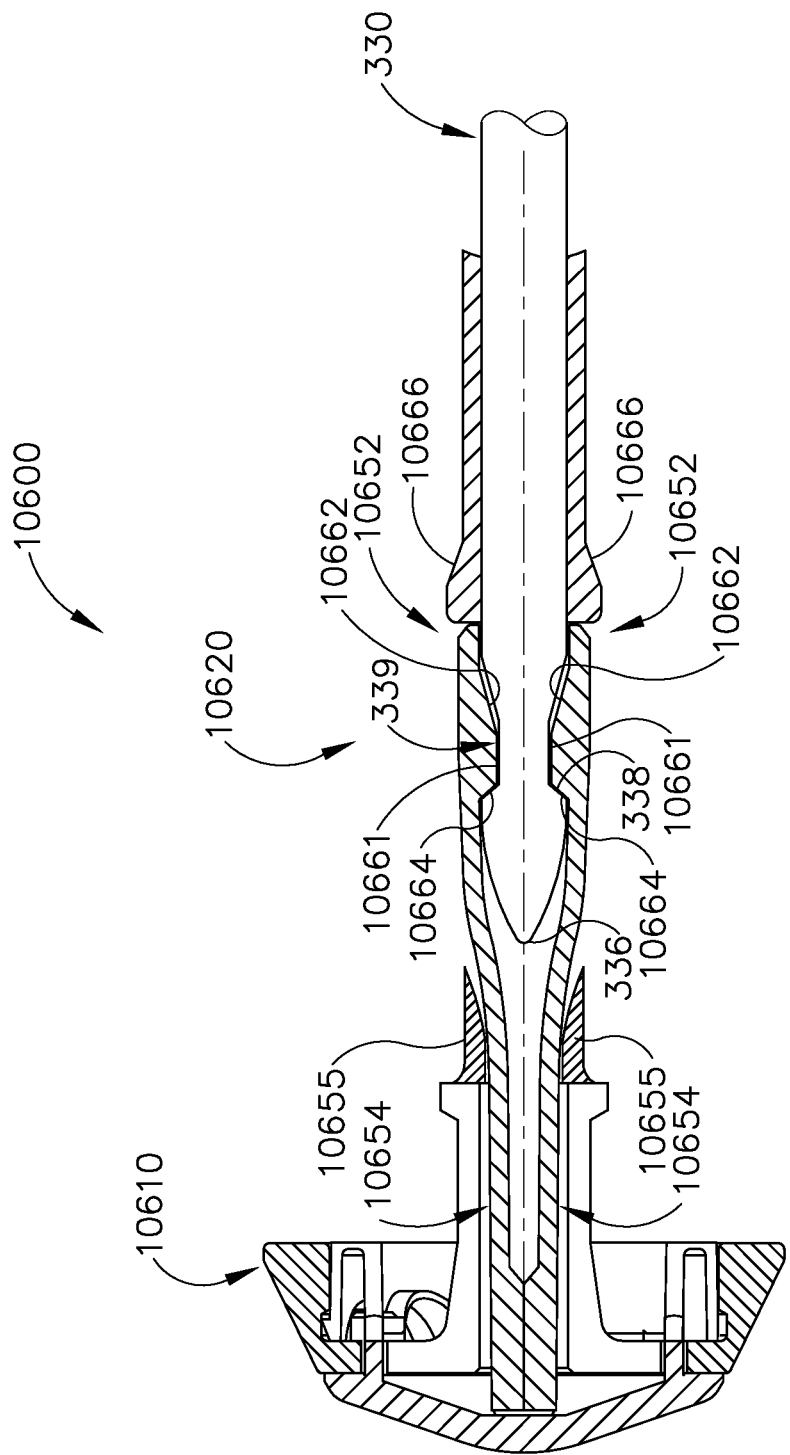
Figure 175:
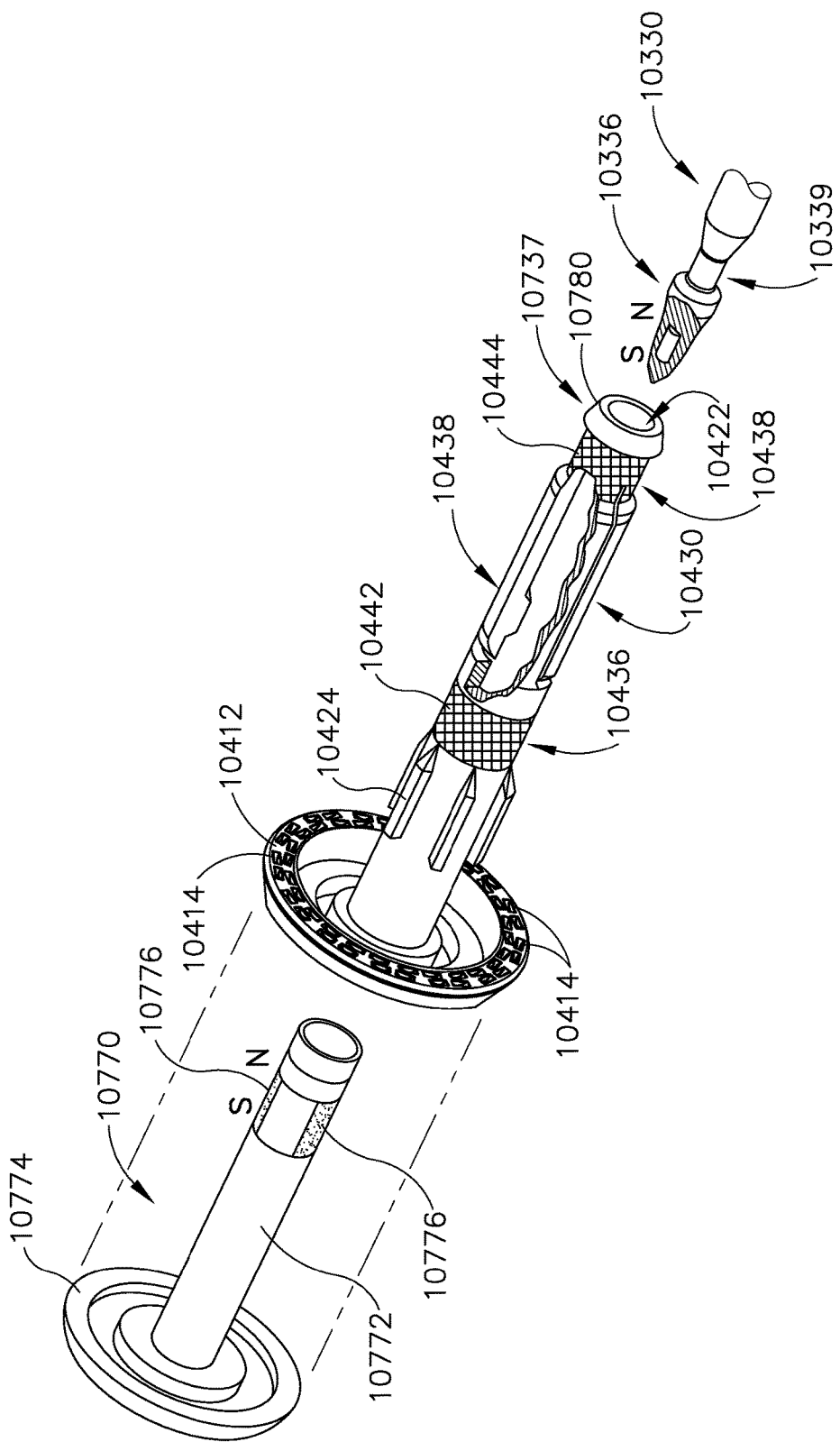
Figure 176A:
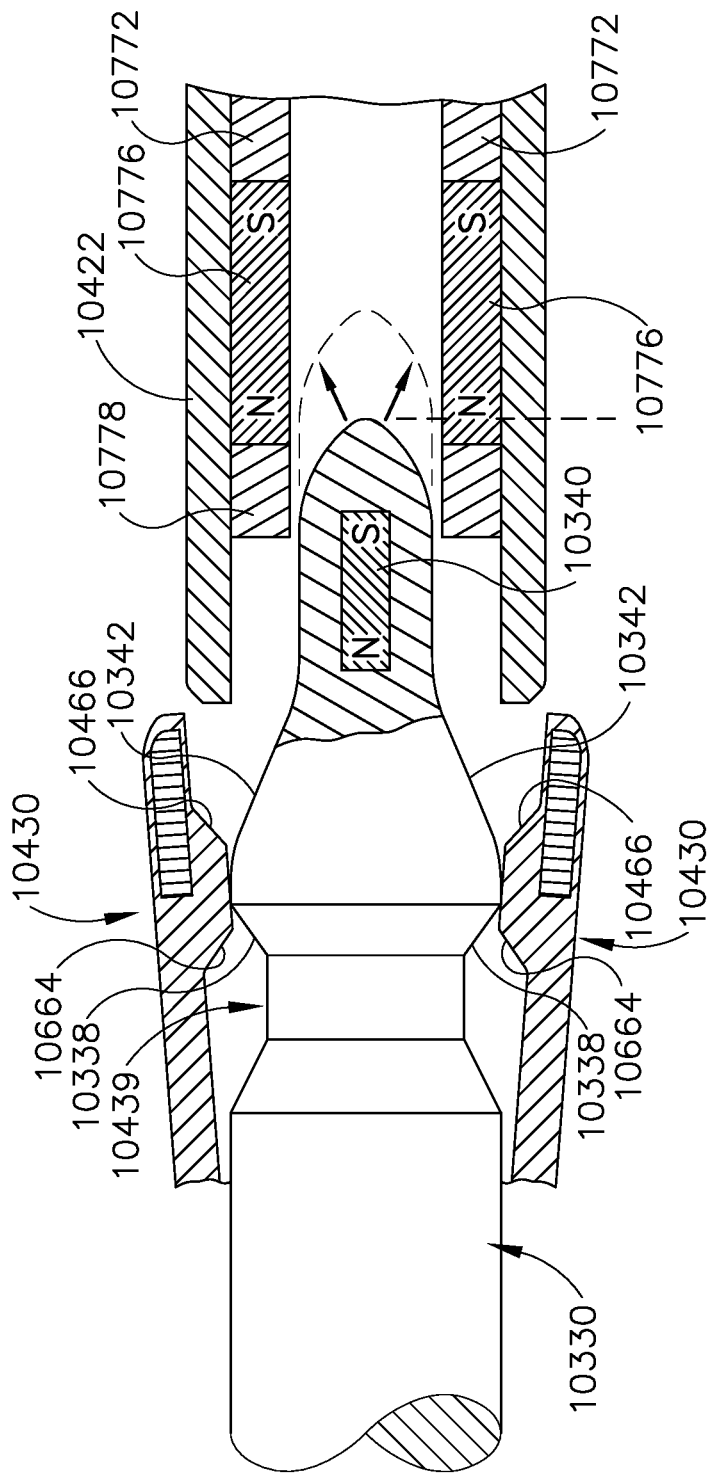
Figure 176B:
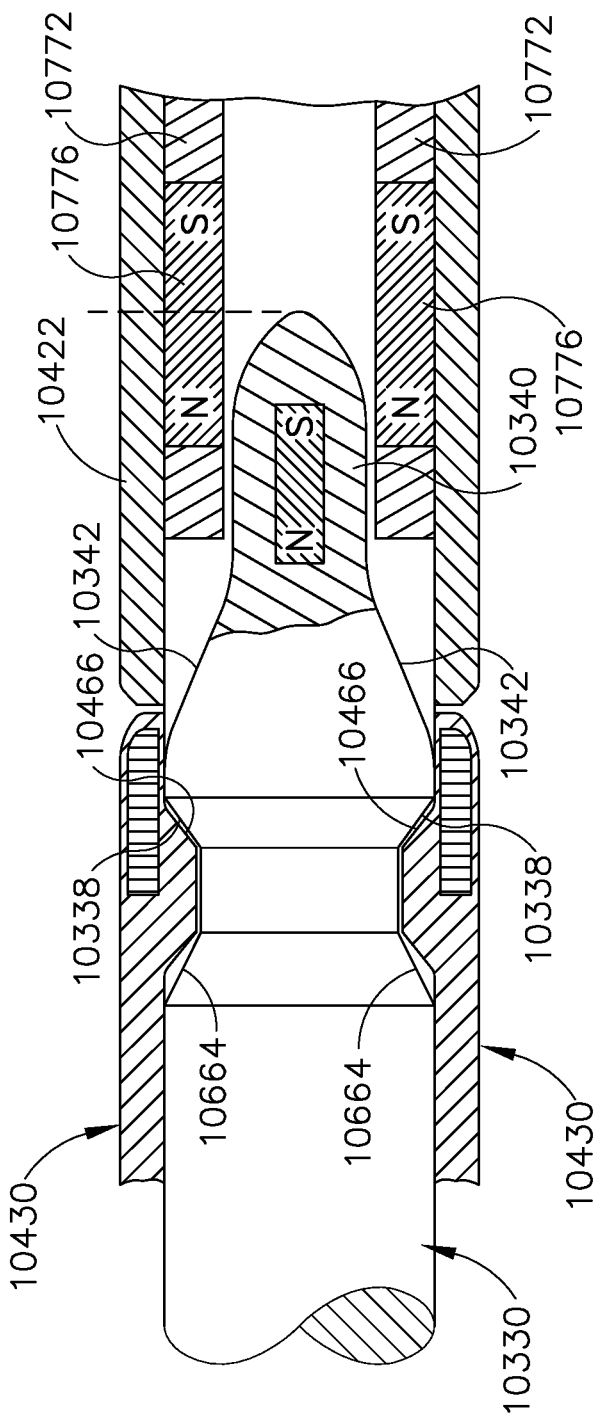

FIG. 85B depicts a side view of the anvil of FIG. 84 in a second position relative to the trocar of FIG. 84;

FIG. 86A depicts a perspective view of the distal end of yet another exemplary alternative circular stapler, with an anvil of the circular stapler positioned about a distal end of a trocar of the circular stapler in a distal position, with a pair of indicator tabs extending from an exterior surface of the anvil;

FIG. 86B depicts a perspective view of the distal end of the circular stapler of FIG. 86A, with the anvil of FIG. 86A positioned about a distal end of the trocar of FIG. 86A and moved into a proximal position, with the indicator tabs of FIG. 86A moved inwardly adjacent the exterior surface of the anvil;

FIG. 87 depicts a cross-sectional side view of an anvil operable for use with any of the circular staplers described herein;

FIG. 88 depicts a cross-sectional side view of the anvil of FIG. 87 positioned about a trocar;

FIG. 89 depicts a cross-sectional side view of the distal end of yet another exemplary alternative circular stapler with an anvil of the circular stapler secured to a trocar of the circular stapler;

FIG. 90A depicts a cross-sectional side view of the anvil of FIG. 89 positioned about the trocar of FIG. 89 in a first position;

FIG. 90B depicts a cross-sectional side view of the anvil of FIG. 89 positioned about the trocar of FIG. 89 in a second position;

FIG. 91 depicts a cross-sectional side view of the distal end of yet another exemplary alternative circular stapler;

FIG. 92A depicts a cross-sectional side view of an adjustment knob of yet another alternative circular stapler, with a clutch of the adjustment knob engaged with a rod of the adjustment member;

FIG. 92B depicts a cross-sectional side view of the adjustment knob of FIG. 92A, with the clutch of FIG. 92A disengaged with the rod of FIG. 92A;

FIG. 93 depicts a perspective view of yet another exemplary alternative circular stapler;

FIG. 94 depicts a perspective view of the circular stapler of FIG. 93, with a battery pack removed from a handle assembly of the circular stapler;

FIG. 95 depicts a perspective view of the battery pack of FIG. 94;

FIG. 96 depicts a partially exploded perspective view of the battery pack of FIG. 94;

FIG. 97A depicts a perspective view of the handle assembly of FIG. 94, with a casing removed from the handle assembly, and with the battery pack of FIG. 94 spaced apart from the handle assembly;

FIG. 97B depicts a perspective view of the handle assembly of FIG. 94, with a casing removed from the handle assembly, and with the battery pack of FIG. 94 coupled with the handle assembly;

FIG. 98 depicts a perspective view of the handle assembly of FIG. 94, with a casing removed from the handle assembly, and with a lower housing of the battery pack of FIG. 94 in a first position relative to the handle assembly;

FIG. 99 depicts a detailed perspective view of the lower housing of FIG. 98 in the first position of FIG. 98, with a lockout sled of the lower housing in a first position relative to a body of the lower housing;

FIG. 100 depicts another detailed perspective view of the lower housing of FIG. 98, with the lockout sled of FIG. 99 in the first position of FIG. 99;

FIG. 101 depicts a perspective view of the handle assembly of FIG. 94, with a casing removed from the handle assembly, and with the lower housing of FIG. 98 moved distally to a second position relative to the handle assembly, and with a lockout flange of the handle assembly received within the lower housing in a first position;

FIG. 102 depicts a detailed perspective view of the lower housing of FIG. 98 in the second position of FIG. 101, with the lockout sled of FIG. 99 remaining in the first position of FIG. 99, and with the lockout flange of FIG. 101 received within the lower housing in the first position of FIG. 101;

FIG. 103 depicts a perspective view of the handle assembly of FIG. 94, with a casing removed from the handle assembly, with the lower housing of FIG. 98 moved distally to a third position relative to the handle assembly such that the lockout flange of FIG. 102 is moved to a second position such that the lockout flange engages the lockout sled of FIG. 99;

FIG. 104 depicts a detailed perspective view of the lower housing of FIG. 98 in the third position of FIG. 103, with the lockout sled of FIG. 99 remaining in the first position of FIG. 99, and with the lockout flange of FIG. 101 received within the lower housing in the second position of FIG. 103 such that the lockout flange engages the lockout sled;

FIG. 105 depicts a perspective view of the handle assembly of FIG. 94, with a casing removed from the handle assembly, with the lower housing of FIG. 98 moved distally to a fourth position relative to the handle assembly such that the lockout flange of FIG. 102 is moved to a third position such that the lockout flange drives the lockout sled of FIG. 99 proximally to a second position;

FIG. 106 depicts a detailed perspective view of the lower housing of FIG. 98 in the fourth position of FIG. 105, with the lockout flange of FIG. 101 received within the lower housing in the third position of FIG. 105 such that the lockout flange drives the lockout sled of FIG. 99 moved into the second position of FIG. 105;

FIG. 107 depicts a perspective view of the handle assembly of FIG. 94, with a casing removed from the handle assembly, with the lower housing of FIG. 98 removed from the handle assembly such that the lockout flange of FIG. 102 is removed from the lower housing, and with the lockout sled of FIG. 99 remaining in the second position of FIG. 105 such that a drain contact of the battery pack of FIG. 104 is biased toward a positive contact of the battery pack;

FIG. 108 depicts a detailed perspective view of the handle assembly of FIG. 94, with the lower housing of FIG. 98 removed from the handle assembly, and with the lockout sled of FIG. 99 remaining in the second position of FIG. 105 such that the drain contact of FIG. 107 is biased toward the positive contact of FIG. 107;

FIG. 109 depicts a detailed perspective view of the handle assembly of FIG. 94, with the lower housing of FIG. 98 removed from the handle assembly, and with the lockout sled of FIG. 99 remaining in the second position of FIG. 105 such that the drain contact of FIG. 107 is biased toward the positive contact of FIG. 107;

FIG. 110 depicts a schematic view of exemplary circuitry operable for use with any of the circular staplers described herein;

FIG. 111 depicts a schematic view of an exemplary alternative circuitry operable for use with any of the circular staplers described herein;

FIG. 112A depicts a side view of an exemplary indicator assembly, with a cam of the indicator assembly in a first rotational position;

FIG. 112B depicts a side view of the indicator assembly of FIG. 112A, with the cam of FIG. 112A moved to a second rotational position so as to actuate a switch of the indicator assembly;

FIG. 113A depicts a top view of a display operable for use within any of the circular staplers described herein, with the display indicating that an anvil is not secured to a trocar;

FIG. 113B depicts a top view of the display of FIG. 113A, with the display indicating that the anvil is secured to a trocar and that the anvil is in a first position;

FIG. 113C depicts a top view of the display of FIG. 113A, with the display indicating that the anvil is secured to a trocar and that the anvil is in a second position;

FIG. 113D depicts a top view of the display of FIG. 113A, with the display indicating that the anvil is secured to a trocar and that the anvil is in a third position;

FIG. 113E depicts a top view of the display of FIG. 113A, with the display indicating that the anvil is secured to a trocar and that the anvil is in a fourth position;

FIG. 114 depicts a schematic view of an exemplary firing indication system that may be incorporated into the circular stapler of FIG. 1;

FIG. 115 depicts a graph of current as a function of time in relation to a power source supplying power to a motor of the firing indication system of FIG. 114;

FIG. 116 depicts a partial perspective view of a handle of a an exemplary firing indication system that may be incorporated into the circular stapler of FIG. 1;

FIG. 117 depicts a partial cutaway perspective view of the firing indication system of FIG. 116;

FIG. 118 depicts a partial perspective view of an exemplary trocar actuation assembly with a tissue release indicator system that may be incorporated into the circular stapler of FIG. 1;

FIG. 119 depicts a perspective view of a bracket of the tissue release indicator system of FIG. 118;

FIG. 120 depicts a side elevational view of the trocar actuation assembly of FIG. 118;

FIG. 121 depicts a broken perspective view of an exemplary tissue release indicator system that may be incorporated into the circular stapler of FIG. 1, where the tissue release indicator system is attached to a rotation knob and a handle;

FIG. 122A depicts a top cross-sectional view of the rotation knob and handle of the tissue release indicator system of FIG. 121, with the knob being rotated in a first direction, and with a detent feature of the knob approaching a tab of the handle;

FIG. 122B depicts a top cross-sectional view of the rotation knob and handle of the tissue release indicator system of FIG. 121, with the knob being rotated further in the first direction, with the detent feature engaging the handle;

FIG. 122C depicts a top cross-sectional view of the rotation knob and handle of the tissue release indicator system of FIG. 121, with the knob being rotated further in the first direction, with the detent feature disengaging the handle to create an audible click;

FIG. 123A depicts a top cross-sectional view of the rotation knob and handle of the tissue release indicator system of FIG. 121, with the knob being rotated in a second direction, and with a detent feature of the knob approaching a tab of the handle;

FIG. 123B depicts a top cross-sectional view of the rotation knob and handle of the tissue release indicator system of FIG. 121, with the knob being rotated further in the second direction, with the detent feature engaging the handle;

FIG. 123C depicts a top cross-sectional view of the rotation knob and handle of the tissue release indicator system of FIG. 121, with the knob being rotated further in the second direction, with the detent feature disengaging the handle to create an audible click;

FIG. 124A depicts a side elevational view of an exemplary trocar actuation assembly including a tissue release indicator that may be incorporated into the circular stapler of FIG. 1, with a trocar actuation rod in a proximal longitudinal position and the tissue release indicator in a first state;

FIG. 124B depicts a side elevational view of the trocar actuation assembly of FIG. 124A, with the trocar actuation rod in a distal position and the tissue release indicator in a second state;

FIG. 125 depicts a perspective view of an exemplary tissue release indicator that may be incorporated into the circular stapler of FIG. 1, where the tissue release indicator comprises a deployable audible/tactile mechanism;

FIG. 126A depicts a side elevational view of the tissue release indicator of FIG. 125 in a pre-deployed position;

FIG. 126B depicts a side elevational view of the tissue release indicator of FIG. 125 in a deployed position while an associated bracket is stationary;

FIG. 126C depicts a side elevational view of the tissue release indicator of FIG. 125 in a deployed position while the bracket is translating longitudinally;

FIG. 127 depicts a prospective view of an exemplary resistance based tissue release indicator that may be incorporated into the circular stapler of FIG. 1;

FIG. 128A depicts a side elevational view of the resistance based tissue release indicator of FIG. 127 with a trocar actuation rod in a first longitudinal position;

FIG. 128B depicts a side elevational view of the resistance based tissue release indicator of FIG. 127 with a trocar actuation rod in a second longitudinal position;

FIG. 128C depicts a side elevational view of the resistance based tissue release indicator of FIG. 127 with a trocar actuation rod in a third longitudinal position;

FIG. 129 depicts a perspective cut away view of an exemplary visual based tissue release indicator that may be incorporated into the circular stapler of FIG. 1;

FIG. 130A depicts a side elevational view of the visual based tissue release indicator of FIG. 129, with a portion of the casing removed, and with a trocar actuation rod in a first longitudinal position;

FIG. 130B depicts a side elevational view of the visual based tissue release indicator of FIG. 129, with a portion of the casing removed, and with a trocar actuation rod in a second longitudinal position;

FIG. 130C depicts a side elevational view of the visual based tissue release indicator of FIG. 129, with a portion of the casing removed, and with a trocar actuation rod in a third longitudinal position;

FIG. 131 depicts a top elevational view of the visual window used in the visual based tissue release indicator of FIG. 129;

FIG. 132 depicts a perspective view of a proximal portion of an exemplary alternative circular stapler;

FIG. 133 depicts a perspective view of a drive bracket assembly of the circular stapler of FIG. 132;

FIG. 134 depicts a partial side elevational view of actuation components in another exemplary alternative circular stapler, with a portion of the stapler shown in cross-section;

FIG. 135 depicts a perspective view of an actuation assembly and strain gauge of the actuation components of FIG. 134;

FIG. 136 depicts a graph showing strain as a function of firing distance during an exemplary firing stroke of the actuation components of FIG. 134;

FIG. 137A depicts a side elevational view of the stapling head actuation assembly of FIG. 13, with the stapling head actuation assembly in an actuated state, with a position sensing assembly;

FIG. 137B depicts a side elevational view of the stapling head actuation assembly and position sensing assembly of FIG. 137A, with the stapling head actuation assembly in a returned state;

FIG. 138 depicts a partial perspective view of a handle assembly of exemplary alternative circular stapler;

FIG. 139 depicts a perspective cut-away view of the circular stapler of FIG. 138, with an anvil bailout assembly in a neutral position visible;

FIG. 140 depicts a detailed perspective view of the anvil bailout assembly of FIG. 139;

FIG. 141 depicts a detailed perspective view of a coupling member of the anvil bailout assembly of FIG. 139;

FIG. 142 depicts side cross-sectional view of the coupling member of FIG. 141, with the cross-section taken along line 142-142 of FIG. 141;

FIG. 143 depicts a detailed perspective view of a trocar actuation rod of the circular stapler of FIG. 138;

FIG. 144 depicts a detailed perspective view of the anvil bailout assembly of FIG. 139, with the anvil bailout assembly in a released position;

FIG. 145 depicts a detailed perspective view of a handle assembly of another exemplary alternative circular stapler;

FIG. 146 depicts a perspective cut-away view of the circular stapler of FIG. 145, with an anvil bailout assembly in a neutral position visible;

FIG. 147 depicts a detailed perspective view of the anvil bailout assembly of FIG. 146, with the anvil bailout assembly in the neutral position;

FIG. 148 depicts a detailed top cross-sectional view of the anvil bailout assembly of FIG. 146, with the cross-section taken along line 148-148 of FIG. 147 and the anvil bailout assembly in the neutral position;

FIG. 149 depicts another detailed top cross-sectional view of the anvil bailout assembly of FIG. 146, with the cross-section taken along line 148-148 of FIG. 147 and the anvil bailout assembly in a released position;

FIG. 150 depicts a detailed side cross-sectional view of a stapling head assembly of the circular stapler of FIG. 145, the stapling head assembly equipped with a knife bailout assembly;

FIG. 151 depicts a detailed side cross-sectional view of the knife bailout assembly of FIG. 150, the knife bailout assembly in a neutral position;

FIG. 152 depicts another detailed side cross-sectional view of the knife bailout assembly of FIG. 150, the knife bailout assembly in a released position;

FIG. 153 depicts a perspective view of still another exemplary alternative circular stapler, with a bailout door removed;

FIG. 154 depicts a detailed perspective view of a proximal portion of the circular stapler of FIG. 153, with the bailout door removed and various bailout features visible;

FIG. 155 depicts a detailed perspective view of a handle assembly of yet another exemplary alternative surgical stapler;

FIG. 156 depicts a detailed perspective cut-away view of the handle assembly of the surgical stapler of FIG. 155, with internal components of a manual stapling head assembly bailout knob visible;

FIG. 157 depicts a detailed side elevational view of a stapling head actuation assembly of the surgical stapler of FIG. 155;

FIG. 158 depicts a detailed side elevational view of an exemplary alternative stapling head actuation assembly that may be readily incorporated into the circular stapler of FIG. 1;

FIG. 159 depicts a detailed side elevational view of a slip clutch the stapling head actuation assembly of FIG. 158, with gears of the slip clutch engaged to transfer torque;

FIG. 160 depicts another detailed side elevational view of the slip clutch of FIG. 159, with the gears slipping to prevent further transfer of torque;

FIG. 161 depicts a side elevational view of an alternative stapling head actuation assembly that may be incorporated into the circular stapler of FIG. 1;

FIG. 162A depicts a partial side elevational view the stapling head actuation assembly of FIG. 22, with a rotary member in a first angular position and a drive bracket in a first linear position;

FIG. 162B depicts a partial side elevational view of the stapling head actuation assembly of FIG. 161, with the rotary member in a second angular position and the drive bracket in a second linear position;

FIG. 162C depicts a partial side elevational view of the stapling head actuation assembly of FIG. 161, with the rotary member in a third angular position and the drive bracket in a third linear position;

FIG. 163A depicts a partial side elevational view of another alternative stapling head actuation assembly that may be incorporated into the circular stapler of FIG. 1, with a rotary member in a first angular position and a drive bracket in a first linear position;

FIG. 163B depicts a partial side elevational view of the stapling head actuation assembly of FIG. 163A, with the rotary member in a second angular position and the drive bracket in a second linear position;

FIG. 163C depicts a partial side elevational view of the stapling head actuation assembly of FIG. 163A, with the rotary member in a third angular position and the drive bracket in a third linear position FIG. 164A depicts a partial side elevational view of another alternative stapling head actuation assembly that may be incorporated into the circular stapler of FIG. 1, with a rotary member in a first angular position and a drive bracket in a first linear position;

FIG. 164B depicts a partial side elevational view of the stapling head actuation assembly of FIG. 164A, with the rotary member in a second angular position and the drive bracket in a second linear position;

FIG. 165A depicts a partial side elevational view of another alternative stapling head actuation assembly that may be incorporated into the circular stapler of FIG. 1, with a drive bracket in a first linear position;

FIG. 165B depicts a partial side elevational view of the stapling head actuation assembly of FIG. 165A, with the drive bracket in a second linear position;

FIG. 165C depicts a partial side elevational view of the stapling head actuation assembly of FIG. 165A, with drive bracket in a third linear position;

FIG. 166A depicts a partial side elevational view of another alternative stapling head actuation assembly that may be incorporated into the circular stapler of FIG. 1, with a drive bracket in a first linear position;

FIG. 166B depicts a partial side elevational view of the stapling head actuation assembly of FIG. 166A, with the drive bracket in a second linear position;

FIG. 166C depicts a partial side elevational view of the stapling head actuation assembly of FIG. 166A, with the drive bracken in a third linear position;

FIG. 167 depicts a perspective view of a circular stapler where the distal end of the shaft assembly is rotatable relative to the casing;

FIG. 168 depicts a side cross-sectional view of the circular stapler of FIG. 167;

FIG. 169 depicts a perspective view of an exemplary alternative anvil suitable for incorporation into the circular stapler of FIG. 1;

FIG. 170A depicts a side elevational view of a trocar of the stapling head assembly of FIG. 6 partially coupled with the anvil of FIG. 169, with the anvil being shown in a cross-section taken along line 170-170 of FIG. 169;

FIG. 170B depicts a side elevational view of a trocar of the stapling head assembly of FIG. 6 fully coupled with the anvil of FIG. 169, with the anvil being shown in a cross-section taken along line 170-170 of FIG. 169;

FIG. 171 depicts a perspective view of another exemplary alternative anvil suitable for incorporation into the circular stapler of FIG. 1;

FIG. 172A depicts a side elevational view of a trocar of the stapling head assembly of FIG. 6 partially coupled with the anvil of FIG. 171, with the anvil being shown in a cross-section taken along line 172-172 of FIG. 171;

FIG. 172B depicts a side elevational view of a trocar of the stapling head assembly of FIG. 6 fully coupled with the anvil of FIG. 171, with the anvil being shown in a cross-section taken along line 172-172 of FIG. 171;

FIG. 173 depicts a perspective view of another exemplary alternative anvil suitable for incorporation into the circular stapler of FIG. 1;

FIG. 174A depicts a side elevational view of a trocar of the stapling head assembly of FIG. 6 partially coupled with the anvil of FIG. 173, with the anvil being shown in a cross-section taken along line 174-174 of FIG. 173;

FIG. 174B depicts a side elevational view of a trocar of the stapling head assembly of FIG. 6 fully coupled with the anvil of FIG. 173, with the anvil being shown in a cross-section taken along line 174-174 of FIG. 173;

FIG. 175 depicts an exploded perspective view of another exemplary alternative anvil and an exemplary alternative trocar, each being suitable for incorporation into the circular stapler of FIG. 1;

FIG. 176A depicts a partial, schematic view of the trocar of FIG. 175 partially coupled with the anvil of FIG. 175; and FIG. 176B depicts a partial, schematic view of the trocar of FIG. 175 fully coupled with the anvil of FIG. 175.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
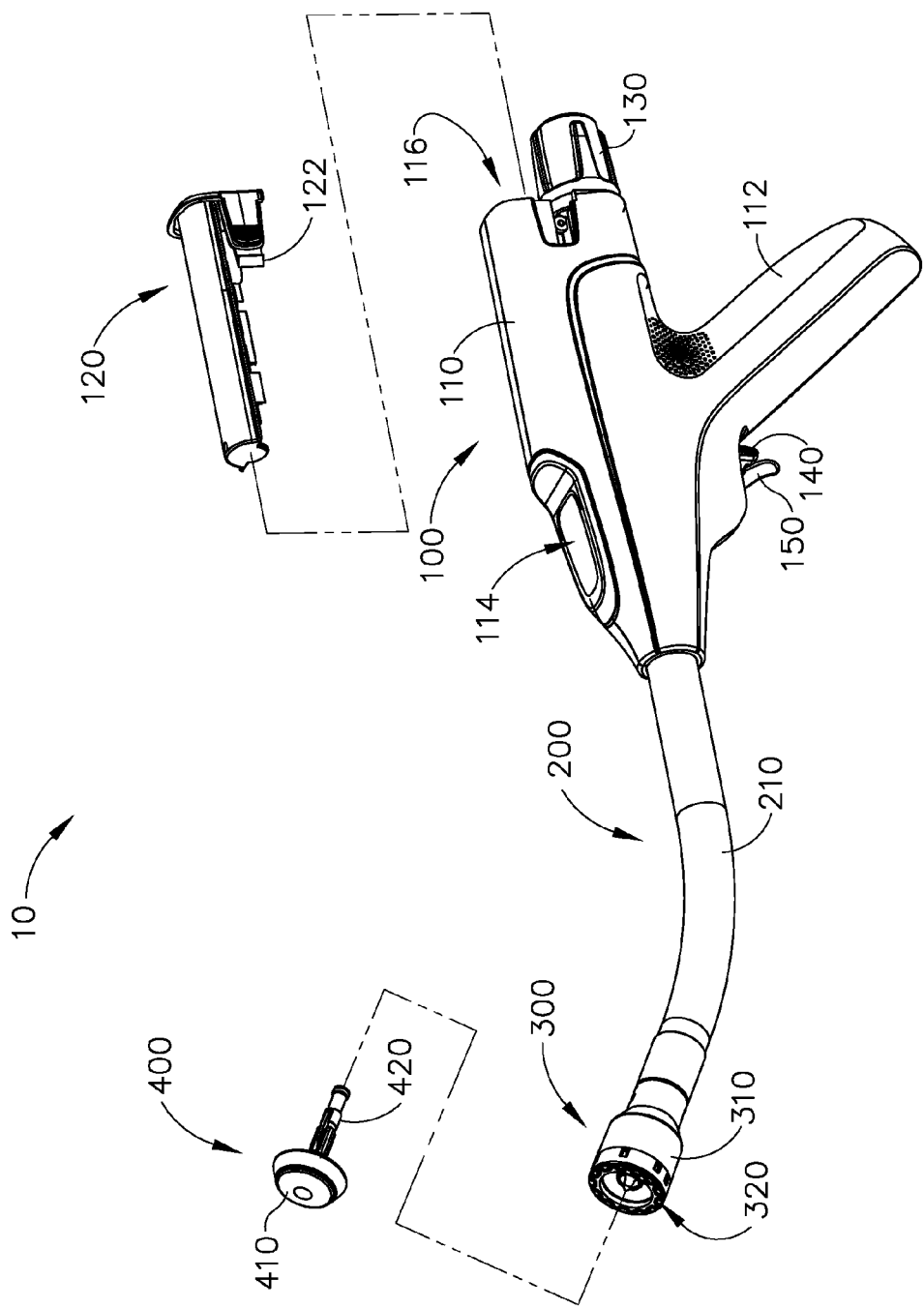
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (110) further includes a window (114) that permits viewing of a movable indicator needle (526) as will be described in greater detail below. In some versions, a series of hash marks, colored regions, and/or other fixed indicators are positioned adjacent to window (114) in order to provide a visual context for indicator needle (526), thereby facilitating operator evaluation of the position of needle (526) within window (114). Various suitable alternative features and configurations for handle assembly (112) will be apparent to those of ordinary skill in the art in view of the teachings herein.

Instrument (10) of the present example further includes a battery pack (120). Battery pack (120) is operable to provide electrical power to a motor (160) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery back (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (100) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 3:
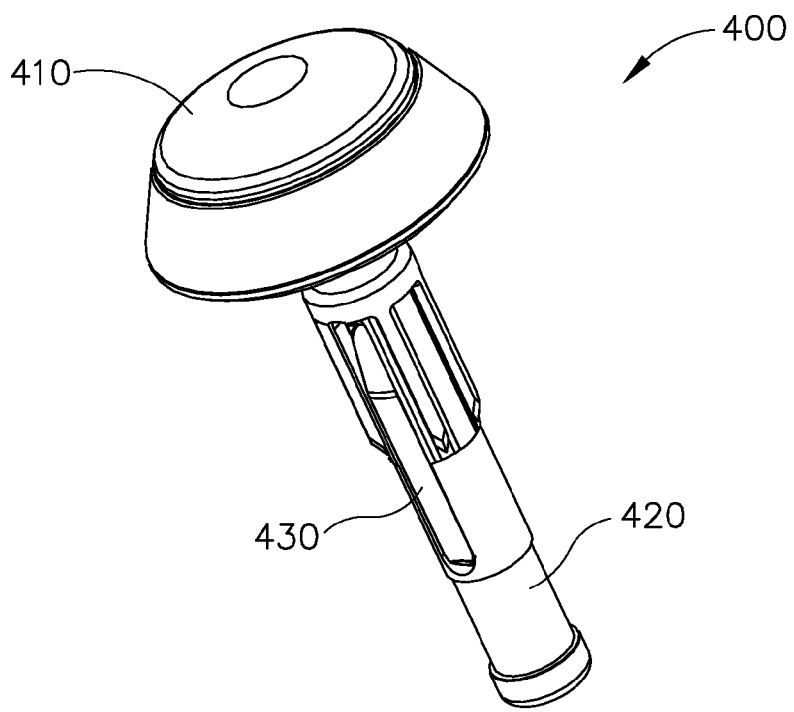
FIG. 3 depicts a perspective view of the anvil of the circular stapler of FIG. 1.
Figure 4:
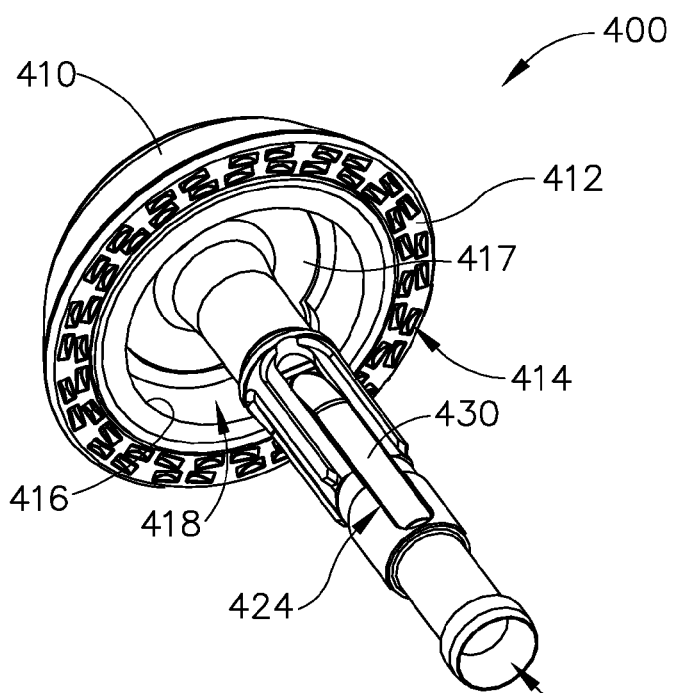
FIG. 4 depicts another perspective view of the anvil of FIG. 3.
Figure 5:
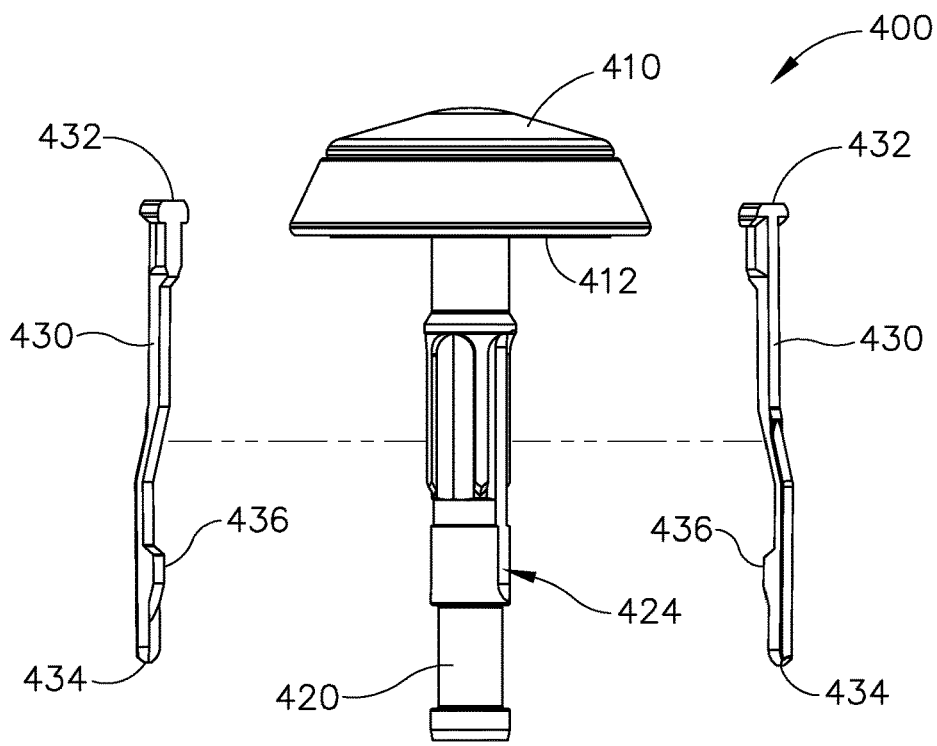
FIG. 5 depicts an exploded side elevational view of the anvil of FIG. 3.

As best seen in FIGS. 3-5, anvil (400) of the present example comprises a head (410) and a shank (420). Head (410) includes a proximal surface (412) that defines a plurality of staple forming pockets (414). Staple forming pockets (414) are arranged in two concentric annular arrays. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to radially inwardly toward the longitudinal axis defined by shank (420). Latch members (430) thus act as retaining clips. This allows anvil (400) to be removably secured to a trocar (330) of stapling head assembly (300) as will be described in greater detail below. It should be understood, however, that latch members (436) are merely optional. Anvil (400) may be removably secured to a trocar (330) using any other suitable components, features, or techniques.

In addition to or in lieu of the foregoing, anvil (400) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

B. Exemplary Stapling Head Assembly

Figure 7:
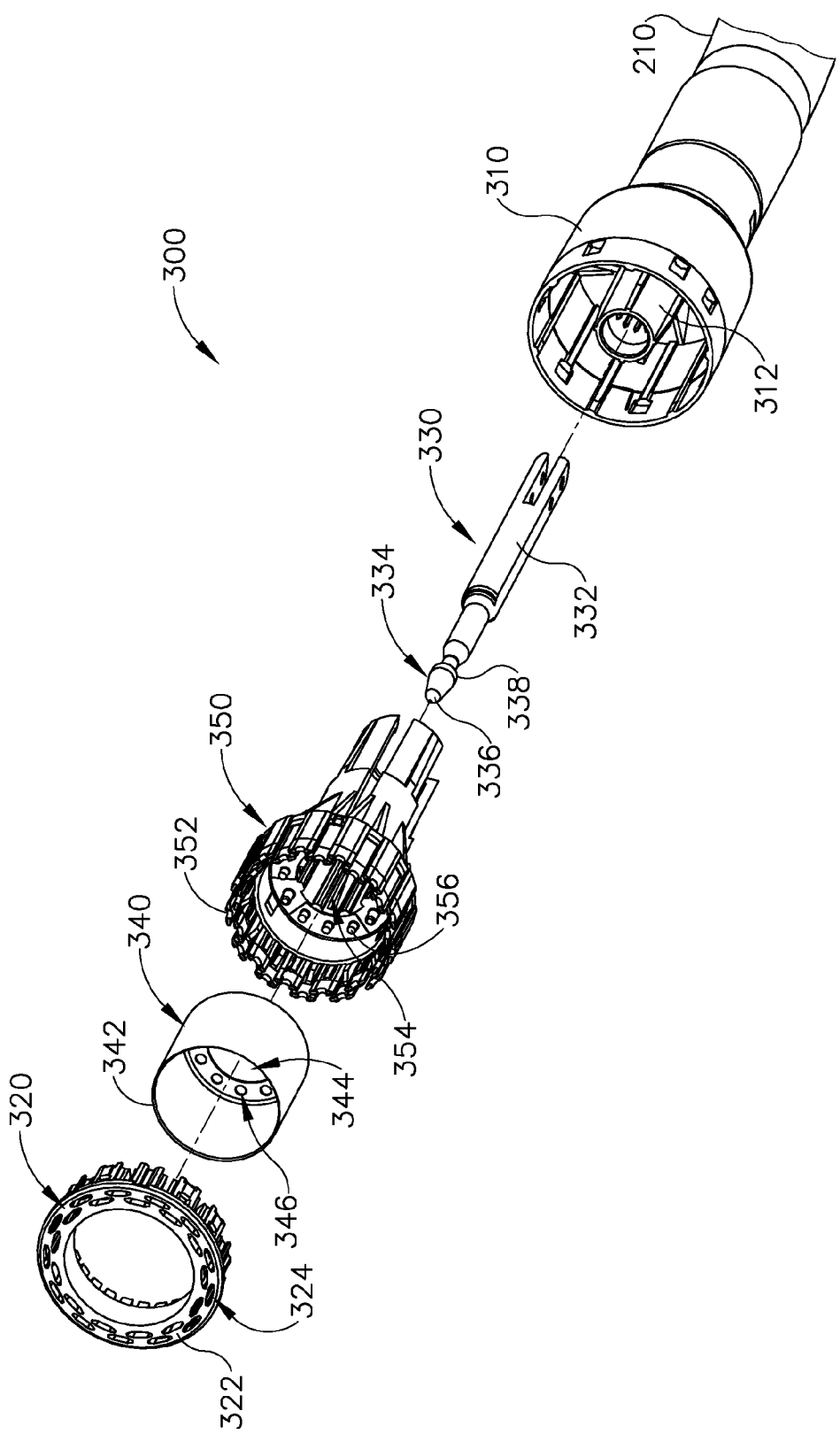
FIG. 7 depicts an exploded perspective view of the stapling head assembly of FIG. 6.

As best seen in FIGS. 6-7, stapling head assembly (300) of the present example is coupled to a distal end of shaft assembly (200) and comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). As will be described in greater detail below, trocar (330) is operable to translate distally and proximally relative to tubular casing (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (420). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive core member (312) of tubular casing (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310). An annular array of openings (346) formed in knife member (340) is configured to complement the annular array of studs (356) of staple driver member (350), such that knife member (340) is fixedly secured to staple driver member (350) via studs (356) and openings (346). Other suitable structural relationships between knife member (340) and stapler driver member (350) will be apparent to those of ordinary skill in the art in view of the teachings herein.

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

As best seen in FIG. 6, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In addition to or in lieu of the foregoing, stapling head assembly (300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

C. Exemplary Shaft Assembly

Figure 8:
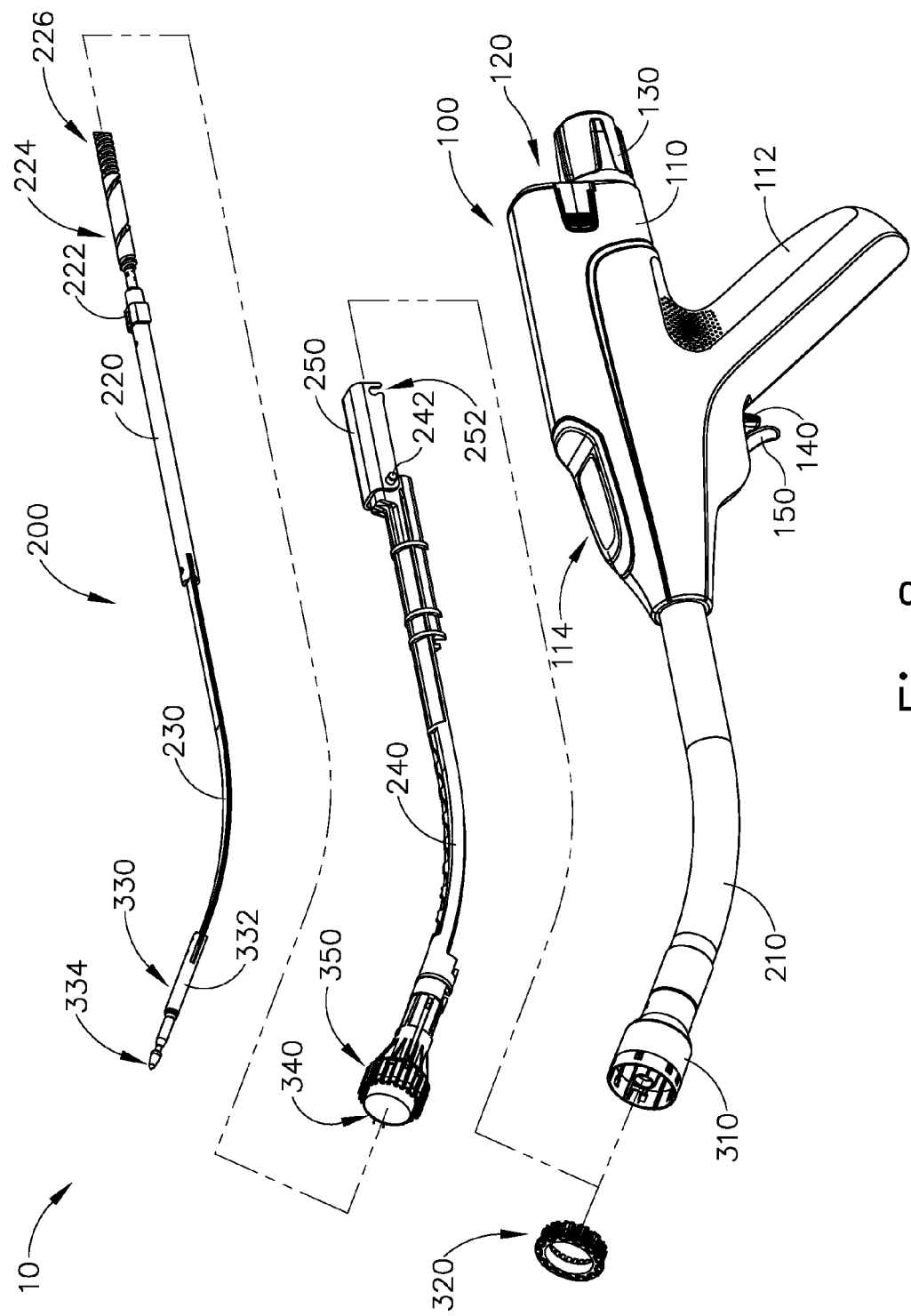
FIG. 8 depicts an exploded perspective view of the circular stapler of FIG. 1, with portions of the shaft assembly shown separately from each other.

FIG. 8 shows various components of shaft assembly (200), which couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226). Details regarding the movement of trocar actuation rod (220) will be described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Details regarding the movement of drive bracket (250) will be described in greater detail below.

While not shown in FIG. 8, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

In addition to or in lieu of the foregoing, shaft assembly (200) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

D. Exemplary Actuator Handle Assembly

Figure 9:
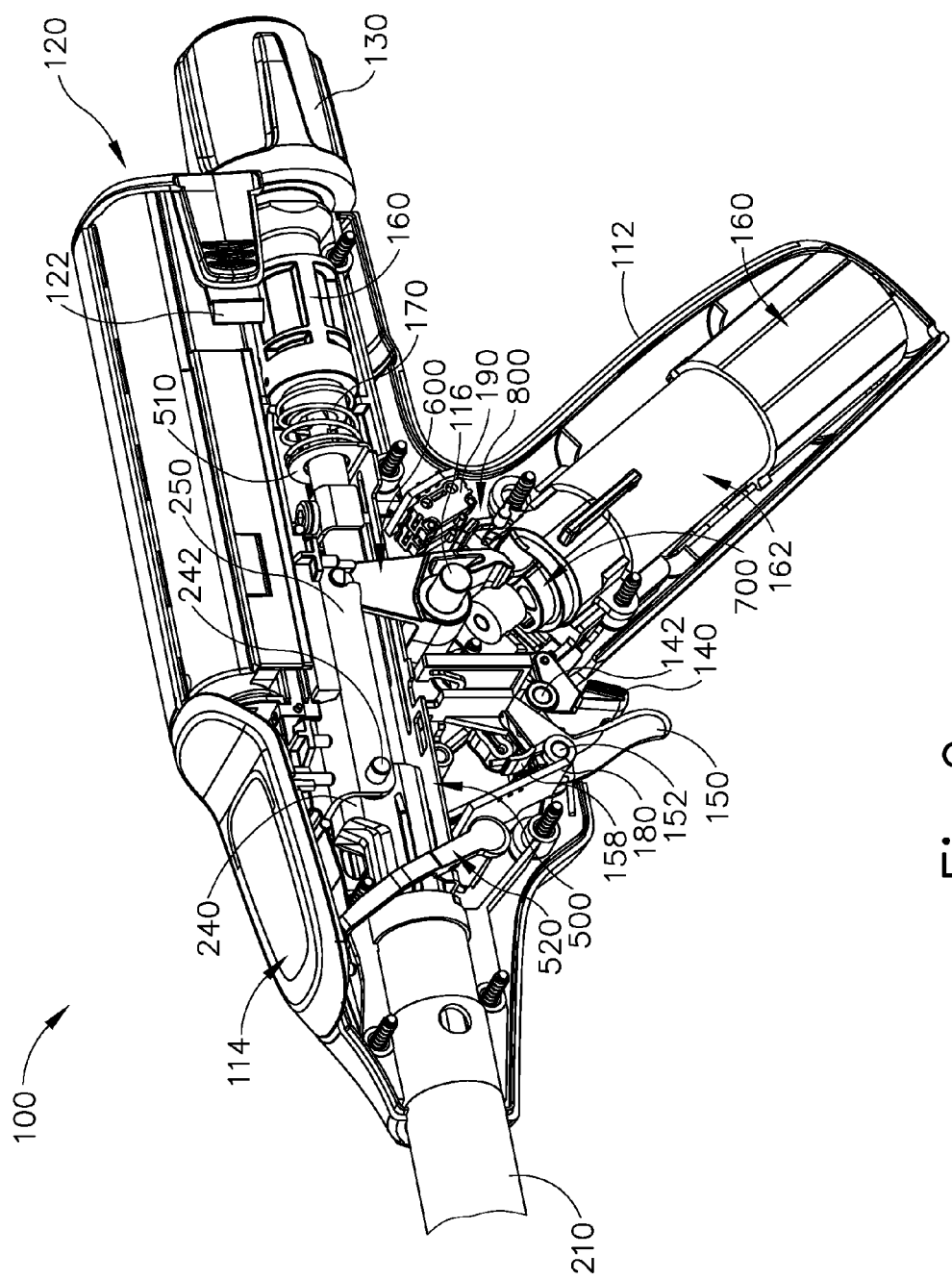
FIG. 9 depicts a perspective view of the handle assembly of the circular stapler of FIG. 1, with a housing half omitted to reveal internal components of the handle assembly.

As shown in FIG. 9, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

1 Exemplary Anvil Actuation Assembly

Knob (130) protrudes proximally from casing (110) of handle assembly and is rotatable relative to casing (110). As shown in FIG. 9, a nut (160) is secured to the distal end of knob (130). In the present example, nut (160) is fixedly secured to the distal end of knob (130) such that nut (160) will rotate unitarily with knob (130). Nut (160) and knob (130) are configured to cooperate with trocar actuation rod (220) to thereby translate trocar actuation rod (220) longitudinally relative to casing (110) in response to rotation of nut (160) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (160) and knob (130). In particular, trocar actuation rod (220) is positioned within handle assembly (100) such that coarse helical threading (224) will selectively engage a thread engagement feature (not shown) within the interior of nut (160); and such that fine helical threading (226) will selectively engage a thread engagement feature (not shown) within the interior of knob (130). In some versions, the thread engagement feature of nut (160) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (160) and knob (130) are rotated relative to casing (110), trocar actuation rod (220) travels proximally through a first range of longitudinal motion where coarse helical threading (224) is engaged with nut (160) to provide a relatively rapid rate of translation. Fine helical threading (226) is not engaged with knob (130) during this range of motion. When nut (160) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (160) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 21C and as described in greater detail below.

2. Exemplary Trigger Lockout Assembly

As noted above, knob may be used to adjust the gap distance (d) between opposing surfaces (412, 322) of anvil (400) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed by staple forming pockets (414). This may result in leakage at the anastomosis site, and in some cases may ultimately lead to the separation of the anatomical lumen sections that are joined at the anastomosis site. If the gap distance (d) is too small, the internal structure of the tissue compressed between surfaces (412, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Figure 10:
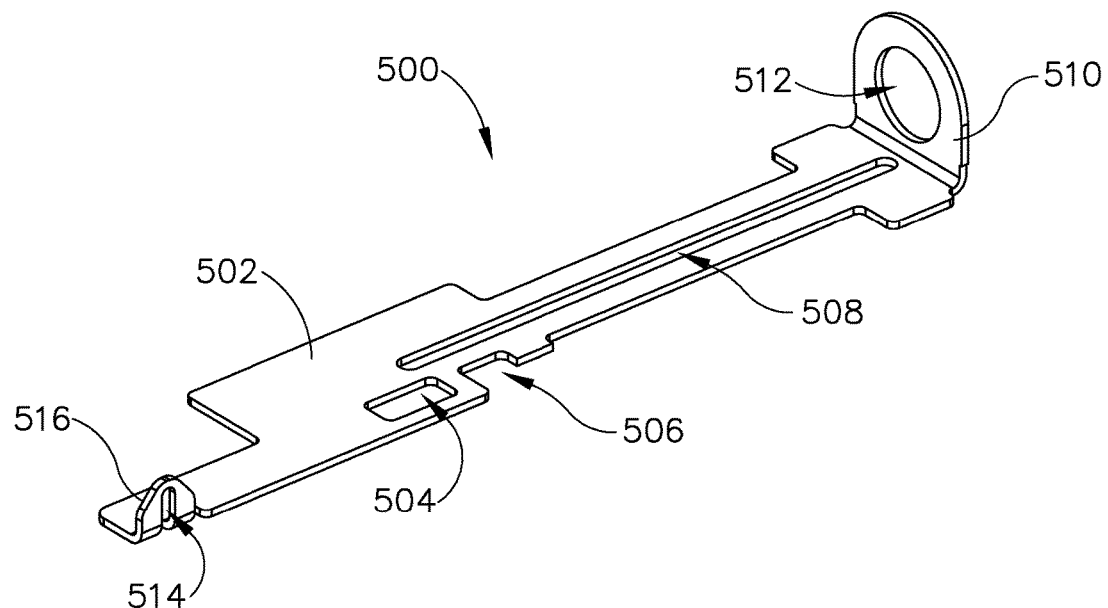
FIG. 10 depicts a perspective view of a bracket of the handle assembly of FIG. 9.

FIGS. 9-12E show components that provide feedback to the operator to indicate whether the gap distance (d) is within an appropriate range; and prevent the operator from actuating stapling head assembly (300) unless the gap distance (d) is within an appropriate range. As best seen in FIGS. 12B-12C, a bracket (500) is configured and positioned to move in response to movement of trocar actuation rod (220). As best seen in FIG. 10, bracket (500) includes a rigid body (502) that defines a first slot (504), a second slot (506), and a third slot (508). An upright feature (510) is positioned at the proximal end of body (502) and defines an opening (512). Trocar actuation rod (220) extends coaxially through opening (512). As shown in FIG. 9, a coil spring (170) is interposed between the proximal end of upright feature (510) and a rigid bulkhead feature that is defined by casing (110) and that forms a support journal for nut (160). The bulkhead is fixed within casing (110) and thereby provides a ground for the proximal end of coil spring (170), such that coil spring (170) resiliently imparts a distal bias to bracket (500) via upright feature (510). Bracket (500) further includes a laterally presented flange (516) at the distal end of body (502). Flange (516) defines a slot (514).

Figure 11:
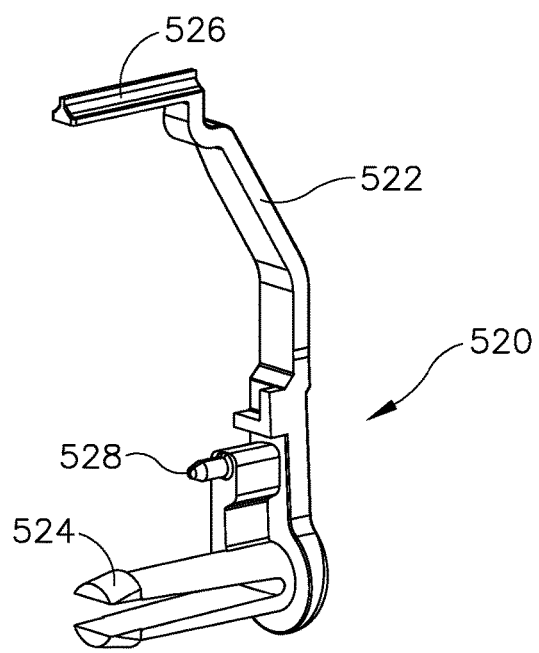
FIG. 11 depicts a perspective view of an indicator member of the handle assembly of FIG. 9.
Figure 12A:
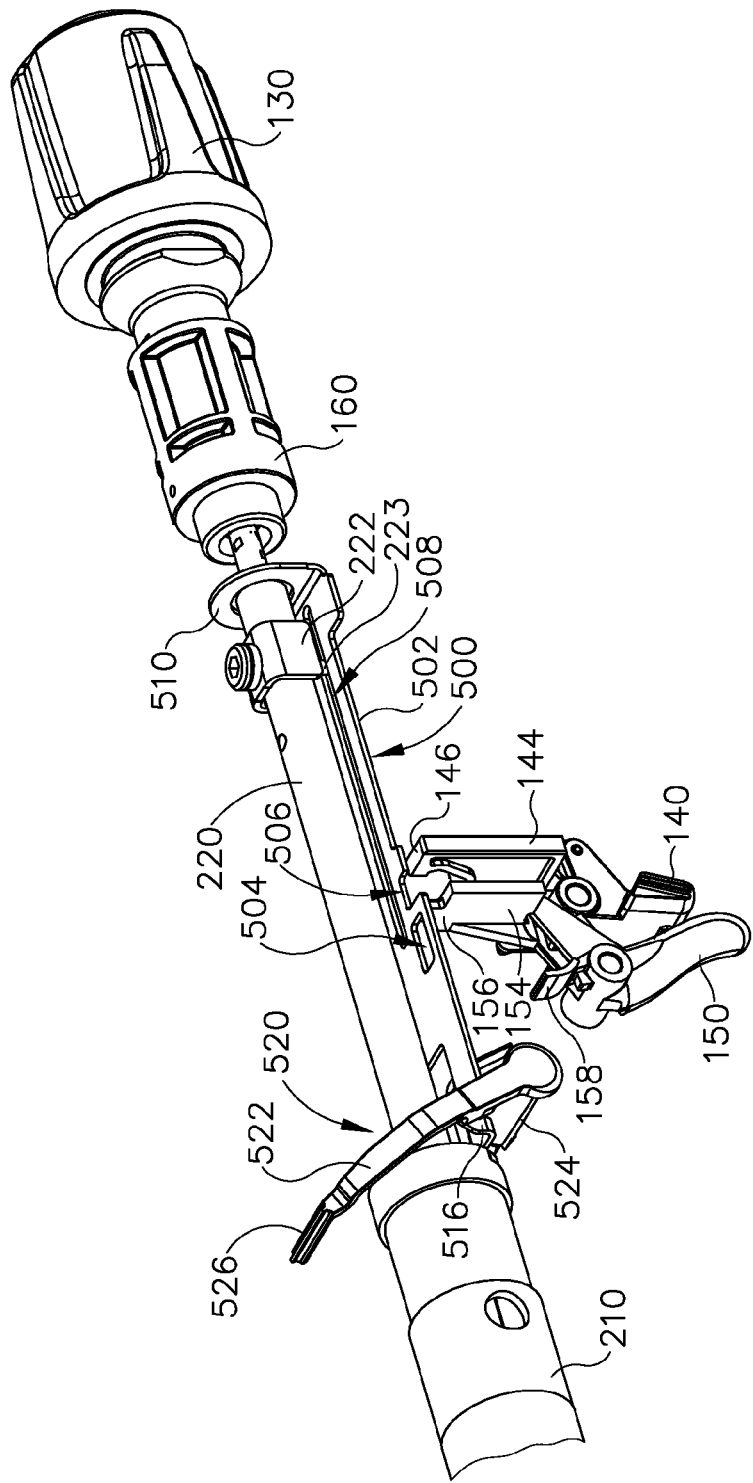
FIG. 12A depicts a perspective view of an anvil actuation assembly of the circular stapler of FIG. 1, an actuation rod in a first position.
Figure 12B:
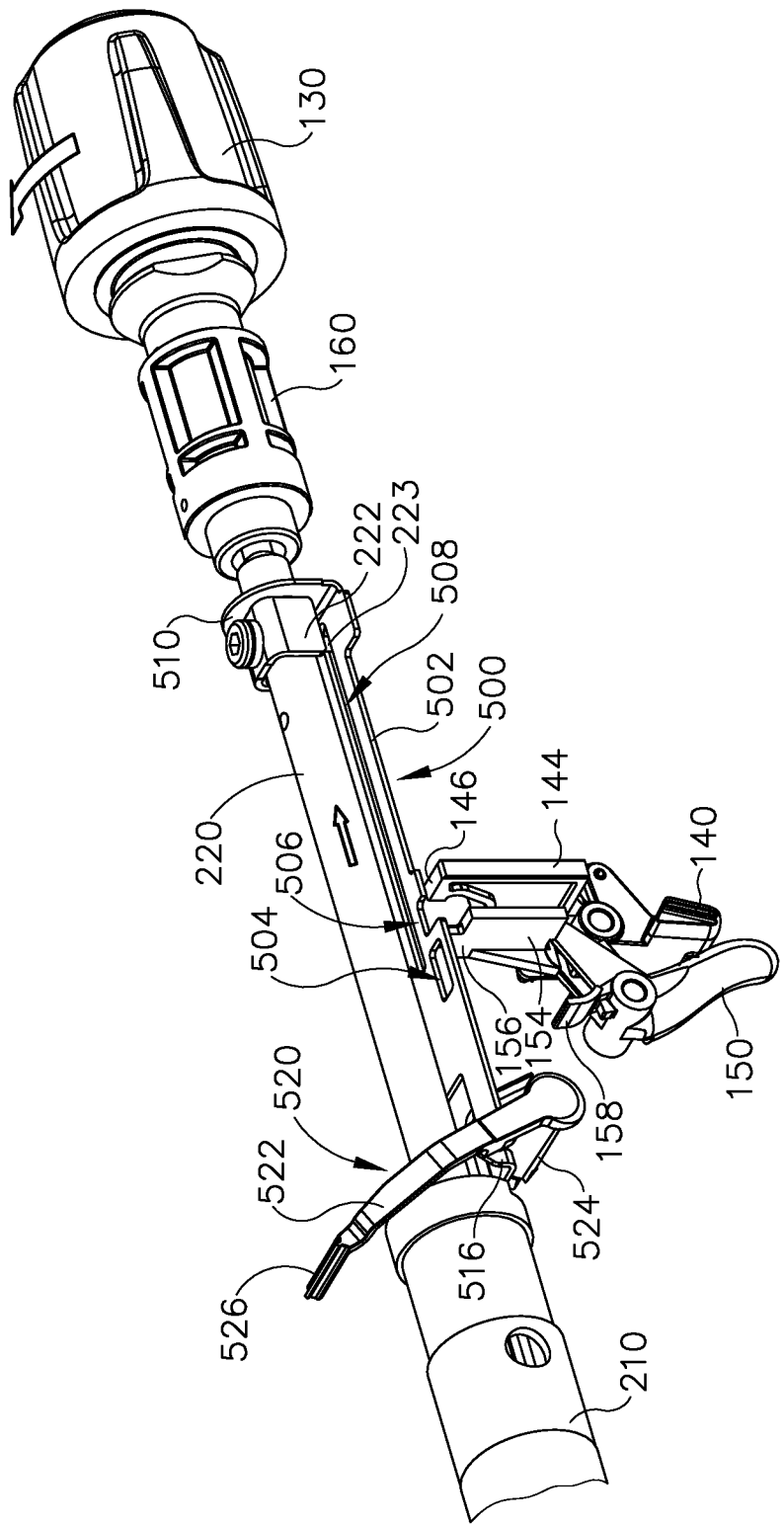
FIG. 12B depicts a perspective view of the anvil actuation assembly of FIG. 12A, with the actuation rod moved to a second position to engage the bracket of FIG. 10.
Figure 12C:
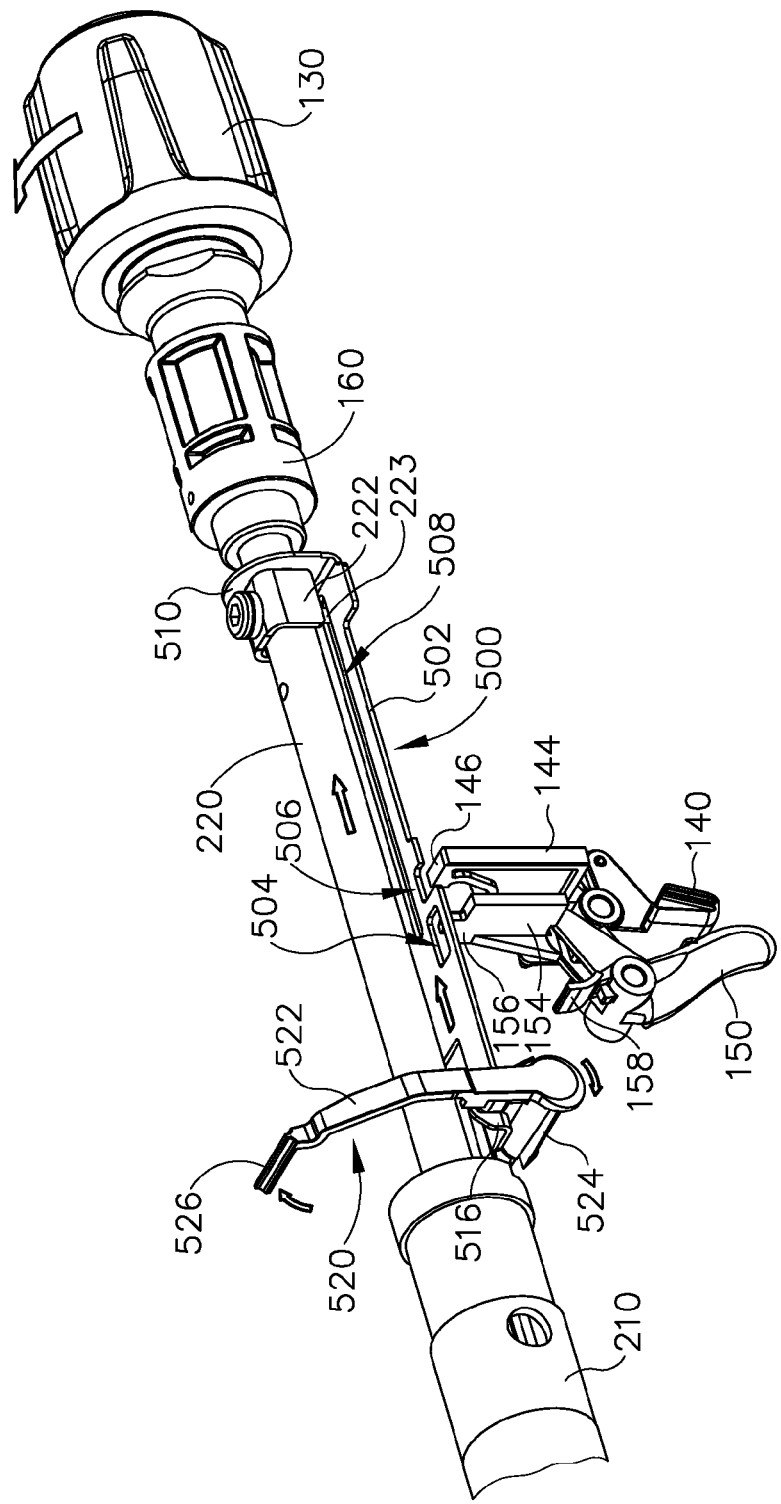
FIG. 12C depicts a perspective view of the anvil actuation assembly of FIG. 12A, with the actuation rod moved to a third position to retract the bracket of FIG. 10 proximally.

As best seen in FIGS. 12B-12C, an indicator member (520) is configured to pivot in response to translation of bracket (500). As best seen in FIG. 11, indicator member (520) comprises an upright arm (522), a snap pin (524) projecting laterally from a lower end of arm (522), an indicator needle (526) projecting laterally from an upper end of arm (522), and a coupling pin (528) projecting laterally from an intermediate region of arm (522). Snap pin (524) is configured to snap into a complementary recess provided by casing (110). Snap pin (524) thereby secures indicator member (520) to casing (110) yet permits indicator member (520) to pivot relative to casing (110) about the longitudinal axis of snap pin (524). Indicator needle (526) is positioned to be visible through window (114) of handle assembly (110) to thereby visually indicate the pivotal position of indicator member (520). Coupling pin (528) is slidably received in slot (514) of flange (516) of bracket (500). This engagement between indicator member (520), casing (110), and bracket (500) provides pivotal movement of indicator member (520) in response to translation of bracket (500).

Bracket (500) is configured to selectively prevent and permit actuation of triggers (140, 150). In particular, slots (504, 506) of bracket (500) are configured to selectively provide clearance for actuation of triggers (140, 150). As shown in FIGS. 12A-12E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (502) of bracket (500) is configured to prevent this movement of first upright member (144) and safety trigger (140) by engaging the upper end (146) of first upright member (144). Body (502) thus blocks movement of first upright member (144) and safety trigger (140)

until bracket (500) is moved to a position where slot (506) is aligned with upper end (146) to thereby provide clearance for upward movement of first upright member (144). It should therefore be understood that safety trigger (140) cannot be pivoted toward pistol grip (112) until slot (506) is positioned over upper end (146).

Similarly, firing trigger (150) is pivotably coupled with a second upright member (154). Second upright member (154) is coupled with casing (110) such that second upright member (154) is configured to translate upwardly in response to pivoting of safety trigger (150) toward pistol grip (112). However, body (502) of bracket (500) is configured to prevent this movement of second upright member (154) and firing trigger (150) by engaging the upper end (156) of second upright member (154). Even if safety trigger (140) is pivoted out of the way to otherwise permit movement of firing trigger (150), body (502) blocks movement of second upright member (154) and firing trigger (150) until bracket (500) is moved to a position where slot (504) is aligned with upper end (156) to thereby provide clearance for upward movement of second upright member (154). It should be understood that, even if safety trigger (140) is pivoted out of the way to otherwise permit movement of firing trigger (150), firing trigger (150) cannot be pivoted toward pistol grip (112) until slot (504) is positioned over upper end (156).

Third slot (508) is configured to receive a downwardly projecting boss (223) of clip (222), which is rigidly secured to trocar actuation rod (220). While casing (110) is configured to allow bracket (500) to translate longitudinally within casing (110), casing (110) includes rails, channels, and/or other features that prevent bracket (500) from rotating within casing (110). Thus, the positioning of boss (223) in slot (508) prevents clip (222) and trocar actuation rod (220) from rotating within casing (110). Boss (223) and slot (508) nevertheless allow bracket (500) to translate longitudinally within casing (110) as will be described in greater detail below.

FIGS. 12A-12E depict the above-described components at various stages of operation. In particular, in FIG. 12A, trocar actuation rod (220) is in a distal-most position, such that trocar (330) is in a distal-most position. At this stage, the operator may couple anvil (400) with trocar (330) by inserting trocar (330) into bore (422) until latch members (430) are secured to head (334) of trocar (330). The operator then rotates knob (130), which rotates nut (160). As knob (130) and nut (160) rotate, engagement between coarse helical threading (224) of trocar actuation rod (220) and the complementary feature of nut (160) causes trocar actuation rod (220) to retract proximally at a relatively rapid rate, such that trocar actuation rod (220) reaches the position shown in FIG. 12B. This provides proximal retraction of trocar actuation rod (220) provides retraction of trocar (330) and anvil (400). As trocar actuation rod (220) moves from the position shown in FIG. 12A to the position shown in FIG. 12B, bracket (500) remains stationary. This is due to the fact that clip (222) is spaced apart from upright feature (510) at the stage shown in FIG. 12A and does not engage upright feature (510) until trocar actuation rod (220) reaches the position shown in FIG. 12B.

After reaching the stage shown in FIG. 12B, the operator may continue rotating knob (130) and nut (160), which causes further proximal retraction of trocar actuation rod (220) as shown in FIG. 12C. This of course causes further proximal retraction of trocar (330) and anvil (400). As trocar actuation rod (220) moves from the position shown in FIG. 12B to the position shown in FIG. 12C, clip (222) bears against bracket (500), driving bracket (500) proximally. This proximal movement of bracket (500) causes indicator member (520) to pivot from the position shown in FIG. 12B to the position shown in FIG. 12C due to the positioning of pin (528) in slot (514) of flange (516).

As indicator member (520) pivots from the position shown in FIG. 12B to the position shown in FIG. 12C, the operator may observe the position of indicator needle (526) through window (114) of handle assembly (110). As noted above, a series of hash marks, colored regions, and/or other fixed indicators may be positioned adjacent to window (114) in order to provide a visual context for indicator needle (526), thereby facilitating operator evaluation of the position of needle (526) within window (114). It should be understood that the position of needle (526) within window (114) will be indicative of the longitudinal position of trocar (330) and anvil (400). The position of needle (526) within window (114) will thus indicate the gap distance (d) between opposing surfaces (412, 322) of anvil (400) and stapling head assembly (300). While observing the position of needle (526) within window (114), the operator may rotate knob (130) clockwise or counterclockwise to further retract or advance trocar (330) and anvil (400), thereby providing fine adjustment of the gap distance (d) until a desired gap distance (d) is reached within an appropriate range.

In order to provide fine control of the gap distance (d) adjustment at the stage shown in FIG. 12C, trocar actuation rod (220) will be at a longitudinal position where fine helical threading (226) is engaged with a complementary feature of knob (130) and coarse helical threading (224) is disengaged from the complementary feature of nut (160). In some versions, coarse helical threading (224) disengages nut (160) and fine helical threading (226) begins to engage knob (130) once trocar actuation rod (220) reaches the longitudinal position shown in FIG. 12B (i.e., when clip (222) first engages upright member (510)). In some other versions, the transition from engagement by coarse helical threading (224) to fine helical threading (226) occurs sometime between the stage shown in FIG. 12B and the stage shown in FIG. 12C. Other suitable stages at which the coarse-to-fine transition may occur will be apparent to those of ordinary skill in the art in view of the teachings herein. It should also be understood that some alternative versions of trocar actuation rod (220) may have just a single threading section, with the pitch of the threading being consistent along the length of the threading. In other words, trocar actuation rod (220) does not necessarily need to have two different sections of threading (224, 226) with different pitches.

At the stage shown in FIG. 12C, slot (506) is aligned with upper end (146) to thereby provide clearance for upward movement of first upright member (144). Similarly, slot (504) is aligned with upper end (156) to thereby provide clearance for upward movement of second upright member (154). In the present example, slots (504, 506) are sized and positioned such that slots (504, 506) only provide clearance for upward movement of upright members (144, 154) when the gap distance (d) is within a clinically acceptable range. By way of example only, a "clinically acceptable range" for the gap distance (d) may be between approximately 0.110 inches and approximately 0.040 inches. As another merely illustrative example, a "clinically acceptable range" for the gap distance (d) may be between approximately 0.110 inches and approximately 0.020 inches. Even when slots (504, 506) are positioned to provide clearance for upward movement of upright members (144, 154) as shown in FIG. 12C, safety trigger (140) will still block pivotal movement of firing trigger (150) about a pin (152) (FIG. 9) when safety trigger (140) is in the non-actuated position shown in FIG. 12C. Thus, in order to enable movement of firing trigger (150), the operator will need to first actuate safety trigger (140) about a pin (142) (FIG. 9) from the position shown in FIG. 12C to the position shown in FIG. 12D.

Figure 12D:
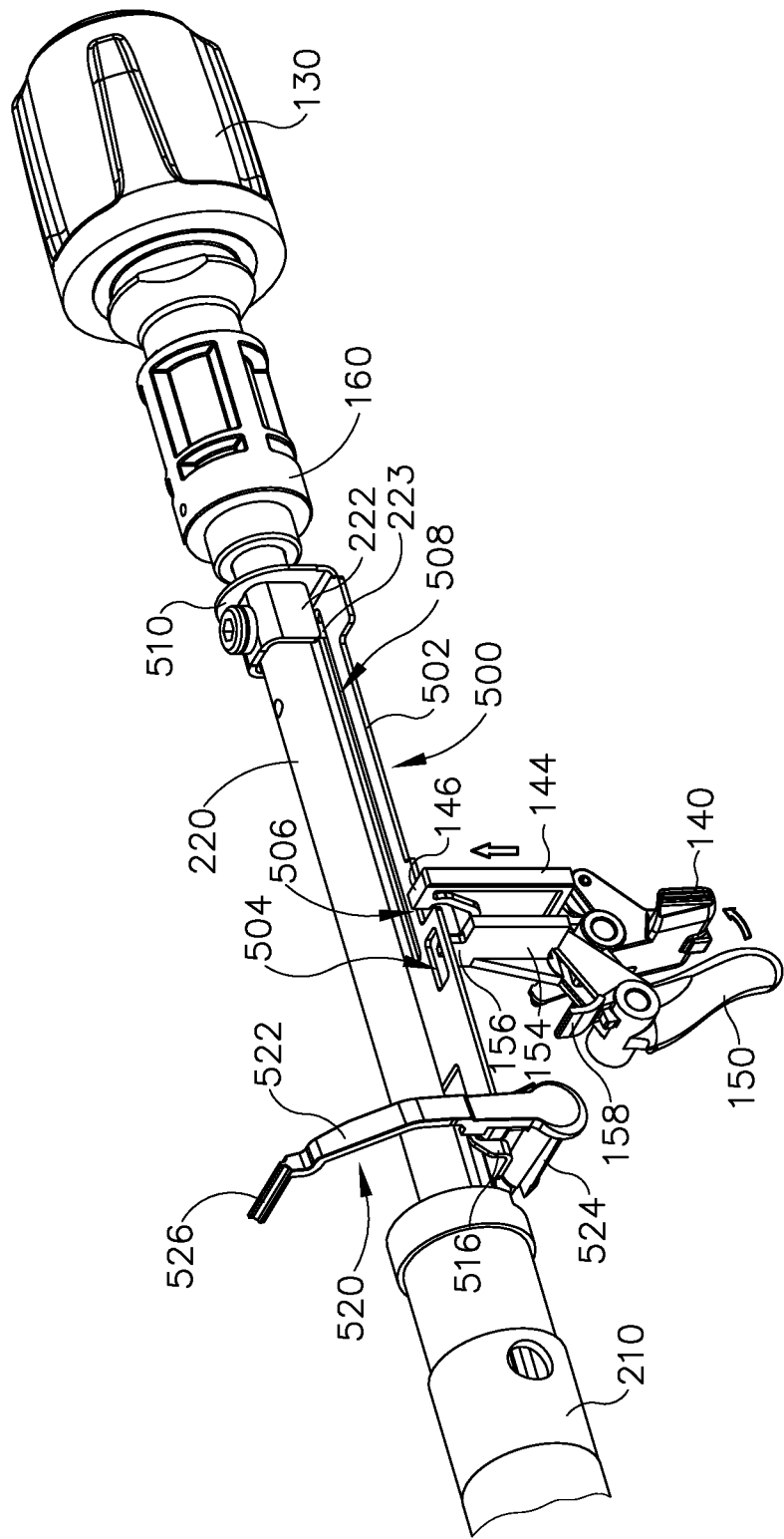
FIG. 12D depicts a perspective view of the anvil actuation assembly of FIG. 12A, with a safety trigger pivoted from a first position to a second position.

As shown in FIG. 12D, upper end (146) passes through slot (506) as safety trigger (140) is pivoted from the position shown in FIG. 12C to the position shown in FIG. 12D. It should be understood that this movement of upper end (146) would not be possible at the stages shown in FIGS. 12A-12B (when the gap distance (d) is too great) because body (502) would physically block upward movement of upright member (144), thereby physically blocking pivotal movement of safety trigger (140). In the present example, a cap (not shown) incorporated into knob (130) prevents knob (130) from rotating to a point where anvil (400) would be retracted too far proximally (such that the gap distance (d) is too small). In some other variations, even if knob (130) were to permit anvil (400) to be retracted too far proximally (such that the gap distance (d) is too small), body (502) would physically block upward movement of upright member (144), thereby physically blocking pivotal movement of safety trigger (140), in the event that the operator retracts trocar (330) and anvil (400) too far proximally (such that the gap distance (d) is too small). Regardless of whether body (502), knob (130), or some other feature prevents actuation when the gap distance (d) would be too small, it should be understood that instrument (10) permits actuation of safety trigger (140) only when the gap distance (d) is within the clinically acceptable range.

Figure 12E:
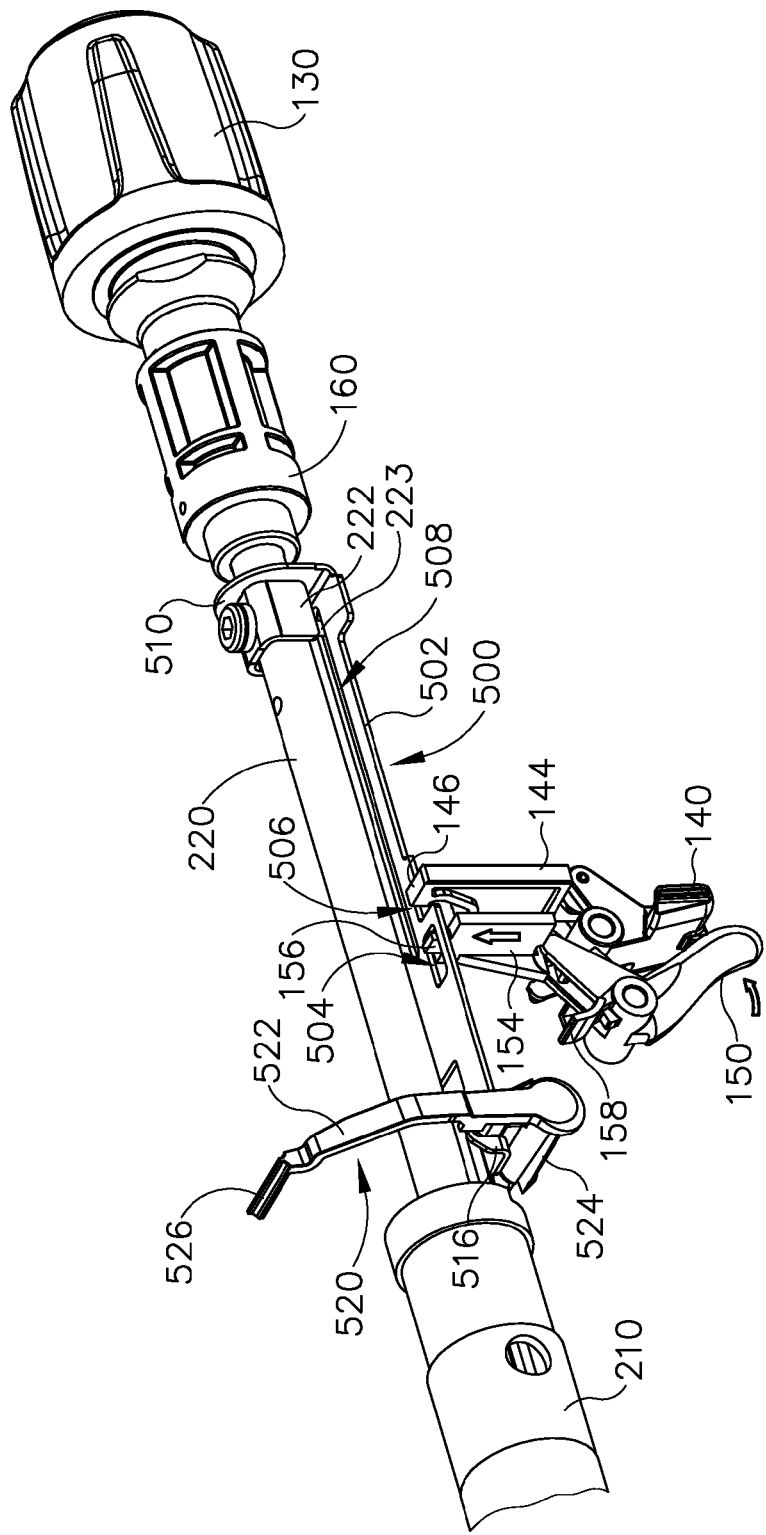
FIG. 12E depicts a perspective view of the anvil actuation assembly of FIG. 12A, with a firing trigger pivoted from a first position to a second position.

As noted above, safety trigger (140) is configured to prevent actuation of firing trigger (150) until safety trigger (140) has been actuated. Once safety trigger (140) has been actuated, the operator may actuate firing trigger (150) from the position shown in FIG. 12D to the position shown in FIG. 12E. As shown in FIG. 12E, upper end (156) passes through slot (504) as firing trigger (150) is pivoted from the position shown in FIG. 12D to the position shown in FIG. 12E. It should be understood that, even in the complete absence of safety trigger (140), this movement of upper end (156) would not be possible at the stages shown in FIGS. 12A-12B (when the gap distance (d) is too great) because body (502) would physically block upward movement of upright member (154), thereby physically blocking pivotal movement of firing trigger (150). It should also be understood that body (502) would also physically block upward movement of upright member (154), thereby physically blocking pivotal movement of firing trigger (150), in the event that the operator retracts trocar (330) and anvil (400) too far proximally (such that the gap distance (d) is too small). Thus, even in the complete absence of safety trigger (140), firing trigger (150) may only be actuated when the gap distance (d) is within the clinically acceptable range.

Firing trigger (150) of the present example includes an integral actuation paddle (158). Paddle (158) pivots forwardly as firing trigger (150) pivots from the position shown in FIG. 12D to the position shown in FIG. 12E. Paddle (158) is configured to actuate a switch of a motor activation module (180), which is shown in FIG. 9, when firing trigger (150) pivots from the position shown in FIG. 12D to the position shown in FIG. 12E. Motor activation module (180) is in communication with battery pack (120) and motor (160), such that motor activation module (180) is configured to provide activation of motor (160) with electrical power from battery pack (120) in response to paddle (158) actuating the switch of motor activation module (180). Thus, motor (160) will be activated when firing trigger (150) is pivoted from the position shown in FIG. 12D to the position shown in FIG. 12E. This activation of motor (160) will actuate stapling head assembly (300) as described in greater detail below.

3. Exemplary Stapling Head Actuation Assembly

FIGS. 13-20D show various components that are operable to actuate stapling head assembly (300). These components include motor (160), a gearbox (162), a rotary cam member (700), a cam follower (600), drive bracket (250) and stapling head assembly driver (240). Gearbox (162) is coupled with a drive shaft of motor (160) and is further coupled with cam member (700). Activation of motor (160) thus causes rotation of cam member (700) via gearbox (162). Various suitable configurations that may be used for gearbox (162) will be apparent to those of ordinary skill in the art in view of the teachings herein. Cam member (700) is configured to interact with cam follower (160) to pivot cam follower (160) in two angular directions about a pin (118) as will be described in greater detail below. Pin (118) is coupled with casing (110). A bushing (701) provides rotary support to cam member (700) relative to casing (110).

Figure 14:
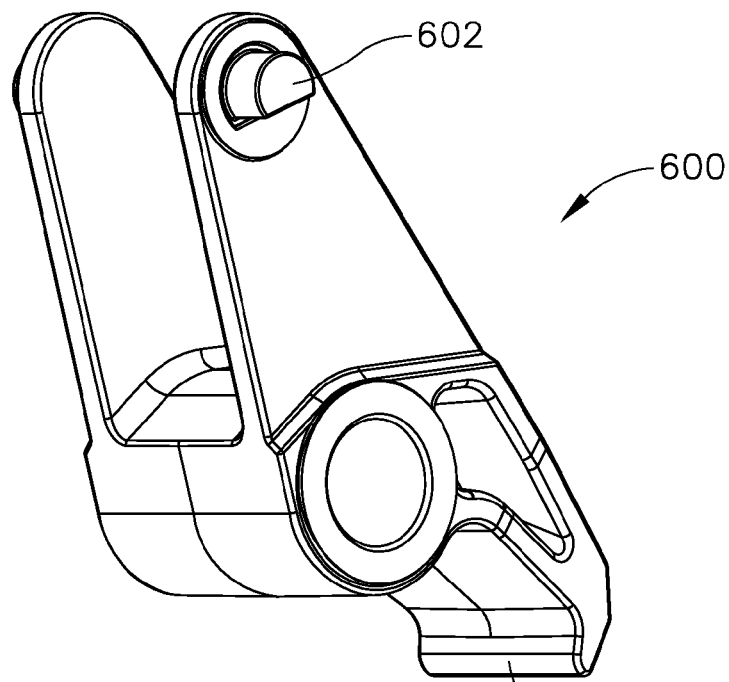
FIG. 14 depicts a perspective view of a cam follower of the stapling head actuation assembly of FIG. 13.
Figure 15:
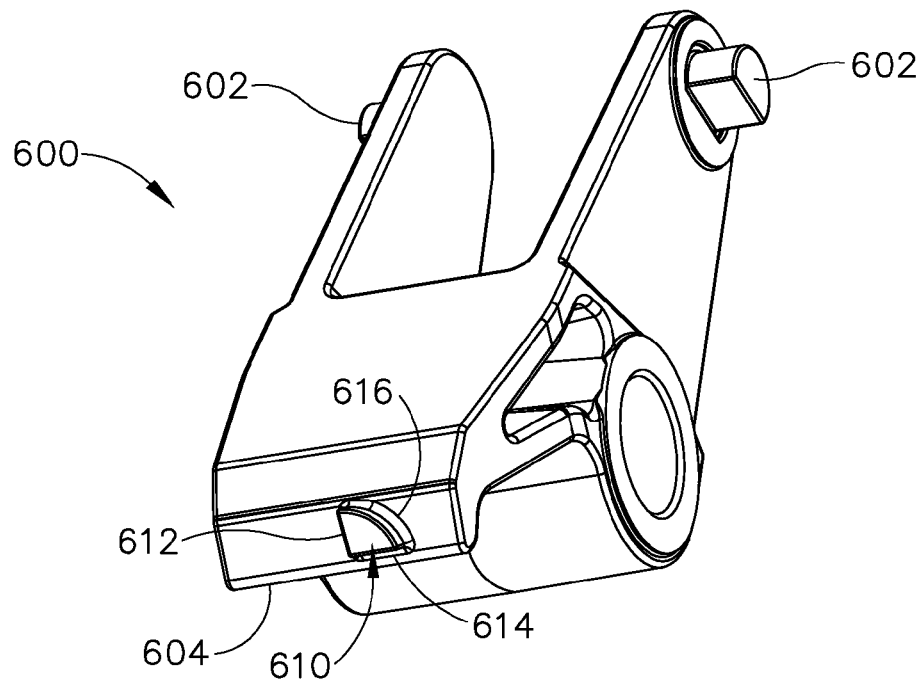
FIG. 15 depicts another perspective view of the cam follower of FIG. 14.

Cam follower (600) is pivotably coupled with drive bracket (250) via a pair of integral pins (602), which are received in complementary notches (252) of drive bracket (250). As shown in FIGS. 14-15, cam follower (600) includes a first bearing feature (604) and a second bearing feature (610). First bearing feature (604) consists of a rounded, horizontally extending surface. Second bearing feature (610) is shaped like a quarter-pie defined by a straight vertical surface (612), a horizontally extending surface (614), and a curved surface (616). Second bearing feature (610) projects proximally relative to first bearing feature (504).

Figure 16:
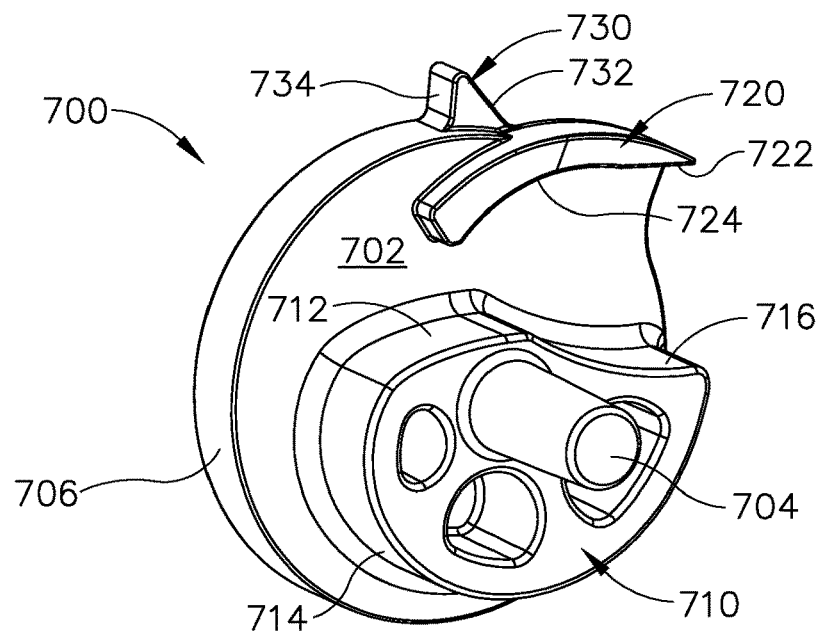
FIG. 16 depicts a perspective view of a rotary cam of the stapling head actuation assembly of FIG. 13.
Figure 17:
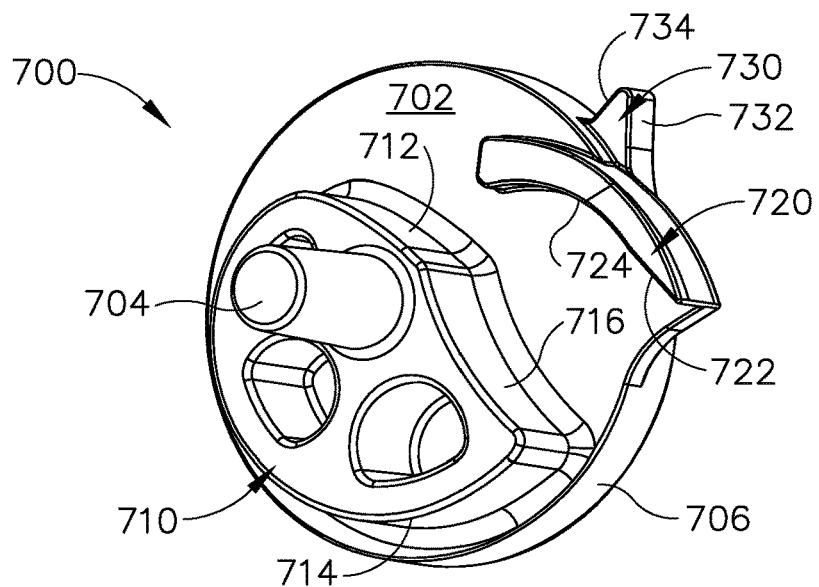
FIG. 17 depicts another perspective view of the rotary cam of FIG. 16.

FIGS. 16-17 show cam member (700) in greater detail. Cam member (700) comprises a distal face (702), a distally projecting post (704), and an outer circumferential surface (706). A first cam feature (710) and a second cam feature (720) project distally from distal face (702). Post (704) engages bushing (701). First cam feature (710) comprises a first surface region (712), a second surface region (714), and a third surface region (716). First surface region (712) is convexly defined by a relatively large radius of curvature, such that first surface region (712) is nearly flat. Second surface region (714) is convexly defined by a progressively increasing radius of curvature. Third surface region (716) is concavely defined by a relatively large radius of curvature. In addition to projecting distally from distal face (702), second cam feature (720) projects outwardly from outer circumferential surface (706). Second cam feature (720) includes a first surface region (722) and a second surface region (724). First surface region (722) is substantially flat while second surface region (724) is concavely curved. The origin of the radius of curvature for each curved surface region (712, 714, 716, 724) is offset from the center of post (704).

Figure 18A:
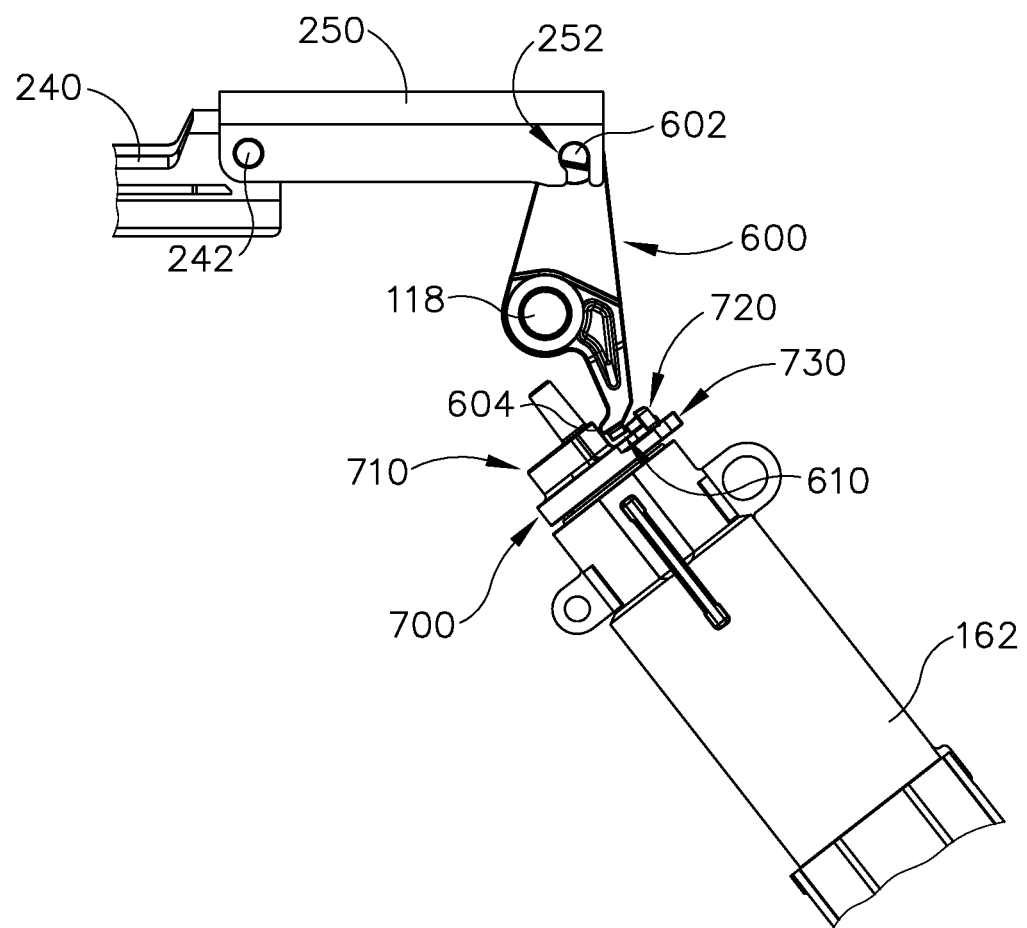
FIG. 18A depicts a side elevational view of the stapling head actuation assembly of FIG. 13, with the rotary cam in a first angular position and the cam follower in a first pivotal position.
Figure 18B:
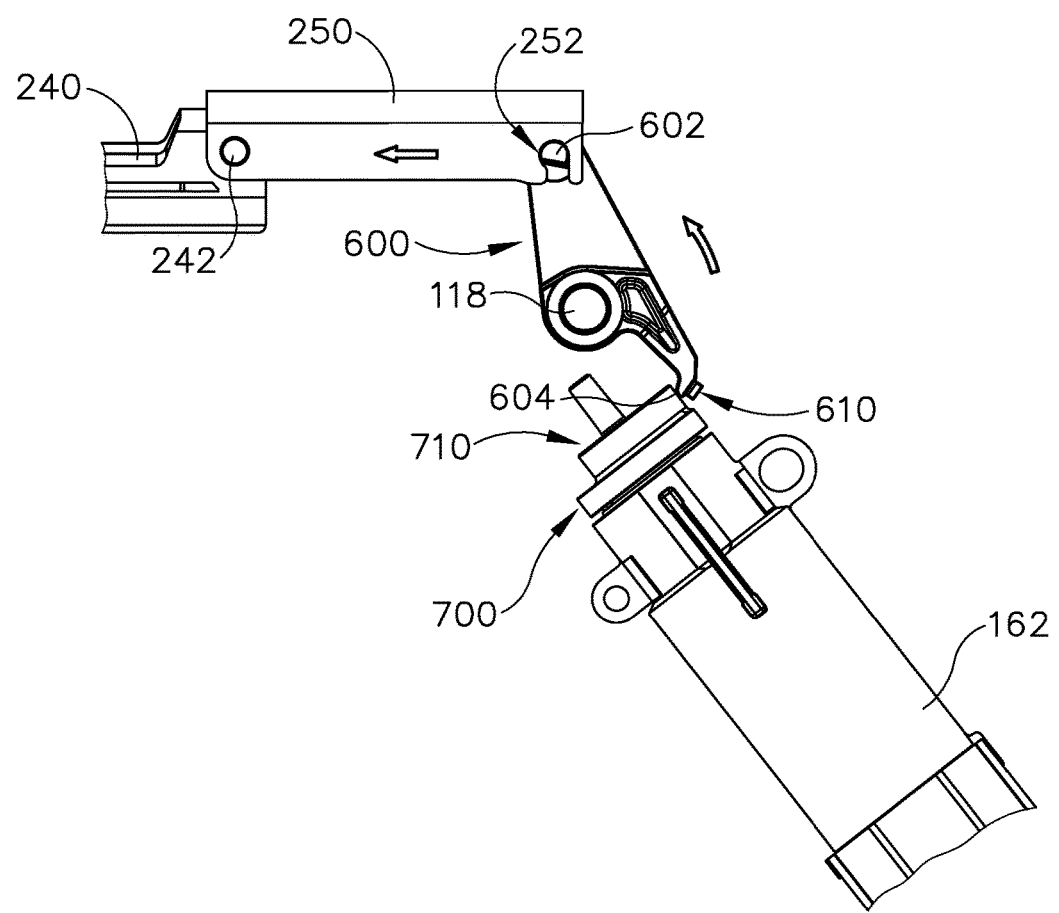
FIG. 18B depicts a side elevational view of the stapling head actuation assembly of FIG. 13, with the rotary cam in a second angular position and the cam follower in a second pivotal position.

FIGS. 18A-18B show the general interaction between cam follower (600) and first and second cam features (710, 720), though this interaction will be described in greater detail below with reference to FIGS. 20A-20D. As cam member (700) is rotated from the position shown in FIG. 18A to the position shown in FIG. 18B, first cam feature (710) bears against first bearing feature (604) of cam follower (600), causing cam follower to pivot about pin (118). In the view shown in FIGS. 18A-18B, cam follower (600) pivots counterclockwise as cam member (700) is rotated from the position shown in FIG. 18A to the position shown in FIG. 18B. As can be seen in the transition from FIG. 18A to FIG. 18B, this counterclockwise pivoting of cam follower (600) drives drive bracket (250) and stapling head assembly driver (240) distally, thereby actuating stapling head assembly (300). As cam member (700) continues to rotate in the same direction back toward the position shown in FIG. 18A, second cam feature (720) engages and bears against second bearing feature (610) of cam follower (600), causing cam follower (600) to pivot clockwise about pin (118). This clockwise pivoting of cam follower (600) about pin (118) retracts drive bracket (250) and stapling head assembly driver (240) proximally back toward the position shown in FIG. 18A.

Figure 19A:
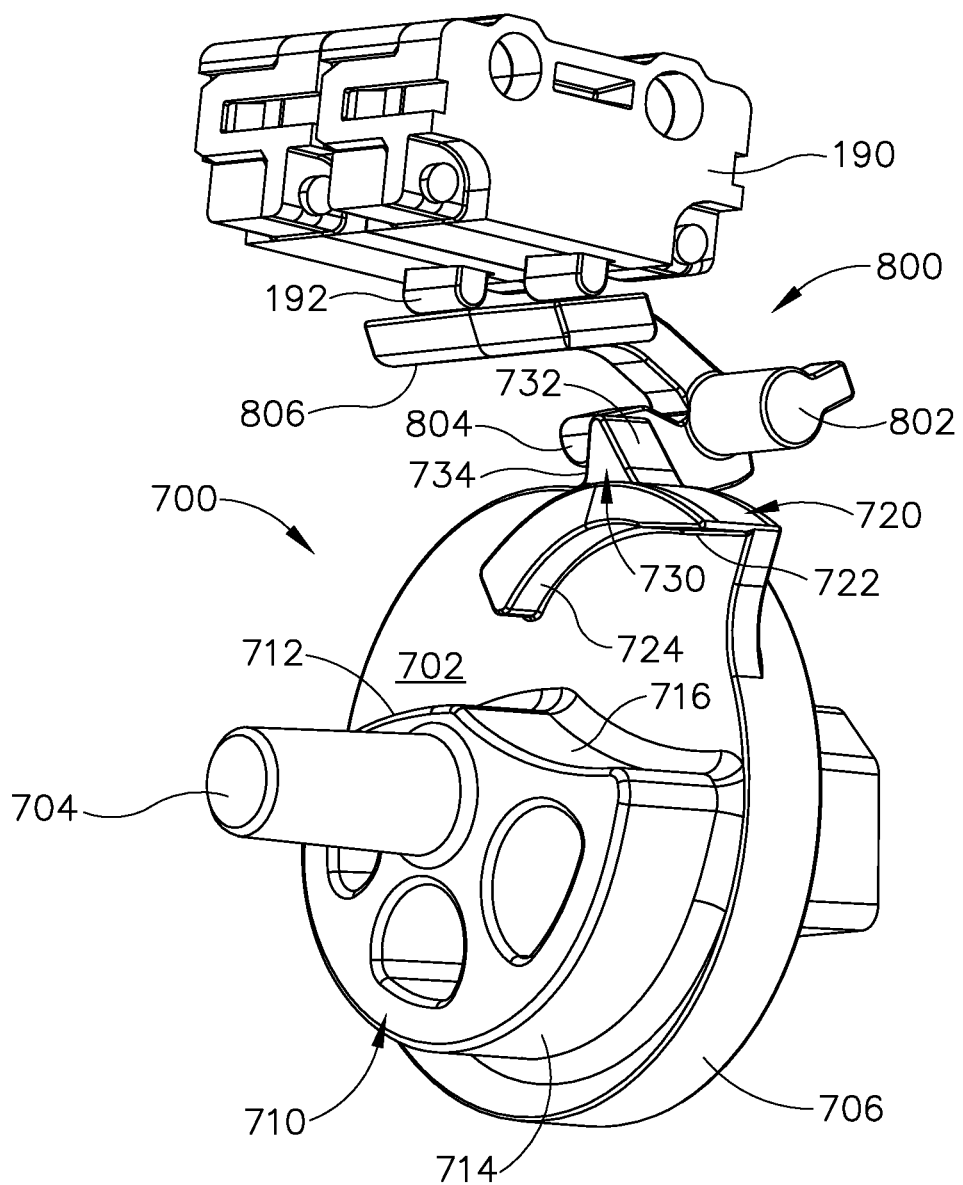
FIG. 19A depicts a perspective view of the rotary cam of FIG. 16, a rocker member, and a stop switch, with the rotary cam in a first angular position and the rocker member in a first pivotal position.
Figure 19B:
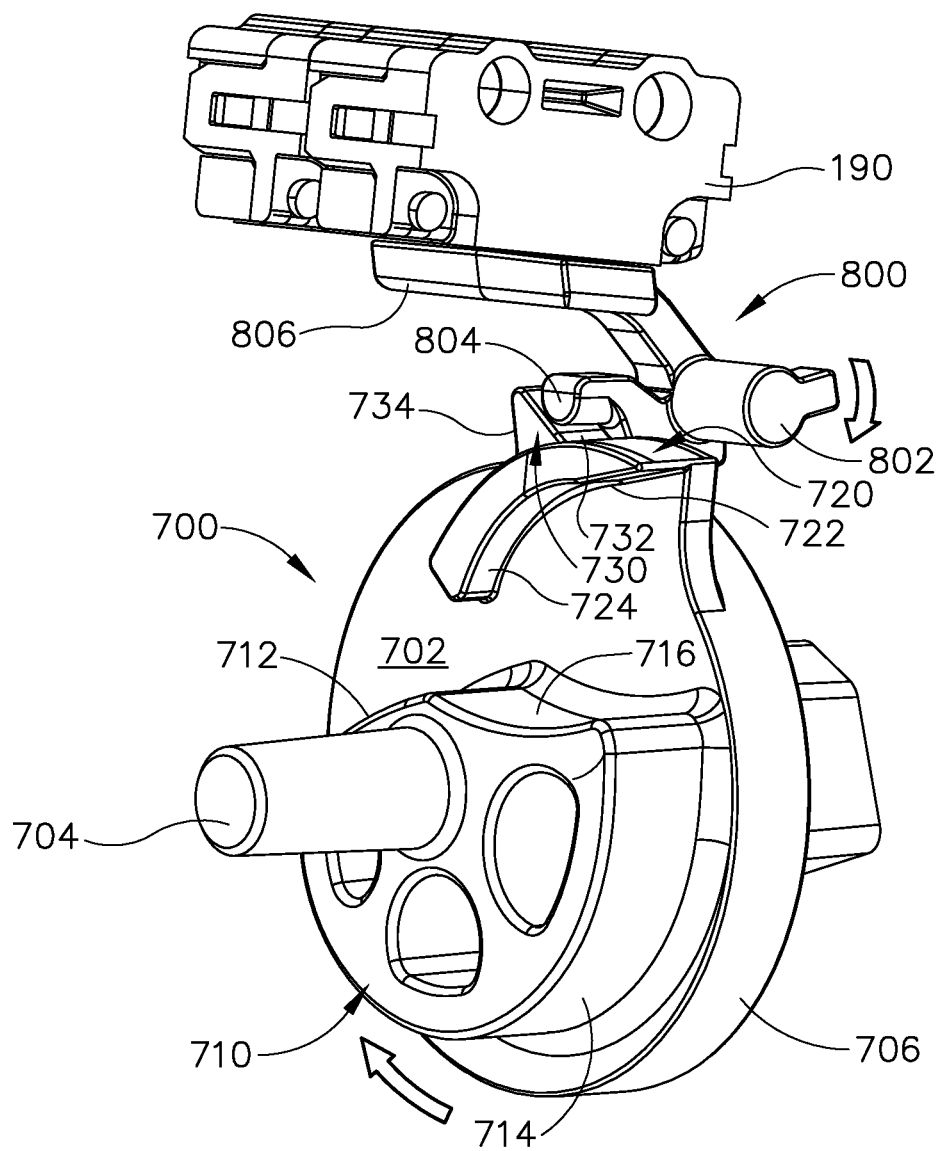
FIG. 19B depicts a perspective view of the rotary cam of FIG. 16, the rocker member of FIG. 19A, and the stop switch of FIG. 19A, with the rotary cam in a fourth angular position and the rocker member in a second pivotal position.

Referring back to FIGS. 16-17, a third cam feature (730) projects outwardly from outer circumferential surface (706). Third cam feature (730) comprises a first surface region (732) and a second surface region (734). First surface region (732) is flat and is oriented generally tangentially relative to outer circumferential surface (706). Second surface region (732) is also flat and is oriented radially outwardly relative to outer circumferential surface (706). Third cam feature (730) is configured to interact with a rocker member (800) as shown in FIGS. 19A-19B. Rocker member (800) comprises an integral pin (802), a bearing member (804), and a paddle (806). Pin (802) is pivotably coupled with casing (110), such that rocker member (800) is pivotable within casing (110) about the longitudinal axis defined by pin (802). Bearing member (804) is configured to interact with third cam feature (730) as will be described in greater detail below. Paddle (806) is configured to actuate a switch button (192) of a short circuit module (190) as will also be described in greater detail below.

FIG. 19A shows cam member (700) in the same position as shown in FIG. 18A. At this stage, second surface region (734) of third cam feature (730) is adjacent to bearing member (804) of rocker member (800). FIG. 19B shows cam member (700) in a position where cam member (700) has been rotated past the position shown in FIG. 18B and back toward the position shown in FIG. 18A. However, cam member (700) has not completed a full revolution. At the stage shown in FIG. 19B, first surface region (732) has engaged and borne against bearing member (804), thereby pivoting rocker member (800) about the longitudinal axis defined by pin (802). This has caused paddle (806) to actuate switch button (192) of short circuit module (190). Short circuit module (190) is configured to prevent motor (160) from further activation when switch button (192) has been actuated. In some versions, short circuit module (190) couples battery pack (120) with a power sink, in addition to short circuiting motor (160), when switch button (192) is actuated. This may result in discharge of battery pack (120) in addition to stopping activation of motor (160) once an actuation stroke of stapling head assembly (300) has been completed. By way of example only, short circuit module (190) may be configured and operable in accordance with at least some of the teachings of U.S. Pub. No. 2015/0083774, issued as U.S. Pat. No. 9,907,552 on Mar. 6, 2018, the disclosure of which is incorporated by reference herein. Other suitable configurations will be apparent to those of ordinary skill in the art in view of the teachings herein.

Figure 20A:
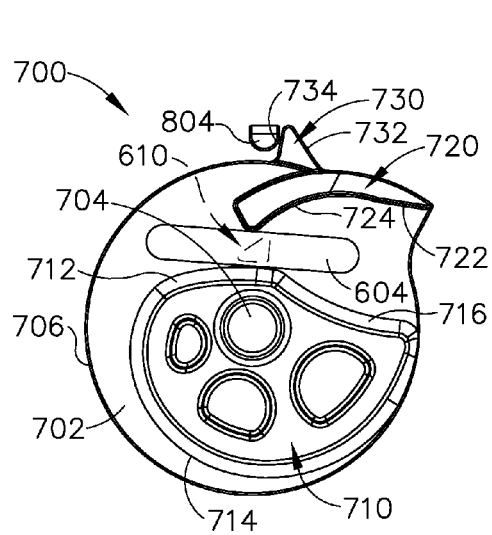
FIG. 20A depicts a schematic end view of the rotary cam of FIG. 16, the cam follower of FIG. 14, and the rocker member of FIG. 19A, with the rotary cam in the first angular position, the cam follower in the first pivotal position, and the rocker member in the first pivotal position.

FIGS. 20A-20D schematically depict the interaction between cam member (700), features of cam follower (600), and features of rocker member (800) as cam member (700) rotates. It should be understood that the rotation of cam member (700) throughout the stages shown in FIGS. 20A-20D is driven by motor (160) and gearbox (162). FIG. 20A shows cam member (700) in the same position as shown in FIGS. 18A and 19A. At this stage, first bearing feature (604) of cam follower (600) is positioned on first surface region (712) and bearing member (804) or rocker member (800) is adjacent to second surface region (734) of third cam feature (730). Also at this stage, knife member (340) and staple driver member (350) are in proximal positions, such that stapling head assembly (300) is in a non-actuated state. As cam member (700) is rotated to the position shown in FIG. 20B, second surface region (714) bears against bearing member (804), thereby driving bearing member (804) upwardly. This causes cam follower (600) to pivot about pin (118) to the position shown in FIG. 18B. Cam follower (600) thus drives knife member (340) and staple driver member (350) distally via drive bracket (250) and stapling head assembly driver (240). Stapling head assembly (300) is thus in an actuated state at the stage shown in FIG. 20B. In some versions, cam member (700) rotates through an angular range of approximately 270° in order to transition stapling head assembly (300) from the non-actuated state to the actuated state.

Figure 20B:
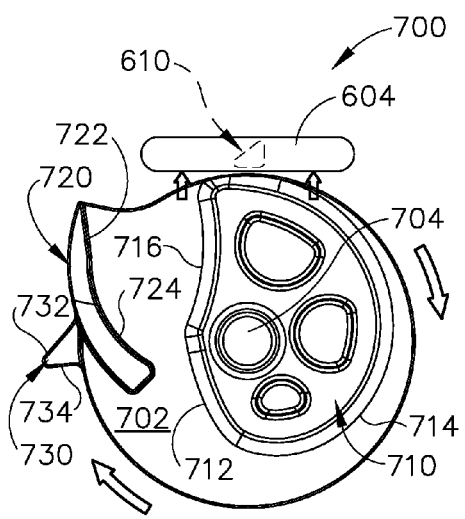
FIG. 20B depicts a schematic end view of the rotary cam of FIG. 16 and the cam follower of FIG. 14, with the rotary cam in the second angular position, the cam follower in the second pivotal position, and the rocker member of FIG. 19A in the first pivotal position.
Figure 20C:
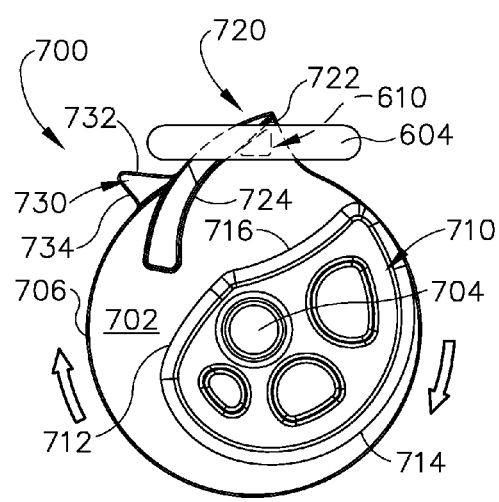
FIG. 20C depicts a schematic end view of the rotary cam of FIG. 16 and the cam follower of FIG. 14, with the rotary cam in a third angular position, the cam follower in the second pivotal position, and the rocker member of FIG. 19A in the first pivotal position.
Figure 20D:
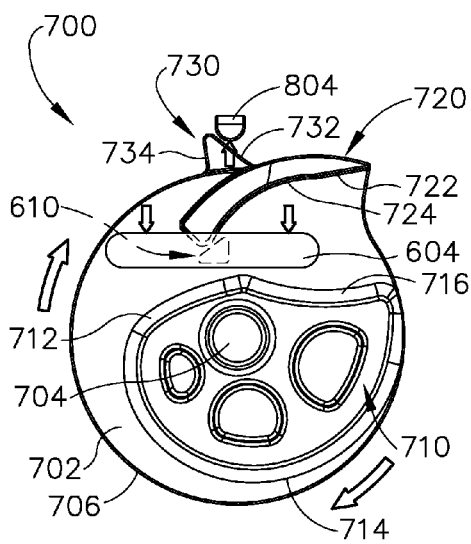
FIG. 20D depicts a schematic end view of the rotary cam of FIG. 16, the cam follower of FIG. 14, and the rocker member of FIG. 19A, with the rotary cam in a fourth angular position, the cam follower in a third pivotal position, and the rocker member in a second pivotal position.

After stapling head assembly (300) has been actuated, cam member (700) continues to rotate to the position shown in FIG. 20C. At this stage, first surface region (722) of second cam member (720) begins to engage curved surface (616) of second bearing feature (610) of cam follower (600). As cam member (700) continues to rotate to the position shown in FIG. 20D, second surface region (724) engages curved surface (616) of second bearing feature (610), driving second bearing feature (610) downwardly. This causes cam follower (600) to pivot about pin (118) back from the position shown in FIG. 18B toward the position shown in FIG. 18A. Cam follower (600) thus drives knife member (340) and staple driver member (350) proximally via drive bracket (250) and stapling head assembly driver (240). In addition, first surface region (732) has engaged and borne against bearing member (804), thereby pivoting rocker member (800) about the longitudinal axis defined by pin (802) at the stage shown in FIG. 20D. Rocker member (800) is thus in the same state in FIG. 20D as shown in FIG. 19B. Short circuit module (190) has thus been actuated at the stage shown in FIG. 20D.

It should be understood from the foregoing that cam member (700) is operable to drive knife member (340) and staple driver member (350) distally, then drive knife member (340) and staple driver member (350) proximally and actuate short circuit module (190) by rotating in a single angular direction through the range of motion shown in FIGS. 20A-20D. Other suitable ways in which knife member (340), staple driver member (350), and short circuit module (190) may be actuated will be apparent to those of ordinary skill in the art in view of the teachings herein.

E. Exemplary Anastomosis Procedure

Figure 21B:
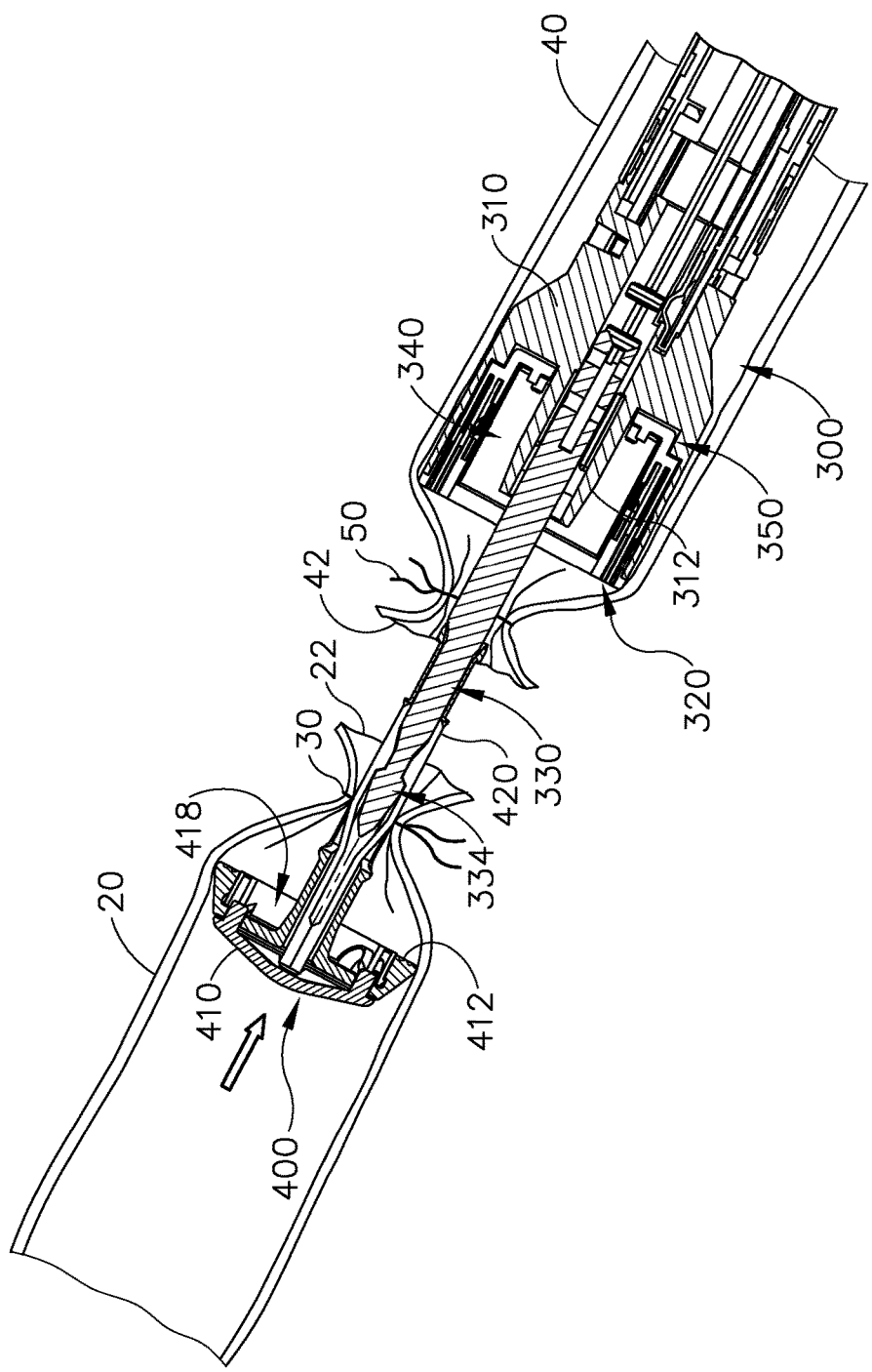
FIG. 21B depicts a cross-sectional side view of the anvil of FIG. 3 positioned within the first section of the digestive tract and the stapling head assembly of FIG. 6 positioned in the second section of the digestive tract, with the anvil secured to the stapling head assembly.
Figure 21C:
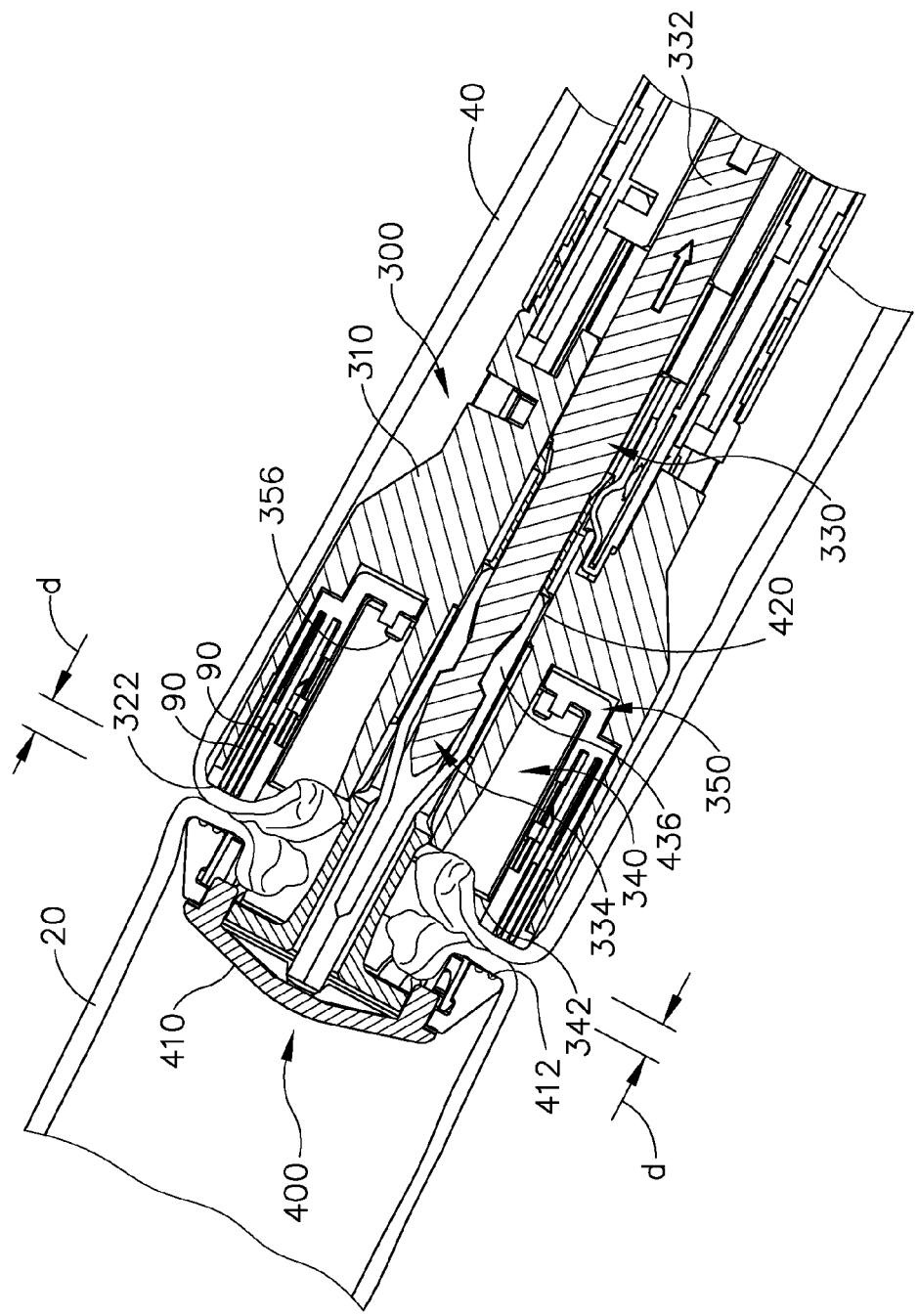
FIG. 21C depicts a cross-sectional side view of the anvil of FIG. 3 positioned within the first section of the digestive tract and the stapling head assembly of FIG. 6 positioned in the second section of the digestive tract, with the anvil retracted toward the stapling head assembly to thereby clamp tissue between the anvil and the stapling head assembly.

FIGS. 21A-21E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 21A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 21A-21E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 21A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Next, anvil (400) is secured to trocar (330) by inserting trocar (330) into bore (422) as shown in FIG. 21B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally (as described above with reference to FIGS. 12A-12C). As shown in FIG. 21C, this proximal retraction of trocar (330) and anvil (400) compresses the tissue of tubular anatomical structures (20, 40) between surfaces (412, 322) of anvil (400) and stapling head assembly (300). The operator observes the position of needle (526) within window (114) to determine whether the gap distance (d) between opposing surfaces (412, 322) of anvil (400) and stapling head assembly (300) is appropriate; and makes any necessary adjustments via knob (130).

Figure 21D:
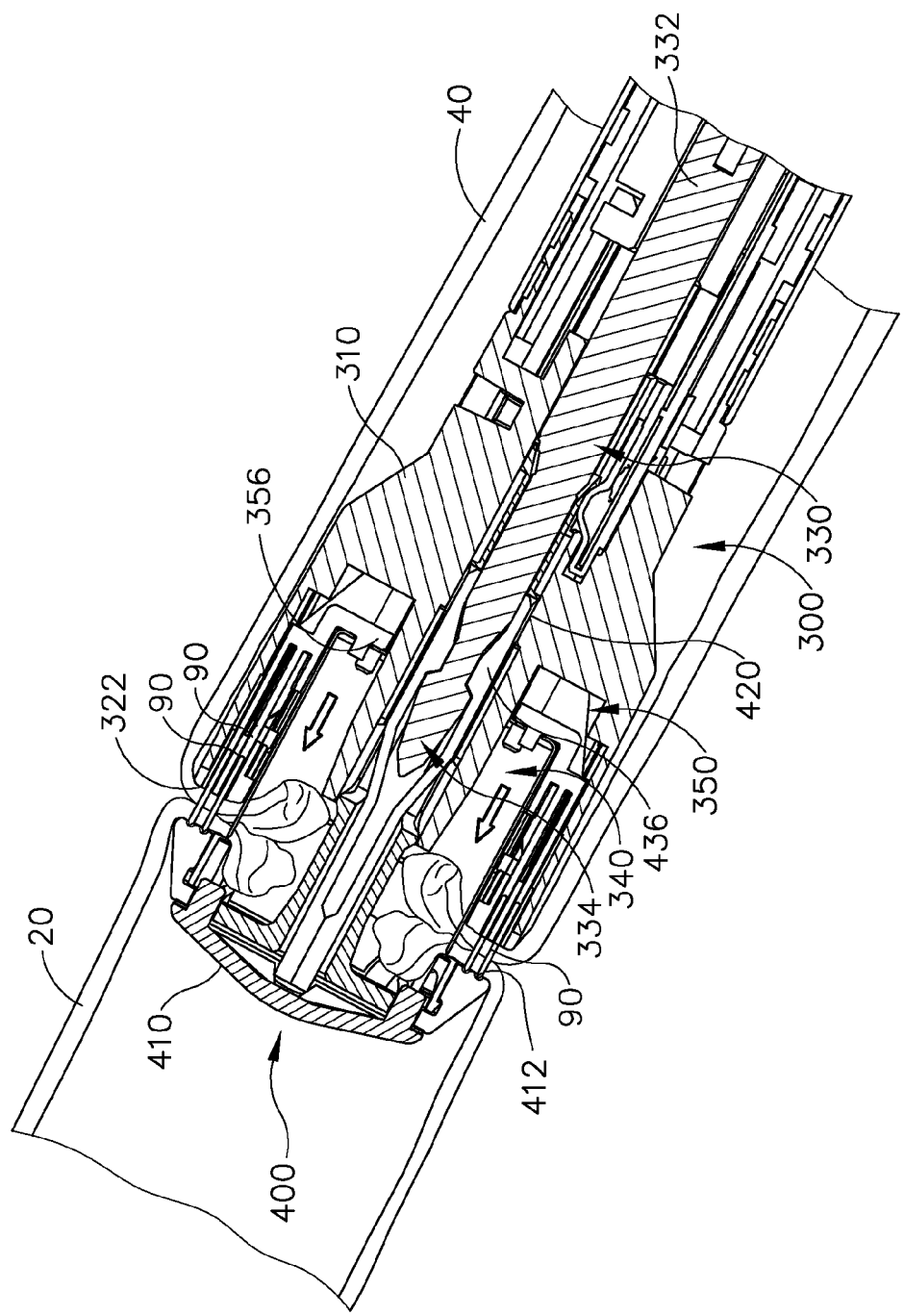
FIG. 21D depicts a cross-sectional side view of the anvil of FIG. 3 positioned within the first section of the digestive tract and the stapling head assembly of FIG. 6 positioned in the second section of the digestive tract, with the stapling head assembly actuated to sever and staple the clamped tissue.

Once the operator has appropriately set the gap distance (d) via knob (130), the operator actuates safety trigger (140) (as shown in FIG. 12D) to enable actuation of firing trigger (150). The operator then actuates firing trigger (150) (as shown in FIG. 12D). This causes paddle (158) to actuate the switch of a motor activation module (180), thereby activating motor to rotate cam member (700) (as shown in FIGS. 20A-20D). This rotation of cam member (700) actuates stapling head assembly (300) by driving knife member (340) and staple driver member (350) distally as shown in FIG. 21D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when the knife member (340) completes a full distal range of motion from the position shown in FIG. 21C to the position shown in FIG. 21D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and knife member (340).

As staple driver member (350) translates distally from the position shown in FIG. 21C to the position shown in FIG. 21D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together.

Figure 21E:
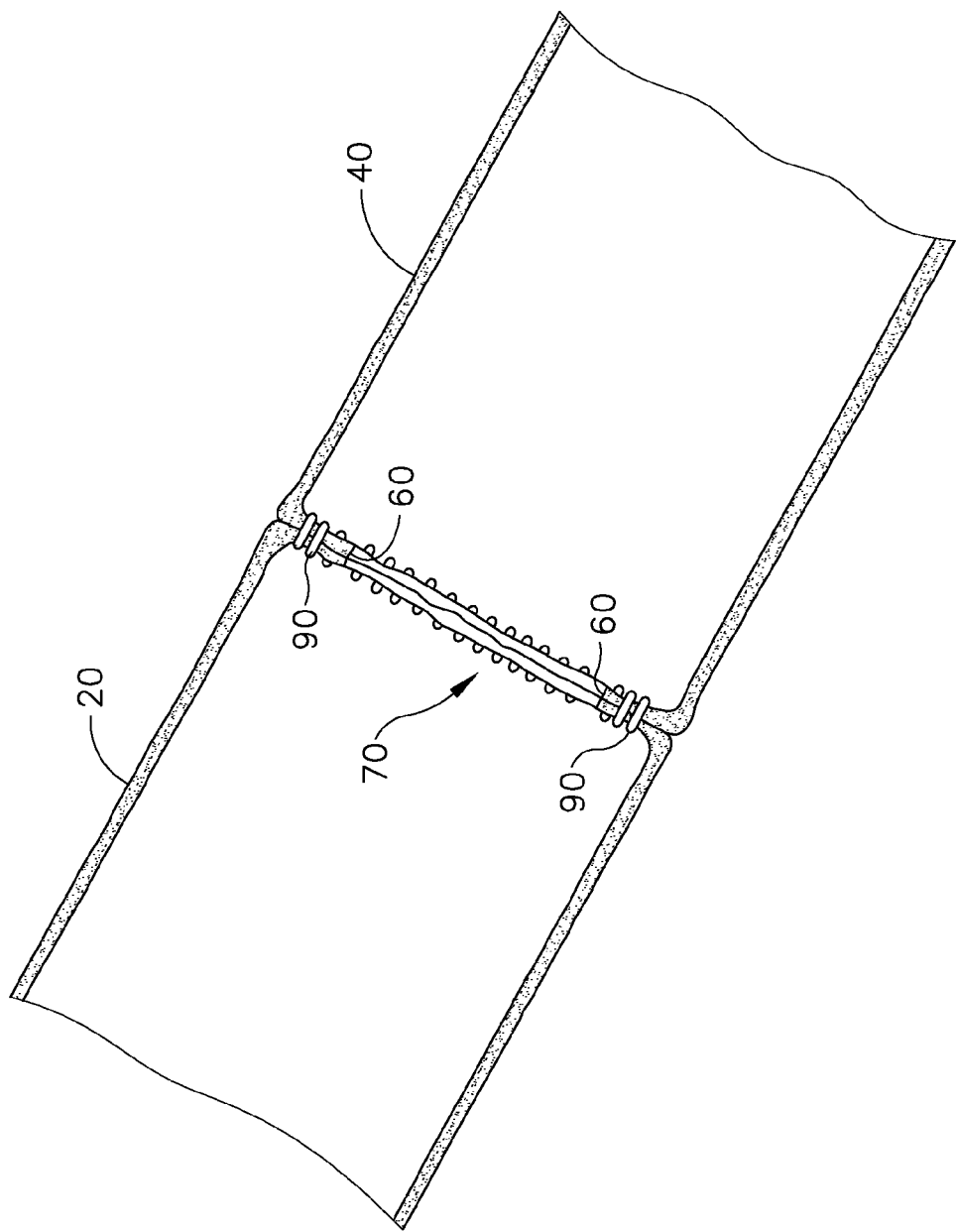
FIG. 21E depicts a cross-sectional side view of the first and second sections of the digestive tract of FIG. 21A joined together at an end-to-end anastomosis.

After the operator has actuated stapling head assembly (300) as shown in FIG. 21D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 21E. The inner diameter of the anastomosis (70) is defined by the severed edge (60) left by knife member (340).

II. Exemplary Alternative Instruments with Anvil Actuation Lockout Features

Although various lockout features are described above with respect to triggers (140, 150) of instrument (10), it may be desirable to provide lockout features that selectively lock out other features of instrument (10). For instance, in an instrument similar to instrument (10) described above, certain lockout features may be included to lock out actuation of an anvil actuation assembly similar to the anvil actuation assembly described above. In particular, such features may prevent an operator from adjusting gap distance (d) after the operator reaches a particular stage of operation of instrument (10) (e.g., after safety trigger (140) is actuated). In such examples, the ability to prevent adjustment of the gap distance (d) after an appropriate gap distance (d) has already been established may be desirable to ensure that the operator completes the anastomosis procedure in a particular sequence of steps comprising adjusting the gap distance followed by the firing procedure.

Examples of anvil lockout features are described in U.S. Pub. No. 2013/0153631, entitled "Feature to Lock Knob of Tissue Stapler," published Jun. 20, 2013, issued as U.S. Pat. No. 9,220,505 on Dec. 29, 2015, the disclosure of which is incorporated by reference herein. While various alternative instruments are described below, other examples will be apparent to those of ordinary skill in the art in view of the teachings herein. It should be further understood that various features and/or structures of the instruments described below may be readily incorporated with other instruments described herein.

A. Exemplary Instrument with Anvil Actuation Rod Lockout Feature

FIG. 22 shows an exemplary alternative surgical circular stapling instrument (1000) that may be used to provide an end-to-end anastomosis between two sections of an anatomical lumen such as a portion of a patient's digestive tract. It should be understood that instrument (1000) of the present example is substantially the same as instrument (10) described above unless otherwise noted herein. For instance, like with instrument (10), instrument (1000) comprises a handle assembly (1010), a shaft assembly (1020), a stapling head assembly (not shown), and an anvil (not shown). Handle assembly (1010) is substantially the same as handle assembly (110) described above and comprises a casing (1012) defining an obliquely oriented pistol grip (1014). Handle assembly (1010) further includes a window (1016) that permits viewing of a movable indicator needle (not shown) as similarly described above.

Like with instrument (10) described above, instrument (1000) is controlled by an operator via knob (1030) and triggers (1040, 1042). Knob (1030), like with knob (130) described above, is operatively connected to shaft assembly (1020) to actuate the anvil. In particular, knob (1030) is rotatable to engage threads (not shown) of shaft assembly (1020) to translate a trocar actuation rod (1022), which ultimately actuates the anvil as similarly described above with respect to shaft assembly (200) of instrument (10).

Triggers (1040, 1042) function similarly to triggers (140, 150) described above. For instance, a safety trigger (1040) may be first actuated by an operator to unblock a firing trigger (1042), to thereby enable activation of the stapling head assembly. Like with safety trigger (140) described above, safety trigger (1040) includes a first upright member (1044) that is generally operable to permit actuation of safety trigger (1040) only after the anvil has been adjusted to define a gap distance (d) that is within a clinically acceptable range. In particular, trocar actuation rod (1022) is operatively connected to a bracket (1024), which includes at least one slot (1026). As similarly described above with respect to slot (506), slot (1026) is configured to receive at least a portion of first upright member (1044) to thereby permit movement of safety trigger (1040). Although not shown, it should be understood that firing trigger (1042) may also include an upright member (not shown) similar to second upright member (154) described above.

Firing trigger (1042) is similar to firing trigger (150) described above. In particular, once safety trigger (1040) has been activated, firing trigger (1042) is operable to initiate actuation of the stapling head assembly. Firing trigger (1042) includes a paddle (1046), which is configured to engage a motor activation module (1050) when firing trigger (1042) is actuated by an operator. Like with motor activation module (180) described above, motor activation module (1050) of the present example initiates the stapling sequence by activating a motor (not shown). The motor then drives a cam member (1052), which in turn drives a cam follower (1054). Cam member (1052) and cam follower (1054) are substantially the same as cam member (700) and cam follower (600) described above, such that cam member (1052) and cam follower (1054) cooperate to drive the stapling head assembly through a stapling sequence.

Figure 23:
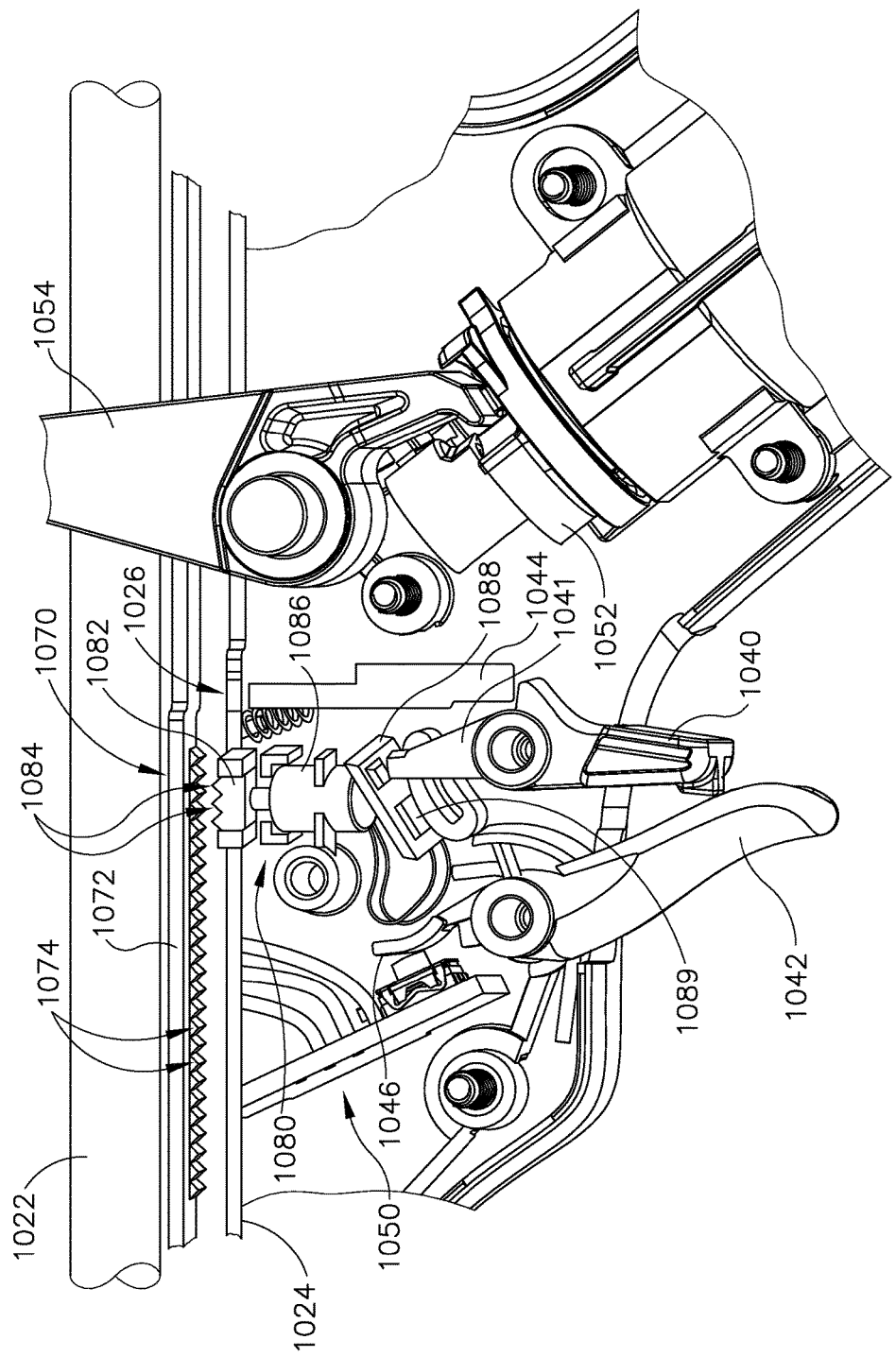
FIG. 23 depicts a side elevational view of an anvil lockout assembly of the handle assembly of FIG. 22, with the anvil lockout assembly in an unlocked position.

Unlike instrument (10) described above, instrument (1000) of the present example comprises an anvil lockout assembly (1070). Anvil lockout assembly (1070) is generally configured to prevent further adjustment of the longitudinal position of the anvil once safety trigger (1040) is actuated. Such a feature may be desirable because lockout of the anvil may prevent an operator from improperly changing the gap distance (d) once a suitable gap (d) distance is reached. Anvil lockout assembly (1070) comprises a lockout member (1072), and an actuation assembly (1080). As is best seen in FIG. 23, lockout member (1072) is fixedly secured to trocar actuation rod (1022). Lockout member (1072) of the present example includes a plurality of triangular teeth (1074) extending downwardly from lockout member (1072). As will be described in greater detail below, teeth (1074) are configured to engage with corresponding teeth (1084) of actuation assembly (1080) to prevent translation of trocar actuation rod (1022).

Although lockout member (1072) of the present example is shown as including teeth (1074), it should be understood that in other examples any other suitable surfacing treatment may be used. For instance, in some examples lockout member (1072) includes a knurled surface, bumps, ridges, detent features, or any other suitable surface treatment or geometry that may be configured to engage with a corresponding surface of actuation assembly (1080) to prevent translation of trocar actuation rod (1022). Additionally, although lockout member (1072) of the present example is shown as being fixedly secured to trocar actuation rod (1022), it should be understood that no such limitation is intended. For instance, in other examples lockout member (1072) is of integral construction with bracket (1024). In such examples, lockout member (1072) may include various features such as slots and/or channels, in addition to teeth (1074), to permit the same functionality of bracket (1024) described above. Of course, various other configurations of lockout member (1072) will be apparent to those of ordinary skill in the art in view of the teachings herein.

Actuation assembly (1080) comprises a lock block (1082), an actuator (1086), and an activation board (1088). Lock block (1082) includes a plurality of teeth (1084), which correspond to teeth (1074) of lockout member (1072). As will be described in greater detail below, lock block (1082) is generally configured to engage with lockout member (1072) to prevent translation of trocar actuation rod (1022).

Lock block (1082) is attached to a portion of actuator (1086). Generally, actuator (1086) is configured to selectively drive lock block (1082) upwardly into engagement with lockout member (1072). Actuator (1086) of the present example comprises a solenoid, although any other suitable mechanical or electro-mechanical actuation mechanism may be used. Actuator (1086) is in communication with activation board (1088). Generally, activation board (1088) is operable to activate actuator (1086) to initiate movement of actuator (1086) to thereby drive lock block (1082) into engagement with lockout member (1072). Activation board (1088) of the present example comprises a button (1089) that is integrated into a printed circuit board. Although not shown, it should be understood that activation board (1088) may include other components suitable for communicating an electrical signal to actuator (1086) such as resistors, capacitors, integrated circuit boards, etc.

Button (1089) is adjacent to safety trigger (1040). As will be described in greater detail below, safety trigger (1040) includes an activation arm (1041) that moves in conjunction with safety trigger (1040) to engage button (1089). Although button (1089) of the present example is shown as an electromechanical push button, it should be understood that in other examples button (1089) may comprise any other suitable electrical switching mechanism. In still other examples, button (1089) may be omitted. In lieu of button (1089), a sensor may be used to replicate the functionality of button (1089) without necessarily requiring direct physical contact between activation board (1088) and safety trigger (1040). Additionally, it should be understood that in examples where actuator (1086) is an entirely mechanical actuator, activation board (1088) may be omitted entirely and safety trigger (1040) may instead be mechanically coupled to actuator (1086) via gears, cams, shafts, etc.

Figure 24:
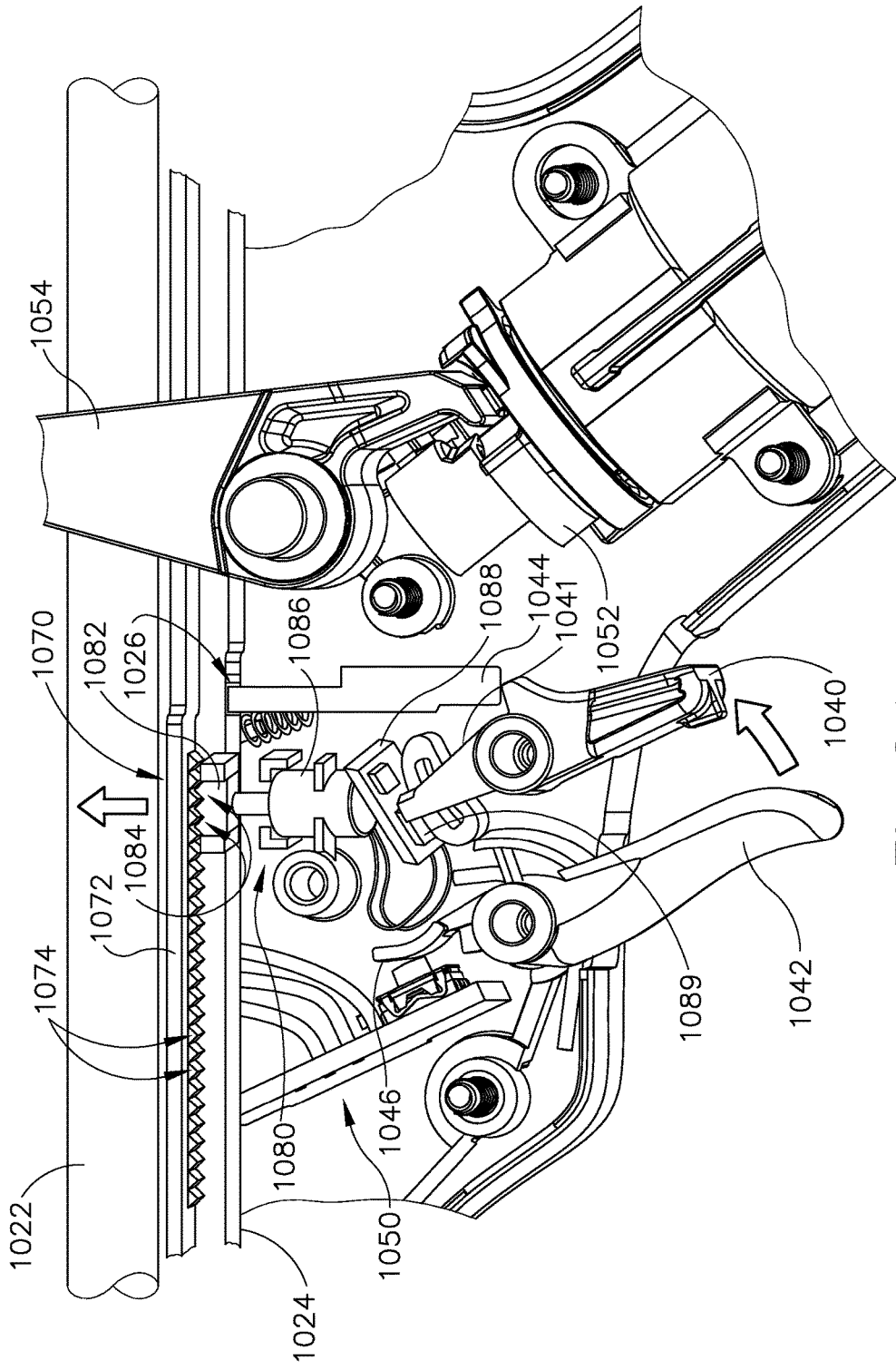
FIG. 24 depicts another side elevational view of the anvil lockout assembly of FIG. 23, with the anvil lockout assembly in a locked position.
Figure 25:
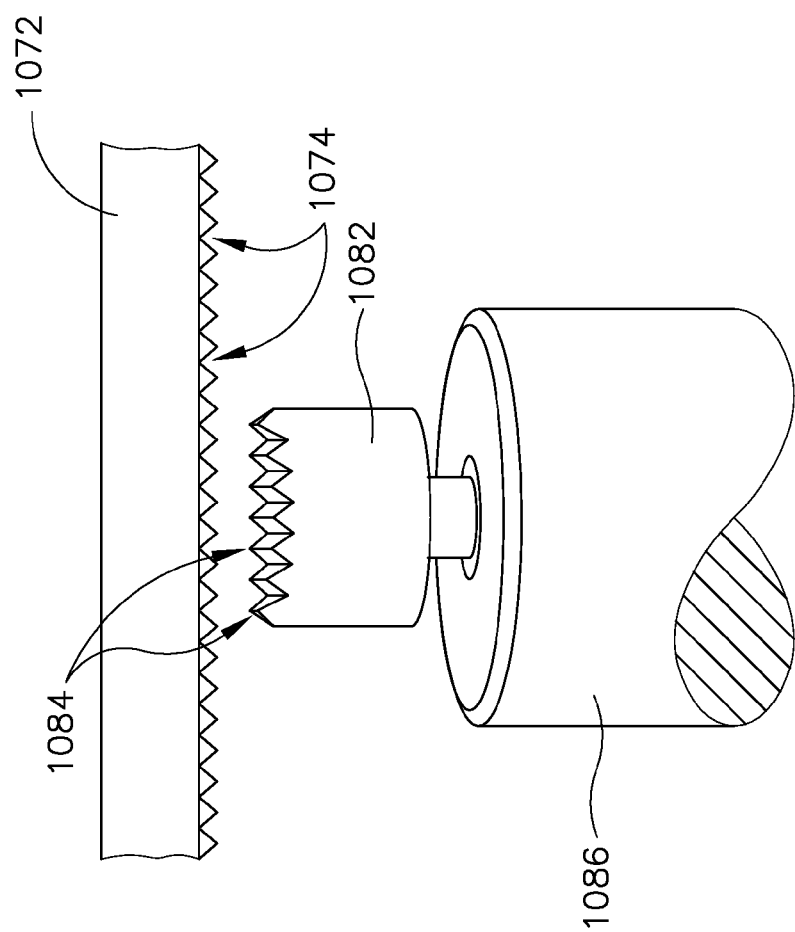
FIG. 25 depicts a detailed side elevational view of the anvil lockout assembly of FIG. 23, with the anvil lockout assembly in the unlocked position.

FIGS. 23-26 show an exemplary sequence of operation of anvil lockout assembly (1070). As can be seen in FIGS. 23 and 25, anvil lockout assembly (1070) initially begins in an unlocked state. In such a state, lock block (1082) is positioned away from lockout member (1072) such that trocar actuation rod (1022) is movable via knob (1030). In particular, safety trigger (1040) is positioned in a non-actuated position such that activation arm (1041) is disposed away from button (1089) of activation board (1088). With activation arm (1041) positioned away from button (1089), activation board (1088) is in an open circuit condition such that no signal is communicated to actuator (1086). Because actuator (1086) of the present example is a solenoid, the open circuit condition of activation board (1088) results in actuator (1086) being in a non-active condition thereby positioning lock block (1082) away from lockout member (1072). Although the unlocked state is described herein as being associated with activation board (1088) being in the open circuit condition, it should be understood that in examples using alternative actuators (1086) described above, activation board (1088) may provide numerous alternative signals to actuator (1086) that correspond to the particular actuator (1086) being used.

Figure 26:
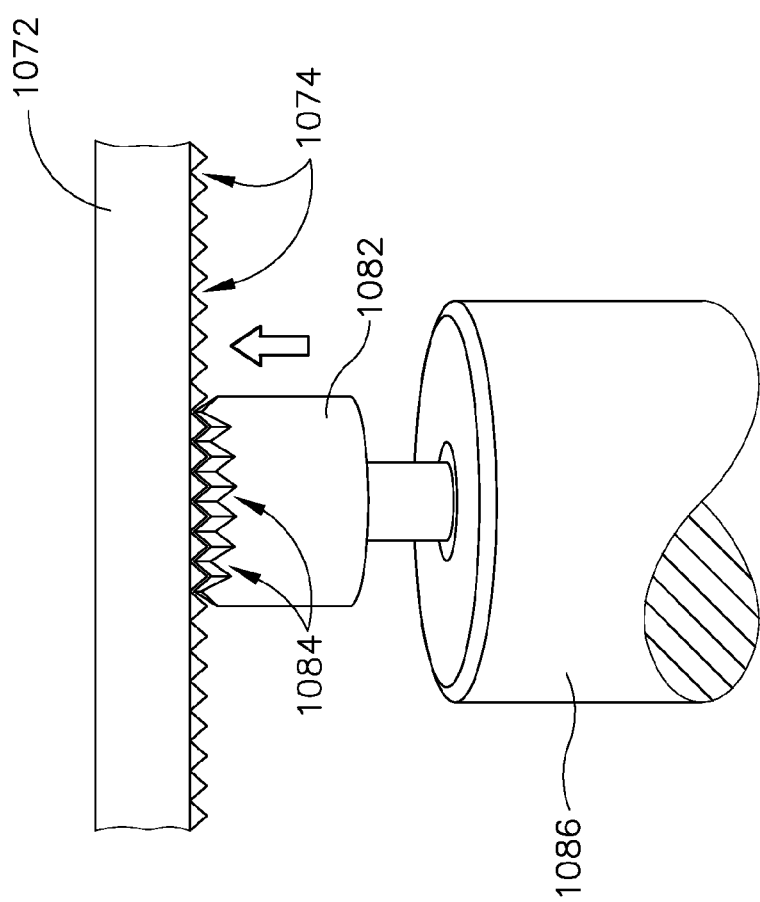
FIG. 26 depicts another detailed side elevational view of the anvil lockout assembly of FIG. 23, with the anvil lockout assembly in the locked position.

FIGS. 24 and 26 show anvil lockout assembly (1070) in a locked state. To transition anvil lockout assembly (1070) to the locked state, an operator may pivot safety trigger (1040) proximally. Proximal movement of safety trigger (1040) correspondingly moves activation arm (1041) toward button (1089) of activation board (1088) until activation arm (1041) engages button (1089). Once an operator has moved safety trigger (1040) to engage button (1089), anvil lockout assembly (1070) will automatically transition to the locked state without further operator intervention. In particular, engagement between button (1089) and activation arm (1041) causes activation board (1088) to transition to a closed circuit condition. When activation board (1088) is in the closed circuit condition, activation board (1088) communicates a signal to actuator (1086). Actuator (1086) then responds to such a signal by driving lock block (1082) upwardly and into engagement with lockout member (1072). With lock block (1082) engaged with lockout member (1072), teeth (1074, 1084) mesh, thereby locking translation of trocar actuation rod (1022).

In some variations, instrument (1000) is also configured to selectively activate actuator (1086) based whether battery pack (120) is fully inserted in socket (116). By way of example only, instrument (1000) may be configured such that anvil lockout assembly (1070) remains in the locked state (by default) until battery pack (120) is fully inserted in socket (116). Once battery pack (120) is fully inserted into socket (116), actuator (1086) is automatically activated transition anvil lockout assembly (1070) to the unlocked state. Anvil lockout assembly (1070) may remain in the unlocked state until the operator pivots safety trigger (1040) proximally as noted above. Once the operator pivots safety trigger (1040) proximally, anvil lockout assembly (1070) may again be transitioned back to the locked state as noted above.

It should therefore be understood that anvil lockout assembly (1070) may prevent translation of trocar actuation rod (1022) when either of the two following conditions are present: (a) battery pack (120) is not fully inserted in socket (116), or (b) safety trigger (1040) has been pivoted proximally. However, anvil lockout assembly (1070) will permit translation of trocar actuation rod (1022) when both of the two following conditions are present: (a) battery pack (120) is fully inserted in socket (116), and (b) safety trigger (1040) has not yet been pivoted proximally.

Various suitable features that may be used to provide activation of anvil lockout assembly (1070) in response to insertion of battery pack (120) into socket (116) will be apparent to those of ordinary skill in the art in view of the teachings herein.

B. Exemplary Instrument with Knob Lockout Actuation Feature

Figure 27:
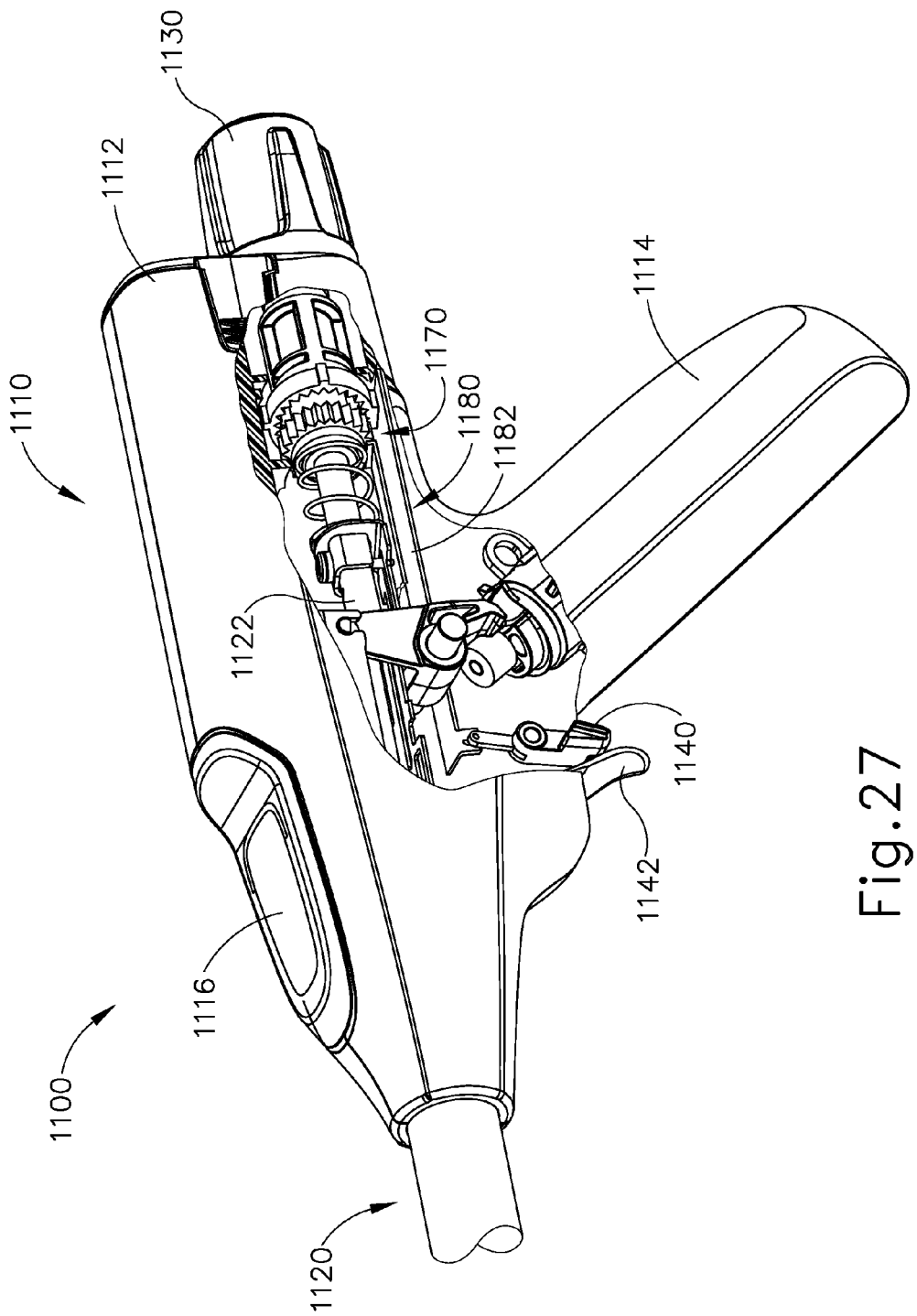
FIG. 27 depicts a detailed perspective cut-away view of a handle assembly of another exemplary alternative circular stapler.

FIG. 27 shows another exemplary alternative surgical circular stapling instrument (1100) that may be used to provide an end-to-end anastomosis between two sections of an anatomical lumen such as a portion of a patient's digestive tract. It should be understood that instrument (1100) of the present example is substantially the same as instrument (10) described above unless otherwise noted herein. For instance, like with instrument (10), instrument (1100) comprises a handle assembly (1110), a shaft assembly (1120), a stapling head assembly (not shown), and an anvil (not shown). Handle assembly (1110) is substantially the same has handle assembly (110) described above and comprises a casing (1112) defining an obliquely oriented pistol grip (1114). Handle assembly (1110) further includes a window (1116) that permits viewing of a movable indicator needle (not shown) as similarly described above.

Like with instrument (10) described above, instrument (1100) is controlled by an operator via knob (1130) and triggers (1140, 1142). Knob (1130), like with knob (130) described above, is operatively connected to shaft assembly (1120) to actuate the anvil. In particular, knob (1130) is rotatable to engage threads (not shown) of shaft assembly (1120) to translate a trocar actuation rod (1122), which ultimately actuates the anvil as similarly described above with respect to shaft assembly (200) of instrument (10).

Triggers (1140, 1142) function similarly as triggers (140, 150) described above. For instance, a safety trigger (1140) may be first actuated by an operator to unblock a firing trigger (1142), to thereby enable activation of the stapling head assembly. Although not shown, it should be understood that like with safety trigger (140) described above, safety trigger (1140) may include an upright member (not shown) that is generally operable to permit actuation of safety trigger (1140) only after the anvil has been adjusted to define a gap distance (d) that is within a clinically acceptable range. Additionally, it should be understood that firing trigger (1142) may also include an upright member (not shown) similar to second upright member (154) described above. Of course, in other examples the upright members may be omitted entirely.

Firing trigger (1142) is similar to firing trigger (150) described above. In particular, once safety trigger (1140) has been activated, firing trigger (1142) is operable to initiate actuation of the stapling head assembly. Firing trigger (1142) includes a paddle (1146), which is configured to engage a motor activation module (not shown) when firing trigger (1142) is advanced by an operator. Like with motor activation module (180) described above, the motor activation module of the present example initiates the stapling sequence by activating a motor (not shown). The motor then drives a cam member (1152), which in turn drives a cam follower (1154). Cam member (1152) and cam follower (1154) are substantially the same as cam member (700) and cam follower (600) described above, such that cam member (1152) and cam follower (1154) cooperate to drive the stapling head assembly through a stapling sequence.

Figure 29:
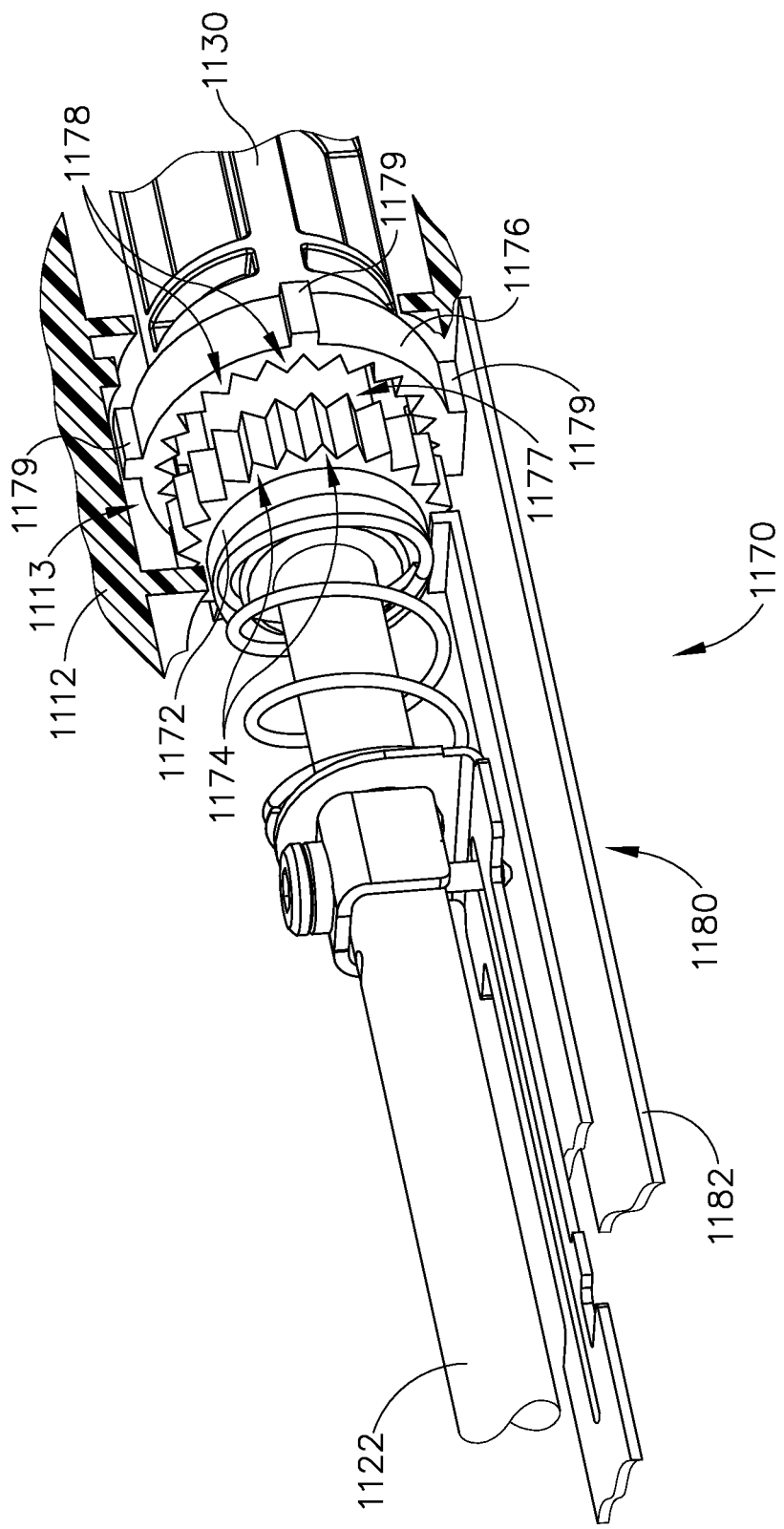
FIG. 29 depicts a detailed perspective view of an anvil lockout assembly of the anvil actuation assembly of FIG. 28, with the anvil lockout assembly in an unlocked position.

Unlike instrument (10) described above, instrument (1100) of the present example comprises an anvil lockout assembly (1170). Anvil lockout assembly (1170) is generally configured to prevent further adjustment of the longitudinal position of the anvil once safety trigger (1140) is actuated. Such a feature may be desirable because lockout of the anvil may prevent an operator from improperly changing the gap distance (d) once a suitable gap distance (d) is reached. Anvil lockout assembly (1170) comprises an inner lockout member (1172), an outer lockout member (1176), and an actuation member (1180). As is best seen in FIG. 29, inner lockout member (1172) is disposed about a portion of a portion of knob (1130) and is fixedly secured thereto Inner lockout member (1172) of the present example includes a plurality of triangular teeth (1174) extending radially outwardly from inner lockout member (1172). As will be described in greater detail below, teeth (1174) are configured to engage with corresponding teeth (1184) of outer lockout member (1176) to prevent rotation of knob (1130), thereby preventing translation of trocar actuation rod (1122).

Outer lockout member (1176) has a generally cylindrical shape and defines an opening (1177) that is sized to receive inner lockout member (1172). The inner diameter of outer lockout member (1176) defines a plurality of teeth (1178), which correspond to teeth (1147) of inner lockout member (1172). As will be described in greater detail below, teeth (1178) are configured to engage teeth (1174) of inner lockout member (1172) to prevent further adjustment of the longitudinal position of anvil, by preventing further rotation of knob (1130). Outer lockout member (1176) further includes a plurality of protrusions (1179) protruding radially outwardly from the outer diameter of outer lockout member (1176). Protrusions (1179) are disposed in corresponding channels (1113) within casing (1112) to rotationally fix outer lockout member (1176) in position while still permitting at least some translation.

Although inner and outer lockout members (1172, 1176) of the present example are shown as including teeth (1174, 1178), it should be understood that in other examples any other suitable surfacing treatment or geometry may be used. For instance, in some examples lockout members (1172, 1176) include corresponding knurled surfaces, bumps, splines, ridges, detent features, or any other suitable surface treatment or geometry that may be configured to correspondingly engage to prevent relative rotational movement between lockout members (1172, 1176).

Actuation member (1180) comprises an elongate body (1182) extending from outer lockout member (1176) to safety trigger (1140). In particular, body (1182) includes a trigger bracket (1184) that is configured to couple with safety trigger (1140). Trigger bracket (1184) includes a channel (1185) that permits bracket (1184) to be pivotably coupled to safety trigger (1140). Similarly, the proximal end of body (1182) is configured to couple with at least one protrusion (1179) of outer lockout member (1176). Accordingly, movement of safety trigger (1140) is transferred to outer lockout member (1176) via actuation member (1180). In other words, outer lockout member (1176) translates longitudinally in response to pivoting of safety trigger (1140). As will be described in greater detail below, outer lockout member (1176) is generally responsive to safety trigger (1140) to selectively lock actuation of the anvil.

Figure 30:
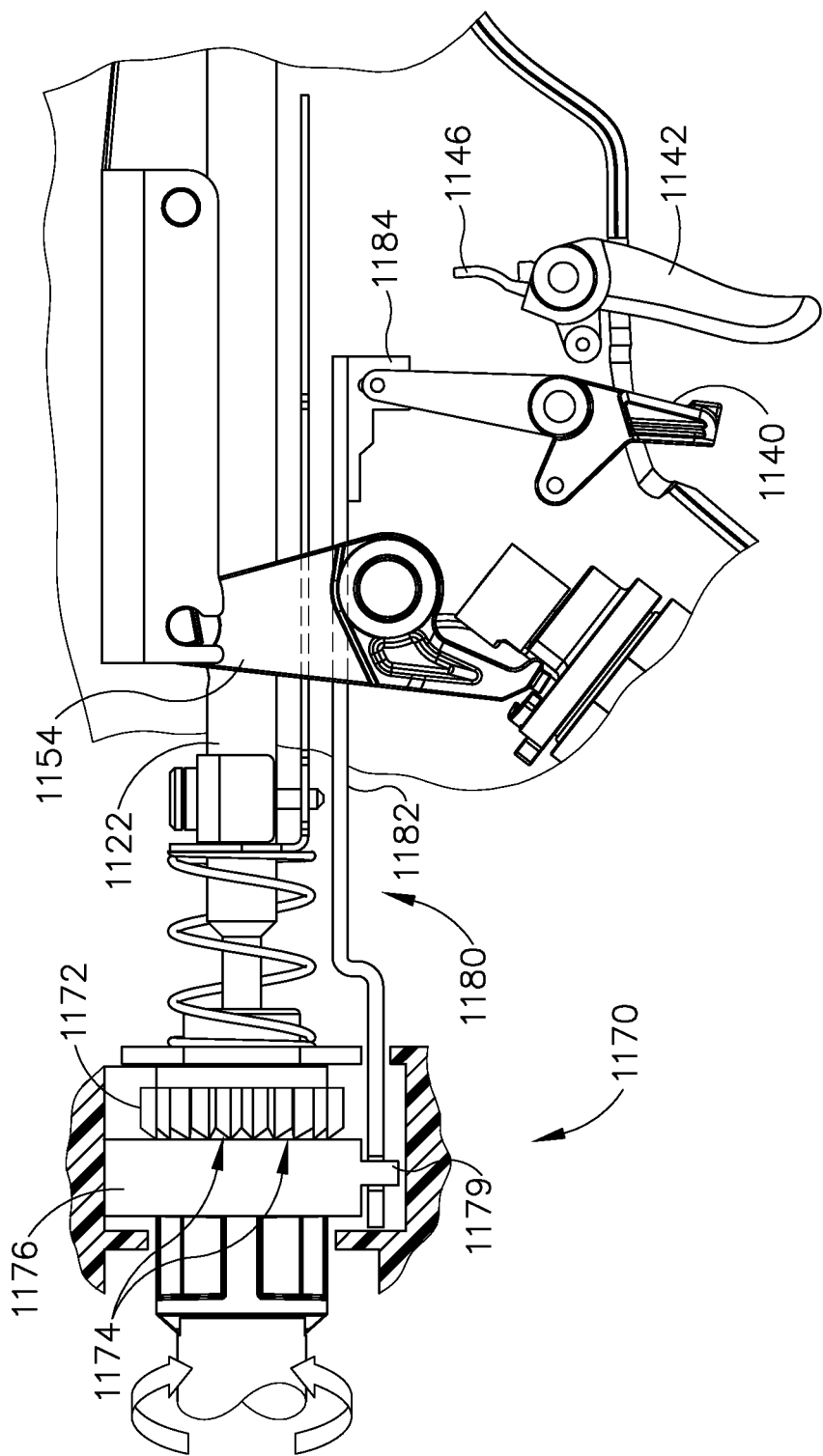
FIG. 30 depicts a detailed side elevational view of the anvil actuation assembly of FIG. 28, with the anvil lockout assembly of FIG. 29 in the unlocked position.
Figure 31:
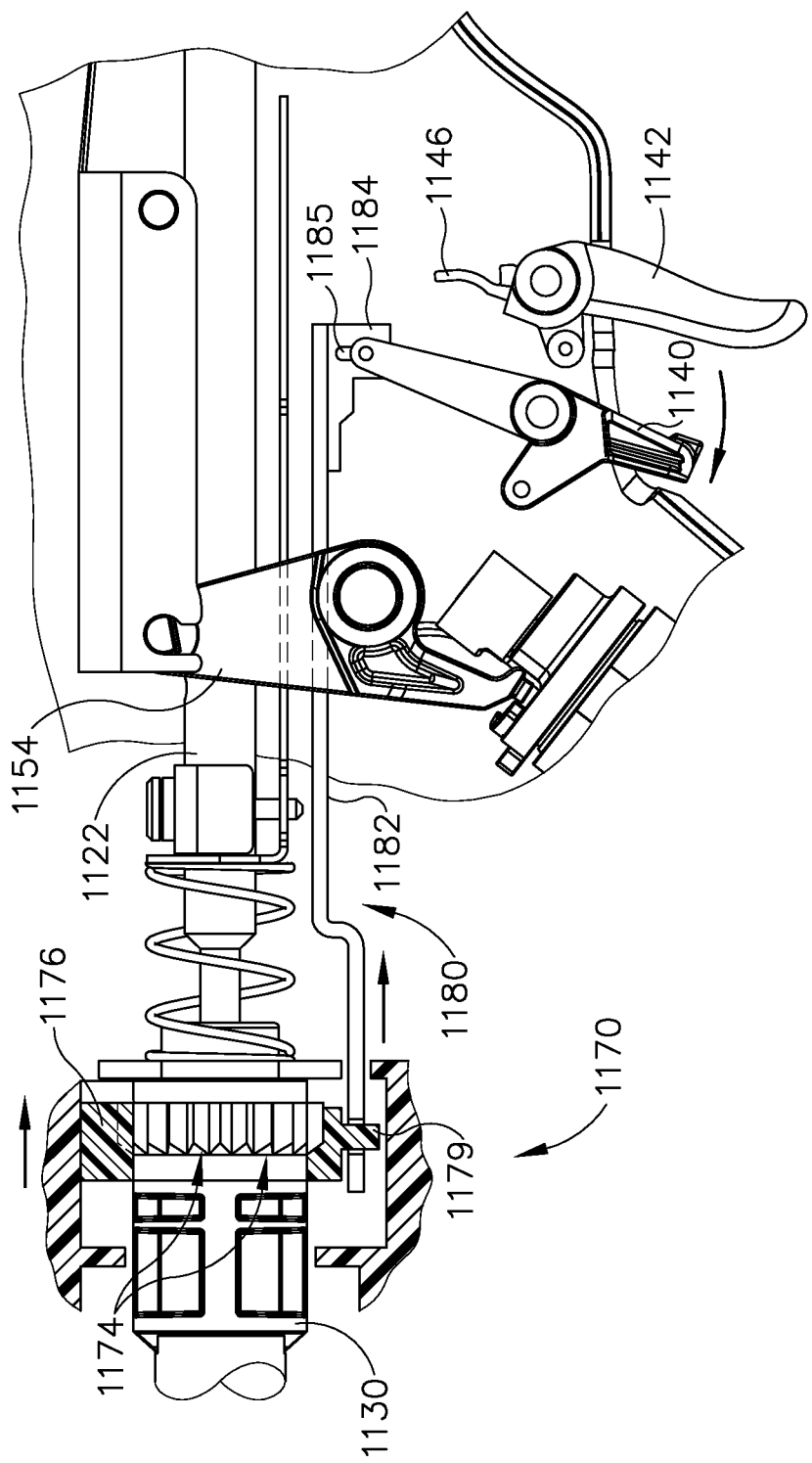
FIG. 31 depicts another detailed side elevational view of the anvil actuation assembly of FIG. 28, with the anvil lockout assembly of FIG. 29 in a locked position.
Figure 32:
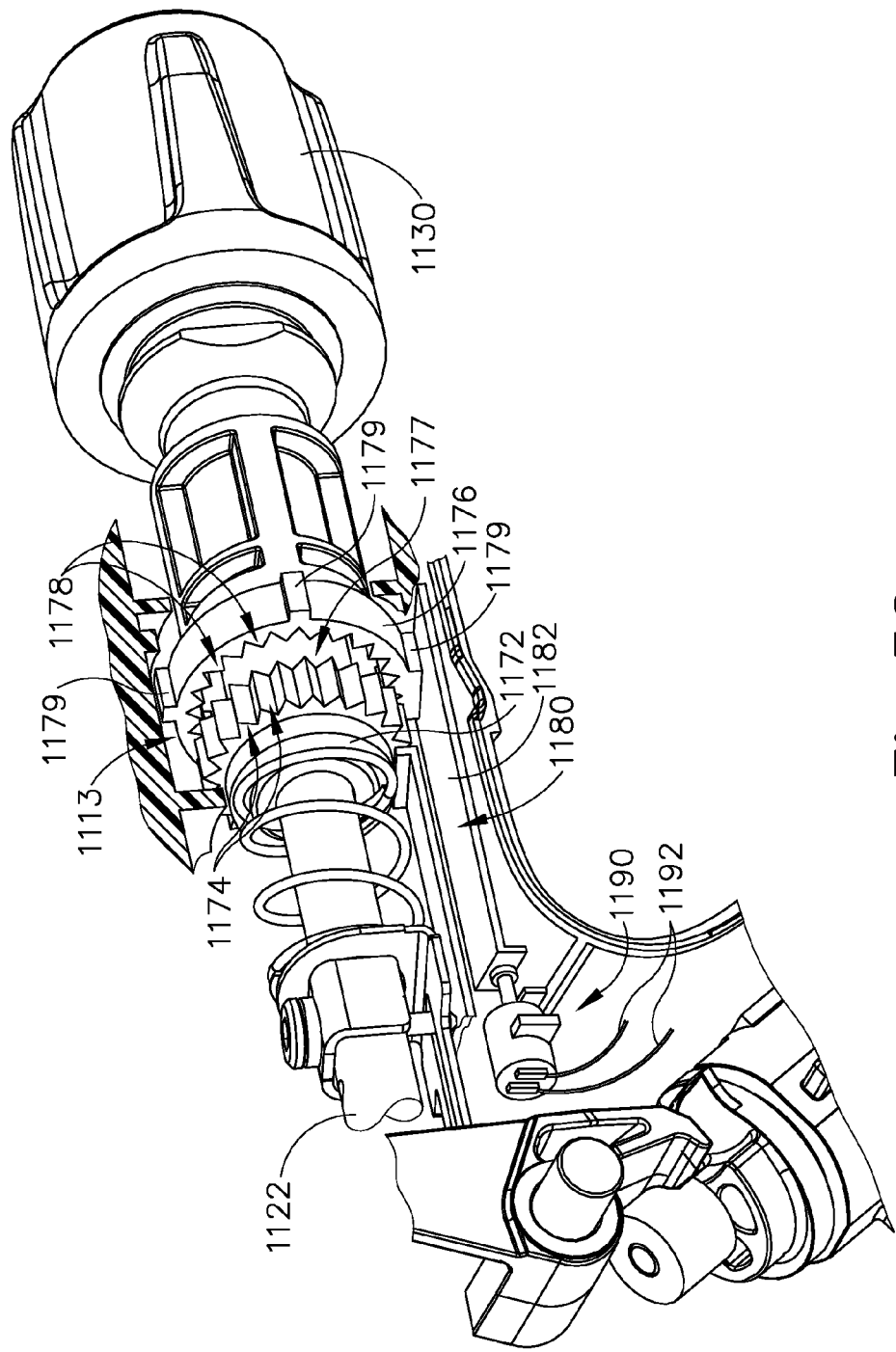
FIG. 32 depicts a detailed perspective view of an alternative configuration of the anvil lockout assembly of FIG. 29.

FIGS. 30-32 show an exemplary sequence of operation of anvil lockout assembly (1170). As can be seen in FIG. 30, anvil lockout assembly (1170) initially begins in an unlocked state. In such a state, outer lockout member (1176) is positioned proximally away from inner lockout member (1172) such that inner lockout member (1172) is freely rotatable relative to outer lockout member (1176). It should be understood that when inner lockout member (1172) is freely rotatable, knob (1130) is similarly freely rotatable such that the longitudinal position of the anvil may be adjusted via trocar actuation rod (1122).

Once the operator has rotated knob (1130) to adjust the longitudinal position of the anvil to achieve an appropriate gap distance (d), it may be desirable to prevent further adjustment of the longitudinal position of the anvil. FIG. 31 shows anvil lockout assembly (1170) in a locked state. To advance anvil lockout assembly (1170) to the locked state, the operator may pivot safety trigger (1140) proximally. Proximal movement of safety trigger (1140) causes safety trigger (1140) to drive actuation member (1180) distally.

Distal movement of actuation member (1180) results in corresponding movement of outer lockout member (1176). As outer lockout member (1176) is moved distally, teeth (1178) of outer lockout member (1176) will begin to engage teeth (1174) of inner lockout member (1176). Once teeth (1178) of outer lockout member (1176) fully engage with teeth (1174) of inner lockout member (1176), outer lockout member (1176) will prevent relative rotational movement of inner lockout member (1172) via protrusions (1179) and casing (1112). Because inner lockout member (1172) is fixedly secured to knob (1130), rotational movement of knob (1130) will also be prevented. With knob (1130) locked in position, further adjustment of the longitudinal position of the anvil will be prevented. With further adjustment of the longitudinal position of the anvil prevented, the operator may then actuate firing trigger (1142) to initiate the stapling sequence as described above with respect to instrument (10).

In some examples, it may be desirable to drive outer lockout member (1176) using other actuation means instead of a mechanical connection as described above. One merely exemplary alternative configuration of instrument (1100) is shown in FIG. 32. As can be seen, instrument (1100) is alternatively equipped with an actuation mechanism (1190) such as a solenoid. Actuation mechanism (1190) is aligned with the longitudinal axis of actuation member (1180) and is fixedly secured to actuation member (1180). To accommodate actuation mechanism (1190), actuation member (1180) may be shortened or otherwise modified to intersect with actuation mechanism (1190). Actuation mechanism (1190) includes a plurality of wires (1192) that may connect to a circuit board, switch, and/or sensor. Although not shown, it should be understood that actuation mechanism (1190) may be actuated using safety trigger (1140) using a similar configuration as safety trigger (1040) of instrument (1000) described above. For instance, actuation of safety trigger (1140) may complete a circuit that activates actuation mechanism (1190), thereby driving lockout member (1176) longitudinally into engagement with lockout member (1172).

In operation, actuation mechanism (1190) generally provides the same function as safety trigger (1140), except actuation mechanism (1190) removes the necessity for actuation member (1180) to extend the entire distance to safety trigger (1140). Although actuation mechanism (1190) is shown and described herein as comprising a solenoid, it should be understood that any other suitable actuator may be used as will be apparent to those of ordinary skill in the art in view of the teachings herein.

In some variations, instrument (1100) is also configured to selectively activate actuation mechanism (1190) based whether battery pack (120) is fully inserted in socket (116). By way of example only, instrument (1100) may be configured such that anvil lockout assembly (1170) remains in the locked state (by default) until battery pack (120) is fully inserted in socket (116). Once battery pack (120) is fully inserted into socket (116), actuation mechanism (1190) is automatically activated transition anvil lockout assembly (1170) to the unlocked state. Anvil lockout assembly (1170) may remain in the unlocked state until the operator pivots safety trigger (1140) proximally as noted above. Once the operator pivots safety trigger (1140) proximally, anvil lockout assembly (1170) may again be transitioned back to the locked state as noted above.

It should therefore be understood that anvil lockout assembly (1170) may prevent translation of trocar actuation rod (1122) when either of the two following conditions are present: (a) battery pack (120) is not fully inserted in socket (116), or (b) safety trigger (1140) has been pivoted proximally. However, anvil lockout assembly (1170) will permit translation of trocar actuation rod (1122) when both of the two following conditions are present: (a) battery pack (120) is fully inserted in socket (116), and (b) safety trigger (1140) has not yet been pivoted proximally.

Figure 33:
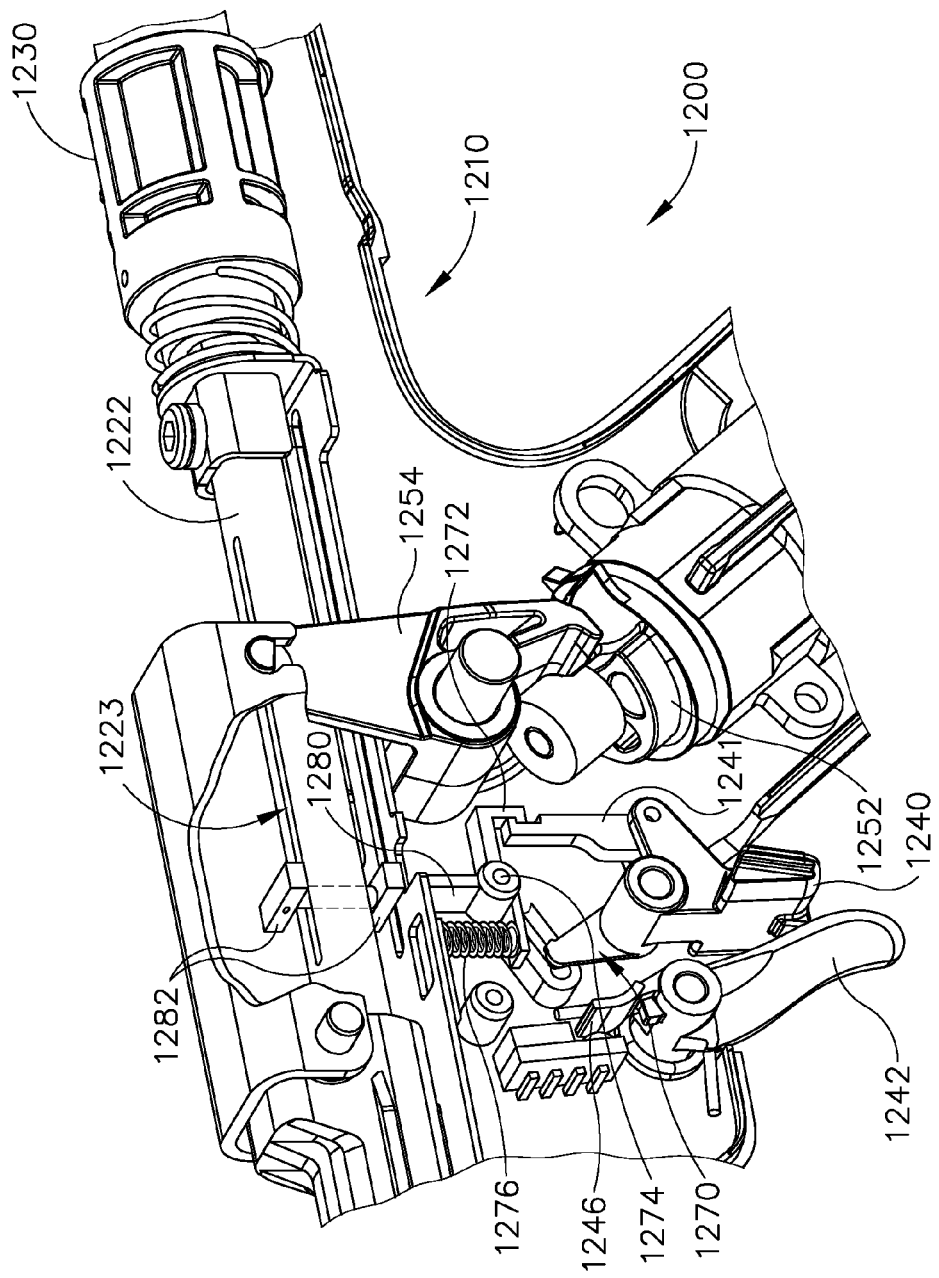
FIG. 33 depicts a detailed perspective cut-away view of yet another exemplary alternative anvil lockout assembly.

Various suitable features that may be used to provide activation of anvil lockout assembly (1170) in response to insertion of battery pack (120) into socket (116) will be apparent to those of ordinary skill in the art in view of the teachings herein III. Exemplary Alternative Lockout Features A. Exemplary Rotatable Anvil Lockout Assembly FIG. 33 shows still another exemplary alternative instrument (1200) that may be used to provide an end-to-end anastomosis between two sections of an anatomical lumen such as a portion of a patient's digestive tract. It should be understood that instrument (1200) of the present example is substantially the same as instrument (10) described above unless otherwise noted herein. For instance, like with instrument (10), instrument (1200) comprises a handle assembly (1210), a shaft assembly (not shown), a stapling head assembly (not shown), and an anvil (not shown). Handle assembly (1210) is substantially the same has handle assembly (110) described above such that further details will not be described herein.

Like with instrument (10) described above, instrument (1200) is controlled by an operator via knob (1230) and triggers (1240, 1242). Knob (1230), like with knob (130) described above, is operatively connected to the shaft assembly to actuate the anvil. In particular, knob (1230) is rotatable to engage threads (not shown) of the shaft assembly to translate a trocar actuation rod (1222), which ultimately actuates the anvil as similarly described above with respect to shaft assembly (200) of instrument (10).

Triggers (1240, 1242) function similarly as triggers (140, 150) described above. For instance, a safety trigger (1240) may be first actuated by an operator to unblock a firing trigger (1242), to thereby enable activation of the stapling head assembly. Although not shown, it should be understood that like with safety trigger (140) described above, safety trigger (1240) may include an upright member (not shown) that is generally operable to permit actuation of safety trigger (1240) only after the anvil has been adjusted to define a gap distance (d) that is within a clinically acceptable range. Additionally, it should be understood that firing trigger (1242) may also include an upright member (not shown) similar to second upright member (154) described above. Of course, in other examples the upright members may be omitted entirely.

Firing trigger (1242) is similar to firing trigger (150) described above. In particular, once safety trigger (1240) has been activated, firing trigger (1242) is operable to initiate actuation of the stapling head assembly. Firing trigger (1242) includes a paddle (1246), which is configured to engage a motor activation module (not shown) when firing trigger (1242) is advanced by an operator. Like with motor activation module (180) described above, the motor activation module of the present example initiates the stapling sequence by activating a motor (not shown). The motor then drives a cam member (1252), which in turn drives a cam follower (1254). Cam member (1252) and cam follower (1254) are substantially the same as cam member (700) and cam follower (600) described above, such that cam member (1252) and cam follower (1254) cooperate to drive the stapling head assembly through a stapling sequence.

Unlike instrument (10) described above, instrument (1200) of the present example comprises an anvil lockout assembly (1270). Anvil lockout assembly (1270) is generally configured to prevent further adjustment of the longitudinal position of the anvil once safety trigger (1240) is actuated. Such a feature may be desirable because lockout of the anvil may prevent an operator from improperly changing the gap distance (d) once a suitable gap distance (d) is reached. Anvil lockout assembly (1270) comprises an actuation member (1272), a pivot (1274), a resilient member (1276) and a lockout member (1280). Actuation member (1272) is configured to engage with a lockout arm (1241) that is attached to safety trigger (1240). As will be described in greater detail below, actuation member (1272) is generally configured to hold anvil lockout assembly (1270) in the position shown in FIGS. 33 and 36 until safety trigger (1240) is actuated.

Resilient member (1276) and actuation member (1272) are disposed on opposite sides of pivot (1274). Pivot (1274) permits actuation member (1272), resilient member (1276) and lockout member (1280) to pivot about an axis defined by pivot (1274). Resilient member (1276) is configured to drive actuation member (1272) and lockout member (1280) in a counter clockwise direction (as seen in FIG. 33) once actuation member (1272) is disengaged from lockout arm (1241) of safety trigger (1240). As will be understood, resilient member (1276) is generally configured to bias anvil lockout assembly (1270) toward a locked position.

Lockout member (1280) extends upwardly from pivot (1274) through a longitudinal slot (1223) in trocar actuation rod (1222). As can be seen, lockout member (1280) is generally positioned perpendicularly relative to the longitudinal axis of trocar actuation rod (1222). Lockout member (1280) includes two blocks (1282) disposed on either side of trocar actuation rod (1222). Blocks (1282) are positioned on lockout member (1280) at a distance that is slightly larger than the outer diameter of trocar actuation rod (1222). As will be described in greater detail below, such a positioning of blocks (1282) enables lockout member (1280) to prevent translation of trocar actuation rod (1222) in at least one direction when lockout member (1280) departs from the perpendicular positioning shown in FIG. 33.

Figure 34:
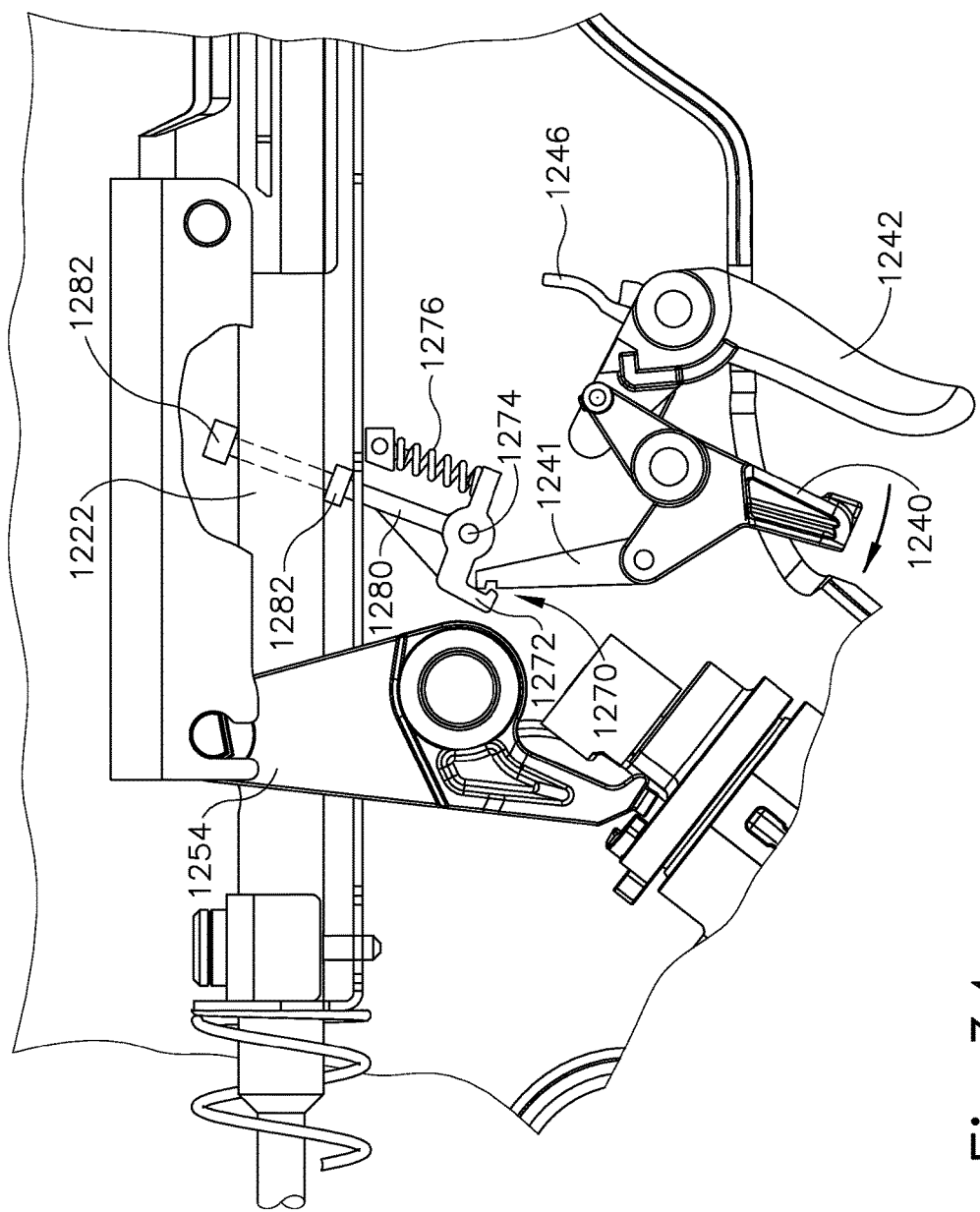
FIG. 34 depicts a detailed side elevational view of the anvil lockout assembly of FIG. 33, with the anvil lockout assembly in an intermediate state between an unlocked position and a locked position.
Figure 35:
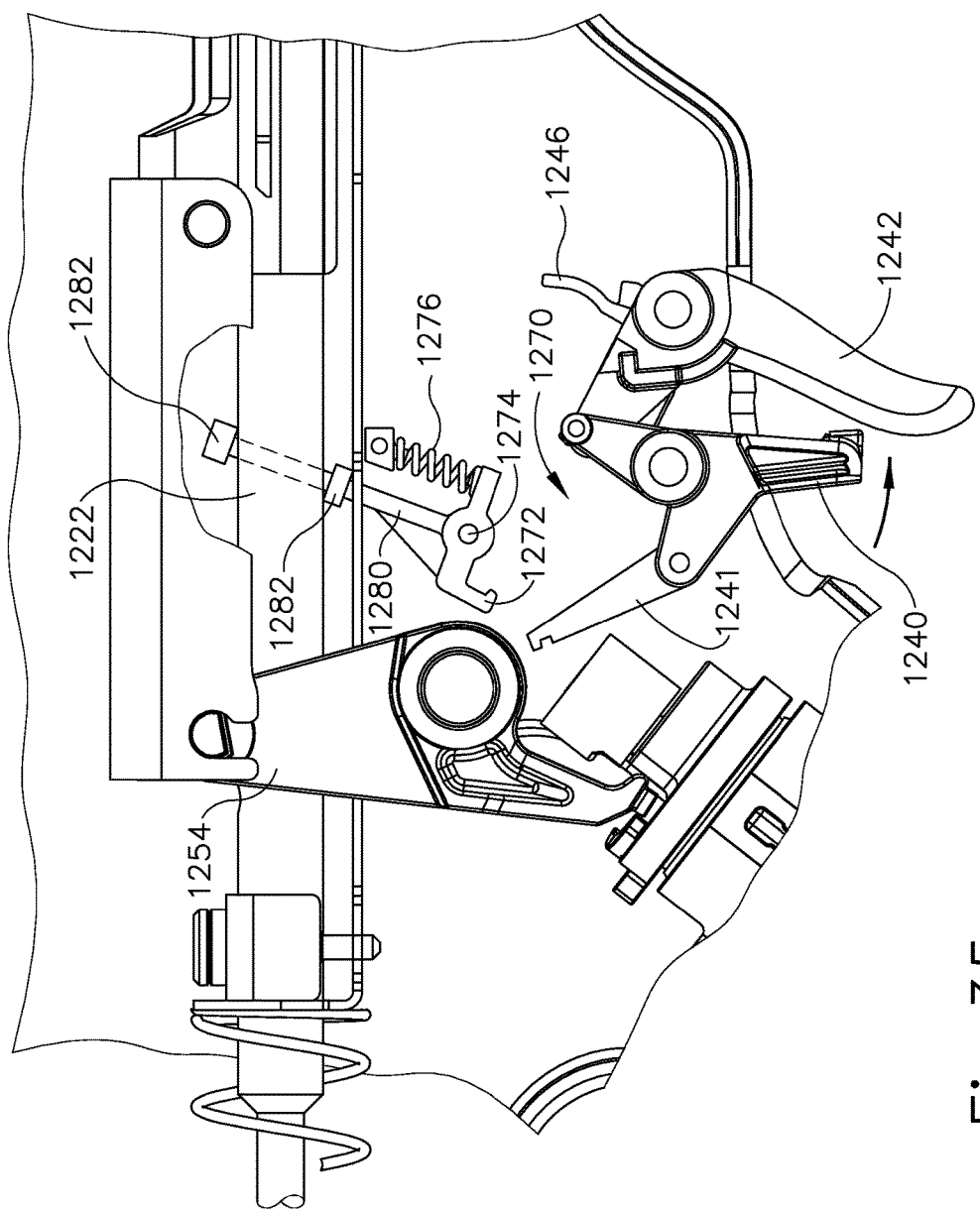
FIG. 35 depicts another detailed side elevational view of the anvil lockout assembly of FIG. 33, with the anvil lockout assembly in the locked position.
Figure 36:
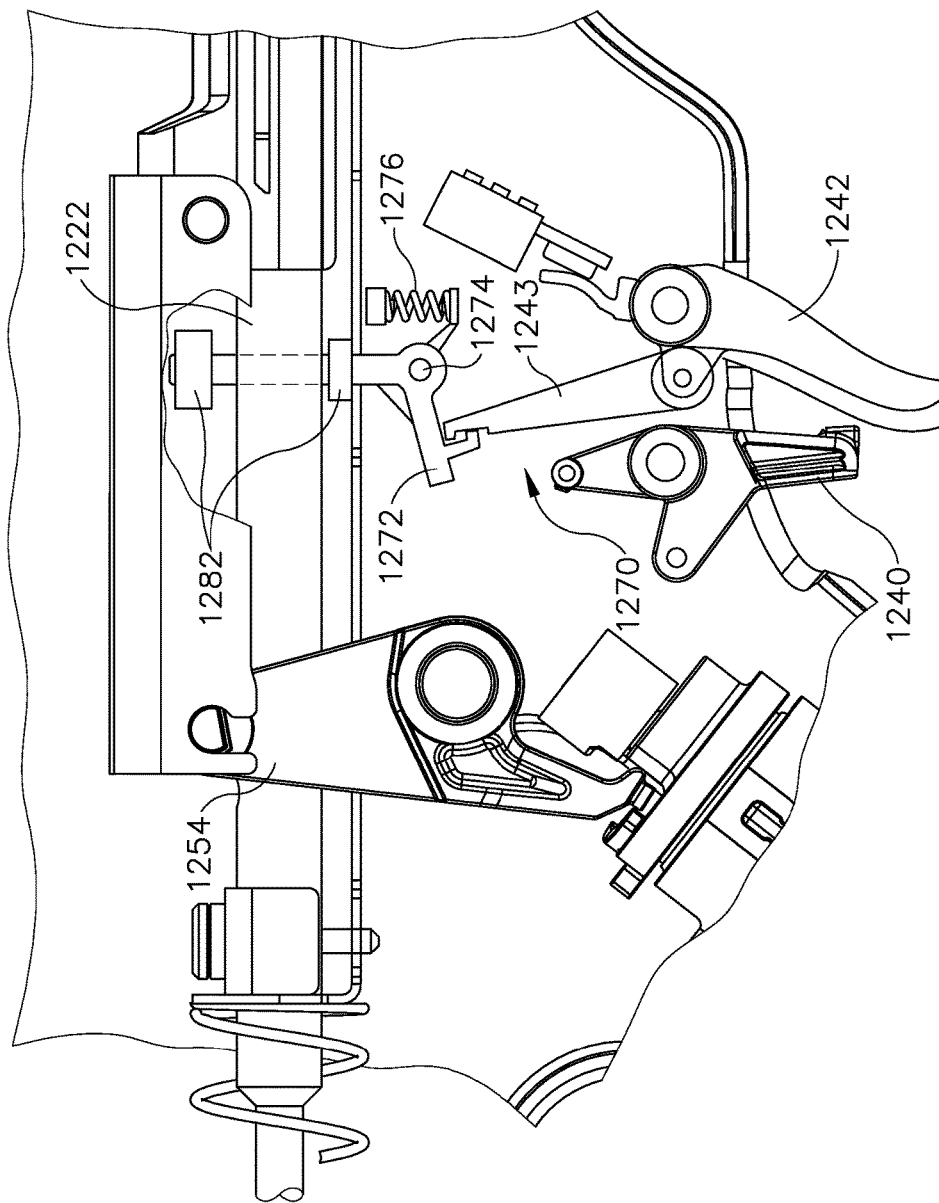
FIG. 36 depicts a detailed side elevational view of an exemplary variation of the anvil lockout assembly of FIG. 33, with the anvil lockout assembly in an unlocked position.

FIGS. 33-36 show an exemplary sequence of operation of anvil lockout assembly (1270). It should be noted that FIG. 33 shows instrument (1200) oriented with the distal end toward the left side of the page, while FIGS. 34-36 show instrument (1200) oriented with the distal end toward the right side of the page. As can be seen in FIG. 33, anvil lockout assembly (1270) is initially in an unlocked position, where trocar actuation rod (1222) is freely translatable within handle assembly (1210). In this position, actuation member (1272) is in engagement with safety trigger (1240), thereby holding anvil lockout assembly (1270) in the unlocked position. Correspondingly, lockout member (1280) is disposed in a position that is perpendicular to the longitudinal axis of trocar actuation rod (1222) such that translation of trocar actuation rod (1222) is not impeded by blocks (1282).

To shift anvil lockout assembly (1270) to the locked position, an operator merely has to actuate safety trigger (1240). Once safety trigger (1240) is actuated, lockout arm (1241) of safety trigger (1240) disengages from actuation member (1272) as shown in FIG. 34. With actuation member (1272) disengaged from lockout arm (1241), resilient member (1276) initiates movement of actuation member (1272) and lockout member (1280) in a clockwise direction (as shown in FIG. 34, but counter clockwise in FIG. 33) about pivot (1274). With lockout member (1280) rotated in a clockwise direction, blocks (1282) bear against the outer diameter of trocar actuation rod (1222), providing friction that prevents further advancement of the anvil via trocar actuation rod (1222).

Once anvil lockout assembly (1270) is in a locked position, lockout assembly (1270) will remain in the locked position. Even if the operator pivots safety trigger (1240) back to a non-actuated position as shown in FIG. 35, this pivotal movement of safety trigger (1240) will have no effect on lockout member (1280) since safety trigger (1240) is completely disengaged from lockout member (1280) as soon as lockout member (1280) pivots to the locking position.

FIG. 36 shows a variation of lockout assembly (1270) where an arm (1243) of firing trigger (1242) is engaged with actuation member (1272). In particular, when firing trigger (1242) is in a non-actuated position as shown in FIG. 36, arm (1243) holds lockout member (1280) in an unlocked state, preventing blocks (1282) from bearing against trocar actuation rod (1222). The operator is thus free to adjust the longitudinal position of the anvil via trocar actuation rod (1222) in the state shown in FIG. 36. However, after the operator pivots safety trigger (1240) to the actuated position, and then pivots firing trigger (1242) to the actuated position, arm (1243) disengages actuation member (1272). This disengagement of arm (1243) from actuation member (1272) allows resilient member (1276) to drive lockout member (1280) about pivot (1274), thereby driving blocks (1282) into trocar actuation rod (1222) to prevent further longitudinal movement of trocar actuation rod (1222). Thus, the variation of FIG. 36 operates substantially identically to the example of FIGS. 33-35 except that firing trigger (1242) releases lockout member (1280) in the variation of FIG. 36 while safety trigger (1240) releases lockout member (1280) in the example of FIGS. 33-35. Still other suitable variations will be apparent to those of ordinary skill in the art in view of the teachings herein.

B. Exemplary Anvil Lockout Assembly Actuated by Cam Follower

Figure 37:
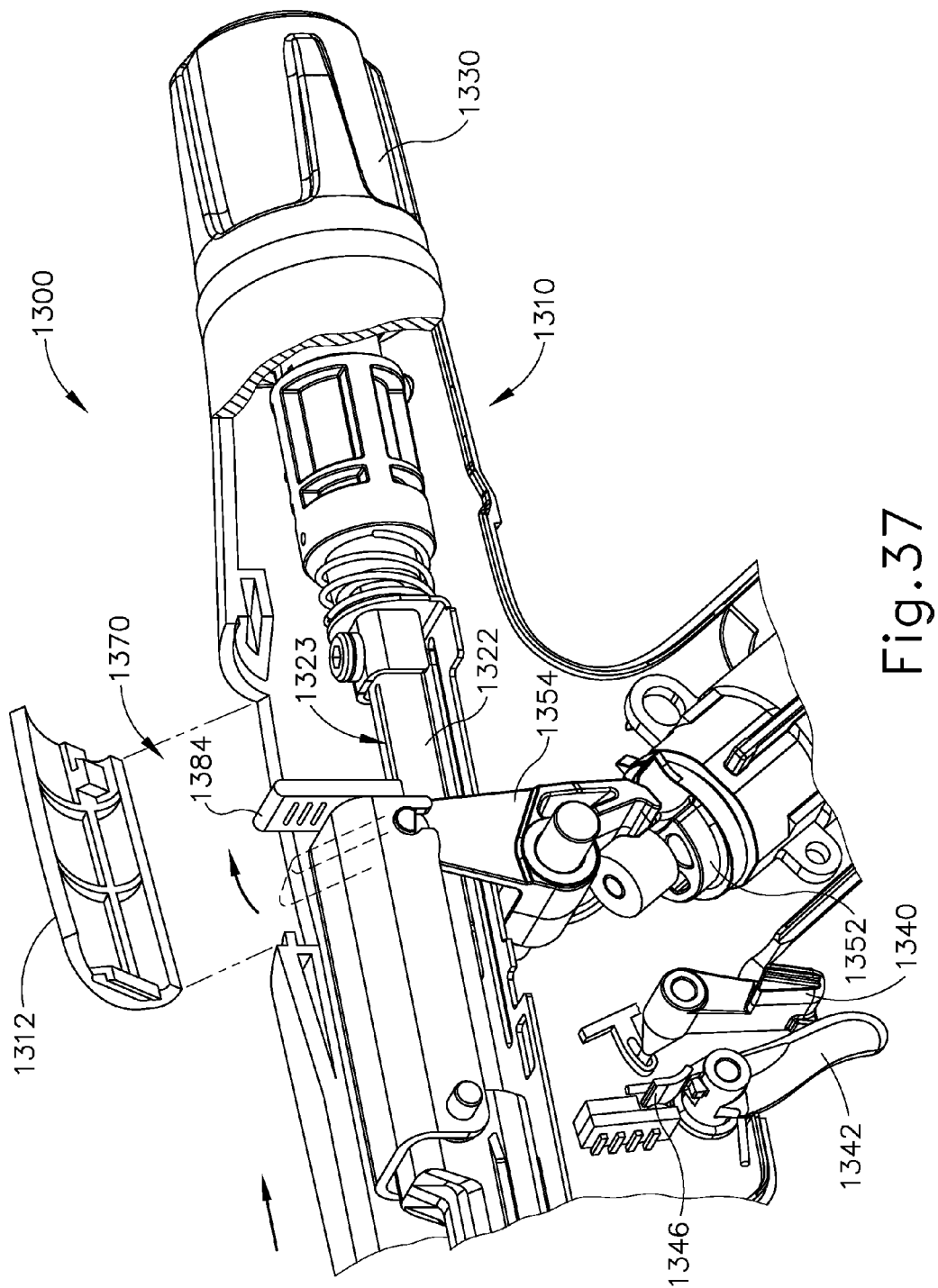
FIG. 37 depicts a detailed perspective cut-away view of yet another exemplary alternative anvil lockout assembly.

FIG. 37 shows yet another exemplary alternative instrument (1300) that may be used to provide an end-to-end anastomosis between two sections of an anatomical lumen such as a portion of a patient's digestive tract. It should be understood that instrument (1300) of the present example is substantially the same as instrument (10) described above unless otherwise noted herein. For instance, like with instrument (10), instrument (1300) comprises a handle assembly (1310), a shaft assembly (not shown), a stapling head assembly (not shown), and an anvil (not shown). Handle assembly (1310) is substantially the same has handle assembly (110) described above such that further details will not be described herein.

Like with instrument (10) described above, instrument (1300) is controlled by an operator via knob (1330) and triggers (1340, 1342). Knob (1330), like with knob (130) described above, is operatively connected to the shaft assembly to actuate the anvil. In particular, knob (1330) is rotatable to engage threads (not shown) of the shaft assembly to translate a trocar actuation rod (1322), which ultimately actuates the anvil as similarly described above with respect to shaft assembly (200) of instrument (10).

Triggers (1340, 1342) function similarly as triggers (140, 150) described above. For instance, a safety trigger (1340) may be first actuated by an operator to unblock a firing trigger (1342), to thereby enable activation of the stapling head assembly. Although not shown, it should be understood that like with safety trigger (140) described above, safety trigger (1340) may include an upright member (not shown) that is generally operable to permit actuation of safety trigger (1340) only after the anvil has been adjusted to a clinically acceptable range. Additionally, it should be understood that firing trigger (1342) may also include an upright member (not shown) similar to second upright member (154) described above. Of course, in other examples the upright members may be omitted entirely.

Firing trigger (1342) is similar to firing trigger (150) described above. In particular, once safety trigger (1340) has been activated, firing trigger (1342) is operable to initiate actuation of the stapling head assembly. Firing trigger (1342) includes a paddle (1346), which is configured to engage a motor activation module (not shown) when firing trigger (1342) is advanced by an operator. Like with motor activation module (180) described above, the motor activation module of the present example initiates the stapling sequence by activating a motor (not shown). The motor then drives a cam member (1352), which in turn drives a cam follower (1354). Cam member (1352) and cam follower (1354) are substantially the same as cam member (700) and cam follower (600) described above, such that cam member (1352) and cam follower (1354) cooperate to drive the stapling head assembly through a stapling sequence.

Figure 38:
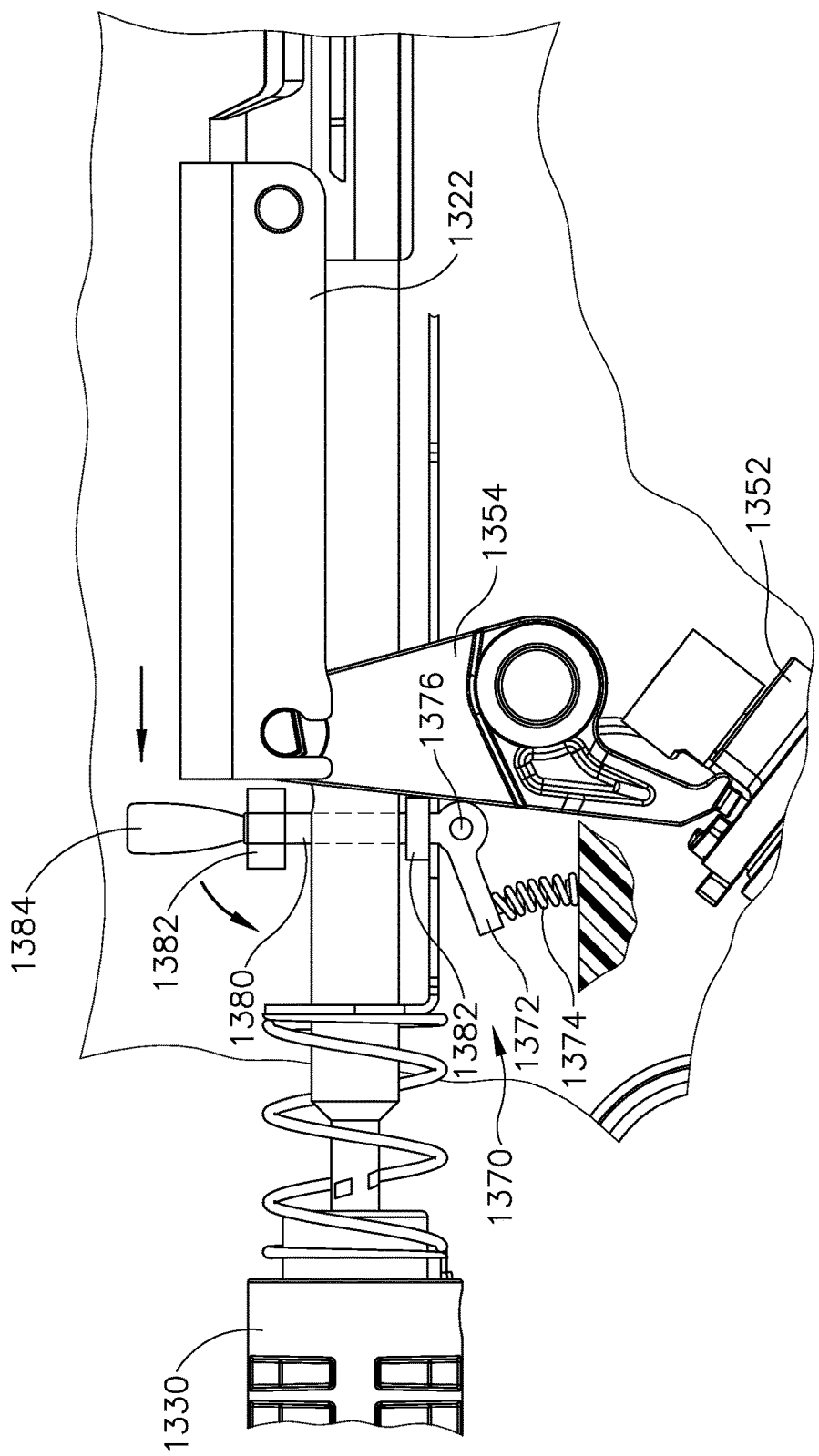
FIG. 38 depicts a detailed side elevational view of the anvil lockout assembly of FIG. 37, with the anvil lockout assembly in an unlocked position.

Unlike instrument (10) described above, instrument (1300) of the present example comprises an anvil lockout assembly (1370). Anvil lockout assembly (1370) is generally configured to prevent further adjustment of the longitudinal position of the anvil once safety trigger (1340) is activated. Such a feature may be desirable because lockout of the anvil may prevent an operator from improperly changing the gap distance (d) once a suitable gap distance (d) is reached. As can be seen in FIGS. 37-38, anvil lockout assembly (1370) comprises a lever arm (1372), a pivot (1376), a resilient member (1374), and a lockout member (1380). Lever arm (1372) is pivotable about pivot (1376) to actuate lockout member (1380) between an unlocked and locked position, as will be described in greater detail below. Resilient member (1374) is in communication with lever arm (1372) and is configured to bias anvil lockout assembly (1370) toward a locked position.

Lockout member (1380) extends upwardly from pivot (1376) through a slot (1323) in trocar actuation rod (1322). Lockout member (1380) comprises a pair of blocks (1382) and a tab (1384). Each block (1382) is disposed on either side of trocar actuation rod (1322). Blocks (1382) are spaced from each other at a distance that is slightly larger than the outer diameter of trocar actuation rod (1322). As will be described in greater detail below, such a spacing of blocks (1382) is configured to permit actuation of trocar actuation rod (1322) when lockout member (1380) is positioned perpendicularly relative to the longitudinal axis of trocar actuation rod (1322); yet blocks (1382) are also configured to lock trocar actuation rod (1322) when lockout member (1380) is positioned at a non-perpendicular angle relative to the longitudinal axis of trocar actuation rod (1322).

Tab (1384) of lockout member (1380) extends upwardly into handle assembly (1310) from the upper end of lockout member (1380). As will be described in greater detail below, tab (1384) is accessible to an operator by removing a panel (1312) of handle assembly (1310) to expose the internal components of instrument (1300). As will also be described in greater detail below, tab (1384) is generally configured to act as a bailout feature, permitting an operator to manually disengage anvil lockout assembly (1370) when anvil lockout assembly (1370) is in a locked position.

Figure 39:
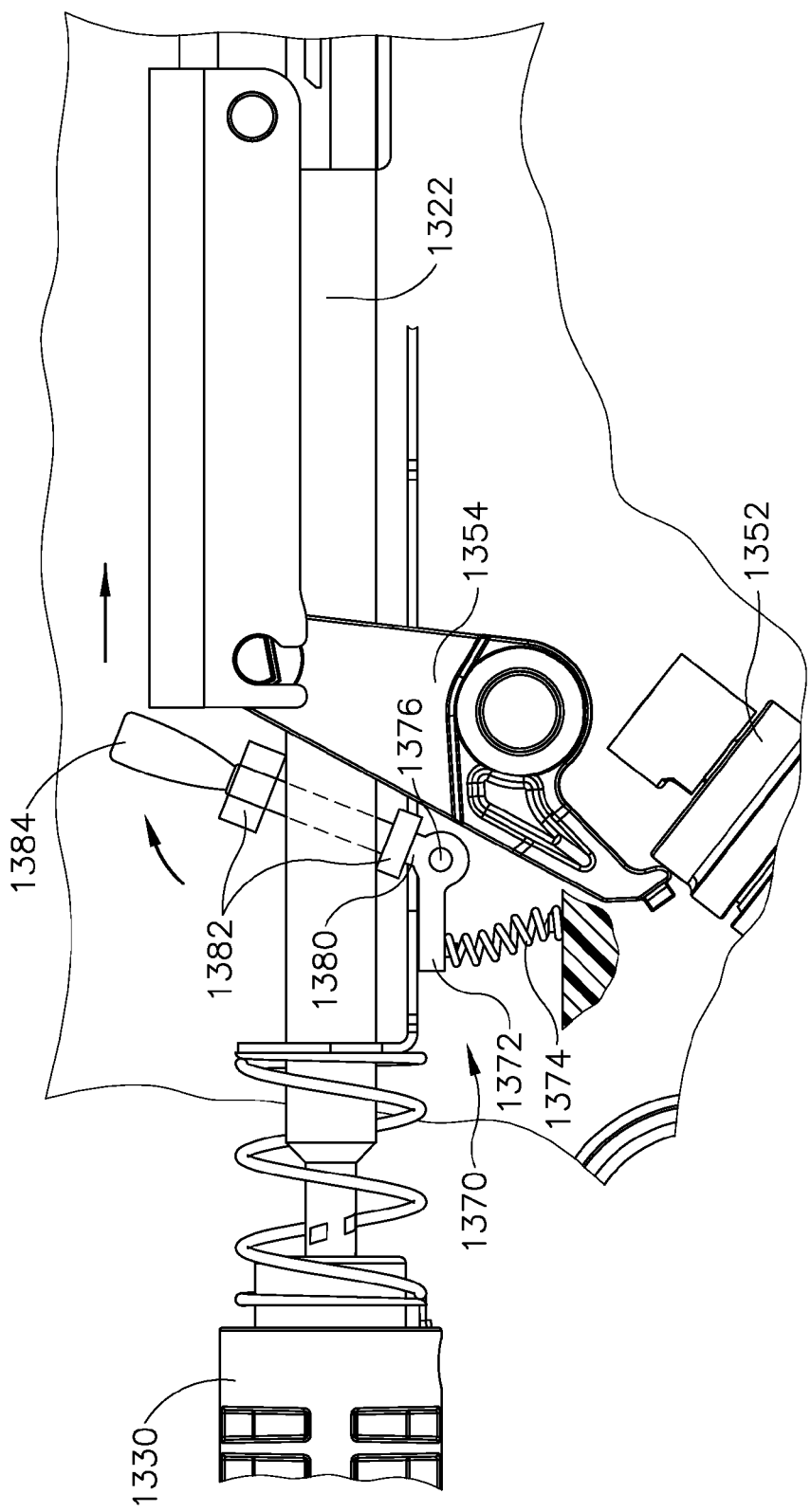
FIG. 39 depicts another detailed side elevational view of the anvil lockout assembly of FIG. 37, with the anvil lockout assembly in a locked position.

FIGS. 38-39 show an exemplary sequence of operation of anvil lockout assembly (1370). As can be seen in FIG. 38, anvil lockout assembly (1370) may initially be unlocked by cam follower (1354) acting on lockout member (1380) against the biasing of resilient member (1374) to align lockout member (1380) in a perpendicular position relative to the longitudinal axis of trocar actuation rod (1322). Thus, it should be understood that unlike other anvil lockout assemblies (1070, 1170, 1270) described above that are controlled by respective safety triggers (1040, 1140, 1240), anvil lockout assembly (1370) of the present example is controlled by the positioning of cam follower (1354).

As can be seen in FIG. 39, as cam follower (1354) is actuated by cam member (1352) during the staple firing sequence, lockout member (1380) is permitted to move to a locked position. In particular, pivotal movement of cam follower (1354) provides clearance for lockout member (1380) to rotate about pivot (1376). With such clearance available, resilient member (1374) acts upon lever arm (1372), driving lever arm (1372) and lockout member (1380) in a clockwise direction. Such movement of lockout member (1380) permits blocks (1382) to bear against the outer diameter of trocar actuation rod (1322), thereby preventing further actuation of trocar actuation rod (1322). It should therefore be understood that the longitudinal position of the anvil will be locked by blocks (1382) as soon as cam follower (1354) as part of the staple firing sequence. As noted above, cam follower (1354) will eventually pivot back from the position shown in FIG. 39 to the position shown in FIG. 38 as the staple firing sequence is fully completed. It should be understood that cam follower (1354) will thus drive lockout member (1380) back to the unlocked position as the staple firing sequence is fully completed. The operator may then translate the anvil distally to assist in releasing tissue to facilitate removal of instrument (1300) from the patient.

In some instances, it may be desirable to bail out of a staple firing sequence before that sequence is completed. In particular, it may be desirable to translate the anvil distally to assist in releasing tissue before cam follower (1354) pivots back to the position shown in FIG. 38. This may occur where, for example, operator error prevents instrument (1300) from being able to complete the full staple firing sequence. To return anvil lockout assembly (1370) to the unlocked position without moving cam follower (1354), the operator may remove panel (1312) of handle assembly (1310) as shown in FIG. 37. With panel (1312) removed, the operator may grasp tab (1384) of lockout member (1380). To unlock lockout member (1380) the operator may pull tab (1384) proximally as shown in FIG. 37. This proximal movement of tab (1384) will disengage blocks (1382) from trocar actuation rod (1322), thereby permitting the operator to actuate trocar actuation rod (1322) to drive the anvil distally to release tissue. Although instrument (1300) is described herein as providing a bailout feature via tab (1384), it should be understood that such a feature is merely optional and may be omitted in some examples.

C. Exemplary Alternative Triggers with Safety Return Feature

Figure 40:
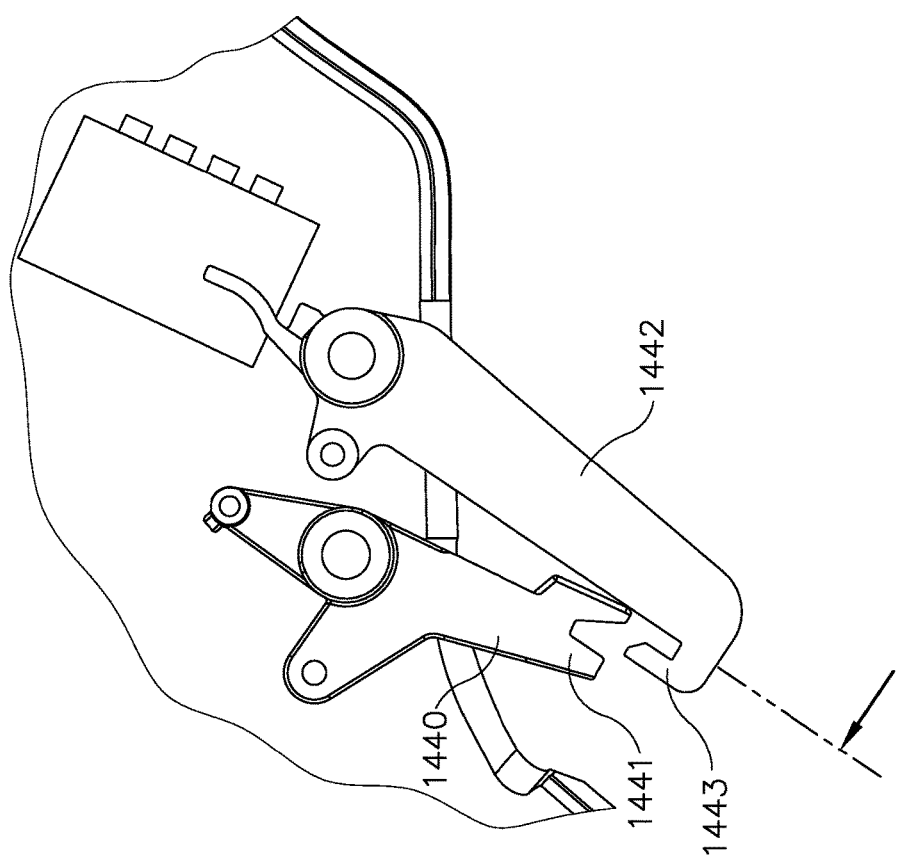
FIG. 40 depicts a side elevational view of an exemplary alternative set of triggers that may be readily incorporated into the circular staplers of FIGS. 1, 22, 27, 33 and 37.

FIG. 40 shows an exemplary set of triggers (1440, 1442) that may be readily incorporated into any of the instruments (10, 1000, 1100, 1200, 1300) described above. Generally, triggers (1440, 1442) are usable to operate instruments (10, 1000, 1100, 1200, 1300) substantially the same as described above. However, unlike other triggers (140, 150, 1040, 1042, 1140, 1142, 1240, 1242, 1340, 1342), triggers (1440, 1442) include other functional features that may improve the general operability of instruments (10, 1000, 1100, 1200, 1300). In particular, triggers (1440, 1442) comprise a safety trigger (1440) and a firing trigger (1442). Generally, firing trigger (1442) is operable to automatically retract safety trigger (1440) to its initial position when firing trigger (1442) returns to its initial position after being actuated.

As can be seen, safety trigger (1440) includes a receiving feature (1441) that is configured to receive at least a portion of firing trigger (1442). Correspondingly, firing trigger (1442) includes a coupling feature (1443) that is configured to be received in receiving feature (1441). As will be described in greater detail below, coupling feature (1443) generally defines a hook shape such that coupling feature (1443) may pull safety trigger (1440) to its initial position.

FIGS. 40-43 show an exemplary sequence of operation of triggers (1440, 1442). As can be seen in FIG. 40, initially triggers (1440, 1442) are disposed in an initial position. It should be understood that the initial position corresponds to the position of triggers (1440, 1442) prior to use by an operator to initiate a stapling sequence. In the initial position, receiving feature (1441) of safety trigger (1440) and coupling feature (1443) of firing trigger (1442) are disengaged from each other such that safety trigger (1440) may move independently relative to firing trigger (1442).

Figure 41:
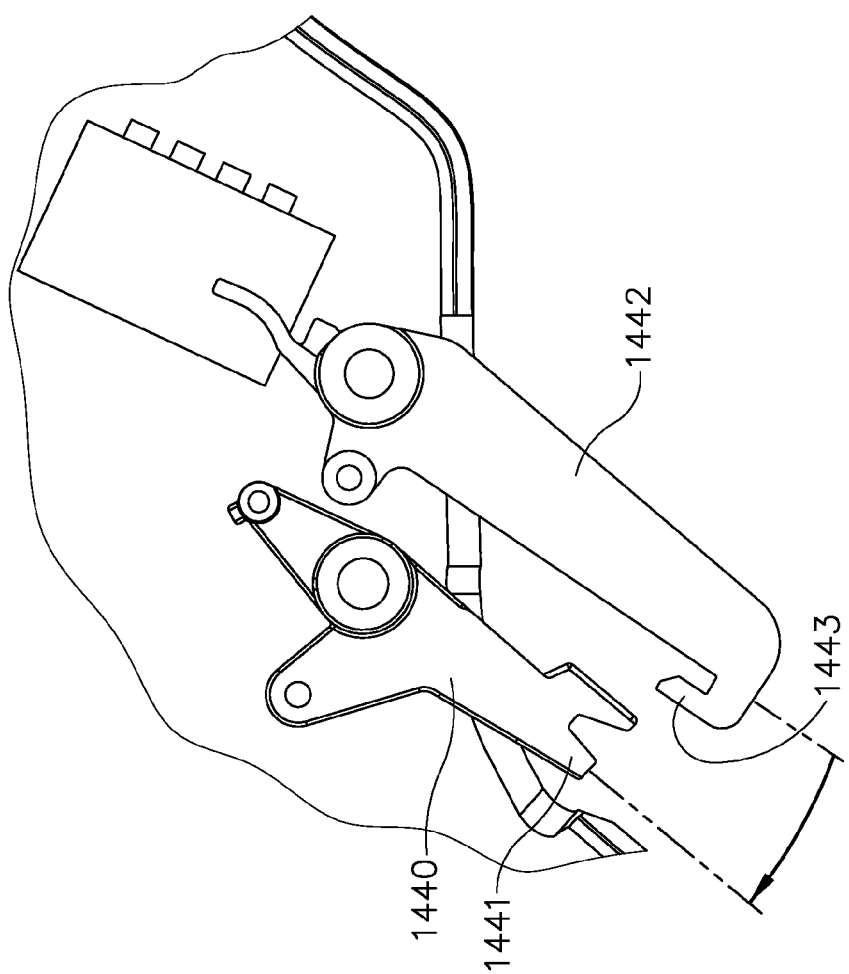
FIG. 41 depicts another side elevational view of the triggers of FIG. 40, with a safety trigger engaged.

As described above with respect to instrument (10), to initiate a stapling sequence, an operator must first actuate safety trigger (1440) to unlock movement of firing trigger (1442). FIG. 41 shows safety trigger (1440) in an actuated position such that firing trigger (1442) is in an unlocked condition where the operator may actuate firing trigger (1442). As can be seen, in this stage receiving feature (1441) of safety trigger (1440) and coupling feature (1443) of firing trigger (1442) remain disengaged from each other and are now offset from each other.

Figure 42:
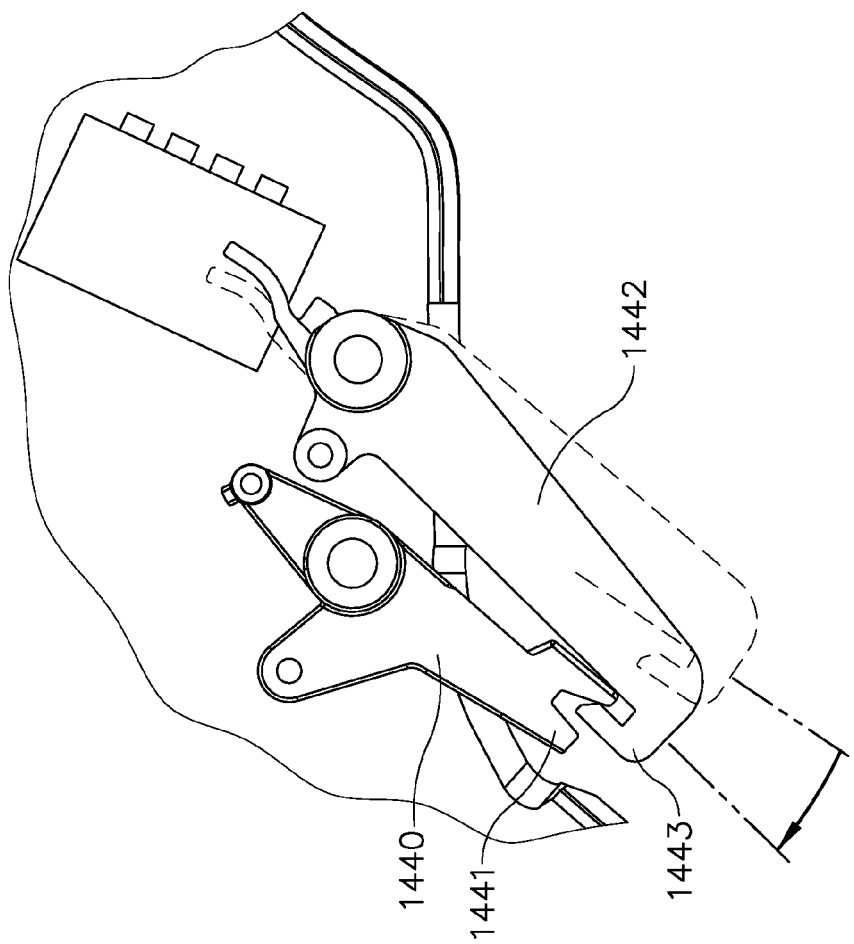
FIG. 42 depicts another side elevational view of the triggers of FIG. 40, with a firing trigger advanced to an activation position and engaged with the safety trigger.

Next, the operator may desire to initiate a stapling sequence by actuating firing trigger (1442) to a firing position. FIG. 42 shows firing trigger (1442) actuated to a position where a firing sequence is initiated. As can be seen by comparing FIGS. 41 and 42, in the process of actuating firing trigger (1442), coupling feature (1443) of firing trigger (1442) enters into receiving feature (1441) of safety trigger (1440) thereby interlocking firing trigger (1442) and safety trigger (1440).

Figure 43:
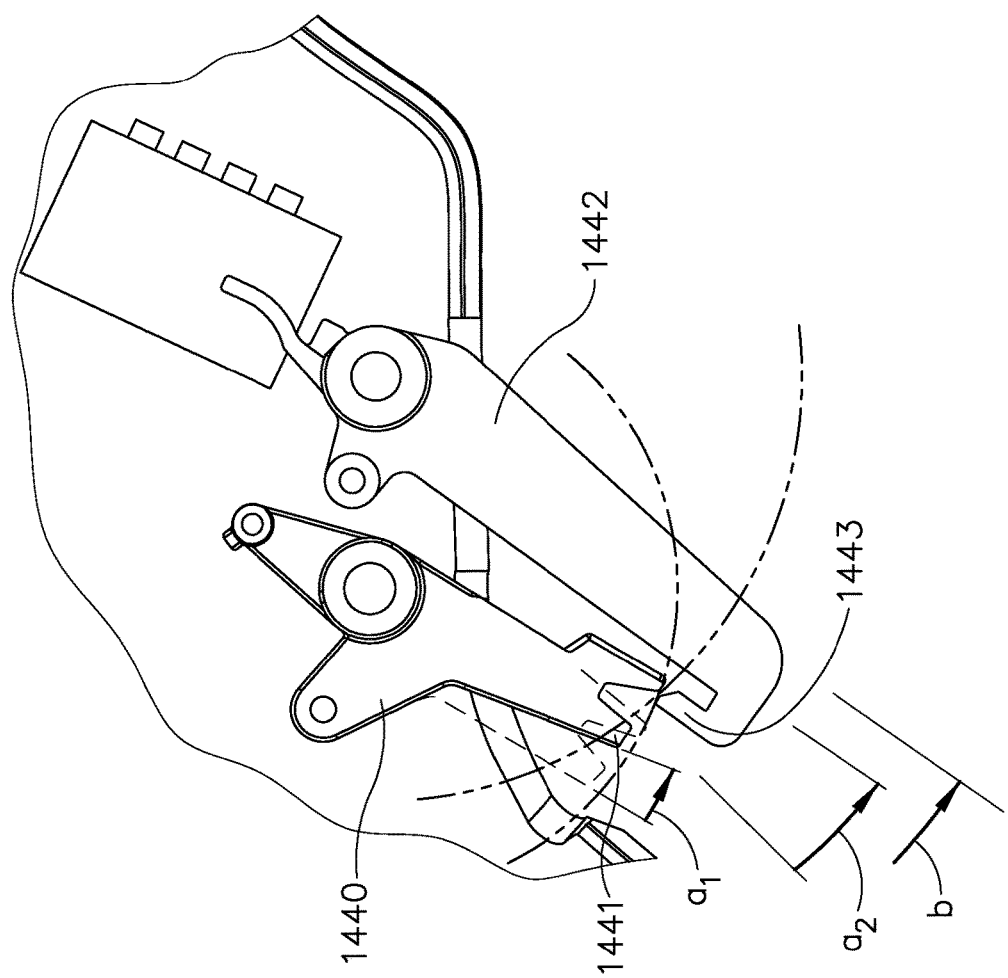
FIG. 43 depicts still another side elevational view of the triggers of FIG. 40, with the firing trigger returning the safety trigger to an initial position.

Once firing trigger (1442) has been actuated to the firing position, the interlocking relationship of coupling feature (1443) and receiving feature (1441) will permit firing trigger (1442) to automatically return safety trigger (1440) toward the initial position of safety trigger (1440). As can be seen in FIG. 43, firing trigger (1442) moves through a return stroke ($a_1$) pulling safety trigger (1440) through a separate safety return stroke ($a_2$). It should be understood that the respective travel paths (shown in phantom in FIG. 43) of safety trigger (1440) and firing trigger (1442) are configured such that coupling feature (1443) remains received within receiving feature (1441) only for the duration of safety return stroke ($a_2$) to pull safety trigger (1440) to its initial position. Once coupling feature (1443) disengages from receiving feature (1441), firing trigger (1442) may continue moving through return stroke ($a_1$), through a travel stroke (b) before returning to the initial position of firing trigger (1442). Although not shown, it should be understood that in some examples firing trigger (1442) may include a resilient feature that may return firing trigger (1442) to the initial position of firing trigger (1442) automatically after an operator releases firing trigger (1442). Of course, such a feature is merely optional and may be omitted in some examples.

D. Exemplary Triggers with Secondary Firing Lockout Feature

Figure 44:
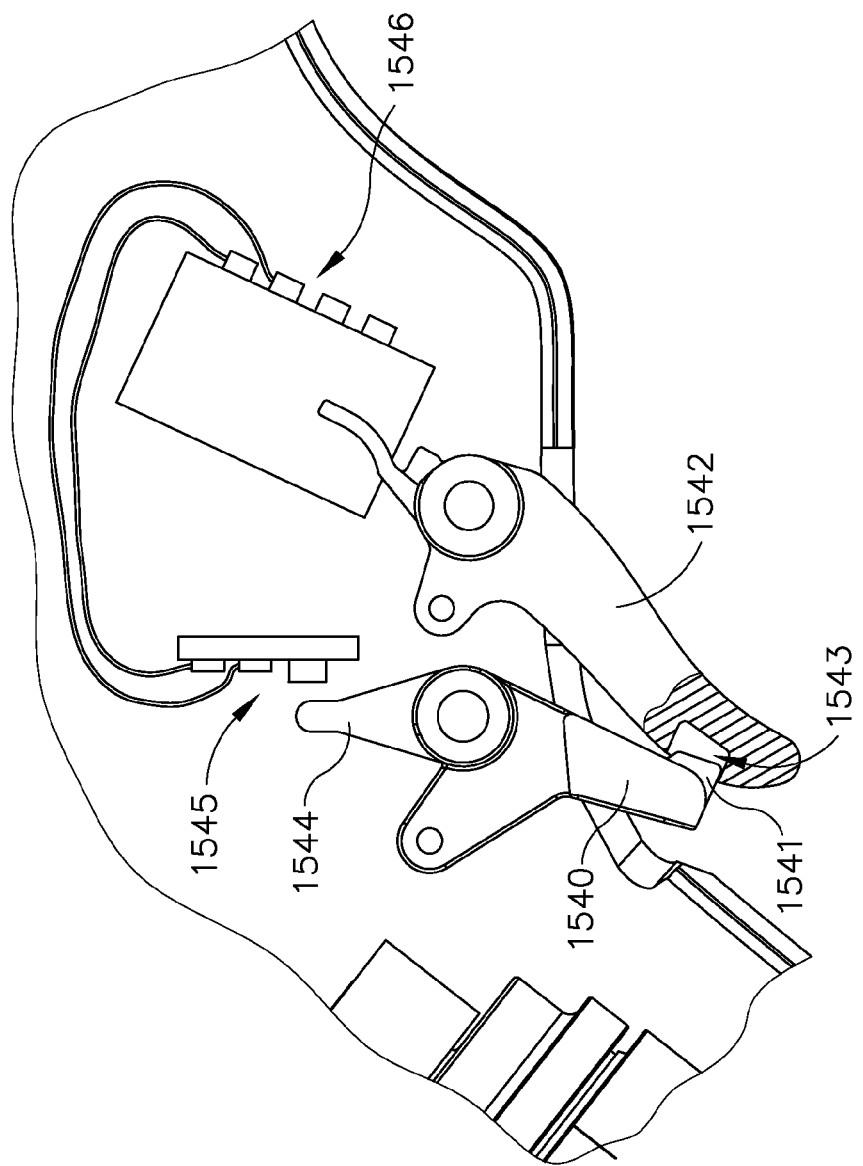
FIG. 44 depicts a side elevational view of another exemplary alternative set of triggers that may be readily incorporated into the circular staplers of FIGS. 1, 22, 27, 33, and 37.

FIG. 44 shows another exemplary set of triggers (1540, 1542) that may be readily incorporated into any of the instruments (10, 1000, 1100, 1200, 1300) described above. Generally, triggers (1540, 1542) are usable to operate instruments (10, 1000, 1100, 1200, 1300) substantially the same as described above. However, unlike other triggers (140, 150, 1040, 1042, 1140, 1142, 1240, 1242, 1340, 1342), triggers (1540, 1542) include other functional features that may improve the general operability of instruments (10, 1000, 1100, 1200, 1300). In particular, triggers (1540, 1542) comprise a safety trigger (1540) and a firing trigger (1542). Safety trigger (1540) is substantially the same as safety trigger (140) described above, except safety trigger (1540) is generally configured to provide both a mechanical stop to firing trigger (1542) and a digital or electrical stop to firing trigger (1542).

As can be seen, safety trigger (1540) includes a stop protrusion (1541) and an actuator (1544). Protrusion (1541) is configured to be received within a corresponding recess (1543) disposed within firing trigger (1542). When protrusion (1541) is received within recess (1543), protrusion prevents actuation of firing trigger (1542) because protrusion (1543) blocks the travel path of firing trigger (1542).

Safety trigger (1540) also includes actuator (1544). Generally actuator (1544) interfaces with a button assembly (1545) to provide a second lockout feature to prevent staple firing while safety trigger (1540) is engaged. In particular, button assembly (1545) is in communication with a motor activation module (1546) that is substantially the same as motor activation module (180) described above. When actuator (1544) of safety trigger (1540) is not engaged with button assembly (1545), a safety circuit of motor activation module (1546) is left in an open state such that motor activation module (180) is electrically inoperable to activate a motor (not shown). With the safety circuit in the open state, even if the operator were somehow able to actuate firing trigger (1542), motor activation module (1546) would not be able to activate the motor in response to actuation of firing trigger (1542). Thus, in the state shown in FIG. 44, the staple firing sequence is mechanically prevented by the pivotal position of safety trigger (1540) and is electrically prevented by the open circuit provided by button assembly (1545) being disengaged by actuator (1544).

However, once safety trigger (1540) is actuated away from firing trigger (1542), actuator (1544) engages button assembly (1545). Once button assembly (1545) is engaged by actuator (1544) the safety circuit of motor activation module (1546) is in a closed state. With the safety circuit in a closed state, subsequent actuation of firing trigger (1542) will initiate a staple firing sequence.

E. Exemplary Firing Lockout Features

Figure 45:
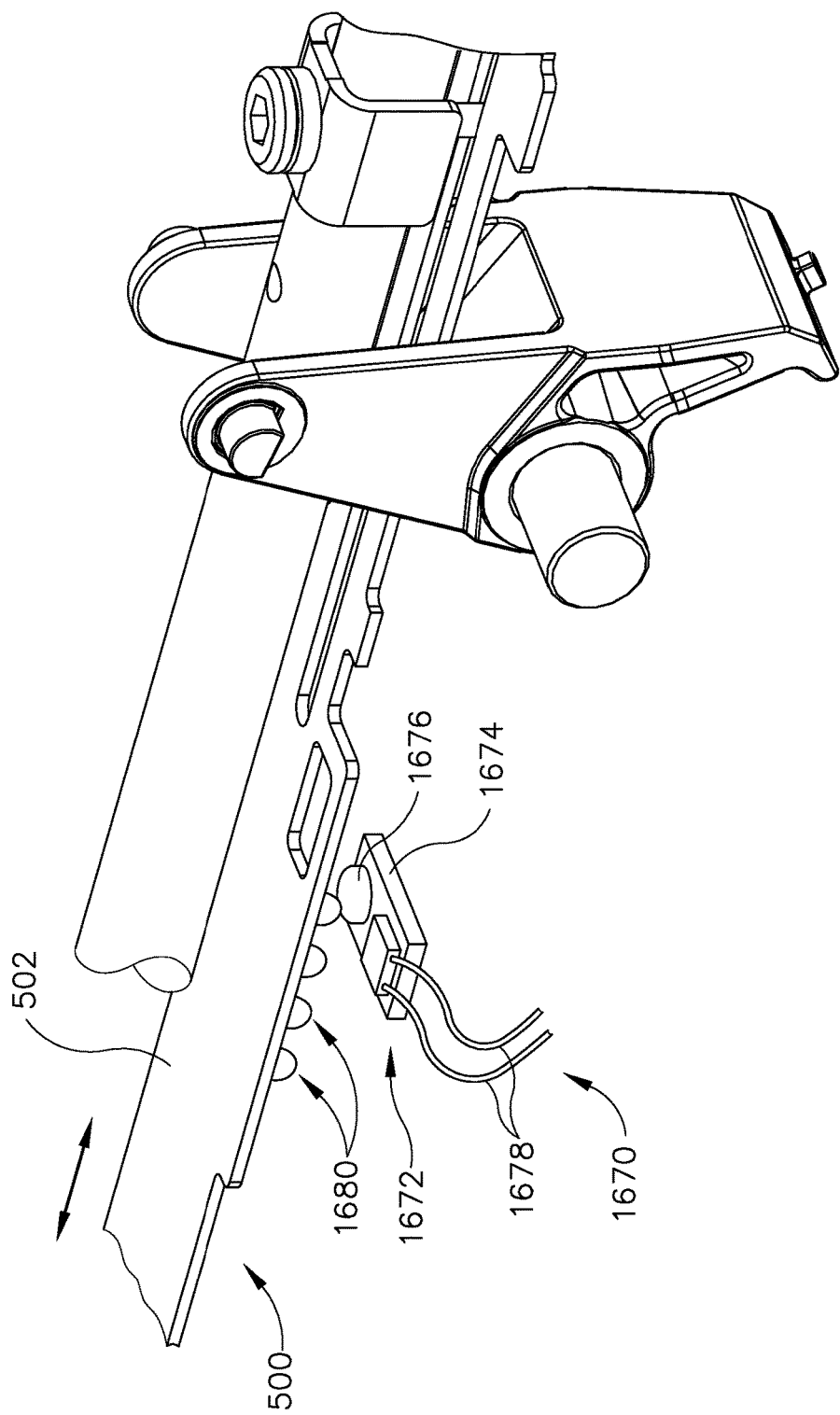
FIG. 45 depicts a detailed perspective view of the anvil actuation assembly of FIG. 12A, with the anvil actuation assembly equipped with a firing lockout assembly.

FIG. 45 shows an exemplary firing lockout assembly (1670) that may be readily incorporated into any of the instruments (10, 1000, 1100, 1200, 1300) described above. Although firing lockout assembly (1670) may be readily incorporated into instruments (10, 1000, 1100, 1200, 1300), firing lockout assembly (1670) is described herein in the context of instrument (10). As described above, instrument (10) includes a first upright member (144) and a second upright member (154) to physically stop triggers (140, 150) from being actuated before anvil (400) is adjusted to a position within a clinically acceptable range. It should be understood that in some examples it may be desirable to provide a separate electronic stop in addition to, or in lieu of upright members (144, 154). Firing lockout assembly (1670) of the present example provides such functionality.

As can be seen, firing lockout assembly (1670) includes a sensor assembly (1672) and a plurality of indicators (1680). Sensor assembly (1672) comprises a circuit board (1674), a sensor (1676), and a plurality of wires (1678). Circuit board (1674) is in communication with sensor (1676) such that sensor (1676) is operable to communicate the presence of indicators (1680) to circuit board (1674). Circuit board (1674) may then communicate signals from sensor (1676) to motor activation module (180) via wires (1678) as will be described in greater detail below.

Indicators (1680) of the present example comprise a plurality of protrusions extending downwardly from body (502) of bracket (500). Correspondingly, sensor (1676) is a push button that is adjacent to indicators (1680) such that each protrusion may actuate the button as body (502) moves relative to sensor (1676). Alternatively, sensor (1676) may comprise a proximity sensor and/or any other suitable kind of sensor (1676) that is responsive to the presence of indicators (1680) adjacent to sensor (1676). Circuit board (1674) is configured to count each actuation of sensor (1676) such that the relative position of body (502) may be calculated as body (502) moves relative to sensor (1676). After circuit board (1674) has calculated a predetermined travel amount for body (502), circuit board (1674) may send a signal via wires (1678) to motor activation module (180) to indicate that motor (160) may be activated using triggers (140, 150). As noted above, the longitudinal positioning of body (502) is associated with the longitudinal positioning of anvil (400). It should therefore be understood that sensor (1676) may be operable to determine whether the gap distance (d) is within the clinically acceptable range. Moreover, feedback from sensor (1676) may be provided to motor activation module (180) such that actuation of firing trigger (150) will only activate motor (160) if feedback from sensor (1676) indicates that the gap distance (d) is within the clinically acceptable range.

Figure 46:
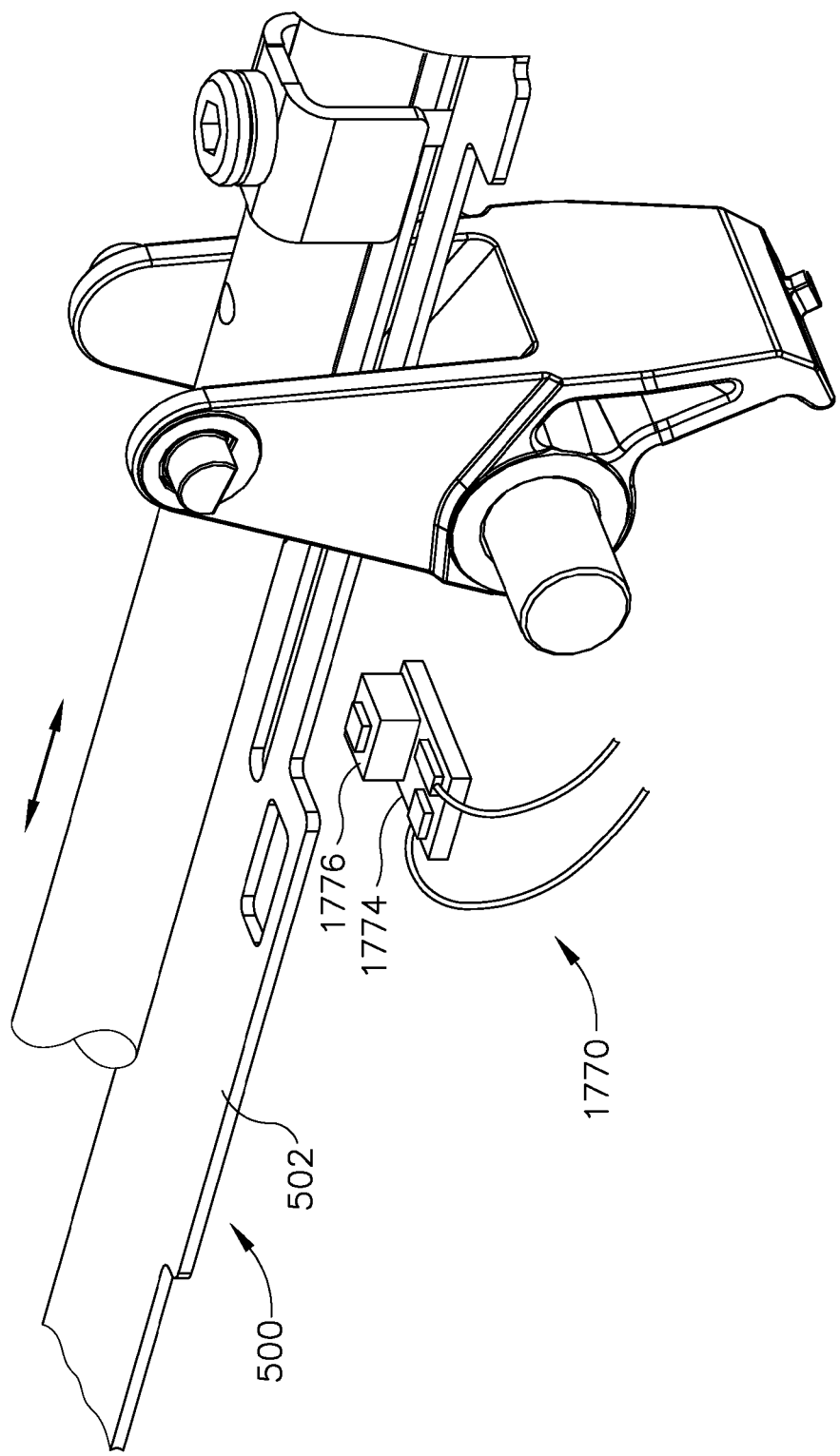
FIG. 46 depicts a detailed perspective view of the anvil actuation assembly of FIG. 12A, with the anvil actuation assembly equipped with an alternative firing lockout assembly.

FIG. 46 shows an exemplary alternative firing lockout assembly (1770). Firing lockout assembly (1770) of this example is substantially the same as firing lockout assembly (1670) described above, except firing lockout assembly (1770) includes a circuit board (1774) equipped with a Hall Effect sensor (1776) instead of a button. Correspondingly, at least a portion of body (502) is magnetized to provide a suitable magnetic field that sensor (1776) may detect. Thus, sensor (1776) may be operable to determine whether the gap distance (d) is within the clinically acceptable range. Moreover, feedback from sensor (1776) may be provided to motor activation module (180) such that actuation of firing trigger (150) will only activate motor (160) if feedback from sensor (1776) indicates that the gap distance (d) is within the clinically acceptable range.

IV. Exemplary Methods for Resetting Instrument for Subsequent Firings

In some instances, it may be desirable to enable resetting of instrument (10) after firing. For example, it may be desirable to fire a single instrument (10) multiple times in a testing or quality control setting. In other situations, after instrument (10) has been used in a procedure, it may be desirable to reset instrument (10) before, during, or after instrument (10) is cleaned, sterilized, and/or otherwise reprocessed for subsequent re-use. The following examples provide techniques by which an already fired instrument (10) may be re-set for subsequent firing.

Figure 47:
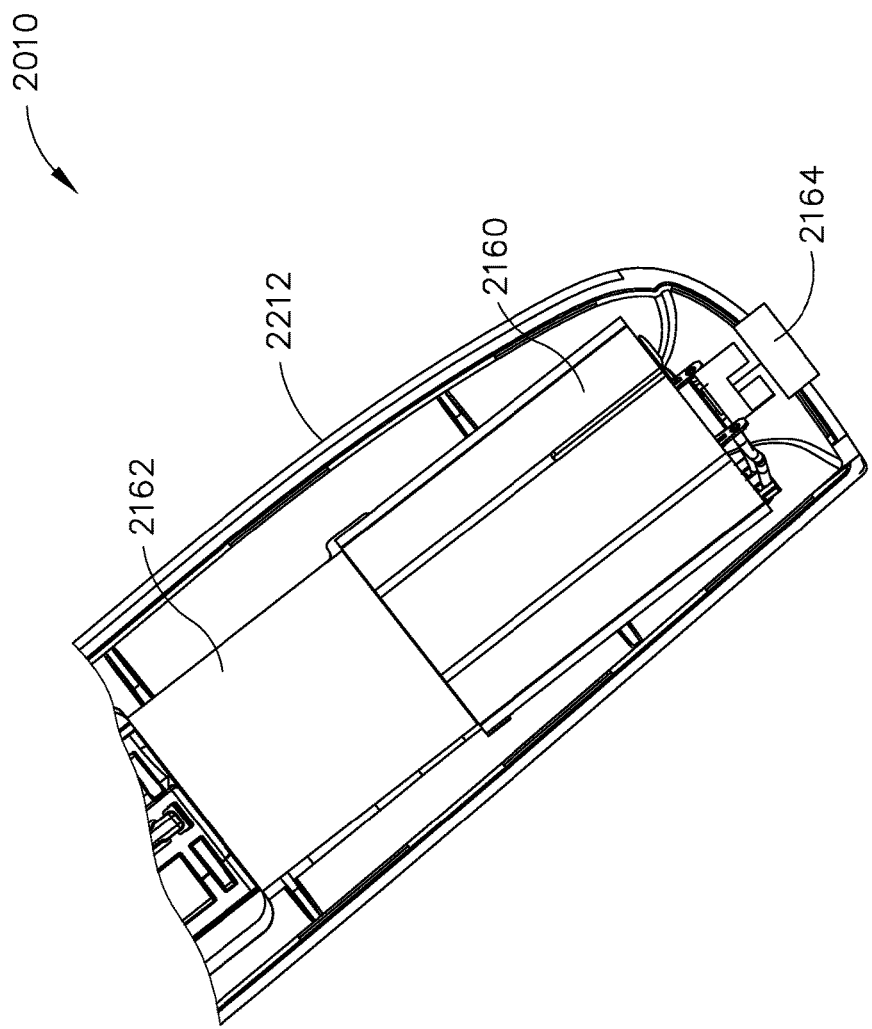
FIG. 47 depicts a detailed side view of a portion of an exemplary alternative circular stapler, shown with a portion of the body removed to show internal components.

FIG. 47 shows a pistol grip (2212) of an exemplary alternative instrument (2010), with a portion of the casing removed to show internal components. Instrument (2010) is configured to operate substantially similarly to instrument (10). Therefore, identical or substantially similar components are marked with the same reference numerals, without further discussion. It should be understood that any components and operabilities of instrument (2010) that are not described explicitly below may be the same as the components and operabilities of instrument (10) described above. Instrument (2010) includes a motor (2160) may be activated like motor (160) described above, such as by actuation of a firing trigger (not shown) that is configured to operate substantially similarly to firing trigger (150) of instrument (10). Moreover, instrument (2010) of the present example includes a safety trigger that is configured and operable like safety trigger (140) discussed above. Instrument (2010) also includes other features of the trigger lockout assembly discussed above and shown best in FIGS. 9-12E.

Instrument (2010) is different than instrument (10) in that instrument (2010) includes a switch (2164) that is in communication with motor (2160). Switch (2164) is operable to reverse the polarity of motor (2160) when switch (2164) is actuated. Thus, it will be understood that actuating switch (2164) changes the direction of rotation of motor (2160), gear box (2162), cam (700), and bushing (701), when motor (2160) is activated by actuation of a firing trigger, such as firing trigger (140) discussed above. Moreover, in order to allow for re-activation of motor (2160) after an actuation stroke of stapling head assembly (300) has been completed, instrument (2010) in some examples does not include a short circuit module, power sink, etc., or other features that prevent subsequent activation of motor (2160) once an actuation stroke of stapling head assembly (300) has been completed. In other examples, instrument (2010) may include such features that prevent re-activation of motor (2160), but such features may be configured to be disabled (i.e., such that they cannot prevent re-activation of motor (2160)).

In the present example, switch (2164) is located at the bottom of pistol grip (2212). In some versions, switch (2164) is exposed such that switch (2164) is accessible without having to disassemble instrument (2010). In some other versions, switch (2164) is positioned within pistol grip (2212) or elsewhere within instrument (2010) such that at least a portion of instrument (2010) must be disassembled in order to access switch (2164). As yet another merely illustrative example, switch (2164) may be recessed within pistol grip (2212) such that switch (2164) may be accessed with a tool inserted through a small opening in pistol grip (2212); yet such that switch (2164) is not conspicuous or easily accessible to the casual operator of instrument (2010). Other suitable ways in which switch (2164) may be positioned and accessible will be apparent to those of ordinary skill in the art in view of the teachings herein. Similarly, various suitable forms that switch (2164) may take will be apparent to those of ordinary skill in the art in view of the teachings herein.

Figure 48:
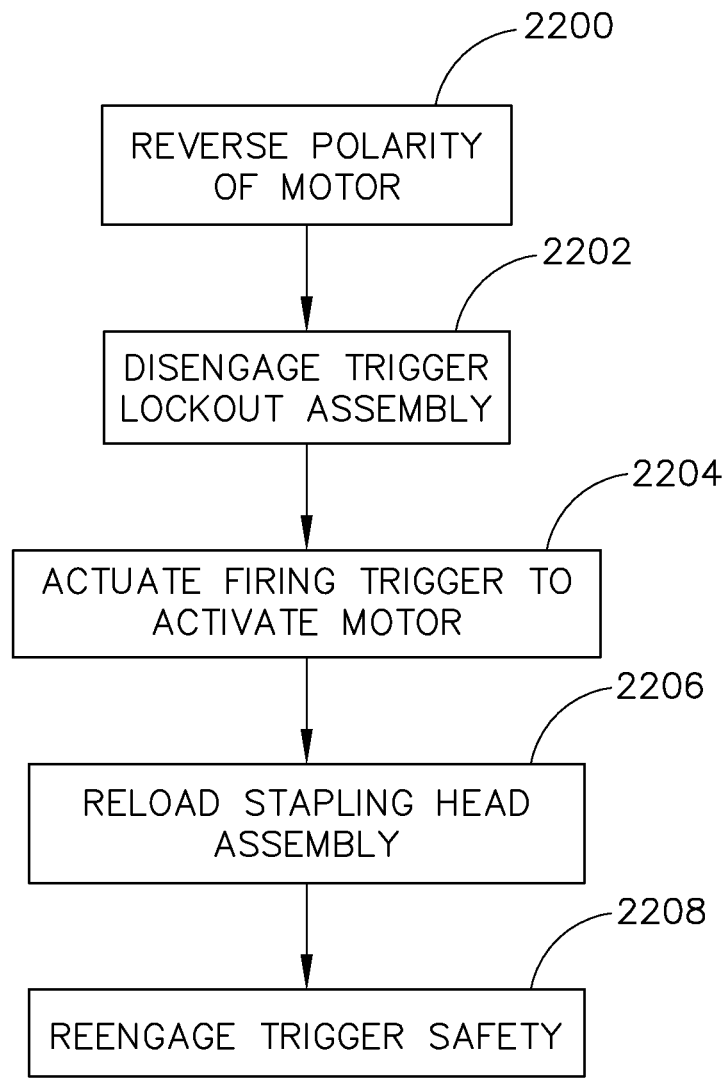
FIG. 48 depicts a flowchart showing steps of an exemplary method of resetting the circular stapler of FIG. 1 or FIG. 47.

FIG. 48 shows a first example of a method of resetting instrument (10, 2010) after firing, such as after an actuation stroke of stapling head assembly (300) of instrument (10, 2010). As shown, the method includes the step of reversing the polarity of motor (160, 2160) (block 2200). In some versions, reversing the polarity includes actuating switch (2164) of instrument (2010), thus reversing the polarity of motor (2160) as discussed above. Other suitable ways in which the polarity of motor (160, 2160) may be reversed will be apparent to those of ordinary skill in the art in view of the teachings herein. The method further includes the step of disengaging trigger lockout assembly (block 2202) as discussed above (e.g., by actuating safety trigger (140)) to allow for firing of trigger (150) and thus activation of motor (160, 2160). Once the trigger lockout assembly is disengaged, the operator may actuate firing trigger (140) to activate motor (160, 2160) (block 2204). Since the polarity of motor (160, 2160) is reversed at this stage, it should be understood that motor (160, 2160) and the associated drive components will move in an direction that is opposite to the direction of motion described above in the context of firing stapling head assembly (300).

FIGS. 50A-50D schematically depict the interaction between cam member (700), features of cam follower (600), and features of rocker member (800) as cam member (700) rotates in response to activation of motor (160, 2160) (block 2204) when the polarity of motor (160, 2160) is reversed. It should be understood that the rotation of cam member (700) throughout the stages shown in FIGS. 50A-50D is driven by motor (160) and gearbox (162). It should be further understood that the interaction between cam member (700), cam follower (600), and features of rocker member (800) occurs essentially in the opposite manner as shown in FIGS. 20A-20D and as described above. Particularly, cam (700) in FIG. 50A is in the same position relative to cam follower (600) and rocker member (800) shown in FIG. 20D; in FIG. 50B is in the same position relative to cam follower (600) and rocker member (800) as shown in FIG. 20C; in FIG. 50C is in the same position relative to cam follower (600) and rocker member (800) as shown in FIG. 20B; and in FIG. 50D is in the same position relative to cam follower (600) and rocker member (800) as shown in FIG. 20A. Of course, as noted above, in the present example, actuation of rocker member (800) does not result in the activation of a short circuit module and/or other features that prevent subsequent uses of instrument (10, 2010). Due to the reversed polarity of motor (160, 2160), activation of motor (160, 2160) causes rotation of cam (700) in an opposite rotational direction that occurred during the prior activation of motor (160, 2160) (e.g., FIGS. 20A-20D) to thereby rotate cam (700) from the position shown in FIG. 50A to the position shown in FIG. 50D.

As motor (160, 2160) is activated at a reversed polarity, cam (700) rotates from the position shown in FIG. 50A to the position in FIG. 50B. Third surface region (716) of first cam feature (710) bears against second bearing feature (610) of cam follower (600), driving second bearing feature (610) upwardly. This causes cam follower (600) to pivot about pin (118) from the position shown in FIG. 18A toward the position shown in FIG. 18B. As cam member (700) is rotated further to the position shown in FIG. 50C, second surface region (714) bears against bearing member (610), such that cam follower (60)) reaches the position shown in FIG. 18B. Cam follower (600) thus drives knife member (340) and staple driver member (350) distally via drive bracket (250) and stapling head assembly driver (240), transitioning stapling head assembly (300) back to the actuated position at the stage shown in FIG. 50C.

As cam (700) rotates further, first bearing feature (604) of cam follower (600) eventually reaches first surface region (712) of cam (700). Second surface region (724) of second cam feature (720) engages second bearing feature (610) of cam follower (600). This causes cam follower (600) to pivot about pin (118) back from the position shown in FIG. 18B toward the position shown in FIG. 18A. Cam follower (600) thus drives knife member (340) and staple driver member (350) proximally via drive bracket (250) and stapling head assembly driver (240). Therefore, first bearing feature (604) of cam follower (600) is again positioned on first surface region (712) and bearing member (610) or rocker member (800) is adjacent to second surface region (734) of third cam feature (730). Also at this stage, knife member (340) and staple driver member (350) are in proximal positions, such that stapling head assembly (300) is returned to a non-actuated state. In some versions, a resilient member (e.g., a coil spring engaged with linearly translating components of the drive assembly such as stapling head assembly driver (240) and/or drive bracket (250); and/or a torsion spring engaged with cam follower (600); etc.) provides a bias to assist in returning cam follower (600) from the position shown in FIG. 50C and FIG. 18B to the position shown in FIG. 50D and FIG. 18A.

It should be understood from the foregoing that rotating cam (700) in an opposite manner of that shown in FIGS. 20A-20D, as shown in FIGS. 50A-D, results in resetting of instrument (10, 2010). With instrument (10, 2010) reset in this fashion, stapling head assembly (300) is in a non-actuated state; and cam (700) and cam follower (600) are in a pre-firing state. Returning back to FIG. 49, at this stage the operator may then reload stapling head assembly (300) with staples (90) (block 2206), and reengage the trigger lockout assembly (block 2208) to prevent undesired firing of instrument (10, 2010) until instrument (10, 2010) is in a state and position where it is ready to be intentionally fired.

Figure 49:
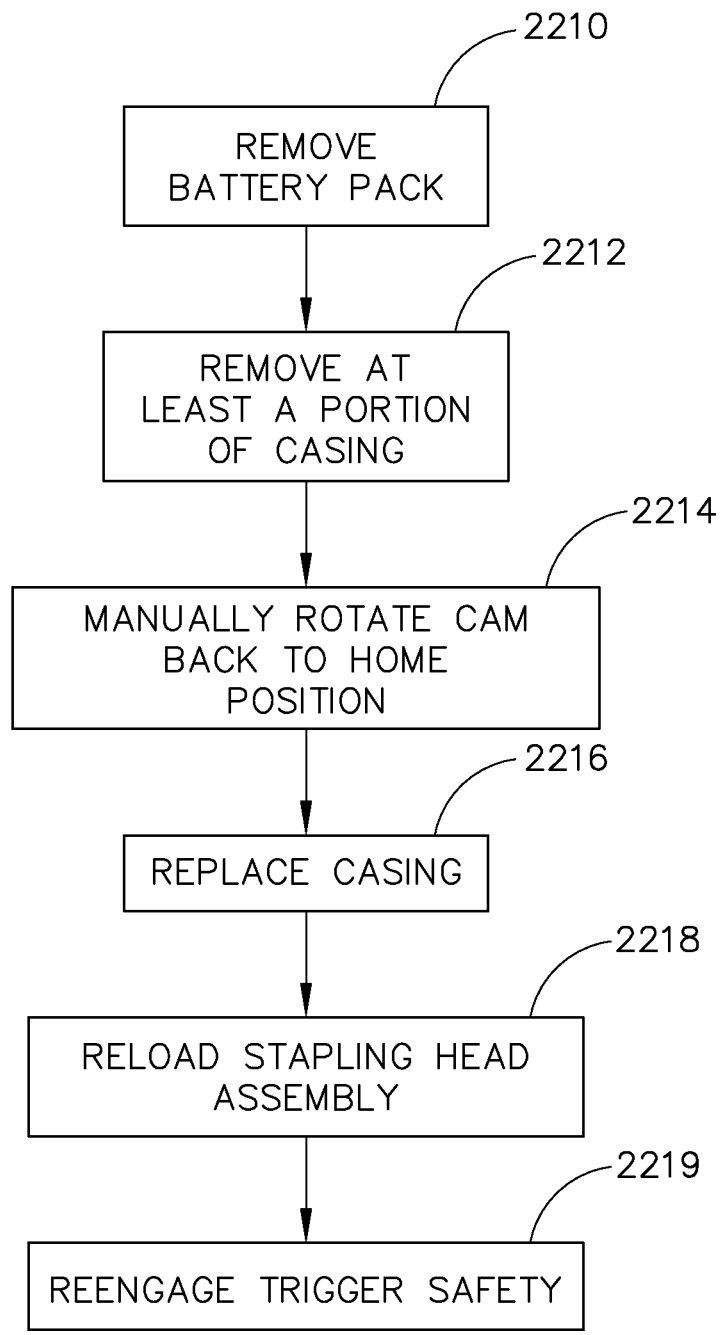
FIG. 49 depicts a flowchart showing steps of an exemplary alternative method of resetting the circular stapler of FIG. 1 or FIG. 47.

In addition to or in lieu of the method described above, an operator may reset instrument (10, 2010) for subsequent firings without activating motor (160, 2160) at all. For instance, FIG. 49 shows another exemplary method of resetting instrument (10, 2010). In this example, the operator may remove battery pack (e.g., battery pack (120)) (block 2210) and remove at least a portion of casing (110) to expose certain internal components of instrument (10, 2010), such as cam (700) (block 2212). Once cam (700) is exposed, the operator may manually rotate cam (700) from the position shown in FIG. 50A (which may be referred to herein as the "fired position") to the position shown in FIG. 50D (which may be referred to herein as the "home position") (block 2214). The user may manually rotate cam (700) by hand or by some sort of tool or device, such as a wrench, screwdriver, or other tool that is configured to provide a rotational force on cam (700). Moreover, cam (700) may include features to enable the use of such tools or devices. Various suitable forms that such features and tools may take will be apparent to those of ordinary skill in the art in view of the teachings herein.

It will be understood that when cam (700) is manually rotated in reverse, the interaction between cam (700), cam follower (600), and rocker member (800), as well as stapling head assembly (300), will be substantially identical to the interaction between cam (700) and such components with motor-driven reversed rotation of cam (700) as described with respect to FIG. 48. Manually rotating cam (700) in an opposite manner of that shown in FIGS. 20A-20D, thus provides the movement shown in FIGS. 50A-50D, resulting in resetting of instrument (10, 2010) as described above. It will be further understood that the operator must subject cam (700) to a sufficient level of rotational force that overcomes the resistance from other components such as cam follower (600), rocker member (800), and stapling head assembly (300), etc.), in order to rotate cam (700) in reverse. Once cam (700) has been manually rotated to the position shown in FIG. 50D, the operator then replaces casing (110) (block 2216), reloads stapling head assembly (300) with staples (90) (block 2218), and reengages the trigger lockout assembly (block 2219) to prevent undesired firing of instrument (10, 2010) until instrument (10, 2010) is in a state and position where it is ready to be intentionally fired.

Figure 51:
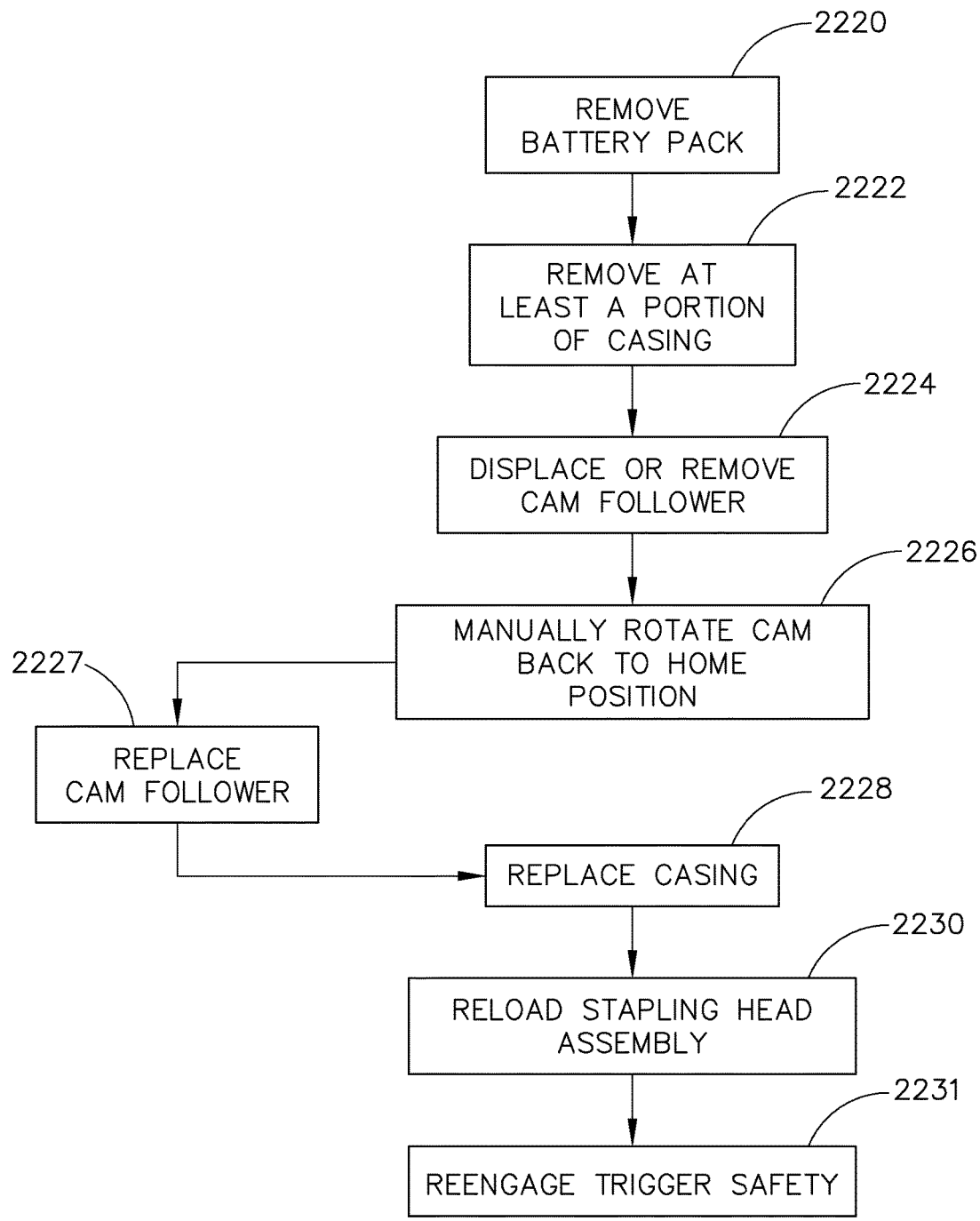
FIG. 51 depicts a flowchart showing steps of another exemplary alternative method of resetting the circular stapler of FIG. 1 or FIG. 47.

FIG. 51 shows another exemplary method of resetting instrument (10, 2010) for subsequent firings without activating motor (160, 2160). The method shown in FIG. 51 may be performed in addition to or in lieu of other methods for resetting instrument (10, 2010). As shown, the operator removes battery pack (120) (block 2220) and removes at least a portion of casing (110) (block 2222) to expose certain internal components of instrument (10, 2010), such as cam (700). Once cam (700) is exposed, the operator displaces or removes cam follower (600) (block 2224) such that cam (700) may be more easily moved from the position shown in FIGS. 20D and 50A to the position shown in FIGS. 20A and 50D (block 2226) without substantially interacting with cam follower (600), stapling head assembly (300), and other components. The operator may manually rotate cam (700) by hand or by some sort of tool or device, such as a wrench, screwdriver, or other tool that is configured to provide a rotational force on cam (700). Moreover, cam (700) may include features to enable the use of such tools or devices.

Once cam (700) has been manually rotated from the fired position back to the home position, the operator may replace cam follower (600) (block 2227) such that cam follower (600) is re-engaged with cam (700). The operator then replaces casing (110) (block 2228), reloads stapling head assembly (300) with staples (90) (block 2230), and reengages the trigger lockout assembly (block 2231) to prevent undesired firing of instrument (10, 2010) until instrument (10, 2010) is in a state and position where it is ready to be intentionally fired.

Figure 52:
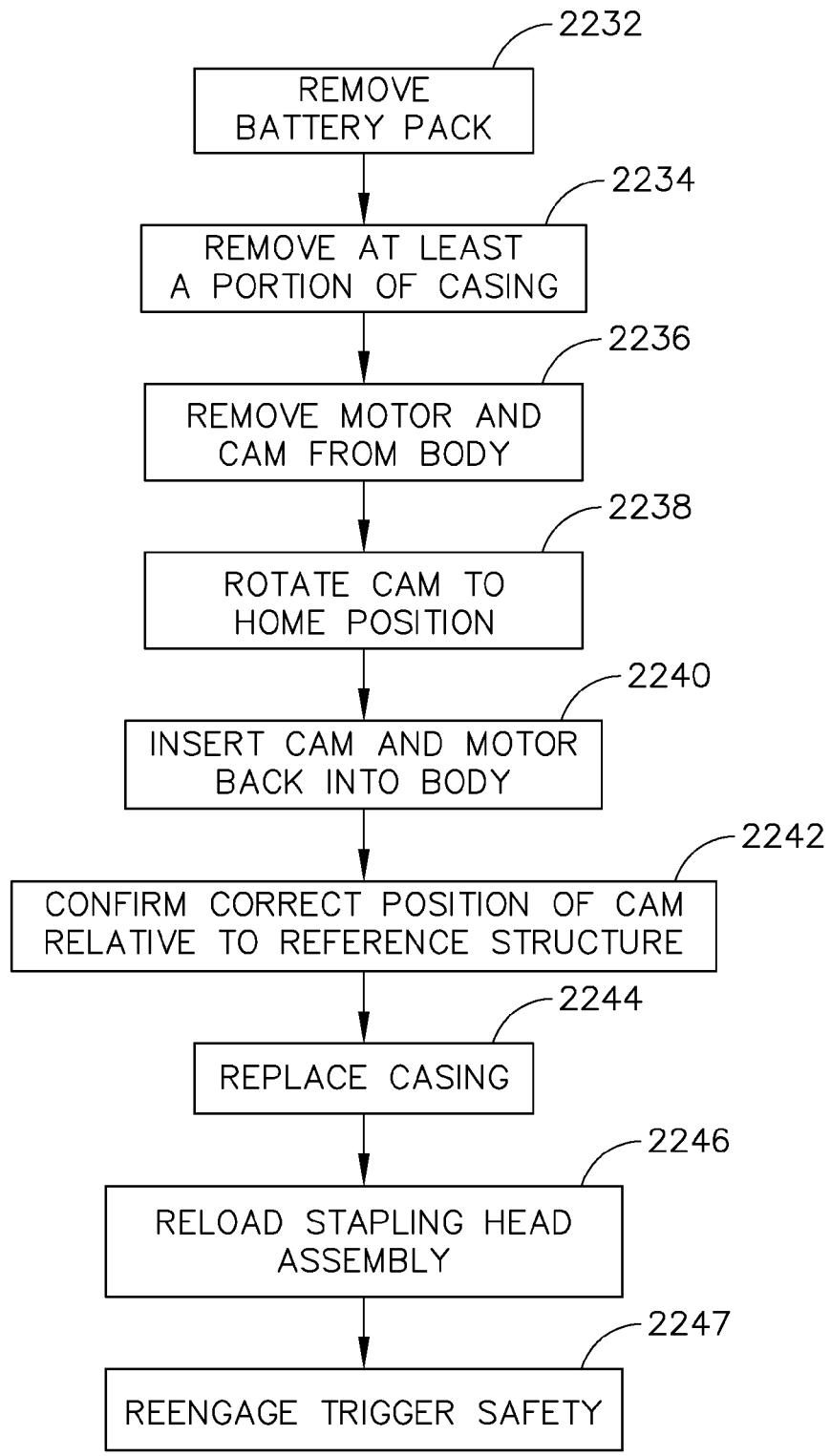
FIG. 52 depicts a flowchart showing steps of another exemplary alternative method of resetting the circular stapler of FIG. 1 or FIG. 47.

FIG. 52 shows another exemplary method of resetting instrument (10, 2010) for subsequent firings without activating motor (160, 2160). The method shown in FIG. 51 may be performed in addition to or in lieu of other methods for resetting a surgical instrument. As shown, the operator removes battery pack (120) (block 2232) and removes at least a portion of casing (110) (block 2234) to expose certain internal components of instrument (10, 2010), such as cam (700). The operator then removes motor (160, 2160), gear box (162, 2162), and cam (700) from handle assembly (200) (block 2236). Once these components are removed from handle assembly (200), the operator rotates cam (700) back to the home position shown in FIGS. 20A and 50D (block 2238). In this regard, motor (160, 2160), gear box (162), and/or cam (700) may include a marking that is angularly positioned to indicate the home position of cam (700) relative to the motor (160, 2160) and/or gear box (162).

Once cam (700) has been manually repositioned to the home position, the operator then inserts cam (700), motor (160, 2160), and gear box (162) back into handle assembly (200) (block 2240) and confirms the correct position of cam (700) relative to a reference structure (block 2242). For instance, the operator may confirm the correct position of third cam feature (730) relative to bearing member (804). If the position of cam (700) is not proper (e.g., as shown in FIGS. 20A and 50D), the operator may further adjust the position of cam (700). Once the proper positioning of cam (700) has been confirmed, the operator replaces casing (110) (block 2244), reloads stapling head assembly (300) with staples (90) (block 2246), and reengages the trigger lockout assembly (block 2247) to prevent undesired firing of instrument (10, 2010) until instrument (10, 2010) is in a state and position where it is ready to be intentionally fired. In some alternative examples, the operator may remove cam (700) and not remove motor (160, 2160) and/or gear box (162). The operator may then replace cam (700) relative to other structures of instrument (10, 2010), in the position shown in FIGS. 20A and 50D.

It should be understood that after any of the processes shown in FIGS. 48-49 and 51-52 are complete, instrument (10, 2010) may again be used to perform an anastomosis procedure such as the procedure shown in FIGS. 21A-21E and described above. In other words, a reset instrument (10, 2010) may be used just like a version of instrument (10, 2010) that had never been used before.

V. Exemplary Anvil Attachment Indicators

In some versions of instrument (10) it may desirable to provide instrument (10) with features that are configured to indicate proper and/or improper attachment of anvil (400) to trocar (330) of stapling head assembly (300). For instance, if anvil (400) is not properly attached to trocar (330), an operator may receive audible and/or tactile feedback indicating improper attachment. Additionally, if anvil (400) is properly attached to trocar (330), an operator may receive audible, tactile, and/or visible feedback indicating proper attachment. In addition or in the alternative, features may be configured to prevent firing of stapling head assembly (300) unless anvil (400) is properly attached to trocar (300). For instance, if anvil (400) is not properly attached to trocar (330), stapling head assembly (300) may be prevented from firing. If anvil (400) is properly attached to trocar (330), firing of stapling head assembly (300) may be enabled. Various examples of such features will be described in greater detail below; while other examples will be apparent to those of ordinary skill in the art in view of the teachings herein. Moreover, the following teachings may be applied to devices that are used in various other contexts.

A. Exemplary Dome Switch Assembly

FIGS. 53A-54B depict a version of stapling head assembly (300) including a switch assembly (3000). It should be understood that this version of stapling head assembly (300) may be readily incorporated into instrument (10). Switch assembly (3000) includes a dome switch (3010) and a resilient actuator spring (3020). Actuator spring (3020) is secured within a cavity (3012) formed within tubular casing (310). Dome switch (3010) is positioned between a pair of flanges (3022, 3024) of actuator spring (3020) such that movement of flange (3022) toward flange (3024) will actuate dome switch (3010). As will be discussed in more detail below, proximal movement of anvil (400), when properly secured to trocar (330), causes movement of flange (3022) toward flange (3024) so as to actuate dome switch (3010). Actuation of dome switch (3010) may provide audible, tactile, and/or visible feedback to an operator indicating proper attachment. Various suitable features that may be used to provide such a response to actuation of dome switch (3010) will be apparent to those of ordinary skill in the art in view of the teachings herein. Additionally or alternatively, actuation of dome switch (3010) may enable firing of stapling head assembly (300). In other words, unless dome switch (3010) has been actuated, stapling head assembly (300) may not be fired in some versions.

Figure 53A:
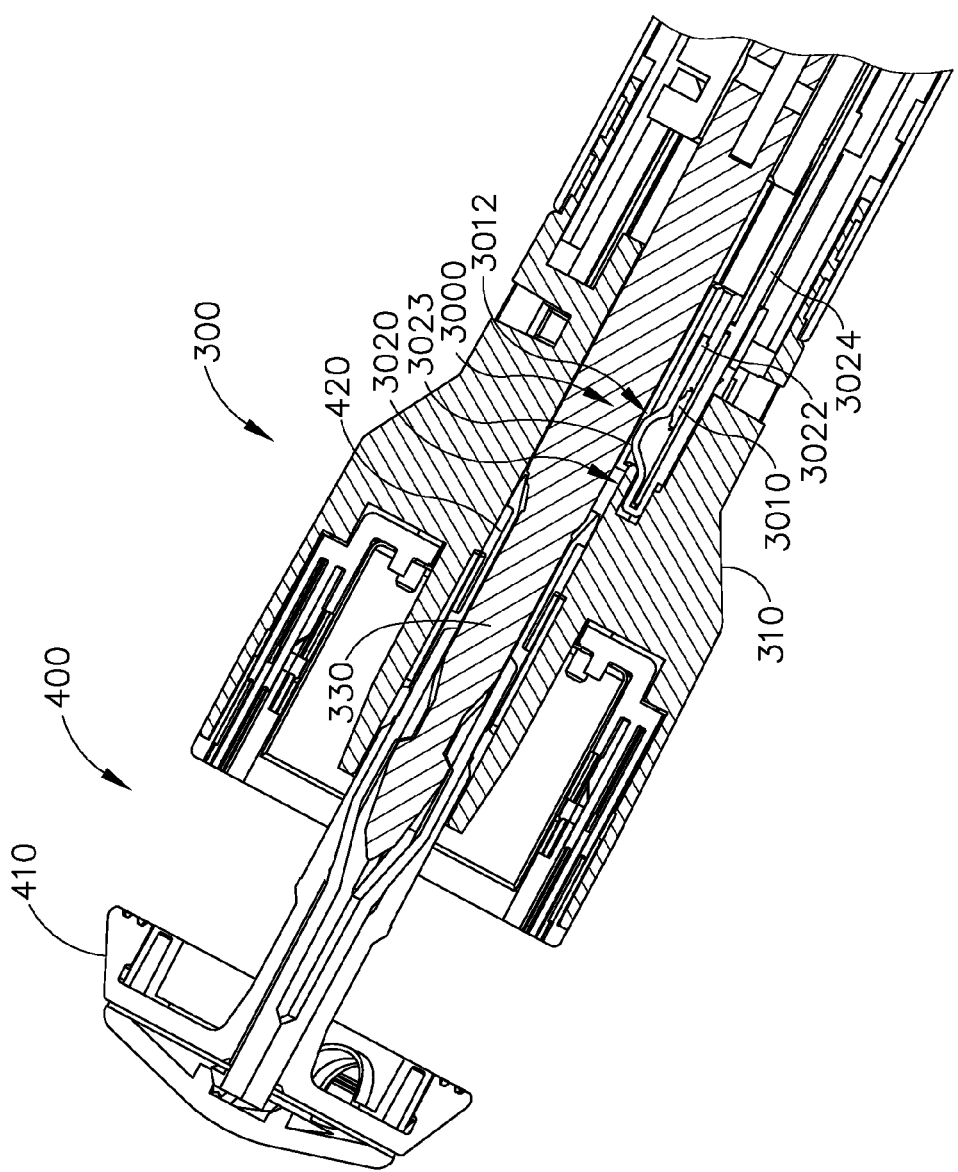
FIG. 53A depicts a cross-sectional side view of the distal end of an exemplary alternative circular stapler, with a contact switch of the circular stapler in an open state.
Figure 53B:
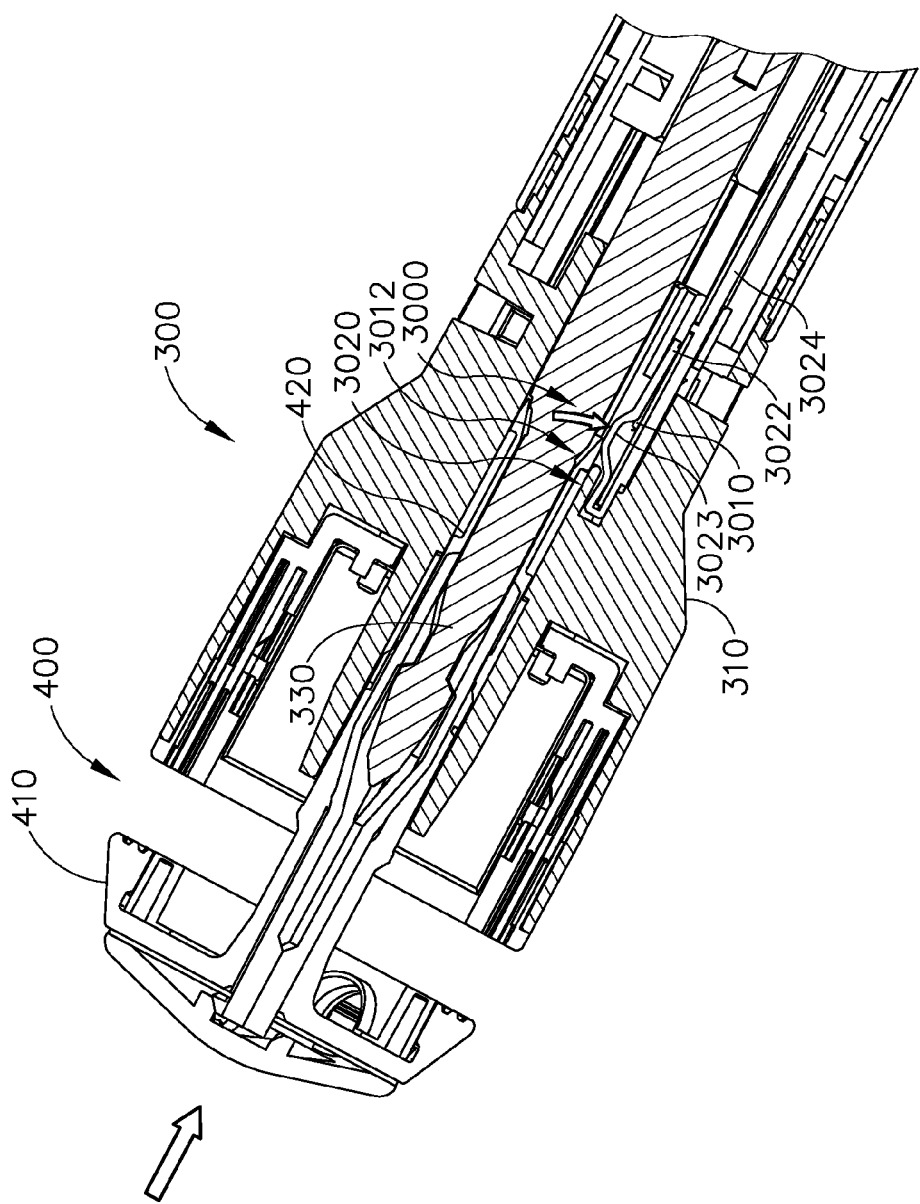
FIG. 53B depicts a cross-sectional side view of the distal end of the circular stapler of FIG. 53A, with the contact switch of FIG. 53A moved into a closed state by proximal translation of a trocar and an anvil of the circular stapler.
Figure 54A:
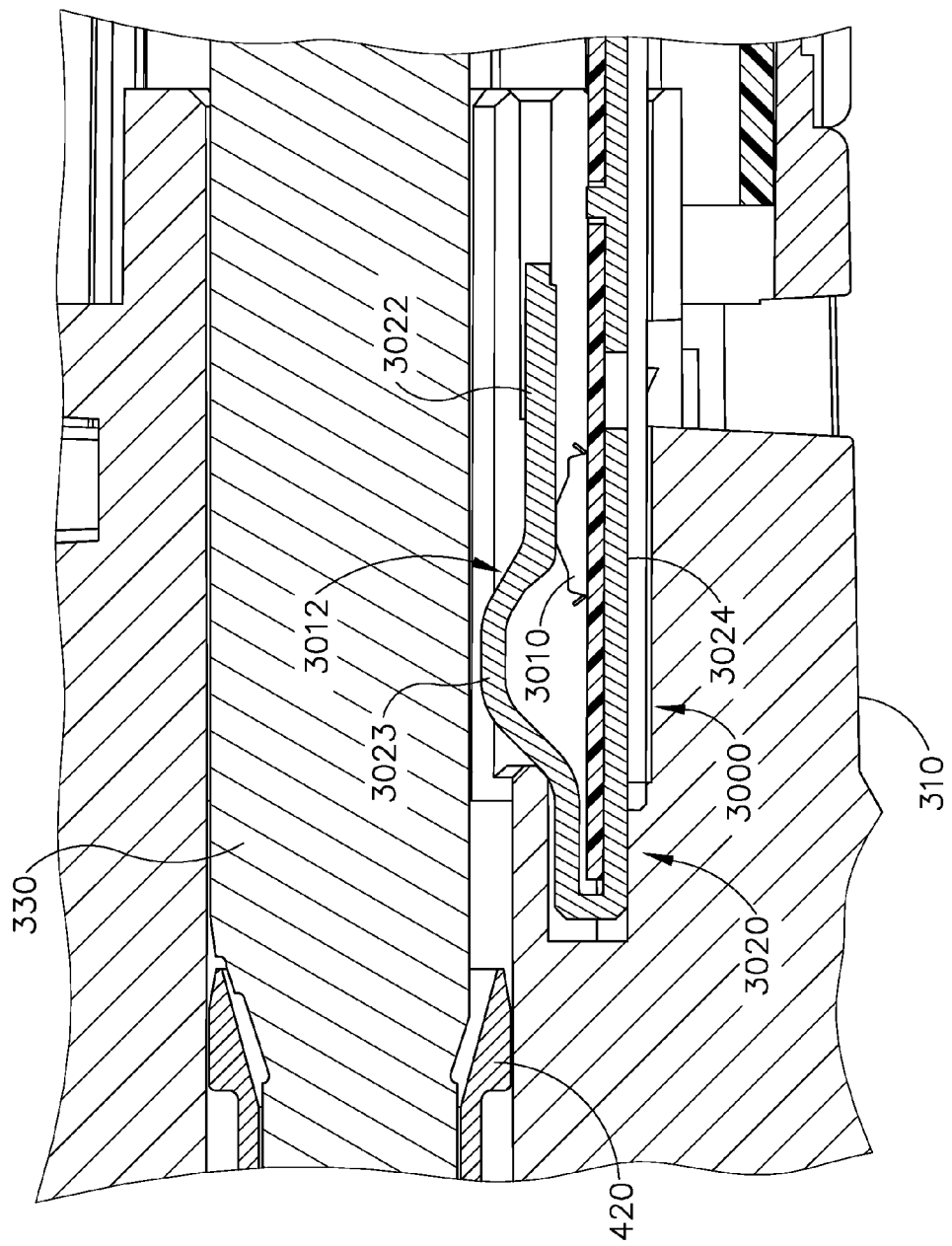
FIG. 54A depicts a cross-sectional side view of the distal end of the circular stapler of FIG. 53A, with the contact switch of FIG. 53A in the open state of FIG. 53A.
Figure 54B:
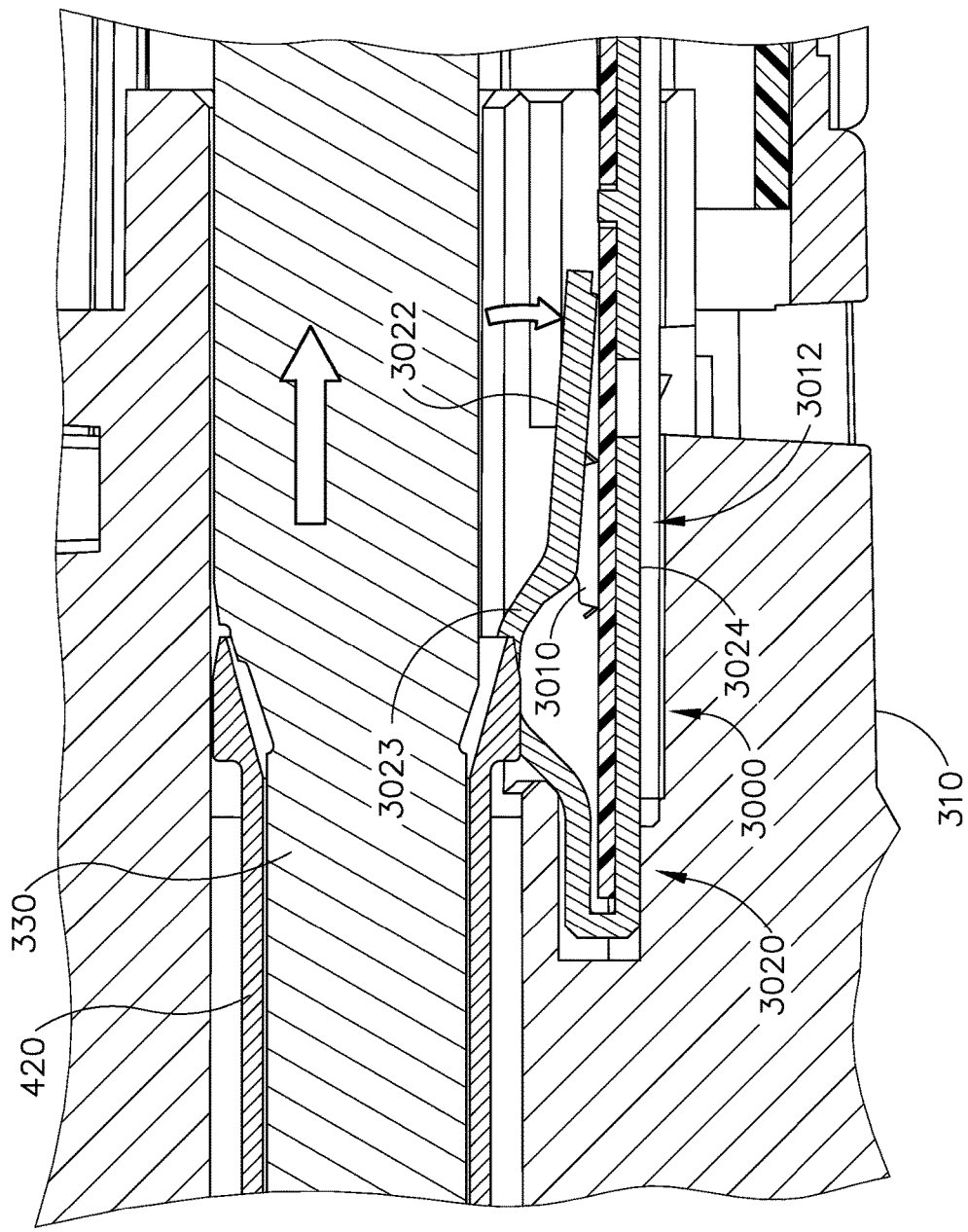
FIG. 54B depicts a cross-sectional side view of the distal end of the circular stapler of FIG. 53A, with the contact switch of FIG. 53A moved into the closed state of FIG. 22B by proximal translation of the trocar and the anvil of the circular stapler.

After anvil (400) is secured to trocar (330), the operator then rotates knob (130) so as to cause trocar (330) and anvil (400) to retract proximally as described above with reference to FIGS. 12A-12C. When trocar (330) and anvil (400) are properly secured to one another, this proximal retraction of trocar (330) and anvil (400) compresses the tissue of tubular anatomical structures (20, 40) between surfaces (412, 322) of anvil (400) and stapling head assembly (300). When trocar (330) and anvil (400) are not properly secured to one another, trocar (330) is retracted proximally without anvil (400) such that the tissue of tubular anatomical structures (20, 40) remains uncompressed. When trocar (330) and anvil (400) are properly secured to one another, as trocar (330) and anvil (400) are refracted proximally, a proximal end of shank (420) of anvil (400) engages a raised portion (3023) of flange (3022) of actuator spring (3020) so as to drive flange (3022) toward flange (3024), thereby actuating dome switch (3010) as shown in FIGS. 53B and 54B. As mentioned above, such actuation of dome switch (3010) may provide audible, tactile, and/or visible feedback to an operator indicating proper attachment. Additionally or alternatively, such actuation of dome switch (3010) may enable firing of stapling head assembly (300). In other words, unless such actuation of dome switch (3010) has been actuated, stapling head assembly (300) may not be fired.

B. Exemplary Contact Switch Assembly

Figure 55:
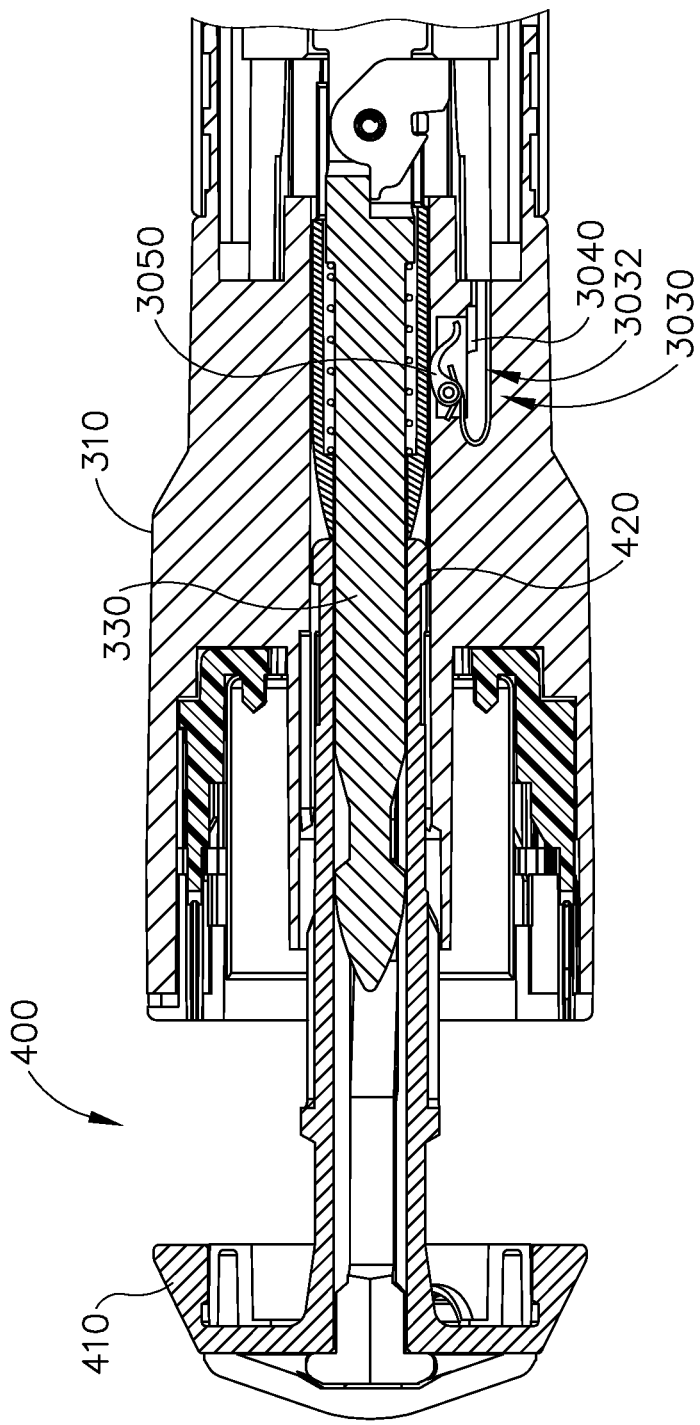
FIG. 55 depicts a cross-sectional side view of the distal end of another exemplary alternative circular stapler.
Figure 56A:
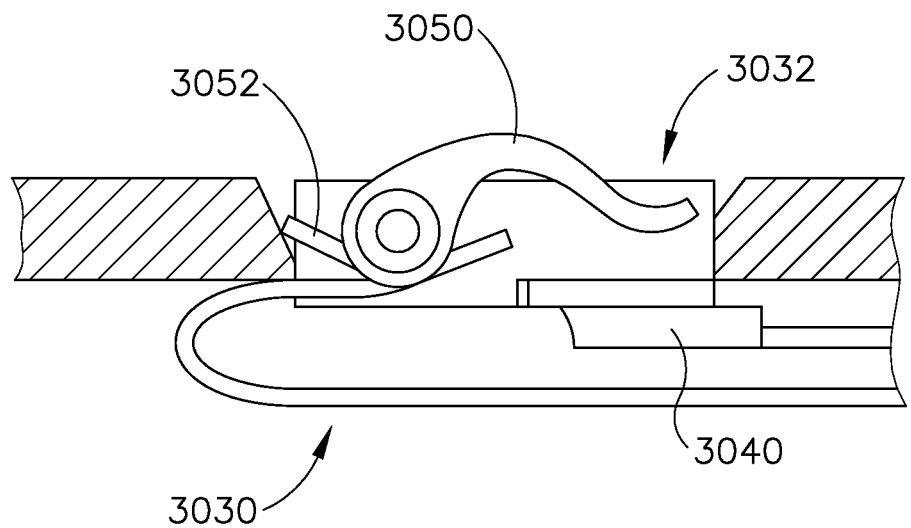
FIG. 56A depicts a detailed cross-sectional side view of the distal end of the circular stapler of FIG. 55, with a contact switch of the circular stapler in an open state.
Figure 56B:
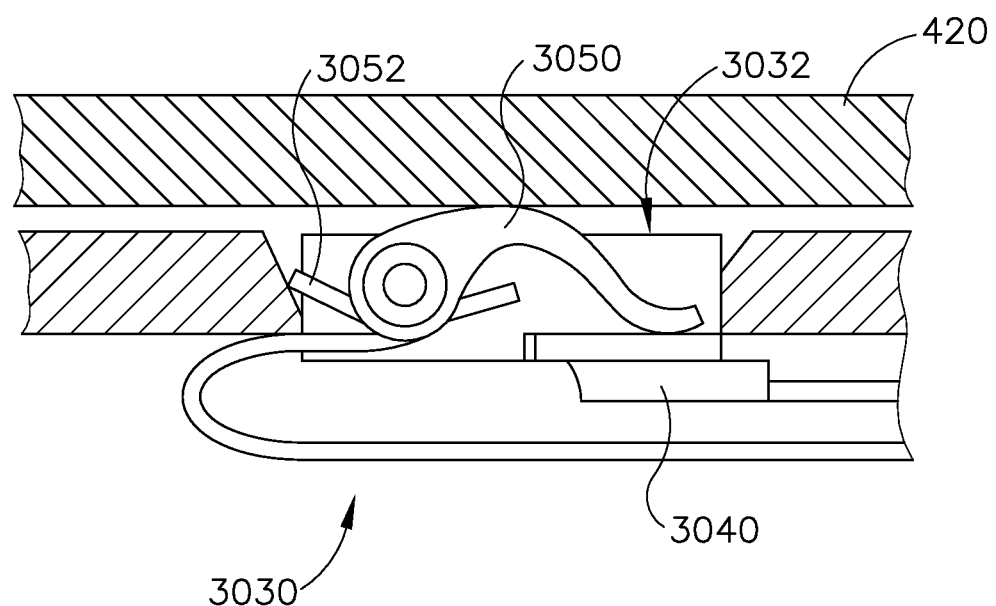
FIG. 56B depicts a detailed cross-sectional side view of the distal end of the circular stapler of FIG. 55, with the contact switch of FIG. 56A moved into a closed state by proximal translation of a trocar and an anvil of the circular stapler.
Figure 57:
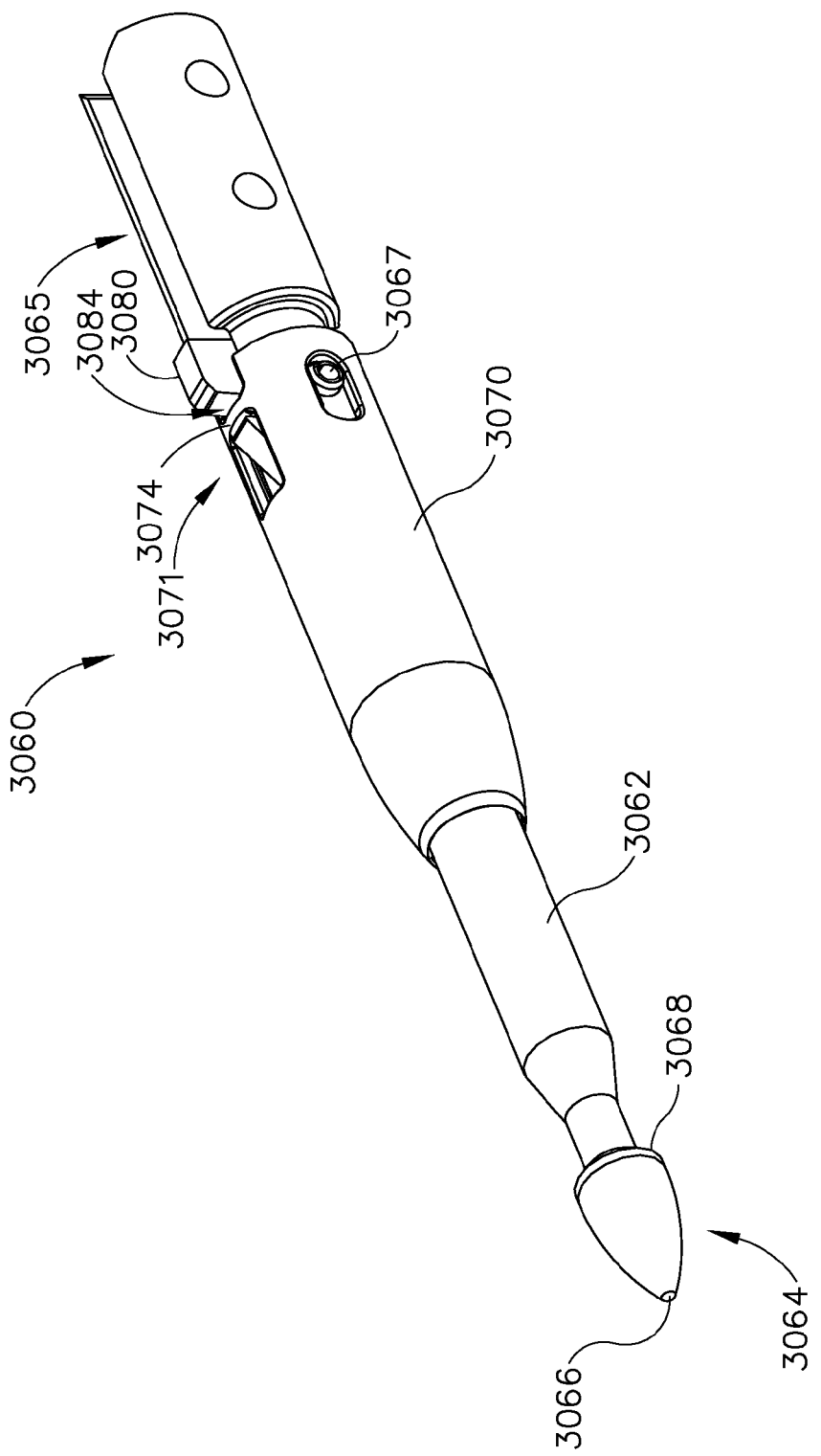
FIG. 57 depicts a perspective view of an exemplary alternative trocar.

FIGS. 55-56B depict a version of stapling head assembly (300) including a switch assembly (3030). It should be understood that this version of stapling head assembly (300) may be readily incorporated into instrument (10). Switch assembly (3030) includes a contact switch (3040) and a rotatable actuator (3020). Actuator (3050) is rotatably secured within a cavity (3032) formed within tubular casing (310) such that actuator (3050) may rotate between a first rotational position (FIG. 56A) and a second rotational position (FIG. 56B). Actuator (3050) is biased toward the first rotational position shown in FIG. 56A via a torsion spring (3052). Contact switch (3040) is positioned adjacent a proximal end of actuator (3050) such that movement of actuator (3050) toward the second rotational position will actuate contact switch (3040) as shown in FIG. 56B. As will be discussed in more detail below, proximal movement of anvil (400), when properly secured to trocar (330), will cause movement of actuator (3050) toward the second rotational position so as to actuate contact switch (3040). Actuation of contact switch (3040) may provide audible, tactile, and/or visible feedback to an operator indicating proper attachment. Various suitable features that may be used to provide such a response to actuation of contact switch (3040) will be apparent to those of ordinary skill in the art in view of the teachings herein. Additionally or alternatively, actuation of contact switch (3040) may enable firing of stapling head assembly (300). In other words, unless contact switch (3040) has been actuated, stapling head assembly (300) may not be fired in some versions.

After anvil (400) is secured to trocar (330), the operator then rotates knob (130) so as to cause trocar (330) and anvil (400) to retract proximally as described above with reference to FIGS. 12A-12C. When trocar (330) and anvil (400) are properly secured to one another, this proximal retraction of trocar (330) and anvil (400) compresses the tissue of tubular anatomical structures (20, 40) between surfaces (412, 322) of anvil (400) and stapling head assembly (300). When trocar (330) and anvil (400) are not properly secured to one another, trocar (330) is retracted proximally without anvil (400) such that the tissue of tubular anatomical structures (20, 40) remains uncompressed. As best seen in FIG. 56B, when trocar (330) and anvil (400) are properly secured to one another, as trocar (330) and anvil (400) are retracted proximally, a proximal end of shank (420) of anvil (400) engages a top surface of actuator (3050) so as to drive actuator (3050) toward the second rotational position so as to actuate contact switch (3040). As mentioned above, such actuation of contact switch (3040) may provide audible, tactile, and/or visible feedback to an operator indicating proper attachment. Additionally or alternatively, such actuation of contact switch (3040) may enable firing of stapling head assembly (300). In other words, unless such actuation of contact switch (3040) has been actuated, stapling head assembly (300) may not be fired.

C. Exemplary Lockout Trocar

FIGS. 57-62C depict an exemplary trocar (3060) that may be readily incorporated into instrument (10) discussed above in place of trocar (330). Trocar (3060) is configured to operate substantially similar to trocar (330) discussed above except for the differences discussed below. For instance, trocar (3060) is operable to translate distally and proximally relative to tubular casing (310) in response to rotation of knob (130). As will be discussed in more detail below, anvil (400) is configured to be attached to trocar (3060) such that translation of trocar (3060) relative to tubular casing (310) is communicated directly to anvil (400) as described above with reference to FIGS. 12A-12C.

Trocar (3060) comprises a shaft (3062) and a head (3064). Head (3064) includes a pointed tip (3066) and an inwardly extending proximal surface (3068). Shaft (3062) thus provides a reduced outer diameter just proximal to head (3064), with surface (3068) providing a transition between the reduced outer diameter of shaft (3062) and the outer diameter of head (3064). While tip (3066) is pointed in the present example, tip (3066) is not sharp. Tip (3066) will thus not easily cause trauma to tissue due to inadvertent contact with tissue. Head (3064) and the distal portion of shaft (3062) are configured for insertion in bore (422) of anvil (400). Proximal surface (3068) and latch shelves (436) have complementary positions and configurations such that latch shelves (436) engage proximal surface (3068) when shank (420) of anvil (400) is fully seated on trocar (3060). Anvil (400) is thus secured to trocar (3060) through a snap fit due to latch members (430).

Figure 58:
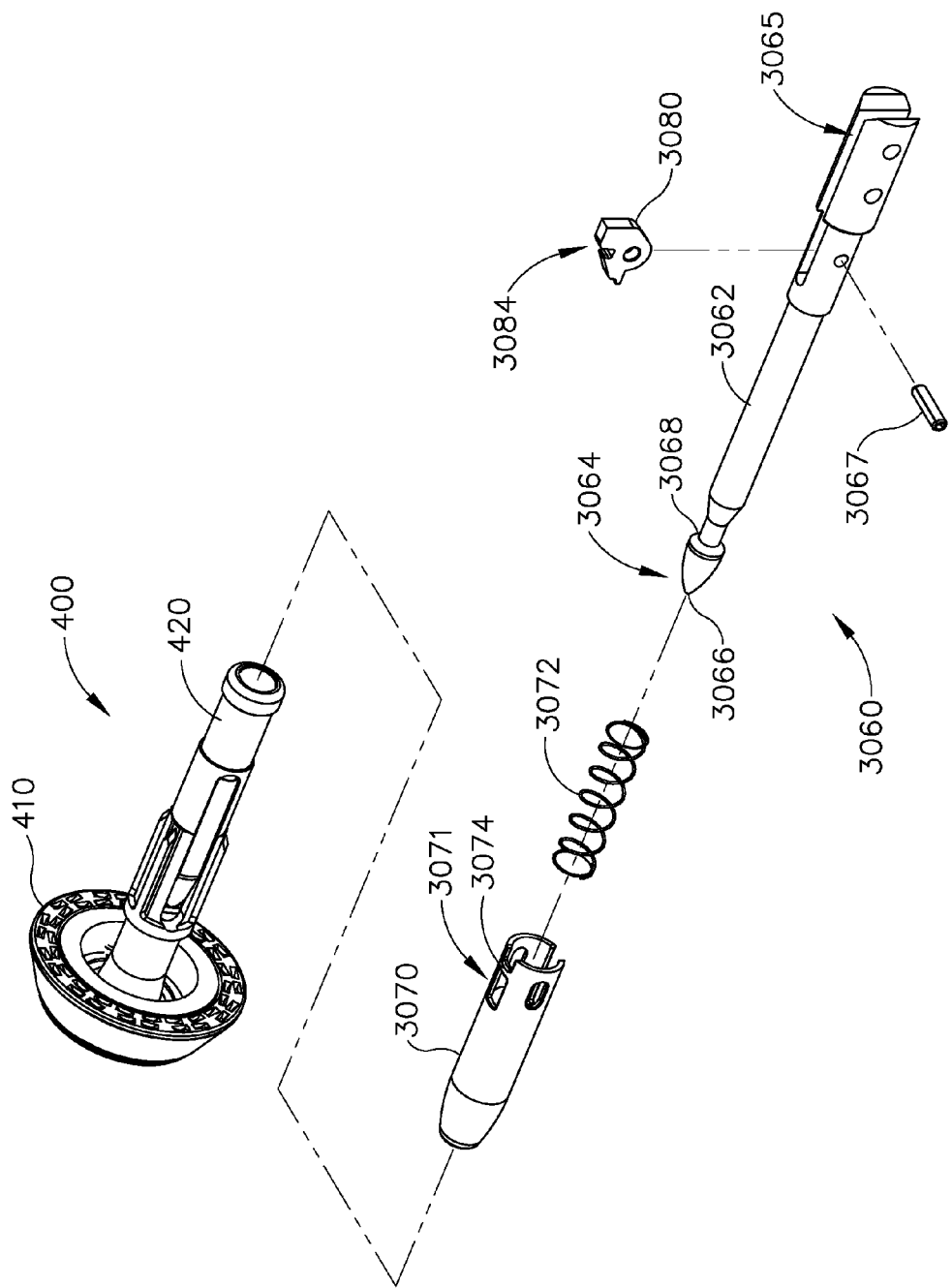
FIG. 58 depicts an exploded perspective view of the trocar of FIG. 57, with an anvil.

Trocar (3060) further comprises a hollow-cylindrical sleeve (3070) and a lockout member (3080). Sleeve (3070) is slidably disposed about shaft (3062) of trocar (3060) such that sleeve (3070) is configured to translate along a length of shaft (3062) between a distal longitudinal position (FIGS. 59B, 60A, 61A) and a proximal longitudinal position (FIGS. 59D, 60C, 61C). As best seen in FIG. 58, a spring (3072), positioned within sleeve (3070) and slidably disposed about shaft (3062), is configured to bias sleeve (3070) toward the distal longitudinal position. Lockout member (3080) is rotatably coupled within a slot (3065) formed in a proximal portion of trocar (3060) via a pin (3067) such that lockout member (3080) is configured to rotate within slot (3065) between a first rotational position (FIGS. 59B, 60A, 61A) and a second rotational position (FIGS. 59D, 60C, 61C). As will be discussed in more detail below, lockout member (3080) further extends through and rotates within a pair of slots (3071) formed within a proximal portion of sleeve (3070). A lateral support member (3074) of sleeve (3070) spans slot (3071) of sleeve (3070) and engages a slot (3084) formed in lockout member (3080) such that, as will be discussed in more detail below, longitudinal translation of sleeve (3070) between the distal longitudinal position and the proximal longitudinal position causes rotation of lockout member (3080) between the first rotational position and the second rotational position and vice versa. Thus, it should be understood that spring (3072) is configured to bias lockout member (3080) toward the first rotational position.

Figure 59A:
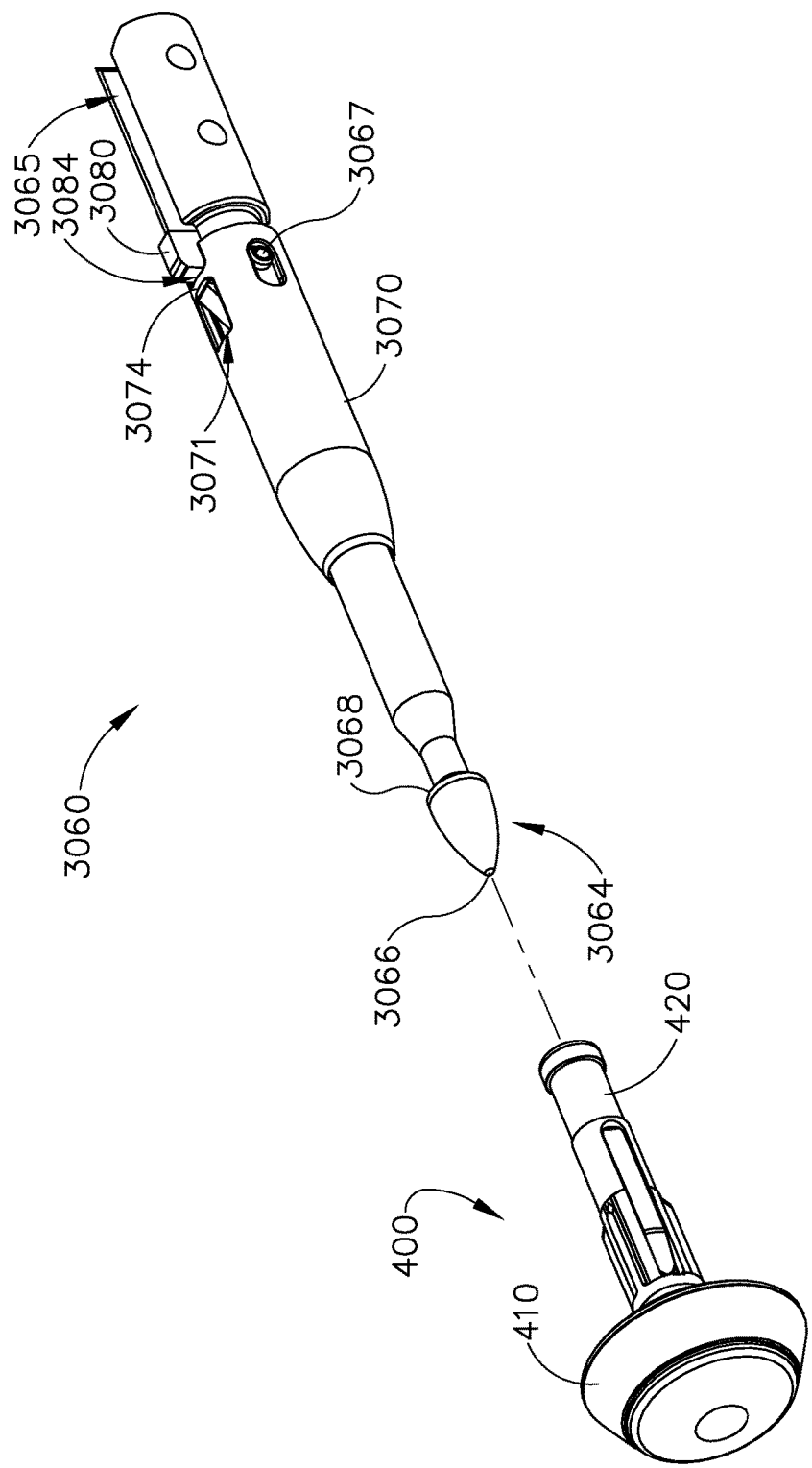
FIG. 59A depicts a perspective view of the trocar of FIG. 57 and the anvil of FIG. 58, with the anvil decoupled from the trocar.
Figure 59B:
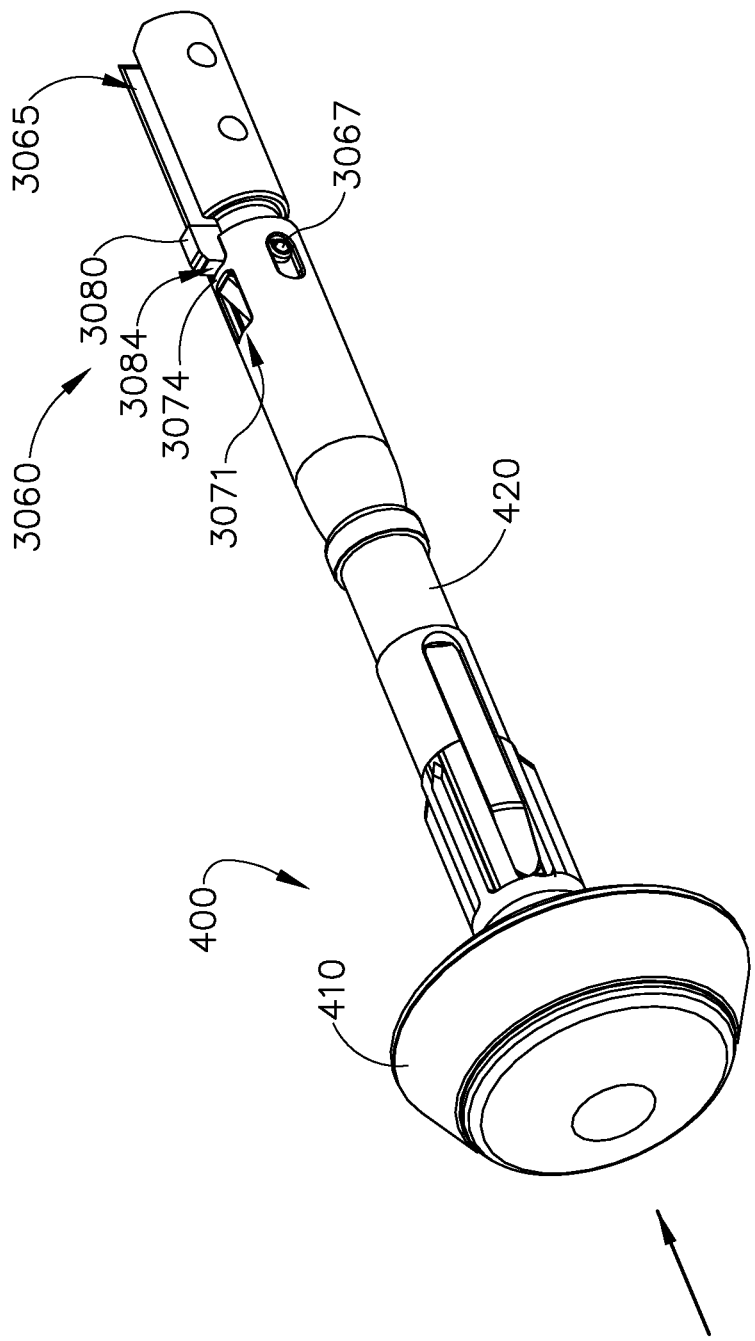
FIG. 59B depicts a perspective view of the trocar of FIG. 57 and the anvil of FIG. 58, with the anvil partially coupled with the trocar.
Figure 59C:
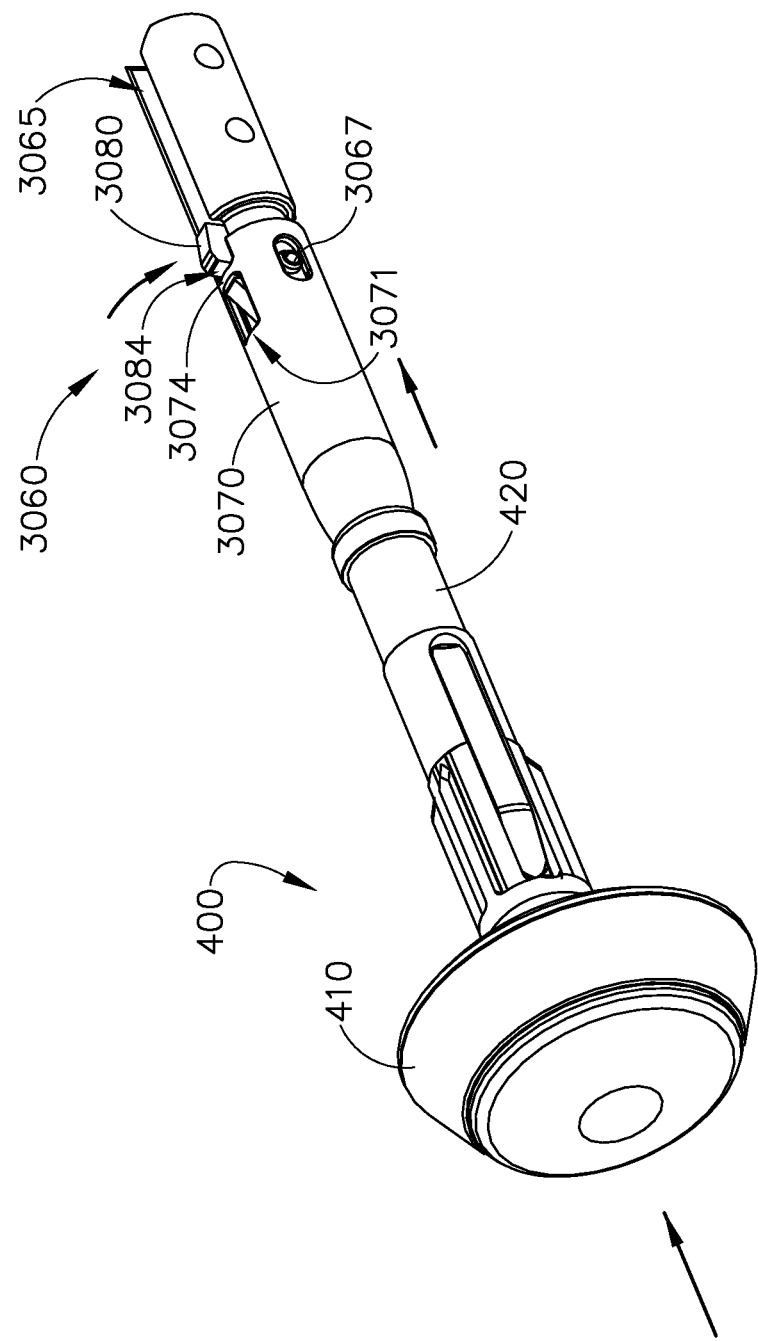
FIG. 59C depicts a perspective view of the trocar of FIG. 57 and the anvil of FIG. 58, with the anvil fully coupled with the trocar.
Figure 59D:
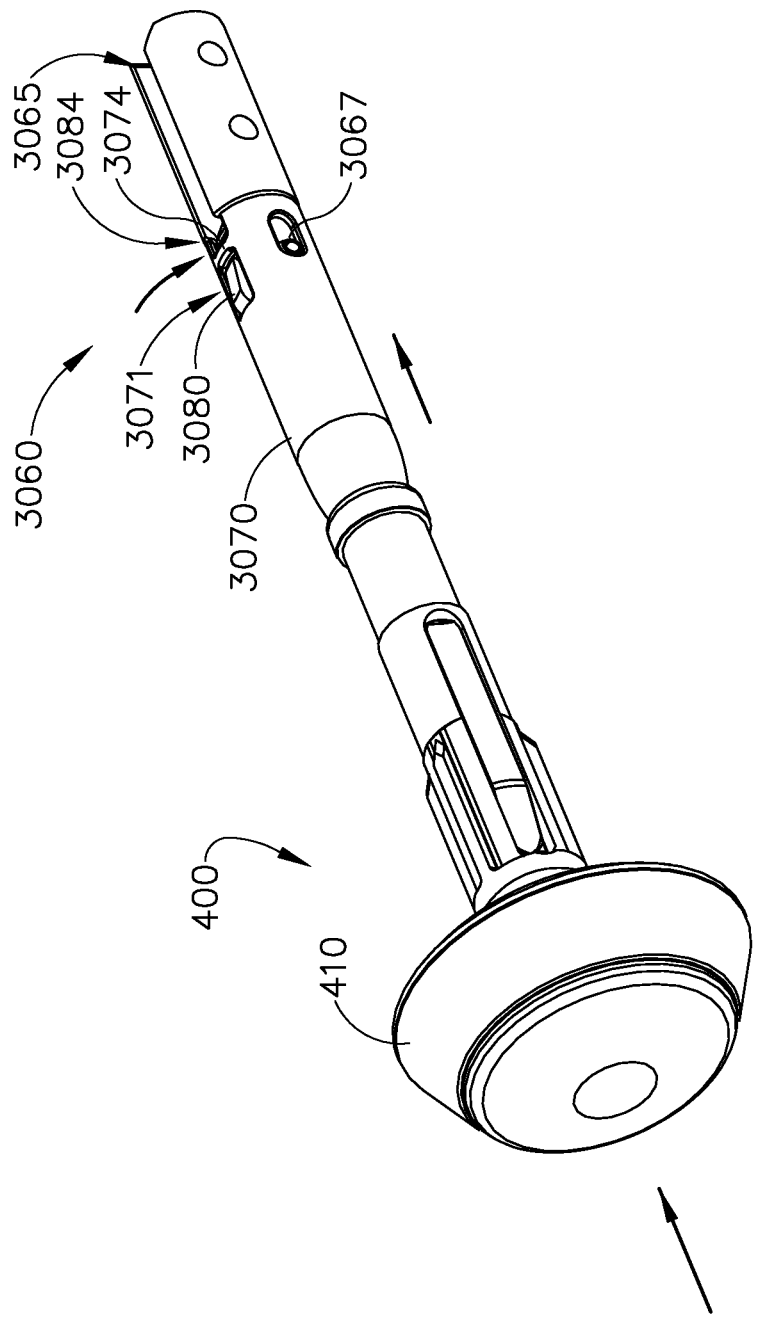
FIG. 59D depicts a perspective view of the trocar of FIG. 57 and the anvil of FIG. 58, with the anvil moved into a fourth position relative to the trocar.

FIG. 59A shows anvil (400) spaced apart from trocar (3060). With anvil (400) in this position, sleeve (3070) is in the distal longitudinal position. As trocar (3060) is initially inserted into bore (422) of shank (420) of anvil (400), a proximal end of shank (420) contacts a distal end of sleeve (3070) as shown in FIG. 59B. As trocar (3060) is further inserted into bore (422), contact between the proximal end of shank (420) and sleeve (3070) drives sleeve (3070) proximally from the distal longitudinal position and into an intermediate position by overcoming the bias of spring (3072) as shown in FIG. 59C. As trocar (3060) is further inserted into bore (422) such that anvil (400) is fully seated on trocar (3060), latch shelves (436) engage proximal surface (3068) of trocar (3060) as discussed above. With anvil (400) fully seated on trocar (3060), sleeve (3070) is driven into the proximal longitudinal position via contact between the proximal end of shank (420) and sleeve (3070) as shown in FIG. 59D.

Figure 60A:
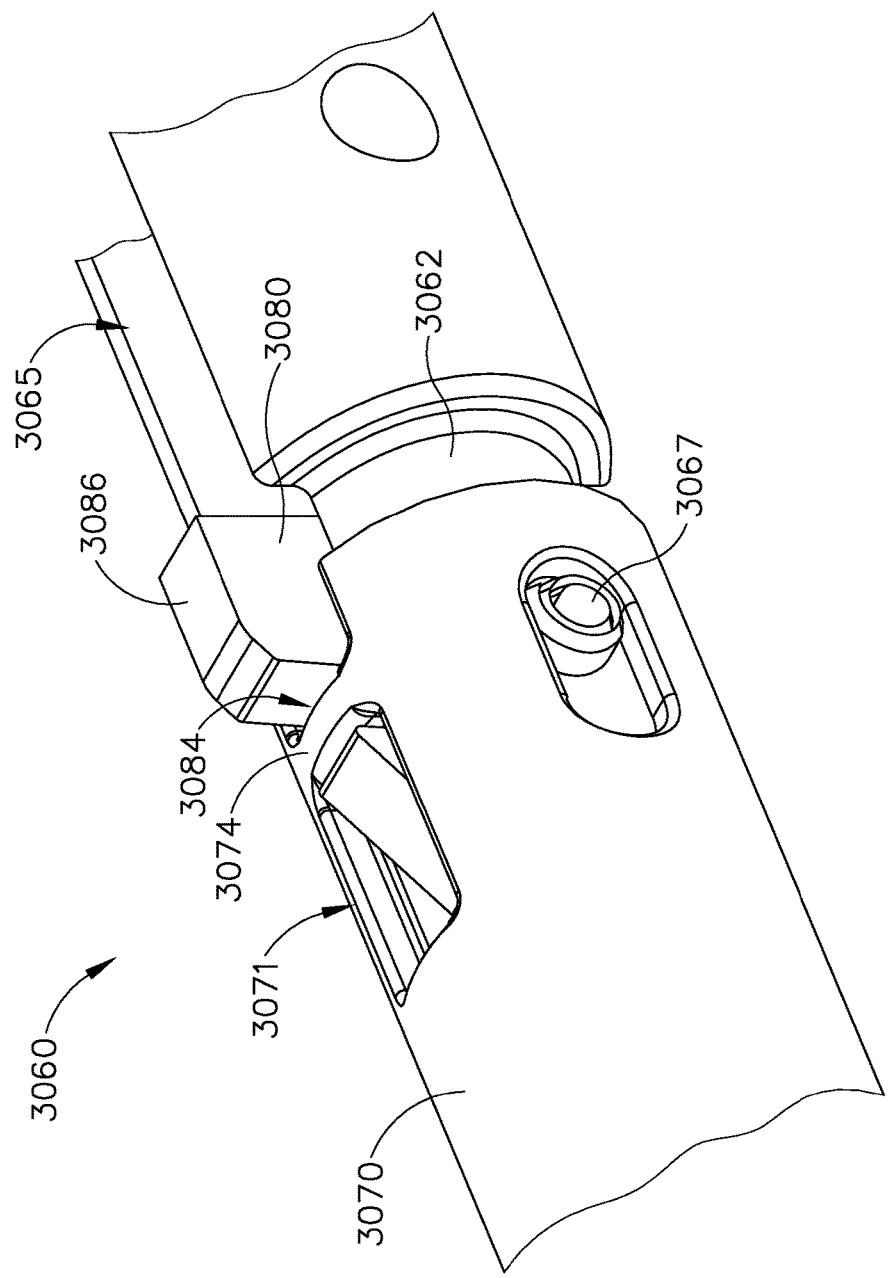
FIG. 60A depicts a detailed perspective view of the trocar of FIG. 57, with a sleeve member of the trocar in a first position, and with a lockout member in a first rotational position.
Figure 60B:
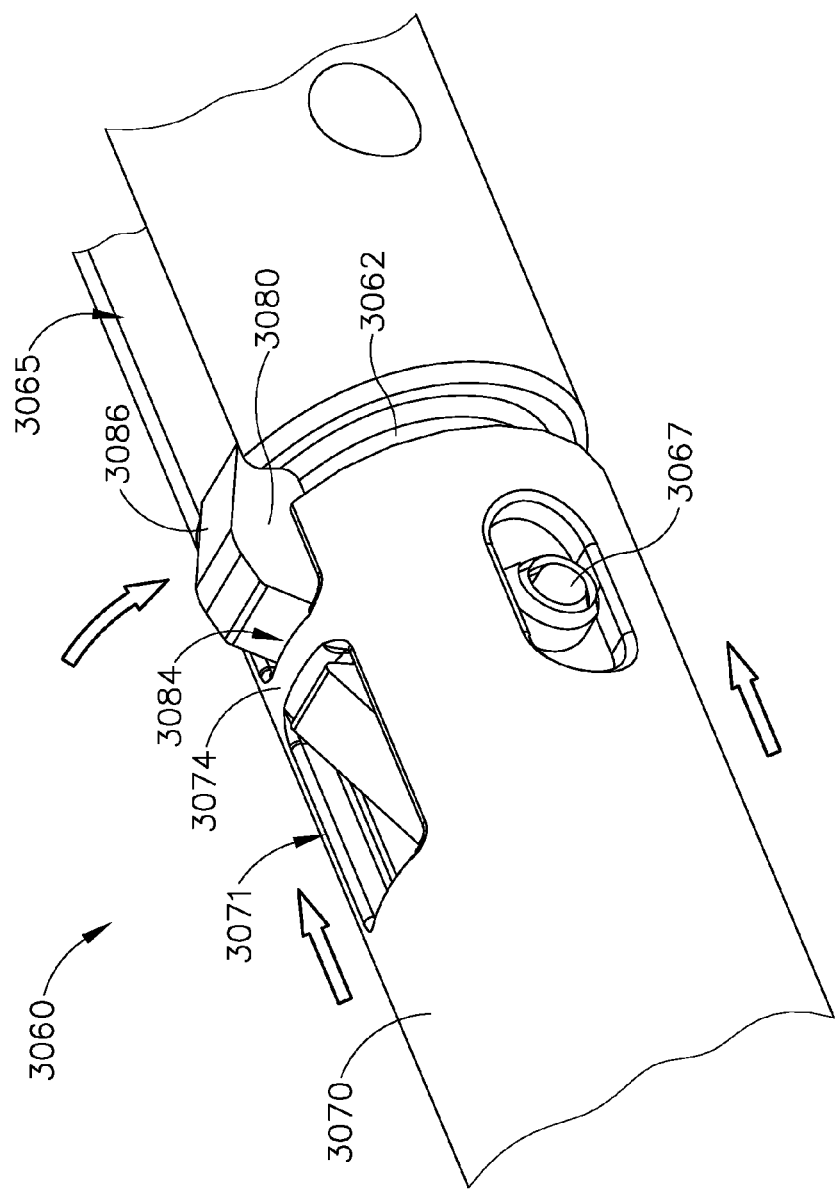
FIG. 60B depicts a detailed perspective view of the trocar of FIG. 57, with the sleeve member of FIG. 60A moved to a second position, and with the lockout member of FIG. 60A moved to a second rotational position by movement of the sleeve member to the second position.
Figure 60C:
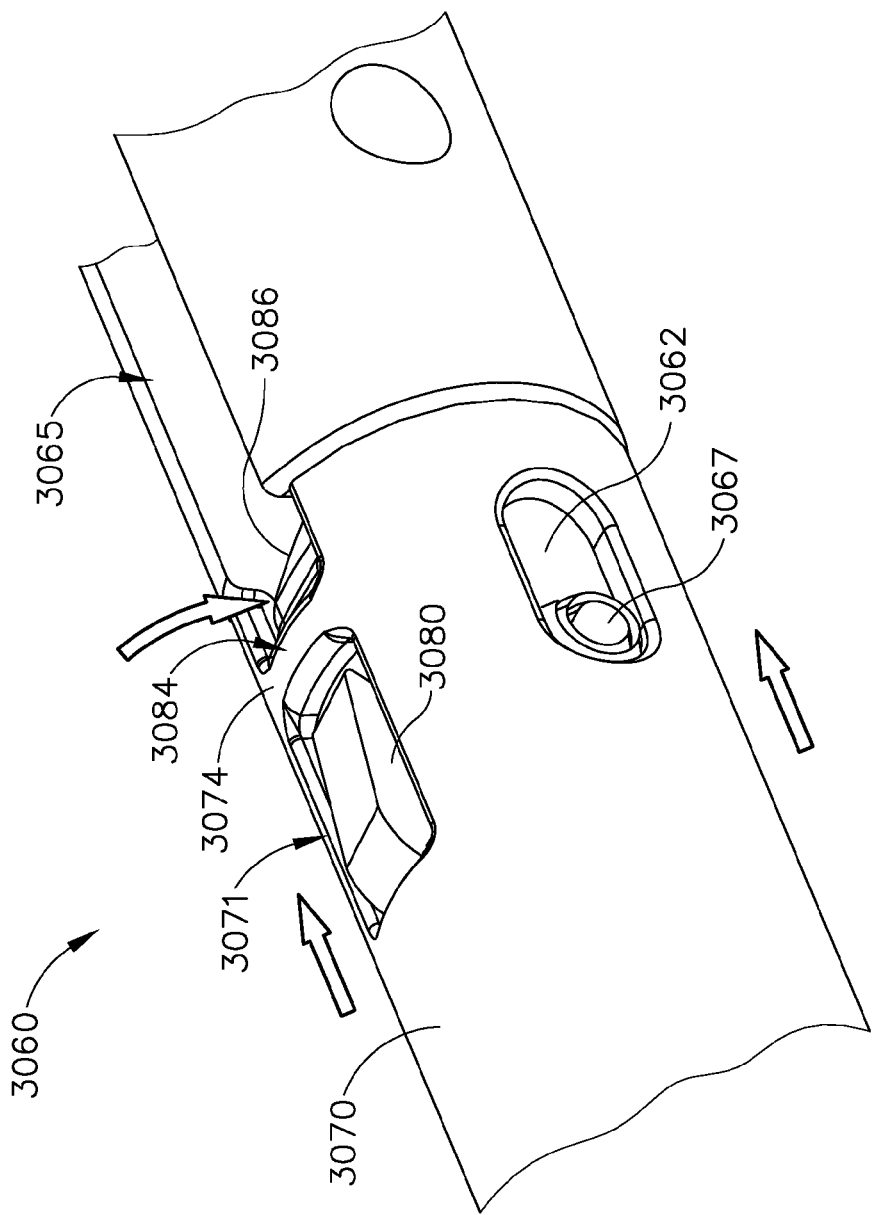
FIG. 60C depicts a detailed perspective view of the trocar of FIG. 57, with the sleeve member of FIG. 60A moved to a third position, and with the lockout member of FIG. 60A moved to a third rotational position by movement of the sleeve member to the third position.
Figure 61A:
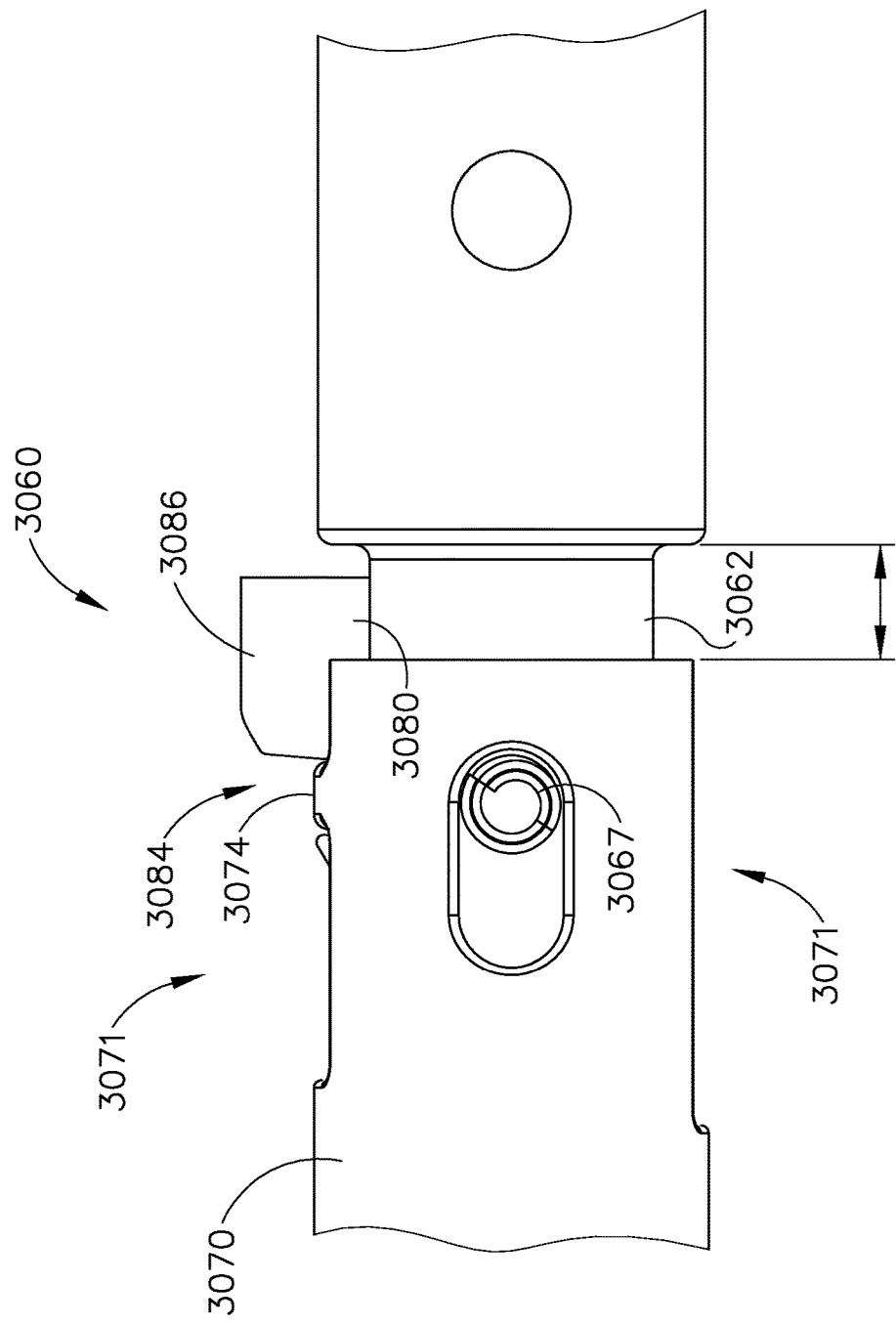
FIG. 61A depicts a detailed side elevational view of the trocar of FIG. 57, with the sleeve member of FIG. 60A in the first position of FIG. 60A, and with the lockout member of FIG. 60A in the first rotational position of FIG. 60A.
Figure 61C:
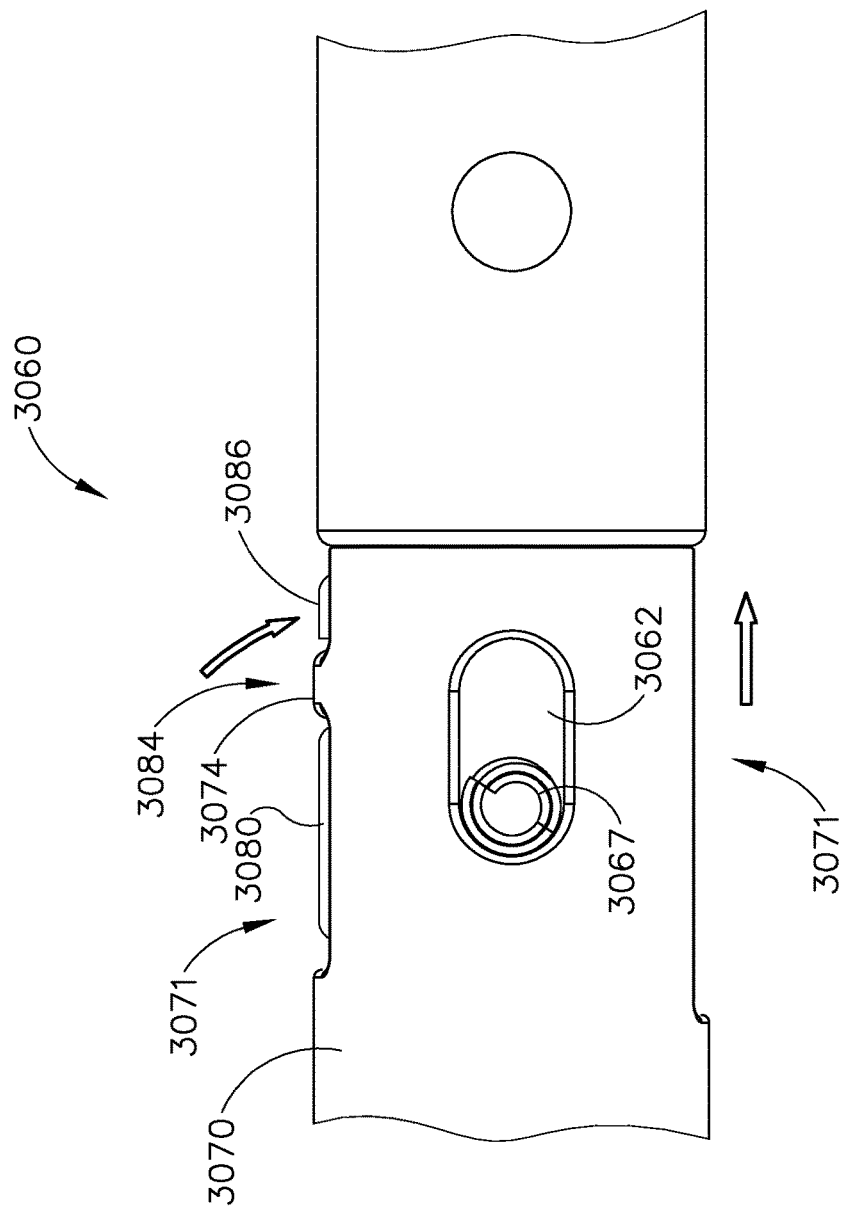
FIG. 61C depicts a detailed side elevational view of the trocar of FIG. 57, with the sleeve member of FIG. 60A moved to the third position of FIG. 60C, and with the lockout member of FIG. 60A moved to the third rotational position of FIG. 60C by movement of the sleeve member to the third position.

FIGS. 60A and 61A show sleeve (3070) in the distal longitudinal position. With sleeve (3070) in the distal longitudinal position, lockout member (3080) is in the first rotational position. As best seen in FIG. 61A, with lockout member (3080) in the first rotational position, a tab (3086) of lockout member (3080) extends transversely through slot (3071) of sleeve (3070). As will be discussed in more detail below, tab (3086) is configured to limit translation of trocar (3060) relative to tubular casing (310). As sleeve (3070) is driven into the intermediate longitudinal position, contact between lateral support member (3074) of sleeve (3070) and slot (3084) of lockout member (3080) causes rotation of lockout member (3080) into an intermediate rotational position as shown in FIGS. 60B and 61B. Finally, as sleeve (3070) is driven into the proximal longitudinal position, contact between lateral support member (3074) of sleeve (3070) and slot (3084) of lockout member (3080) causes rotation of lockout member (3080) into the second rotational position as shown in FIGS. 60C and 61C. As best seen in FIG. 61C, with lockout member (3080) in the second rotational position, tab (3086) of lockout member (3080) is rotated completely into sleeve (3070) such that trocar (3060) has a substantially cylindrical profile.

Figure 62A:
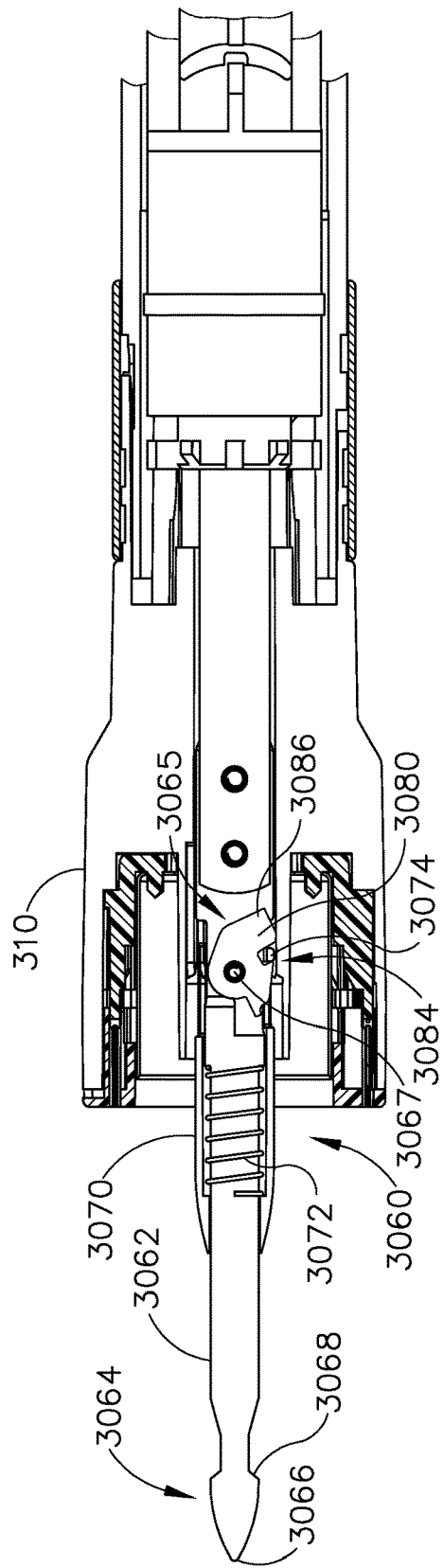
FIG. 62A depicts a cross-sectional side view of the distal end of yet another exemplary alternative circular stapler incorporating the trocar of FIG. 57, with the trocar of FIG. 57 in a first position, with the sleeve member of FIG. 60A in the first position of FIG. 60A, and with the lockout of FIG. 60A in the third rotational position of FIG. 60C.
Figure 62B:
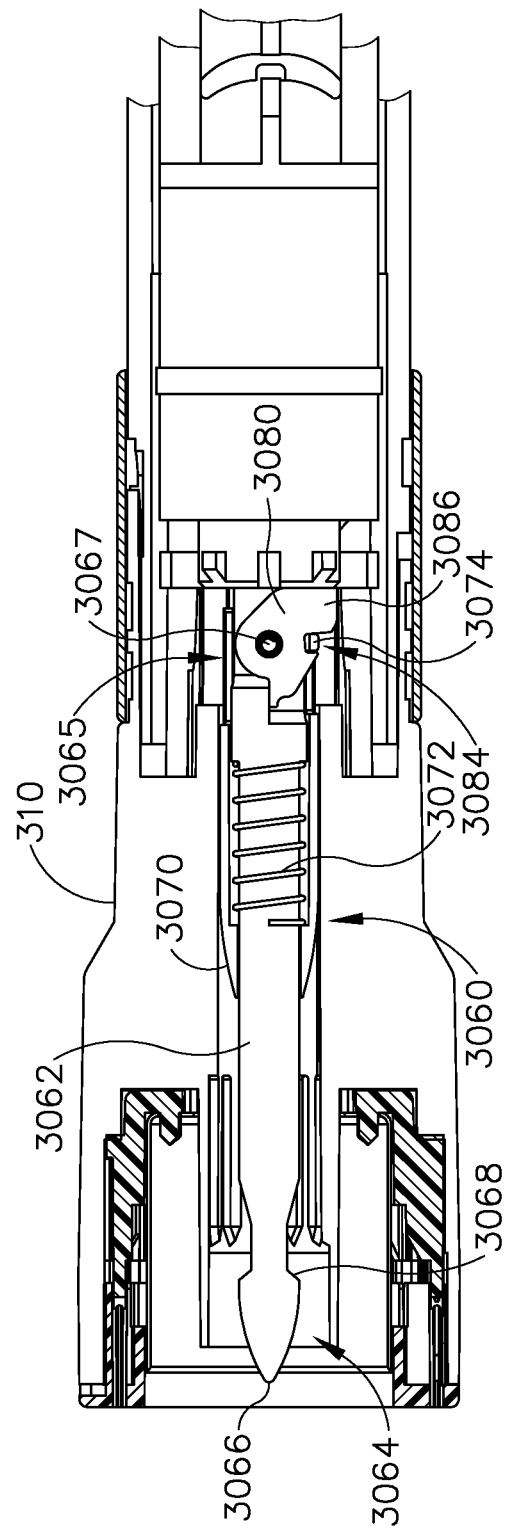
FIG. 62B depicts a cross-sectional side view of the distal end of the circular stapler of FIG. 62A, with the trocar of FIG. 57 moved to a second position, with the sleeve member of FIG. 60A in the first position of FIG. 60A, and with the lockout member of FIG. 60A moved to the first rotational position of FIG. 60A.
Figure 62C:
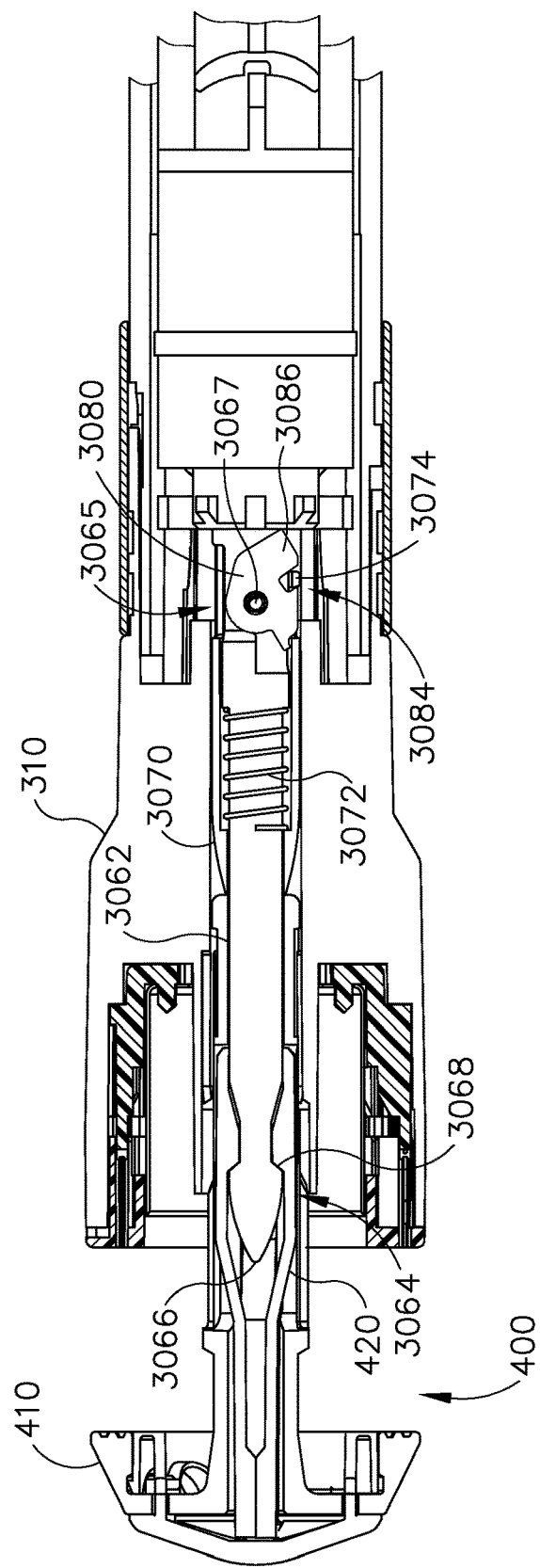
FIG. 62C depicts a cross-sectional side view of the distal end of the circular stapler of FIG. 62A, with the trocar of FIG. 57 moved to a third position, with the sleeve member of FIG. 60A moved to the third position of FIG. 60C, and with the lockout tab of FIG. 60A in the third rotational position.

As shown in FIGS. 62A and 62B, if an operator attempts to proximally retract trocar (3060) in the absence of anvil (400) or with anvil (400) not properly attached to trocar (3060), tab (3086) of lockout member (3080) is configured to limit proximal translation of trocar (3060). In particular, in the absence of anvil (400), sleeve (3070) is biased toward the distal longitudinal position via spring (3072) such that lockout member (3080) is rotated into the first rotational position. As mentioned above, with lockout member (3080) in the first rotational position, tab (3086) of lockout member (3080) extends transversely through slot (3071) of sleeve (3070). As shown in FIG. 62B, in the first rotational position, tab (3086) of lockout member (3080) engages tubular casing (310) so as to prevent proximal translation of trocar (3060). Alternatively, with anvil (400) properly attached to trocar (3060), lockout member (3080) is driven into the second rotational position such that tab (3086) of lockout member (3080) is rotated completely into sleeve (3070) such that trocar (3060) may be further proximally translated.

1 Exemplary Circuit Opening Trocar

In some versions of trocar (3060), tab (3086) of lockout member (3080) may be configured to prevent firing of stapling head assembly (300) unless anvil (400) is properly attached to trocar (300). For instance, as shown in FIGS. 63A-64B, if an operator attempts to proximally retract trocar (3060) in the absence of anvil (400) or with anvil (400) not properly attached to trocar (3060), tab (3086) of lockout member (3080) is configured to prevent firing of stapling head assembly (300). In particular, in the absence of anvil (400), sleeve (3070) is biased toward the distal longitudinal position via spring (3072) such that lockout member (3080) is rotated into the first rotational position. As mentioned above, with lockout member (3080) in the first rotational position, tab (3086) of lockout member (3080) extends transversely through slot (3071) of sleeve (3070).

Figure 63A:
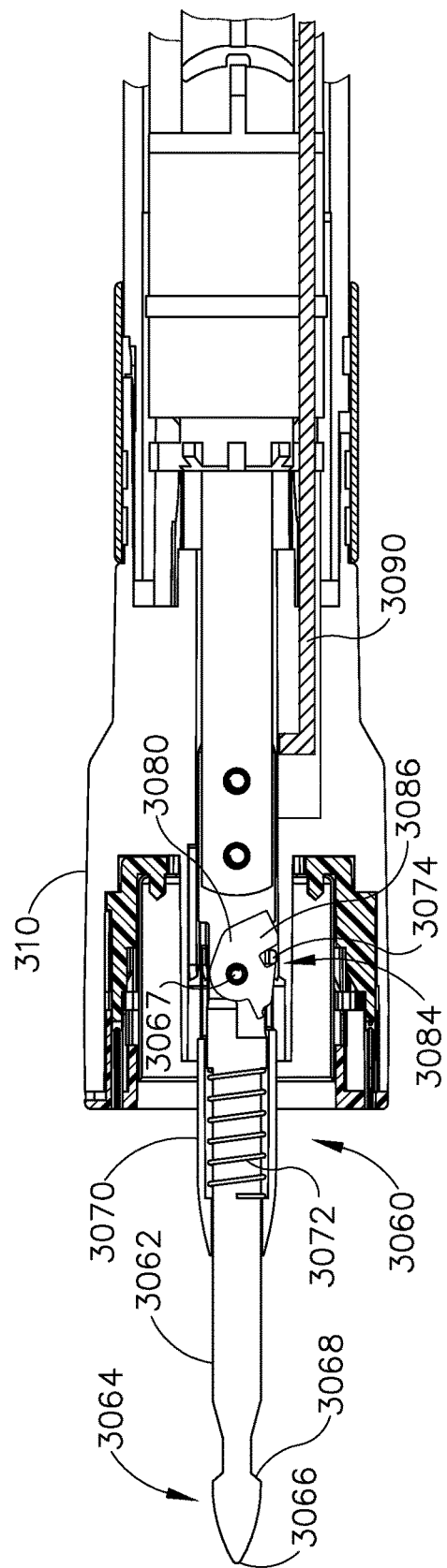
FIG. 63A depicts a cross-sectional side view of the distal end of yet another exemplary alternative circular stapler, with a trocar of the circular stapler in a first position, with a lockout member in a first rotational position, and with a link member in a first position.
Figure 63B:
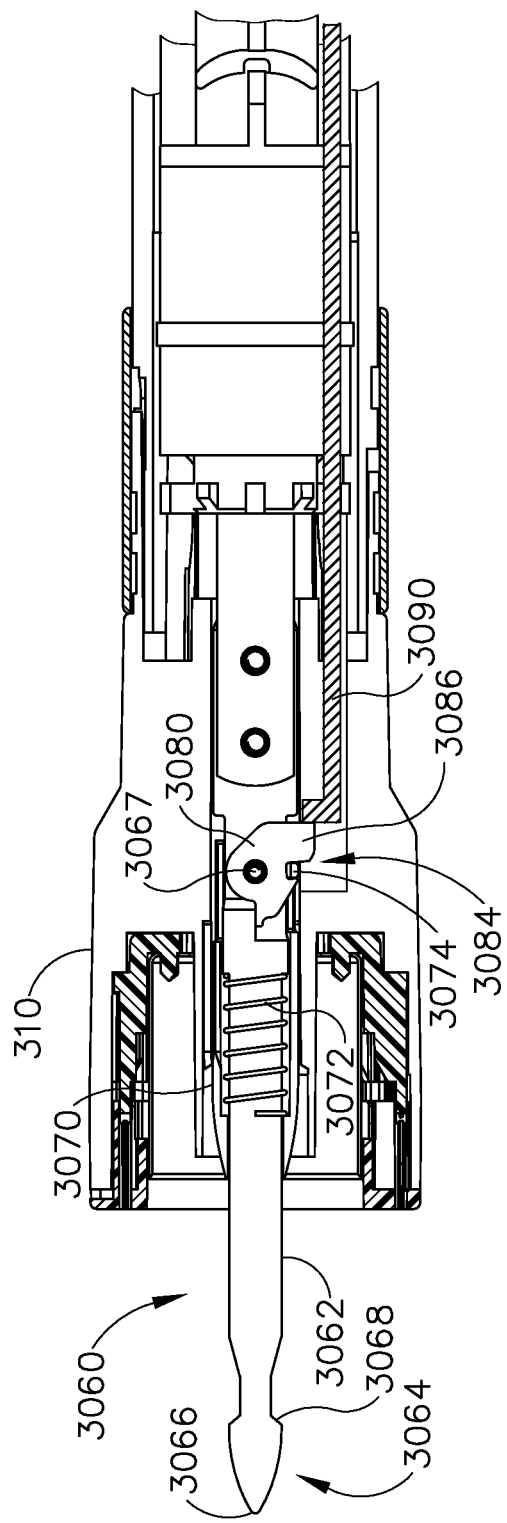
FIG. 63B depicts a cross-sectional side view of the distal end of the circular stapler of FIG. 63A, with the trocar of FIG. 63A moved to a second position, with the lockout member of FIG. 63A moved to a second rotational position so as to engage the link member of FIG. 63A, and with the link member remaining in the first position.
Figure 63C:
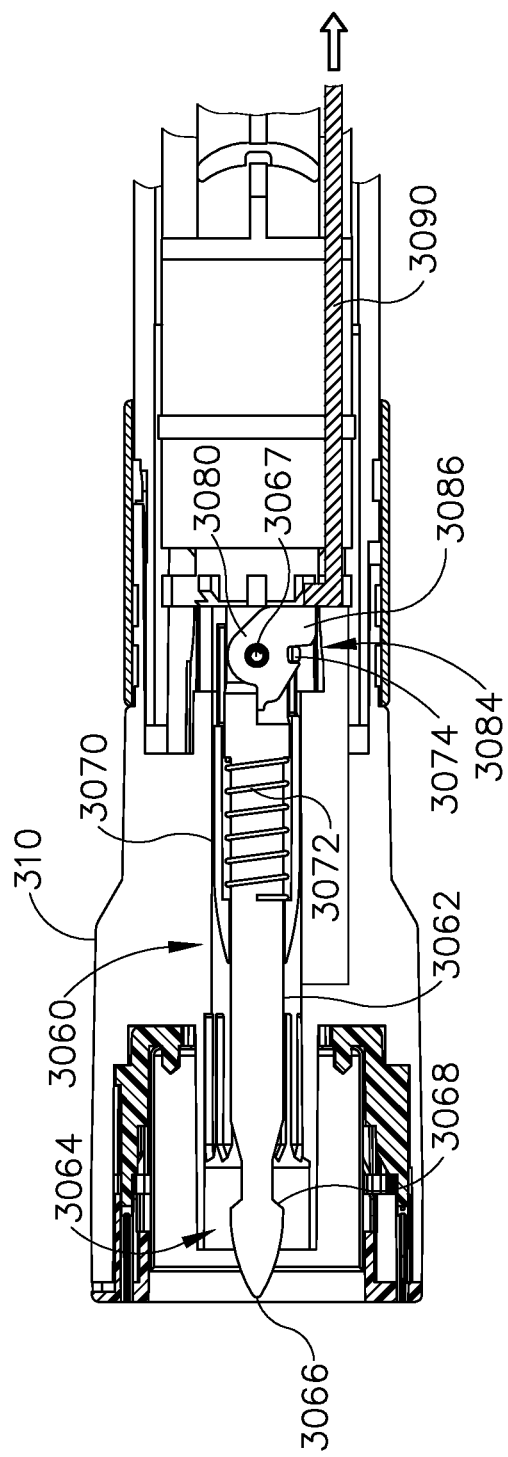
FIG. 63C depicts a cross-sectional side view of the distal end of the circular stapler of FIG. 63A, with the trocar of FIG. 63A moved to a third position, with the lockout member of FIG. 63A remaining in the second rotational position, and with the link member of FIG. 63A moved to a second position.
Figure 63D:
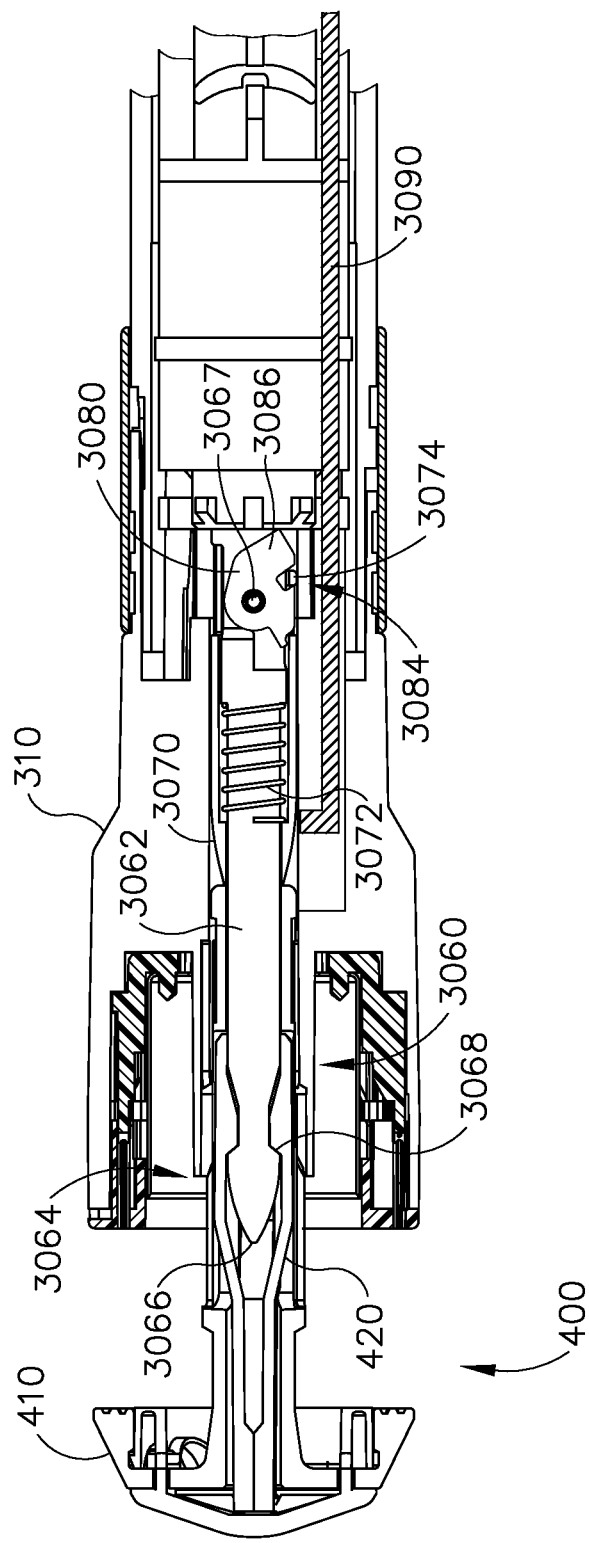
FIG. 63D depicts a cross-sectional side view of the distal end of the circular stapler of FIG. 63A, with the trocar of FIG. 63A in the third position of FIG. 63C, with the lockout member of FIG. 63A remaining in the first rotational position of FIG. 63A, and with the link member of FIG. 63A remaining in the first position of FIG. 63A.
Figure 64A:
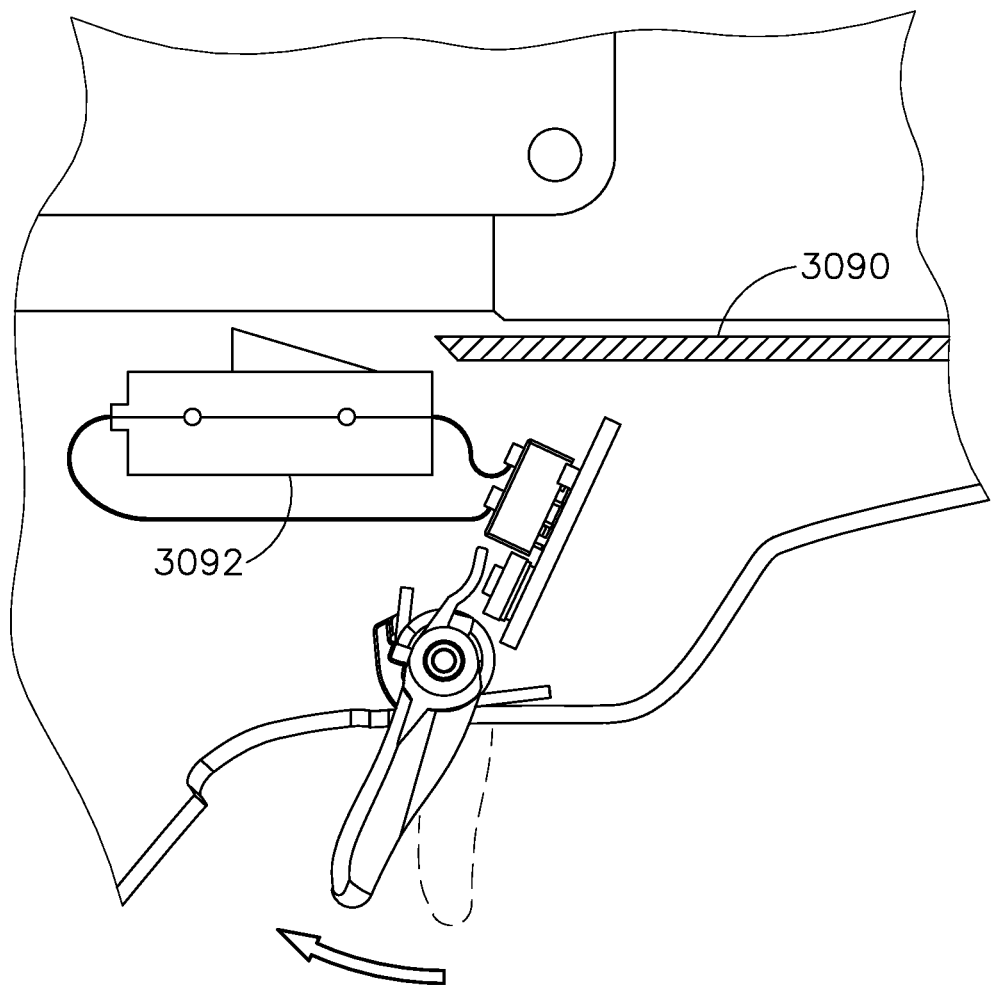
FIG. 64A depicts a cross-sectional side view of a contact switch of the circular stapler of FIG. 63A, with the contact switch in a closed state, and with the link member of FIG. 63A in the first position of FIG. 63A.
Figure 64B:
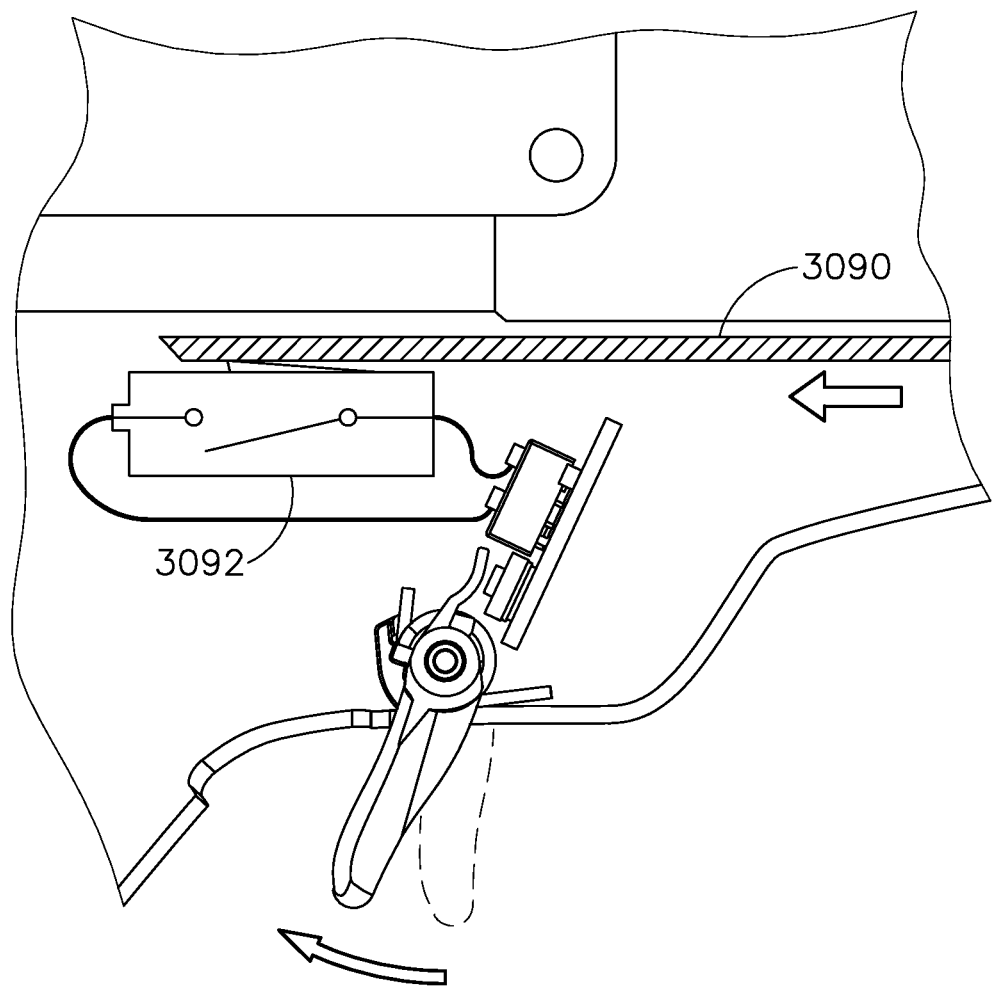
FIG. 64B depicts a cross-sectional side view of the contact switch of FIG. 64A, with the contact switch moved to an open position by movement of the link member of FIG. 63A to the second position of FIG. 63C.

As shown in FIG. 63B, with lockout member (3080) in the first rotational position, tab (3086) of lockout member (3080) is configured to engage a longitudinally translatable link member (3090). Link member (3090) is slidably disposed within tubular casing (310) and extends along the length of shaft assembly (200) into handle assembly (100) such that link member (3090) is configured to translate within and relative to tubular casing (310) and shaft assembly (200). As trocar (3060) is driven proximally relative to tubular casing (310), engagement between tab (3086) and link member (3090) causes proximal longitudinal translation of link member (3090) as shown in FIG. 63C. As shown in FIGS. 64A and 64B, as link member (3090) is translated proximally, a proximal end of link member (3090) is configured to move a switch (3092) from a closed state (FIG. 64A) to an open state (FIG. 64B) so as to prevent firing of stapling head assembly (300). Alternatively, with anvil (400) properly attached to trocar (3060), lockout member (3080) is driven into the second rotational position such that tab (3086) of lockout member (3080) is rotated completely into sleeve (3070) such that trocar (3060) may be proximally retracted without causing proximal longitudinal translation of link member (3090) as shown in FIG. 63D. In the absence of proximal longitudinal translation of link member (3090), switch (3092) remains in the closed position, permitting firing of stapling head assembly (300).

2. Exemplary Circuit Opening Trocar

Figure 65A:
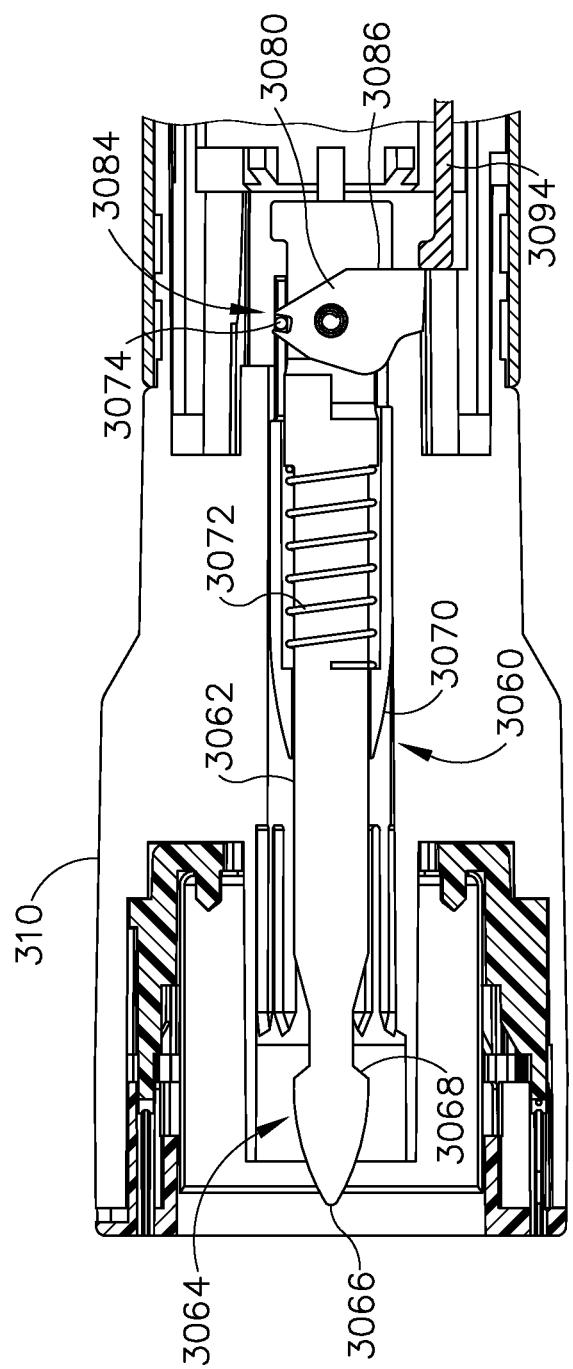
FIG. 65A depicts a cross-sectional side view of the distal end of yet another exemplary alternative circular stapler, with a lockout member in a first rotational position.
Figure 65B:
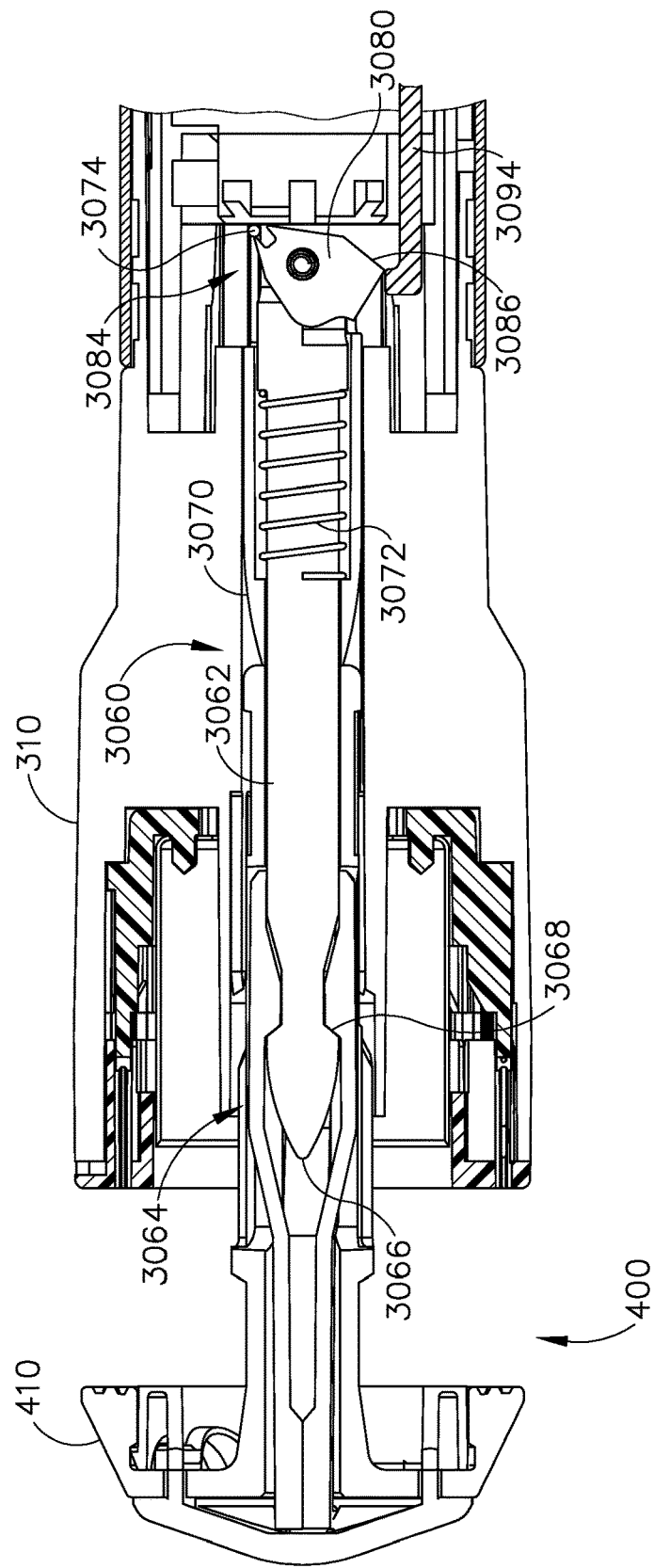
FIG. 65B depicts a cross-sectional side view of the distal end of the circular stapler of FIG. 65A, with the lockout member of FIG. 65A moved to a second rotational position so as to engage a link member of the circular stapler.
Figure 66A:
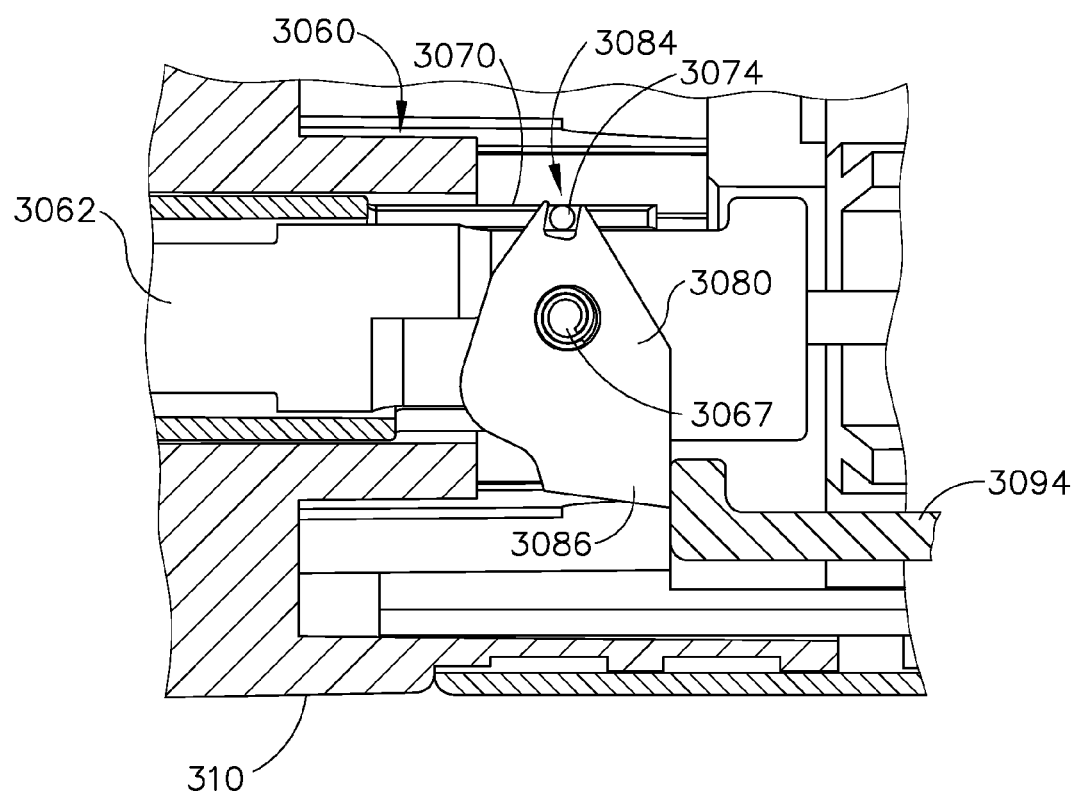
FIG. 66A depicts a detailed cross-sectional side view of the distal end of the circular stapler of FIG. 65A, with the lockout member of FIG. 65A in the second rotational position of FIG. 65B so as to engage the link member of FIG. 65B, and with a trocar of the circular stapler in a distal longitudinal position.
Figure 66B:
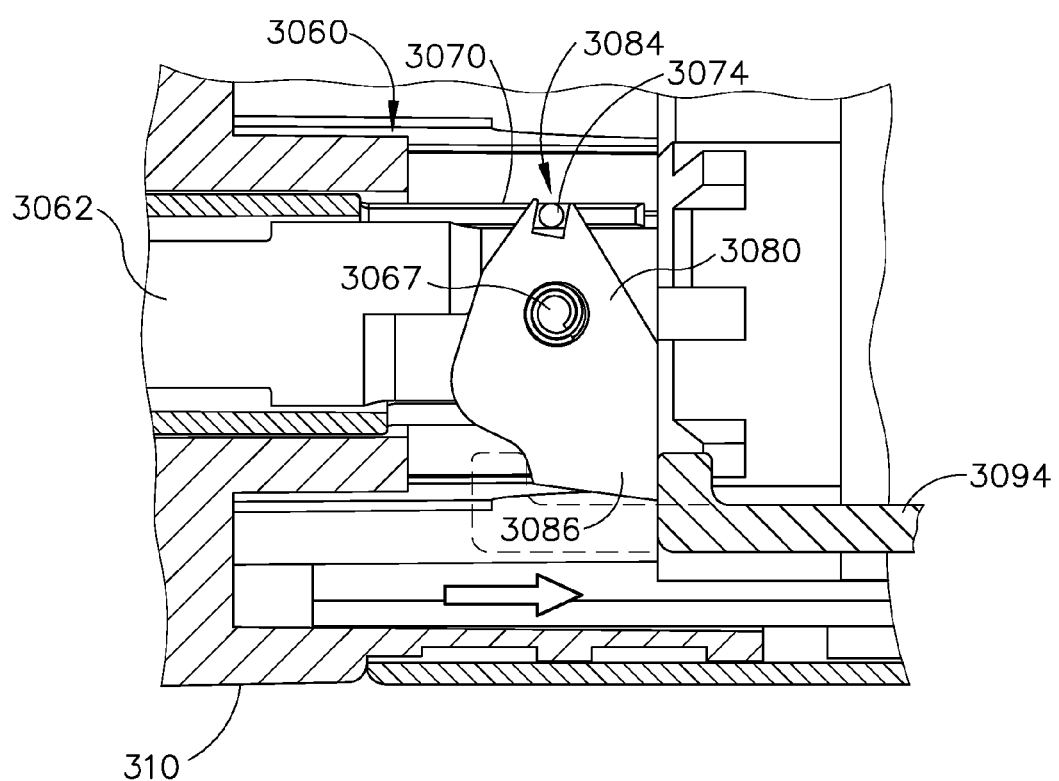
FIG. 66B depicts a detailed cross-sectional side view of the distal end of the circular stapler of FIG. 65A, with the lockout member of FIG. 65A in the second rotational position of FIG. 65B so as to engage the link member of FIG. 65B, and with the link member moved to a proximal longitudinal position by movement of the trocar to a proximal longitudinal position.
Figure 67A:
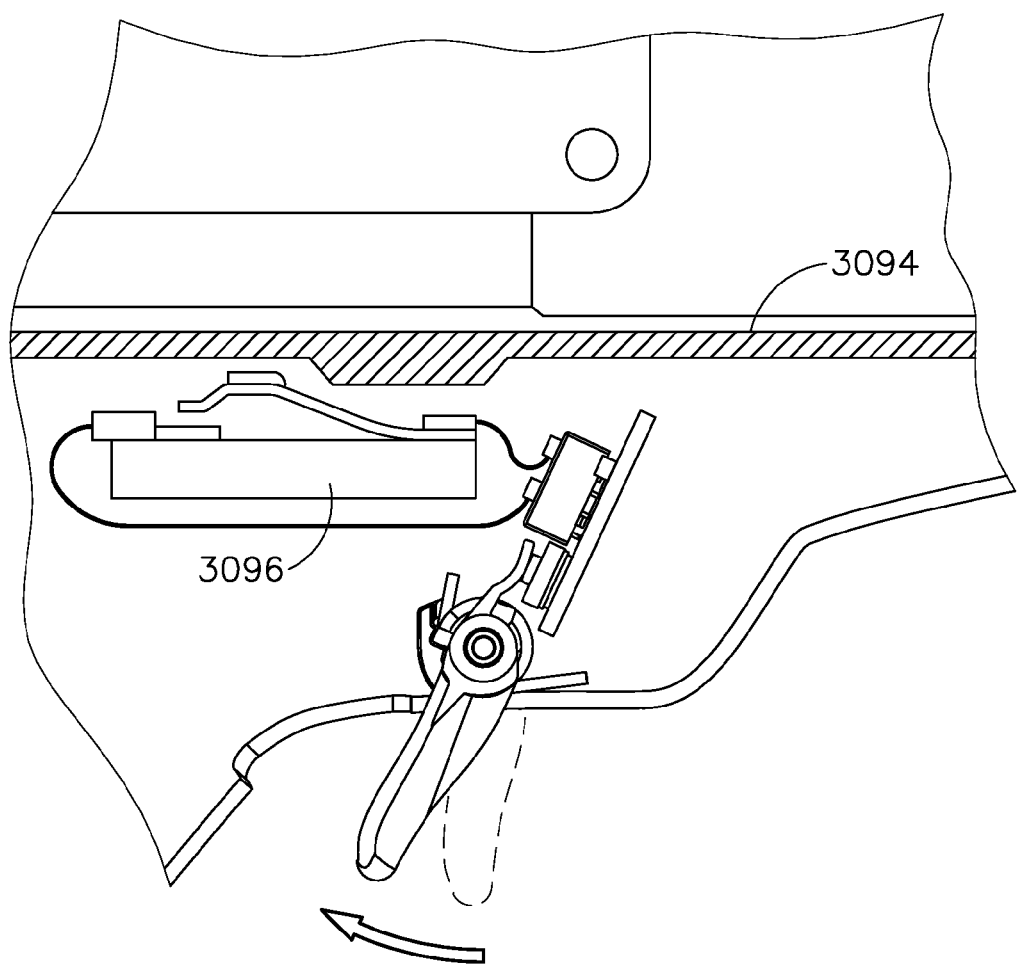
FIG. 67A depicts a cross-sectional side view of a contact switch of the circular stapler of FIG. 65A, with the contact switch in an open state, and with the link member of FIG. 65B in the first position of FIG. 66A.
Figure 67B:
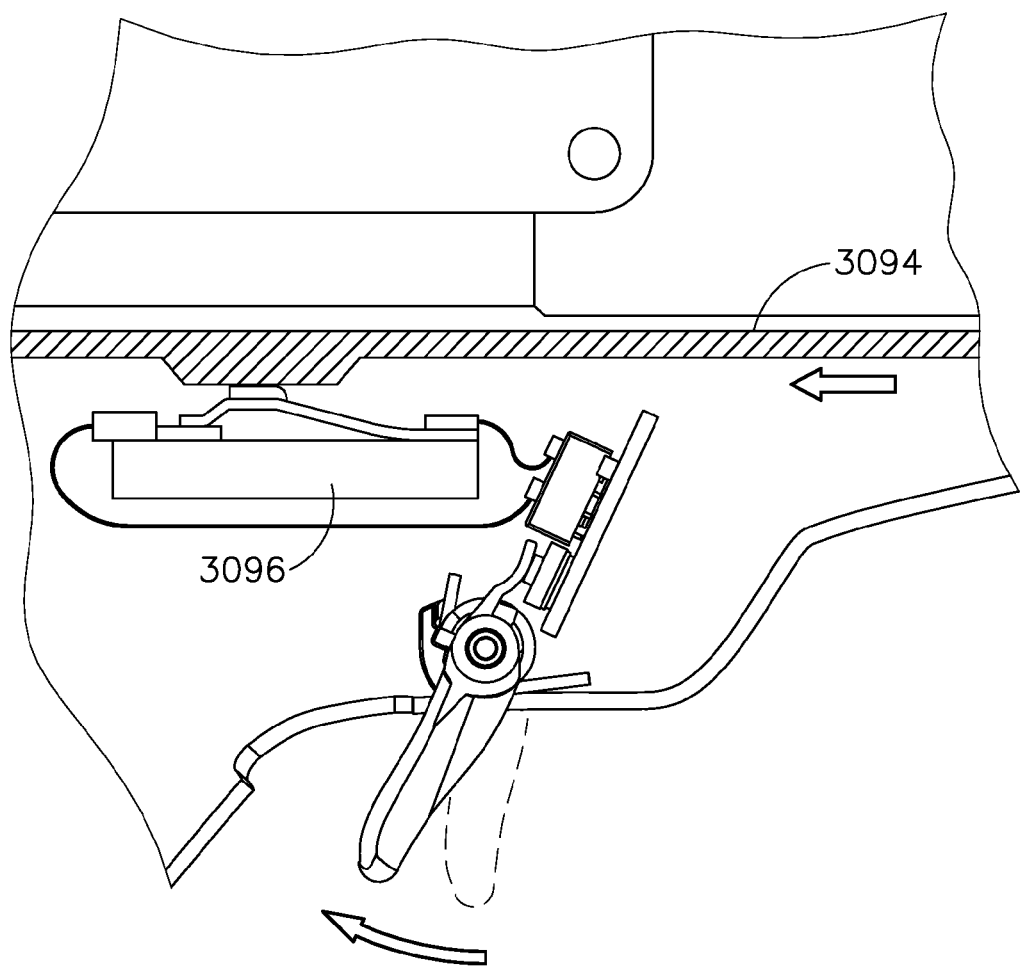
FIG. 67B depicts a cross-sectional side view of the contact switch of FIG. 67A, with the contact switch moved to a closed state by movement of the link member of FIG. 65B to the second position of FIG. 66B.

In other versions of trocar (3060), translation of sleeve (3070) from the distal longitudinal position to the proximal longitudinal position is configured to drive lockout member (3080) from the second rotational position to the first rotational position. In other words, lockout member (3080) of the present example operates opposite of lockout member (3080) discussed above in that such versions of trocar (3060), tab (3086) extends transversely through slot (3071) of sleeve (3070) when anvil (400) is properly secured to trocar (3060). As shown in FIGS. 65A-67B, in the absence of anvil (400), sleeve (3070) is biased toward the distal longitudinal position via spring (3072) such that lockout member (3080) is rotated into the second rotational position. In the present example, with lockout member (3080) in the second rotational position, tab (3086) of lockout member (3080) is rotated completely into sleeve (3070). Alternatively, with anvil (400) properly attached to trocar (3060), lockout member (3080) is driven into the first rotational position such that tab (3086) of lockout member (3080) extends transversely through slot (3071) of sleeve (3070). As shown in FIGS. 65B and 66A, with lockout member (3080) in the first rotational position, tab (3086) of lockout member (3080) is configured to engage a longitudinally translatable link member (3094). Link member (3094) is slidably disposed within tubular casing (310) and extends along the length of shaft assembly (200) into handle assembly (100) such that link member (3094) is configured to translate within and relative to tubular casing (310) and shaft assembly (200). As trocar (3060) is driven proximally relative to tubular casing (310), engagement between tab (3086) and link member (3094) causes proximal longitudinal translation of link member (3094) as shown in FIG. 66B. As shown in FIGS. 67A and 67B, as link member (3094) is translated proximally, a proximal end of link member (3094) is configured to move a switch (3096) from an open state (FIG. 67A) to a closed state (FIG. 67B) so as to permit firing of stapling head assembly (300). It should be understood that in some versions, switch (3096) may be closed via movement of bracket (500) as discussed above in addition to or in lieu of link member (3094).

3. Exemplary Trocar with Contact Switch

Figure 68A:
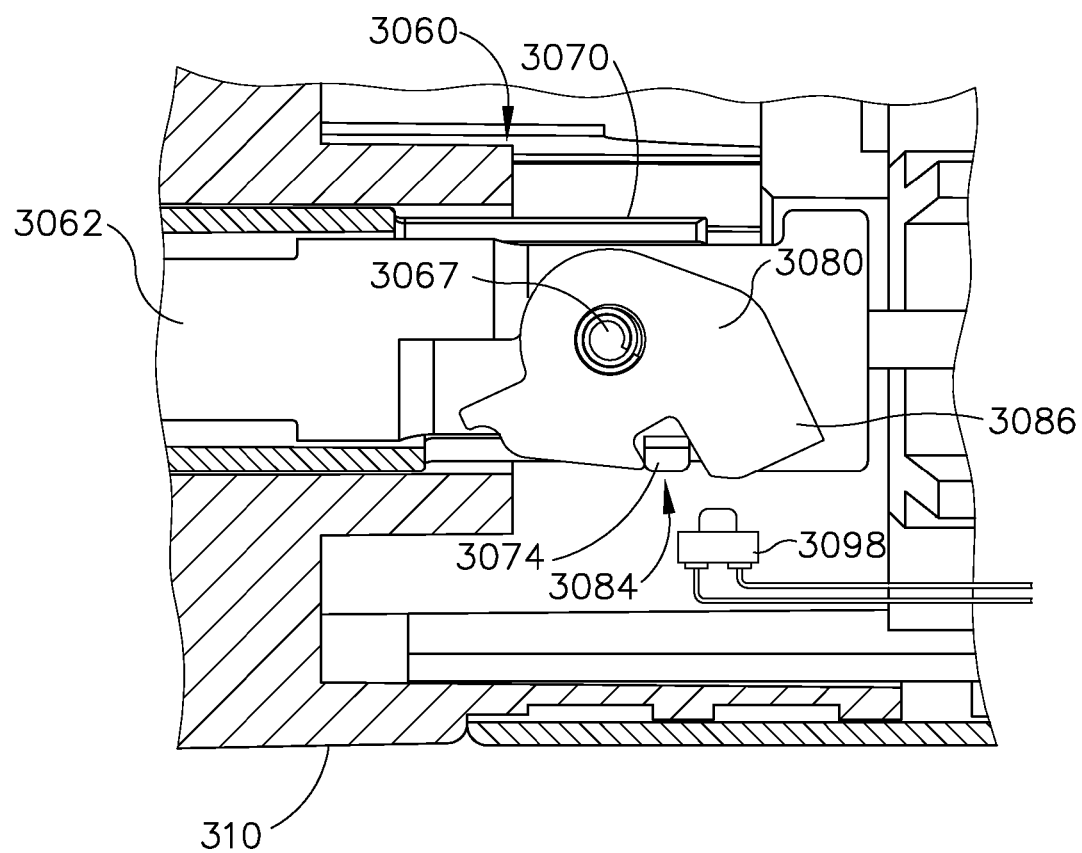
FIG. 68A depicts a cross-sectional side view of the distal end of yet another exemplary alternative circular stapler, with a lockout member in a first rotational position, and with a contact switch in an open state.
Figure 68B:
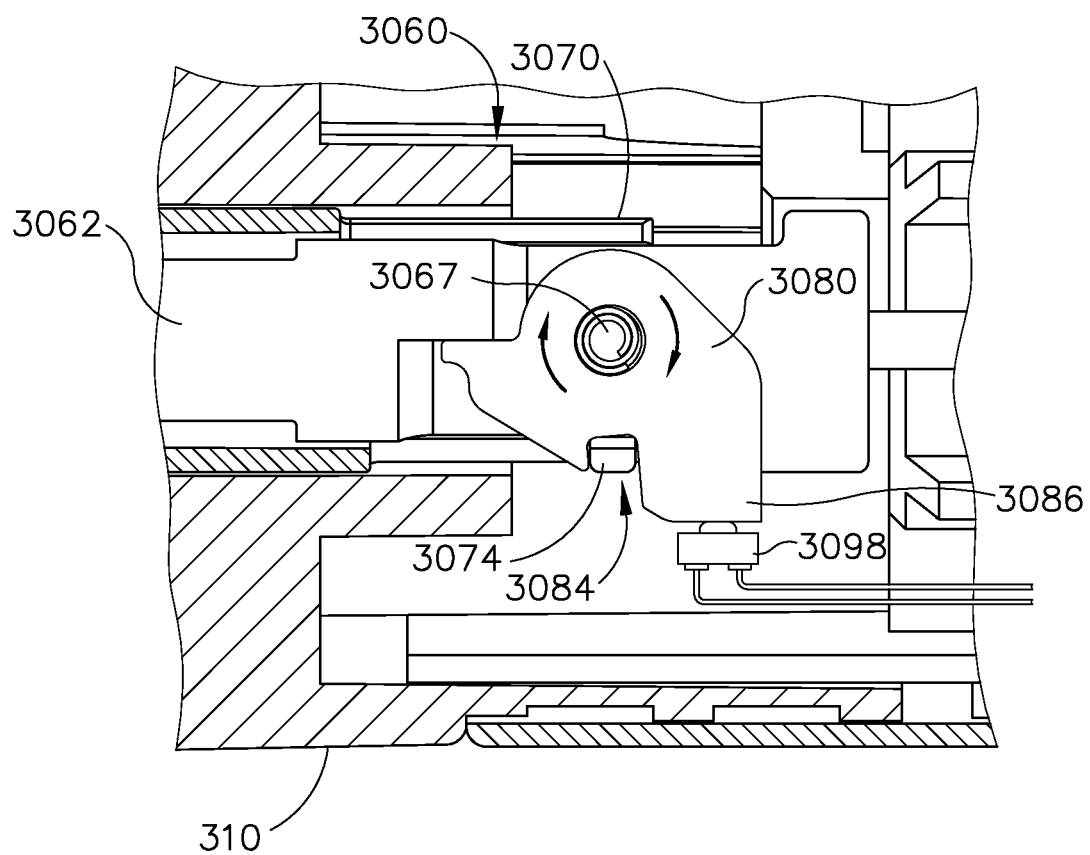
FIG. 68B depicts a cross-sectional side view of the distal end of the circular stapler of FIG. 68A, with the lockout tab of FIG. 68A rotated to a second rotational position so as to close the contact switch of FIG. 68A.

In some versions of trocar (3060), tab (3086) of lockout member (3080) may be configured to prevent firing of stapling head assembly (300) unless anvil (400) is properly attached to trocar (300). For instance, as shown in FIGS. 68A and 68B, if an operator attempts to proximally retract trocar (3060) in the absence of anvil (400) or with anvil (400) not properly attached to trocar (3060), tab (3086) of lockout member (3080) is configured to prevent firing of stapling head assembly (300). In particular, in the absence of anvil (400), sleeve (3070) is biased toward the distal longitudinal position via spring (3072) such that lockout member (3080) is rotated into the first rotational position. As mentioned above, with lockout member (3080) in the first rotational position, tab (3086) of lockout member (3080) extends transversely through slot (3071) of sleeve (3070). As shown in FIG. 68B, with lockout member (3080) in the first rotational position, tab (3086) of lockout member (3080) is configured to engage a contact switch (3098) so as to move contact switch (3098) from a closed state (FIG. 68A) to an open state (FIG. 68B) (or vice versa) so as to prevent firing of stapling head assembly (300). Alternatively, with anvil (400) properly attached to trocar (3060), lockout member (3080) is driven into the second rotational position such that tab (3086) of lockout member (3080) is rotated completely into sleeve (3070) such that tab (3086) of lockout member (3080) does not engage contact switch (3098) such that contact switch (3098) remains in the close state to thereby permit firing of stapling head assembly (300).

4. Exemplary Trocar and Lockout Rod

Figure 69:
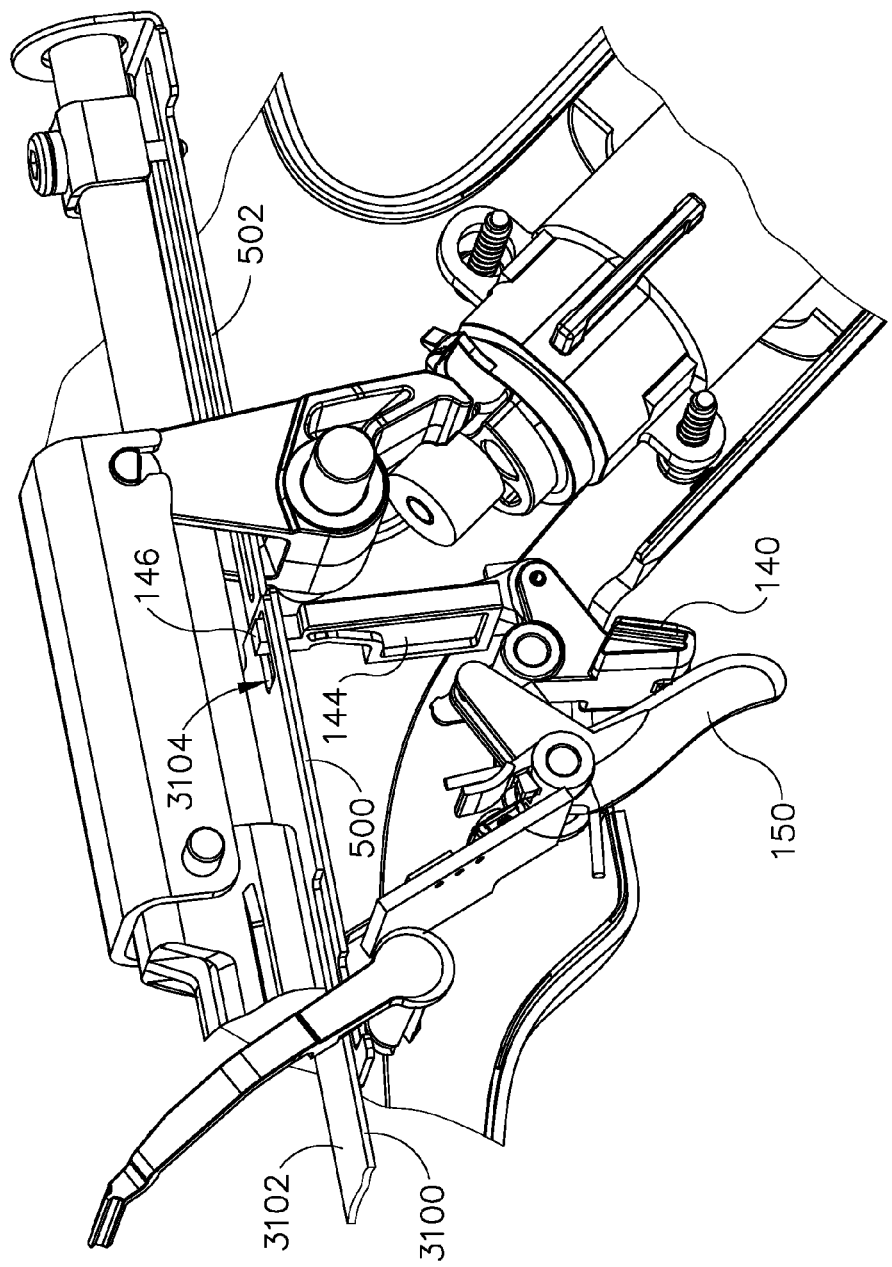
FIG. 69 depicts a perspective view of components of yet another exemplary alternative circular stapler.

As discussed above, in some versions of trocar (3060), translation of sleeve (3070) from the distal longitudinal position to the proximal longitudinal position will drive lockout member (3080) from the second rotational position to the first rotational position. In other words, in such versions of trocar (3060), tab (3086) extends transversely through slot (3071) of sleeve (3070) when anvil (400) is properly secured to trocar (3060). With lockout member (3080) in the first rotational position, tab (3086) of lockout member (3080) is configured to engage a longitudinally translatable lockout member (3100). As best seen in FIG. 69, lockout member (3100) includes a rigid body (3012) that defines a slot (3104).

As will be discussed in more detail below, lockout member (3100) is configured to selectively prevent and permit actuation of triggers (140, 150), similar to how bracket (500) selectively prevents and permits actuation of triggers (140, 150) as discussed above. In particular, slot (3104) of lockout member (3100) is configured to selectively provide clearance for actuation of triggers (140, 150). As shown in FIGS. 12A-12E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (3102) of lockout member (3100) is configured to prevent this movement of first upright member (144) and safety trigger (140) by engaging the upper end (146) of first upright member (144). Body (3102) thus blocks movement of first upright member (144) and safety trigger (140)

until lockout member (3100) is moved to a position where slot (3104) is aligned with upper end (146) to thereby provide clearance for upward movement of first upright member (144). It should therefore be understood that safety trigger (140) cannot be pivoted toward pistol grip (112) until slot (3104) is positioned over upper end (146). When lockout member (3100) is moved to a position to provide clearance for upward movement of first upright member (144), safety trigger (140) may be pivoted out of the way to permit movement of firing trigger (150).

Figure 70A:
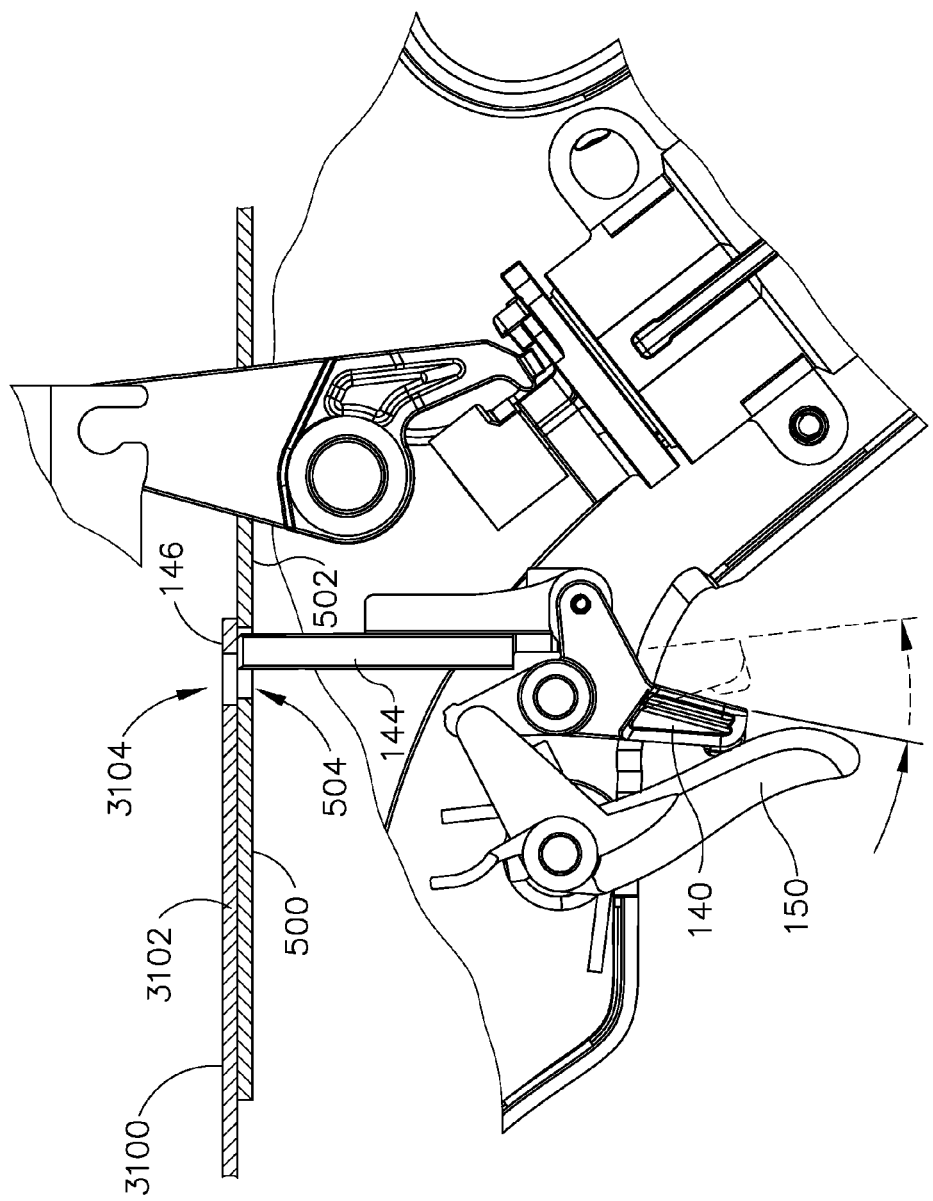
FIG. 70A depicts a side view of an anvil actuation assembly of the circular stapler of FIG. 69; with an actuation rod in a first position; and with a lockout rod in a first position.

Lockout member (3100) is slidably disposed within tubular casing (310) and extends along the length of shaft assembly (200) into handle assembly (100) such that lockout member (3100) is configured to translate within and relative to tubular casing (310) and shaft assembly (200). As trocar (3060) is driven proximally relative to tubular casing (310), engagement between tab (3086) and lockout member (3100) will cause proximal longitudinal translation of lockout member (3100) from a distal longitudinal position (FIG. 70A) to a proximal longitudinal position (FIG. 70B), similar to link member (3094) discussed above. As lockout member (3100) is translated proximally, lockout member (3100) is moved to a position where slot (3104) is aligned with upper end (146) to thereby provide clearance for upward movement of first upright member (144) as shown in FIG. 70B. When lockout member (3100) is moved to the position shown in FIG. 70B, slot (3104) provides clearance for upward movement of first upright member (144) such that safety trigger (140) may be pivoted out of the way to thereby permit movement of firing trigger (150).

D. Exemplary Trocar with Integral Switch

Figure 71:
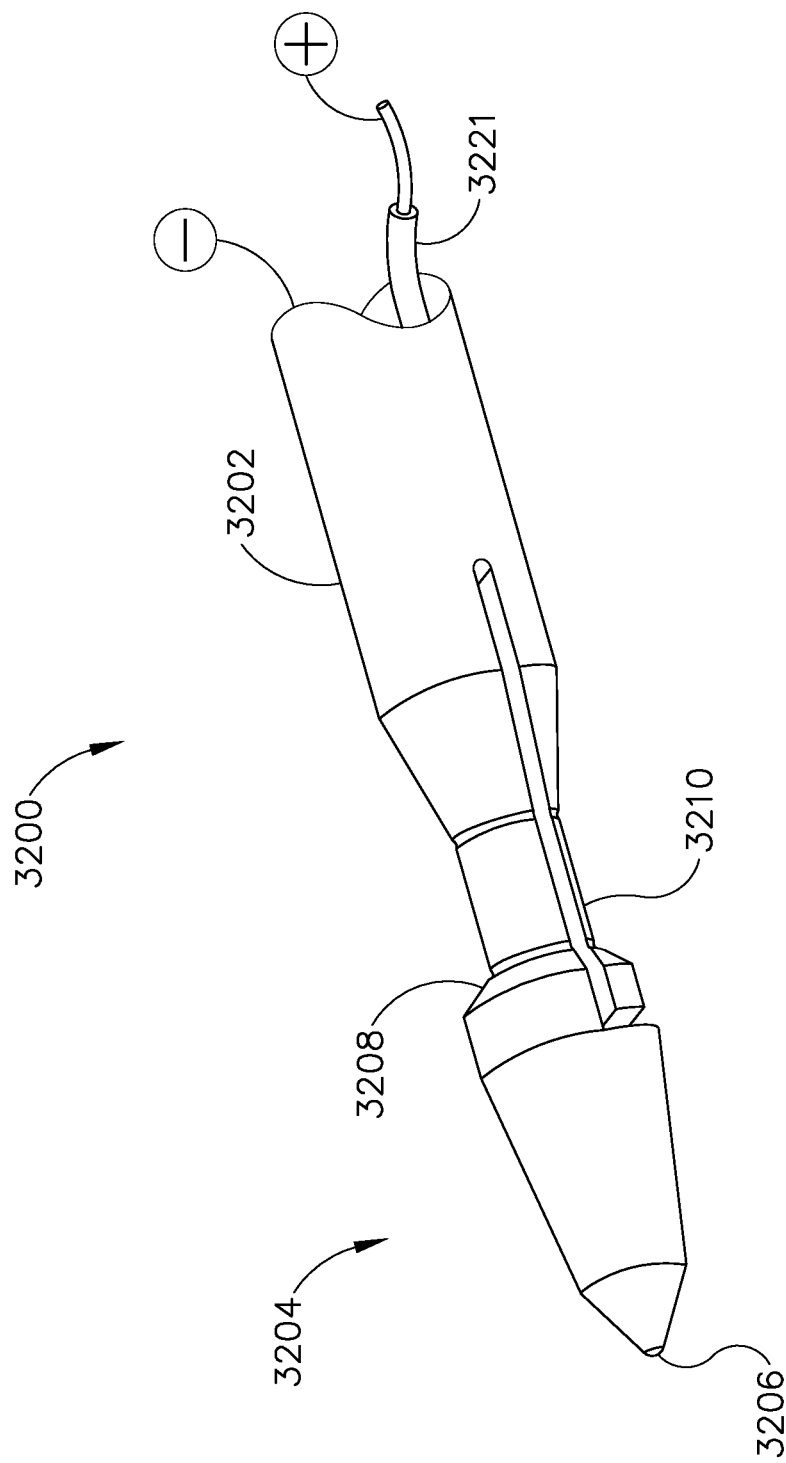
FIG. 71 depicts a perspective view of the distal end of an exemplary alternative trocar.
Figure 72A:
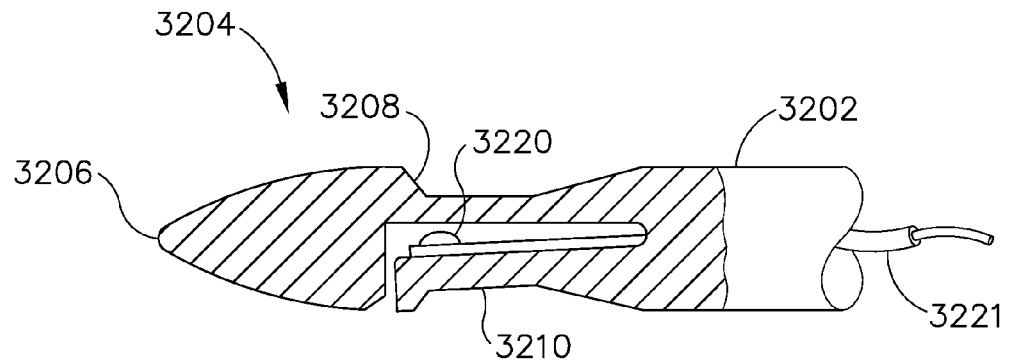
FIG. 72A depicts a cross-sectional side view of the distal end of the trocar of FIG. 71, with a contact switch of the trocar in an open state.
Figure 72B:
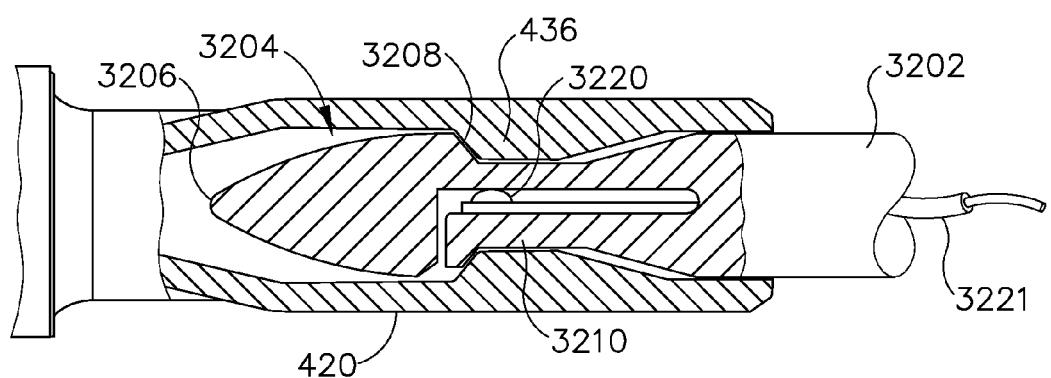
FIG. 72B depicts a cross-sectional side view of the distal end of the trocar of FIG. 71, with the contact switch of FIG. 72A moved to a closed state.

FIGS. 71-72B depict another exemplary trocar (3200) that may be readily incorporated into instrument (10) discussed above in place of trocar (330). Trocar (3200) of this example is configured to operate substantially similar to trocars (330, 3060) discussed above except for the differences discussed below. For instance, trocar (3200) is operable to translate distally and proximally relative to tubular casing (310) in response to rotation of knob (130). As will be discussed in more detail below, anvil (400) is configured to be attached to trocar (3200) such that translation of trocar (3200) relative to tubular casing (310) is communicated directly to anvil (400) as described above with reference to FIGS. 12A-12C.

Trocar (3200) comprises a shaft (3202) and a head (3204). Head (3204) includes a pointed tip (3206) and an inwardly extending proximal surface (208). Shaft (3202) thus provides a reduced outer diameter just proximal to head (3204), with surface (3208) providing a transition between that reduced outer diameter of shaft (3202) and the outer diameter of head (3204). While tip (3206) is pointed in the present example, tip (3206) is not sharp. Tip (3206) will thus not easily cause trauma to tissue due to inadvertent contact with tissue. Head (3204) and the distal portion of shaft (3202) are configured for insertion in bore (422) of anvil (400). Proximal surface (3208) and latch shelves (436) have complementary positions and configurations such that latch shelves (436) engage proximal surface (3208) when shank (420) of anvil (400) is fully seated on trocar (3200). Anvil (400) is thus secured to trocar (3200) through a snap fit due to latch members (430).

A sidewall of shaft (3202) of trocar (3200) defines a resilient-cantilevered tab (3210). Tab (3210) is formed in trocar (3200) proximal to head (3204) and includes a portion of surface (3208) at its distal end. Tab (3210) is configured to move inwardly and outwardly relative to a hollow interior of trocar (3200). A contact switch (3220) is secured to an interior surface of tab (3210). Contact switch (3220) is in communication with a control circuit (not shown) of instrument (10) via a wire (3221), the control circuit being configured to control firing of stapling head assembly (300). Contact switch (3220) is positioned such that as tab (3210) is driven inwardly, contact switch (3220) is actuated via contact with an opposing interior surface of trocar (3200). In the absence of anvil (400) or with anvil (400) not properly attached to trocar (3200), tab (3210) is biased outwardly to the position shown in FIG. 72A such that contact switch (3220) is not actuated. With anvil (400) properly attached to trocar (3200), contact between an interior surface of shank (420) of anvil (400) drives tab (3210) inwardly to the position shown in FIG. 72B such that contact switch (3220) is actuated. In particular, as discussed above, proximal surface (3208) and latch shelves (436) have complementary positions and configurations such that latch shelves (436) engage proximal surface (3208) when shank (420) of anvil (400) is fully seated on trocar (3200). Contact between latch shelves (436) and proximal surface (3208) when shank (420) of anvil (400) is fully seated on trocar (3200) drives tab (3210) inwardly to the position shown in FIG. 72B such that contact switch (3220) is actuated. Actuating contact switch (3220) will enable firing of stapling head assembly (300). When contact switch (3220) is not actuated, stapling head assembly (300) may not be fired.

E. Exemplary Trocar with Integral Circuit

Figure 73:
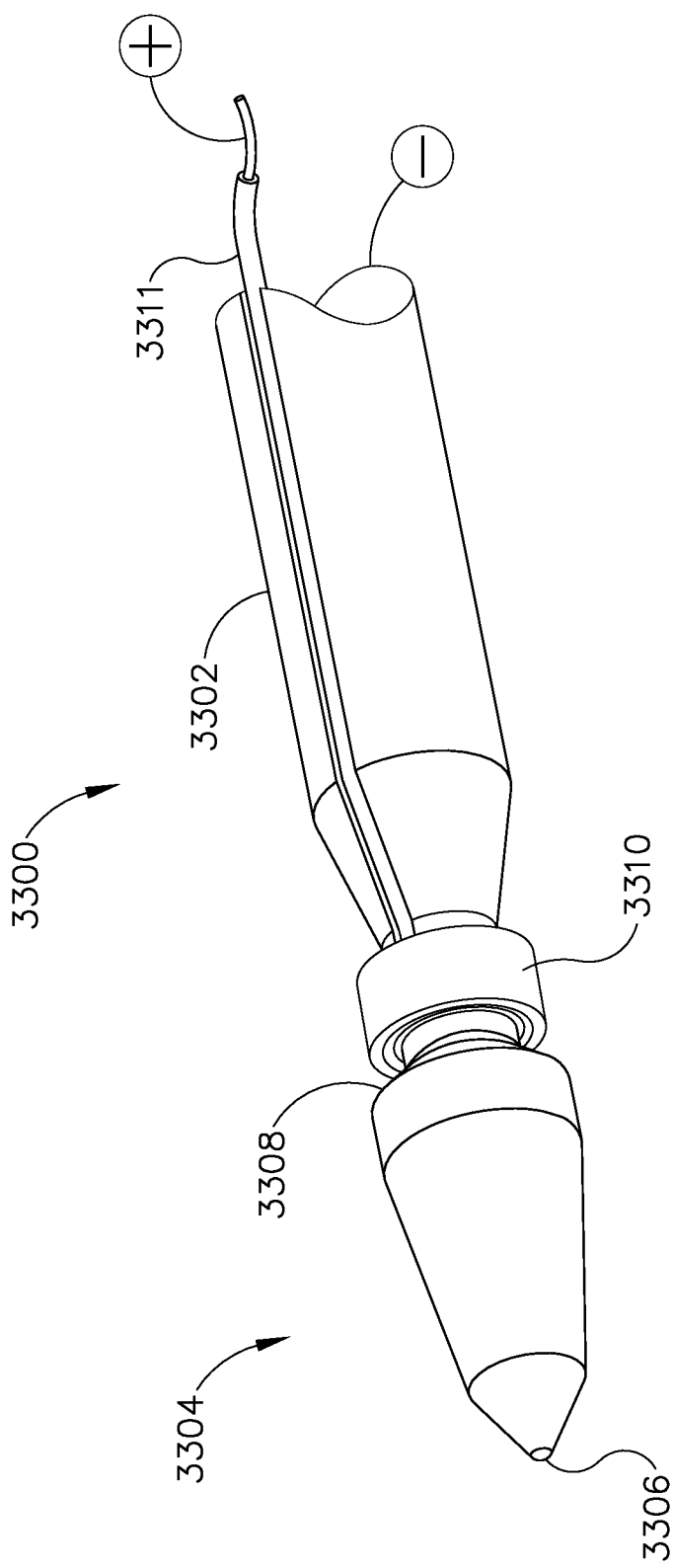
FIG. 73 depicts a perspective view of the distal end of another exemplary alternative trocar.
Figure 74A:
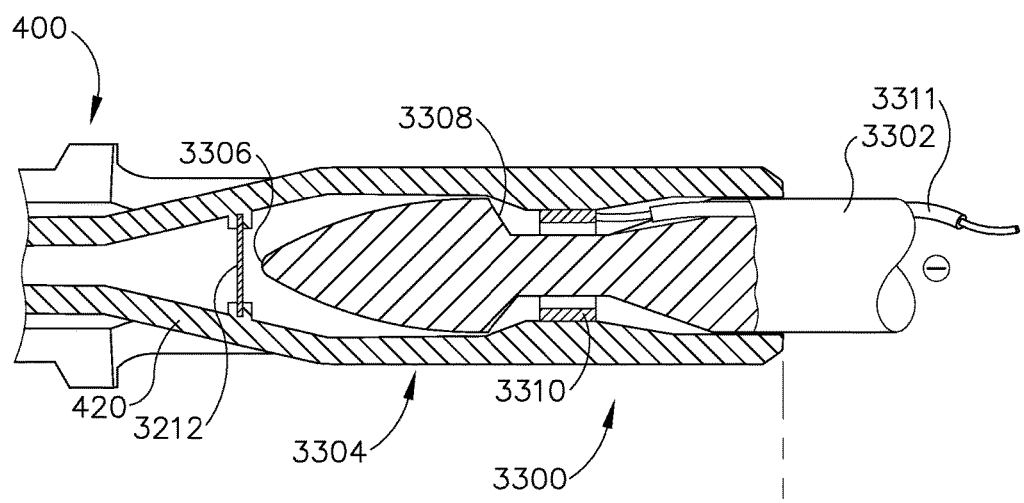
FIG. 74A depicts a cross-sectional side view of the distal end of the trocar of FIG. 73, with a circuit of the trocar in an open state.

FIGS. 73-74A depict an exemplary trocar (3300) that may be readily incorporated into instrument (10) discussed above in place of trocar (330). Trocar (3300) of this example is configured to operate substantially similar to trocars (330, 3060, 3200) discussed above except for the differences discussed below. For instance, trocar (3300) is operable to translate distally and proximally relative to tubular casing (310) in response to rotation of knob (130). As will be discussed in more detail below, anvil (400) is configured to be attached to trocar (3300) such that translation of trocar (3300) relative to tubular casing (310) is communicated directly to anvil (400) as described above with reference to FIGS. 12A-12C.

Trocar (3300) comprises a shaft (3302) and a head (3304). Head (3304) includes a pointed tip (3306) and an inwardly extending proximal surface (208). Shaft (3302) thus provides a reduced outer diameter just proximal to head (3304), with surface (3308) providing a transition between that reduced outer diameter of shaft (3302) and the outer diameter of head (3304). While tip (3306) is pointed in the present example, tip (3306) is not sharp. Tip (3306) will thus not easily cause trauma to tissue due to inadvertent contact with tissue. Head (3304) and the distal portion of shaft (3302) are configured for insertion in bore (422) of anvil (400). Proximal surface (3308) and latch shelves (436) have complementary positions and configurations such that latch shelves (436) engage proximal surface (3308) when shank (420) of anvil (400) is fully seated on trocar (3300). Anvil (400) is thus secured to trocar (3300) through a snap fit due to latch members (430).

Trocar (3300) includes an electrical contact surface (3310) disposed about a portion of shaft (3302) proximal to head (3304). Contact surface (3310) is in communication with a control circuit (not shown) of instrument (10) via a wire (3311), the control circuit being configured to control firing of stapling head assembly (300). Contact surface (3310) electrically isolated from shaft (3302) of trocar (3300).

Figure 74B:
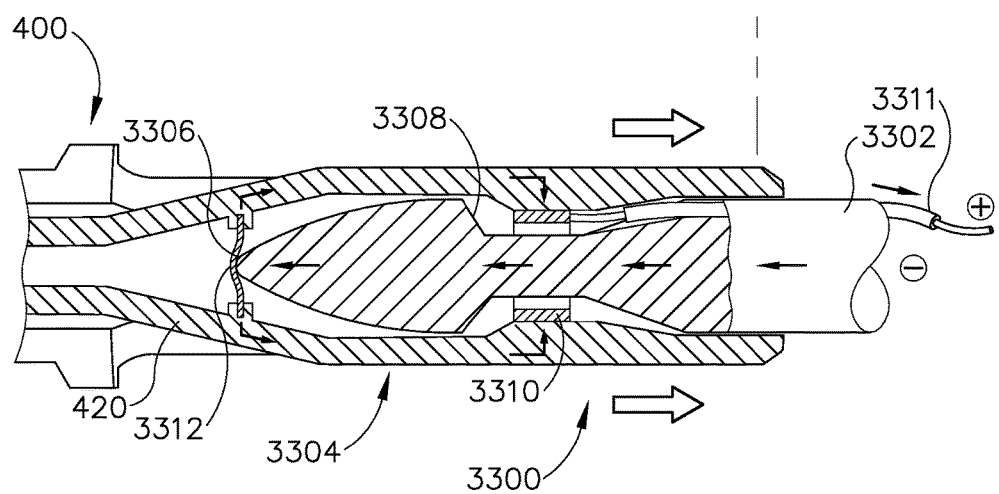
FIG. 74B depicts a cross-sectional side view of the distal end of the trocar of FIG. 73, with the circuit of FIG. 74A in a closed state.

Anvil (400) of the present example further includes an electrical contact surface (3312) that is positioned within shank (420) of anvil (400). Contact surface (3312) is in electrical communication with shank (420) of anvil (400). Contact surfaces (3310, 3312), shaft (3302), shank (420), and wire (3311) are configured to form part of an electrical circuit that selectively enables firing of stapling head assembly (300). In the absence of anvil (400) or with anvil (400) not properly attached to trocar (3300), the electrical circuit is in an open state as shown in FIG. 74A because tip (3306) of trocar (3300) is not in contact with contact surface (3312) of anvil (400). With anvil (400) properly attached to trocar (3300) as shown in FIG. 74B, tip (3306) of trocar (3300) contacts contact surface (3312) of anvil (400), thus providing a path for electrical continuity between shaft (3302) of trocar (3300) and contact surface (3312) of anvil (400). In addition, shank (420) contacts contact surface (3310) of trocar (3300), thereby providing a path for electrical continuity between shank (420) and contact surface (3310). Since shank (420) is also in electrical continuity with contact surface (3312), and since contact surface (3310) is in electrical continuity with wire (3311), it should be understood that the above described contacts provide electrical continuity between shaft (3302) of trocar (3300) and wire (3311) at the stage shown in FIG. 74B. This closes the circuit that enables stapling head assembly (300) to be fired. Until this circuit is closed, stapling head assembly (300) may not be fired. In other words, as in other examples herein, stapling head assembly (300) may not be fired until anvil (400) is fully seated on trocar (3300).

VI. Exemplary Trocar with Piercing Features

In some versions of instrument (10) it may desirable to provide trocar (330) with features configured to improve the ability of trocar (330) to pierce or penetrate tissue. For instance, it may be desirable to provide trocar (330) with features that are configured to prevent "tenting" of the tissue as trocar (330) is pushed through the tissue. Various examples of such features will be described in greater detail below; while other examples will be apparent to those of ordinary skill in the art in view of the teachings herein. Moreover, the following teachings may be applied to devices that are used in various other contexts.

Figure 75:
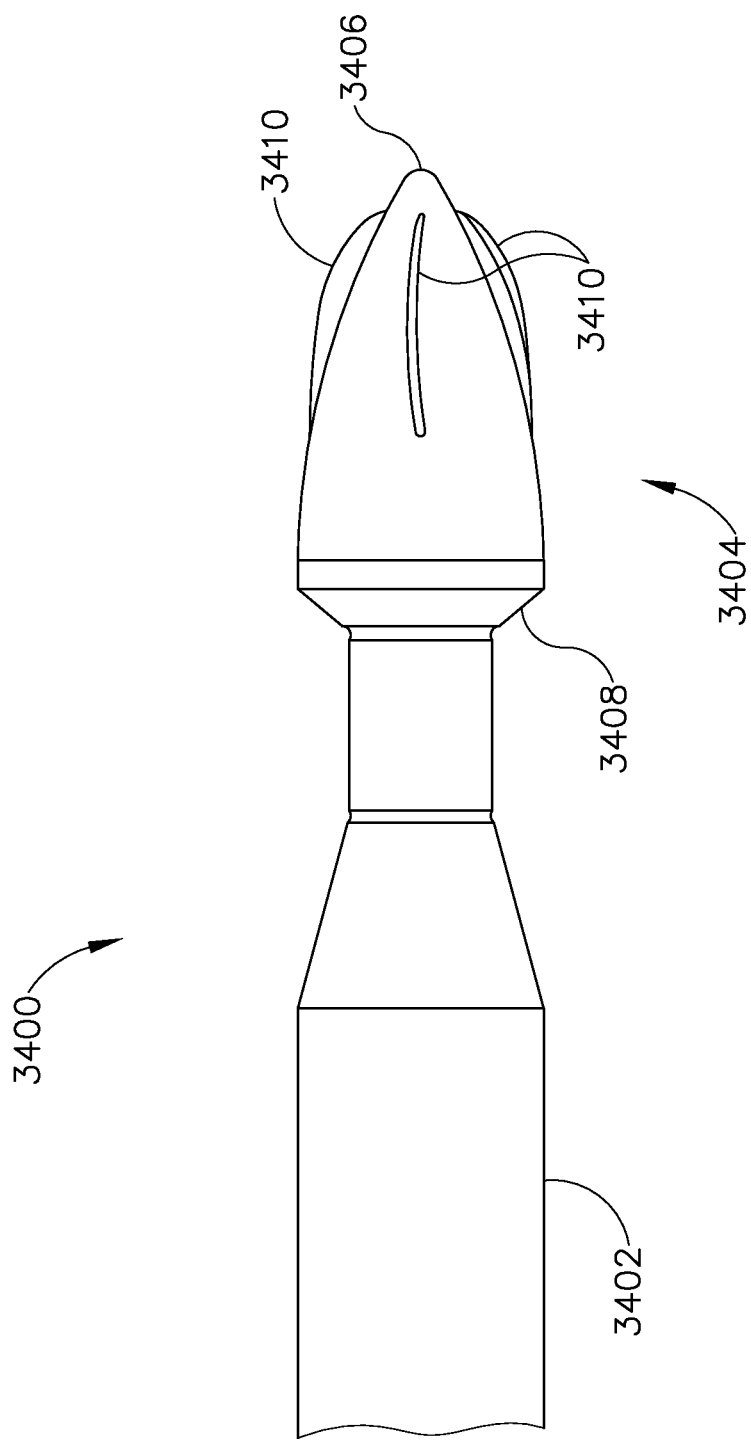
FIG. 75 depicts a side view of the distal end of yet another exemplary alternative trocar.
Figure 76A:
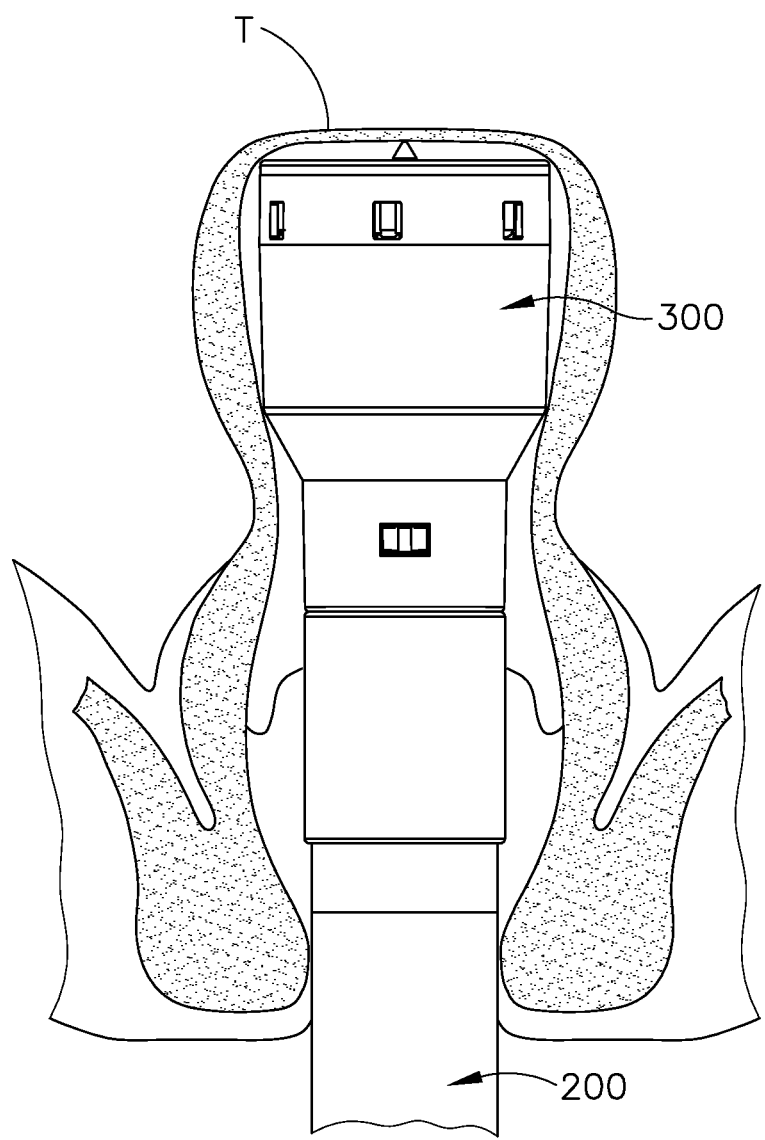
FIG. 76A depicts a side view of the trocar of FIG. 75, with the trocar in a first position.
Figure 76B:
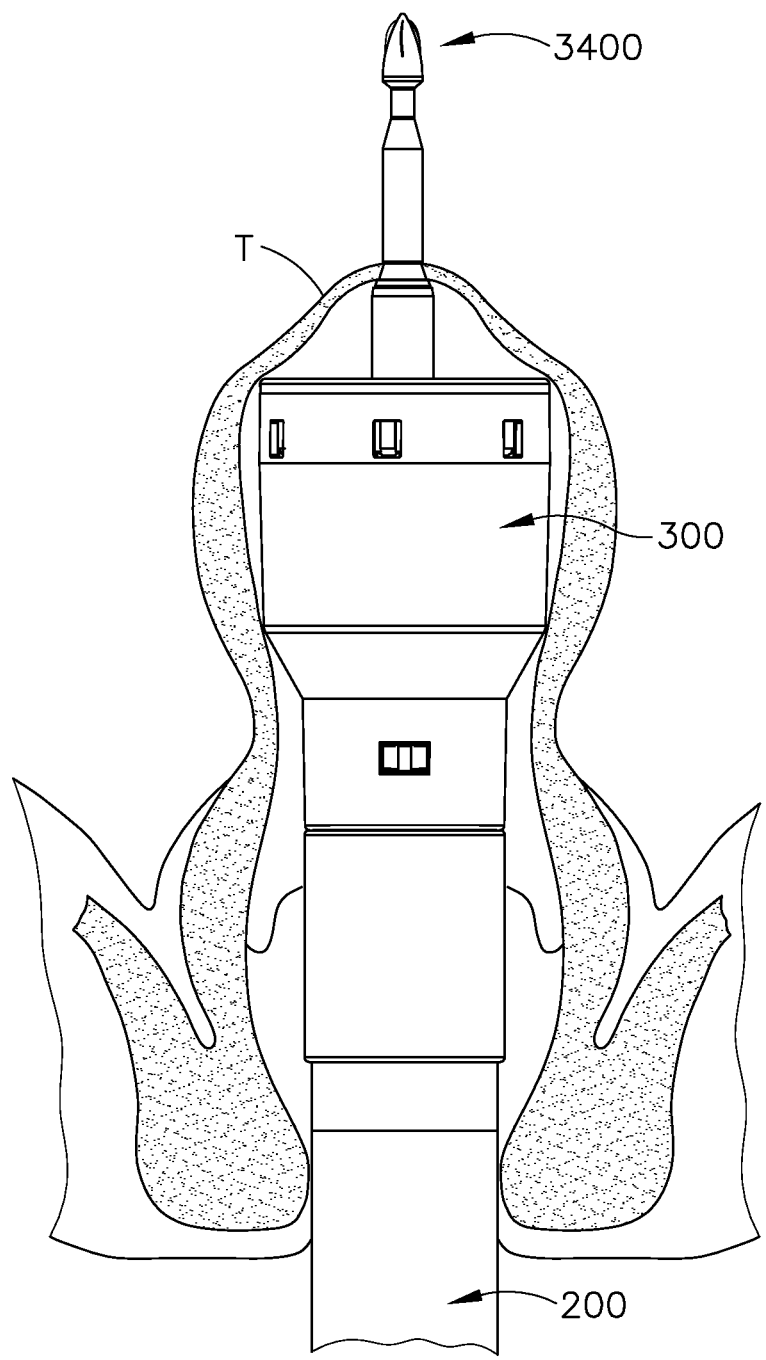
FIG. 76B depicts a side view of the trocar of FIG. 75, with the trocar moved to a second position.

FIGS. 75-76B depict an exemplary trocar (3400) that may be readily incorporated into instrument (10) discussed above in place of trocar (330). Trocar (3400) of this example is configured to operate substantially similar to trocars (330, 3060, 3200, 3300) discussed above except for the differences discussed below. For instance, trocar (3400) is operable to translate distally and proximally relative to tubular casing (310) in response to rotation of knob (130). In addition, anvil (400) may be attached to trocar (3400) such that translation of trocar (3400) relative to tubular casing (310) is communicated directly to anvil (400) as described above with reference to FIGS. 12A-12C.

Trocar (3400) comprises a shaft (3402) and a head (3404). Head (3404) includes a pointed tip (3406) and an inwardly extending proximal surface (208). Shaft (3402) thus provides a reduced outer diameter just proximal to head (3404), with surface (3408) providing a transition between that reduced outer diameter of shaft (3402) and the outer diameter of head (3404). While tip (3406) is pointed in the present example, tip (3406) is not sharp. Tip (3406) will thus not easily cause trauma to tissue due to inadvertent contact with tissue. Head (3404) and the distal portion of shaft (3402) are configured for insertion in bore (422) of anvil (400). Proximal surface (3408) and latch shelves (436) have complementary positions and configurations such that latch shelves (436) engage proximal surface (3408) when shank (420) of anvil (400) is fully seated on trocar (3400). Anvil (400) is thus secured to trocar (3400) through a snap fit due to latch members (430).

Trocar (3400) of the present example further includes a plurality of ribs (3410) extending from an exterior surface of head (3404) along a length of head (3404). Ribs (3410) may be sharp or relatively blunt. Ribs (3410) are configured to improve the ability of trocar (3400) to pierce tissue (T) by severing and/or spreading the tissue as trocar (3400) passes through the tissue (T), as shown in FIGS. 76A and 76B. For instance, ribs (3410) may be configured to prevent "tenting" of the tissue (T) as trocar (330) pierces and/or penetrates the tissue (T).

VII. Exemplary Routines for Surgical Stapler

Figure 77A:
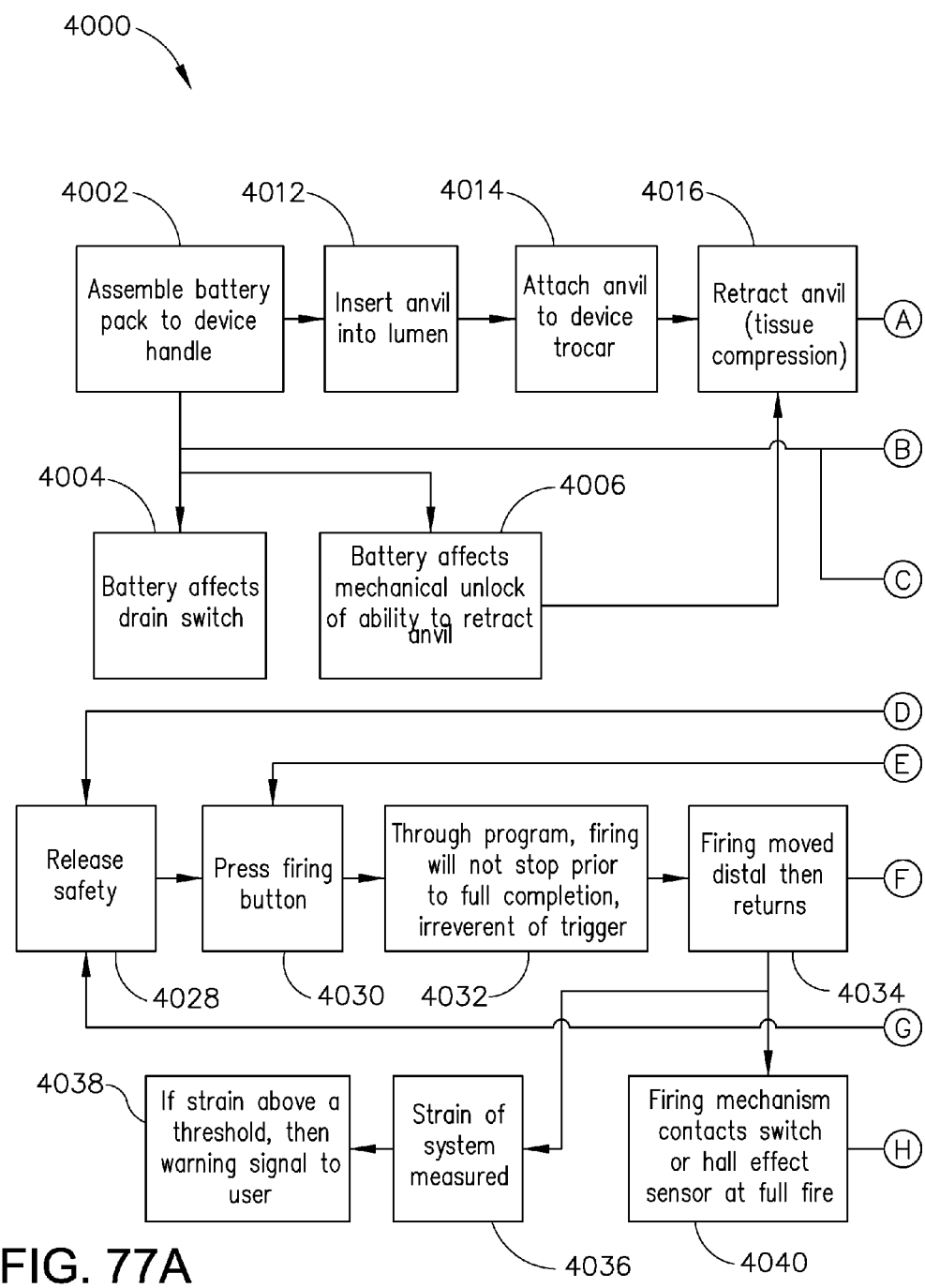
FIGS. 77A-77B depict a flow chart showing exemplary steps of operating the circular stapler of FIG. 1.
Figure 77B:
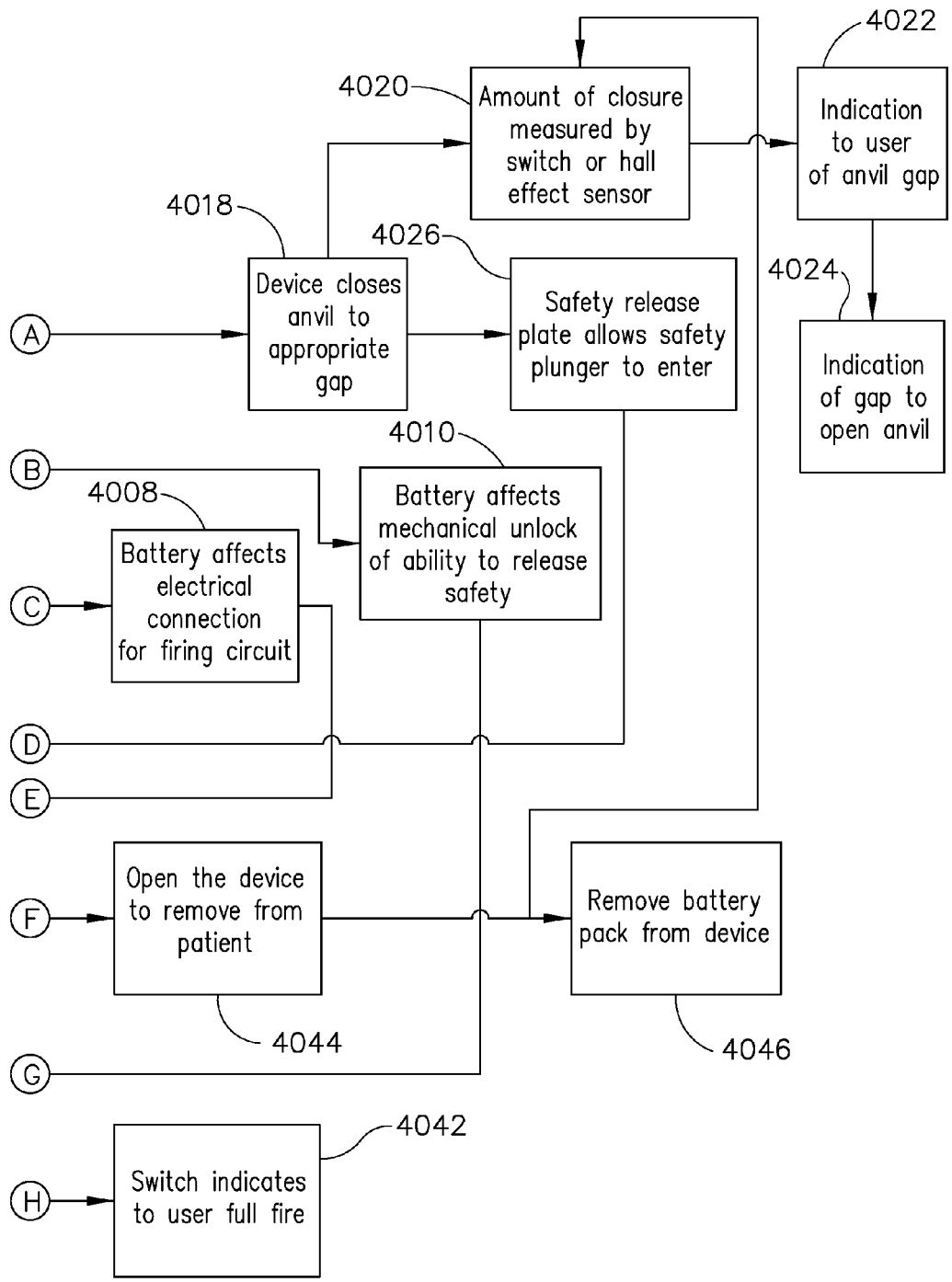

While the sequence described above with reference to FIGS. 21A-21E relate to how instrument (10) may be used by an operator in a surgical procedure, it should be understood that there are various routines that may be performed within instrument (10) before, during, and after the procedure depicted in FIGS. 21A-21E. FIGS. 77A-77B show various steps in an exemplary process (4000) that may be carried out through instrument (10) before, during, and after the procedure depicted in FIGS. 21A-21E. It should be understood that various steps of process (4000) are merely optional and may be omitted if desired.

In the present example, process (4000) begins with an operator inserting battery pack (120) into socket (116) of handle assembly (100), as shown in block (4002). In some versions, the insertion of battery back (120) into socket (116) will automatically trigger one or more additional steps in process (4000). For instance, as shown in block (4004), the insertion of battery back (120) into socket (116) may automatically activate a drain switch that begins to drain power from battery pack (120). By way of example only, such automatic drainage of power from battery pack (120) may be provided in accordance with at least some of the other teachings herein. In addition or in the alternative, automatic drainage of power from battery pack (120) may be provided in accordance with at least some of the teachings below with reference to FIGS. 78A-78F. Other suitable ways in which power may be automatically drained from battery pack (120) upon insertion of battery back (120) into socket (116) will be apparent to those of ordinary skill in the art in view of the teachings herein. Alternatively, in some versions the step shown in block (4004) is simply omitted.

In addition to or as an alternative to automatically initiating drainage of power from battery pack (120), the insertion of battery pack (120) into socket (116) may also mechanically unlock the ability to retract trocar (330) and anvil (400) proximally, as shown in block (4006). By way of example only, such unlocking of the ability to retract trocar (330) and anvil (400) proximally may be provided in accordance with at least some of the other teachings herein. Other suitable ways in which the ability to retract trocar (330) and anvil (400) proximally may be automatically unlocked upon insertion of battery back (120) into socket (116) will be apparent to those of ordinary skill in the art in view of the teachings herein. Alternatively, in some versions the step shown in block (4006) is simply omitted.

It should also be understood that the insertion of battery pack (120) into socket (116) may provide a necessary electrical connection within the circuit that actuates stapling head assembly (300), as shown in block (4008). In other words, in the absence of battery pack (120), the circuit that actuates stapling head assembly will lack a necessary electrical connection. In some other versions, instrument (10) is capable of receiving electrical power from some other source, such that battery pack (120) need not necessarily be inserted into socket (116) in order to complete a circuit that is operable to actuate stapling head assembly (300).

In some versions, the insertion of battery pack (120) into socket (116) may also mechanically unlock the ability to actuate safety trigger (140), as shown in block (4010). Various suitable ways in which the insertion of battery pack (120) into socket (116) may mechanically unlock the ability to actuate safety trigger (140) will be apparent to those of ordinary skill in the art in view of the teachings herein. Alternatively, in some versions the step shown in block (4010) is simply omitted.

Regardless of whether (or the extent to which) the steps shown in blocks (4004, 4006, 4008, 4010) are ultimately included in process (4000), process (400) may proceed with insertion of anvil (400) into anatomical structure (20), as shown in block (4012). This step is also shown in FIG. 21A as discussed above. Continuing on with process (4000) as shown in FIGS. 77A-77B, anvil (400) is then secured to trocar (330) as shown in block (4014). This step is also shown in FIG. 21B as discussed above. Continuing on with process (4000) as shown in FIGS. 77A-77B, anvil (400) and trocar (330) are then retracted proximally to compress the tissue of anatomical structures (20, 40), as shown in block (4016). This step is also shown in FIG. 21C as discussed above. The operator rotates knob (130) in order to achieve an appropriate gap distance (d), as shown in block (4018). This step is also shown in FIGS. 12B-12C and 21C as discussed above.

In some instances, instrument (10) includes electromechanical features that monitor the gap distance (d) and provide feedback to the operator relating to the gap distance (d). By way of example only, such features may be provided in accordance with at least some of the other teachings herein. Other suitable ways in which an instrument (10) may monitor the gap distance (d) and provide feedback to the operator relating to the gap distance (d) will be apparent to those of ordinary skill in the art in view of the teachings herein. For those versions of instrument (10) that do have this capability, process (4000) includes such monitoring of the gap distance (d) as shown in block (4020). Instrument (10) may provide audible, visual, and or tactile feedback relating to the gap distance (d) as shown in block (4022). In the event that the gap distance (d) falls below the clinically acceptable range (i.e., anvil (400) is getting too close to stapling head assembly (300)), instrument (10) my provide an indication to the operator to indicate that anvil (400) needs to be advanced distally to increase the gap distance (d), as shown in block (4024).

Regardless of whether instrument (10) includes electromechanical features that monitor the gap distance (d) and provide feedback to the operator relating to the gap distance (d), bracket (500) will move to a position where it unblocks actuation of safety trigger (140) when the gap distance (d) reaches the clinically acceptable range, as shown in block (4026). Such positioning of bracket (500) is also shown in FIG. 12C as described above. The operator may actuate safety trigger (140) once bracket (500) has moved into the unblocking position, as shown in block (4028). Such actuation of safety trigger (140) is also shown in FIG. 12D as described above. Once safety trigger (130) has been actuated, the operator may then actuate firing trigger (150), as shown in block (4030). Such actuation of firing trigger (150) is also shown in FIG. 12E as described above.

Once the operator actuates firing trigger (150), instrument (10) will complete an actuation stroke of stapling head assembly (300), regardless of what the operator does next with firing trigger (150), as shown in block (4032). In other words, the assembly that actuates stapling head assembly (300) (i.e., motor (160) and the rest of the components that couple motor (160) with stapling head assembly (300)) will effectively be fully committed to actuating stapling head assembly (300) once the operator actuates firing trigger (150), even if the operator further manipulates firing trigger (150). By way of example only, instrument (10) may include components that provide full commitment to the actuation of stapling head assembly (300) in response to actuation of firing trigger (150) in accordance with at least some of the teachings of U.S. Pub. No. 2015/0083774, entitled "Control Features for Motorized Surgical Stapling Instrument," published Mar. 26, 2015, issued as U.S. Pat. No. 9,907,552 on Mar. 6, 2018, the disclosure of which is incorporated by reference herein. Alternatively, instrument (10) may include components that provide full commitment to the actuation of stapling head assembly (300) in response to actuation of firing trigger (150) in accordance with the teachings below.

The actuation stroke of stapling head assembly (300) includes the distal and proximal motion of various components, as shown in block (4034). This alternating motion is shown in FIGS. 18A-18B and in FIGS. 20A-20D as described above. The distal motion is also shown in FIG. 21D as described above.

In some versions of instrument (10), while the firing mechanism completes the actuation stroke of stapling head assembly (300), instrument (10) may include features that detect strain within the firing mechanism as shown in block (4036). By way of example only, such sensing may be provided in accordance with at least some of the other teachings herein. Other suitable ways in which instrument (10) may incorporate features that sense strain in the firing system be apparent to those of ordinary skill in the art in view of the teachings herein. Alternatively, such features may be omitted such that the step shown in block (4036) is omitted. In the event that such features are included, instrument (10) may provide an audible, visual, and/or tactile indication in the event that the sensing feature(s) detected that the strain has exceeded a threshold, as shown in block (4038).

In addition to or as an alternative to features that detect strain in the firing mechanism during the actuation stroke of stapling head assembly (300), some versions of instrument (10) may include a switch or other kind of sensor that detects whether a portion of the firing mechanism has traveled to an expected distance during the actuation stroke, as indicated in block (4040). By way of example only, such sensing may be provided in accordance with at least some of the other teachings herein. Other suitable ways in which instrument (10) may incorporate features that sense whether the firing mechanism has completed sufficient travel will be apparent to those of ordinary skill in the art in view of the teachings herein. Alternatively, such features may be omitted such that the step shown in block (4040) is omitted. In the event that such features are included, instrument (10) may provide an audible, visual, and/or tactile indication in the event that the sensing feature(s) detected that the actuation stroke of stapling head assembly (300) was successfully completed, as shown in block (4042).

Once stapling head assembly (300) has been successfully actuated, anvil (400) may be advanced distally from stapling head assembly (300) and instrument (10) may be withdrawn from the patient, as shown in block (4044). After instrument (10) has been withdrawn from the patient, the operator may remove battery pack (120) from handle assembly (100), as shown in block (4046).

As noted above, the above-described steps of process (4000) are merely illustrative examples. Instrument (10) may be used in various other ways as will be apparent to those of ordinary skill in the art in view of the teachings herein. In addition, instrument (10) may have various other functionalities as will be apparent to those of ordinary skill in the art in view of the teachings herein.

VIII. Exemplary Control Circuits for Surgical Stapler

As noted above with reference to block (4032), it may be desirable to ensure that the firing mechanism for stapling head assembly (300) completes a full actuation stroke in response to actuation of firing trigger (150). In other words, it may be desirable to prevent subsequent manipulation of firing trigger (150) from having any effect on the firing mechanism completing the actuation stroke of stapling head assembly (300). In some instances, instrument (10) may incorporate mechanical features that ensure completion of a full actuation stroke of stapling head assembly (300) in response to actuation of firing trigger (150), regardless of subsequent manipulation of firing trigger (150). Examples of such mechanical features are described in U.S. Pub. No. 2015/0083774, entitled "Control Features for Motorized Surgical Stapling Instrument," published Mar. 26, 2015, issued as U.S. Pat. No. 9,907,552 on Mar. 6, 2018, the disclosure of which is incorporated by reference herein. In addition to or as an alternative to using such mechanical features, instrument (10) may include electronic components that ensure completion of a full actuation stroke of stapling head assembly (300) in response to actuation of firing trigger (150), regardless of subsequent manipulation of firing trigger (150). Several examples of such electrical features are described in greater detail below, while further examples will be apparent to those of ordinary skill in the art in view of the teachings herein.

A. Exemplary Relay-Based Control Circuit for Surgical Stapler

FIGS. 78A-78F show an exemplary circuit (4100) that may be readily incorporated into instrument (10). In particular, circuit (4100) includes components that may be incorporated into motor activation module (180) and short circuit module (190). Circuit (4100) further includes battery pack (120), motor (160), a battery drain module (4112), and a feedback module (4130).

In the present example, motor activation module (180) includes a switch (4120) and a relay (4122). Switch (4120) is configured to be closed by paddle (158) of firing trigger (150) when firing trigger (150) is pivoted from the position shown in FIG. 12D to the position shown in FIG. 12E. By way of example only, switch (4120) may comprise a single pole single throw (SPST) momentary tactile switch. Alternatively, switch (4120) may take any other suitable form. Relay (4122) comprises a conventional polarized double pole double throw (DPDT) relay, such that relay (4122) includes a pair of integral switches (4124). Motor activation module (180) is in communication with motor (160) and battery pack (120) via feedback module (4130).

Short circuit module (190) of the present example comprises a pair of switches (4140). Switches (4140) are configured to be actuated by paddle (806) of rocker member (800) when rocker member is pivoted from the position shown in FIGS. 19A and 20A-20C to the position shown in FIGS. 19B and 20D. Short circuit module (190) is in communication with motor (160) and motor activation module (4120) via feedback module (4130).

Battery drain module (4112) of the present example comprises a pair of resistors and a positive temperature coefficient (PTC) current limiting device. By way of example only, battery drain module (4112) may be constructed and operable in accordance with at least some of the other teachings herein. Battery drain module (4112) is in communication with a switch (4110), with battery (120), and with feedback module (4130).

Feedback module (4130) of the present example comprises a pair of backlight light emitting diodes (LEDs) (4132) and an indicator LED (4134). Backlight LEDs (4132) are configured and positioned to provide backlight illumination to a display that is provided in window (114). As noted above, window (114) is operable to reveal the position of indicator needle (526) as the operator adjusts the gap distance (d) between opposing surfaces (412, 322) of anvil (400) and stapling head assembly (300). Backlight LEDs (4132) may thus assist in visualization of the position of indicator needle (526) in window (114). In addition or in the alternative, window (114) may include a backlit display that is configured and operable in accordance with at least some of the other teachings herein. In addition or in the alternative, window (114) may include a backlit display that is configured and operable in accordance with at least some of the other teachings herein. Other suitable displays that may be provided through window (114) and backlit by LEDs (4132) will be apparent to those of ordinary skill in the art in view of the teachings herein. It should also be understood that backlight LEDs (4132) are merely optional and may be omitted if desired.

Indicator LED (4134) is configured to illuminate, change color, or otherwise react to an operational condition associated with instrument (10). For instance, indicator LED (4134) may be configured to provide visual feedback indicating whether anvil (400) is fully coupled with trocar (330). Indicator LED (4134) may thus be in communication with anvil (400) detection features such as those taught elsewhere herein. In addition or in the alternative, indicator LED (4134) may be configured to provide visual feedback indicating whether stapling head assembly (300) is in a ready to fire state. Indicator LED (4134) may thus be in communication with anvil (400) features such as those taught elsewhere herein. In addition or in the alternative, indicator LED (4134) may be configured to provide visual feedback indicating whether anvil (400) has been sufficiently advanced away from stapling head assembly (300) after a firing stapling head assembly (300) has been actuated and before instrument (10) is removed from the patient. Indicator LED (4134) may thus be in communication with anvil (400) position detection features such as those taught elsewhere herein. In addition or in the alternative, indicator LED (4134) may be configured to provide visual feedback indicating a level of stress within the firing mechanism for stapling head assembly (300) and/or indicating whether stapling head assembly (300) has been fully actuated. Indicator LED (4134) may thus be in communication with sensing components such as those taught elsewhere herein. Still other conditions that may be indicated through indicator LED (4134) will be apparent to those of ordinary skill in the art in view of the teachings herein. It should also be understood that feedback module (4130) may include any suitable number of indicator LEDs (4134); or may simply lack an indicator LED (4134) altogether.

Figure 78A:
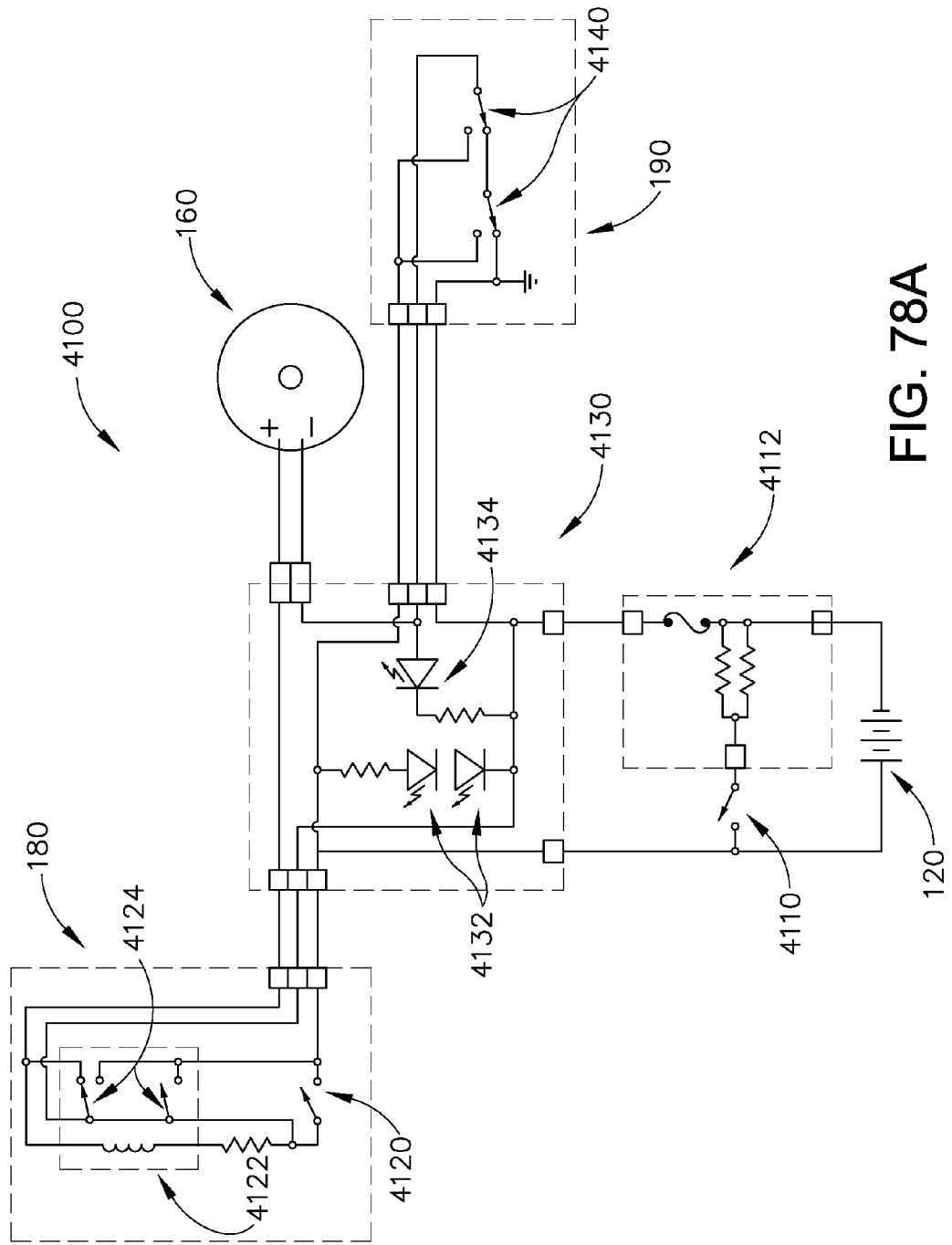
FIG. 78A depicts a schematic view of an exemplary control circuit that may be incorporated into the circular stapler of FIG. 1, in a first state of operation.

As a sequence, FIGS. 78A-78F show the various states of circuit (4100) during operation of instrument (10). In particular, FIG. 78A shows circuit (4100) in a state before battery pack (120) is inserted into handle assembly (10).

Figure 78B:
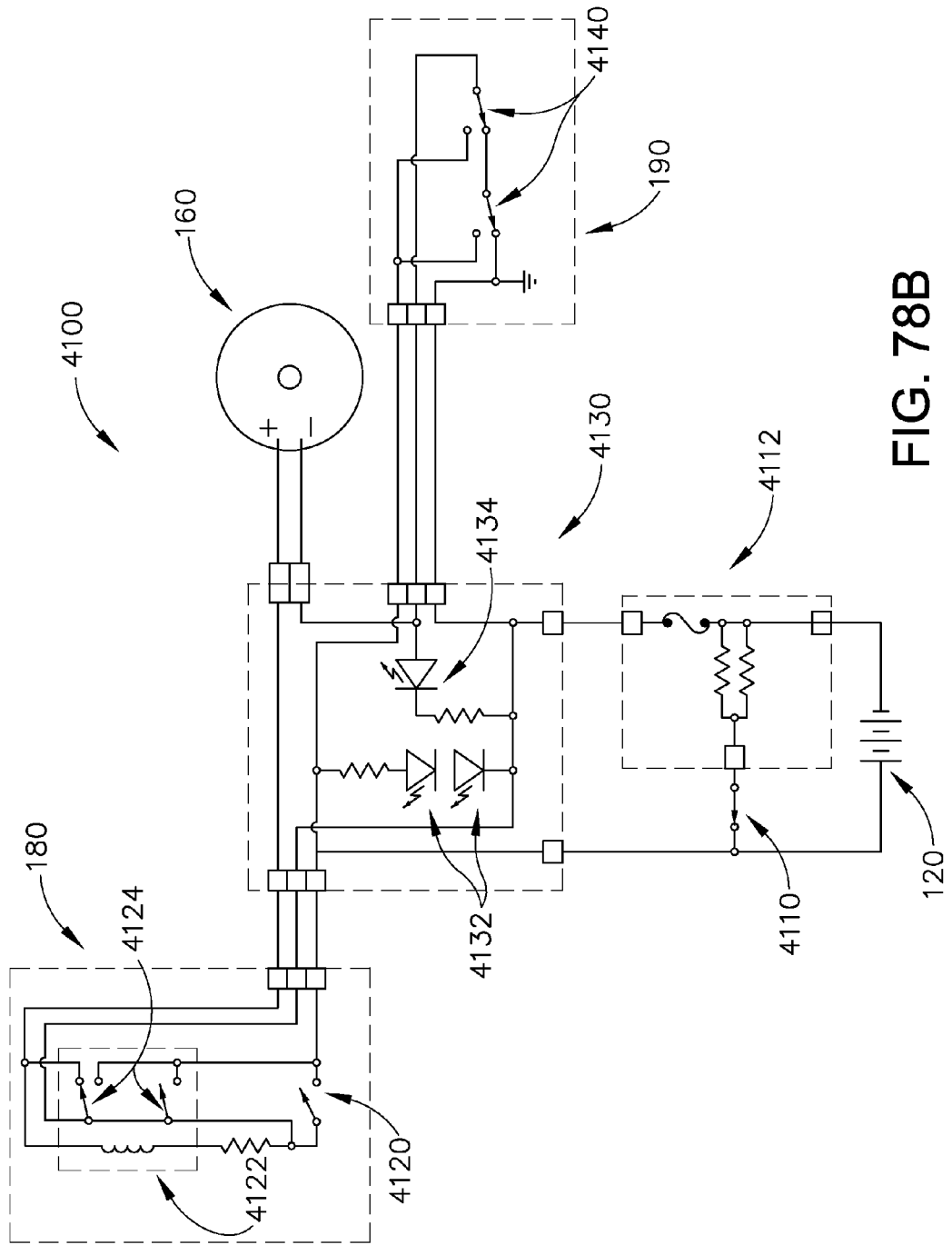
FIG. 78B depicts a schematic view of the control circuit of FIG. 78A, in a second state of operation.

FIG. 78B shows circuit (4100) in a state where battery pack (120) has been inserted into handle assembly (10). The insertion of battery pack (120) into handle assembly (10) has automatically closed switch (4110), such that battery pack (120) is electrically coupled with battery drain module (4112). This corresponds with block (4004) from process (4000) of FIGS. 77A-77B. As noted above, switch (4110) may be closed by insertion of battery pack (120) in accordance with at least some of the other teachings herein. It should also be understood that backlight LEDs (4132) may illuminate in response to insertion of battery pack (120) in handle assembly (100).

Figure 78C:
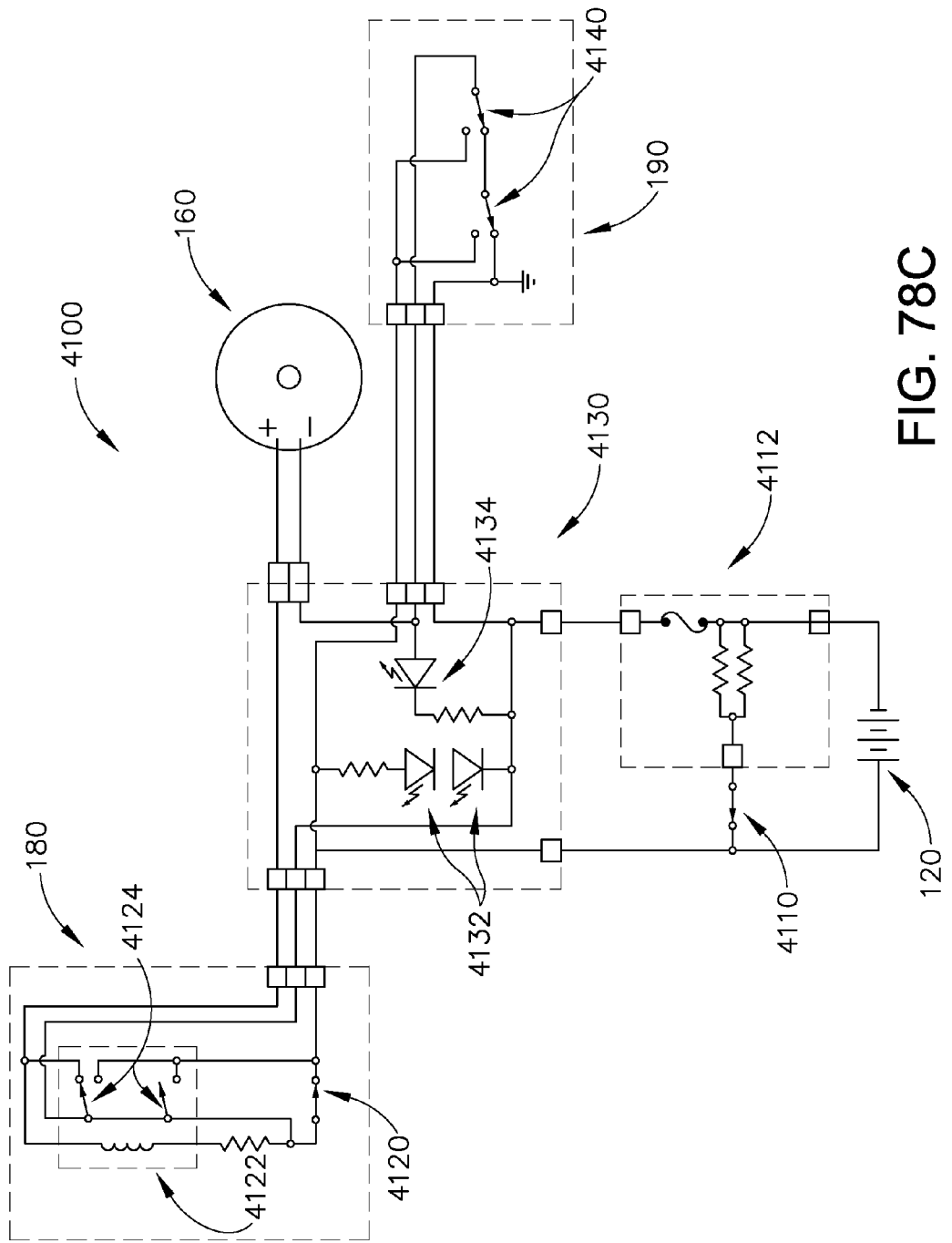
Figure 78D:
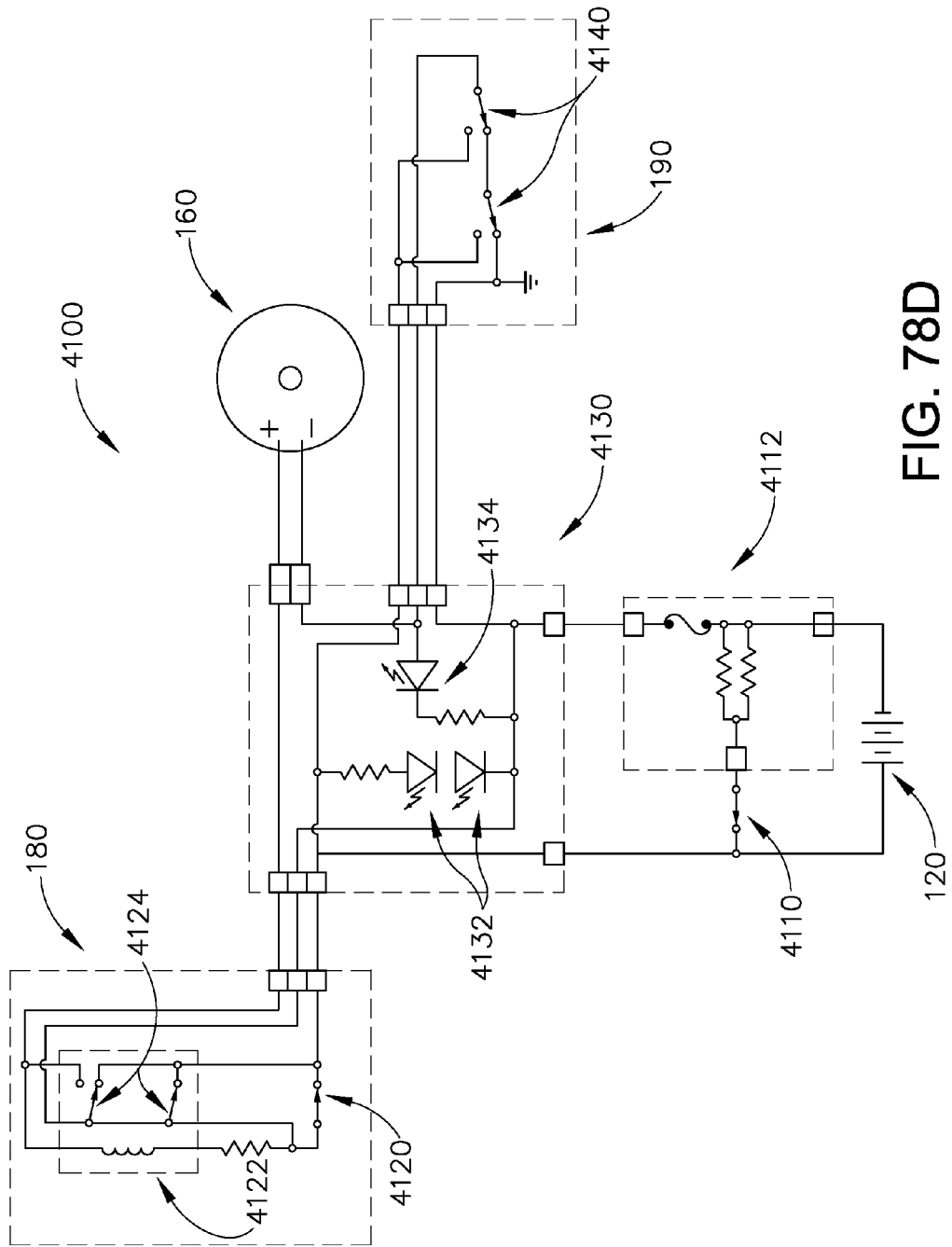

FIG. 78C shows circuit (4100) in a state where the operator has actuated firing trigger (150), thereby closing switch (4120). This corresponds with block (4030) from process (4000) of FIGS. 77A-77B. Relay (4122) is configured to automatically and immediately actuate both switches (4124) in response to closure of switch (4120), as shown in FIG. 78D. Such actuation of switches (4124) is provided by relay (4122) through activation of a magnet in response to closure of switch (4120), as is known in the art. Closure of switches (4124) will complete a circuit between battery (120) and motor (160), thereby causing motor (160) to actuate the firing mechanism of stapling head assembly (300) as described above.

Figure 78E:
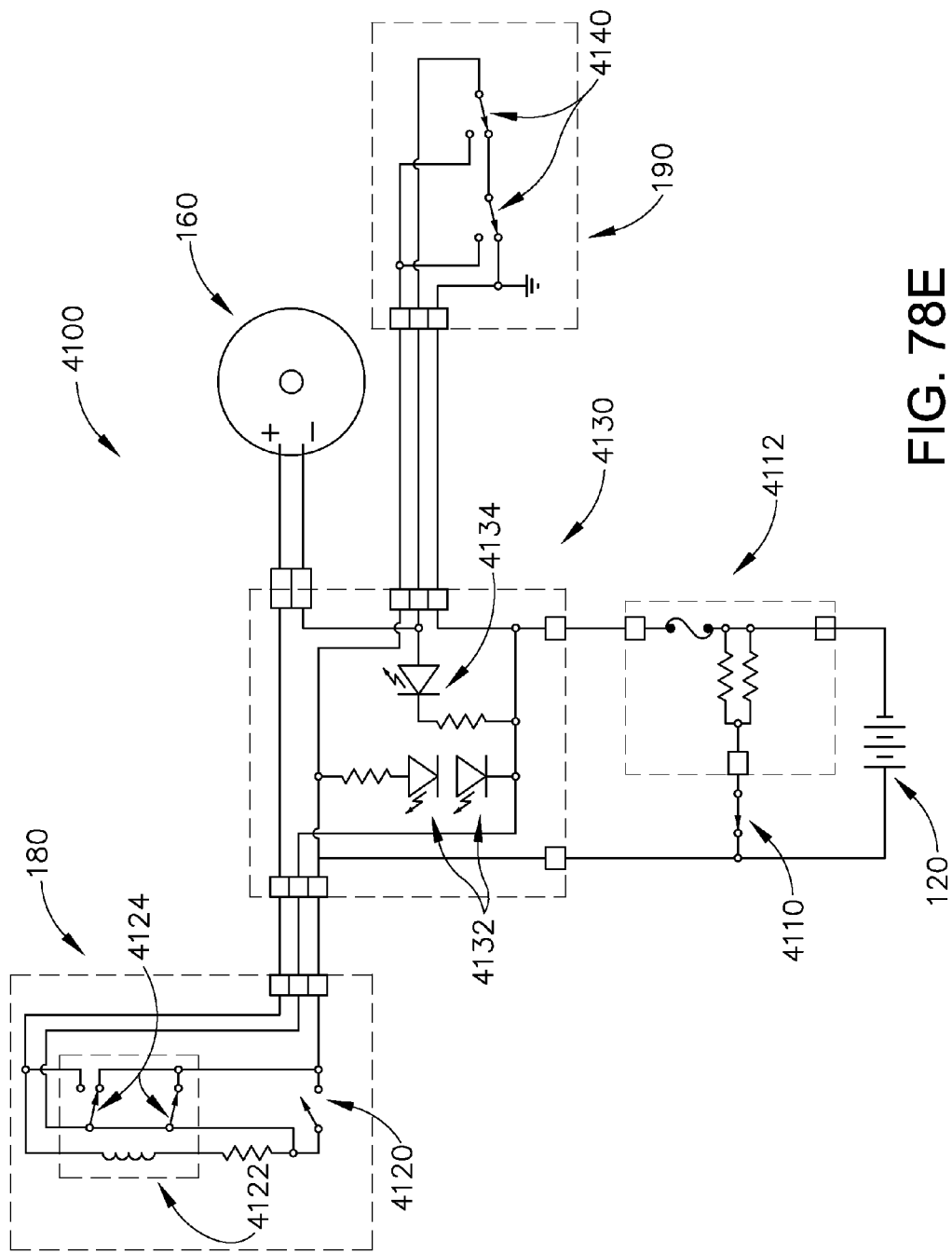

Relay (4122) of the present example is configured such that, once switches (4124) are transitioned from the state shown in FIGS. 78A-78C to the state shown in FIG. 78D, switches (4124) will remain in the state shown in FIG. 78D regardless of what subsequently happens with switch (4120). In particular, FIG. 78E shows switch (4120) transitioned back to the open state (e.g., by the operator releasing a grip on firing trigger (150) or intentionally moving trigger (150) back from the position shown in FIG. 12E to the position shown in FIG. 12D, etc.). Despite switch (4120) being transitioned back to the open state as shown in FIG. 78E, switches (4124) remain in the state first shown in FIG. 78D. In other words, switches (4124) maintain completion of the circuit between battery (120) and motor (160), thereby ensuring that motor (160) will complete actuation of the firing mechanism of stapling head assembly (300) even with switch (4120) transitioned back to the open state. Relay (4122) thus provides a commitment to completion of the actuation stroke in accordance with block (4032).

Figure 78F:
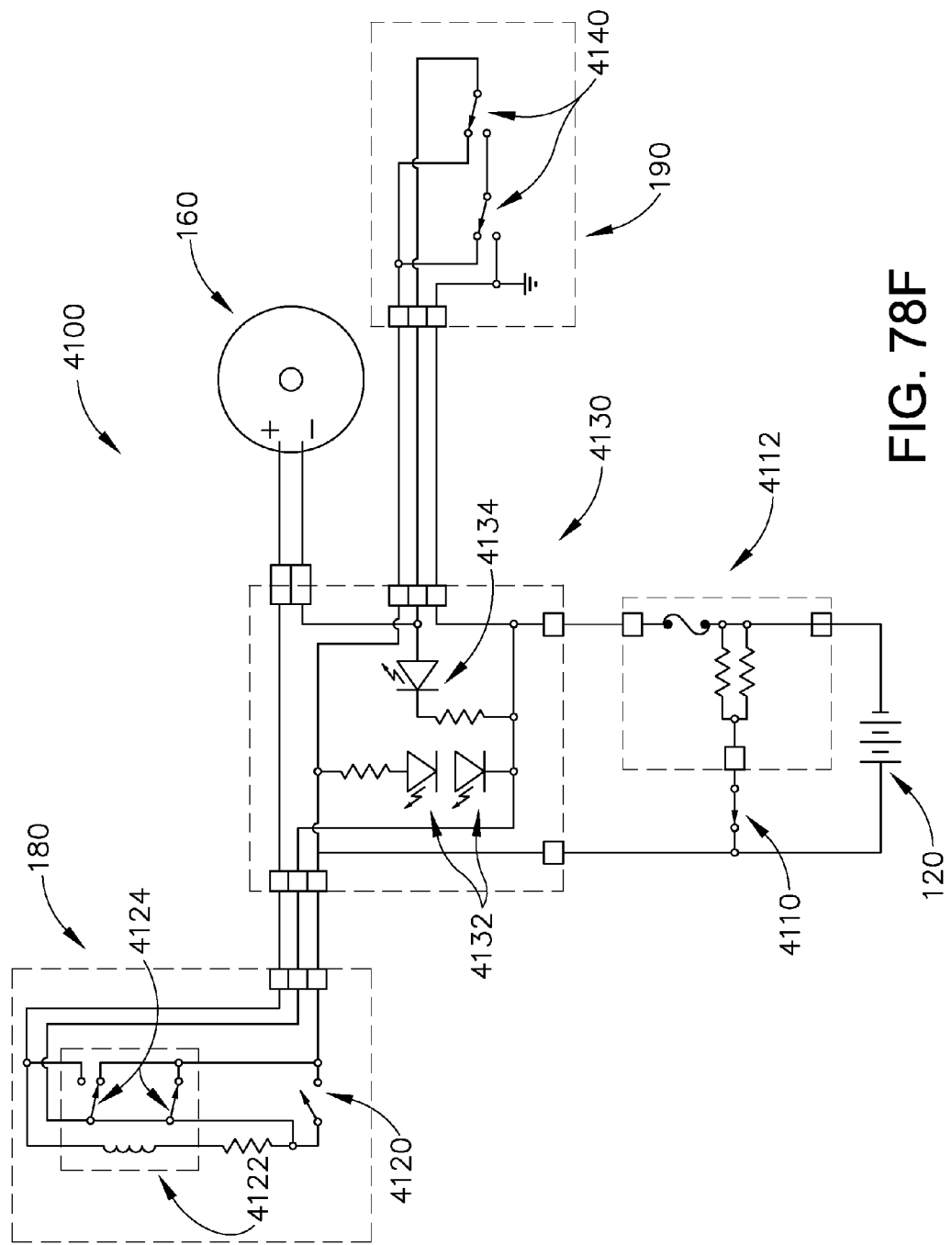

FIG. 78F shows circuit (4000) in a state where paddle (806) of rocker member (800) has changed the state of switches (4140). In this state, switches (4140) provide a short for circuit motor (160). In addition to decoupling motor (160) from battery (120), this short circuiting of motor (160) provides a braking effect on motor (160). By way of example only, this effect may be provided in accordance with at least some of the teachings of U.S. Pub. No. 2015/0083774, entitled "Control Features for Motorized Surgical Stapling Instrument," published Mar. 26, 2015, issued as U.S. Pat. No. 9,907,552 on Mar. 6, 2018, the disclosure of which is incorporated by reference herein. At this stage of operation, the operator may translate anvil (400) distally to release tissue from between opposing surfaces (412, 322) of anvil (400) and stapling head assembly (300) and then remove instrument (10) from the patient in accordance with block (4044). In the event that the operator fails to subsequently remove battery pack (120) from handle assembly (100) in accordance with block (4046), battery drain module (4112) will continue to drain power from battery pack (120) until no power is left in battery pack (120). It should also be understood that, since relay (4122) comprises a conventional polarized double pole double throw (DPDT) relay, an operator may not successfully cause motor (160) to operate in reverse simply by reversing the polarity of the voltage applied to motor (160) via relay (4122).

Figure 79:
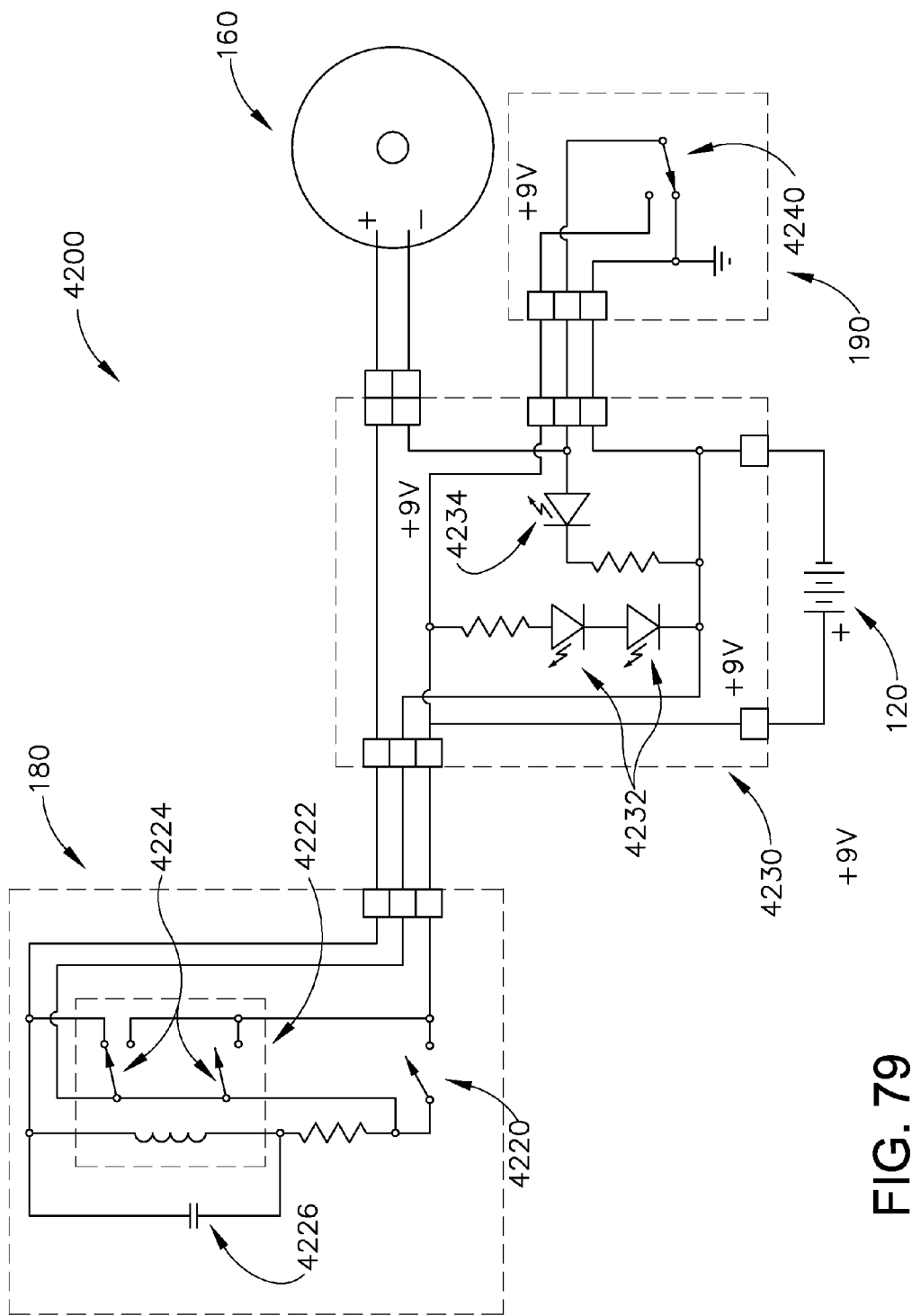

FIG. 79 shows another exemplary circuit (4200), which is a merely illustrative variation of circuit (4100). Circuit (4200) of this example thus also includes components that may be incorporated into motor activation module (180) and short circuit module (190). Circuit (4200) further includes battery pack (120), motor (160), and a feedback module (4230). While circuit (4200) of this example lacks a battery drain module, it should be understood that a battery drain module (similar to a battery drain module (4112) or otherwise configured) may be readily incorporated into circuit (4200).

Short circuit module (190) of circuit (4200) is substantially identical to short circuit module (190) of circuit (4100) except that short circuit module (190) of circuit (4200) includes just one switch (4240) instead of two switches (4140). Feedback module (4230) of circuit (4200) is substantially identical to feedback module (4130) of circuit (4100). In particular, feedback module (4230) of circuit (4200) includes a pair of backlight light emitting diodes (LEDs) (4232) and an indicator LED (4234). LEDs (4232, 4234) are configured and operable just like LEDs (4132, 4134) of circuit (4100).

Motor activation module (180) of circuit (4200) is substantially identical to motor activation module (180) of circuit (4100). In particular, motor activation module (180) of circuit (4200) includes a switch (4220) and a relay (4222). Switch (4220) is configured to be closed by paddle (158) of firing trigger (150) when firing trigger (150) is pivoted from the position shown in FIG. 12D to the position shown in FIG. 12E. Relay (4222) comprises a conventional double pole double throw (DPDT) relay, such that relay (4222) includes a pair of integral switches (4224). As described above with respect to relay (4122), relay (4222) of circuit (4200) provides a commitment to completion of the actuation stroke in accordance with block (4032) of FIGS. 77A-77B. In particular, once switch (4120) is actuated by paddle (158) of firing trigger (150), switches (4224) maintain completion of the circuit between battery (120) and motor (160), thereby ensuring that motor (160) will complete actuation of the firing mechanism of stapling head assembly (300) even if switch (4220) is transitioned back to the open state.

Unlike motor activation module (180) of circuit (4100), motor activation module (180) of circuit (4200) further includes a hold-up capacitor (4226). Hold-up capacitor (4226) is applied across the electromechanical coil of relay (4222). Hold-up capacitor (4226) is configured to prevent mechanical shock from impacting the performance of relay (4222). For instance, as noted above, some versions of anvil (400) include a breakable washer within annular recess (418). This washer is broken by knife member (340) when knife member (340) completes a full distal range of motion from the position shown in FIG. 21C to the position shown in FIG. 21D. When knife member (340) breaks the washer, this breakage of the washer may provide a mechanical shock (e.g., similar to a mechanical shock encountered when a piece of rigid plastic is broken). This mechanical shock may be communicated along shaft assembly (200) to components in handle assembly (100). In instances, this mechanical shock may tend to jar one or both switches (4224) back to the open state, which may disrupt completion of the firing stroke. Even in the presence of such mechanical shock, hold-up capacitor (4226) may maintain activation of relay (4222), maintaining power to motor (160) and thereby ensuring undisturbed completion of the firing stroke.

B. Exemplary Transistor-Based Control Circuit for Surgical Stapler

Figure 80:
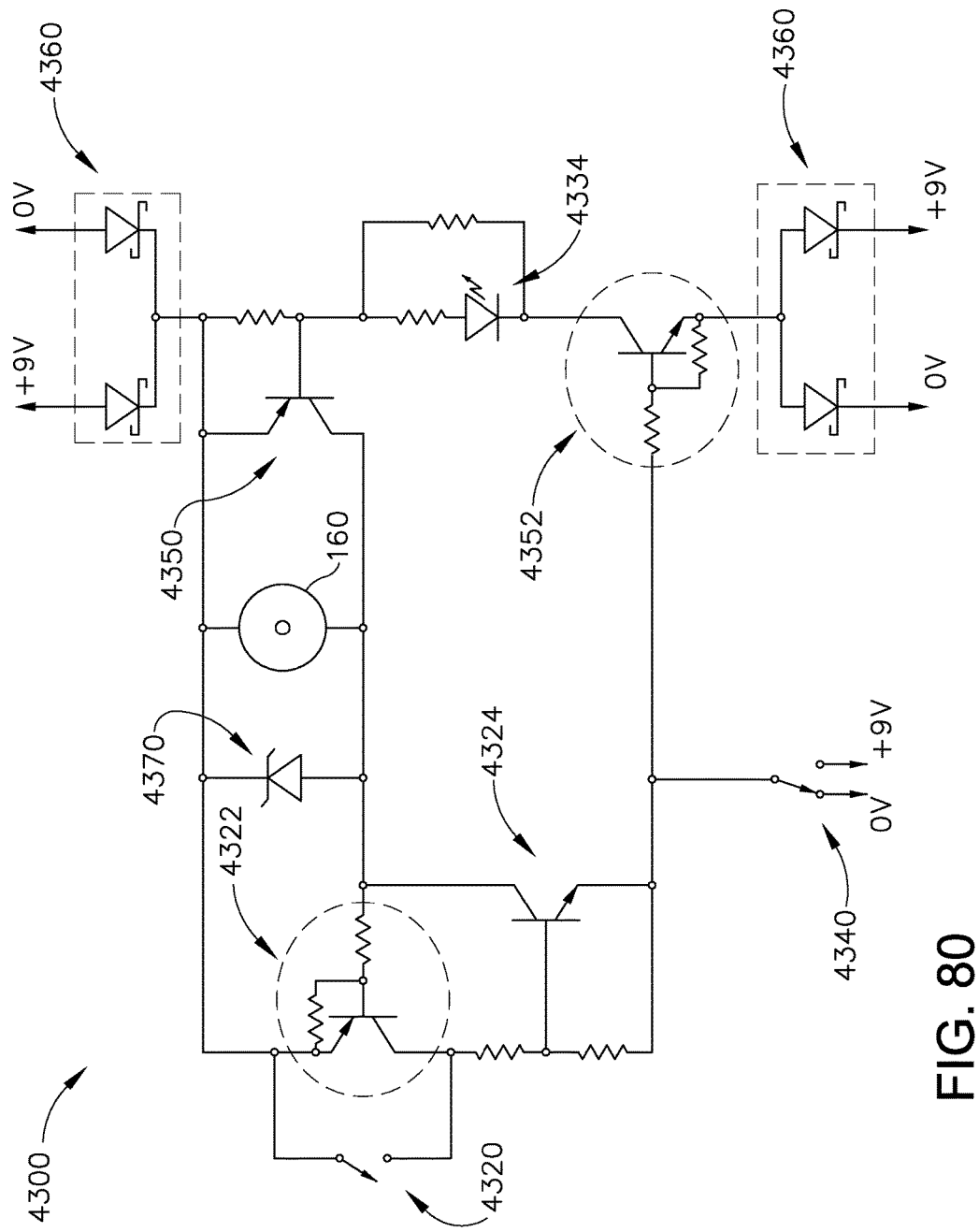

FIG. 80 shows another exemplary circuit (4300) that may be readily incorporated into instrument (10). In particular, circuit (4300) includes components that may be incorporated into motor activation module (180) and short circuit module (190). Circuit (4300) comprises a firing switch (4320), a stop switch (4340), a set of bipolar transistors (4322, 4324, 4350, 4352), and an indicator LED (4334). Circuit (4300) is in communication with battery pack (not shown in FIG. 80) via two sets of dual schottky diodes (4360). Diodes (4360) maintain current flow in a single direction.

Firing switch (4320) is configured to be closed by paddle (158) of firing trigger (150) when firing trigger (150) is pivoted from the position shown in FIG. 12D to the position shown in FIG. 12E. By way of example only, switch (4320) may comprise a single pole single throw (SPST) momentary tactile switch. Alternatively, switch (4320) may take any other suitable form. Stop switch (4340) is configured to be actuated by paddle (806) of rocker member (800) when rocker member is pivoted from the position shown in FIGS. 19A and 20A-20C to the position shown in FIGS. 19B and 20D.

Latching transistor (4322) is configured to provide a function similar to that provided by relays (4122, 4222) described above. In particular, latching transistor (4322) is configured to cooperate with a driver transistor (4322) to activate motor (160) in response to closure of firing switch (4320); and to maintain activation of motor (160) through the completion of the firing stroke even in the event that firing switch (4320) transitions back to an open state prior to completion of the firing stroke. In other words, latching transistor (4322) provides a commitment to completion of the actuation stroke in accordance with block (4032) of FIGS. 77A-77B. Various suitable ways in which transistors (4322, 4324) may be constructed and operable will be apparent to those of ordinary skill in the art in view of the teachings herein. A snubber diode (4370) further provides a current path for motor generated voltage. Snubber diode (4370) thus snubs or limits the voltage that the rest of circuit (4300) might otherwise be exposed to. It should be understood that power interruptions will not cause behavioral anomalies in circuit (4300). For instance, power interruptions may be due to high current draws such as those caused by a weak battery or electrical contacts that are not being fully contacted. Such interruptions may have a duration that is less than a second, and in some cases milliseconds.

Stop switch (4340) is configured to activate a motor brake transistor (4350) and a motor brake pre-driver transistor (4352) to provide braking of motor (160) upon completion of the firing stroke as described above. Various suitable ways in which transistors (4350, 4352) may be constructed and operable will be apparent to those of ordinary skill in the art in view of the teachings herein.

Indicator LED (4334) is configured to illuminate, change color, or otherwise react to an operational condition associated with instrument (10). For instance, indicator LED (4334) may be configured to provide visual feedback indicating whether anvil (400) is fully coupled with trocar (330). Indicator LED (4334) may thus be in communication with anvil (400) detection features such as those taught elsewhere herein. In addition or in the alternative, indicator LED (4334) may be configured to provide visual feedback indicating whether stapling head assembly (300) is in a ready to fire state. Indicator LED (4334) may thus be in communication with anvil (400) features such as those taught elsewhere herein. In addition or in the alternative, indicator LED (4334) may be configured to provide visual feedback indicating whether anvil (400) has been sufficiently advanced away from stapling head assembly (300) after a firing stapling head assembly (300) has been actuated and before instrument (10) is removed from the patient. Indicator LED (4334) may thus be in communication with anvil (400) position detection features such as those taught elsewhere herein. In addition or in the alternative, indicator LED (4334) may be configured to provide visual feedback indicating a level of stress within the firing mechanism for stapling head assembly (300) and/or indicating whether stapling head assembly (300) has been fully actuated. Indicator LED (4334) may thus be in communication with sensing components such as those taught elsewhere herein. Still other conditions that may be indicated through indicator LED (4334) will be apparent to those of ordinary skill in the art in view of the teachings herein. It should also be understood that circuit (4300) may include any suitable number of indicator LEDs (4334); or may simply lack an indicator LED (4334) altogether

C. Exemplary Microprocessor-Based Control Circuit for Surgical Stapler

Figure 81:
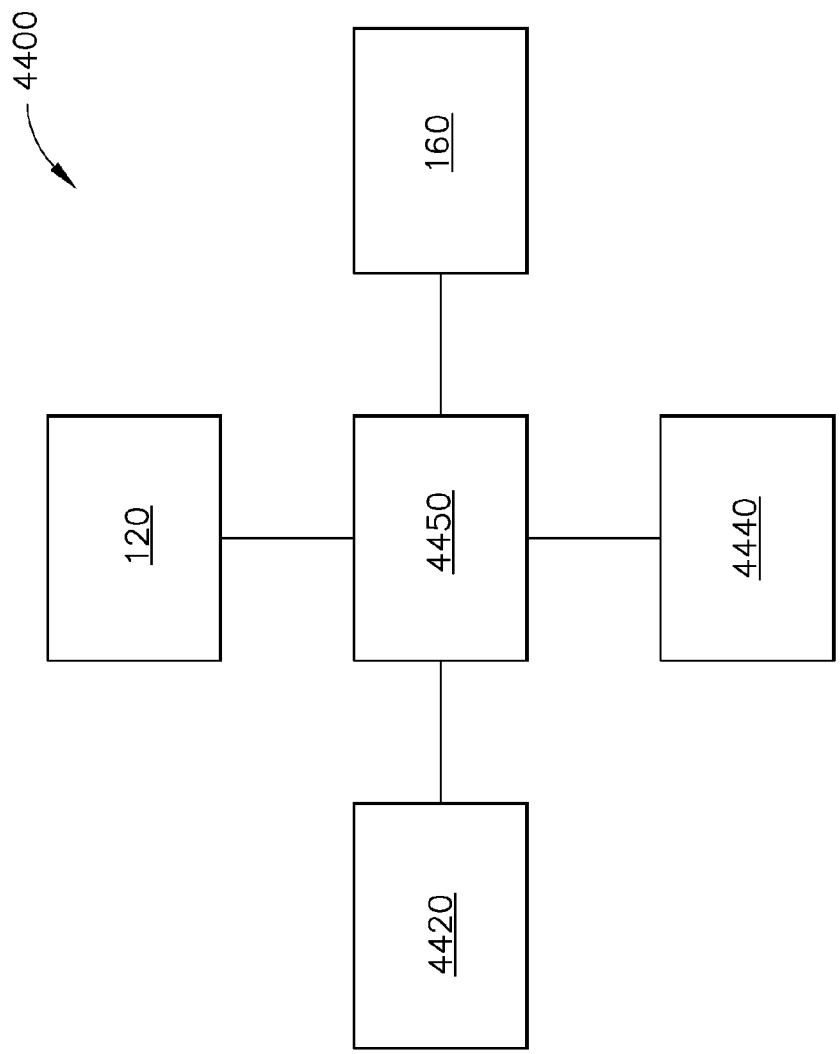

FIG. 81 shows another exemplary circuit (4400) that may be readily incorporated into instrument (10). In particular, circuit (4400) includes battery pack (120), motor (160), a firing switch (4420), a stop switch (4440), and a microprocessor (4450). Firing switch (4420) is configured to be closed by paddle (158) of firing trigger (150) when firing trigger (150) is pivoted from the position shown in FIG. 12D to the position shown in FIG. 12E. By way of example only, switch (4420) may comprise a single pole single throw (SPST) momentary tactile switch. Alternatively, switch (4420) may take any other suitable form. Stop switch (4440) is configured to be actuated by paddle (806) of rocker member (800) when rocker member is pivoted from the position shown in FIGS. 19A and 20A-20C to the position shown in FIGS. 19B and 20D.

Microprocessor (4450) is configured to serve as a central hub for the other components of circuit (4400). In addition, microprocessor (4450) is programmed to activate motor (160) in response to closure of firing switch (4420); and to maintain activation of motor (160) through the completion of the firing stroke even in the event that firing switch (4420) transitions back to an open state prior to completion of the firing stroke. In other words, microprocessor (4450) provides a commitment to completion of the actuation stroke in accordance with block (4032) of FIGS. 77A-77B. Microprocessor (4450) is also configured to provide braking of motor (160) upon completion of the firing stroke as described above. Microprocessor (4450) thus provides a single, comprehensive alternative to relays (4122, 4222) and transistors (4322, 4324, 4350, 4352) as described above. Various suitable ways in which microprocessor (4450) may be constructed and operable will be apparent to those of ordinary skill in the art in view of the teachings herein. In some versions, microprocessor (4450) is configured in accordance with, operable in accordance with, and/or placed in an arrangement with other components in accordance with at least some of the teachings of U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

IX. Exemplary "Readiness" Indicators

In some versions of instrument (10) it may be desirable to provide instrument (10) with features that are configured to indicate the "readiness" of instrument (10) to actuate stapling head assembly (300). For instance, such features may indicate any one or more of the following conditions: whether battery pack (120) is appropriately attached; whether anvil (400) is appropriately attached with stapling head assembly (300); whether the gap distance (d) between opposing surfaces (412, 322) of anvil (400) and stapling head assembly (300) is appropriate; and/or whether battery pack (120) has sufficient charge to complete actuation of stapling head assembly (300). In addition, features may be provided to prevent actuation of stapling head assembly (300) unless instrument (10) is "ready" and/or to prevent subsequent actuation of stapling head assembly (300) after a single use. For instance, such features may cause the charge to be drained from battery pack (120) after a first use of battery pack (120) so as to prevent subsequent use of battery pack (120). Various examples of such features will be described in greater detail below; while other examples will be apparent to those of ordinary skill in the art in view of the teachings herein. Moreover, the following teachings may be applied to devices that are used in various other contexts.

A. Exemplary Rotation Knob Lockout Features

Figure 82:
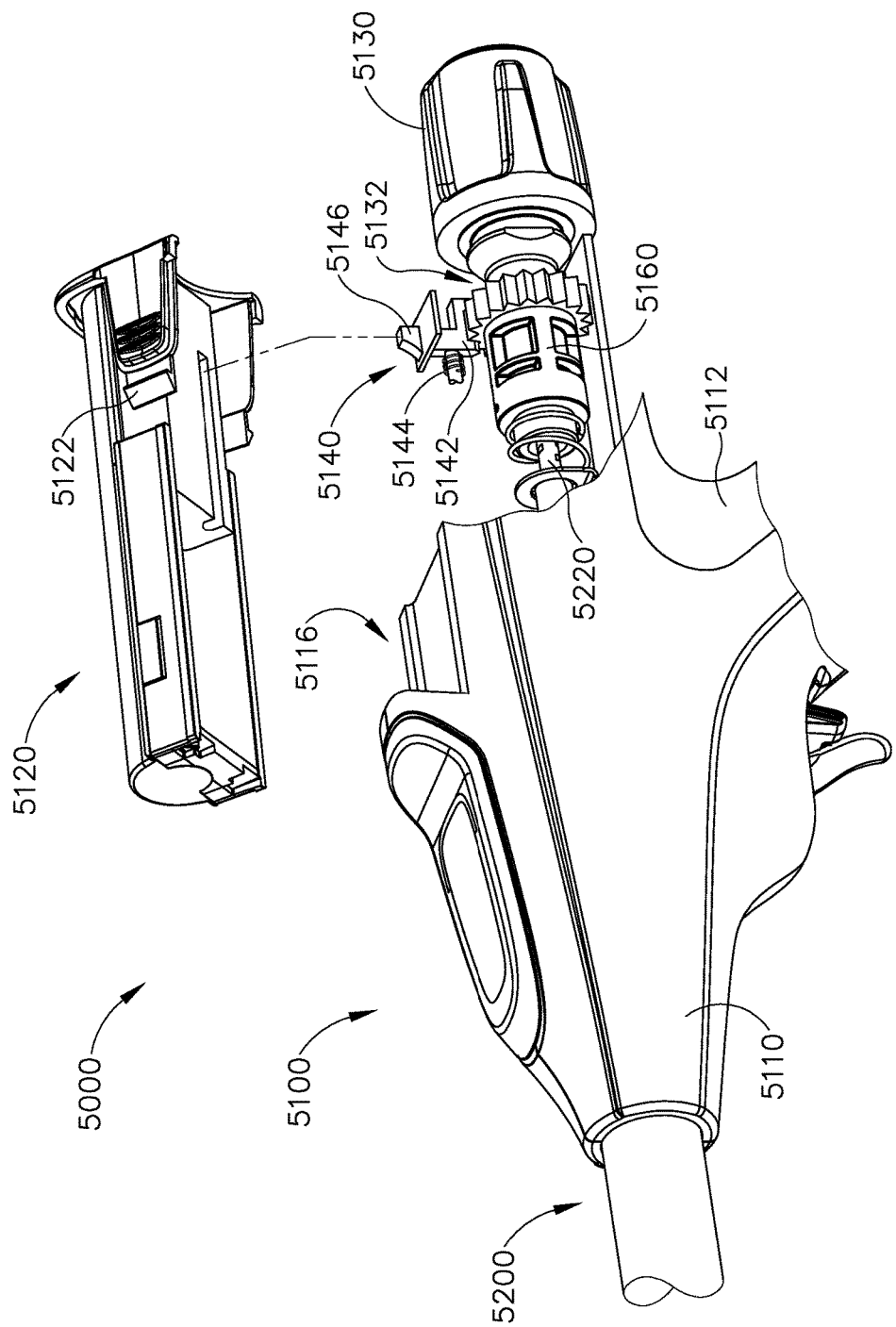
Figure 83A:
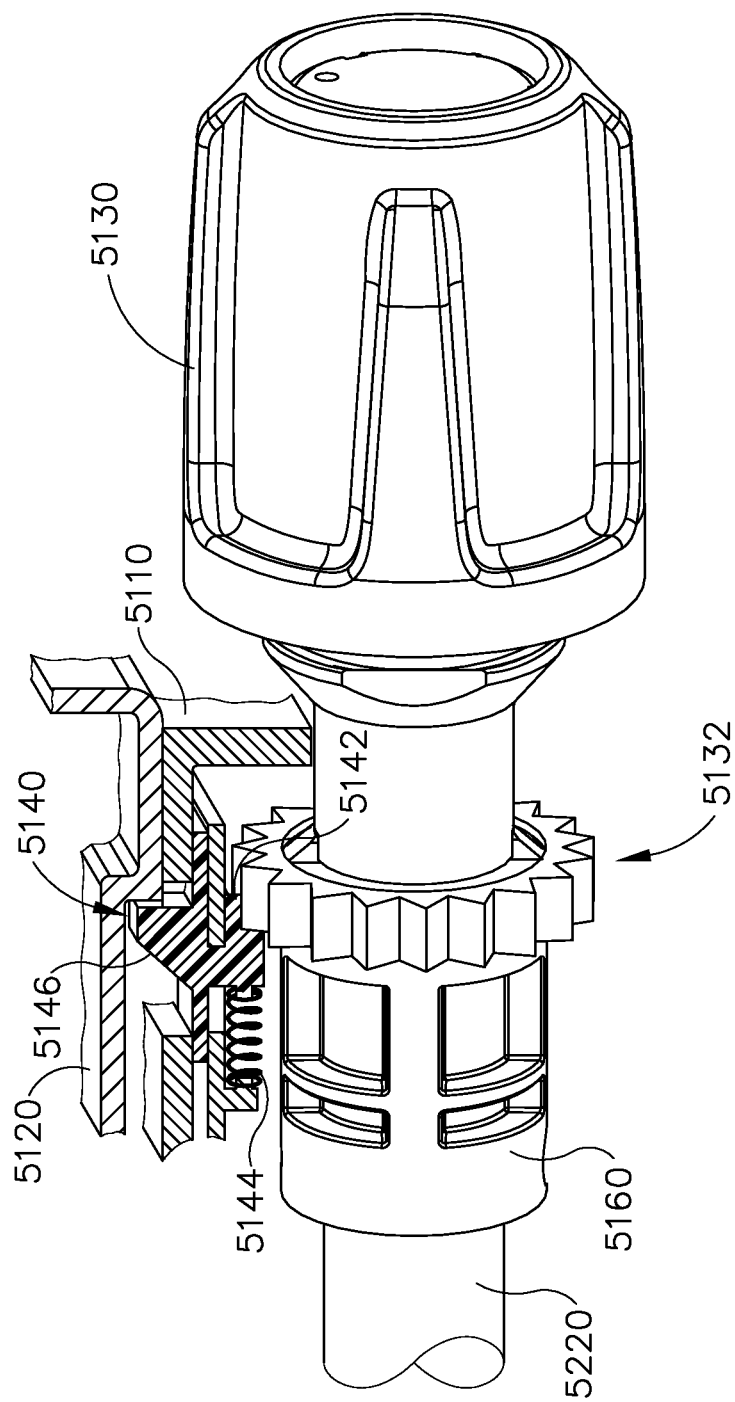
Figure 83B:
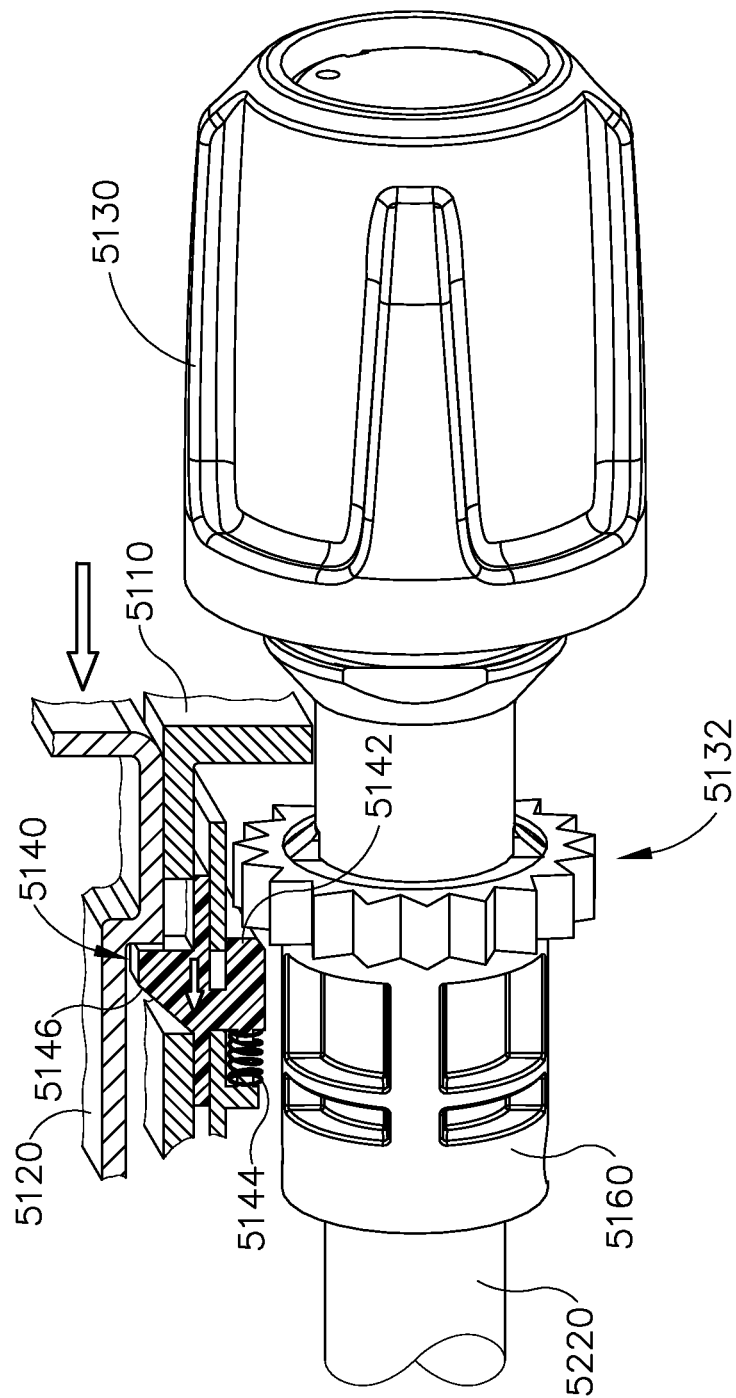

FIGS. 82-83B show an exemplary surgical circular stapling instrument (5000) that is configured to operate substantially similar to instrument (10) discussed above except for any differences discussed below. For instance, instrument (5000) may be used to provide an end-to-end anastomosis between two sections of an anatomical lumen such as a portion of a patient's digestive tract. Instrument (5000) of this example comprises a handle assembly (5100), a shaft assembly (5200), a stapling head assembly (not shown), and an anvil (not shown). Instrument (5100) of the present example further includes a battery pack (5120) that is configured to operate substantially similar to battery pack (120) discussed above except for any differences discussed below. Battery pack (5120) is removable from handle assembly (5100). In particular, battery pack (5120) may be inserted into a socket (5116) defined by casing (5110). Once battery pack (5120) is fully inserted in socket (5116), latches (5122) of battery pack (5120) may resiliently engage interior features of casing (5110) to provide a snap fit.

Handle assembly (5100) comprises a casing (5110) defining an obliquely oriented pistol grip (5112). A knob (5130) at the proximal end of handle assembly (5100) is rotatable relative to casing (5110) to provide precise clamping of the tissue between the anvil and the stapling head assembly as discussed above with reference to knob (130) of instrument (10). In particular, a nut (5160) is secured to the distal end of knob (5130). In the present example, nut (5160) is fixedly secured to the distal end of knob (5130) such that nut (5160) will rotate unitarily with knob (5130). Nut (5160) and knob (5130) are configured to cooperate with a trocar actuation rod (5220) to thereby translate trocar actuation rod (5220) longitudinally relative to casing (5110) in response to rotation of nut (5160) and knob (5130) relative to casing (5110). As discussed above with reference to instrument (10), a trocar (not shown) will translate longitudinally relative to shaft assembly (5200) in response to translation of trocar actuation rod (5220) relative to outer shaft assembly (5200) and casing (5110).

Nut (5160) of this example comprises a plurality of outwardly extending teeth (5132) that are disposed in an array that is angularly spaced about an exterior circumference of nut (5160). As will be discussed in more detail below, teeth (5132) of nut (5160) are configured to engage a lockout sled (5140) of handle assembly (5100) to thereby prevent rotation of knob (5130) in the absence of battery pack (5120) or when battery pack (5120) is not properly secured in socket (5116) of handle assembly (5100). Lockout sled (5140) is slidably secured to an interior of casing (5110) within handle assembly (5100) such that lockout sled (5140) is translatable between a proximal position (FIG. 83A) and a distal position (FIG. 83B). A spring (5144) biases lockout sled (5140) toward the proximal position.

As shown in FIG. 83A, in the absence of battery pack (5120) or when battery pack (5120) is not properly secured in socket (5116), with lockout sled (5140) in the proximal position, a lower flange (5142) of lockout sled (5140) engages teeth (5132) of nut (5160) to thereby prevent rotation of knob (5130).

As shown in FIG. 83B, when battery pack (5120) is properly secured in socket (5116), contact between battery pack (5120) and an upper flange (5146) lockout sled (5140) drives lockout sled (5140) distally against the bias of spring (5144) into the distal position. In the distal position, lower flange (5142) of lockout sled (5140) disengages teeth (5132) of nut (5160) so as to permit rotation of knob (5130). It should therefore be appreciated that in the absence of battery pack (5120) or when battery pack (5120) is not properly secured in socket (5116) of handle assembly (5100), the trocar cannot be translated longitudinally relative to shaft assembly (5200); and when battery pack (5120) is properly secured in socket (5116), the trocar can be translated longitudinally relative to shaft assembly (5200).

B. Exemplary Pinhole Indicator

FIGS. 84-85B show an exemplary trocar (5200) and anvil (5240) that are configured to operate substantially similar to trocar (330) and anvil (400) discussed above respectively except for any differences discussed below. For instance, trocar (5200) is operable to translate distally and proximally relative to tubular casing (310) in response to rotation of knob (130) as discussed above. As will be discussed in more detail below, anvil (5240) is configured to be attached to trocar (5200) such that translation of trocar (5200) relative to tubular casing (310) is communicated directly to anvil (5240) as described above with reference to FIGS. 12A-12C.

Trocar (5200) comprises a shaft (5202) and a head (5204). Head (5204) includes a pointed tip (5206) and an inwardly extending proximal surface (5208). Shaft (5202) thus provides a reduced outer diameter just proximal to head (5204), with surface (5208) providing a transition between that reduced outer diameter of shaft (5202) and the outer diameter of head (5204). While tip (5206) is pointed in the present example, tip (5206) is not sharp. Tip (5206) will thus not easily cause trauma to tissue due to inadvertent contact with tissue. Anvil (5240) of the present example comprises a head (5242) and a shank (5244). Head (5242) includes a proximal surface (not shown) that defines a plurality of staple forming pockets (not shown). Shank (5244) defines a bore (5246). Head (5204) and the distal portion of shaft (5202) are configured for insertion in bore (5246) of anvil (5240). Anvil (5240) is configured to be secured to trocar (5200) in a snap-fit manner when anvil (5240) is fully seated on trocar (5200) as discussed above with reference to instrument (10). In addition to or in lieu of the foregoing, anvil (5240) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein.

Still other suitable configurations will be apparent to one of ordinary skill in the art in view of the teachings herein.

Anvil (5240) includes a pinhole (5248) formed in a sidewall of shank (5244). Pinhole (5248) extends completely through the sidewall of shank (5244) thus providing an operator with visual access through the sidewall of shank (5244) and into bore (5246) of shank (5244). Trocar (5200) includes a marker region (5210) formed in or disposed about an exterior surface of shaft (5202) of trocar (5200). Marker region (5210) is visually distinguishable from the remainder of shaft (5202). For instance, marker region (5210) may comprise a painted region, a decal, and/or a colored band disposed about shaft (5202).

As shown in FIG. 85A, when anvil (5240) is not fully seated on trocar (5200), marker region (5210) is only partially visible via pinhole (5248). In other words, when anvil (5240) is not fully seated on trocar (5200), marker region (5210) extends only partially across the diameter pinhole (5248).

As shown in FIG. 85B, when anvil (5240) is fully seated on trocar (5200), marker region (5210) is completely visible via pinhole (5248). In other words, when anvil (5240) is fully seated on trocar (5200), marker region (5210) extends completely across the diameter pinhole (5248). Thus, it should be understood that pinhole (5248) and marker region (5210) provide an operator with an indication of whether anvil (5240) is fully seated on trocar (5200). It should also be understood that the operator may visualize marker region (5210) through pinhole (5248) directly, endoscopically, or in any other suitable fashion.

C. Exemplary Indicator Latch Members

FIGS. 86A and 86B show an exemplary anvil (5300) that is configured to operate substantially similar to anvils (400, 5240) discussed above except for any differences discussed below. For instance, anvil (5300) is configured to be attached to trocars (330, 5200) discussed above such that translation of trocars (330, 5200) relative to tubular casing (310) is communicated directly to anvil (5300) as described above with reference to FIGS. 12A-12C.

Anvil (5300) of the present example comprises a head (5310) and a shank (5320). Head (5310) includes a proximal surface (5312) that defines a plurality of staple forming pockets (5314). Staple forming pockets (5314) are arranged in two concentric annular arrays. In some other versions, staple forming pockets (5314) are arranged in three or more concentric annular arrays. Staple forming pockets (5314) are configured to deform staples as the staples are driven into staple forming pockets (5314). For instance, each staple forming pocket (5314) may deform a generally "U" shaped staple into a "B" shape as is known in the art.

Shank (5320) defines a bore (5322) and includes a pair of pivoting latch members (5330) positioned in bore (5322). Latch members (5330) are configured to operate substantially similar to latch members (430) discussed above except for any differences discussed below. Latch members (5330) are positioned within a pair of lateral openings (5324), which are formed through the sidewall of shank (5320). Lateral openings (5324) provide clearance for latch members (5330) to deflect radially outwardly from a longitudinal axis defined by shank (5320) such that latch members (5330) may be passed over head (334) of trocar (330). However, latch members (5330) are configured to resiliently bias distal ends (5334) and latch shelves (not shown) of latch members (5330) radially inwardly toward the longitudinal axis defined by shank (5320). Latch members (5330) thus act as retaining clips. This allows anvil (5300) to be removably secured to a trocars (330, 5240) of stapling head assembly (300). For instance, as discussed above with reference to anvil (400), trocar (330) is configured for insertion in bore (5322) of anvil (5320). Proximal surface (338) of trocar (330) and the latch shelves of latch members (5330) have complementary positions and configurations such that when latch members (5330) deflect radially inwardly, the latch shelves engage proximal surface (338) when shank (5320) of anvil (5300) is fully seated on trocar (330). Anvil (5300) is thus secured to trocar (330) through a snap fit due to latch members (5330).

Distal end (5334) of each latch member (5330) includes a marker region (5340). Marker regions (5340) are visually distinguishable from the remainder of latch members (5330) and shank (5320). For instance, marker regions (5340) may comprise a painted region, a decal, and/or a colored band secured to distal ends (5334). As shown in FIG. 86A, when latch members (5330) are deflected outwardly, marker regions (5340) are exposed relative to shank (5320) and are thus visible to an operator so as to indicate to the operator that anvil (5300) is not fully seated on trocar (330). When anvil (5300) fully seated on trocar (330), latch members (5330) deflect inwardly as discussed above such that marker regions (5340) are obscured by shank (5320) and thus indicate to the operator that anvil (5300) is fully seated on trocar (330). It should be understood that the operator may inspect for the visibility of marker regions (5340) through direct vizualization, endoscopically, or in any other suitable fashion.

In addition to or in lieu of the foregoing, anvil (5300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

D. Exemplary Anvil with Integral Circuit

Figure 28:
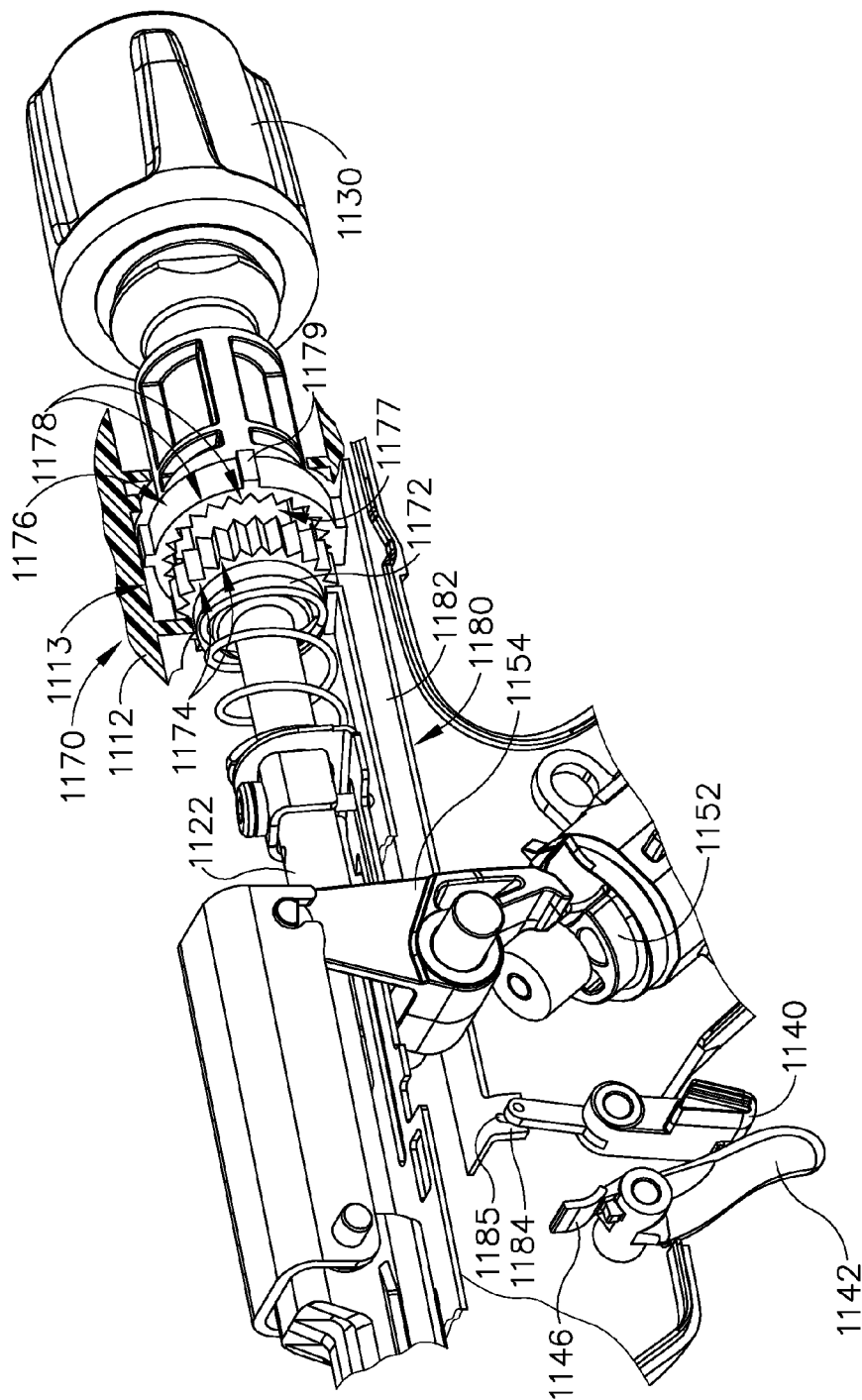
FIG. 28 depicts a detailed perspective view of an anvil actuation assembly of the handle assembly of FIG. 27.

FIGS. 87 and 28 depict an exemplary anvil (5350) that is configured to operate substantially similar to anvils (400, 5240, 5300) discussed above except for any differences discussed below. For instance, anvil (5350) is configured to be attached to trocars (330, 5200) discussed above such that translation of trocars (330, 5200) relative to tubular casing (310) is communicated directly to anvil (5350) as described above with reference to FIGS. 12A-12C.

Anvil (5350) of the present example comprises a head (5360) and a shank (5370). Shank (5370) defines a bore (5372). Anvil (5350) further includes a pair of electrical contact surfaces (5380, 5382) positioned within bore (5372) of shank (5370). Contact surfaces (5380, 5382) are in electrical communication with a transmitter (5384) via wires (5386). As will be discussed in more detail below, transmitter (5384) is configured to emit a signal operable to actuate audible, tactile, and/or visible feedback to an operator indicating proper attachment of anvil (5350) to trocar (330). A first electrical contact surface (5380) is positioned for contact with an exterior surface of shaft (332) of trocar (330). A second electrical contact surface (5382) is positioned for contact with surface (338) of trocar (330). In the present example, at least the exterior surface of trocar (330) comprises an electrically conductive material.

When anvil (5350) is not attached to trocar (330), an electrical circuit defined by contact surfaces (5380, 5382) and wires (5386) is in an open state as shown in FIG. 87. As shown in FIG. 88, with anvil (5350) properly attached to trocar (330), contact between the exterior surface of shaft (332) of trocar (330) and electrical contact surface (5380);

and between surface (338) of trocar (330) and electrical contact surface (5382) completes and closes the electrical circuit defined by contact surfaces (5380, 5382) and wires (5386) so as to actuate transmitter (5384). Actuation of transmitter (5384) causes a signal (5390) to be emitted from transmitter (5384). Signal (5390) is configured to actuate an indicator (not shown) so as to cause the indicator to emit audible, tactile, and/or visible feedback to an operator so as to indicate proper attachment of anvil (5350) to trocar (330). In some instances, the indicator is positioned within handle assembly (110). In some other instances, the indicator is positioned external to instrument (10). In still other instances, the indicator is positioned within anvil (5350). For instance, an LED light on anvil (5350) may serve as the indicator, such that the light illuminates in response to closure of the circuit defined by trocar (330), contact surfaces (5380, 5382), and wires (5386). Other suitable forms that the indicator may take, and other suitable locations for the indicator, will be apparent to those of ordinary skill in the art in view of the teachings herein.

E. Exemplary Snap-Fit Anvil and Trocar

FIGS. 89-90B show an exemplary trocar (5400) and anvil (5440) that are configured to operate substantially similar to trocars (330, 5200) and anvils (400, 5240, 5300, 5350) discussed above respectively except for any differences discussed below. For instance, trocar (5400) is operable to translate distally and proximally relative to tubular casing (310) in response to rotation of knob (130) as discussed above. As will be discussed in more detail below, anvil (5440) is configured to be attached to trocar (5400) such that translation of trocar (5400) relative to tubular casing (310) is communicated directly to anvil (5440) as described above with reference to FIGS. 12A-12C.

Trocar (5400) comprises a shaft (5402) and a head (5404). Head (5404) includes a pointed tip (5406). While tip (5406) is pointed in the present example, tip (5406) is not sharp. Tip (5406) will thus not easily cause trauma to tissue due to inadvertent contact with tissue. Head (5404) is generally conically shaped. A proximal end of head (5404) is flared outwardly so as to present a conical lip (5410) which is raised relative to the remainder of head (5404).

Anvil (5440) of the present example comprises a head (5442) and a shank (5444). Shank (5444) defines a bore (5446). Bore (5446) defines a distal chamber (5447) configured to receive head (5404) of trocar (5400) so as to selectively secure anvil (5440) with trocar (5400). A proximal end of chamber (5447) includes a raised conical lip (5448) which defines a proximal opening (5449). As best seen in FIG. 90A, raised conical lip (5448) of bore (5446) and raised conical lip (5410) of head (5404) present mating angular surfaces. A diameter of raised conical lip (5410) of head (5404) is greater than a diameter of conical lip (5448) of chamber (5447) such that head (5404) must be forced into chamber (5447). In particular, as trocar (5404) is forced distally relative to anvil (5440), the mating angular surfaces presented by raised conical lips (5410, 5448) cause compression and/or deflection of one or both raised conical lips (5410, 5448) such that head (5404) of trocar (5400) may be passed into chamber (5447). Once head (5404) is positioned within chamber (5447), raised conical lips (5410, 5448) return to their original shape such that head (5404) is locked within chamber (5447) as shown in FIG. 90B.

In addition to or in lieu of the foregoing, anvil (5440) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

F. Exemplary Anvil Proximity Sensor

FIG. 91 depicts an exemplary anvil (5500) that is configured to operate substantially similar to anvils (400, 5240, 5300, 5440) discussed above except for any differences discussed below. For instance, anvil (5500) is configured to be attached to trocars (330, 5200, 5400) discussed above such that translation of trocars (330, 5200, 5400) relative to tubular casing (310) is communicated directly to anvil (5500) as described above with reference to FIGS. 12A-12C.

Anvil (5500) of the present example comprises a head (5510) and a shank (5520). Head (5510) includes a proximal surface (5512). Proximal surface (5512) terminates at an inner edge (5516), which defines an outer boundary of an annular recess (5518) surrounding shank (5520). As discussed above, knob (130) may be used to adjust the gap distance (d) between opposing surfaces (5512, 322) of anvil (5500) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed as discussed above. This may result in leakage at the anastomosis site, and in some cases may ultimately lead to the separation of the anatomical lumen sections that are joined at the anastomosis site. If the gap distance (d) is too small, the internal structure of the tissue compressed between surfaces (5512, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Shank (5520) includes a magnet (5530) that is secured within an exterior surface of shank (5520) such that translation of anvil (5500) causes concurrent translation of magnet (5530). Magnet (5530) of the present example is secured within a portion of shank (5520) located within annular recess (5518) Inner core member (312) of stapling head assembly (300) includes a Hall Effect sensor (5532). Hall Effect sensor (5532) is configured to sense a magnetic field emitted from magnet (5530). In particular, as anvil (5500) translates distally and proximally relative to tubular casing (310) of stapling head assembly (300), an output voltage of Hall Effect sensor (5532) varies in response to translation of magnet (5530) toward and away from Hall Effect sensor (5532).

Hall Effect sensor (5532) is in electrical communication with a control circuit (not shown) that is configured to control firing of stapling head assembly (300). When anvil (5500) is appropriately positioned relative to stapling head assembly (300) (i.e., an appropriate gap distance (d) exists between opposing surfaces (322, 5512)), a predetermined voltage, or range of voltages, is communicated from Hall Effect sensor (5532) to the control unit so as to indicate to the control unit that anvil (5500) is appropriately positioned. In response, the control circuit permits firing of stapling head assembly (300). Otherwise, when anvil (5500) is not appropriately positioned relative to stapling head assembly (300), a predetermined voltage, or range of voltages, is communicated from Hall Effect sensor (5532) to the control circuit so as to indicate to the control unit that anvil (5500) is not appropriately positioned. In response, the control unit prohibits firing of stapling head assembly (300).

In addition to or as an alternative to selectively enabling/disabling firing of stapling head assembly (300) based on signals from Hall Effect sensor (5532), the control circuit and/or some other circuit may be configured to provide some form of audible, tactile, and/or visible feedback to the operator, with the feedback being indicative of whether the gap distance (d) is within an appropriate range. For instance, the feedback may be provided once the gap distance (d) reaches an appropriate range. Alternatively, the feedback may be provided during the entire time that the position of anvil (5500) is being adjusted, with the feedback changing based on whether the gap distance (d) is within an appropriate range. The feedback may be provided in any of the various forms described herein. Other suitable ways in which feedback may be provided based on the gap distance (d) will be apparent to those of ordinary skill in the art in view of the teachings herein.

G. Exemplary Force Limiting Knob

FIGS. 92A and 92B depict an exemplary knob (5550) that is configured to operate substantially similar to knob (130) discussed above except for any difference discussed below. For instance, knob (5550) may be positioned at a proximal end of handle assembly (100) in place of knob (130), and may be rotated relative to casing (110) to provide precise clamping of the tissue between anvil (400) and the stapling head assembly (300) as discussed above with reference to knob (130) of instrument (10).

As discussed above with reference to knob (130), knob (5550) may be used to adjust the gap distance (d) between opposing surfaces (312, 322) of anvil (400) and stapling head assembly (300). Limiting a compressive force applied to the tissue compressed between surfaces (312, 322) may be critical to the success of an anastomosis. For instance, if the compressive force is too great, the internal structure of the tissue compressed between surfaces (312, 322) may be damaged to the point where the structural integrity of the tissue is compromised. This may prevent the tissue from adequately holding the formed staples, which again may result in leakage or other failure of the anastomosis.

Knob (5550) protrudes proximally from casing (110) of handle assembly (100) and is rotatable relative to casing (110). As discussed above with reference to knob (130), knob (5550) is configured to cooperate with nut (160) and trocar actuation rod (220) to thereby translate trocar actuation rod (220) longitudinally relative to casing (110) in response to rotation of nut (160) and knob (5550) relative to casing (110). Also as discussed above, trocar (330) will translate longitudinally relative to outer sheath (210) in response to translation of trocar actuation rod (220) relative to outer sheath (210) and casing (110).

Unlike knob (130) described above, knob (5550) of this example is coupled with nut (160) via a clutch assembly (5560). Clutch assembly (5560) includes a gear (5562). Gear (5562) is slidably disposed about a shaft (5566), which is positioned within an interior of knob (5550) such that gear (5562) is operable to translate along the length of shaft (5566). Gear (5562) is, however, secured to shaft (5566) (e.g., via slot-and-key) such that gear (5562) is unable to rotate about shaft (5566) and such that rotation of knob (5550) is causes rotation of gear (5562). As shown in FIG. 92A, gear (5562) is resiliently biased via a spring (5568) to engage teeth (5564) formed in a proximal end of nut (160) such that rotation of gear (5562) is configured to cause concurrent rotation of nut (160).

As discussed above, knob (5550) may be used to adjust the gap distance (d) between opposing surfaces (312, 322) of anvil (400) and stapling head assembly (300). As knob (5550) is rotated to adjust the gap distance (d) so as to compress tissue between surfaces (312, 322), a compressive force applied to the tissue increases. As this compressive force increases, the torque required to rotate knob (5550) increases. As shown in FIG. 92B, once this torque reaches a predetermined level, gear (5562) will disengage teeth (5564) of nut (160) by overcoming the bias of spring (5568). When gear (5562) disengages teeth (5564), further rotation of gear (5562) will cause gear (5562) to slip relative to nut (160) such that further rotation of knob (5550) is not communicated to nut (160). The slipping of gear (5562) relative to nut (160) in response to the torque exceeding a certain level will prevent further compression of the tissue between surfaces (312, 322). In other words, the torque threshold provided by slipping of gear (5562) will restrict the amount of compression that may be achieved between surfaces (312, 322).

H. Exemplary Self-Draining Battery Pack

FIGS. 93-109 depict instrument (10) including an exemplary battery pack (5600) that is configured to operate substantially similar to battery pack (120) discussed above except for any difference discussed below. For instance, battery pack (5600) is operable to provide electrical power to a motor (160) in pistol grip (112) as discussed above with reference to battery pack (120). Battery pack (5600) is removable from handle assembly (100). In particular, as shown in FIGS. 93-94 and 97A-97B, battery pack (5600) may be inserted into socket (116) defined by casing (110). Once battery pack (5600) is fully inserted in socket (116), latches (5602) of battery pack (5600) may resiliently engage interior features of casing (110) to provide a snap fit. To remove battery pack (5600), the operator may press latches (5602) inwardly to disengage latches (5602) from the interior features of casing (110) then pull battery pack (5600) proximally from socket (116). It should be understood that battery pack (5600) and handle assembly (100) may have complementary electrical contacts, pins and sockets, and/or other features that provide paths for electrical communication from battery pack (5600) to electrically powered components in handle assembly (100) when battery pack (5600) is inserted in socket (116).

As best seen in FIGS. 95 and 36, battery pack (5600) includes an upper housing (5610) and a lower housing (5620). Upper housing (5610) and lower housing (5620) are configured to be secured to one another in a snap-fit manner so as to provide a rigid casing that encloses a plurality of batteries (5630). Lower housing (5620) includes a positive battery contact (5622) configured to connect with a positive terminal of batteries (5630) and a negative battery contact (5624) configured to connect with a negative terminal of batteries (5630). Lower housing (5620) further includes a drain contact (5626). A proximal end of positive battery contact (5622) is biased toward drain contact (5626). As will be discussed in more detail below, contact between positive battery contact (5622) and drain contact (5626) is configured to drain batteries (5630) of power. It should be understood that housing (110) of instrument (10) and upper housing (5610) and batteries (5630) of battery pack (5630) have been omitted from FIGS. 98-109 to assist in understanding operation of battery pack (5600).

Lower housing (5620) includes a lockout sled (5628) that is slidably disposed within a channel (5621) formed within lower housing (5620) such that lockout sled (5628) is configured to translate longitudinally within channel (5621)

relative to lower housing (5620). As shown in FIGS. 98-100, in an initial position, lockout sled (5628) positioned within channel (5621) between drain contact (5626) and the proximal end of positive battery contact (5622) so as to prevent contact between drain contact (5626) and positive battery contact (5622).

As shown in FIGS. 101-102, as battery pack (5600) is inserted into socket (116) of housing (110), a flange (111) of housing (110) passes through an opening (5618) formed in a distal end of lower housing (5620) toward channel (5621) of lower housing (5620).

As shown in FIGS. 103-104, as battery pack (5600) is further inserted into socket (116) of housing (110), flange (111) passes further through opening (5618) and into channel (5621) such that a proximal end of flange (111) comes into contact with a distal end of lockout sled (5628).

As shown in FIGS. 105-106, as battery pack (5600) is further inserted into socket (116) of housing (110) to a point where battery pack (5600) is fully seated within socket (116), flange (111) passes further through opening (5618) and into channel (5621) such that flange (111) drives lockout sled (5628) proximally within channel (5621). In this position, lockout sled (5628) is no longer between positive battery contact (5622) and drain contact (5626). However, flange (111) is now positioned between positive battery contact (5622) and drain contact (5626). Thus, it should be understood that as battery pack (5600) is passed into socket (116), lockout sled (5628) and flange (111) cooperate to prevent contact between positive battery contact (5622) and drain contact (5626).

As best seen in FIG. 106, as lockout sled (5628) is driven proximally, a detent (5629) of lockout sled (5628) engages a detent (5619) formed in a sidewall of channel (5621) so as to "lock" lockout sled (5628) in the proximal position. As shown in FIGS. 107-109, as battery pack (5600) is removed, flange (111) is removed from lower housing (5620) such that flange (111) is no longer between positive battery contact (5622) and drain contact (5626). Thus, with lockout sled (5628) in the proximal position, the proximal end of positive battery contact (5622) contacts drain contact (5626) so as to drain batteries (5630) of power. Thus, it should be understood that insertion and removal of battery pack (5600) from housing (110) will ultimately drain batteries (5630). In other words, battery pack (5600) will be drained of power after a single use. Such power drainage will further eliminate potential energy available from battery contacts (5622, 5624) so as to limit the chances of battery pack (5600) igniting combustible materials upon disposal.

In addition, as shown in FIGS. 110-111, battery pack (5600) may include a positive temperature coefficient (PTC) current limiting device (5650). PTC limiting device (5650) may comprise materials that experience an increase in electrical resistance upon an increase in temperature. PTC limiting device (5650) is configured to control current during discharge so as to minimize any temperature rise in battery pack (5600) and/or its components. For instance, PTC limiting device (5650) may be configured to limit the temperature of battery pack (5600) and/or its components to below a flash point of common materials encountered during use or upon disposal. Various suitable materials and configurations that may be used to form PTC limiting device (5650) will be apparent to those of ordinary skill in the art in view of the teachings herein.

I. Exemplary Cycling-Complete Indicator

As discussed above, paddle (806) is configured to actuate a switch button (192) of a short circuit module (190). Short circuit module (190) is configured to prevent motor (160) from further activation when switch button (192) has been actuated. As shown in FIGS. 112A and 112B, paddle (806) may further be configured to actuate a switch (5700). Switch (5700) is operable to actuate an audible, tactile, and/or visible feedback feature (e.g., an LED) (not shown) so as to indicate completion of the firing cycle. Alternatively, switch button (192) may be operable to actuate an audible, tactile, and/or visible feedback feature in addition to actuating short circuit module (190).

J. Exemplary Anvil Position Indicator

FIGS. 113A-113E depict an exemplary gap distance indicator (5800). Indicator (5800) includes an electronic display (e.g., an LED display) that depicts a position of a visual representation of an anvil (5810) at varying longitudinal positions relative to a visual representation of a stapling head assembly (5820). It should therefore be appreciated that indicator (5800) depicts a gap distance (d) between opposing surfaces of anvil (5810) and stapling head assembly (5820). For instance, as shown in FIG. 113A, indicator (5800) depicts anvil (5810) at a distal longitudinal position relative to stapling head assembly (5820) when gap distance (d) is greatest. FIGS. 113B-113D depict anvil (5810) as anvil (5810) is translated progressively proximally toward stapling head assembly (5820) to a proximal longitudinal position as shown in FIG. 113E when gap distance (d) is smallest. It should be appreciated that the depiction of anvil (5810) and stapling head assembly (5820) may correspond to any anvil or shaft assembly described herein. By way of example only, the position of the depiction of anvil (5810) in relation to the depiction of stapling head assembly (5820) is based on signals from Hall Effect sensor (5532) as described above. Other suitable ways in which indicator (5800) may be driven to visually depict the gap distance (d) will be apparent to those of ordinary skill in the art in view of the teachings herein.

In some versions, indicator (5800) comprises an array of LEDs or other illuminating features. A circuit may selectively illuminate those illuminating features to indicate the gap distance (d).

Indicator (5800) further includes an anvil attachment indicator (5830) that is configured to indicate when any of the anvils described above have been appropriately attached to the trocars described above. For instance, in FIG. 113A, indicator (5830) indicates that anvil (5810) is not attached to stapling head assembly (5820); whereas in FIGS. 58B-58E, indicator (5830) indicates that anvil (5810) is appropriately attached to stapling head assembly (5820). By way of example only, the state of indicator (5830) may be based on the presence, absence, or character of a signal (5390) emitted from transmitter (5384) as described above. Other suitable ways in which indicator (5830) may be driven to visually indicate whether the anvil has been appropriately attached to the trocar will be apparent to those of ordinary skill in the art in view of the teachings herein.

In addition to or in lieu of the foregoing, indicator (5800) may provide visual, audible, and/or tactile feedback indicating proper insertion of a battery pack (120, 5120, 5600) into handle assembly (100, 5100). For instance, when battery pack (120, 5120, 5600) is fully inserted into handle assembly (100, 5100), a circuit in handle assembly (100, 5100) may automatically illuminate a backlight in indicator (5800). Other suitable ways in which a feature of handle assembly (100, 5100) may provide feedback indicating proper insertion of a battery pack (120, 5120, 5600) into handle assembly (100, 5100) will be apparent to those of ordinary skill in the art in view of the teachings herein.

In some variations of instrument (10), a circuit may monitor the voltage of battery pack (120) while battery pack (120) is under an electrical load. Such a circuit may further prevent activation of motor (160), and thereby prevent actuation of stapling head assembly (300), if the voltage of battery pack (120) is below a certain predetermined level while battery pack (120) is under an electrical load. In other words, motor (160) and stapling head assembly (300) may be rendered inoperable if battery pack (120) lacks a predetermined minimal voltage under an electrical load. In addition to or as an alternative to rendering motor (160) and stapling head assembly (300) inoperable, the circuit may provide a visual indication of the voltage level of battery pack (120) through indicator (5800) or otherwise.

Similarly, some variations of instrument (10) may include one or more features (e.g., a sensor, etc.) that is/are configured to authenticate battery pack (120). In the event that an operator attempts to couple a non-authentic battery pack (120) with handle assembly (100), instrument (10) may provide visual, audible, and/or tactile feedback indicating that the battery pack (120) is non-authentic. For instance, indicator (5800) may include a feature that provides visual indication that battery pack (120) is non-authentic. In addition or in the alternative, indicator (5800) may include a feature that provides visual indication that battery pack (120) is authentic. Various suitable ways in which a battery pack (120) may be authenticated, as well as various ways in which the instrument (10) may provide an operator with feedback indicating whether battery pack (120) is authentic, will be apparent to those of ordinary skill in the art in view of the teachings herein.

In addition to or in lieu of the foregoing features, indicator (5800) may also be operable to indicate whether stapling head assembly (300) is in a non-actuated state, when safety trigger (140) has been actuated such that stapling head assembly (300) Is ready to fire, when stapling head assembly (300) is engaged in a firing stroke, when stapling head assembly (300) has completed a firing stroke, and/or any other suitable information. Various suitable ways in which circuitry may drive indicator (5800) to provide such feedback in response to such conditions will be apparent to those of ordinary skill in the art in view of the teachings herein. Similarly, other kinds of conditions that may be conveyed through indicator (5800) and variations thereof will be apparent to those of ordinary skill in the art in view of the teachings herein.

X. Exemplary Firing Indication System

In some instances, it may be desirable for an operator to verify complete actuation of stapling head assembly (300). In particular, it may be helpful for an operator to know when staple driver member (350) has driven staples (90) and cutting edge (342) of knife member (340) has successfully sheared off excess tissue so the operator can determine when it is appropriate to drive anvil (400) distally away from stapling head assembly (300), thereby increasing the gap distance (d) to facilitate release of tissue between surfaces (412, 322) before removing instrument (10) from the patient. The following are merely illustrative examples of various ways to indicate when the firing of staple driver member (350) and knife member (340) has been completed. Other variations or appropriate combinations of present examples and/or other variations will be apparent to one having ordinary skill in the art in view of the teachings herein.

A. Microprocessor Firing Indication System

FIG. 114 depicts a block diagram of an exemplary system (6000) that may be readily incorporated into instrument (10) in order to indicate when stapling head assembly (300) has been fully actuated. System (6000) of this example comprises a microprocessor (6002) that is in communication with a power source (6001), a motor (6003), and an indicator (6004). Power source (6001) is configured to provide electrical power to motor (6003) when an operator activates the appropriate firing mechanisms (not shown). By way of example only, motor (6003) may comprise motor (160) described above; and power source (6001) may comprise battery pack (120) described above.

Indicator (6004) may be located anywhere on, within, or near the instrument in order to appropriately communicate information to an operator. For example, indicator (6004) could comprise an auditory feedback feature (capable of generating a variety of sounds when activated) that is located inside or outside surgical instrument. Additionally, indicator (6004) may include an LED light located within a translucent portion of the body of instrument, capable of emitting light outside surgical stapler to communicate information to operator. Indicator (6004) could also be positioned outside the body of instrument in such a manner to communicate appropriate information to operator. Indicator (6004) could also comprise an LCD screen attached to the body of instrument or separated from instrument. In some instances, indicator (6004) is viewable through window (114) or is otherwise placed at the location of window (114). Various suitable forms that indicator (6004) may take, as well as various places where indicator (6004) may be located, will be apparent to those of ordinary skill in the art in view of the teachings herein.

Microprocessor (6002) is electrically coupled to both power source (6001) and motor (6003). Therefore, microprocessor (6002) is capable of measuring the electrical current supplied from power source (6001) to motor (6003). Of course, any other means of measuring current could be utilized instead of microprocessor (6002). As best shown in FIG. 115, current supplied from power source (6001) to motor (6003) increases once appropriate firing mechanisms have been activated. Once motor has completed its course of travel, as exemplified in FIG. 20D, power source (6001) is no longer driving staple driver member (350) or knife member (340). This is shown approximately around the point of cut shown on FIG. 115. Because power source (6001) is no longer driving staple driver member (350) or knife member (340), the current level measured by microprocessor (6002) drops as compared to when power source (6001) was powering motor (6003).

Once microprocessor (6002) detects a drop in current associated with completion of actuation of stapling head assembly (300), microprocessor (6002) then activates indicator (6004). Indicator (6004) thus signals to an operator that the current level of power provided from power source (6001) to motor (6003) has dropped, signifying a completion of actuation of stapling head assembly (300). It should be noted that while microprocessor (6002) measures current supplied from power source (6001) to motor (6003), microprocessor (6002) does not have to strictly measure current or be connected to both power source (6001) and motor (6003) in order to determine completion of the firing process. For example, microprocessor (6002) could be in communication with only power source (6001) and indicator (6004) and measure the drop in potential of power source (6001) caused by activation of motor (6003). Other suitable configurations and techniques that may be used to measure activation and deactivation of motor (6003) will be apparent to a person having ordinary skill in the art in view of the teachings herein.

B. Physical Firing Indication System

FIGS. 116-117 depict various features that may be utilized to verify complete actuation of stapling head assembly (300). These features may be readily incorporated into instrument (10). Instead of measuring electrical properties between supply source (6001) and motor (6003), the features depicted in FIGS. 116-117 measure the physical positioning of components that actuate stapling head assembly (300). It should be understood that the physical location of components that actuate stapling head assembly (300) may indicate whether stapling head assembly (300) is in a fired state or an un-fired state.

FIG. 116 shows a casing (6107), an indication light (6101), a transparent indicator window (6105), and an indicator marking (6102) located on drive bracket (6103). It should be noted that casing (6107) is substantially similar to casing (110) mentioned above. Additionally, drive bracket (6103) is substantially similar to drive bracket (250) mentioned above. Transparent indicator window (6105) and indicator marking (6102) are used in tandem to visually display the physical location of drive bracket (6103). Transparent indicator window (6105) and casing (6107) include fixed markings that provide reference points to compare the location of indicator marking (6102) against in order to determine the position of drive bracket (6103). It should be understood that, based on the location of indicator marking (6102) relative to the predetermined markings on transparent indicator window (6105) and casing (6107), an operator may determine if stapling head assembly (300) has completed actuation.

For instance, when stapling head assembly (300) is in an unfired state, drive bracket (6103) will be in a proximal position, such that indicator marking (6102) will also be in a proximal position. In the proximal position, indicator marking (6102) will be viewable though transparent indicator window (6105) adjacent to an "X" or some other indication, thereby indicating to the operator that stapling head assembly (300) is in an unfired state. When stapling head assembly (300) is in a fired state or has been fired, drive bracket (6103) will be advanced to a distal position, such that indicator marking (6102) will also be advanced to a distal position. In the distal position, indicator marking (6102) will be viewable through transparent indicator window (6105) adjacent to a check mark or some other indication, therefore indicating to the operator that stapling head assembly (300) has been fired.

Indicator light (6101) works separately and independently from indicator marking (6102) and transparent indicator window (6105). It should therefore be understood that an instrument may include indicator light (6101) yet lack indicator marking (6102) and transparent indicator window (6105). Similarly, an instrument may include indicator marking (6102) and transparent indicator window (6105) yet lack indicator light (6101). As shown in FIG. 117, in the present example indicator light (6101) is in communication with a switch (6106) via wiring (6107). Indicator light (6101) and switch (6106) are both secured to casing (6107). Switch (6106) is operable to pivot based on contact with a protrusion (6104). Pivoting of switch (6106) will activate indicator light (6101), such that indicator light (6101) will illuminate when protrusion (6104) actuates switch (6106). Indicator light (6101) may be configured to illuminate at different colors based on the angular direction that switch (6106) is pivoted, or for any other reason that would be apparent to a personal having ordinary skill in the art in view of the teachings herein.

Protrusion (6104) is fixed to drive bracket (6103). Protrusion (6104) extends from drive bracket (6103) at a location such that protrusion (6104) will actuate switch (6106) based on the firing status of stapling head assembly (300). For instance, when stapling head assembly (300) is in an unfired state, drive bracket (6103) will be in a proximal position. Therefore, protrusion (6104) will also be in a proximal position such that protrusion (6104) is spaced away from switch (6106). Because protrusion (6104) has yet to rotate switch (6106) in any angular direction, indicator light (6101) remains turned off (i.e., non-illuminated), thereby indicating to an operator that stapling head assembly (300) is in an unfired state. When stapling head assembly (300) is in a fired state or has been fired, drive bracket (6103) will be moved to a distal position, such that protrusion (6104) will also be moved to a distal position. As protrusion (6104) travels from a proximal position to a distal position, protrusion (6104) will rotate switch (6106) in a first angular direction. Because protrusion (6104) has rotated switch in a first angular direction, indicator light (6101) illuminates at a first color of light, thereby indicating to the operator that stapling head assembly (300) has been fired.

Additionally, protrusion (6104) may be configured to actuate switch (6106) a second time when drive bracket (6103) returns to the proximal position after stapling head assembly (300) has stapled and severed tissue. If protrusion (6104) is positioned on drive bracket (6103) in this manner, protrusion will (6104) translate from a distal position back to a proximal position, therefore rotating switch (6106) in a second angular direction that is opposite to the direction in which switch (6106) rotates during distal translation of drive bracket (6103). Because protrusion (6104) has rotated switch in a second angular direction, indicator light (6101) may illuminate at a second color of light, thereby indicating to the operator that the full stroke for stapling head assembly (300) has been completed. In other words, protrusion (6104) may rotate switch (6106) in a first angular direction to indicate when stapling and severing tissue occurs, then protrusion (6104) may rotate switch (6106) in a second angular direction to indicate when stapling head assembly (300) has completed its entire course of travel.

For exemplary purposes, switch (6106) may be configured to only light up only when protrusion (6104) has rotated switch (6106) in either a first angular direction or a second angular direction. Switch (6106) may be capable of only lighting up indicator light (6101) with one color, but blinking when rotating in a first angular direction and remaining lit when rotating in a second-opposite angular direction. Indicator light (6101) might use other forms of indicating, such as auditory rather than visual. Other suitable variations will be apparent to one having ordinary skill in the art in view of the teachings herein.

XI. Exemplary Anvil Position Indicators

As mentioned above, after the operator has actuated stapling head assembly (300) as shown in FIG. 21D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). In some instances, it may be desirable for an operator to know when knob (130) has been sufficiently rotated to have driven anvil (400) far enough away from stapling head assembly (300) in order to increase an appropriate gap distance (d) to facilitate release of tissue between surfaces (412, 322). The following are merely illustrative examples of various ways to indicate when anvil (400) and stapling head assembly (300) have a sufficient gap distance (d) to facilitate release of tissue between surfaces (412, 322) of anvil (400) and stapling head assembly (300). Other variations or appropriate combinations of present examples and/or other variations will be apparent to one having ordinary skill in the art in view of the teachings herein.

A. Electric Contact Switch Indicator

FIGS. 118-120 depict a switch system (6200) that is operable to indicate a sufficient gap distance (d) to facilitate proper release of stapled tissue between surface (412, 322) of anvil (400) and stapling head assembly (300). Switch system (6200) may be readily incorporated into instrument (10). Switch system (6200) comprises a trocar actuation rod (6201), a bracket (6202) coupled with trocar actuation rod (6201), a switch (6205) fixed to casing (6206), a counter (6207) and an indicator (6208). Trocar actuation rod (6201) is substantially similar to trocar actuation rod (220) mentioned above. Therefore, it should therefore be understood that trocar (330) and anvil (400) will translate longitudinally relative to outer sheath (210) in response to translation of trocar actuation rod (6201) relative to outer sheath (210). Bracket (6202) is substantially similar to bracket (500) mentioned above. However, bracket (6202) of this example further comprises a linear array of markers (6203) that are arranged in a longitudinally extending array along a path that is parallel with the longitudinal direction defined by trocar actuation rod (6201). Bracket (6202) is configured and positioned to move longitudinally in response to longitudinal movement of trocar actuation rod (6201).

Adjacent markers (6203) of the linear array of markers (6203) are positioned equidistantly apart. Markers (6203) are positioned along bracket (6202) in order to compress and release switch (6205) while trocar actuation rod (6201) distally actuates trocar (330) away from stapling head assembly (300) to create a sufficient gap distance (d) to release tissue. In other words, markers (6203) are driven distally with bracket (6202) and trocar actuation rod (6201), markers (6203) successively engage fixed switch (6205). In some versions, markers (6203) physically press against switch (6205) and thereby actuate switch (6205) through direct contact. In some other versions, switch (6205) comprises a proximity sensor, an optical sensor, or some other kind of sensor that is responsive to passage of markers (6203) over switch (6205) without necessarily having to come into direct contact with markers (6203).

Switch (6205) is coupled to a counter (6207) (which may be similar to microprocessor (6002)) via wiring (6204). Counter (6207) counts the number of times markers (6203) compress and release switch (6205). Since markers (6203) are spaced apart equidistantly, each compression and release of switch (6205) correlates to a predetermined distance (y) of travel by bracket (6202), trocar actuation rod (6201) and anvil (400). Therefore, once switch (6205) is compressed and released a predetermined number of times, counter (6207) will be able to determine when a sufficient gap distance (d) is created to facilitate release of tissue between surfaces (412, 322).

As shown in FIG. 120, it is important that markers (6203) are distanced far enough from each other to allow switch (6205) to fully compress and release, thereby ensuring each segment of predetermined distance (y) is accounted for by counter (6207). Additionally, while switch (6205) is currently shown as being linearly actuated, switch may also count marks through angular rotation or any other means apparent to one having ordinary skill in the art in view of the teachings herein. Also, linear array of markers (6203) can be substituted for one marker (6203) that is placed to engage switch (6405) precisely at the point where a sufficient gap distance (d) is defined for safe removal of tissue from surfaces (412, 322) of anvil (400) and stapling head assembly (300).

Once counter (6207) determines that switch (6205) has been actuated a sufficient number of times indicating an appropriate gap distance (d), counter (6207) activates indicator (6208). Activation of indicator (6208) may indicate to the operator that a sufficient gap distance (d) has been created to release tissue between surfaces (412, 322). The operator may then remove instrument (10) from the patient. By way of example only, indicator (6208) may provide an audible tone, an automated voice response, a textual indication, a graphical indication, illumination of a light, vibration of pistol grip (112), and/or any other suitable form of audible, visual, and/or tactile feedback. Various suitable forms that indicator (6208) may take will be apparent to one of ordinary skill in the art in view of the teachings herein.

B. Knob Detent Feature Indicator

FIGS. 121-123C depict an exemplary knob detent indicator (6300) that is operable to indicate a sufficient gap distance (d) to facilitate proper release of stapled tissue between surface (412, 322) of anvil (400) and stapling head assembly (300). Knob detent indicator (6300) may be readily incorporated into instrument (10). As best seen in FIG. 121, knob detent indicator (6300) comprises a knob (6304), a handle assembly (6301), and a proximal shaft segment (6305) unitarily coupled to a distal shaft segment (6306). Handle assembly (6301) is substantially similar to handle assembly (100) mentioned above, except that handle assembly (6301) comprises a resilient tab (6302) that is configured to interact with knob (6304) as will be described in greater detail below. Tab (6302) extends proximally from handle assembly (6301) and is oriented along a circumferential path.

Knob (6304) is substantially the same as knob (130) described above, except that knob (6304) further comprises an annular array of detents (6303) configured to interact with resilient tab (6306) of handle assembly (6301) as will be described in greater detail below. Detents (6303) extend distally from knob (6304) and are arranged in an annular array at a radius corresponding to the location of tab (6302) in relation to the longitudinal axis shared by shaft segments (6305, 6306). Proximal shaft segment (6305) and distal shaft segment (6306) unitarily connect knob (6304) with nut (160) so knob (6304) and nut (160) rotate together unitarily as described above.

As mentioned above, the operator rotates knob (6304) after actuating stapling head assembly (300) as shown in FIG. 21D in order to increase gap distance (d). Increasing gap distance (d) helps to facilitate release of the tissue between surfaces (412, 322). Detents (6303) are annularly spaced apart in equal angular segments and are configured to interact with resilient tab (6302) to provide an audible/tactile response in the form of a "click" when each individual detent (6303) passes over resilient tab (6302). Since detents (6303) are spaced apart in equal angular segments, each time a detent (6303) and resilient tab (6302) interact to provide an audible/tactile click, the operator may thus be informed that trocar actuation rod (220) has traveled a predetermined distance in either a proximal direction or a distal direction depending on the direction of rotation. Since the operator can determine how far trocar actuation rod (220) has traveled based on audible/tactile feedback from detents (6303) and resilient tab (6302), the operator can determine when a sufficient gap distance (d) is created to facilitate proper release of stapled tissue by counting a predetermined number of audible/tactile clicks associated with a sufficient gap distance (d). Once the predetermined number of audible/tactile clicks are counted, the operator may confirm that a sufficient gap distance (d) has been created to release tissue between surfaces (412, 322) of anvil (400) and stapling head assembly (300). The operator may thus be informed that anvil (400) has reached a position where it is proper to remove instrument (10) from the patient.

Since distal actuation of trocar actuation rod (220) is more relevant than proximal actuation of trocar actuation rod (220) when creating sufficient gap distance (d) to facilitate proper release of stapled tissue, it may be desirable to create a different level of audible/tactile response based on the direction of knob (6304) rotation. However, creating different audible/tactile responses based off direction of knob (6304) rotation is completely optional.

As shown in FIGS. 122A-C, annular array of detents (6303) is configured to interact with resilient tab (6302) of handle (6301) to make relatively loud or pronounced clicks when rotation of knob (6304) translates trocar actuation rod (220) in a distal direction. Each detent (6303) is defined by a gradual slope (6308) extending obliquely from the distal face of knob (6304) and a steep slope (6307) extending either normal or obliquely from the distal face of knob (6304). As seen in FIG. 122B when knob (6304) is rotated in a first direction, gradual slope (6308) makes contact with resilient tab (6302), displacing resilient tab a predetermined distance based on the apex of detent (6303). As best seen in FIG. 122C, when gradual slope (6308) of detent (6303) is no longer in contact with resilient tab (6302), resilient tab (6302) pops back into a non-deformed state. However, because of the drastic change in slope between gradual slope (6308) and steep slope (6307), resilient tab (6302) is not gradually released into a non-deformed state, so resilient tab (6302) makes a loud clicking noise. As mentioned above, each time resilient tab (6302) makes this noise, the operator may hear and/or feel the click and thereby understand that trocar actuation rod (220) has traveled a predetermined distance.

As shown in FIGS. 123A-C, annular array of detents (6303) is configured to interact with resilient tab (6302) of handle (6301) to make relatively soft or subdued clicks when rotation of knob (6304) translates trocar actuation rod (220) in a proximal direction. FIGS. 123A-B show knob (6304) rotated in a second direction (opposite to the first direction associated with FIGS. 122A-122C) so that steep slope (6307) displaces resilient tab to the predetermined apex of detent (6303). However, as best seen in FIG. 123C, when steep slope (6307) is no longer in contact with resilient tab (6302), resilient tab (6302) is gradually placed back a non-deformed state through contact with gradual slope (6308). The gradual release of resilient tab (6302) makes a 'soft' click as compared to the 'loud' click when knob (6303) is rotated in the first direction. Therefore, an operator will be able to determine which direction trocar actuation rod (220) is translating based on the sound of the click, and will also be able to determine the distance traveled by trocar actuation rod (220) based on the number of clicks that are heard and/or felt.

C. Hall Effect Sensor Indicator

FIGS. 1126A-1126B depict a hall effect sensor indicator system (6400) that is operable to indicate a sufficient gap distance (d) to facilitate proper release of stapled tissue between surfaces (412, 322) of anvil (400) and stapling head assembly (300). Hall Effect sensor indicator system (6400) may be readily incorporated into instrument (10). Hall Effect sensor indicator system (6400) comprises a Hall Effect sensor (6401), a trocar actuation rod (6404), a magnet (6405), and an indicator (6407) attached to knob (6406). Hall Effect sensor (6401) is fixed relative to a casing (6402). Hall Effect sensor (6401) is connected to indicator (6407) via wiring (6403) such that Hall Effect sensor (6401) effectively acts as a switch to activate indicator (6407) as will be described in greater detail below. Knob (6406), casing (6402), and trocar actuation rod (6404) are substantially the same as knob (130), casing (110), and actuation rod (220) mentioned above. Therefore, it should therefore be understood that trocar (330) will translate longitudinally relative to outer sheath (210) in response to translation of trocar actuation rod (6404) relative to outer sheath (210). Additionally, rotation of knob (6406) translates trocar actuation rod (6404). However, magnet (6405) is strategically fixed to trocar actuation rod (6404) such that Hall Effect sensor (6401) is directly adjacent to magnet when trocar actuation rod (6404) is positioned in such a way to define a sufficient gap distance (d) to facilitate proper release of stapled tissue.

Hall Effect sensor (9401) acts as a switch to turn on indicator (6407). Therefore, when Hall Effect sensor (9401) is not adjacent to magnet, the switch is effectively off, leaving indicator (6407) in an inactivated state. However, when Hall Effect sensor (6401) is directly adjacent to magnet, the switch is effectively on, turning indicator (6407) into an activated state. In the present example, indicator (6407) comprises an LED that illuminates when magnet (6405) actuates Hall Effect sensor (9401). Of course, indicator (6407) may take any other suitable form and may provide feedback to the operator in the form of audible, visual, and/or tactile feedback.

As shown in FIG. 1126A, when tissue has been severed and staples administered, an operator may start rotating knob to push trocar actuation rod (6404) in a distal direction to facilitate proper release of stapled tissue. As trocar actuation rod (6404) travels in the distal direction, magnet (6405) travels closer towards Hall Effect sensor (6401). As mentioned above, once magnet (6405) is adjacent to Hall Effect sensor (6401), trocar actuation rod (6404) is positioned in such a way to define a sufficient gap distance (d) to facilitate proper release of stapled tissue. Therefore, Hall Effect sensor (6401) switches indicator (6407) to an activated state, allowing operator to confirm that a sufficient gap distance (d) has been created to release tissue between surfaces (412, 322) of anvil (400) and stapling head assembly (300). The operator may thus be informed that anvil (400) has reached a position where it is proper to remove instrument (10) from the patient.

D. Deployable Audible Mechanism Indicator

FIGS. 125-34C depict an exemplary deployable indicator system (6500) that provides audible feedback to indicate a sufficient gap distance (d) to facilitate proper release of stapled tissue between surfaces (412, 322) of anvil (400) and stapling head assembly (300). Deployable indicator system (6500) may be readily incorporated into instrument (10). Deployable indicator system (6500) comprises a rotary cam feature (6512) that is driven by gearbox (6502), a clicking mechanism (6509) that is slidably coupled to casing (6508), a resilient member (6507) with one end engaging clicking mechanism (6509) and one end fixed to casing (6508), and a bracket (6511). Gearbox (6502) is substantially similar to gearbox (162) in the fact gearbox (6502) is driven by motor (not shown) and drives rotary cam member (6512) to drive stapling head assembly (300).

Rotary cam member (6512) in substantially similar to rotary cam member (700) described above. Rotary cam member (6512) comprises a first cam feature (6503), a second cam feature (6513), and a third cam feature (not shown) substantially similar to the first cam feature (710), second cam feature (720), and a third cam feature (730) of rotary cam member (700), respectively. However, unlike cam member (700) described above, cam member (6512) of the present example comprises an additional fourth cam feature (6505). As best seen in FIGS. 34A-34C, fourth cam feature (6505) slopes in a radial path on top of first cam feature (6503) in such a way that the sloped face of fourth cam feature (6505) engages the proximal end of clicking mechanism (6509) when rotary cam member (6512) is driven by gearbox (6502).

Bracket (6511) is substantially similar to bracket (500) described above. Bracket (6511) is configured and positioned to translate longitudinally in response to movement of trocar actuation rod (6514). Trocar actuation rod (6514) is substantially similar to trocar actuation rod (220) described above. It should therefore be understood that trocar (330) and anvil (400) will translate longitudinally relative to outer sheath (210) in response to translation of trocar actuation rod (6514) relative to outer sheath (210). Unlike bracket (500) described above, bracket (6511) of the present example also comprises a set of teeth (6510) positioned in a longitudinally extending array that is parallel with the longitudinal direction defined by trocar actuation rod (6514). As will be described in greater detail below, teeth (6510) are configured to engage clicking mechanism (6509) when clicking mechanism (6509) is in a deployed position.

As noted above, clicking mechanism (6509) is slidably coupled to casing (6508) in such a way that clicking mechanism (6509) can slide along a linear path. Resilient member (6507) has one end fixed to casing (6508) and another end fixed to clicking mechanism (6509). As best seen in FIG. 34A, resilient member (6507) biases clicking mechanism (6509) toward cam feature (6505) and away from bracket (6511) so that clicking mechanism (6509) is resiliently biased to disengage from linear array of teeth (6510) in a pre-deployed position.

FIGS. 34A-34C depict the above-described components at various stages of operation. FIG. 34A shows deployable indicator system (6500) in a pre-deployed position. In a pre-deployed position, clicking mechanism (6509) is biased in a proximal position away from bracket (6511). Rotary cam member (6512) is positioned in a similar position as that of cam member (700) shown in FIGS. 18A, 19A, and 20A. Therefore, at this stage, knife member (340) and staple driver member (350) are in proximal positions, such that stapling head assembly (300) is in a non-actuated state.

FIG. 34B shows deployable indicator system (6500) in a post-deployed position. In a post-deployed position, rotary cam member (6512) is positioned in a similar position as that of cam member (700) shown in FIG. 20D. Therefore, at this state, knife member (340) and staple driver member (350) have been actuated both distally and proximally, completing the cutting and stapling motion. However, as noted above, fourth cam feature (6505) has been rotated such that the sloped face of fourth cam feature (6505) engages clicking mechanism (6509), thereby displacing clicking mechanism (6509) in a distal direction toward bracket (6511) in opposition to the bias provided by resilient member (6507). It is important to note, at this point, clicking mechanism (6509) is positioned at a level capable of interacting with linear array of teeth (6510) if bracket (6511) is translated longitudinally.

FIG. 34C shows deployable indicator system (6500) in a post-deployed position while bracket (6511) is being actuated via trocar actuation rod (6514) and knob (130). As can be seen, the distal end of clicking mechanism (6509) is in contact with linear array of teeth (6510) such that linear actuation of bracket (6511) drags teeth (6510) over clicking mechanism (6509) to make an audible noise. In other words, clicking mechanism (6509) provides a pawl that ratchets along teeth (6510) as bracket (6511) translates longitudinally. Teeth (6510) may be positioned along bracket (6511) such that any audible clicking between teeth (6510) and deployed clicking mechanism (6509) indicate to the operator that a sufficient gap distance (d) has been created to release tissue between surfaces (412, 322) of anvil (400) and stapling head assembly (300), signaling that removal of instrument is proper. Additionally, teeth (6510) may be positioned along bracket (65111) such that a predetermined number of clicks between teeth (6510) and deployed clicking mechanism (6509) will indicate to the operator that a sufficient gap distance (d) has been created to release tissue between surfaces (412, 322) of anvil (400) and stapling head assembly (300), thereby indicating that that removal of instrument (10) from the patient is proper.

E. Increased Resistance Indicator

FIGS. 127-128C depict an exemplary resistance indicator system (6600) that is operable to indicate a sufficient gap distance (d) to facilitate proper release of stapled tissue between surfaces (412, 322) of anvil (400) and stapling head assembly (300). Resistance system (6600) may be readily incorporated into instrument (10). Resistance indicator system (6600) comprises a trocar actuation rod (6606) and a resistance spring (6612) that is partially fixed to a casing (6601). Trocar actuation rod (6606) is substantially similar to trocar actuation rod (220) described above. It should therefore be understood that trocar (330) and anvil (400) will translate longitudinally relative to outer sheath (210) in response to translation of trocar actuation rod (6606) relative to outer sheath (210). Unlike trocar actuation rod (220), trocar actuation rod (6606) of the present example defines a cutout (6608) comprising an angled guide surface (6607), a flat surface (6609), and a resistant surface (6610). Both resistant surface (6610) and guide surface (6607) slope inwardly toward flat surface (6609) from exterior (6612) of trocar actuation rod (6606).

Resistance spring (6612) comprises a fixed member (6605) located within a channel (6602) of casing (6601), a distal leg (6603), a proximal leg (6611), and a deforming surface (6604) in between distal leg (6603) and proximal leg (6611). Resistance spring (6612) is configured to deform is response to distal actuation of trocar actuation rod (6606) as will be described in greater detail below.

FIGS. 128A-128C depict the above-described components at various stages of operation. FIG. 128A shows resistance indicator system (6600) at a state where knife member (340) and staple driver member (350) have been actuated both distally and proximally, completing the cutting and stapling motion but before the gap distance (d) has been enlarged to facilitate release of stapled tissue between surfaces (412, 322). At this state, distal leg (6603) of resistance spring (6605) is in contact with guide surface (6607) of cutout (6608). Guide surface (6607) is in contact with distal leg (6603) until the apex of resistance spring (6612) is in contact with flat surface (6009). However, it is important to note that guide surface (6607) does not need to be in contact with distal leg (6603) at this stage.

As trocar actuation rod (6606) is advanced distally in order to enlarge gap distance (d) for removal of tissue between surfaces (412, 322), the apex of resistance spring (6612) contacts flat surface (6009) while distal leg (6603) is no longer in contact with guide surface (6607). Fixed member (6605) of resistance spring (6612) prevents resistance spring (6612) from translating distally with trocar actuation rod (6606). Trocar actuation rod (6606) is further advanced distally until deforming surface (6604) makes contact with resistance surface (6610) as shown in FIG. 128B.

Resistant surface (6610) is positioned on trocar actuation rod (6606) to make contact with deforming surface (6604) of spring (6612) when a sufficient gap distance (d) has been created. As a result of resistant surface (6610) making contact with deforming surface, the operator will then feel an increased resistance while turning knob (130) to translate trocar actuation rod (6606) further distally. This increase is resistance occurs because resistant surface (6610) of trocar actuation rod (6606) must exert additional force to deform resistance spring (6612). Resistant surface (6610) is sloped in such a manner as to push resistance spring (6612) downwardly as trocar actuation rod (6606) travels further distally. Resistance spring (6612) has sufficient column strength not to buckle when forced by actuation of resistance surface (6610). At this stage, the additional resistance provided by spring (6612) and cutout (6608) provide tactile feedback to the operator, indicating that trocar actuation rod (6606) has been advanced to a distance that provides a sufficiently large gap between surfaces (412, 322) to facilitate removal of instrument (10) from the patient.

In the event that the operator drives trocar actuation rod (6606) further distally from the position shown in FIG. 128B, resistance surface (6610) and deforming surface (6604) will cooperate to eventually transition spring (6612) to a collapsed state as shown in FIG. 128C. When spring (6612) reaches this collapsed state, the resistance to further rotation of knob (130) may drop suddenly. This sudden drop of resistance to knob (130) rotation may provide further tactile feedback to the operator indicating that trocar actuation rod (6606) has been advanced to a distance that provides a sufficiently large gap between surfaces (412, 322) to facilitate removal of instrument (10) from the patient. In some instances, though, the operator may remove instrument (10) from the patient when the above described components are in the state shown in FIG. 128B, such that the components do not ever reach the state shown in FIG. 128C.

F. Dual Mode Visual Indicator

FIGS. 129-131 depict an exemplary indicator system (6700) that is configured to provide another form of visual feedback to indicate a sufficient gap distance (d) to facilitate proper release of stapled tissue between stapling head assembly (300) and anvil (400). Indicator system (6700) may be readily incorporated into instrument (10). Indicator system (6700) comprises an indicator window (6707), an indicator panel (6708), a backlight (6708), a pivoting indicator member (6711), and a tissue release indicator (6705).

Indicator window (6707) is substantially the same as window (114) described above. Indicator member (6711) is positioned between indicator window (6707) and indicator panel (6708). Indicator member (6711) is substantially the same as indicator member (520) described above. Indicator member (6711) is configured to pivot in response to translation of a bracket (6702), which is substantially the same as bracket (500) described above. Bracket (6702) is configured to translate in response to translation of a trocar actuation rod (6701), which is substantially the same as trocar actuation rod (220) described above.

It should be understood from the foregoing that the operator may view indicator member (6711) through window (6707) to determine whether the gap distance (d) is within the appropriate range before the operator actuates stapling head assembly (300). As shown in FIG. 131, indicator panel (6708) may provide fixed indicia (6720) that provide reference points for the operator to view the moving indicator member (6711) against. Backlight (6708) may provide illumination that facilitates viewing of indicator member (6711) against indicator panel (6708) through indicator window (6707). FIGS. 130A-130B show indicator member (6711) moving above indicator member (6711) in response to proximal movement of trocar actuation rod (6701) and bracket (6702) as the operator adjusts the gap distance (d) between opposing surfaces (412, 322) of anvil (400) and stapling head assembly (300) before actuating stapling head assembly (300).

Tissue release indicator (6705) is fixed to trocar actuation rod (6701). Tissue release indicator (6705) comprises an anchor portion (6713), a stem (6709), an optional extension arm (6704), a spring arm (6706), and a distal tab (6714). Anchor portion (6713) is fixedly secured to trocar actuation rod (6701). Stem (6709) projects upwardly from anchor portion (6713) through a slot (6710) formed in a stapling head assembly driver (6715). Slot (6710) of stapling head assembly driver (6715) provides sufficient clearance for stem (6709) that enables tissue release indicator (6705) and trocar actuation rod (6701) to move together independently relative to stapling head assembly driver (6715). As shown in FIG. 129, extension arm (6704) may be provided to extend proximally to secure spring arm (6706) to stem (6709). Alternatively, as shown in FIGS. 130A-130C, spring arm (6706) may be secured directly to stem (6709). In both versions, distal tab (6714) is provided at the free distal end of spring arm (6706).

Spring arm (6706) is resiliently biased to urge distal tab (6714) upwardly toward window (6707). However, during the initial stages of operation before anvil (400) is retracted to bring surfaces (412, 322) within the appropriate range of gap distance (d) to actuate stapling head assembly (300), distal tab (6714) is positioned underneath indicator panel (6708) and is thus obscured by indicator panel (6708) as shown in FIG. 130A. The stage of operation shown in FIG. 130A corresponds with the stages of operation shown in FIGS. 21A-21B as described above.

Once anvil (400) is retracted to a position where surfaces (412, 322) are within the appropriate range of gap distance (d) to actuate stapling head assembly (300), distal tab (6714) clears the proximal end of indicator panel (6708), such that spring arm (6706) drives distal tab (6714) upwardly as shown in FIG. 130B. At this stage, the operator will actuate stapling head assembly (300) as described above. The stage of operation shown in FIG. 130B thus corresponds with the stages of operation shown in FIGS. 21C-21D as described above.

After stapling head assembly (300) is actuated, the operator may wish to advance anvil (400) distally to increase the gap distance (d), to thereby facilitate release of the tissue between surfaces (412, 322), to thereby facilitate removal of instrument (10) from the patient as described above in relation to FIG. 21E. As the operator advances anvil (400) distally via trocar actuation rod (6701), distal tab (6714) also travels distally. As shown in FIG. 130C, distal tab (6714) is positioned between window (6707) and indicator panel (6708) as distal tab (6714) travels distally during this stage of operation. The operator may thus visually observe the position of distal tab (6714) against indicator panel (6708) through window (6707) in order to receive visual feedback that is indicative of the expanded gap distance (d). Referring back to FIG. 131, the associated region of indicator panel (6708) may provide fixed indicia (6722) that serve as reference points for the operator to view the moving distal tab (6714) against. Again, backlight (6708) may provide illumination that facilitates viewing of distal tab (6714) against indicator panel (6708) through indicator window (6707).

It should be understood from the foregoing that indicator panel (6708) is configured to provide two different kinds of visual feedback—one indicating whether a suitable gap distance (d) has been achieved before stapling head assembly (300) has been actuated; and another indicating whether the gap distance (d) has been sufficiently increased to facilitate release of the tissue between surfaces (412, 322), to thereby facilitate removal of instrument (10) from the patient. It should be understood that the example of indicator panel (6708) shown in FIG. 131 is merely illustrative. Various other suitable forms that indicator panel (6708) may take will be apparent to those of ordinary skill in the art in view of the teachings herein.

XII. Exemplary Circular Stapling Instrument with Firing State Indicator

It may be desirable to provide one or more features in instrument (10) that will provide the operator with feedback relating to the state of components that are used to actuate stapling head assembly (300). Such feedback may be indicative of the stage of the actuation stroke at which stapling head assembly (300) currently is. For instance, in versions where anvil (400) includes a washer that is broken by knife member (340) when the knife member (340) completes a full distal range of motion from the position shown in FIG. 21C to the position shown in FIG. 21D, the washer may provide an increasing load on the actuation components, followed by a sudden drop in the load as soon as the washer is broken. If position feedback indicates a full travel distance by knife member (340) but load feedback does not indicate breakage of the washer, the combination of such feedback may indicate that knife member (340) might not have sufficiently severed tissue. Load related feedback may also be indicative of operator error or other conditions that may lead to an unsuccessful anastomosis (70). For instance, if the operator has not positioned instrument (10) properly, the actuation components may encounter a relatively high, intolerable or otherwise unacceptable load. If the operator is informed of this situation, the operator may reposition instrument (10) or take other corrective action. Load related feedback may also be indicative of proper completion of an actuation stroke, providing confirmation to the operator that instrument (10) is ready for removal from the patient.

The following examples relate to features that may be readily incorporated into instrument (10) to indicate a load encountered by components that are used to actuate stapling head assembly (300). It should be understood that these examples are merely illustrative. The load indicating features described below may be used for any of the purposes noted above, among others. Other ways in which such load related feedback may be used will be apparent to those of ordinary skill in the art in view of the teachings herein.

A. Exemplary Mechanical Load Sensor

FIGS. 132-133 show a portion of an instrument (7000) that is an exemplary variation of instrument (10). Instrument (7000) of this example comprises a handle assembly (7100) and a shaft assembly (7200). Except for the differences explicitly noted below, instrument (7000) may be constructed and operable just like instrument (10) described above. Handle assembly (7100) comprises a casing (7110) defining an obliquely oriented pistol grip (7112). Handle assembly (110) further includes a window (7114) that permits viewing of a movable indicator needle like indicator needle (526) described above. In addition, handle assembly includes triggers (7140, 7150) that are configured and operable just like triggers (140, 150) described above.

Shaft assembly (7200) comprises an outer sheath (7210), a trocar actuation rod (7220), and a stapling head assembly driver (7240). Trocar actuation rod (7220) is coupled with a knob (7130), which is located at the proximal end of handle assembly (7100) and is rotatable relative to casing (7110) to adjust the longitudinal position of trocar actuation rod (7220). Like trocar actuation rod (220) described above, trocar actuation rod (7220) may be translated to adjust the position of an anvil (similar to anvil (400)) in relation to a stapling head assembly (similar to stapling head assembly (300)) that is located at the distal end of shaft assembly (7200). Stapling head assembly driver (7240) is coupled with a motor (not shown) in pistol grip (7112). The motor is operable to translate stapling head assembly driver (7240), just like motor (160) is operable to translate stapling head assembly driver (240), to actuate the stapling head assembly at the distal end of shaft assembly (7200).

Stapling head assembly driver (7240) is coupled with the motor via a drive bracket (7250), which is a variation of drive bracket (250) described above. As shown in FIG. 133, drive bracket (7250) of this example comprises a proximal portion (7252) and a distal portion (7254), which are joined together by a resilient member (7256). The proximal end of stapling head assembly driver (7240) is directly secured to the distal end of distal portion (7254). Proximal portion (7252) is directly coupled with a cam follower (not shown) that is substantially identical to cam follower (600) described above. As proximal portion (7252) is driven distally by the motor via the cam follower, resilient member (7256) communicates the distal driving forces to distal portion (7254), enabling the distal driving forces to be further communicated to stapling head assembly driver (7240). In the present example, resilient member (7256) comprises a substantially stiff coil spring that is operable to substantially avoid deformation during an actuation stroke during normal operation of instrument (7000). However, when relatively high loads are encountered by drive bracket (7250) during the actuation stroke, resilient member (7256) will compressibly deform to some degree.

As also shown in FIG. 133, an indicator panel (7192) is fixedly secured to proximal portion (7252) of drive bracket (7250) via a collar (7280) and arm (7282). An indicator needle (7194) is fixedly secured to distal portion (7254) of drive bracket (7250) via a collar (7290) and arm (7292). Indicator needle (7194) is positioned in front of indicator panel (7192). Indicator panel (7192) includes fixed indicia that facilitate viewing of the position of needle (7194) in relation to panel (7192) along an axis that is parallel to the longitudinal axis of drive bracket (7250). As shown in FIG. 132, casing (7110) of handle assembly (7100) defines a window (7190) through which an operator may view panel (7192) and needle (7194). As drive bracket (7250) translates distally during a firing stroke, the operator may watch the position of needle (7194) in relation to panel (7192) along an axis that is parallel to the longitudinal axis of drive bracket (7250). If the actuation assembly does not encounter any unacceptably high loads, needle (7194) and the indicia on panel (7192) will provide visual feedback to the operator indicating that the load on the actuation assembly is within an acceptable range. However, if the actuation assembly encounters an unacceptably high load, resilient member (7256) will compress and thereby deform to a point where the position of needle (7194) in relation to indicia on panel (7192) will provide visual feedback to the operator indicating that the load on the actuation assembly is higher than acceptable. The operator may then take corrective action.

In addition to providing visual feedback to the operator through movement of needle (7194) relative to indicia on panel (7192) in response to the actuation assembly encountering an unacceptably high load, resilient member (7256) may also prevent proximal portion (7252) of drive bracket (7250) from transferring unacceptably high driving forces to distal portion (7254) of drive bracket (7250). In other words, when distal portion (7254) encounters resistance to further distal translation to the point where resilient member (7256) begins to deform, further distal advancement of proximal portion (7252) may simply deform resilient member (7256) rather than transferring further distal movement to distal portion (7254). Resilient member (7256) may thus restrict the force that may be applied to distal portion (7254) by proximal portion (7252). A suitable spring constant that may be selected for resilient member (7256) in order to achieve the results described herein will be apparent to those of ordinary skill in the art in view of the teachings herein.

It should be understood that panel (7192) will move longitudinally with drive bracket (7250) during the actuation stroke in this example. Thus, window (7190) may be sized to enable viewing of the entire panel (7192) during the full actuation stroke. Alternatively, window (7190) may be sized such that at least a portion of panel (7192) is only viewable during a portion of the actuation stroke.

While resilient member (7256), panel (7192), and needle (7194) are disclosed as being part of the firing assembly that is coupled with a motor in this example, it should be understood that a similar resilient member (7256), panel (7192), and needle (7194) may be incorporated into the anvil actuation assembly. For instance, trocar actuation rod (7220) may be broken into two segments that are separated by a resilient member like resilient member (7256). A panel (e.g., like panel (7192)) may be secured to one of the segments and a needle (e.g., like needle (7194)) may be secured to the other segment. The resilient member may communicate longitudinal forces between the two segments and deform in response to significant loads. However, it should be understood that the relevant loads against these segments would be distally oriented while the relevant loads against portions (7252, 7254) would be proximally oriented.

In the event that the operator observes an indication via panel (7192) and needle (7194) that the stapling head firing assembly and/or the anvil actuation assembly is encountering an unacceptably high load, the operator may actuate a bailout feature (7002) to decouple components of instrument (7000) that are under the load, thereby facilitating prompt removal of instrument (7000) from the patient. Bailout feature (7002) includes a lever (7004) that is pivotably coupled to casing (7110). The operator may thus pivot lever (7004) relative to casing (7100) to actuate bailout feature (7002). In some versions, bailout feature is operable to provide separation of two segments of trocar actuation rod (7220) thereby relieving compression between tissue that is compressed between surfaces (412, 322) of anvil (400) and stapling head assembly (300). By way of example only, bailout feature (7002) may be constructed and operable in accordance with at least some of the other teachings herein. Other suitable ways in which a bailout feature may be configured and operable will be apparent to those of ordinary skill in the art in view of the teachings herein. Alternatively, instrument (7000) may simply lack a bailout feature.

B. Exemplary Electromechanical Load Sensor

FIGS. 134-135 show a portion of another instrument (7300) that is an exemplary variation of instrument (10). Instrument (7300) of this example comprises a handle assembly (7400) and a shaft assembly (7500). Except for the differences explicitly noted below, instrument (7300) may be constructed and operable just like instrument (10) described above. Handle assembly (7400) comprises a casing (7410) with a window (7414) that permits viewing of a movable indicator needle like indicator needle (526) described above. In addition, handle assembly includes triggers (7440, 7450) that are configured and operable just like triggers (140, 150) described above.

Shaft assembly (7500) comprises an outer sheath (7510), a trocar actuation rod (7520), and a stapling head assembly driver (7540). Trocar actuation rod (7520) is coupled with a knob (not shown), which is located at the proximal end of handle assembly (7400) and is rotatable relative to casing (7410) to adjust the longitudinal position of trocar actuation rod (7520). Like trocar actuation rod (220) described above, trocar actuation rod (7520) may be translated to adjust the position of an anvil (similar to anvil (400)) in relation to a stapling head assembly (similar to stapling head assembly (300)) that is located at the distal end of shaft assembly (7500). Stapling head assembly driver (7540) is coupled with a motor (not shown) via a gearbox (7362), cam (7370), cam follower (7360), drive bracket (7550), and actuator extension (7552). The motor is operable to thereby translate stapling head assembly driver (7240), just like motor (160) is operable to translate stapling head assembly driver (240), to actuate the stapling head assembly at the distal end of shaft assembly (7200).

While instrument (7000) includes a mechanical load sensor as provided by resilient member (7256), panel (7192), and needle (7194), instrument (7300) of the present example comprises an electromechanical load sensor. In particular, as shown in FIG. 135, a strain gauge (7580) is positioned on driver (7540). Strain gauge (7580) comprises a conductive foil pattern that is configured to deform in response to longitudinal strain (i.e., compression) being provided on driver (7540). Strain gauge (7580) provides a change in resistance or voltage in based on the degree of such deformation, as will be apparent to those of ordinary skill in the art in view of the teachings herein. Various suitable forms that strain gauge (7580) may take will be apparent to those of ordinary skill in the art in view of the teachings herein.

Strain gauge (7580) provides a pair of longitudinally extending contact strips (7582, 7584) that are in electrical communication with the conductive foil pattern. A pair of fixed position contacts (7592, 7594) are in sliding contact with contact strips (7582, 7584). Contacts (7592, 7594) are fixedly secured within casing (7410). Contacts (7592, 7594) comprise leaf springs that are resiliently biased to engage contact strips (7582, 7584) such that contacts (7592, 7594) maintain electrical continuity with contact strips (7582, 7584) throughout the longitudinal range of travel of driver (7540) during the firing stroke of the stapling head assembly.

Referring back to FIG. 134, contacts (7592, 7594) are further coupled with a processing module (7586), which is operable to process signals from strain gauge (7580). By way of example only, processing module (7586) may comprise a Wheatstone bridge circuit, a comparator circuit, a microprocessor, an application specific integrated circuit (ASIC), and/or any other suitable components. Various suitable components and arrangements that may be used to form processing module (7586) will be apparent to those of ordinary skill in the art in view of the teachings herein.

As also shown in FIG. 134, an indicator (7588) is positioned in window (7414). Indicator (7588) is in communication with processing module (7586) and is configured to provide the operator with visual feedback based on the load on driver (7540) as sensed through strain gauge (7580). By way of example only, indicator (7588) may comprise a light emitting diode (LED) that is operable to illuminate when strain gauge (7580) and processing module (7586) sense that the load on driver (7540) has exceeded a threshold. As another merely illustrative example, indicator (7588) may comprise a liquid crystal display (LCD) feature that provides some form of visual feedback to the operator to indicate when strain gauge (7580) and processing module (7586) sense that the load on driver (7540) has exceeded a threshold. Other suitable forms that indicator (7588) may take, as well as other suitable ways in which indicator (7588) may provide visual feedback based on load conditions sensed by strain gauge (7580) and processing module (7586), will be apparent to those of ordinary skill in the art in view of the teachings herein.

FIG. 136 shows a graph plotting an example of the load that may be encountered by driver (7540) during an actuation stroke of the stapling head assembly. The x-axis of the graph represents the full distal range of longitudinal travel by driver (7540); and the y-axis the compressive strain encountered by driver (7540) during that range of travel. A first leg (7600) of the plot shows the increasing compressive strain encountered by driver (7540) as driver (7540) advances distally through a first portion of the distal range of motion. A peak (7602) of the plot shows the point at which a washer in the anvil has been broken by the knife member of the stapling head assembly. A second leg (7604) of the plot shows how the compressive load quickly drops after the washer has been broken and driver (7540) completes the remaining second portion of the distal range of motion.

FIG. 136 also shows a broken line (7610) indicating a threshold strain level. Processing module (7586) may be configured to compare the sensed strain against this threshold level and trigger some form of indication through indicator (7588) when the sensed strain exceeds this threshold level. In the example shown, the sensed strain has exceeded the threshold level indicated by the line (7610) before reaching the peak (7602). Thus, processing module (7586) would have activated the indicator (7588) before reaching peak (7602). In some versions, the threshold level associated with broken line (7610) represents a load that is unacceptable or undesirable for normal operation of instrument (7300). In such instances, processing module (7586) may activate indicator (7588) when the load exceeds the threshold. In some other versions, the threshold level associated with broken line (7610) represents a load that processing module (7586) would expect driver (7540) to exceed during normal operation of instrument (7300). In such instances, processing module (7586) may activate indicator (7588) when the load fails to exceed the threshold despite completion of an actuation stroke. In still other versions, both kinds of thresholds may be used, such that processing module (7586) may drive indicator (7588) based on whether the load stays below the upper threshold yet exceeds the lower threshold.

In addition to or as an alternative to comparing sensed strain against a threshold and activating indicator (7588) accordingly, processing module (7586) may focus on when second leg (7604) reaches an endpoint (7606), indicating completion of the firing stroke for stapling head assembly. It should be understood that the reaching of endpoint (7606) may be detected based on feedback from strain gauge (7580). When processing module (7586) determines that endpoint (7606) has been reached, processing module (7586) may alert the operator via indicator (7588). In addition or in the alternative, processing module (7586) may process this data in combination with positioning data as described below, and provide the operator with some form of notification via indicator (7588) based on the processing of the combined data.

While strain gauge (7580) is disclosed as being part of the firing assembly that is coupled with a motor in this example, it should be understood that a similar strain gauge (7580) may be incorporated into the anvil actuation assembly. For instance, a strain gauge (7580) may be integrated into or onto trocar actuation rod (7520). The strain gauge (7580) may sense loads on trocar actuation rod (7520) during actuation of trocar actuation rod (7520) and during actuation of driver (7540). It should be understood that the relevant loads against trocar actuation rod (7520) would be distally oriented while the relevant loads driver (7540) would be proximally oriented.

In the event that the operator observes an indication via indicator (7588) that the stapling head firing assembly and/or the anvil actuation assembly is encountering an unacceptably high load, the operator may actuate a bailout feature (not shown) to decouple components of instrument (7300) that are under the load, thereby facilitating prompt removal of instrument (7300) from the patient. Such a bailout feature may be constructed and operable like bailout feature (7002) described above. Other suitable ways in which a bailout feature may be configured and operable will be apparent to those of ordinary skill in the art in view of the teachings herein. Alternatively, instrument (7300) may simply lack a bailout feature.

C. Exemplary Position Sensor

In addition to or as an alternative to providing a sensor that is operable to sense strain within drive components that actuate a stapling head assembly like stapling head assembly (300) it may be desirable to provide a sensor that is operable to sense positioning of drive components that actuate a stapling head assembly like stapling head assembly (300). FIGS. 137A-137B show one merely illustrative example of a stapling head actuation assembly (7700) that provides position sensing capabilities. It should be understood that stapling head actuation assembly (7700) may be readily incorporated into any of the instruments (10, 7000, 7300) described herein. Stapling head actuation assembly (7700) of this example comprises a motor (not shown), gearbox (162), rotary cam (700), cam follower (600), drive bracket (250), and stapling head assembly driver (240), all of which are configured and operable just like the same components in instrument (10) as described above. However, in this example drive bracket (250) includes an integral permanent magnet (7702). Magnet (7702) is fixedly secured to drive bracket (250) such that magnet will travel distally with drive bracket (250) (FIG. 137A) and proximally with drive bracket (250) as stapling head actuation assembly (7700) completes a full actuation stroke. While magnet (7702) is secured to drive bracket (250) in this example, it should be understood that magnet (7702) may be secured to any other moving component of stapling head actuation assembly (7700).

Stapling head actuation assembly (7700) of the present example also includes a distal Hall Effect sensor (7710) and a proximal Hall Effect sensor (7720). Sensors (7710, 7720) are fixedly secured within casing (110). Each sensor (7710, 7720) is configured to generate a voltage in response to movement of magnet (7702) into proximity of sensor (7710, 7720). In particular, when drive bracket (250) is driven distally as shown in FIG. 137A, the resulting distal positioning of magnet (7702) will generate a voltage in Hall Effect sensor (7710). When drive bracket (250) is retracted proximally as shown in FIG. 137B, the resulting proximal positioning of magnet (7702) will generate a voltage in Hall Effect sensor (7720).

Sensors (7710, 7720) are in communication with a processing module (7730), which is further in communication with an indicator (7740). Processing module (7730) is operable to process signals from sensors (7710, 7720) and drive indicator (7740) based on those signals. Processing module (7730) may also be in communication with a load sensor such as strain gauge (7580) and/or any other suitable sensor(s); and may process data from such sensors to drive indicator (7740) based on such data and combinations thereof. By way of example only, processing module (7730) may comprise a Wheatstone bridge circuit, a comparator circuit, a microprocessor, an application specific integrated circuit (ASIC), and/or any other suitable components. Various suitable components and arrangements that may be used to form processing module (7730) will be apparent to those of ordinary skill in the art in view of the teachings herein.

Indicator (7740) is in communication with processing module (7730) and is configured to provide the operator with visual feedback based at least in part on the longitudinal position of drive bracket (250) as sensed by sensors (7710, 7720). For instance, if processing module (7730) determines based on feedback from sensors (7710, 7720) that drive bracket (250) did not travel enough distally during an actuation stroke, processing module (7730) may activate indicator (7740) to provide the operator with a visual indication of this condition. Similarly, if processing module (7730) determines based on feedback from sensors (7710, 7720) that drive bracket (250) did not travel enough proximally at the completion of the actuation stroke, processing module (7730) may activate indicator (7740) to provide the operator with a visual indication of this condition. By way of example only, indicator (7740) may comprise a light emitting diode (LED) that is operable to illuminate when stapling head actuation assembly (7700) has completed a full actuation stroke. As another merely illustrative example, indicator (7740) may comprise a liquid crystal display (LCD) feature that provides some form of visual feedback to the operator to indicate when stapling head actuation assembly (7700) has completed a full actuation stroke. Other suitable forms that indicator (7740) may take, as well as other suitable ways in which indicator (7740) may provide visual feedback based on positioning conditions sensed by sensors (7710, 7720), will be apparent to those of ordinary skill in the art in view of the teachings herein.

While only two sensors (7710, 7720) are used in this example, it should be understood that any other suitable number of sensors may be used. Increasing the number of sensors may provide finer granularity in tracking the longitudinal position of drive bracket (250) in real time during an actuation stroke. Such capabilities may enhance the quality and/or quantity of information that may be provided to the operator via indicator (7740). For instance, indicator (7740) may be driven to provide a first indication (e.g., yellow light, etc.) to indicate when drive bracket (250) (and hence knife member (340)) has been advanced to less than 25% of the distal range of the drive stroke; then a second indication (e.g., red light, etc.) to indicate when drive bracket (250) (and hence knife member (340)) has been advanced to at least 25% of the distal range of the drive stroke. It should also be understood that Hall Effect sensors are just one example of a form that sensors (7710, 7720) may take. By way of example only, sensors (7710, 7720) may alternatively comprise optical sensors, an encoder assembly, and or any other suitable kind of sensors. Various suitable alternative forms that sensors (7710, 7720) may take will be apparent to those of ordinary skill in the art in view of the teachings herein.

As noted above, processing module (7730) may process data from at least two different kinds of sensors associated with stapling head actuation assembly (7700). For instance, processing module (7730) may process a combination of load data from strain gauge (7580) and position data from sensors (7710, 7720). By way of example only, processing module (7730) may determine that drive bracket (250) has reached the full distal extent of its range of travel when sensor (7710) detects magnet (7702). If processing module (7730) has not detected that the load sensed by train gauge (7580) has surpassed peak (7602) and suddenly decreased per second leg (7604) as shown in FIG. 136 by the time sensor (7710) detects magnet (7702), processing module (7730) may activate an appropriate notification through indicator (7740). Such a combination of conditions may indicate that the washer in anvil (400) was not broken by knife member (340), which may indicate that the tissue was not sufficiently cut by knife member (340).

Processing module (7730) may also process data from one or more sensors that are integrated into the actuation assembly for anvil (400). For instance, such sensors may be configured to sense whether anvil (400) is fully seated on trocar (330), the position of anvil (400) relative to stapling head assembly (300), the load being encountered by trocar actuation rod (220), and/or other data relating to conditions associated with anvil (400). Merely illustrative examples of sensors that are configured to sense conditions associated with anvil (400) are disclosed elsewhere herein. Various other suitable sensors that may be in communication with processing module (7730), various conditions that such sensors may detect, various ways in which processing module (7730) may process the associated data in combination with data from sensors (7710, 7720), and various ways in which processing module (7730) may drive indicator (7740) based on such processing will be apparent to those of ordinary skill in the art in view of the teachings herein.

XIII. Exemplary Alternative Instruments with Bailout Features

Although anvil (400) of instrument (10) is described above as being adjustable and/or movable in response to rotation of knob (130), it may be desirable in some instances to provide additional control over movement of anvil (400). In particular, it may be desirable to provide a bailout feature that is operable to quickly release anvil (400) from a retracted position to thereby quickly decompress tissue that is disposed between opposing surfaces (412, 322) of anvil (400) and stapling head assembly (300). The bailout features described herein may be desirable because an operator may encounter circumstances creating the need or desire to immediately abort an anastomosis procedure, once such a procedure has begun. While various alternative instruments are described below, other examples will be apparent to those of ordinary skill in the art in view of the teachings herein. It should be further understood that various features and/or structures of the instruments described below may be readily incorporated with other instruments described herein.

A. Exemplary Instrument with Threaded Bailout Mechanism

FIG. 138 shows an exemplary alternative surgical circular stapling instrument (8000) that may be used to provide an end-to-end anastomosis between two sections of an anatomical lumen such as a portion of a patient's digestive tract. It should be understood that instrument (8000) of the present example is substantially the same as instrument (10) described above unless otherwise noted herein. For instance, like with instrument (10), instrument (8000) comprises a handle assembly (8010), a shaft assembly (8020), a stapling head assembly (not shown), and an anvil (not shown). Handle assembly (8010) is substantially the same has handle assembly (110) described above and comprises a casing (8012) defining an obliquely oriented pistol grip (8014). Handle assembly (8010) further includes a window (8016) that permits viewing of a movable indicator needle (not shown) as similarly described above.

Like with instrument (10) described above, instrument (8000) is controlled by an operator via knob (8030) and triggers (8040, 8042). Knob (8030), like with knob (130) described above, is operatively connected to shaft assembly (8020) to actuate the anvil. In particular, knob (8030) is rotatable to engage threads (not shown) of shaft assembly (8020) to translate a trocar actuation rod (8022), which ultimately actuates the anvil as similarly described above with respect to shaft assembly (200) of instrument (10).

Triggers (8040, 8042) function similarly as triggers (140, 150) described above. For instance, a safety trigger (8040) may be first actuated by an operator to permit activation of the stapling head assembly. Instrument (8000) further includes a firing trigger (8042), which is similar to firing trigger (150) described above. In particular, once safety trigger (8040) has been activated, firing trigger (8042) is operable to initiate actuation of the stapling head assembly. Firing trigger (8042) includes a paddle (not shown), which is configured to engage a motor activation module (not shown) when firing trigger (8042) is advanced by an operator. Like with motor activation module (180) described above, the motor activation module of the present example initiates the stapling sequence by activating a motor (not shown). The motor then drives a cam member (not shown), which in turn drives a cam follower (8054). The cam member and cam follower (8054) are substantially the same as cam member (700) and cam follower (600) described above, such that the cam member and cam follower (8054) operate cooperatively to drive the stapling head assembly through a stapling sequence.

Unlike instrument (10) described above, instrument (8000) of the present example comprises an anvil bailout assembly (8070). Anvil bailout assembly (8070) is generally configured to permit the trocar and anvil to be quickly disengaged by releasing tension in trocar actuation rod (8022) after the trocar and anvil have been adjusted via knob (8030). Such a feature may be desirable because an operator may desire to quickly release any compressive force supplied by the anvil during an anastomosis procedure. As can be seen in FIG. 139, anvil bailout assembly (8070) comprises a release member (8072), a pawl member (8076), and a coupling member (8080). Release member (8072) extends through casing (8012) of handle assembly (8010) and is configured for grasping by an operator. In particular, release member (8072) includes a plurality of gripping features (8074), which are configured to permit grasping by an operator to pivot release member (8072) relative to handle assembly (8010). As will be described in greater detail below, release member (8072) is generally pivotable relative to handle assembly (8010) to drive anvil bailout assembly (8070) to release tension in trocar actuation rod (8022), thereby releasing the trocar and anvil.

Pawl member (8076) is in communication with release member (8070). As is best seen in FIG. 140, pawl member (8076) includes an engagement portion (8078) that is generally configured to drive anvil bailout assembly (8070) via pivotable movement of release member (8072). In particular, pawl member (8076) is coupled to release member (8072) such that pivoting of release member (8072) in a counter clockwise direction results in corresponding pivoting of pawl member (8076) in a counter clockwise direction. Pivoting of pawl member (8076) in a counter clockwise direction results in engagement portion (8078) applying a driving force to coupling member (8080), as will be described in greater detail below.

Pawl member (8076) further includes a resilient member (8079). In the present example resilient member (8079) is a coil spring that is configured to resiliently bias pawl member (8076) toward the position shown in FIG. 140. As will be described in greater detail below, resilient member (8079) is configured to maintain engagement between engagement portion (8078) of pawl member (8076) and at least a portion of coupling member (8080).

Coupling member (8080) is shown in FIGS. 141 and 26. As can be seen, coupling member (8080) comprises a generally cylindrical sheath. As will be described in greater detail below, coupling member (8080) is generally configured to be rotatably driven by pawl member (8076) relative to trocar actuation rod (8022) to expand the effective length of trocar actuation rod (8022). The outer diameter of coupling member (8080) comprises a plurality of tangentially oriented, longitudinally extending ratchet teeth (8082). Ratchet teeth (8082) of the present example are generally triangular and are configured to engage with pawl member (8076) to create a pawl and ratchet mechanism. Accordingly, each ratchet tooth (8082) is oriented in a particular tangential direction to sucessively engage pawl member (8076) as pawl member (8076) is used to advance coupling member (8080).

The interior of coupling member (8080) is shown in FIG. 142. As can be seen, the inner diameter of coupling member (8080) includes two sets of threads (8084, 8086) disposed therein. Each set of threads (8084, 8086) are generally the same, except threads (8084) have a pitch orientation that is opposite to the pitch orientation of threads (8086). As will be described in greater detail below, the opposing nature of threads (8084, 8086) is configured to engage with corresponding threads (8025, 8027) of trocar actuation rod (8022) to couple trocar actuation rod (8022) and lengthen or shorten the effective length of trocar actuation rod (8022).

As can be seen in FIG. 143, trocar actuation rod (8022) comprises a proximal part (8024) and a distal part (8026). Each part (8024, 8026) is a discrete shaft that forms a single whole. Trocar actuation rod (8022) is thus formed by coupled parts (8024, 8026) via coupling member (8080). The distal end of proximal part (8024) includes a threaded portion (8025) and is configured to abut the proximal end of distal part (8026). Similarly, the proximal end of distal part (8026) includes a threaded portion (8027) and is configured to abut the distal end of proximal part (8024).

Each threaded portion (8025, 8027) is configured to engage with corresponding threads (8084, 8086) of coupling member (8080). Thus, threaded portions (8025, 8027) are likewise configured with opposing pitch orientations. Because of this, it should be understood that rotation of coupling member (8080) relative to parts (8024, 8026) will generally result in opposing longitudinal translation of each part (8024, 8026) of trocar actuation rod (8022). By way of example only, threaded portions (8025, 8027) and threads (8084, 8086) of the present example are configured such that clockwise rotation of coupling member (8080) results in each part (8024, 8026) of trocar actuation rod (8022) moving away from the other. Similarly, counter clockwise rotation of coupling member (8080) will result in each part (8024, 8026) of trocar actuation rod (8022) moving closer to the other. Although threaded portions (8025, 8027) and threads (8084, 8086) of the present example are described herein as having a particular relationship with rotation of coupling member (8080), it should be understood that no such limitation is intended and in other examples coupling member may be configured to have any suitable relationship as will be apparent to those of ordinary skill in the art in view of the teachings herein.

An exemplary mode of operation of anvil bailout assembly (8070) can be seen by comparing FIGS. 140 and 28. As can best be seen in FIG. 140, anvil bailout assembly (8070) is initially in a neutral state. It should be understood that in the neutral state anvil bailout assembly (8060) generally has no impact on the functioning of instrument (8000). In particular, coupling member (8080) is positioned via anvil bailout assembly (8070) such that proximal part (8024) of trocar actuation rod (8022) abuts distal part (8026) of trocar actuation rod (8022) such that trocar actuation rod (8022) comprises a length that is substantially the same as trocar actuation rod (220) described above. Correspondingly, release member (8072) is disposed in a position that is generally downwardly oriented to position pawl member (8076) away from coupling member (8080). In other words, pawl member (8076) does not contact teeth (8082) or any other portion of coupling member (8080) during rotation of knob (8030) to adjust the longitudinal position of the trocar and anvil relative to the stapling head assembly via trocar actuation rod (8022).

In some instances, an operator may desire to quickly bail out of an anastomosis procedure. This may require quickly releasing the trocar and anvil to unload the compression on tissue that is clamped between the anvil and the stapling head assembly. To quickly release the trocar and anvil, the operator may generally grasp release member (8072) and pull release member (8072) upwardly, as shown in FIG. 144. Movement of release member (8072) upwardly drives pawl member (8076) into engagement with a tooth (8082) of coupling member (8080), such that pawl member (8076) causes coupling member (8080) to rotate about the longitudinal axis of trocar actuation rod (8022). In the present example, coupling member (8080) is driven in a clockwise direction. Trocar actuation rod (8022) remains rotationally stationary while this occurs.

As described above, threads (8084, 8086) of coupling member (8080) are configured to engage threaded portions (8025, 8027) of trocar actuation rod (8022). Due to the opposing pitch orientations of threads (8025, 8027, 8084, 8086), the above-described rotation of coupling member (8080) relative to trocar actuation rod (8022) urges parts (8024, 8026) longitudinally away from each other. As proximal and distal parts (8024, 8026) are driven apart, this increases the effective length of trocar actuation rod (8022), relieving some of the compression being applied to the tissue by the anvil against the stapling head assembly.

The operator may push release member (8072) downwardly back to the position shown in FIG. 140, causing pawl member (8078) to ratchet along the tooth (8082) without causing corresponding rotation of coupling member (8080).

The operator may then again pull release member (8072) upwardly to the position shown in FIG. 144, causing pawl member (8076) to engage the next tooth (8082) and thereby rotate coupling member (8080) yet again relative to trocar actuation rod (8022), thereby driving parts (8024, 8026) longitudinally away from each other by another increment. The operator may repeat this process as many times as desired to incrementally increase the effective length of trocar actuation rod (8022), thereby incrementally decreasing the compression being applied to the tissue by the anvil against the stapling head assembly. With the tension on the anvil by trocar actuation rod (8022) being relieved, the operator may more easily extract instrument (8000) from the patient without causing damage to surrounding tissue.

It should be understood that rotating member (8080) has sufficient length such that pawl member (8076) may engage teeth (8082) while rotating member (8080) and trocar actuation rod (8022) are at various different longitudinal positions. In other words, anvil bailout assembly (8070) may be effectively operated before the anvil significantly compresses tissue against the stapling head assembly. It should also be understood that in some examples anvil bailout assembly (8070) may include gears, levers, or other features to create a mechanical advantage between the movement of release member (8072) and the movement of pawl member (8076). Other suitable variations will be apparent to those of ordinary skill in the art in view of the teachings herein.

B. Exemplary Instrument with Pin Release Bailout Features

FIGS. 145-146 show an exemplary alternative surgical circular stapling instrument (8100) that may be used to provide an end-to-end anastomosis between two sections of an anatomical lumen such as a portion of a patient's digestive tract. It should be understood that instrument (8100) of the present example is substantially the same as instrument (10) described above unless otherwise noted herein. For instance, like with instrument (10), instrument (8100) comprises a handle assembly (8110), a shaft assembly (8120), a stapling head assembly (not shown), and an anvil (not shown). Handle assembly (8110) is substantially the same has handle assembly (110) described above and comprises a casing (8112) defining an obliquely oriented pistol grip (8114). Handle assembly (8110) further includes a window (8116) that permits viewing of a movable indicator needle (not shown) as similarly described above.

Like with instrument (10) described above, instrument (8100) is controlled by an operator via knob (8130) and triggers (8140, 8142). Knob (8130), like with knob (130) described above, is operatively connected to shaft assembly (8120) to actuate the anvil. In particular, knob (8130) is rotatable to engage threads (not shown) of shaft assembly (8120) to translate a trocar actuation rod (8122), which ultimately actuates the anvil as similarly described above with respect to shaft assembly (200) of instrument (10).

Triggers (8140, 8142) function similarly as triggers (140, 150) described above. For instance, a safety trigger (8140) may be first actuated by an operator to permit activation of the stapling head assembly. Instrument (8100) further includes a firing trigger (8142), which is similar to firing trigger (150) described above. In particular, once safety trigger (8140) has been activated, firing trigger (8142) is operable to initiate actuation of the stapling head assembly. Firing trigger (8142) includes a paddle (not shown), which is configured to engage a motor activation module (not shown) when firing trigger (8142) is advanced by an operator. Like with motor activation module (180) described above, the motor activation module of the present example initiates the stapling sequence by activating a motor (not shown). The motor then drives a cam member (not shown), which in turn drives a cam follower (8154). The cam member and cam follower (8154) are substantially the same as cam member (700) and cam follower (600) described above, such that the cam member and cam follower (8154) operate cooperatively to drive the stapling head assembly through a stapling sequence.

Unlike instrument (10) described above, instrument (8100) of the present example comprises an anvil bailout assembly (8170). Anvil bailout assembly (8170) is generally configured to permit the trocar and anvil to be quickly disengaged by releasing tension in trocar actuation rod (8122) after the trocar and anvil have been adjusted via knob (8130). Such a feature may be desirable because an operator may desire to quickly release any compressive force supplied by the anvil during an anastomosis procedure. As can be seen in FIG. 147, anvil bailout assembly (8170) comprises a release member (8172) and a coupling member (8180). Release member (8172) is disposed on the exterior of casing (8112) of handle assembly (8110) and is configured for grasping by an operator. In particular, release member (8172) comprises a gripping portion (8173) and a lever portion (8176). Gripping portion (8173) is configured to be grasped by an operator and includes a plurality of gripping features (8174) to improve the general grippability of gripping portion (8173).

Lever portion (8176) extends distally from gripping portion (8173) and is generally configured to permit release member (8072) to pivot relative to handle assembly (8110). The distal end of lever portion (8176) is pivotably secured to casing (8112) of handle assembly (8110) by a pin (8177) or other suitable pivotable coupling. Lever portion (8176) further includes a bore (8178) disposed distally of the proximal end of lever portion (8176). As will be described in greater detail below, bore (8178) is generally configured to secure coupling member (8180) to lever portion (8176). As will also be described in greater detail below, release member (8172) is generally pivotable relative to handle assembly (8110) to drive anvil bailout assembly (8170) to release tension in trocar actuation rod (8122), thereby releasing the trocar and anvil.

Coupling member (8180) is shown in FIGS. 147-149. As can be seen, coupling member (8180) comprises a generally cylindrical pin. Coupling member (8180) extends laterally from lever portion (8176) of release member (8072). In particular, coupling member (8180) is disposed in bore (8178) of lever portion (8176). In the present example, coupling member (8180) is held in bore (8178) by an interference or friction fit. Additionally, adhesives, other bonding agents, and/or other features may be used to secure coupling member (8180) to lever portion (8176). Although coupling member (8180) is described herein as being a separate component from release member (8172), it should be understood that in some examples coupling member (8180) may be integral with release member (8172).

As will be described in greater detail below, coupling member (8180) is generally configured to be moved by release member (8172) relative to trocar actuation rod (8122) to decouple two parts (8124, 8126) of trocar actuation rod (8122). As is best seen in FIG. 148, coupling member (8180) extends laterally from lever portion (8176) of release member (8172) through an opening (8123) in trocar actuation rod (8122).

Similarly to trocar actuation rod (8022) described above, trocar actuation rod (8122) of the present example comprises a proximal part (8124) and a distal part (8126). However, unlike proximal part (8024) described above, proximal part (8124) of the present example comprises a slotted female end (8125), while distal part (8126) comprises an elongate male end (8127). As will be described in greater detail below, male end (8127) of distal part (8126) is configured to be inserted into female end (8125) of proximal part (8124) such that parts (8124, 8126) of trocar actuation rod (8122) may be releasably coupled by coupling member (8180). Trocar actuation rod (8122) translates longitudinally in response to rotation of knob (8130) to adjust the longitudinal position of the anvil and the trocar relative to the stapling head assembly. Since coupling member (8180) is disposed in both parts (8124, 8126) of trocar actuation rod (8122), coupling member (8180) will translate longitudinally with trocar actuation rod (8122). Casing (8112) may include a slot and/or any other suitable features to accommodate such translation of coupling member (8180) relative to casing (8112) as trocar actuation rod (8122) translates relative to casing (8112). In addition, casing (8112) may include a slot and/or any other suitable features to accommodate translation of release member (8172) that may occur relative to casing (8112) as coupling member (8180) and trocar actuation rod (8122) translate relative to casing. Thus, while bailout assembly (8170) is in a neutral position, bailout assembly (8170) holds parts (8124, 8126) together and allows trocar actuation rod (8122) to translate as the operator adjusts the position of the anvil and trocar.

FIGS. 148 and 33 show an exemplary mode of operation of anvil bailout assembly (8170). As can be seen in FIG. 148, anvil bailout assembly (8170) initially begins in a neutral position. In the initial position, anvil bailout assembly (8170) is positioned such that operation of instrument (8100) is not substantially impacted by anvil bailout assembly (8170). In particular, release member (8172) is disposed relatively flush with handle assembly (8110). With release member (8172) in such a position, coupling member (8180) is disposed in opening (8183) of trocar actuation rod (8122), thereby coupling proximal and distal ends (8124, 8126) of trocar actuation rod (8122) together. Although trocar actuation rod (8122) is coupled via coupling member (8180), it should be understood that trocar actuation rod (8122) remains relatively free to translate as the operator rotates knob (8130).

In some instances, an operator may desire to quickly bail out of an anastomosis procedure. This may require quickly releasing the trocar and anvil to unload the compression on tissue that is clamped between the anvil and the stapling head assembly. To release the trocar and anvil, the operator may transition anvil bailout assembly (8170) to a released position as shown in FIG. 149. As can be seen, to transition anvil bailout assembly (8170) to the released position, an operator may grasp gripping portion (8173) of release member (8172) and pull release member (8172) outwardly away from handle assembly (8110). Pulling release member (8172) outwardly causes release member (8172) to pivot about pin (8177). Such pivoting motion of release member (8172) correspondingly pulls coupling member (8180) out of opening (8123) in trocar actuation rod (8122). With coupling member (8180) pulled from opening (8123), distal part (8126) of trocar actuation rod (8122) is permitted to decouple from proximal part (8124) of trocar actuation rod (8122), thereby relieving compression being applied to the tissue by the anvil against the stapling head assembly.

In some instances it may be desirable for instrument (8100) to also include features to quickly release a cylindraceous knife member (8150), similar to cylindraceous knife member (340) described above. For instance, as described above with respect to knife member (340), knife member (8150) may be driven separately from the anvil. Thus, in such examples it may be desirable to include a knife bailout assembly (8190) to quickly release knife member (8150) in addition to or in lieu of anvil bailout assembly (8170).

FIG. 150 shows instrument (8100) of the present example equipped with knife bailout assembly (8190). Knife bailout assembly (8190) comprises a pair of cables (8192), a force director (8194), and a pair of pins (8196). Cables (8192) extend proximally from the distal end of shaft assembly (8120) to the handle assembly (8110). Although not shown, it should be understood that in the present example, the proximal end of cables (8192) are attachable to release member (8172) of anvil bailout assembly (8170) such that actuation of anvil bailout assembly (8170) also results in actuation of knife bailout assembly (8190). In examples where knife bailout assembly (8190) is included in lieu of anvil bailout assembly (8170), it should be understood that handle assembly (8110) may include features such as levers, triggers, or etc. that permit actuation of knife bailout assembly (8190) from handle assembly (8110). It should also be understood that, in examples where both anvil bailout assembly (8170) and knife bailout assembly (8190) are included, assemblies (8170, 8190) may be actuated by separate, independently operable release members.

The distal ends of cables (8192) are threaded through force director (8194). In particular, force director (8194) is secured to stationary inner core member (8132), which is similar to inner core member (312). Force director (8194) includes a pair of redirecting features (8195) that redirect each cable (8192) approximately 90° from a longitudinal travel direction to a transverse travel direction. As will be described in greater detail below, such a redirection permits cables (8192) to actuate pins (8196). Although not shown, it should be understood that redirecting features (8195) may comprise friction management features such as wheels, pulleys, ball bearings, etc. to permit cables (8192) to move smoothly with low friction over redirecting features (8195).

Each pin (8196) is attached to the distal end of a corresponding cable (8192). An outwardly extending portion (8198) of each pin (8196) extends laterally though an opening (8151) in knife member (8150) and into a staple driver member (8135), which is similar to staple driver member (350). Pins (8196) thus releasably couple knife member (8150) to staple driver member (8135). As will be described in greater detail below, pins (8196) generally function to permit knife member (8150) to function as similarly described above with respect to knife member (340) until knife bailout assembly (8190) is actuated by an operator. Knife member (8150) and staple driver member (8135) will operate just like knife member (340) and staple driver member (350) as described above when knife member (8150) is secured to staple driver member (8135) via pins (8196).

FIGS. 151-152 show an exemplary mode of operation of knife bailout assembly (8190). As can be seen in FIG. 151, knife bailout assembly (8190) is initially in a neutral state where knife bailout assembly (8190) does not generally impact the operation of instrument (8100). As can be seen, in the neutral state, each pin (8196) is positioned through knife member (8150) and into staple driver member (8135). This positioning permits the normal operation of knife member (8150) by permitting a feature of shaft assembly (8120) similar to stapling head assembly driver (240) to actuate knife member (8150) and staple driver member (8135) together. Each cable (8192) is correspondingly relatively free from tension to permit each pin (8196) to move along with knife member (8150). In other words, cables (8192) provide enough slack to freely accommodate distal travel of knife member (8150) and staple driver member (8135) as knife member (8150) and staple driver member (8135) are actuated during normal operation.

If an operator desires to release knife member (8150) to abort or otherwise bail out of an anastomosis procedure, an operator may actuate knife bailout assembly (8190) to the position shown in FIG. 152. FIG. 152 shows knife bailout assembly (8190) is in a released state. In the released state, each pin (8196) is pulled from opening (8151) of knife member (8150) such that knife member (8150) is no longer held in position by each pin (8196). To pull each pin (8196) from opening (8151) of knife member (8150), the operator may apply tension to each cable (8192) by pulling proximally on cables (8192). In examples where knife bailout assembly (8190) is included in addition to anvil bailout assembly (8170), cables (8192) may be pulled by actuating release member (8172) of anvil bailout assembly (8170) or by actuating a separate feature that is independent of anvil bailout assembly (8170). In examples where knife bailout assembly (8190) is included in lieu of anvil bailout assembly (8170), the tensioning of cables (8192) may comprise actuating a lever arm, wheel, or other feature. Alternatively, cables (8192) may merely extend from handle assembly (8110) and an operator may simply pull directly on cables (8192) themselves.

When knife bailout assembly (8190) is in a released state, tissue that has not yet been cut by knife member (8150) may drive knife member (8150) proximally to or toward the position shown in FIG. 152. In some versions where an anvil bailout assembly (8170) is included in addition to a knife bailout assembly (8190), the operator may wish to actuate knife bailout assembly (8190) first and then actuate anvil bailout assembly (8170). This may facilitate removal of anvil (8104) from the patient, particularly when non-severed tissue might otherwise be stuck between knife member (8150) and anvil (8104).

XIV. Exemplary Alternative Bailout Features

A. Exemplary Bailout Door

FIG. 153 shows still another exemplary alternative instrument (8200) that may be used to provide an end-to-end anastomosis between two sections of an anatomical lumen such as a portion of a patient's digestive tract. It should be understood that instrument (8200) of the present example is substantially the same as instrument (10) described above unless otherwise noted herein. For instance, like with instrument (10), instrument (8200) comprises a handle assembly (8210), a shaft assembly (8220), and a stapling head assembly (8232). Handle assembly (8210) comprises a casing (8212) and is substantially the same has handle assembly (110) described above such that further details will not be described herein.

Like with instrument (10) described above, instrument (8200) is controlled by an operator via knob (8230) and triggers (8240, 8242). Knob (8230), like with knob (130) described above, is operatively connected to shaft assembly (8220) to actuate an anvil (8234) of stapling head assembly (8232). In particular, knob (8230) is rotatable to engage threads (not shown) of the shaft assembly to translate a trocar actuation rod (not shown), which ultimately actuates anvil (8234) as similarly described above with respect to shaft assembly (200) of instrument (10).

Triggers (8240, 8242) function similarly as triggers (140, 150) described above. For instance, a safety trigger (8240) may be first actuated by an operator to permit activation of stapling head assembly (8232). Instrument (1200) further includes a firing trigger (8242), which is similar to firing trigger (150) described above. In particular, once safety trigger (8240) has been activated, firing trigger (8242) is operable to initiate actuation of stapling head assembly (8232). Firing trigger (8242) is configured to engage a motor activation module (not shown) when firing trigger (8242) is advanced by an operator. Like with motor activation module (180) described above, the motor activation module of the present example initiates the stapling sequence by activating a motor (not shown). The motor then drives a cam member (not shown), which in turn drives a cam follower (not shown). The cam member and the cam follower are substantially the same as cam member (700) and cam follower (600) described above, such that the cam member and the cam follower operate cooperatively to drive stapling head assembly (8232) through a stapling sequence.

Unlike instrument (10) described above, instrument (8200) of the present example comprises a shaft rotation knob (8290). Shaft rotation knob (8290) is disposed distally of handle assembly (8210) and is configured to rotate shaft assembly (8220). In particular, shaft rotation knob (8290) permits an operator to rotate shaft assembly (8220) 360° in either a clockwise or counter clockwise direction (as shown in phantom in FIG. 153) about a longitudinal axis extending distally from handle assembly (8210). Although not shown, it should be understood that in some examples all or some of the internal components of shaft assembly (8220) may be rotatable to facilitate rotation of shaft assembly (8220). Of course, shaft rotation knob (8290) is merely optional and may be omitted in some examples. The rotatability of shaft assembly (8220) is not at all required for any of the other teachings herein to apply.

Also unlike instrument (10) described above, instrument (8200) of the present example comprises a bailout door (8213). Bailout door (8213) comprises a removable portion of casing (8212) and is generally configured to selectively cover certain bailout features (8270) as will be described in greater detail below. As is best seen in FIG. 154, bailout door (8213) comprises a plurality of latch features (8214) and an actuation member (8215). Latch features (8214) are configured to selectively secure bailout door (8213) to handle assembly (8210) through a snap fit. In some examples, latch features (8214) may be resiliently biased or otherwise configured to act as a latch, button, or lever to permit release of bailout door (8213) from handle assembly (8210).

Actuation member (8215) protrudes laterally from bailout door (8213). Actuation member (8215) is generally configured to engage features that are covered by bailout door (8213). In particular, and as will be described in greater detail below, actuation member (8215) is configured to engage a switch (8280) that is disposed inside casing (8212) to signal to instrument (8200) when bailout door (8213) is removed.

As described above, bailout door (8213) is configured to cover bailout features (8270) of instrument (8200). Bailout features (8270) of the present example comprise a release member (8272) and a switch (8280). Release member (8272) is similar to release members (8072, 8172) described above with respect to instruments (8000, 8100). Although not shown, it should be understood that release member (8272) of the present example is in communication with certain bailout mechanisms (not shown). The bailout mechanisms may comprise mechanisms similar to those described above with respect to anvil bailout assembly (8070), anvil bailout assembly (8170), and/or knife bailout assembly (8190) of instruments (8000, 8100) described above. Of course, any other suitable bailout mechanisms may be used as will be apparent to those of ordinary skill in the art in view of the teachings herein.

Switch (8280) is in communication with internal circuitry of instrument (8200). As described above, switch (8280) is configured to be actuated by actuation member (8215) of bailout door (8213). This relationship between switch (8280) and actuation member (8215) permits switch (8280) to communicate to the internal circuitry of instrument (8200) whether bailout door (8213) is attached or removed from handle assembly (8210). Although not shown, it should be understood that the internal circuitry of instrument (8200) may be configured to deactivate motors or other actuators of instrument (8200) upon receiving a signal from switch (8280) that bailout door (8213) has been removed. Thus, switch (8280) is configured to operate as a bailout feature by powering instrument (8200) off when bailout door (8213) is removed. Alternatively, in some examples switch (8280) may activate a reversing sequence that causes instrument (8200) to return to an unactuated state (e.g., the state prior to initiation of a surgical procedure). Of course, some other versions may provide no impact at all on any drive components when switch (8280) is actuated or non-actuated.

Instrument (8200) of the present example further includes an indicator (8216). Indicator (8216) is generally configured to display the status of instrument (8200), including communicating to an operator whether bailout door (8213) has been removed. Indicator (8216) of the present example may be included in addition or in lieu of a window (not shown) similar to window (114) of instrument (10) described above. Indicator (8216) of the present example comprises a liquid crystal display (LCD) screen, although any other suitable mechanism may be used such as light emitting diodes or mechanically driven needle indicators. Indicator (8216) is in communication with switch (828) such that indicator (8216) is configured to provide a visual indication that bailout door (8213) has been removed. In addition or in the alternative, indicator (8216) may provide a visual indication that release member (8272) has been actuated. Various suitable ways in which indicator (8216) may provide one or more indications, and various ways in which indicator (8216) may be triggered to provide such indications, will be apparent to those of ordinary skill in the art in view of the teachings herein.

B. Exemplary Manual Stapling Head Assembly Bailout Feature

FIGS. 155-156 show yet another exemplary alternative instrument (8300) that may be used to provide an end-to-end anastomosis between two sections of an anatomical lumen such as a portion of a patient's digestive tract. It should be understood that instrument (8300) of the present example is substantially the same as instrument (10) described above unless otherwise noted herein. For instance, like with instrument (10), instrument (8300) comprises a handle assembly (8310), a shaft assembly (8320), a stapling head assembly (not shown), and an anvil (not shown). Handle assembly (8310) comprises as casing (8312) is substantially the same has handle assembly (110) described above such that further details will not be described herein.

Like with instrument (10) described above, instrument (8300) is controlled by an operator via knob (8330) and triggers (8340, 8342). Knob (8330), like with knob (130) described above, is operatively connected to shaft assembly (8320) to actuate the anvil of the stapling head assembly. In particular, knob (8330) is rotatable to engage threads (not shown) of the shaft assembly to translate a trocar actuation rod (8322), which ultimately actuates the anvil as similarly described above with respect to shaft assembly (200) of instrument (10).

Triggers (8340, 8342) function similarly as triggers (140, 150) described above. For instance, a safety trigger (8340) may be first actuated by an operator to permit activation of stapling head assembly (8332). Instrument (8300) further includes a firing trigger (8342), which is similar to firing trigger (150) described above. In particular, once safety trigger (8340) has been activated, firing trigger (8342) is operable to initiate actuation of the stapling head assembly. Firing trigger (8342) is configured to engage a motor activation module (not shown) when firing trigger (8242) is advanced by an operator. Like with motor activation module (180) described above, the motor activation module of the present example initiates the stapling sequence by activating a motor (8350).

As best seen in FIG. 157, motor (8350) is operable to drive a cam member (8352), which in turn drives a cam follower (8354) to drive a bracket (8355) and stapling head assembly driver (8356) similar to bracket (250) and stapling head assembly driver (240), respectively, described above. Cam member (8352) is substantially the same as cam member (700) described above. Cam follower (8352) is substantially the same as cam follower (600) described above. Bracket (8355) is substantially the same as bracket (250) described above. Stapling head assembly driver (8356) is substantially the same as sapling head assembly driver (240). Thus, the stapling head assembly of instrument (8300) is driven just like stapling head assembly (300) described above.

Unlike instrument (10) described above, instrument (8200) of the present example comprises an anvil bailout assembly (8370) and a side window (8380). Anvil bailout assembly (8370) includes a release member (8372) that is similar to release members (8072, 8172) described above. Although not shown, it should be understood that release member (8372) is in communication with various mechanisms similar to those described above with respect to anvil bailout assemblies (8070, 8170) of instruments (8000, 8100) described above. Thus, anvil bailout assembly (8370) is operable to selectively release the anvil by pivoting release member (8372) like with anvil bailout assemblies (8070, 8170) of instruments (8000, 8100) described above. In other words, bailout assembly (8370) is operable to quickly release tension in trocar actuation rod (8355), thereby quickly releasing any compressive force supplied by the anvil during an anastomosis procedure.

Side window (8380) is similar in function to window (114) described above with respect to instrument (10). However, unlike window (114), side window (8380) is disposed on the side of handle assembly (8310). Although not shown, it should be understood that in some examples side window (8380) may be positioned on both sides of handle assembly (8310) because such positioning may generally promote ease of use. In some versions, side window (8380) includes an indicator (8382) that is operable to indicate a load being applied to instrument (8300). For instance, indicator (8382) may indicate a compressive load being applied to stapling head assembly driver (8356). Various suitable features that may be used to couple indicator (8382) with stapling head assembly driver (8356) to enable indicator (8382) to indicate the load being applied to stapling head assembly driver (8356) will be apparent to those of ordinary skill in the art in view of the teachings herein. As another merely illustrative example, indicator (8382) may indicate a compressive load being applied to trocar actuation rod (8322). Various suitable features that may be used to couple indicator (8382) with trocar actuation rod (8322) to enable indicator (8382) to indicate the load being applied to trocar actuation rod (8322) will be apparent to those of ordinary skill in the art in view of the teachings herein. Similarly, various suitable forms that indicator (8382) may take will be apparent to those of ordinary skill in the art in view of the teachings herein. Alternatively, indicator (8382) may be omitted.

Also unlike instrument (10) described above, instrument (8300) of the present example comprises a manual stapling head assembly bailout knob (8390). Bailout knob (8390) is generally configured to move telescopically and rotate to selectively rotate motor (8350) to thereby actuate stapling head assembly driver (8356) manually. As can be seen in FIGS. 156-157, bailout knob (8390) is configured to selectively communicate with a manual driver (8351) protruding proximally from motor (8350). Manual driver (8351) is in direct communication with a drive shaft (8353) of motor (8350). Thus, when bailout knob (8390) is coupled with driver (8351), rotation of bailout knob (8390) results in corresponding rotation of drive shaft (8353). Otherwise, drive shaft (8353) is driven by motor (8350) during normal operation of instrument (8300).

As described above, bailout knob (8390) is configured to selectively communicate with manual driver (8351) of motor (8350). In particular, casing (8312) of handle assembly (8310) comprises knob attachment features (8313), which are configured to translatably and rotatably fasten bailout knob (8390) to handle assembly (8310). Attachment features (8313) of the present example are spring loaded to resiliently bias a drive feature (8392) of bailout knob (8390) away from manual driver (8351). Thus, bailout knob (8390) is initially positioned by attachment features (8313) such that drive feature (8392) is disengaged from manual driver (8351), such that rotation of bailout knob (8390) has no impact on instrument (8300).

In an exemplary mode of operating bailout knob (8390), an operator may manually retract stapling head assembly driver (8356), thereby manually retracting staple driver member (350) and knife member (340) proximally, by actuating bailout knob (8390). In particular, the operator may first push bailout knob (8390) distally toward motor (8350) to engage drive feature (8392) of bailout knob (8390) with manual driver (8351) of motor (8350). Once drive feature (8392) is engaged with manual driver (8351), the operator may rotate bailout knob (8390) to manually actuate drive shaft (8353). Such rotation in turn drives drive cam member (8352). Cam member (8352) then drives cam follower (8354) to thereby retract bracket (8355) and stapling head assembly driver (8356) proximally. In some instances, the operator may be prompted to actuate bailout knob (8390) in this fashion in response to indicator (8382) indicating that stapling head assembly driver (8356) is experiencing an undesirably high compressive load.

XV. Exemplary Alternative Stapling Head Actuation Assembly

FIG. 158 shows an exemplary stapling head actuation assembly (8470) that may be readily incorporated into instruments (10, 8000, 8100, 8200, 8300) described above. It should be understood that stapling head actuation assembly (8470) of the present example may be used in lieu of cam member (700) and cam follower (600) described above with respect to instrument (10). Stapling head actuation assembly (8470) comprises a first drive shaft (8472), a second drive shaft (8480), and a lead screw assembly (8490). First drive shaft (8472) is in communication with a motor (8450) that is similar to motor (160) described above with respect to instrument (10). In particular, motor (8450) includes a motor gear (8451) that meshes with a corresponding drive gear (8474) on first drive shaft (8472). Thus, motor (8450) is configured to drive first drive shaft (8472) via motor gear (8451) and drive gear (8474).

The end of first drive shaft (8472) opposite to drive gear (8474) includes a first slip gear (8476). First slip gear (8476) comprises a crown gear and is configured to mesh with a corresponding second slip gear (8482) of second drive shaft (8480). As will be described in greater detail below, first slip gear (8476) together with second slip gear (8482) are configured to act as a clutch to prevent stapling head actuation assembly (8470) from exerting more than a predetermined amount of force on tissue via a stapling head assembly.

As described above, second drive shaft (8480) comprises second slip gear (8482) that is in communication with first slip gear (8476) of first drive shaft (8472). Like first slip gear (8476), second slip gear (8482) of the present example comprises a crown gear. A resilient member (8484) is disposed adjacent to second slip gear (8482). Resilient member (8484) of the present example is shown as a coil spring, although any suitable resilient mechanism may be used. Resilient member (8484) bears against second slip gear (8482) to urge second slip gear (8482) into engagement with first slip gear (8476). As will be described in greater detail below, this permits first slip gear (8476) and second slip gear (8482) to act as a clutch for motor (8450).

The end of second drive shaft (8480) opposite to second slip gear (8482) includes a bevel gear (8486). Bevel gear (8486) is configured to mesh with a corresponding spur gear (8492) of lead screw assembly (8490). As will be described in greater detail below, bevel gear (8486) generally configured to be driven by second drive shaft (8480) to drive shaft (8480) to drive lead screw assembly (8490). In some alternative versions, gears (8486, 8492) comprise complementary helical gears.

Lead screw assembly (8490) comprises spur gear (8492) and a lead screw member (8496). As described above, spur gear (8492) is configured to mesh with bevel gear (8486) of second drive shaft (8480). Additionally, spur gear (8492) comprises an opening (8494) in spur gear (8492). Opening (8494) is configured to receive lead screw member (8496). The inner diameter of opening (8494) includes a series of threads (not shown). As will be described in greater detail below, the threads of opening (8494) are configured to engage with corresponding threads (8498) of lead screw member (8496) to thereby drive lead screw member (8496), spur gear (8492) serves as a drive nut.

Lead screw member (8496) is generally cylindrical in shape. Lead screw member (8496) further comprises threads (8498) on its outer diameter. The distal end of lead screw member (8496) is rotatably secured to a stapling head assembly driver (8456). As will be described in greater detail below, lead screw member (8496) is generally configured to translate via engagement between threads (8498) of lead screw member and the threads of spur gear (8492) to drive stapling head assembly via stapling head assembly driver (8456).

In an exemplary mode of operation, motor (8451) drives first drive shaft (8472) via gars (8451, 8474). First drive shaft (8472) then drives second drive shaft (8480) via slip gears (8476, 8482). Second drive shaft (8480) then drives lead screw assembly (8490) via bevel gear (8486) and spur gear (8492). In particular, spur gear (8482) is rotated by bevel gear (8486). As spur gear (8482) is rotated, the threads of the inner diameter of opening (8494) in spur gear (8482) engage threads (8498) of lead screw member (8496). Engagement between the threads of opening (8494) and threads (8498) of lead screw member (8496) drive lead screw member (8496) distally. As lead screw assembly (8490) is driven distally, stapling head assembly driver (8456) is correspondingly driven distally to actuate the stapling head assembly.

As the stapling head assembly is actuated to drive a knife member and staples through tissue, the torque required to drive lead screw assembly (8490) increases. Generally, slip gears (8476, 8482) are configured to communicate rotation of first drive shaft (8472) to drive second drive shaft (8480) until a predetermined amount of torque is reached. Then slip gears (8476, 8482) will begin to slip relative to each other. As can be seen in FIG. 159, resilient member (8484) of second drive shaft (8480) urges slip gears (8476, 8482) into engagement. However, when the amount of torque required to communicate rotation of first drive shaft (8472) to drive second drive shaft (8480) exceeds a certain threshold, resilient member (8484) will compress and slip gears (8476, 8482) will begin to slip as shown in FIG. 160 such that rotation of first drive shaft (8472) is no longer communicated to drive second drive shaft (8480). Thus, slip gears (8476, 8482) act as a clutching mechanism to restrict the force that may be used to actuate stapling head assembly. Such restriction may be desirable to prevent failure of an anastomosis that might otherwise be at least partially created by the stapling head assembly. In other words, when an unusually high amount of torque is required to actuate the stapling head assembly, this may indicate a problem that may create a risk of a failed anastomosis. It may be better for the outcome of the procedure if the stapling head assembly is not fully actuated under such conditions. The slipping of slip gears may thus provide no anastomosis in lieu of providing a failed or risky anastomosis.

XVI. Exemplary Alternative Stapling Head Actuation Assemblies

In some instances, it may be desirable to provide an alternative assembly to actuate stapling head assembly (300). Such an alternative actuation assembly may be integrated into instrument (10) in place of the actuation assembly shown in FIGS. 13-20D and described above. Such an alternative actuation assembly may be driven by motor (160) and may provide both distal translation of stapling head assembly driver (240) and proximal translation of stapling head assembly driver (240) in response to rotation by motor (160) in just a single angular direction (e.g., through an angular range of just less than 360°). Such an alternative actuation assembly may also be used in conjunction with gearbox (162) or may permit gearbox (162) to be omitted altogether. Regardless, such an alternative actuation assembly may be capable of providing a high drive load that is sufficient to fully actuate stapling head assembly (300), including breakage of a breakable washer within annular recess (418) of anvil (400) if such an anvil (400) is used. Several merely illustrative examples of alternative assemblies to actuate stapling head assembly (300) are described in greater detail below. It should be understood that the assemblies described below may be readily incorporated into instrument (10) in place of the actuation assembly shown in FIGS. 13-20D and described above.

A. Rotary Link Based Firing and Return System

FIG. 161 shows various components of a stapling head actuation assembly (9000) that is operable to actuate stapling head assembly (300). These components include a motor (9001), a motor drive shaft (9007) that is driven by motor (9001), a primary drive gear (9022), an idler gear (9022), an idler shaft (9024), a secondary drive gear (9014), a rotary member (9013), a link (9009), a drive bracket (9004), and a stapling head assembly driver (9005). Motor (9001) is similar to motor (160) described above. In particular, motor (9001) is coupled with motor drive shaft (9007) and is further coupled with drive gear (9020). Therefore, activation of a motor (9001) causes rotation of drive gear (9020). Various suitable configurations that may be used for motor (9001) will be apparent to those of ordinary skill in the art in view of the teachings herein.

In the present example, assembly (9000) lacks a gearbox that is analogous to gearbox (162), though it should be understood that a gearbox and/or any other suitable components may be interposed between motor (9001) and drive gear (9020) to provide desired operational characteristics (e.g., torque, speed, etc.). Idler gear (9022) meshes with drive gear (9020) such that rotation of drive gear (9020) will rotate idler gear (9022). Idler gear (9022) is fixedly secured to idler shaft (9024). Drive gear (9014) is also fixedly secured to idler shaft (9024). It should therefore be understood that rotation of drive gear (9020) will rotate drive gear (9014) via idler gear (9022) and idler shaft (9024). Of course, any other suitable components may be interposed between motor (9001) and drive gear (9014). For instance, FIGS. 162A-162C show a variation of stapling head actuation assembly (9000) where gears (9020, 9022) and idler shaft (9024) are omitted. In this variation, drive gear (9014) is secured to drive shaft (9007) and is thereby driven directly by motor (9001).

In the version of stapling head actuation assembly (9000) shown in FIG. 161 and the version of stapling head actuation assembly (9000) shown in FIGS. 162A-162C, rotary member (9013) is pivotably fixed to casing (9003) via pin (9011). Drive gear (9014) is configured to rotate rotary member (9013) in a clockwise angular direction about a pin (9011) as will be described in greater detail below. Pin (9011) is coupled with casing (9003), such that rotary member (9013) is only capable of rotating relative to casing (9003). Casing (9003) of this example is substantially similar to casing (110) described above.

Trocar actuation rod (9002) is substantially similar to trocar actuation rod (220) described above. In the present example, trocar actuation rod (9002) is presumed to be located at a position to define a desirable "clinically acceptable range" for gap distance (d). So while trocar actuation rod (9002) is in fact movable, trocar actuation rod (9002) is assumed to be stationary through the stages shown in FIGS. 162A-162C.

Drive bracket (9004) is substantially similar to drive bracket (250) described above, except that drive bracket (9004) is pivotably coupled to link (9009) via pin (9008) instead of being pivotably coupled to cam follower (600). Drive bracket (9004) is fixed to stapling head assembly driver (9005) via pin (9006). However, drive bracket (9004) and stapling head assembly driver (9005) may instead be formed as a single unitary piece if desired. Stapling head assembly driver (9005) is substantially similar to stapling head assembly driver (240) described above. Therefore, it should be understood that staple driver member (350) will translate longitudinally relative to trocar actuation rod (9002) in response to translation of stapling head assembly driver (9005) and drive bracket (9005) relative to trocar actuation rod (9002).

Rotary member (9013) includes a semi-annular array of laterally presented teeth (9012) on one side of pin (9011) and a rotary arm (9015) on the other side of pin (9011). Teeth (9012) extend along a quarter-pie angular range perimeter of rotary member (9013). Teeth (9012) are configured to complement drive gear (9014) in such a way that rotation of drive gear (9014) drives rotary member (9013) in an angular direction about pin (9011). Once drive gear (9014) reaches the termination of the quarter-pie perimeter of rotary member (9013), drive gear (9014) and teeth (9013) may disengage in such a manner that rotary member (9013) is no longer is capable of engaging drive gear (9014). After drive gear (9014) and teeth (9013) disengage, rotary member (9013) is then incapable of angular movement about pin (9011). In the present example, however, motor (9001) is not activated in a manner that would provide disengagement of drive gear (9014) from teeth (9013). Instead, motor (9001) is deactivated before drive gear (9014) disengages teeth (9013).

Rotary arm (9015) extends generally tangentially in relation to pin (9011) and pivotably couples to link (9009) via pin (9010). Link (9009) is also pivotably coupled to drive bracket (9004) via pin (9008). While rotary member (9013) is limited to rotational movement about pin (9011), and drive bracket (9004) is limited to linear translation relative to outer sheath (210), link (9009) is capable of both linear translation and rotation. Therefore, link (9009) converts the angular movement of rotary member (9013) into linear movement of drive bracket (9004). In other words, the angular position of rotary member (9013) directly corresponds to a linear position of drive bracket (9004).

FIGS. 162A-162C schematically depict the interaction between drive gear (9014), rotary member (9013), link (9009), drive bracket (9004), and stapling head assembly driver (9005). It should be understood that the rotation of drive gear (9014) throughout the stages shown in FIGS. 162A-162C is driven by motor (9001). It should also be understood that the variation of stapling head actuation assembly (9000) shown in FIG. 161 will operate substantially identically to the variation of stapling head actuation assembly (9000) shown in FIGS. 162A-162C.

FIG. 162A shows stapling head actuation assembly (9000) in a first, pre-firing configuration. Drive gear (9014) is located on a proximal portion of the semi-annular array of teeth (9012). The angular location of rotary member (9013), and therefore the angular location of rotary arm (9015) as shown in FIG. 162A corresponds to the most proximal location of drive bracket (9004). At this stage, the proximal end of link (9009), as defined by pin (9010) is located at its highest vertical placement relative to the distal end of link (9009), as defined by pin (9008). At this stage, knife member (340) and staple driver member (350) are in proximal positions, such that stapling head assembly driver (9005) and therefore stapling head assembly (300) are in a non-actuated state.

As drive gear (9014) is rotated by motor drive shaft (9007), this causes drive gear (9014) to travel along the semi-annular array of teeth (9012), thereby rotating rotary member (9013) about pin (9011) to the position shown in FIG. 162B. The angular location of rotary member (9013), and therefore the angular location of rotary arm (9015) as shown in FIG. 162B, corresponds to the most distal location of drive bracket (9004). Rotary member (9013) and link (9009) thus drive knife member (340) and staple driver member (350) distally via drive bracket (9004) and stapling head assembly driver (9005). Stapling head assembly (300) is thus in an actuated state at the stage shown in FIG. 162B. In the present example, drive gear (9014) is located at a position that is approximately mid-way along the length of the semi-annular array of teeth (9012) at the stage shown in FIG. 162B.

At the stage shown in FIG. 162B, pins (9008, 9010, 9011) are aligned with each other along a single axis. It is important to note that at this point, the proximal end of link (9009), as defined by pin (9010) is located at the same vertical level relative to the distal end of link (9009), as defined by pin (9008). This occurs because vertically fixed pins (9011, 9008) are located at the same vertical level. While this placement is optional, it may provide optimal torque to force transfer while knife member (340) and staple driver member (350) are in their most distal position, helping ensure knife member (340) and staple driver member (350) properly operate. However, as described below, this placement of vertically fixed pins (9011, 9008) is optional.

After stapling head assembly (300) has been actuated through a full distal drive stroke as shown in the transition from FIG. 162A to FIG. 162B, drive gear (9014) continues to rotate in the same angular direction, therefore rotating rotary member (9013) to the position shown in FIG. 162C. At this stage, rotary arm (9015) and link (9009) have pulled drive bracket (9004) and stapling head assembly driver (9005) proximally. The proximal end of link (9009), at pin (9010), is located at a vertical level that is lower than the vertical level of the distal end of link (9009), at pin (9008). At this stage, knife member (340) and staple driver member (350) are back to proximal positions, such that stapling head assembly driver (9005) and therefore stapling head assembly (300) are back in a non-actuated state. In the present example, drive gear (9014) is located at the distal end of the semi-annular array of teeth (9012) at the stage shown in FIG. 162C.

Optionally, rotary gear (9014) may keep rotating past the location shown on FIG. 162C so that teeth (9012) disengage from drive gear (9014). This may help ensure that actuation of knife member (340) and staple driver member (350) only occurs once. Additionally or alternatively, motor (9001) may be utilized to rotate drive shaft (9007) in one direction. Therefore, the quarter-pie array of teeth (9012) ensures that actuation of knife member (340) and staple driver member (350) only occurs once.

FIGS. 163A-163C show various components of another exemplary stapling head actuation assembly (9400) that is operable to actuate stapling head assembly (300). These components include a motor (9401), a motor drive shaft (9407) that is driven by motor (9401), a drive gear (9414), a rotary member (9413), a link (9409), a drive bracket (9404), and a stapling head assembly driver (9405). Motor (9401) is similar to motor (160) described above. In particular, motor (9401) is coupled with motor drive shaft (9407) and is further coupled with drive gear (9414). Therefore, activation of motor (9401) causes rotation of drive gear (9414). Various suitable configurations that may be used for motor (9401) will be apparent to those of ordinary skill in the art in view of the teachings herein. In the present example, assembly (9400) lacks a gearbox that is analogous to gearbox (162), though it should be understood that a gearbox and/or any other suitable components may be interposed between motor (9401) and drive gear (9414) to provide desired operational characteristics (e.g., torque, speed, etc.).

Rotary member (9413) is pivotably fixed to casing (9403) via pin (9411). Drive gear (9414) is configured to rotate rotary member (9413) in an angular direction about a pin (9411) as will be described in greater detail below. Pin (9411) is coupled with casing (9403), such that rotary member (9413) is only capable of rotating relative to casing (9403). Casing (9403) is substantially similar to casing (110) described above.

Trocar actuation rod (9402) is substantially similar to trocar actuation rod (220) described above. In the present example, trocar actuation rod (9402) is presumed to be located at a position to define a desirable "clinically acceptable range" for gap distance (d). So while trocar actuation rod (9402) is in fact movable, trocar actuation rod (9402) is assumed to be stationary through the stages shown in FIGS. 163A-163C.

Drive bracket (9404) is substantially similar to drive bracket (250) described above, except that drive bracket (9404) is pivotably coupled to link (9409) via pin (9408) instead of being pivotably coupled to cam follower (600). Drive bracket (9404) is fixed to stapling head assembly driver (9405) via pin (9406). However, drive bracket (9404) and stapling head assembly driver (9405) may instead be formed as a single unitary piece if desired. Stapling head assembly driver (9405) is substantially similar to stapling head assembly driver (240) described above. Therefore, it should be understood that staple driver member (350) will translate longitudinally relative to trocar actuation rod (9402) in response to translation of stapling head assembly driver (9405) and drive bracket (9405) relative to trocar actuation rod (9402).

Rotary member (9413) includes a semi-annular array of laterally presented teeth (9412) on one side of pin (9411) and a rotary arm (9415) on the other side of pin (9411). Teeth (9412) extend along a quarter-pie angular range along the perimeter of rotary member (9413). Teeth (9412) are configured to complement drive gear (9414) in such a way that rotation of drive gear (9414) drives rotary member (9413) in an angular direction about pin (9411). Once drive gear (9414) reaches the termination of the array of teeth (9412), drive gear (9414) and teeth (9412) may disengage in such a manner that rotary member (9413) is no longer is capable of engaging drive gear (9414). After drive gear (9414) and teeth (9412) disengage, rotary member (9413) is then incapable of angular movement about pin (9411). In the present example, however, motor (9401) is not activated in a manner that would provide disengagement of drive gear (9414) from teeth (9412). Instead, motor (9401) is deactivated before drive gear (9414) disengages teeth (9412).

Rotary arm (9415) extends outwardly relative to pin (9411) and pivotably couples to link (9409) via pin (9410). Link (9409) is also pivotably coupled to drive bracket (9404) via pin (9408). While rotary member (9413) is limited to rotational movement about pin (9411) and drive bracket (9404) is limited to linear translation relative to outer sheath (210), link (9409) is capable of both linear translation and rotation. Therefore, link (9409) converts the angular movement of rotary member (9413) into linear movement of drive bracket (9404). In other words, the angular position of rotary member (9413) directly corresponds to a linear position of drive bracket (9404).

FIGS. 163A-163C schematically depict the interaction between drive gear (9414), rotary member (9413), link (9409), drive bracket (9404), and stapling head assembly driver (9405). It should be understood that the rotation of drive gear (9414) throughout the stages shown in FIGS. 163A-163C is driven by motor (9401).

FIG. 163A shows stapling head actuation assembly (9400) in a first, pre-firing configuration. Drive gear (9414) is located on a proximal portion of the semi-annular array of teeth (9412). The angular location of rotary member (9413), and therefore the angular location of rotary arm (9415) as shown in FIG. 163A, corresponds to the most proximal location of drive bracket (9404). At this stage, knife member (340) and staple driver member (350) are in proximal positions, such that stapling head assembly driver (9405) and therefore stapling head assembly (300) are in a non-actuated state.

As drive gear (9414) is rotated by motor drive shaft (9407), this causes drive gear (9414) to travel along the semi-annular array of teeth (9412), thereby rotating rotary member (9413) about pin (9411) to the position shown in FIG. 163B. The angular location of rotary member (9413), and therefore the angular location of rotary arm (9415) as shown in FIG. 163B, corresponds to the most distal location of drive bracket (9404). Rotary member (9413) and link (9409) thus drive knife member (340) and staple driver member (350) distally via drive bracket (9404) and stapling head assembly driver (9405). Stapling head assembly (300) is thus in an actuated state at the stage shown in FIG. 163B. In the present example, drive gear (9414) is located at a position that is approximately mid-way along the length of the semi-annular array of teeth (9412) at the stage shown in FIG. 163B. At the stage shown in FIG. 163B, pins (9408, 9410, 9411) are aligned with each other along a single axis, which is obliquely oriented relative to the longitudinal axis of stapling head assembly driver (9405). This placement is merely optional, providing alignment of pins (9408, 9410, 9411) along a single axis at this stage may After stapling head assembly (300) has been actuated through a full distal drive stroke as shown in the transition from FIG. 163A to FIG. 163B, drive gear (9414) continues to rotate in the same angular direction, therefore rotating rotary member (9413) to the position shown in FIG. 163C. At this stage, rotary arm (9415) and link (9409) have pulled drive bracket (9404) and stapling head assembly driver (9405) proximally. Thus, at this stage, knife member (340) and staple driver member (350) are back to proximal positions, such that stapling head assembly driver (9405) and therefore stapling head assembly (300) is back in a non-actuated state. In the present example, drive gear (9414) is located at the distal end of the semi-annular array of teeth (9412) at the stage shown in FIG. 163C.

Optionally, rotary gear (9414) may keep rotating past the location shown on FIG. 163C so that teeth (9412) disengage from drive gear (9414). This may help ensure that actuation of knife member (340) and staple driver member (350) only occurs once. Additionally or alternatively, motor (9401) may be utilized to rotate drive shaft (9407) in one direction. Therefore, the quarter-pie array of teeth (9412) ensures that actuation of knife member (340) and staple driver member (350) only occurs once.

B. Rotary Pawl Based Firing and Return System

FIGS. 164A-164B show various components of another exemplary stapling head actuation assembly (9100) that is operable to actuate stapling head assembly (300). These components include a motor (9101), a motor drive shaft (9107) that is driven by motor (9101), a drive gear (9114), a rotary member (9113), a pin (9116) coupled to a torsion spring (9110), a drive bracket (9104), and a stapling head assembly driver (9105). Motor (9101) is similar to motor (160) described above. In particular, motor (9101) is coupled with motor drive shaft (9107) and is further coupled with drive gear (9114). Therefore, activation of motor (9101) causes rotation of drive gear (9114). Various suitable configurations that may be used for motor (9101) will be apparent to those of ordinary skill in the art in view of the teachings herein. In the present example, assembly (9100) lacks a gearbox that is analogous to gearbox (162), though it should be understood that a gearbox and/or any other suitable components may be interposed between motor (9101) and drive gear (9114) to provide desired operational characteristics (e.g., torque, speed, etc.).

Rotary member (9113) is pivotably fixed to casing (9103) via pin (9111). Drive gear (9114) is configured to rotate rotary member (9113) in an angular direction about a pin (9111) as will be described in greater detail below. Pin (9111) is coupled with casing (9103), such that rotary member (9113) is only capable of rotating relative to casing (9103). Casing (9103) is substantially similar to casing (110) described above.

Trocar actuation rod (9102) is substantially similar to trocar actuation rod (220) described above. In the present example, trocar actuation rod (9102) is presumed to be located at a position to define a desirable "clinically acceptable range" for gap distance (d). So while trocar actuation rod (9102) is in fact movable, it is assumed to be stationary through the stages shown in FIGS. 164A-164B.

Drive bracket (9104) is substantially similar to drive bracket (250) described above, except that drive bracket (9104) defines a recess (9109) that receives pawl (9108) instead of being pivotably coupled to cam follower (600). Drive bracket (9104) is fixed to stapling head assembly driver (9105) via pin (9106). However, drive bracket (9104) and stapling head assembly driver (9105) may instead be formed as a single unitary piece if desired. Stapling head assembly driver (9105) is substantially similar to stapling head assembly driver (240) described above. Therefore, it should be understood that staple driver member (350) will translate longitudinally relative to trocar actuation rod (9102) in response to translation of stapling head assembly driver (9105) and drive bracket (9105) relative to trocar actuation rod (9102).

Rotary member (9113) includes a semi-annular array of teeth (9112) on one side of pin (9111) and a rotary arm (9115) on the other side of pin (9111). Teeth (9112) extend along a quarter-pie angular range along the perimeter of rotary member (9113). Teeth (9112) are configured to complement drive gear (9114) in such a way that rotation of drive gear (9114) drives rotary member (9113) in an angular direction about pin (9111). Once drive gear (9014) reaches the termination of the array of teeth (9112), drive gear (9114) and teeth (9112) may disengage in such a manner that rotary member (9113) is no longer is capable of engaging drive gear (9114). After drive gear (9114) and teeth (9112) disengage, rotary member (9113) is then incapable of angular movement about pin (9111). In the present example, however, motor (9101) is not activated in a manner that would provide disengagement of drive gear (9114) from teeth (9112). Instead, motor (9101) is deactivated before drive gear (9114) disengages teeth (9112).

Rotary arm (9115) extends outwardly relative to pin (9111) and pivotably couples to the proximal end of pawl (9108) via pin (9116). Pin (9116) is also coupled to resiliently biased torsion spring (9110). Torsion spring (9110) is attached to both pawl (9108) and rotary arm (9115). Distal end of pawl (9108) is located within recess (9109) of drive bracket (9104). Torsion spring (9110) is positioned in such a way as to bias pawl (9108) against the proximal portion of recess (9109), therefore biasing drive bracket (9104) in a proximal direction.

FIGS. 164A-164B schematically depict the interaction between drive gear (9114), rotary member (9113), pawl (9108), drive bracket (9104), and stapling head assembly driver (9105). It should be understood that the rotation of drive gear (9014) throughout the stages shown in FIGS. 164A-164B is driven by motor (9101).

FIG. 164A shows stapling head actuation assembly (9100) in a first, pre-firing configuration. Drive gear (9114) is located in a proximal portion of the semi-annular array of teeth (9112). The angular location of rotary member (9113), and therefore the angular location of rotary arm (9115) as shown in FIG. 164A, corresponds to the most proximal location of drive bracket (9104). Additionally, as mentioned before, pawl (9108) is resiliently biased against the proximal portion of recess (9109), therefore further pushing drive bracket (9104) in a proximal direction. At this stage, knife member (340) and staple driver member (350) are in proximal positions, such that stapling head assembly driver (9105) and therefore stapling head assembly (300) are in a non-actuated state.

As drive gear (9114) is rotated by motor drive shaft (9007), this causes drive gear (9014) to travel along the semi-annular array of teeth (9012), thereby rotating rotary member (9113) to the position shown in FIG. 164B. Rotary member (9113) pushes pawl (9108) against the distal portion of recess (9109), thereby actuating drive bracket (9104) and stapling head assembly driver (9105) in a distal direction. Stapling head assembly (300) is thus in an actuated state at the stage shown in FIG. 164B. Torsion spring (9110) has a spring constant strong enough to allow pawl (9108) to push drive bracket (9104) in the distal direction without having pawl (9108) over-rotate around pin (9116), thereby slipping out of recess (9109). In other words, torsion spring (9110) has a large enough spring contact to keep pawl (9108) within recess (9109) while pawl (9108) pushes drive bracket (9104) distally.

After stapling head assembly (300) has been actuated through a full distal drive stroke as shown in the transition from FIG. 164A to FIG. 164B, motor (9101) rotates shaft (9107) and gear (9114) in a reverse direction, thereby pivoting rotary arm (9115) about pin (9111) back to the position shown in FIG. 164A. As rotary arm (9115) pivots back to the position shown in FIG. 164A, pawl (9108) pulls drive bracket (9104) and stapling head assembly driver (9105) proximally back to the position shown in FIG. 164A. The bias imposed by torsion spring (9110) maintains engagement between pawl (9108) and bracket (9104). At this stage, knife member (340) and staple driver member (350) are back to proximal positions, such that stapling head assembly driver (9105) and therefore stapling head assembly (300) is back in a non-actuated state.

In some alternative versions, a resilient member resiliently urges drive bracket (9104) and stapling head assembly driver (9105) proximally, such that motor (9101) is simply deactivated to allow the resilient member to return drive bracket (9104) and stapling head assembly driver (9105) from the position shown in FIG. 164B back to the position shown in FIG. 164A. In such versions, deactivated motor (9101) may allow shaft (9107) to rotate freely. Thus, motor (9101) need not necessarily be reversed in order to return drive bracket (9104) and stapling head assembly driver (9105) from the position shown in FIG. 164B back to the position shown in FIG. 164A. Other suitable ways in which drive bracket (9104) and stapling head assembly driver (9105) may be returned from the position shown in FIG. 164B back to the position shown in FIG. 164A will be apparent to those of ordinary skill in the art in view of the teachings herein.

C. Direct Gear Based Firing and Return System

FIGS. 165A-165C show various components of another exemplary stapling head actuation assembly (9200) that is operable to actuate stapling head assembly (300). These components include a motor (9201), a motor drive shaft (9207) that is driven by motor (9201), a drive gear assembly (9209), a drive bracket (9204), and a stapling head assembly driver (9205). Motor (9201) is similar to motor (160) described above. In particular, motor (9201) is coupled with motor drive shaft (9207) and is further coupled with a first bevel gear (9212). Therefore, activation of motor (9201) causes rotation of first bevel gear (9212). Various suitable configurations that may be used for motor (9201) will be apparent to those of ordinary skill in the art in view of the teachings herein. In the present example, assembly (9200) lacks a gearbox that is analogous to gearbox (162), though it should be understood that a gearbox and/or any other suitable components may be interposed between motor (9201) and first bevel gear (9212) to provide desired operational characteristics (e.g., torque, speed, etc.).

Drive gear assembly (9209) comprises first bevel gear (9212), a second bevel gear (9210), and a spur gear (9211) extending around the circumference of second bevel gear (9210). First bevel gear (9212) is attached to the distal end of motor drive shaft (9207) and is configured to rotate in two angular directions as determined by motor drive shaft (9207). First bevel gear (9212) and second bevel gear (9210) are connected by complementary teeth in such a way that rotation of first bevel gear (9212) about a first axis drives rotation of second bevel gear (9210) about a second axis that is perpendicular to the first axis. Second bevel gear (9210) is rotatably coupled to pin (9213) which is also fixed to casing (9203). Therefore, while first bevel gear (9212) and second bevel gear (9210) unitarily rotate with each other relative to casing (9203), gears (9212, 9210) are incapable of translating relative to casing (9203). Spur gear (9211) is unitarily fixed to the circumference of second bevel gear (9210). Therefore, spur gear (9211) also rotates in response to first bevel gear (9212). Casing (9203) is substantially similar to casing (110) described above.

Trocar actuation rod (9202) is substantially similar to trocar actuation rod (220) described above. In the present example, trocar actuation rod (9202) is presumed to be located at a position to define a desirable "clinically acceptable range" for gap distance (d). So while trocar actuation rod (9202) is in fact movable, it is assumed to be stationary through the stages shown in FIGS. 165A-165C.

Drive bracket (9204) is substantially similar to drive bracket (250) described above, except that drive bracket (9204) comprises a spur rack (9208). Spur rack (9208) is configured to mate with spur gear (9211) of drive gear assembly (9209) instead of being pivotably coupled to cam follower (600). Therefore, rotation of spur gear (2011) translates drive bracket (9204) longitudinally due to spur gear (2011) driving spur rack (9208). Drive bracket (9204) is fixed to stapling head assembly driver (9205) via pin (9206). However, drive bracket (9204) and stapling head assembly driver (9205) may instead be formed together as a single unitary piece if desired. Stapling head assembly driver (9205) is substantially similar to stapling head assembly driver (240) described above. Therefore, it should be understood that staple driver member (350) will translate longitudinally relative to trocar actuation rod (9202) in response to translation of stapling head assembly driver (9205) and drive bracket (9205) relative to trocar actuation rod (9202).

FIGS. 165A-165C schematically depict the interaction between drive gear assembly (9209), drive bracket (9204), and stapling head assembly driver (9205). It should be understood that the rotation of drive gear assembly (9209) throughout the stages shown in FIGS. 165A-165C is driven by motor (9201).

FIG. 165A shows stapling head actuation assembly (9200) in a first, pre-firing configuration. Spur gear (9211) of drive gear assembly (9209) is located on a distal portion of spur rack (9208) of drive bracket (9204). At this stage, knife member (340) and staple driver member (350) are in proximal positions, such that stapling head assembly driver (9205) and therefore stapling head assembly (300) are in a non-actuated state.

As first bevel gear (9212) is rotated by motor drive shaft (9207) in a first angular direction, this causes second bevel gear (9210) and spur gear (9211) to rotate about pin (9213) in a clockwise direction. Spur gear (9211) translates drive bracket (9204) via spur rack (9208) in a distal direction to the position shown in FIG. 165B. Drive gear assembly (9209) thus drives knife member (340) and staple driver member (350) distally via drive bracket (9204) and stapling head assembly driver (9205). Stapling head assembly (300) is thus in an actuated states at the stage shown in FIG. 162B.

After drive bracket (9204) reaches the position shown in FIG. 165B, first bevel gear (9212) is rotated by motor drive shaft (9207) in reverse in a second angular direction. This reversal causes second bevel gear (9210) and spur gear (9211) to rotate about pin (9213) in a counterclockwise direction. Spur gear (9211) translates drive bracket (9204) via spur rack (9208) in a proximal direction to the position shown in FIG. 165C. At this stage, knife member (340) and staple driver member (350) are back to proximal positions, such that stapling head assembly driver (9205) and therefore stapling head assembly (300) are back in a non-actuated state.

D. Lead Screw Based Firing and Return System

FIGS. 166A-166C show various components of another stapling head actuation assembly (3200) that are operable to actuate stapling head assembly (300). These components include a motor (9301), a motor drive shaft (9307) that is driven by motor (9301), a first spur gear (9315) coupled to the distal end of motor drive shaft (9307), a second spur gear (9214) coupled to the proximal end of an extending shaft (9313), a bevel gear (9311) coupled to the distal end of extending shaft (9313), a third spur gear (9309), a drive nut (9308) with interior threading, a lead screw (9310), a drive bracket (9304), and a stapling head assembly driver (9305).

Motor (9301) is similar to motor (160) described above. In particular, motor (9301) is coupled with motor drive shaft (9307) and is further coupled with spur gear (9315). Therefore, activation of motor (9301) causes rotation of spur gear (9315). Various suitable configurations that may be used for motor (9301) will be apparent to those of ordinary skill in the art in view of the teachings herein. In the present example, assembly (9300) lacks a gearbox that is analogous to gearbox (162), though it should be understood that a gearbox and/or any other suitable components may be interposed between motor (9301) and first bevel gear (9312) to provide desired operational characteristics (e.g., torque, speed, etc.).

Trocar actuation rod (9302) is substantially similar to trocar actuation rod (220) described above. In the present example, trocar actuation rod (9302) is presumed to be located at a position to define a desirable "clinically acceptable range" for gap distance (d). So while trocar actuation rod (9302) is in fact movable, it is assumed to be stationary through the stages shown in FIGS. 165A-165C.

First spur gear (9315) connects with second spur gear (9314) in such a way that rotation of first spur gear (9315) rotates second spur gear (9314). Second spur gear is fixedly secured to extending shaft (9313). Extending shaft (9313) is rotatably secured to casing (9303). Bevel gear (9311) is fixedly secured to the distal end of extending shaft (9313) so that bevel gear (9311) rotates unitarily with second spur gear (9314). Bevel gear (9311) has teeth that complement the teeth of third spur gear (9309) so that rotation of bevel gear (9311) rotates third spur gear (9309). In some variations, gears (9311, 9309) have meshing helical teeth or threads. It should be understood that gear (9311) rotates about an axis that is obliquely oriented relative to (and laterally offset from) the axis about which gear (9309) rotates. Various suitable ways in which gears (9311, 9309) may be engaged will be apparent to those of ordinary skill in the art in view of the teachings herein.

Third spur gear (9309) encompasses and is fixed to the circumference of drive nut (9308). Drive nut (9308) is rotatably coupled to casing (9303) such that casing (9303) permits drive nut (9308) to rotate within casing (9303) yet permits drive nut (9308) to rotate within casing (9303). Drive nut (9308) comprises internal threading that mates with external threading of lead screw (9310). Lead screw (9310) is permitted to translate within casing (9303) but is prevented from rotating in casing (9303). Lead screw (9310) translates longitudinally in response to rotation of drive nut (9308).

Drive bracket (9304) is substantially similar to drive bracket (250) described above, except that the proximal end of drive bracket (9304) is fixedly secured to lead screw (9310) instead of being pivotably coupled to cam follower (600). Thus, rotation of drive nut (9308) translates drive bracket (9204) longitudinally due to internal threading of drive nut (9308) driving lead screw (9310), which is fixed to proximal end (9312) of drive bracket (9204). Drive bracket (9304) is fixed to stapling head assembly driver (9305) via pin (9306). However, drive bracket (9304) and stapling head assembly driver (9305) may instead be formed together as a single unitary piece if desired. Stapling head assembly driver (9305) is substantially similar to stapling head assembly driver (240) described above. Therefore, it should be understood that staple driver member (350) will translate longitudinally relative to trocar actuation rod (9302) in response to translation of stapling head assembly driver (9305) and drive bracket (9305) relative to trocar actuation rod (9302).

FIGS. 166A-166C schematically depict the interaction between motor drive shaft (9307), first spur gear (9315), second spur gear (9314), extending shaft (9313), bevel gear (9311), third spur gear (9309), drive nut (9308), lead screw (9310), drive bracket (9304) and stapling head assembly driver (9305). It should be understood that the rotation of first spur gear (9315) throughout the stages shown in FIGS. 166A-166C is driven by a motor similar to motor (160) and gearbox (9301).

FIG. 166A shows stapling head actuation assembly (9300) in a first, pre-firing configuration. Drive nut (9308) is located at a distal position along lead screw (9310), thereby holding drive bracket (9304) in a proximal position. At this stage, knife member (340) and staple driver member (350) are in proximal positions, such that stapling head assembly driver (9305) and therefore stapling head assembly (300) are in a non-actuated state.

As first spur gear (9315) is rotated by motor drive shaft (9307) in a first angular direction, this causes second spur gear (9314), extending shaft (9313) and bevel gear (9311) to rotate in a second (opposite) direction. Bevel gear (9311) engages spur gear (9309) to rotate spur gear (9311). Spur gear (9311) drives drive nut (9308) to rotate. Internal threading of drive nut (9308) then drives lead screw (9310) in a distal direction. Lead screw (9310) translates drive bracket (9304) in a distal direction to the position shown in FIG. 166B. Motor (9301) thus drives knife member (340) and staple driver member (350) distally via drive bracket (9304) and stapling head assembly driver (9305). Stapling head assembly (300) is thus in an actuated state at the stage shown in FIG. 166B.

After drive bracket (9304) reaches the position shown in FIG. 166B, first spur gear (9315) is rotated by motor drive shaft (9307) in reverse to a second angular direction. This reversal causes second spur gear (9314), extending shaft (9313), and bevel gear (9311) to rotate in a reverse direction. Bevel gear (9311) engages spur gear (9309) to rotate spur gear (9211) in reverse. Spur gear (9311) drives drive nut (9308) to rotate in reverse. Internal threading of drive nut (9308) then drives lead screw (9310) in a proximal direction. Lead screw (9310) translates drive bracket (9304) back in a proximal direction to the position shown in FIG. 166C. At this stage, knife member (340) and staple driver member (350) are back to proximal positions, such that stapling head assembly driver (9205) and therefore stapling head assembly (300) are back in a non-actuated state.

XVII. Circular Stapler with Rotatable Shaft

In some instances, it may be desirable to rotate a shaft (9502) relative to a handle assembly (9503) of a circular stapler (9500). In particular, it may be desirable from an ergonomic standpoint to enable an operator to rotate shaft (9502) relative to handle assembly (9503), particularly when shaft (9502) includes a preformed bend. This may enable the operator to more easily position a stapling head assembly (9530) in relation to handle assembly (9503). Such rotatability thus might benefit an operator by limiting arm or hard motion required of the operator in order to place circular stapler (9500) in the proper location or orientation required to fire circular stapler (9500).

FIG. 167 depicts circular stapler (9500) with handle assembly (9503), shaft (9502), and a rotator knob (9501) configured to rotate shaft (9502) relative to handle assembly (9503). Rotator knob (9501) comprises an array of gripping features (9504) that are configured to be gripped by user.

FIG. 168 depicts a cross-sectional view of rotator knob (9501) slidably attached to rotatable shaft (9502) in such a way that rotator knob (9501) can translate along shaft (9502) and rotate shaft (9502) about the longitudinal axis. A trocar actuation band (9511) is unitarily fixed to distal end of trocar actuation rod (9508) by trocar band holder (9509) in such a way that trocar actuation band (9511) rotates and translates with distal trocar actuation rod (9508). Proximal trocar actuation rod (9506) is within handle assembly (9503) and terminates at trocar actuation rod ball joint (9507). Trocar actuation rod ball joint (9507) rotatably connects proximal trocar actuation rod (9506) with distal trocar actuation rod (9508).

Similarly, proximal end stapling head assembly driver (9512) is within handle assembly (9503) and terminates at stapling head assembly driver ball joint (9513). Stapling head assembly driver ball joint (9513) rotatably connects proximal stapling head assembly driver (9512) and distal end stapling head assembly driver (9514).

Rotator knob (9501) comprises grip (9504) and strip (9505) unitarily coupled to grip (9504). Strip (9505) extends into both distal end stapling head assembly driver (9514) and trocar actuation band (9511). Therefore, when rotator knob (9501) rotates about shaft (9502), strip (9505) causes trocar actuation band (9511), trocar band holder (9509), distal trocar actuation rod (9508), and distal stapling head assembly driver (9514) to unitarily rotate relative to proximal end stapling head assembly driver (9512) and proximal trocar actuation rod (9506) due to ball joints (9507, 9513). Since rotator knob (9501) is slidably connected to rotatable shaft (9502), trocar actuation band (9511), trocar band holder (9509), distal trocar actuation rod (9508), and distal stapling head assembly driver (9514) are also able to translate relative to rotatable shaft (9502). Of course, any other means known in the art in view of the teachings herein may be utilized to rotate rotatable shaft (9502). It should also be understood that one or more features may be provided to selectively lock the angular position of shaft (9502) relative to handle assembly (5503).

XVIII. Exemplary Alternative Features for Coupling Anvil and Stapling Head Assembly As noted above, prior to performing an anastomosis procedure, anvil (400) may be coupled to trocar (330) of stapling head assembly (300) after purse string sutures (30) are applied about anvil (400) and stapling head assembly (330) to substantially secure anatomical structures (20, 40) relative to anvil (400) and stapling head assembly (330). In some instances, it may be difficult to grasp anvil (400) without risking damage to the anvil (400) itself or tissue. For example, it may be difficult to couple trocar (330) to anvil (400) if a grasping instrument (e.g., a conventional surgical grasping instrument) is grasping one of latch members (430), for example. Moreover, reducing the amount of components in anvil (400) may reduce the likelihood of tissue interference and/or injury during use of anvil (400) and instrument (10), and may reduce manufacturing costs.

FIGS. 169-170B show an exemplary alternative anvil (10400) that is suitable for incorporation into a surgical instrument, such as surgical instrument (10). Particularly, anvil (10400) is configured to removably couple with shaft assembly (200) of instrument (10). However, anvil (10400) includes several different features that further enable an operator to couple anvil (10400) to the stapling head assembly (300) of shaft assembly (200), particularly to trocar (330) of stapling head assembly (300). When anvil (10400) is removably coupled to stapling head assembly (300), anvil (10400) and stapling head assembly (300) are configured to cooperate to manipulate tissue in the same manner discussed above with respect to anvil (400), including clamping the tissue, cutting the tissue, and stapling the tissue. In the following discussion of anvil (10400), the terms "distal" and "proximal" (and variations thereof) will be used with reference to the orientation of anvil (10400) when anvil (10400) is coupled with shaft assembly (200) of instrument (10). Thus, proximal features of anvil (10400) will be closer to the operator of instrument (10); while distal features of anvil (10400) will be further from the operator of instrument (10).

As best seen in FIGS. 169-170B, anvil (10400) of the present example comprises a head (10410) and a shank (10420). Head (10410) is configured to be substantially similar to head (410). Head (10410) includes a proximal surface (10412) that defines a plurality of staple forming pockets (10414). Staple forming pockets (10414) are arranged in two concentric annular arrays. In some other versions, staple forming pockets (10414) are arranged in three or more concentric annular arrays. Staple forming pockets (10414) are configured to deform staples as the staples are driven into staple forming pockets (10414), in the same manner as discussed above with respect to staple forming pockets (414). For instance, each staple forming pocket (10414) may deform a generally "U" shaped staple into a "B" shape as is known in the art.

Shank (10420) defines a bore or lumen (10422), splines (10424), grab zones (10436, 10438), and an engagement feature. In the present example, the engagement feature comprises latch members (10430). Splines (10424) are provided in order to allow the operator to properly angularly align anvil (10400) relative to stapling head assembly. Particularly, in the present example, splines (10424) include a substantially identical angular spacing as splines (313) of inner core member (312) of tubular casing (310) (FIGS. 6-7), such that the operator may visually observe the position of splines (10424) in relation to splines (313) in order to verify proper angular alignment of anvil (10400) in relation to stapling head assembly (300). Anvil (10400) and stapling head assembly (300) are configured such that when splines (10424) are aligned with respective splines (313) of inner core member (312) of tubular casing (310), staple forming pockets (10414) of anvil (10400) are aligned with staple openings (324) (FIGS. 6-7). In some other versions, inner core member (312) includes a plurality of interior guide channels that are configured to receive splines (10424) in order to provide proper angular alignment of anvil (10400) in relation to stapling head assembly (300). Such guide channels may include tapered distal portions that provide camming features to engage splines (10424) and thereby rotate anvil (10400) into alignment as needed when anvil (10400) is proximally retracted relative to stapling head assembly (300). Other suitable ways of providing or promoting proper angular alignment of anvil (10400) in relation to stapling head assembly (300) will be apparent to those of ordinary skill in the art in view of the teachings herein.

In the example shown, grab zones (10436, 10438) are provided with a textured surface (10442, 10444), respectively, to enhance the grip of a grasping instrument on shank (10420) while, for example, an operator couples anvil (10400) with trocar (330). Grab zones (10436, 10438) may also provide a visual indication to indicate where anvil (10400) should be engaged by a grasping instrument. Grab zone (10436) is positioned distal to latch members (10430) such that an operator may grasp grab zone (10436) without accidentally grasping, and potentially damaging latch members (10430) or tissue that is captured by the purse string suture (30), as discussed above with respect to FIGS. 21A-B. A portion of grab zone (10438) is positioned coincident with a proximal end or portion (10452) of latch members (10430). However, because latch members (10430) are connected to shank (10420) at proximal ends (10452) and because latch members (10430) pivot at a point at or near proximal ends (10452), the force or moment on latching members associated with an operator grasping grab zone (10438) is less likely to result in damage to latch members (10430).

As shown, textured surfaces (10442, 10444) include a knurled configuration. However, one or both of textured surfaces (10442, 10444) may include additional or alternative features that are integral or non-integral with shank (10420). The additional or alternative features may be, for example, a coating or alternative textures such as longitudinally extending ridges, annular ridges, etc. Other suitable configurations of textured surfaces (10442, 10444) will be apparent to persons skilled in the art in view of the teachings herein. Shank (10420) defines a first portion (10446) that is positioned distally of a second portion (10448). Second portion (10448) includes a smaller cross-sectional dimension (e.g., diameter) than first portion (10446) (in the configuration shown in FIGS. 22, 170B). Shank (10420) further defines a tapered portion (10450) between the first and second portions (10446, 10448). In other examples, however, the relative dimensions of different portions of shank (10420) may be different than those shown in FIGS. 169-170B. In the present example, textured surface (10444) is positioned coincident with second portion (10448).

Latch members (10430) are in communication with lumen (10422) such that when trocar (330) is received within lumen (10422), latch members (10430) secure anvil (10400) to trocar (330). As shown, latch members (10430) include a proximal end (10452) and a distal end (10454) and are integral with shank (10420). In the present example, each of latch member (10430) is formed at least in part from creating a pair of opposing longitudinal slits (10456) (e.g., cutouts) in shank (10420) and a transverse slit (10458) between the ends of longitudinal slits (10456). Transverse slits (10458) more particularly extend around a longitudinal axis (10460) of anvil (10400). Therefore, due to the configuration of the present example, latch members (10430) are configured to deflect outwardly about a point at or near proximal ends (10452) of latch members (10430). As seen best in FIG. 169, in the present example, longitudinal slits (10456) extend along first portion (10446), tapered portion (10450), and second portion (10448), but do not extend fully to and through the proximal end of shank (10420). Thus, proximal end (10457) of shank (10420) is radially fixed relative to axis (10460). Therefore, shank (10420) presents a proximal end (10457) that is more rigid than the portion of shank (10420) that is coincident with the slits (10456, 10458) and latch members (10430), thereby reducing the likelihood of damaging the shank (10420) (e.g., the latch members (10430)). Moreover, the absence of slits (10456) at proximal end (10457) of shank (10420) may reduce the likelihood of unwanted tissue interference before, during, and after the operator attempts to couple anvil (10400) to trocar (330).

In the present example, latch members (10430) are resiliently biased to the position shown in FIGS. 22 and 170B. Each latch members (10430) includes a radially inward protrusion (10461) including a proximal cam surface (10462) and a distal cam surface (10464). Cam surfaces (10462, 10464) are configured to provide radially outward flexing and radially inward flexing of latch members (10430), respectively, as trocar (330) is directed into lumen (10422). In particular, as trocar (330) is directed into lumen (10422), head (336) of trocar (330) rides against proximal cam surface (10462) and causes latch members (10430) to flex outwardly, as shown in FIG. 170A. As trocar (330) moves further distally, proximal surface (338) of trocar (330) rides against distal cam surface (10464) and allows latch members (10430) to flex back inwardly, as shown in FIG. 170B. Thus, anvil (10400) is removably coupled to stapling head assembly (300), enabling anvil (10400) and stapling head assembly (300) to cooperate to manipulate tissue as discussed herein, in a substantially similar manner as anvil (400) and stapling head assembly (300).

FIGS. 171-172B show another exemplary alternative anvil (10500) that is suitable for incorporation into a surgical instrument, such as surgical instrument (10). Anvil (10500) is configured to operate substantially similar to anvil (400, 10400), except for the differences discussed below. Anvil (10500) of the present example comprises a head (10510) and a shank (10520). Head (10510) is configured to operate substantially similarly to head (410, 10410). In that regard, head (10400) includes a proximal surface (10512) that defines a plurality of staple forming pockets (10514). Staple forming pockets (10514) are arranged in two concentric annular arrays. In some other versions, staple forming pockets (10514) are arranged in three or more concentric annular arrays. Staple forming pockets (10514) are configured to deform staples as the staples are driven into staple forming pockets (10514), in the same manner as discussed above with respect to staple forming pockets (414, 10414). For instance, each staple forming pocket (10514) may deform a generally "U" shaped staple into a "B" shape as is known in the art.

Shank (10520) defines a lumen (10522), splines (10536), grab zones (10538, 10540), and an engagement feature. In the present example, the engagement feature comprises resilient members (10530). Splines (10536) are provided in order to allow the operator to properly angularly align anvil (10500) relative to stapling head assembly. Particularly, in the present example, splines (10536) include a substantially identical angular spacing as splines (313) of inner core member (312) of tubular casing (310) (FIGS. 6-7), such that the operator may visually observe the position of splines (10536) in relation to splines (313) in order to verify proper angular alignment of anvil (10500) in relation to stapling head assembly (300). Anvil (10500) and stapling head assembly (300) are configured such that when splines (10524) are aligned with respective splines (313) of inner core member (312) of tubular casing (310), staple forming pockets (10514) of anvil (10500) are aligned with staple openings (324) (FIGS. 6-7). In some other versions, inner core member (312) includes a plurality of interior guide channels that are configured to receive splines (10524) in order to provide proper angular alignment of anvil (10500) in relation to stapling head assembly (300). Such guide channels may include tapered distal portions that provide camming features to engage splines (10524) and thereby rotate anvil (10500) into alignment as needed when anvil (10500) is proximally retracted relative to stapling head assembly (300). Other suitable ways of providing or promoting proper angular alignment of anvil (10500) in relation to stapling head assembly (300) will be apparent to those of ordinary skill in the art in view of the teachings herein.

In the example shown, grab zones (10538, 10540) are provided with a textured surface (10542, 10544), respectively, to enhance the grip of a grasping instrument on shank (10520) while, for example, an operator couples anvil (10500) with trocar (330). Grab zones (10538, 10540) may also provide a visual indication to indicate where anvil (10400) should be engaged by a grasping instrument. Grab zone (10538) is positioned distal to latch members (10430), and grab zone (10540) is positioned proximal to latch members (10430), such that an operator may grasp grab zone (10538, 10540) without accidentally grasping, and potentially damaging resilient members (10530) or tissue that is captured by the purse string suture (30), as discussed above with respect to FIGS. 21A-B.

As shown, textured surfaces (10542, 10544) include a knurled configuration. However, one or both of textured surfaces (10542, 10544) may include additional or alternative features that are integral or non-integral with shank (10520). The additional or alternative features may be, for example, a coating or alternative textures such as longitudinally extending ridges, annular ridges, etc. Other suitable configurations of textured surfaces (10542, 10544) will be apparent to persons skilled in the art in view of the teachings herein. As shown in the present example, shank (10520) includes the same cross-sectional dimension at each grab zone (10538, 10540). In other examples, however, the relative dimensions of different portions of shank (10520) may be different than those shown in FIGS. 171-172B.

Resilient members (10530) are in communication with lumen (10522) such that when trocar (330) is received within lumen (10522), resilient members (10530) secure anvil (10500) to trocar (330). As shown, resilient members (10530) include a proximal portion (10552), a distal portion (10554), and an intermediate portion (10555) therebetween. In the present example, resilient members (10530) are integral with shank (10520). In particular, resilient members (10530) are formed at least in part by the presence of longitudinal slits (10556), such that forming slits (10556) in shank (10520) facilitates deformation of the portions of shank (10520) defining resilient members (10530). Slits (10556) extend generally between grab zone (10538) and grab zone (10540), but do not extend fully to and through the proximal end (10537) of shank (10520). Thus, proximal end (10537) of shank (10520) is radially fixed relative to the longitudinal axis (10560) of shank (10520). Therefore, shank (10520) presents a proximal end (10537) that is more rigid than the portion of shank (10520) that is coincident with the slits (10556) and resilient members (10530), thereby reducing the likelihood of damaging the shank (e.g., the latch members (10430)). Moreover, the absence of slits (10456) at proximal end (10537) of shank (10520) may reduce the likelihood of unwanted tissue interference before, during, and after the operator attempts to couple anvil (10500) to trocar (330). Proximal end (10537) further includes a frustoconical shaped portion (10570) defining a lip (10572).

In the present example, intermediate portion (10555) includes a radially inward projection (10562) extending toward longitudinal axis (10560) of anvil (10500) and a radially outward projection (10564) extending away from axis (10560). Therefore, intermediate portion (10555) defines a portion of shank (10520) that includes a greater cross-sectional dimension than other portions of shank (10520), such as portions of shank coincident with grab zones (10538, 10540). In some versions, intermediate portion (10555) is marked in red or has some other visual indication that indicates to an operator that intermediate portion (10555) should not be grasped with a grasping instrument. Otherwise, if the operator grasps anvil (10500) by intermediate portion (10555), this may prevent intermediate portion (10555) from properly flexing outwardly as described below as the operator attempts to secure anvil (10500) to trocar (330).

In the example shown, radially inward projection (10562) includes a proximal cam surface (10566) and a distal cam surface (10568) that are configured to cause radially outward flexing and radially inward flexing, respectively, of resilient members (10530) as trocar (330) is directed into lumen (10522). In particular, as trocar (330) is directed into lumen (10522), proximal portion of head (336) of trocar (330) rides against proximal cam surface (10566) and causes resilient members (10530) to bow outwardly, as shown in FIG. 172A. As trocar (330) moves further distally, proximal surface (338) of trocar (330) rides against distal cam surface (10568) and allows resilient members (10530) to flex back inwardly, as shown in FIG. 172B. As shown, annular groove (339) of trocar receives inward projection (10562). Thus, anvil (10500) is removably coupled to stapling head assembly (300), enabling anvil (10500) and stapling head assembly (300) to cooperate to manipulate tissue as discussed herein.

FIGS. 173-174B show another exemplary alternative anvil (10600) that is suitable for incorporation into a surgical instrument, such as surgical instrument (10). Particularly, anvil (10600) is configured to removably couple with shaft assembly (200) of instrument (10). However, anvil (10600) includes several different features that further enable an operator to couple anvil (10600) to the stapling head assembly (300) of shaft assembly (200), particularly to trocar (330) of stapling head assembly (300). When anvil (10600) is removably coupled to stapling head assembly (300), anvil (10600) and stapling head assembly (300) are configured to cooperate to manipulate tissue in the same manner discussed above with respect to anvil (400), including clamping the tissue, cutting the tissue, and stapling the tissue. In the following discussion of anvil (10600), the terms "distal" and "proximal" (and variations thereof) will be used with reference to the orientation of anvil (10600) when anvil (10600) is coupled with shaft assembly (200) of instrument (10). Thus, proximal features of anvil (10600) will be closer to the operator of instrument (10); while distal features of anvil (10600) will be further from the operator of instrument (10).

As best seen in FIGS. 173-174B, anvil (10600) of the present example comprises a head (10610) and a shank (10620). Head (10610) is configured to be substantially similar to head (410). Head (10610) includes a proximal surface (10612) that defines a plurality of staple forming pockets (10614). Staple forming pockets (10614) are arranged in two concentric annular arrays. In some other versions, staple forming pockets (10614) are arranged in three or more concentric annular arrays. Staple forming pockets (10614) are configured to deform staples as the staples are driven into staple forming pockets (10614), in the same manner as discussed above with respect to staple forming pockets (414, 10414, 10514). For instance, each staple forming pocket (10614) may deform a generally "U" shaped staple into a "B" shape as is known in the art.

Shank (10620) defines a lumen (10622) and an engagement feature. In the present example, the engagement feature comprises latch members (10630). Each latch member (10630) is formed at least in part from creating a pair of opposing longitudinal slits (10656) (e.g., cutouts) in shank (10620) and a transverse slit (10658) between the ends of longitudinal slits (10656). Transverse slits (10658) more particularly extend around a longitudinal axis (10660) of anvil (10600). Latch members include a proximal end (10652) and a distal end (10654) that extends into head (10610) of anvil (10600). Anvil (10600) includes a pivot limiting member (10655) that limits the pivoting of latch members outwardly relative to axis (10660). Therefore, due to the configuration of the present example, latch members (10630) are configured to pivot about a point at or near distal ends (10652) of latch members (10630), but are limited in the amount of pivoting due to the presence of member (10655).

As seen best in FIG. 173, in the present example, longitudinal slits (10656) extend along a portion that is between the proximal and distal ends (10657, 10659) of shank, but do not extend fully to and through the proximal end (10657) of shank (10620). Thus, proximal end (10657) of shank (10620) is radially fixed relative to axis (10460). Therefore, shank (10620) presents a proximal end (10657) that is more rigid than the portion of shank (10620) that is coincident with the slits (10656, 10658) and latch members (10630), thereby reducing the likelihood of damaging the shank (10620) (e.g., the latch members (10630)). Moreover, the absence of slits (10656) at proximal end (10657) of shank (10620) may reduce the likelihood of unwanted tissue interference before, during, and after the operator attempts to couple anvil (10400) to trocar (330). Furthermore, as best seen in FIGS. 174A-B, proximal ends (10652) of latch members (10630) are tapered in order to prevent unwanted tissue interference during use of anvil (10600). A tapered, increased cross-sectional dimension portion (10666) is provided on shank (10620) adjacent to slits (10658) to further prevent tissue interference. For instance, portion (10666) may prevent tissue from snagging on proximal ends (10652) of latch members (10630) and/or entering slits (10658), even when latch members (10630) are being deflected outwardly by trocar (330).

In the present example, latch members (10630) are resiliently biased to the position shown in FIGS. 26 and 174B. Each latch members (10630) includes a radially inward protrusion including (10661) a proximal cam surface (10662) and a distal cam surface (10664). Cam surfaces (10662, 10664) are configured to provide radially outward flexing and radially inward flexing, respectively, as trocar (330) is directed into lumen (10622). In particular, as trocar (330) is directed into lumen (10622), head (336) of trocar (330) rides against proximal cam surface (10662) and causes latch members (10630) to flex outwardly, as shown in FIG. 174A. As trocar (330) moves further distally, proximal surface (338) of trocar (330) rides against distal cam surface (10664) and allows latch members (10630) to flex back inwardly, as shown in FIG. 170B. Thus, anvil (10600) is removably coupled to stapling head assembly (300), enabling anvil (10600) and stapling head assembly (300) to cooperate to manipulate tissue as discussed herein, in a substantially similar manner as anvil (400) and stapling head assembly (300).

In the example shown, anvil (10600) does not include some of the features included in or on anvils (400, 10400, 10500). However, in other examples, anvil (10600) may include such features of anvils (400, 10400, 10500), such as grab zones (10436, 10438, 10538, 10540), splines (10424, 10536), and other features shown in FIGS. 169-172B.

FIGS. 175-176A show another exemplary alternative anvil (10700) that is suitable for incorporation into a surgical instrument, such as surgical instrument (10). Particularly, anvil (10700) is configured to removably couple with shaft assembly (200) of instrument (10). However, anvil (10700) includes several different features that further enable an operator to couple anvil (10700) to the stapling head assembly (300) of shaft assembly (200), particularly to trocar (330) of stapling head assembly (300). When anvil (10700) is removably coupled to stapling head assembly (300), anvil (10700) and stapling head assembly (300) are configured to cooperate to manipulate tissue in the same manner discussed above with respect to anvil (400), including clamping the tissue, cutting the tissue, and stapling the tissue. In the following discussion of anvil (10700), the terms "distal" and "proximal" (and variations thereof) will be used with reference to the orientation of anvil (10700) when anvil (10700) is coupled with shaft assembly (200) of instrument (10). Thus, proximal features of anvil (10700) will be closer to the operator of instrument (10); while distal features of anvil (10700) will be further from the operator of instrument (10). FIGS. 175-176A also show a modified trocar (10330) that includes magnetic features that are configured to be magnetically coupled to magnetic features of anvil (10700), as discussed in more detail below.

Anvil (10700) of the present example includes features that are substantially similar to anvil (10400). For that reason, features of anvil (10700) that are substantially similar or identical to features of anvil (10400) are labeled with the same reference numbers without further discussion below. One of the differences between anvil (10400) and anvil (10700) is that anvil (10700) utilizes magnetic features, in addition to mechanical coupling features, to couple anvil (10700) with trocar (10300). Particularly, first head portion (10710) and shank (10722) receive a tubular member (10770) that includes a shaft (10772) and second head portion (10774). When shaft (10772) is received relative to head (10710) and shank (10722), first and second head portions (10710, 10774) collectively define a head of anvil (10700). As shown in the present example, shaft (10772) includes a magnetic feature (10776) with respective north and south poles (N, S). As seen best in FIGS. 176A-B, when shaft (10772) is received in shank (10722), proximal end (10778) of shaft (10772) is positioned distal to slits (10458) and therefore distal to latch members (10430). Proximal end (10737) further includes a frustoconical shaped portion (10780) defining a lip that is similar to the lip (10572) shown in FIGS. 172A-B.

Trocar (10330) is configured to operate substantially similar to trocar (330). Particularly, trocar (10330) is suitable as an alternative to trocar (330) in a stapling head assembly (300) of a surgical instrument, such as instrument (10). Trocar is different from trocar (330) in that trocar (10330) includes a modified, elongate head (10336) that is configured to accommodate a magnetic feature (10340) that includes a north pole (N) proximally and a south pole (S) distally. Trocar (10330) also includes a proximal cam feature (10338) and a distal cam feature (10342).

In the present example, magnetic features (10340, 10776) each comprise a discrete permanent magnet, such that magnetic feature (10340) is a separate component embedded in or coupled to trocar (10330) and magnetic feature (10776) are is a separate component embedded in or coupled to shaft (10772). By way of example only, magnetic feature (10776) may be in the form of an annular cuff or other cylindraceous structure. In some other versions, magnetic feature (10776) comprises a pair of discrete magnets that are located at the same longitudinal position along shaft (10772). It should also understood that one or both of magnetic features (10340, 10776) may comprise an electromagnet. In other examples, magnetic features (10330, 10776) may be portions of trocar (10330) and/or tube (10772) that are magnetized as would be understood by persons skilled in the art. Additionally or alternatively, magnetic features (10340, 10776) may be a combination of any of the magnetic elements described herein.

As trocar (10330) is directed into lumen (10422), proximal cam feature (10338) of head (10336) of trocar (10330) rides against proximal cam surface (10464) and causes latch members (10430) to flex outwardly, as shown in FIG. 176A. As trocar (330) moves further distally, proximal surface (338) of trocar (330) rides against distal cam surface (10466) and allows latch members (10430) to flex back inwardly, as shown in FIG. 176B.

It should be understood that the south pole (S) of magnetic feature (10340) is substantially adjacent to the north pole (N) of magnetic feature (10776) at the stage shown in FIG. 176B. Thus, in addition to the mechanical coupling shown in FIG. 176B, magnetic feature (10340) is magnetically coupled to magnetic feature (10776) of shaft (10772), thus adding an additional measure of protection against an undesired decoupling of anvil (10700) from trocar (10330) (i.e., by requiring additional force to undesirably decouple anvil (10700) from trocar (10330)). Thus, with anvil (10400) removably coupled to stapling head assembly (300), anvil (10400) and stapling head assembly (300) are able to cooperate to manipulate tissue as discussed herein, in a substantially similar manner as anvil (400) and stapling head assembly (300). In addition to enhancing the security of the coupling between anvil (10440) and trocar (10330), magnetic features (10340, 10776) may cooperate to draw anvil (10440) proximally into full engagement with trocar (10330), such as when anvil (10440) is positioned as shown in FIG. 176A. In other words, the magnetic force of magnetic features (10340, 10776) may enable the operator to simply release anvil (10440) at the stage shown in FIG. 176A, with magnetic features (10340, 10776) cooperating to provide the final proximal movement of anvil (10440) to fully seat trocar (10333) in anvil (10440).

XIX. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, issued as U.S. Pat. No. 8,408,439 on Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of operating a surgical instrument, wherein the surgical instrument comprises:
   (a) a body;
   (b) a shaft assembly extending distally from the body;
   (c) a stapling head assembly located at the distal end of the shaft assembly, wherein the stapling head assembly comprises a distal surface, wherein the stapling head assembly is operable to drive an annular array of staples through the distal surface;
   (d) an anvil, wherein the anvil is configured to couple with the stapling head assembly;
   (e) an anvil adjustment assembly, wherein the anvil adjustment assembly comprises a translating member, wherein the translating member is operable to translate relative to the body along a longitudinal axis defined by the body to thereby adjust the longitudinal position of the anvil relative to the distal surface of the stapling head assembly;
   (f) a first trigger, wherein the first trigger is operable to actuate the stapling head assembly to thereby drive the annular array of staples through the distal surface toward the anvil; and
   (g) a lockout assembly, wherein the lockout assembly comprises an electrically powered braking feature, wherein the electrically powered braking feature further comprises an actuator that defines an enclosure and a lock member that extends from inside the enclosure from a retracted position to an extended position, wherein the lockout assembly is configured to transition between a first state and a second state, wherein:
      (i) in the first state, the lockout assembly is configured to permit translation of the translating member, and
      (ii) in the second state, the lockout assembly is configured to prevent translation of the translating member;
   wherein the method comprises:
   (a) providing the lockout assembly in the first state to permit translation of the translating member, wherein in the first state the electrically powered braking feature is separated at a distance from the translating member;

(b) translating the translating member; and
(c) transitioning the lockout assembly to the second state to prevent further translation of the translating member by linearly translating the lock member of the electrically powered braking feature away from the enclosure defined by the actuator to be in contact with the translating member.

2. The method of claim 1, further comprising initially providing the lockout assembly in the second state, wherein the act of providing the lockout assembly in the first state comprises transitioning the lockout assembly from the second state to the first state.

3. The method of claim 2, wherein the body defines a socket configured to receive a battery pack, wherein the act of transitioning the lockout assembly from the second state to the first state comprises inserting a battery pack in the socket.

4. The method of claim 1, wherein the lockout assembly further comprises a second trigger, wherein the second trigger is movable between a non-actuated position and an actuated position, wherein the act of transitioning the lockout assembly to the second state comprises actuating the second trigger.

5. The method of claim 4, further comprising actuating the first trigger to thereby actuate the stapling head assembly.

6. The method of claim 5, wherein the second trigger is configured to prevent actuation of the first trigger when the second trigger is in the non-actuated position, wherein the act of actuating the second trigger is performed before the act of actuating the first trigger.

7. The method of claim 5, wherein the translating member is configured to prevent actuation of the second trigger based on the longitudinal position of the anvil relative to the distal surface of the stapling head assembly.

8. The method of claim 7, wherein the act of translating the translating member further comprises translating the translating member from a position where the translating member prevents actuation of the second trigger to a position that enables actuation of the second trigger.

9. The method of claim 1, wherein the electrically powered braking feature comprises a solenoid, wherein the act of transitioning the lockout assembly to the second state comprises activating the solenoid.

10. The method of claim 9, wherein the activated solenoid drives the lock member into engagement with the translating member to thereby prevent translation of the translating member.

11. The method of claim 10, wherein the act of providing the lockout assembly in the first state comprises disengaging the lock member from the translating member.

12. The method of claim 1, wherein in the first state, the lockout assembly is further configured to prevent actuation of the first trigger, and wherein in the second state, the lockout assembly is further configured to permit actuation of the first trigger.

13. The method of claim 1, further comprising:
(a) positioning the anvil in a first anatomical structure;
(b) positioning the stapling head assembly in a second anatomical structure;
(c) securing the anvil to the stapling head assembly; and
(d) actuating the stapling head assembly to drive the annular array of staples through tissue of the first anatomical structure and through tissue of the second anatomical structure.

14. The method of claim 1, wherein the lockout assembly includes an activation board, wherein transitioning the lockout assembly to the second state further comprises activating the activation board to initiate movement of the actuator to drive the lock member into locking engagement with the translating member.

15. The method of claim 14, wherein the activation board comprises a button, wherein transitioning the lockout assembly to the second state further comprises moving an activation arm toward the button of the activation board until the activation arm contacts the button.

16. The method of claim 14, wherein transitioning the lockout assembly to the second state further comprises communicating a signal from the activation board to the actuator causing the actuator to respond to the signal by driving the lock member into locking engagement with the translating member.

17. The method of claim 1, wherein the lock member includes a plurality of teeth, wherein the translating member includes a corresponding plurality of teeth, wherein transitioning the lockout assembly to the second state further comprises linearly translating the lock member so that the plurality of teeth of the lock member lockingly engage the plurality of corresponding teeth of the translating member.

18. A method of operating a surgical instrument, wherein the surgical instrument comprises:
(a) a stapling head assembly, wherein the stapling head assembly comprises a plurality of staples;
(b) a clamping member, wherein the clamping member comprises a plurality of staple forming features;
(c) a clamping drive assembly, wherein the clamping drive assembly is operable to drive the clamping member toward and away from the stapling head assembly;
(d) a firing assembly, wherein the firing assembly is operable to actuate the stapling head assembly to thereby drive the staples toward the staple forming features; and
(e) a lockout assembly, wherein the lockout assembly is operable to selectively lock the clamping drive assembly and thereby prevent actuation of the clamping drive assembly in response to a first operational condition, wherein the lockout assembly is further operable to selectively lock the clamping drive assembly and thereby prevent actuation of the clamping drive assembly in response to a second operational condition, wherein the second operational condition is different from the first operational condition, wherein the lockout assembly comprises an electrically activated actuator, wherein the electrically activated actuator comprises an enclosure and an arm that linearly translates away from the enclosure defined by the electrically powered actuator between a retracted position and an extended position;
wherein the method comprises:
(a) providing the surgical instrument in the first operational condition where the lockout assembly is in a locked state;
(b) removing the first operational condition to transition the lockout assembly to an unlocked state; and
(c) providing the second operational condition to transition the lockout assembly back to the locked state by an operator manually actuating a safety trigger of the firing assembly which causes the arm of the electrically activated actuator to linearly translate away from the enclosure defined by the electrically powered actuator from the retracted position to the extended position to prevent actuation of the clamping drive assembly.

19. The method of claim 18, wherein the surgical instrument comprises a body defining a battery socket, wherein the act of removing the first operational condition comprises inserting a battery into the battery socket of the body.

20. A method of operating a surgical instrument, wherein the surgical instrument comprises:
(a) a stapling head assembly, wherein the stapling head assembly comprises a plurality of staples;
(b) a clamping member, wherein the clamping member comprises a plurality of staple forming features;
(c) a clamping drive assembly, wherein the clamping drive assembly is operable to drive the clamping member toward and away from the stapling head assembly;
(d) a firing assembly, wherein the firing assembly is operable to actuate the stapling head assembly to thereby drive the staples toward the staple forming features;
(e) a first lockout assembly, wherein the first lockout assembly is configured to prevent actuation of the firing assembly unless the clamping member is within a predefined range of distance from the stapling head assembly; and
(f) a second lockout assembly, wherein the second lockout assembly is configured to prevent actuation of the clamping drive assembly during activation of the firing assembly, wherein the second lockout assembly comprises an electrically activated actuator, wherein the electrically activated actuator comprises an enclosure and an arm that linearly translates away from the enclosure between a retracted position and an extended position;

wherein the method comprises:
(a) positioning the clamping member within the predefined range of distance from the stapling head assembly;
(b) activating the first lockout assembly to permit actuation of the firing assembly;
(c) activating the electrically activated actuator of the second lockout assembly, so that the arm of the electrically activated actuator linearly translates away from the enclosure from the retracted position to the extended position to thereby prevent actuation of the clamping drive assembly during activation of the firing assembly; and
(d) actuating the firing assembly.

* * * * *